(12) United States Patent
Ding et al.

(10) Patent No.: US 11,845,937 B2
(45) Date of Patent: Dec. 19, 2023

(54) RNAI AGENTS FOR INHIBITING EXPRESSION OF DUX4, COMPOSITIONS THEREOF, AND METHODS OF USE

(71) Applicant: Arrowhead Pharmaceuticals, Inc., Pasadena, CA (US)

(72) Inventors: Zhi-Ming Ding, Waunakee, WI (US); Jonathan Van Dyke, Burke, WI (US); Xiaokai Li, Middleton, WI (US); Anthony Nicholas, Oregon, WI (US); Casi M. Schienebeck, Deerfield, WI (US); Tao Pei, Middleton, WI (US); Zhao Xu, Brookfield, WI (US); Teng Ai, Middleton, WI (US); Susan Phan, Fitchburg, WI (US); Susan Ramos-Hunter, Hendersonville, TN (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 0 days.

(21) Appl. No.: 18/181,199

(22) Filed: Mar. 9, 2023

(65) Prior Publication Data
US 2023/0265430 A1 Aug. 24, 2023

Related U.S. Application Data

(63) Continuation of application No. PCT/US2021/049871, filed on Sep. 10, 2021.

(60) Provisional application No. 63/214,742, filed on Jun. 24, 2021, provisional application No. 63/077,272, filed on Sep. 11, 2020.

(51) Int. Cl.
*C12N 15/113* (2010.01)
*A61K 47/64* (2017.01)
*A61P 21/00* (2006.01)

(52) U.S. Cl.
CPC ............ *C12N 15/113* (2013.01); *A61K 47/64* (2017.08); *A61P 21/00* (2018.01); *C12N 2310/14* (2013.01); *C12N 2310/314* (2013.01); *C12N 2310/321* (2013.01); *C12N 2310/3513* (2013.01)

(58) Field of Classification Search
CPC ....... A61K 47/64; A61P 21/00; C12N 15/113; C12N 2310/14; C12N 2310/314; C12N 2310/321; C12N 2310/3513
USPC ..... 435/6.1, 91.1, 91.31, 455, 458; 530/300; 514/44 A; 536/23.1, 24.5
See application file for complete search history.

(56) References Cited

U.S. PATENT DOCUMENTS

| 4,522,811 A | 6/1985 | Eppstein et al. |
|---|---|---|
| 5,994,076 A | 11/1999 | Chenchik et al. |
| 5,998,203 A | 12/1999 | Matulic-Adamic et al. |
| 6,352,829 B1 | 3/2002 | Chenchik et al. |
| 6,489,455 B2 | 12/2002 | Chenchik et al. |
| 9,828,640 B2 | 11/2017 | Cao et al. |
| 10,301,649 B2 | 5/2019 | Harper et al. |
| 10,538,763 B2 | 1/2020 | Rigo et al. |
| 2005/0026164 A1 | 2/2005 | Zhou |
| 2005/0244851 A1 | 11/2005 | Blume et al. |
| 2005/0244969 A1 | 11/2005 | Kupper et al. |
| 2005/0272080 A1 | 12/2005 | Palma et al. |
| 2006/0024715 A1 | 2/2006 | Liu et al. |
| 2007/0237754 A1 | 10/2007 | Kupper et al. |
| 2013/0035287 A1 | 2/2013 | Kupper et al. |
| 2013/0288976 A1 | 10/2013 | van der Maarel et al. |
| 2014/0186311 A1 | 7/2014 | Kupper et al. |
| 2018/0147256 A1 | 5/2018 | Van Der Maarel et al. |
| 2019/0105312 A1 | 4/2019 | Cacace et al. |

FOREIGN PATENT DOCUMENTS

| EP | 3636778 A1 | 4/2020 |
|---|---|---|
| WO | 1996013610 | 5/1996 |
| WO | 2000053722 A2 | 9/2000 |
| WO | 2004044123 A2 | 5/2004 |
| WO | 2004045543 A2 | 6/2004 |
| WO | 2004048511 A2 | 6/2004 |
| WO | 2006006948 A2 | 1/2006 |
| WO | 2008022309 A2 | 2/2008 |
| WO | 2011104169 A1 | 9/2011 |
| WO | 2012024535 A2 | 2/2012 |
| WO | 2012083185 A2 | 6/2012 |
| WO | 2012087983 A1 | 6/2012 |

(Continued)

OTHER PUBLICATIONS

U.S. Appl. No. 18/181,311 (Year: 2023).*
Altenhafer, et al.; "Synthesis of a novel cyclopropyl phosphonate nucleotide as a phosphate mimic"; Chemical Communications (Jun. 2021) (DOI:10.1039/d1cc02328d).
Ansseau, et al.; "DUX4 Is Up-Regulated in FSHD. It induces the MYF5 Protein and Human Myoblast Proliferation"; PLos ONE; vol. 4, Issue 10; 2009.
Ansseau, Eugenie; "Antisense strategies against DUX4 as a therapeutic approach for FSHD"; Proceedings of the Belgian Royal Academies of Medicine; vol. 3: 194-204; 2014.
Ansseau, et al.; "Antisense Oligonucleotides Used to Target the DUX4 mRNA as Therapeutic Approaches in FaciosScapuloHumeral Muscular Dystrophy (FSHD)"; Genes; 8, 93; 2017; doi:10.3390/genes8030093.

(Continued)

*Primary Examiner* — Jane J Zara
(74) *Attorney, Agent, or Firm* — Paul VanderVelde; Robert M. Teigen; Meibo Chen

(57) ABSTRACT

Described are RNAi agents, compositions that include RNAi agents, and methods for inhibition of a double homeobox 4 (DUX4) gene. The DUX4 RNAi agents and RNAi agent conjugates disclosed herein inhibit the expression of a DUX4 gene. Pharmaceutical compositions that include one or more DUX4 RNAi agents, optionally with one or more additional therapeutics, are also described. Delivery of the described DUX4 RNAi agents to skeletal muscle cells in vivo, provides for inhibition of DUX4 gene expression and a reduction in DUX4 levels, which can provide a therapeutic benefit to subjects, including human subjects, suffering from certain skeletal muscle-related diseases or disorders including Facioscapulohumeral Muscular Dystrophy (FSHD).

22 Claims, 47 Drawing Sheets

Specification includes a Sequence Listing.

(56) References Cited

FOREIGN PATENT DOCUMENTS

| | | |
|---|---|---|
| WO | 2013016352 A1 | 1/2013 |
| WO | 2013032829 A1 | 3/2013 |
| WO | 2013158141 A1 | 10/2013 |
| WO | 2014071340 A1 | 5/2014 |
| WO | 2016115490 A1 | 7/2016 |
| WO | 2016170348 A2 | 10/2016 |
| WO | 2017053995 A1 | 3/2017 |
| WO | 2017173411 A1 | 10/2017 |
| WO | 2017214112 A1 | 12/2017 |
| WO | 2018057863 A1 | 3/2018 |
| WO | 2018085415 A1 | 5/2018 |
| WO | 2019060432 A2 | 3/2019 |
| WO | 2019070741 A1 | 4/2019 |
| WO | 2019071147 A1 | 4/2019 |
| WO | 2019115711 A1 | 6/2019 |
| WO | 2020028134 A1 | 2/2020 |
| WO | 2020028864 A1 | 2/2020 |
| WO | 2020142479 A1 | 7/2020 |
| WO | 2021188390 A1 | 9/2021 |
| WO | 2022045366 A1 | 3/2022 |
| WO | 2022051332 A1 | 3/2022 |

OTHER PUBLICATIONS

Banerji, et al.; "Skeletal muscle regeneration in facioscapulohumeral muscular dystrophy is correlated with pathological severity"; Human Molecular Genetics; vol. 29, Issue 16; 2746-2760; 2020.

Banerji, et al.; Pathomechanisms and biomarkers in facioscapulohumeral muscular dystrophy: roles of DUX4 and PAX7; EMBO Mol. Med.; 2021; e13695.

Bao, et al.; "Targeting mRNA for the treatment of facioscapulohumeral muscular dystrophy"; Intractable & Rare Diseases Research; 5(3): 168-176; 2016.

Barro, et al.; "Myoblasts from affected and non-affected FSHD muscles exhibit morphological differentiation defects"; J. Cell. Mol. Med.; vol. 14, No. 102; pp. 275-289; 2010.

Bosnakovski, et al.; "p53-independent DUX4 pathology in cell and animal models of facioscapulohumeral muscular dystrophy"; Disease Models & Mechanisms; 10:1211-1216; 2017; doi: 10.1242/dmm.030064.

Bosnakovski, et al.; "Muscle pathology from stochastic low level DUX4 expression in an FSHD mouse model"; Nat. Commun. 8(1): 550; 2017; doi: 10.1038/s41467-017-99730-1.

Bosnakovski, et al.; "Muscle pathology from stochastic low level DUX4 expression in an FSHD mouse model"; Nat. Commun. 8(1):550; 2017; doi:10.1038/s41467-017-99730-1. (Supplementary Material).

Bosnakovski, et al.; "Author Correction: Muscle pathology from stochastic low level DUX4 expression in an FSHD mouse model"; Nat. Commun. 9(1):856; 2018; doi:10.1038/s41467-018-03449-9.

Bosnakovski, et al.; "Low level DUX4 expression disrupts myogenesis through deregulation of myogenic gene expression"; Scientific Reports; 8:16957; 2018.

Cadavid, et al.; "Development and Evaluation of a whole-body MRI imaging protocol and analysis algorithms to measure changes in skeletal muscle in FSHD"; Fulcrum Therapeutics; Publication; Oct. 1, 2020.

Campbell, et al.; "Facioscapulohumeral dystrophy: activating an early embryonic transcriptional program in human skeletal muscle"; Human Molecular Genetics; vol. 27, No. R2; R153-R162; 2018.

Caron, et al.; "A Human Pluripotent Stem Cell Model of Facioscapulohumeral Muscular Dystrophy-Affected Skeletal Muscles"; Stem Cells Translational Medicine; 5:1145-1161; 2016.

Chen, et al.; "Morpholino-mediated Knockdown of DUX4 Toward Facioscapulohumeral Muscular Dystrophy Therapeutics"; Molecular Therapy; vol. 24, No. 8; 1405-1411; 2016.

Czauderna, et al.; "Structural variations and stabilizing modifications of synthetic siRNAs in mammalian cells"; Nucleic Acids Research; vol. 31, No. 11; 2705-2716; 2003.

Dai, et al.; Single-molecule optical mapping enables accurate molecular diagnosis of facioscapulohumeral muscular dystrophy (FSHD); Mar. 21, 2018; doi: https://doi.org/10.1101/286104.

Dai, et al.; Single-molecule optical mapping enables quantitative measurement of D4Z4 repeats in facioscapulohumeral muscular dystrophy (FSHD); J. Med. Genet.; 57:109-120; 2020.

Dandapat, et al.; "Dominant Lethal Pathologies in Male Mice Engineered to Contain an X-Linked DUX4 Transgene"; Cell Reports; 8; 1484-1496; 2014.

Deenan, et al.; "Population-based incidence and prevalence of facioscapulohumeral dystrophy"; Neurology; 83 (12):1056-1059; 2014.

Ding, Zhi-Ming; "Facioscapulohumeral Muscular Dystrophy (FSHD)"; Presentation; Arrowhead Pharmaceuticals; Nov. 15, 2018.

Dixit, et al.; "DUX4, a candidate gene of facioscapulohumeral muscular dystrophy, encodes a transcriptional activator of PTIX1"; PNAS; vol. 104, No. 46; 18157-18162; 2007.

Dmitriev, et al.; DUX4-induced constitutive DNA damage and oxidative stress contribute to aberrant differentiation of myoblasts from FSHD patients; Free Radical Biology and Medicine; vol. 99; 244-258; 2016.

Dong, et al.; "Structural basis of DUX4/IGH-driven transactivation"; Leukemia; 32:1466-1476; 2018.

Ehrlich, et al.; "Deciphering transcription dysregulation in FSH muscular dystrophy"; Journal of Human Genetics; 57; 477-484; 2012.

Eidahl, et al.; "Mouse Dux is myotoxic and shares partial functional homology with its human paralog DUX4"; Human Molecular Genetics; vol. 25, No. 20; 4577-4589; 2016.

Gall, et al.; "Therapeutic Strategies Targeting DUX4 in FSHD"; Journal of Clinical Medicine; 2020; 9, 2886; doi:10.3390/jcm9092886.

Geng, et al.; "DUX4 Activates Germline Genes, Retroelements, and Immune Mediators: Implications for Facioscapulohumeral Dystrophy"; Developmental Cell; 22; 38-51; 2012.

Giesige, et al.; "AAV-mediated follistatin gene therapy improves functional outcomes in the TIC-DUX4 mouse model of FSHD"; JCI Insight; 3(22); 2018; e123538; https://doi.org/10.1172/jci.insight.123538.

Greef, et al.; "Clinical features of facioscapulohumeral muscular dystrophy 2"; Neurology; 75; 1548-1544; 2010.

Gruncay, Ashley K; "Evaluation of LNA Gapmer efficacy in FSHD patients' muscle cells"; ERA; University of Alberta; Thesis; Spring 2016; doi:https://doi.org/10.7939/R32V2CS35.

Hamel, et al.; "Facioscapulohumeral Muscular Dystrophy: Update on Pathogenesis and Future Treatments"; Neurotherapeutics; 15:863-871; 2018.

Haynes, et al.; "Sporadic DUX4 expression in FSHD myocytes is associated with incomplete repression by the PRC2 complex and gain of H3K9 acetylation on the contracted D474 allele"; Epigenetics & Chromatin; 11:47; 2018.

Himeda, et al.; "Identification of Epigenetic Regulators of DUX4-fl for Targeted Therapy of Facioscapulohumeral Muscular Dystrophy"; Molecular Therapy; vol. 26, No. 7; 1797-1807; 2018.

Jagannathan, et al.; "Model systems of DUX4 expression recapitulate the transcriptional profile of FSHD cells"; Human Molecular Genetics; vol. 25, No. 20; 4419-4431; 2016.

Jagannathan, et al.; "Quantitative proteomics reveals key roles for post-transcriptional gene regulation in the molecular pathology of facioscapulohumeral muscular dystrophy"; Elife; 8:e41740; 2019.

Jones, et al.; "Facioscapulohumeral muscular dystrophy family studies of DUX4 expression: evidence for disease modifiers and a quantitative model of pathogenesis" Human Molecular Genetics; vol. 21, No. 20; 4419-4430; 2012.

Jones, et al.; "Facioscapulohumeral muscular dystrophy family studies of DUX4 expression: evidence for disease modifiers and a quantitative model of pathogenesis" Human Molecular Genetics; vol. 21, No. 20; 4419-4430; 2012. (Supplementary Data).

Jones, et al.; "A cre-inducible DUX4 transgenic mouse model for investigating facioscapulohumeral muscular dystrophy"; PLoS ONE; 13(2): e0192657. https://doi.org/10.1371/journal.pone.0192657.2018.

Jones, et al.; "Transgenic mice expressing tunable levels of DUX4 develop characteristic facioscapulohumeral muscular dystrophy-

(56) References Cited

OTHER PUBLICATIONS like pathophysiology ranging in severity"; Skelet. Muscle; 10(1):8; 2020; doi:10.1186/s13395-020-00227-4.
Kalantari, et al.; "Regulatin of mammalian transcripition and splicing by Nuclear RNAi"; Nucleic Acids Res.; 44(2):524-537; 2016.
Knopp, et al.; "DUX4 induces a transcriptome more characteristic of a less-differentiated cell state and inhibits myogenesis"; Journal of Cell Science; 129; 3816-3813; 2016; doi:10.1242/jcs.180372.
Lang, et al.; "Double Homeobox Protein DUX 4 in the Human Lung: Expression under Normal and Pathological Conditions"; Global Journal of Pathology and Microbiology; 2; 1-9; 2014.
Lek, et al.; "Emerging preclinical animal models for FSHD"; Trends Mol. Med.; 21(5): 295-306; 2015; doi:10.1016/j.molmed.2015.02.011.
Lim, et al.; "DICER/AGO-dependent epigenetic silencing of D474 repeats enhanced by exogenous siRNA suggests mechanisms and therapies for FSHD"; Human Molecular Genetics; vol. 24, No. 17; 4817-4828; 2015.
Lim, et al.; "DUX4 Transcript Knockdown with Antisense 2'-O-Methoxyethyl Gapmers for the Treatment of Facioscapulohumeral Muscular Dystrophy"; Molecular Therapy; vol. 29, No. 2; 2021.
Lu-Nguyen, et al.; "Systemic antisense therapeutics inhibiting DUX4 expression ameliorates FSHD-like pathology in an FSHD mouse model"; Human Molecular Genetics; vol. 30, No. 15; 1398-1412; 2021.
Marsollier, et al.; "Antisense targeting of 3' end elements involved in DUX4 mRNA processing is an efficient therapeutic strategy for facioscapulohumeral dystrophy: a new gene-silencing approach"; Human Molecular Genetics; vol. 25, No. 8; 1468-1478; 2016.
Marsollier, et al.; "Targeting the Polyadenylation Signal of Pre-mRNA: A New Gene Silencing Approach for Facioscapulohumeral Dystrophy"; Int. J. Mol. Sci.; 19; 347; 2018.
Mitsuhashi, et al.; "Functional domains of the FSHD-associated DUX4 protein"; Biology Open; 7; 2018; doi.10.1242/bio.033977.
Olivia; et al.; "Clinically Advanced p38 Inhibitors Suppress DUX4 Expression in Cellular and Animal Models of Facioscapulohumeral Muscular Dystrophy"; J. Pharmacol. Exp. Ther.; vol. 370, Issue 2; 219-230; 2019.
Peart, et al.; "A distal auxiliary element facilitates cleavage and polyadenylation of Dux4 mRNA in the pathogenic haplotype of FSHD"; Hum. Genet.; 136:1291-1301; 2017.
Petek, et al.; "A cross sectional study of two independent cohorts identifies serum biomarkers for jacioscapulohumeral muscular dystrophy (FSHD)"; Neuromuscular Disorders; 26; 405-413; 2016.
Rickard, et al.; "Endogenous DUX4 expression in FSHD myotubes is sufficient to cause cell death and disrupts RNA splicing and cell migration pathways"; Human Molecular Genetics; vol. 24, No. 20; 5901-5914; 2015.
Rojas, et al.; "p38α Regulates Expression of DUX4 in a Model of Facioscapulohumeral Muscular Dystrophy"; J. Pharmacol. Exp. Ther.; 374:489-498; 2020.
Ronco, et al.; "Design of a biomarker of DUX4 activity to evaluate losmapimod treatment effect in FSHD Phase 2 trials"; Fulcrum Therapeutics; Publication; Oct. 30, 2019.
Ronco, et al.; "A Biomarker of Aberrant DUX4 Activity to Evaluate Losmapimod Treatment Effect in FSHD Phase 2 Trials"; Fulcrum Therapeutics; Publication; Oct. 1, 2020.
Sacconi, et al.; "Facioscapulohumeral muscular dystrophy"; Biochimica et Biophysica Acta; 1852; 607-614; 2015.
Sharma, et al.; "DUX4 Differentially Regulates Transcriptomes of Human Rhabdomyosarcoma and Mouse C2C12 Cells"; Plos One; vol. 8; Issue 5; 2013.
Snider, et al.; "Facioscapulohumeral Dystrophy: Incomplete Suppression of a Retrotransposed Gene"; PLoS Genetics; vol. 6, Issue 10; 2010.
Statland, MD, Jeffrey; "What we know, what we think we know, what we have left to learn"; University of Rochester; FSHD Patient Day 2014.
Statland, et al.; "Muscle Pathology Grade for Facioscapulohumeral Muscular Dystrophy Biopsies"; Muscle Nerve; 52(4):521-526; 2015.
Stein, et al.; "Clinical Features of Facioscapulohumeral Muscular Dystrophy (FSHD)"; J. Neurol. Psychol.; 2(2): 2; 2013.
Tassin, et al.; "FSHD Myotubes with Different Phenotypes Exhibit Distinct Proteomes"; Plos One; vol. 7, Issue 12; 2012.
Tassin, et al.; "DUX4 expression of FSHD muscle cells: how could such a rare protein cause a myopathy?"; J. Cell. Mol. Med.; vol. 17, No. 1; 76-89; 2013.
Tawil, et al.; "Facioscapulohumeral dystrophy: the path to consensus on pathophysiology"; Skeletal Muscle; 4:12; 2014.
Tawil, et al.; "Evidence-based guideline summary: Evaluation, diagnosis, and management of facioscapulohumeral muscular dystrophy"; Neurology; 85:357-364; 2015.
Tawil, et al.; Clinical trial preparedness in facioscapulohumeral muscular dystrophy: Clinical, tissue, and imaging outcome measures May 29-30, 2015, Rochester, New York; Neuromuscular Disorders; 26; 181-186; 2016.
Vanderplanck, et al.; "The FSHD Atrophic Myotube Phenotype Is Caused by DUX4 Expression"; Plos One; vol. 6; Issue 10; 2011.
Vanderplanck, et al.; "Overexpression of the double homeodomain protein DUX4c interferes with myofibrillogenesis and induces clustering of myonuclei"; Skeletal Muscle; 8:2; 2018.
Wallace, et al.; "RNAi Therapy for Dominant Muscular Dystrophies and Other Myopathies"; D. Duan (ed.); Muscle Gene Therapy; 2010; doi:10.1007/978-1-4419-1207-7_7.
Wallace, et al.; "RNA Interference Inhibits DUX4-induced Muscle Toxicity In Vivo: Implications for a Targeted FSHD Therapy"; Molecular Therapy; vol. 20, No. 7; 1417-1423; 2012.
Wallace, et al.; "Pre-clinical Safety and Off-Target Studies to Support Translation of AAV-Mediated RNAi Therapy for FSHD"; Mol. Ther. Methods Clinc. Dev.; 8:121-130; 2017.
Wong, et al.; "Longitudinal measures of RNA expression and disease activity in FSHD muscle biopsies"; Human Molecular Genetics; vol. 29, No. 6; 1030-1044; 2020.
Yao, et al.; "DUX4-induced gene expression is the major molecular signature in FSHD skeletal muscle"; Human Molecular Genetics; vol. 23, No. 20; 5342-5352; 2014.
Ciszewski, et al.; "G-quadruplex ligands mediate downregulation of DUX4 expression"; Nucleic Acids Research; vol. 48, No. 8; 4179-4194; 2020.
Clapp, et al.; "Evolutionary Conservation of a Coding Function for D474, the Tandem DNA Repeat Mutated in Facioscapulohumeral Muscular Dystrophy"; The American Journal of Human Genetics; vol. 81; 264-279; 2007.

\* cited by examiner

SEQUENCE LISTING

```
Sequence total quantity: 245
SEQ ID NO: 1            moltype = RNA  length = 1574
FEATURE                 Location/Qualifiers
source                  1..1574
                        mol_type = mRNA
                        organism = Homo sapiens
SEQUENCE: 1
atggccctcc cgacaccctc ggacagcacc ctccccgcgg aagcccgggg acgaggacgg   60
cgacggagac tcgtttggac cccgagccaa agcgaggccc tgcgagcctg ctttgagcgg  120
aacccgtacc cgggcatcgc caccagagaa cggctgcc aggccatcgg cattccggag    180
cccagggtcc agatttggtt tcagaatgag aggtcacgcc agctgaggca gcaccggcgg  240
gaatctcggc cctggcccgg gagacgcggc ccgccagaag gccggcgaaa gcggaccgcc  300
gtcaccggat cccagaccgc cctgctcctc cgagcctttg agaaggatcg ctttccaggc  360
atcgccgccc gggaggagct ggccagagag acgggcctcc cggagtccag gattcagatc  420
tggtttcaga atcgaagggc caggcacccg ggacagggtg gcagggcgcc cgcgcaggca  480
ggcggcctgt gcagcgcggc ccccggcggg ggtcaccctg ctccctcgtg ggtcgccttc  540
gcccacaccg gcgcgtgggg aacgggggctt cccgcacccc acgtgccctg cgcgcctggg  600
gctctcccac aggggggcttt cgtgagccag gcagcgaggg ccgcccccgc gctgcagccc  660
agccaggccg cgccggcaga ggggatctcc caacctgccc cggcgcgcgg ggatttcgcc  720
tacgccgccc cggctcctcc ggacggggcg ctctcccacc ctcaggctcc tcgctggcct  780
ccgcaccgg gcaaaagccg ggaggaccgg gacccgcagc gcgacggcct gccgggcccc   840
tgcgcggtgg cacagcctgg gcccgctcaa gcggggccgc agggccaagg ggtgcttgcg  900
ccacccacgt cccagggag tccgtggtgg ggctggggcc ggggtcccca ggtcgccggg   960
gcggcgtggg aaccccaagc cggggcagct ccacctcccc agcccgcgcc cccggacgcc  1020
tccgcctccg cgcggcaggg gcagatgcaa ggcatcccgg cgccctccca ggcgctccag  1080
gagccggcgc cctggtctgc actccctgc ggcctgctgc tggatgagct cctggcgagc   1140
ccggagtttc tgcagcaggc gcaacctctc ctagaaacgg aggcccgggg ggagctggag  1200
gcctcggaag aggccgcctc gctggaagca cccctcagcg aggaagaata ccgggctctg  1260
ctggaggagc tttaggacgc ggggtctagg cccggtgaga gactccacac cgcggagaac  1320
tgccattctt tcctgggcat cccgggatc ccagagccgg cccaggtacc agcagacctg   1380
cgcgcagtgc gcacccggc tgacgtgcaa gggagctcgc tggcctctct gtgcccttgt   1440
tcttccgtga aattctggct gaatgtctcc ccccaccttc cgacgctgtc taggcaaacc  1500
tggattagag ttacatctcc tggatgatta gttcagagat atattaaaat gccccctccc  1560
tgtggatcct atag                                                    1574

SEQ ID NO: 2            moltype = RNA  length = 1574
FEATURE                 Location/Qualifiers
source                  1..1574
                        mol_type = mRNA
                        organism = Homo sapiens
SEQUENCE: 2
atggccctcc cgacaccctc ggacagcacc ctccccgcgg aagcccgggg acgaggacgg   60
cgacggagac tcgtttggac cccgagccaa agcgaggccc tgcgagcctg ctttgagcgg  120
aacccgtacc cgggcatcgc caccagagaa cggctgcc aggccatcgg cattccggag    180
cccagggtcc agatttggtt tcagaatgag aggtcacgcc agctgaggca gcaccggcgg  240
gaatctcggc cctggcccgg gagacgcggc ccgccagaag gccggcgaaa gcggaccgcc  300
gtcaccggat cccagaccgc cctgctcctc cgagcctttg agaaggatcg ctttccaggc  360
```

-continued

```
atcgccgccc gggaggagct ggccagagag acgggcctcc cggagtccag gattcagatc   420
tggtttcaga atcgaaggc  caggcacccg ggacagggtg gcagggcgcc cgcgcaggca   480
ggcggcctgt gcagcgcggc ccccggcggg ggtcaccctg ctccctcgtg ggtcgccttc   540
gcccacaccg gcgcgtgggg aacgggcttt cccgcacccc acgtgccctg cgcgcctggg   600
gctctcccac aggggctttt cgtgagccag gcagcgaggg cgcccccgc  gctgcagccc   660
agccaggccg cgccggcaga ggggatctcc caacctgccc cggcgcgcgg ggatttcgcg   720
tacgccgccc cggctcctcc ggacggggcg ctctcccacc ctcaggctcc tcggtggcct   780
ccgcacccgg gcaaaagccg ggaggaccgg gacccgcagc gcgacggcct gccgggcccc   840
tgcgcggtgg cacagcctgg gcccgctcaa gcggggccgc agggccaagg ggtgcttgcg   900
ccacccacgt cccagggag  tccgtggtgg ggctggggcc ggggtcccca ggtcgccggg   960
gcggcgtggg aacccaagc  cggggcagct ccacctcccc agcccgcgcc cccggacgcc  1020
tccgcctccg cgcggcaggg gcagatgcaa ggcatcccgg cgcctcccca ggcgctccag  1080
gagccggcgc cctggtctgc actcccctgc ggcctgctgc tggatgagct cctggcgagc  1140
ccggagtttc tgcagcaggc gcaacctctc ctagaaacgg agccccggg  ggagctggag  1200
gcctcggaag aggccgcctc gctggaagca cccctcagcg aggaagaata ccgggctctg  1260
ctggaggagc tttaggacgc ggggtctagg cccgtgaga  gactccactc cgcggagaac  1320
tgcctttctt tcctgggcat cccggggatc ccagagccgg cccaggtacc agcagacctg  1380
cgcgcagtgc gcaccccggc tgacgtgcaa gggagctcgc tggcctctct gtgccctgt   1440
tcttccgtga aattctggct gaatgtctcc ccccaccttc cgacgctgtc taggcaaacc  1500
tggattagag ttacatctcc tggatgatta gttcagagat atattaaaat gccccctccc  1560
tgtggatcct atag                                                    1574

SEQ ID NO: 3            moltype = RNA   length = 19
FEATURE                 Location/Qualifiers
source                  1..19
                        mol_type = other RNA
                        organism = synthetic construct
SEQUENCE: 3
ggattcagat ctggtttca                                                  19

SEQ ID NO: 4            moltype = RNA   length = 19
FEATURE                 Location/Qualifiers
source                  1..19
                        mol_type = other RNA
                        organism = synthetic construct
SEQUENCE: 4
gattcagatc tggtttcaa                                                  19

SEQ ID NO: 5            moltype = RNA   length = 19
FEATURE                 Location/Qualifiers
source                  1..19
                        mol_type = other RNA
                        organism = synthetic construct
SEQUENCE: 5
ccttgttctt ccgtgaaat                                                  19

SEQ ID NO: 6            moltype = RNA   length = 19
FEATURE                 Location/Qualifiers
source                  1..19
                        mol_type = other RNA
                        organism = synthetic construct
SEQUENCE: 6
gttcttccgt gaaattcta                                                  19

SEQ ID NO: 7            moltype = RNA   length = 19
FEATURE                 Location/Qualifiers
source                  1..19
                        mol_type = other RNA
                        organism = synthetic construct
SEQUENCE: 7
acctggatta gagttacat                                                  19

SEQ ID NO: 8            moltype = RNA   length = 19
FEATURE                 Location/Qualifiers
source                  1..19
                        mol_type = other RNA
                        organism = synthetic construct
SEQUENCE: 8
ctggatgatt agttcagaa                                                  19

SEQ ID NO: 9            moltype = RNA   length = 19
FEATURE                 Location/Qualifiers
source                  1..19
                        mol_type = other RNA
                        organism = synthetic construct
SEQUENCE: 9
atgattagtt cagagatat                                                  19

SEQ ID NO: 10           moltype = RNA   length = 19
```

-continued

```
FEATURE                 Location/Qualifiers
source                  1..19
                        mol_type = other RNA
                        organism = synthetic construct
SEQUENCE: 10
tgaaaccaga tctgaatcc                                                    19

SEQ ID NO: 11           moltype = RNA   length = 19
FEATURE                 Location/Qualifiers
source                  1..19
                        mol_type = other RNA
                        organism = synthetic construct
SEQUENCE: 11
agaaaccaga tctgaatcc                                                    19

SEQ ID NO: 12           moltype = RNA   length = 19
FEATURE                 Location/Qualifiers
source                  1..19
                        mol_type = other RNA
                        organism = synthetic construct
SEQUENCE: 12
ngaaaccaga tctgaatcc                                                    19

SEQ ID NO: 13           moltype = RNA   length = 19
FEATURE                 Location/Qualifiers
source                  1..19
                        mol_type = other RNA
                        organism = synthetic construct
SEQUENCE: 13
ngaaaccaga tctgaatcn                                                    19

SEQ ID NO: 14           moltype = RNA   length = 19
FEATURE                 Location/Qualifiers
source                  1..19
                        mol_type = other RNA
                        organism = synthetic construct
SEQUENCE: 14
ttgaaaccag atctgaatc                                                    19

SEQ ID NO: 15           moltype = RNA   length = 19
FEATURE                 Location/Qualifiers
source                  1..19
                        mol_type = other RNA
                        organism = synthetic construct
SEQUENCE: 15
atgaaaccag atctgaatc                                                    19

SEQ ID NO: 16           moltype = RNA   length = 19
FEATURE                 Location/Qualifiers
source                  1..19
                        mol_type = other RNA
                        organism = synthetic construct
SEQUENCE: 16
ntgaaaccag atctgaatc                                                    19

SEQ ID NO: 17           moltype = RNA   length = 19
FEATURE                 Location/Qualifiers
source                  1..19
                        mol_type = other RNA
                        organism = synthetic construct
SEQUENCE: 17
ntgaaaccag atctgaatn                                                    19

SEQ ID NO: 18           moltype = RNA   length = 19
FEATURE                 Location/Qualifiers
source                  1..19
                        mol_type = other RNA
                        organism = synthetic construct
SEQUENCE: 18
atttcacgga agaacaagg                                                    19

SEQ ID NO: 19           moltype = RNA   length = 19
FEATURE                 Location/Qualifiers
source                  1..19
                        mol_type = other RNA
                        organism = synthetic construct
SEQUENCE: 19
ttttcacgga agaacaagg                                                    19
```

| | | |
|---|---|---|
| SEQ ID NO: 20<br>FEATURE<br>source | moltype = RNA   length = 19<br>Location/Qualifiers<br>1..19<br>mol_type = other RNA<br>organism = synthetic construct | |
| SEQUENCE: 20<br>ntttcacgga agaacaagg | | 19 |
| SEQ ID NO: 21<br>FEATURE<br>source | moltype = RNA   length = 19<br>Location/Qualifiers<br>1..19<br>mol_type = other RNA<br>organism = synthetic construct | |
| SEQUENCE: 21<br>ntttcacgga agaacaagn | | 19 |
| SEQ ID NO: 22<br>FEATURE<br>source | moltype = RNA   length = 19<br>Location/Qualifiers<br>1..19<br>mol_type = other RNA<br>organism = synthetic construct | |
| SEQUENCE: 22<br>tagaatttca cggaagaac | | 19 |
| SEQ ID NO: 23<br>FEATURE<br>source | moltype = RNA   length = 19<br>Location/Qualifiers<br>1..19<br>mol_type = other RNA<br>organism = synthetic construct | |
| SEQUENCE: 23<br>aagaatttca cggaagaac | | 19 |
| SEQ ID NO: 24<br>FEATURE<br>source | moltype = RNA   length = 19<br>Location/Qualifiers<br>1..19<br>mol_type = other RNA<br>organism = synthetic construct | |
| SEQUENCE: 24<br>nagaatttca cggaagaac | | 19 |
| SEQ ID NO: 25<br>FEATURE<br>source | moltype = RNA   length = 19<br>Location/Qualifiers<br>1..19<br>mol_type = other RNA<br>organism = synthetic construct | |
| SEQUENCE: 25<br>nagaatttca cggaagaan | | 19 |
| SEQ ID NO: 26<br>FEATURE<br>source | moltype = RNA   length = 19<br>Location/Qualifiers<br>1..19<br>mol_type = other RNA<br>organism = synthetic construct | |
| SEQUENCE: 26<br>atgtaactct aatccaggt | | 19 |
| SEQ ID NO: 27<br>FEATURE<br>source | moltype = RNA   length = 19<br>Location/Qualifiers<br>1..19<br>mol_type = other RNA<br>organism = synthetic construct | |
| SEQUENCE: 27<br>ttgtaactct aatccaggt | | 19 |
| SEQ ID NO: 28<br>FEATURE<br>source | moltype = RNA   length = 19<br>Location/Qualifiers<br>1..19<br>mol_type = other RNA<br>organism = synthetic construct | |
| SEQUENCE: 28<br>ntgtaactct aatccaggt | | 19 |
| SEQ ID NO: 29<br>FEATURE<br>source | moltype = RNA   length = 19<br>Location/Qualifiers<br>1..19<br>mol_type = other RNA<br>organism = synthetic construct | |
| SEQUENCE: 29<br>ntgtaactct aatccaggn | | 19 |

```
SEQ ID NO: 30           moltype = RNA  length = 19
FEATURE                 Location/Qualifiers
source                  1..19
                        mol_type = other RNA
                        organism = synthetic construct
SEQUENCE: 30
ttctgaacta atcatccag                                                    19

SEQ ID NO: 31           moltype = RNA  length = 19
FEATURE                 Location/Qualifiers
source                  1..19
                        mol_type = other RNA
                        organism = synthetic construct
SEQUENCE: 31
atctgaacta atcatccag                                                    19

SEQ ID NO: 32           moltype = RNA  length = 19
FEATURE                 Location/Qualifiers
source                  1..19
                        mol_type = other RNA
                        organism = synthetic construct
SEQUENCE: 32
ntctgaacta atcatccag                                                    19

SEQ ID NO: 33           moltype = RNA  length = 19
FEATURE                 Location/Qualifiers
source                  1..19
                        mol_type = other RNA
                        organism = synthetic construct
SEQUENCE: 33
ntctgaacta atcatccan                                                    19

SEQ ID NO: 34           moltype = RNA  length = 19
FEATURE                 Location/Qualifiers
source                  1..19
                        mol_type = other RNA
                        organism = synthetic construct
SEQUENCE: 34
atatctctga actaatcat                                                    19

SEQ ID NO: 35           moltype = RNA  length = 19
FEATURE                 Location/Qualifiers
source                  1..19
                        mol_type = other RNA
                        organism = synthetic construct
SEQUENCE: 35
ttatctctga actaatcat                                                    19

SEQ ID NO: 36           moltype = RNA  length = 19
FEATURE                 Location/Qualifiers
source                  1..19
                        mol_type = other RNA
                        organism = synthetic construct
SEQUENCE: 36
ntatctctga actaatcat                                                    19

SEQ ID NO: 37           moltype = RNA  length = 19
FEATURE                 Location/Qualifiers
source                  1..19
                        mol_type = other RNA
                        organism = synthetic construct
SEQUENCE: 37
ntatctctga actaatcan                                                    19

SEQ ID NO: 38           moltype = RNA  length = 19
FEATURE                 Location/Qualifiers
source                  1..19
                        mol_type = other RNA
                        organism = synthetic construct
SEQUENCE: 38
ggattcagat ctggtttca                                                    19

SEQ ID NO: 39           moltype = RNA  length = 19
FEATURE                 Location/Qualifiers
source                  1..19
                        mol_type = other RNA
                        organism = synthetic construct
SEQUENCE: 39
```

```
ggattcagat ctggtttct                                                    19

SEQ ID NO: 40          moltype = RNA  length = 19
FEATURE                Location/Qualifiers
source                 1..19
                       mol_type = other RNA
                       organism = synthetic construct
SEQUENCE: 40
ggattcagat ctggtttcn                                                    19

SEQ ID NO: 41          moltype = RNA  length = 19
FEATURE                Location/Qualifiers
source                 1..19
                       mol_type = other RNA
                       organism = synthetic construct
SEQUENCE: 41
ngattcagat ctggtttcn                                                    19

SEQ ID NO: 42          moltype = RNA  length = 19
FEATURE                Location/Qualifiers
source                 1..19
                       mol_type = other RNA
                       organism = synthetic construct
SEQUENCE: 42
gattcagatc tggtttcaa                                                    19

SEQ ID NO: 43          moltype = RNA  length = 19
FEATURE                Location/Qualifiers
source                 1..19
                       mol_type = other RNA
                       organism = synthetic construct
SEQUENCE: 43
gattcagatc tggtttcat                                                    19

SEQ ID NO: 44          moltype = RNA  length = 19
FEATURE                Location/Qualifiers
source                 1..19
                       mol_type = other RNA
                       organism = synthetic construct
SEQUENCE: 44
gattcagatc tggtttcan                                                    19

SEQ ID NO: 45          moltype = RNA  length = 19
FEATURE                Location/Qualifiers
source                 1..19
                       mol_type = other RNA
                       organism = synthetic construct
SEQUENCE: 45
nattcagatc tggtttcan                                                    19

SEQ ID NO: 46          moltype = RNA  length = 19
FEATURE                Location/Qualifiers
source                 1..19
                       mol_type = other RNA
                       organism = synthetic construct
SEQUENCE: 46
ccttgttctt ccgtgaaat                                                    19

SEQ ID NO: 47          moltype = RNA  length = 19
FEATURE                Location/Qualifiers
source                 1..19
                       mol_type = other RNA
                       organism = synthetic construct
SEQUENCE: 47
ccttgttctt ccgtgaaaa                                                    19

SEQ ID NO: 48          moltype = RNA  length = 19
FEATURE                Location/Qualifiers
source                 1..19
                       mol_type = other RNA
                       organism = synthetic construct
SEQUENCE: 48
ccttgttctt ccgtgaaan                                                    19

SEQ ID NO: 49          moltype = RNA  length = 19
FEATURE                Location/Qualifiers
source                 1..19
                       mol_type = other RNA
                       organism = synthetic construct
```

-continued

```
SEQUENCE: 49
ncttgttctt ccgtgaaan                                                           19

SEQ ID NO: 50           moltype = RNA   length = 19
FEATURE                 Location/Qualifiers
source                  1..19
                        mol_type = other RNA
                        organism = synthetic construct
SEQUENCE: 50
gttcttccgt gaaattcta                                                           19

SEQ ID NO: 51           moltype = RNA   length = 19
FEATURE                 Location/Qualifiers
source                  1..19
                        mol_type = other RNA
                        organism = synthetic construct
SEQUENCE: 51
gttcttccgt gaaattctt                                                           19

SEQ ID NO: 52           moltype = RNA   length = 19
FEATURE                 Location/Qualifiers
source                  1..19
                        mol_type = other RNA
                        organism = synthetic construct
SEQUENCE: 52
gttcttccgt gaaattctn                                                           19

SEQ ID NO: 53           moltype = RNA   length = 19
FEATURE                 Location/Qualifiers
source                  1..19
                        mol_type = other RNA
                        organism = synthetic construct
SEQUENCE: 53
nttcttccgt gaaattctn                                                           19

SEQ ID NO: 54           moltype = RNA   length = 19
FEATURE                 Location/Qualifiers
source                  1..19
                        mol_type = other RNA
                        organism = synthetic construct
SEQUENCE: 54
acctggatta gagttacat                                                           19

SEQ ID NO: 55           moltype = RNA   length = 19
FEATURE                 Location/Qualifiers
source                  1..19
                        mol_type = other RNA
                        organism = synthetic construct
SEQUENCE: 55
acctggatta gagttacaa                                                           19

SEQ ID NO: 56           moltype = RNA   length = 19
FEATURE                 Location/Qualifiers
source                  1..19
                        mol_type = other RNA
                        organism = synthetic construct
SEQUENCE: 56
acctggatta gagttacan                                                           19

SEQ ID NO: 57           moltype = RNA   length = 19
FEATURE                 Location/Qualifiers
source                  1..19
                        mol_type = other RNA
                        organism = synthetic construct
SEQUENCE: 57
ncctggatta gagttacan                                                           19

SEQ ID NO: 58           moltype = RNA   length = 19
FEATURE                 Location/Qualifiers
source                  1..19
                        mol_type = other RNA
                        organism = synthetic construct
SEQUENCE: 58
ctggatgatt agttcagaa                                                           19

SEQ ID NO: 59           moltype = RNA   length = 19
FEATURE                 Location/Qualifiers
source                  1..19
                        mol_type = other RNA
```

```
                              organism = synthetic construct
SEQUENCE: 59
ctggatgatt agttcagat                                                       19

SEQ ID NO: 60           moltype = RNA   length = 19
FEATURE                 Location/Qualifiers
source                  1..19
                        mol_type = other RNA
                        organism = synthetic construct
SEQUENCE: 60
ctggatgatt agttcagan                                                       19

SEQ ID NO: 61           moltype = RNA   length = 19
FEATURE                 Location/Qualifiers
source                  1..19
                        mol_type = other RNA
                        organism = synthetic construct
SEQUENCE: 61
ntggatgatt agttcagan                                                       19

SEQ ID NO: 62           moltype = RNA   length = 19
FEATURE                 Location/Qualifiers
source                  1..19
                        mol_type = other RNA
                        organism = synthetic construct
SEQUENCE: 62
atgattagtt cagagatat                                                       19

SEQ ID NO: 63           moltype = RNA   length = 19
FEATURE                 Location/Qualifiers
source                  1..19
                        mol_type = other RNA
                        organism = synthetic construct
SEQUENCE: 63
atgattagtt cagagataa                                                       19

SEQ ID NO: 64           moltype = RNA   length = 19
FEATURE                 Location/Qualifiers
source                  1..19
                        mol_type = other RNA
                        organism = synthetic construct
SEQUENCE: 64
atgattagtt cagagatan                                                       19

SEQ ID NO: 65           moltype = RNA   length = 19
FEATURE                 Location/Qualifiers
source                  1..19
                        mol_type = other RNA
                        organism = synthetic construct
SEQUENCE: 65
ntgattagtt cagagatan                                                       19

SEQ ID NO: 66           moltype = RNA   length = 21
FEATURE                 Location/Qualifiers
modified_base           1
                        mod_base = um
modified_base           1^2
                        mod_base = OTHER
                        note = phosphorothioate linkage
modified_base           2
                        mod_base = OTHER
                        note = 2'-fluoroguanosine
modified_base           2^3
                        mod_base = OTHER
                        note = phosphorothioate linkage
modified_base           3
                        mod_base = OTHER
                        note = 2'-O-methyladenosine
modified_base           3^4
                        mod_base = OTHER
                        note = phosphorothioate linkage
modified_base           4
                        mod_base = OTHER
                        note = 2'-fluoroadenosine
modified_base           5
                        mod_base = OTHER
                        note = 2'-O-methyladenosine
modified_base           6
                        mod_base = OTHER
```

```
                        note = 2'-fluorocytidine
modified_base           7
                        mod_base = cm
modified_base           8
                        mod_base = OTHER
                        note = 2'-fluoroadenosine
modified_base           9
                        mod_base = gm
modified_base           10
                        mod_base = OTHER
                        note = 2'-fluoroadenosine
modified_base           11
                        mod_base = um
modified_base           12
                        mod_base = OTHER
                        note = 2'-fluorocytidine
modified_base           13
                        mod_base = um
modified_base           14
                        mod_base = OTHER
                        note = 2'-fluoroguanosine
modified_base           15
                        mod_base = OTHER
                        note = 2'-O-methyladenosine
modified_base           16
                        mod_base = OTHER
                        note = 2'-fluoroadenosine
modified_base           17
                        mod_base = um
modified_base           18
                        mod_base = OTHER
                        note = 2'-fluorocytidine
modified_base           19
                        mod_base = cm
modified_base           20
                        mod_base = OTHER
                        note = 2'-fluorouridine
modified_base           20^21
                        mod_base = OTHER
                        note = phosphorothioate linkage
modified_base           21
                        mod_base = gm
source                  1..21
                        mol_type = other RNA
                        organism = synthetic construct
SEQUENCE: 66
tgaaaccaga tctgaatcct g                                              21

SEQ ID NO: 67           moltype = RNA   length = 21
FEATURE                 Location/Qualifiers
modified_base           1
                        mod_base = um
modified_base           1^2
                        mod_base = OTHER
                        note = phosphorothioate linkage
modified_base           2
                        mod_base = OTHER
                        note = 2'-fluorouridine
modified_base           2^3
                        mod_base = OTHER
                        note = phosphorothioate linkage
modified_base           3
                        mod_base = gm
modified_base           3^4
                        mod_base = OTHER
                        note = phosphorothioate linkage
modified_base           4
                        mod_base = OTHER
                        note = 2'-fluoroadenosine
modified_base           5
                        mod_base = OTHER
                        note = 2'-O-methyladenosine
modified_base           6
                        mod_base = OTHER
                        note = 2'-fluoroadenosine
modified_base           7
                        mod_base = cm
modified_base           8
                        mod_base = OTHER
```

| | |
|---|---|
| | note = 2'-fluorocytidine |
| modified_base | 9 |
| | mod_base = OTHER |
| | note = 2'-O-methyladenosine |
| modified_base | 10 |
| | mod_base = OTHER |
| | note = 2'-fluoroguanosine |
| modified_base | 11 |
| | mod_base = OTHER |
| | note = 2'-O-methyladenosine |
| modified_base | 12 |
| | mod_base = OTHER |
| | note = 2'-fluorouridine |
| modified_base | 13 |
| | mod_base = cm |
| modified_base | 14 |
| | mod_base = OTHER |
| | note = 2'-fluorouridine |
| modified_base | 15 |
| | mod_base = gm |
| modified_base | 16 |
| | mod_base = OTHER |
| | note = 2'-fluoroadenosine |
| modified_base | 17 |
| | mod_base = OTHER |
| | note = 2'-O-methyladenosine |
| modified_base | 18 |
| | mod_base = OTHER |
| | note = 2'-fluorouridine |
| modified_base | 19 |
| | mod_base = cm |
| modified_base | 20 |
| | mod_base = OTHER |
| | note = 2'-fluorocytidine |
| modified_base | 20^21 |
| | mod_base = OTHER |
| | note = phosphorothioate linkage |
| modified_base | 21 |
| | mod_base = um |
| source | 1..21 |
| | mol_type = other RNA |
| | organism = synthetic construct |
| SEQUENCE: 67 | |
| ttgaaaccag atctgaatcc t | 21 |
| | |
| SEQ ID NO: 68 | moltype = RNA length = 21 |
| FEATURE | Location/Qualifiers |
| modified_base | 1 |
| | mod_base = um |
| modified_base | 1^2 |
| | mod_base = OTHER |
| | note = phosphorothioate linkage |
| modified_base | 2 |
| | mod_base = OTHER |
| | note = 2'-fluoroadenosine |
| modified_base | 2^3 |
| | mod_base = OTHER |
| | note = phosphorothioate linkage |
| modified_base | 3 |
| | mod_base = gm |
| modified_base | 3^4 |
| | mod_base = OTHER |
| | note = phosphorothioate linkage |
| modified_base | 4 |
| | mod_base = OTHER |
| | note = 2'-fluoroadenosine |
| modified_base | 5 |
| | mod_base = OTHER |
| | note = 2'-O-methyladenosine |
| modified_base | 6 |
| | mod_base = OTHER |
| | note = 2'-fluorouridine |
| modified_base | 7 |
| | mod_base = um |
| modified_base | 8 |
| | mod_base = OTHER |
| | note = 2'-fluorouridine |
| modified_base | 9 |
| | mod_base = cm |

| | | |
|---|---|---|
| modified_base | 10 | |
| | mod_base = OTHER | |
| | note = 2'-fluoroadenosine | |
| modified_base | 11 | |
| | mod_base = cm | |
| modified_base | 12 | |
| | mod_base = OTHER | |
| | note = 2'-fluoroguanosine | |
| modified_base | 13 | |
| | mod_base = gm | |
| modified_base | 14 | |
| | mod_base = OTHER | |
| | note = 2'-fluoroadenosine | |
| modified_base | 15 | |
| | mod_base = OTHER | |
| | note = 2'-O-methyladenosine | |
| modified_base | 16 | |
| | mod_base = OTHER | |
| | note = 2'-fluoroguanosine | |
| modified_base | 17 | |
| | mod_base = OTHER | |
| | note = 2'-O-methyladenosine | |
| modified_base | 18 | |
| | mod_base = OTHER | |
| | note = 2'-fluoroadenosine | |
| modified_base | 19 | |
| | mod_base = cm | |
| modified_base | 20 | |
| | mod_base = OTHER | |
| | note = 2'-fluoroadenosine | |
| modified_base | 20^21 | |
| | mod_base = OTHER | |
| | note = phosphorothioate linkage | |
| modified_base | 21 | |
| | mod_base = gm | |
| source | 1..21 | |
| | mol_type = other RNA | |
| | organism = synthetic construct | |
| SEQUENCE: 68 | | |
| tagaatttca cggaagaaca g | | 21 |
| | | |
| SEQ ID NO: 69 | moltype = RNA  length = 21 | |
| FEATURE | Location/Qualifiers | |
| modified_base | 1 | |
| | mod_base = um | |
| modified_base | 1^2 | |
| | mod_base = OTHER | |
| | note = phosphorothioate linkage | |
| modified_base | 2 | |
| | mod_base = OTHER | |
| | note = 2'-fluorouridine | |
| modified_base | 2^3 | |
| | mod_base = OTHER | |
| | note = phosphorothioate linkage | |
| modified_base | 3 | |
| | mod_base = cm | |
| modified_base | 3^4 | |
| | mod_base = OTHER | |
| | note = phosphorothioate linkage | |
| modified_base | 4 | |
| | mod_base = OTHER | |
| | note = 2'-fluorouridine | |
| modified_base | 5 | |
| | mod_base = gm | |
| modified_base | 6 | |
| | mod_base = OTHER | |
| | note = 2'-fluoroadenosine | |
| modified_base | 7 | |
| | mod_base = OTHER | |
| | note = 2'-O-methyladenosine | |
| modified_base | 8 | |
| | mod_base = OTHER | |
| | note = 2'-fluorocytidine | |
| modified_base | 9 | |
| | mod_base = um | |
| modified_base | 10 | |
| | mod_base = OTHER | |
| | note = 2'-fluoroadenosine | |
| modified_base | 11 | |

```
                        mod_base = OTHER
                        note = 2'-O-methyladenosine
modified_base           12
                        mod_base = OTHER
                        note = 2'-fluorouridine
modified_base           13
                        mod_base = cm
modified_base           14
                        mod_base = OTHER
                        note = 2'-fluoroadenosine
modified_base           15
                        mod_base = um
modified_base           16
                        mod_base = OTHER
                        note = 2'-fluorocytidine
modified_base           17
                        mod_base = cm
modified_base           18
                        mod_base = OTHER
                        note = 2'-fluoroadenosine
modified_base           19
                        mod_base = gm
modified_base           20
                        mod_base = OTHER
                        note = 2'-fluoroguanosine
modified_base           20^21
                        mod_base = OTHER
                        note = phosphorothioate linkage
modified_base           21
                        mod_base = OTHER
                        note = 2'-O-methyladenosine
source                  1..21
                        mol_type = other RNA
                        organism = synthetic construct
SEQUENCE: 69
ttctgaacta atcatccagg a                                               21

SEQ ID NO: 70           moltype = RNA  length = 21
FEATURE                 Location/Qualifiers
modified_base           1
                        mod_base = OTHER
                        note = 2'-O-methyladenosine
modified_base           1^2
                        mod_base = OTHER
                        note = phosphorothioate linkage
modified_base           2
                        mod_base = OTHER
                        note = 2'-fluorouridine
modified_base           2^3
                        mod_base = OTHER
                        note = phosphorothioate linkage
modified_base           3
                        mod_base = um
modified_base           3^4
                        mod_base = OTHER
                        note = phosphorothioate linkage
modified_base           4
                        mod_base = OTHER
                        note = 2'-fluorouridine
modified_base           5
                        mod_base = cm
modified_base           6
                        mod_base = OTHER
                        note = 2'-fluoroadenosine
modified_base           7
                        mod_base = cm
modified_base           8
                        mod_base = OTHER
                        note = 2'-fluoroguanosine
modified_base           9
                        mod_base = gm
modified_base           10
                        mod_base = OTHER
                        note = 2'-fluoroadenosine
modified_base           11
                        mod_base = OTHER
                        note = 2'-O-methyladenosine
modified_base           12
                        mod_base = OTHER
```

|  |  |
|---|---|
| | note = 2'-fluoroguanosine |
| modified_base | 13 |
| | mod_base = OTHER |
| | note = 2'-O-methyladenosine |
| modified_base | 14 |
| | mod_base = OTHER |
| | note = 2'-fluoroadenosine |
| modified_base | 15 |
| | mod_base = cm |
| modified_base | 16 |
| | mod_base = OTHER |
| | note = 2'-fluoroadenosine |
| modified_base | 17 |
| | mod_base = OTHER |
| | note = 2'-O-methyladenosine |
| modified_base | 18 |
| | mod_base = OTHER |
| | note = 2'-fluoroguanosine |
| modified_base | 19 |
| | mod_base = gm |
| modified_base | 20 |
| | mod_base = OTHER |
| | note = 2'-fluoroguanosine |
| modified_base | 20^21 |
| | mod_base = OTHER |
| | note = phosphorothioate linkage |
| modified_base | 21 |
| | mod_base = cm |
| source | 1..21 |
| | mol_type = other RNA |
| | organism = synthetic construct |

SEQUENCE: 70
atttcacgga agaacaaggg c                                              21

|  |  |
|---|---|
| SEQ ID NO: 71 | moltype = RNA length = 21 |
| FEATURE | Location/Qualifiers |
| modified_base | 1 |
| | mod_base = OTHER |
| | note = 2'-O-methyladenosine |
| modified_base | 1^2 |
| | mod_base = OTHER |
| | note = phosphorothioate linkage |
| modified_base | 2 |
| | mod_base = OTHER |
| | note = 2'-fluorouridine |
| modified_base | 2^3 |
| | mod_base = OTHER |
| | note = phosphorothioate linkage |
| modified_base | 3 |
| | mod_base = gm |
| modified_base | 3^4 |
| | mod_base = OTHER |
| | note = phosphorothioate linkage |
| modified_base | 4 |
| | mod_base = OTHER |
| | note = 2'-fluorouridine |
| modified_base | 5 |
| | mod_base = OTHER |
| | note = 2'-O-methyladenosine |
| modified_base | 6 |
| | mod_base = OTHER |
| | note = 2'-fluoroadenosine |
| modified_base | 7 |
| | mod_base = cm |
| modified_base | 8 |
| | mod_base = OTHER |
| | note = 2'-fluorouridine |
| modified_base | 9 |
| | mod_base = cm |
| modified_base | 10 |
| | mod_base = OTHER |
| | note = 2'-fluorouridine |
| modified_base | 11 |
| | mod_base = OTHER |
| | note = 2'-O-methyladenosine |
| modified_base | 12 |
| | mod_base = OTHER |
| | note = 2'-fluoroadenosine |
| modified_base | 13 |

```
                        mod_base = um
modified_base           14
                        mod_base = OTHER
                        note = 2'-fluorocytidine
modified_base           15
                        mod_base = cm
modified_base           16
                        mod_base = OTHER
                        note = 2'-fluoroadenosine
modified_base           17
                        mod_base = gm
modified_base           18
                        mod_base = OTHER
                        note = 2'-fluoroguanosine
modified_base           19
                        mod_base = um
modified_base           20
                        mod_base = OTHER
                        note = 2'-fluorouridine
modified_base           20^21
                        mod_base = OTHER
                        note = phosphorothioate linkage
modified_base           21
                        mod_base = um
source                  1..21
                        mol_type = other RNA
                        organism = synthetic construct
SEQUENCE: 71
atgtaactct aatccaggtt t                                              21

SEQ ID NO: 72           moltype = RNA   length = 21
FEATURE                 Location/Qualifiers
modified_base           1
                        mod_base = OTHER
                        note = 2'-O-methyladenosine
modified_base           1^2
                        mod_base = OTHER
                        note = phosphorothioate linkage
modified_base           2
                        mod_base = OTHER
                        note = 2'-fluorouridine
modified_base           2^3
                        mod_base = OTHER
                        note = phosphorothioate linkage
modified_base           3
                        mod_base = OTHER
                        note = 2'-O-methyladenosine
modified_base           3^4
                        mod_base = OTHER
                        note = phosphorothioate linkage
modified_base           4
                        mod_base = OTHER
                        note = 2'-fluorouridine
modified_base           5
                        mod_base = cm
modified_base           6
                        mod_base = OTHER
                        note = 2'-fluorouridine
modified_base           7
                        mod_base = cm
modified_base           8
                        mod_base = OTHER
                        note = 2'-fluorouridine
modified_base           9
                        mod_base = gm
modified_base           10
                        mod_base = OTHER
                        note = 2'-fluoroadenosine
modified_base           11
                        mod_base = OTHER
                        note = 2'-O-methyladenosine
modified_base           12
                        mod_base = OTHER
                        note = 2'-fluorocytidine
modified_base           13
                        mod_base = um
modified_base           14
                        mod_base = OTHER
                        note = 2'-fluoroadenosine
```

```
modified_base      15
                   mod_base = OTHER
                   note = 2'-O-methyladenosine
modified_base      16
                   mod_base = OTHER
                   note = 2'-fluorouridine
modified_base      17
                   mod_base = cm
modified_base      18
                   mod_base = OTHER
                   note = 2'-fluoroadenosine
modified_base      19
                   mod_base = um
modified_base      20
                   mod_base = OTHER
                   note = 2'-fluorocytidine
modified_base      20^21
                   mod_base = OTHER
                   note = phosphorothioate linkage
modified_base      21
                   mod_base = cm
source             1..21
                   mol_type = other RNA
                   organism = synthetic construct
SEQUENCE: 72
atatctctga actaatcatc c                                          21

SEQ ID NO: 73      moltype = RNA  length = 21
FEATURE            Location/Qualifiers
modified_base      1
                   mod_base = OTHER
                   note = 5 -cyclopropyl phosphonate-2 -O-methyluridine
modified_base      1^2
                   mod_base = OTHER
                   note = phosphorothioate linkage
modified_base      2
                   mod_base = OTHER
                   note = 2'-fluoroadenosine
modified_base      2^3
                   mod_base = OTHER
                   note = phosphorothioate linkage
modified_base      3
                   mod_base = gm
modified_base      3^4
                   mod_base = OTHER
                   note = phosphorothioate linkage
modified_base      4
                   mod_base = OTHER
                   note = 2'-fluoroadenosine
modified_base      5
                   mod_base = OTHER
                   note = 2'-O-methyladenosine
modified_base      6
                   mod_base = OTHER
                   note = 2'-fluorouridine
modified_base      7
                   mod_base = um
modified_base      8
                   mod_base = OTHER
                   note = 2'-fluorouridine
modified_base      9
                   mod_base = cm
modified_base      10
                   mod_base = OTHER
                   note = 2'-fluoroadenosine
modified_base      11
                   mod_base = cm
modified_base      12
                   mod_base = OTHER
                   note = 2'-fluoroguanosine
modified_base      13
                   mod_base = gm
modified_base      14
                   mod_base = OTHER
                   note = 2'-fluoroadenosine
modified_base      15
                   mod_base = OTHER
                   note = 2'-O-methyladenosine
modified_base      16
```

|  |  |
|---|---|
| | mod_base = OTHER |
| | note = 2'-fluoroguanosine |
| modified_base | 17 |
| | mod_base = OTHER |
| | note = 2'-O-methyladenosine |
| modified_base | 18 |
| | mod_base = OTHER |
| | note = 2'-fluoroadenosine |
| modified_base | 19 |
| | mod_base = cm |
| modified_base | 20 |
| | mod_base = OTHER |
| | note = 2'-fluoroadenosine |
| modified_base | 20^21 |
| | mod_base = OTHER |
| | note = phosphorothioate linkage |
| modified_base | 21 |
| | mod_base = gm |
| source | 1..21 |
| | mol_type = other RNA |
| | organism = synthetic construct |
| SEQUENCE: 73 | |
| tagaatttca cggaagaaca g | 21 |
| | |
| SEQ ID NO: 74 | moltype = RNA  length = 21 |
| FEATURE | Location/Qualifiers |
| modified_base | 1 |
| | mod_base = OTHER |
| | note = 5'-cyclopropyl phosphonate-2'-O-methyluridine |
| modified_base | 1^2 |
| | mod_base = OTHER |
| | note = phosphorothioate linkage |
| modified_base | 2 |
| | mod_base = OTHER |
| | note = 2'-fluorouridine |
| modified_base | 2^3 |
| | mod_base = OTHER |
| | note = phosphorothioate linkage |
| modified_base | 3 |
| | mod_base = cm |
| modified_base | 3^4 |
| | mod_base = OTHER |
| | note = phosphorothioate linkage |
| modified_base | 4 |
| | mod_base = OTHER |
| | note = 2'-fluorouridine |
| modified_base | 5 |
| | mod_base = gm |
| modified_base | 6 |
| | mod_base = OTHER |
| | note = 2'-fluoroadenosine |
| modified_base | 7 |
| | mod_base = OTHER |
| | note = 2'-O-methyladenosine |
| modified_base | 8 |
| | mod_base = OTHER |
| | note = 2'-fluorocytidine |
| modified_base | 9 |
| | mod_base = um |
| modified_base | 10 |
| | mod_base = OTHER |
| | note = 2'-fluoroadenosine |
| modified_base | 11 |
| | mod_base = OTHER |
| | note = 2'-O-methyladenosine |
| modified_base | 12 |
| | mod_base = OTHER |
| | note = 2'-fluorouridine |
| modified_base | 13 |
| | mod_base = cm |
| modified_base | 14 |
| | mod_base = OTHER |
| | note = 2'-fluoroadenosine |
| modified_base | 15 |
| | mod_base = um |
| modified_base | 16 |
| | mod_base = OTHER |
| | note = 2'-fluorocytidine |
| modified_base | 17 |

```
                         mod_base = cm
modified_base            18
                         mod_base = OTHER
                         note = 2'-fluoroadenosine
modified_base            19
                         mod_base = gm
modified_base            20
                         mod_base = OTHER
                         note = 2'-fluoroguanosine
modified_base            20^21
                         mod_base = OTHER
                         note = phosphorothioate linkage
modified_base            21
                         mod_base = OTHER
                         note = 2'-O-methyladenosine
source                   1..21
                         mol_type = other RNA
                         organism = synthetic construct
SEQUENCE: 74
ttctgaacta atcatccagg a                                              21

SEQ ID NO: 75            moltype = RNA  length = 21
FEATURE                  Location/Qualifiers
modified_base            1
                         mod_base = OTHER
                         note = 5 -cyclopropyl phosphonate-2 -O-methyluridine
modified_base            1^2
                         mod_base = OTHER
                         note = phosphorothioate linkage
modified_base            2
                         mod_base = OTHER
                         note = 2'-fluoroguanosine
modified_base            2^3
                         mod_base = OTHER
                         note = phosphorothioate linkage
modified_base            3
                         mod_base = OTHER
                         note = 2'-O-methyladenosine
modified_base            3^4
                         mod_base = OTHER
                         note = phosphorothioate linkage
modified_base            4
                         mod_base = OTHER
                         note = 2'-fluoroadenosine
modified_base            5
                         mod_base = OTHER
                         note = 2'-O-methyladenosine
modified_base            6
                         mod_base = OTHER
                         note = 2'-fluorocytidine
modified_base            7
                         mod_base = cm
modified_base            8
                         mod_base = OTHER
                         note = 2'-fluoroadenosine
modified_base            9
                         mod_base = gm
modified_base            10
                         mod_base = OTHER
                         note = 2'-fluoroadenosine
modified_base            11
                         mod_base = um
modified_base            12
                         mod_base = OTHER
                         note = 2'-fluorocytidine
modified_base            13
                         mod_base = um
modified_base            14
                         mod_base = OTHER
                         note = 2'-fluoroguanosine
modified_base            15
                         mod_base = OTHER
                         note = 2'-O-methyladenosine
modified_base            16
                         mod_base = OTHER
                         note = 2'-fluoroadenosine
modified_base            17
                         mod_base = um
modified_base            18
```

```
                        mod_base = OTHER
                        note = 2'-fluorocytidine
modified_base           19
                        mod_base = cm
modified_base           20
                        mod_base = OTHER
                        note = 2'-fluorouridine
modified_base           20^21
                        mod_base = OTHER
                        note = phosphorothioate linkage
modified_base           21
                        mod_base = gm
source                  1..21
                        mol_type = other RNA
                        organism = synthetic construct
SEQUENCE: 75
tgaaaccaga tctgaatcct g                                              21

SEQ ID NO: 76           moltype = RNA  length = 21
FEATURE                 Location/Qualifiers
modified_base           1
                        mod_base = OTHER
                        note = 5 -cyclopropyl phosphonate-2 -O-methyluridine
modified_base           1^2
                        mod_base = OTHER
                        note = phosphorothioate linkage
modified_base           2
                        mod_base = OTHER
                        note = 2'-fluorouridine
modified_base           2^3
                        mod_base = OTHER
                        note = phosphorothioate linkage
modified_base           3
                        mod_base = gm
modified_base           3^4
                        mod_base = OTHER
                        note = phosphorothioate linkage
modified_base           4
                        mod_base = OTHER
                        note = 2'-fluoroadenosine
modified_base           5
                        mod_base = OTHER
                        note = 2'-O-methyladenosine
modified_base           6
                        mod_base = OTHER
                        note = 2'-fluoroadenosine
modified_base           7
                        mod_base = cm
modified_base           8
                        mod_base = OTHER
                        note = 2'-fluorocytidine
modified_base           9
                        mod_base = OTHER
                        note = 2'-O-methyladenosine
modified_base           10
                        mod_base = OTHER
                        note = 2'-fluoroguanosine
modified_base           11
                        mod_base = OTHER
                        note = 2'-O-methyladenosine
modified_base           12
                        mod_base = OTHER
                        note = 2'-fluorouridine
modified_base           13
                        mod_base = cm
modified_base           14
                        mod_base = OTHER
                        note = 2'-fluorouridine
modified_base           15
                        mod_base = gm
modified_base           16
                        mod_base = OTHER
                        note = 2'-fluoroadenosine
modified_base           17
                        mod_base = OTHER
                        note = 2'-O-methyladenosine
modified_base           18
                        mod_base = OTHER
                        note = 2'-fluorouridine
```

```
modified_base        19
                     mod_base = cm
modified_base        20
                     mod_base = OTHER
                     note = 2'-fluorocytidine
modified_base        20^21
                     mod_base = OTHER
                     note = phosphorothioate linkage
modified_base        21
                     mod_base = um
source               1..21
                     mol_type = other RNA
                     organism = synthetic construct
SEQUENCE: 76
ttgaaaccag atctgaatcc t                                              21

SEQ ID NO: 77        moltype = RNA   length = 21
FEATURE              Location/Qualifiers
modified_base        1
                     mod_base = um
modified_base        1^2
                     mod_base = OTHER
                     note = phosphorothioate linkage
modified_base        2
                     mod_base = OTHER
                     note = 2'-fluorouridine
modified_base        2^3
                     mod_base = OTHER
                     note = phosphorothioate linkage
modified_base        3
                     mod_base = gm
modified_base        3^4
                     mod_base = OTHER
                     note = phosphorothioate linkage
modified_base        4
                     mod_base = OTHER
                     note = 2'-fluoroadenosine
modified_base        5
                     mod_base = OTHER
                     note = 2'-O-methyladenosine
modified_base        6
                     mod_base = OTHER
                     note = 2'-fluoroadenosine
modified_base        7
                     mod_base = cm
modified_base        8
                     mod_base = OTHER
                     note = 2'-fluorocytidine
modified_base        9
                     mod_base = OTHER
                     note = 2'-O-methyladenosine
modified_base        10
                     mod_base = OTHER
                     note = 2'-fluoroguanosine
modified_base        11
                     mod_base = OTHER
                     note = 2'-O-methyladenosine
modified_base        12
                     mod_base = OTHER
                     note = 2'-fluorouridine
modified_base        13
                     mod_base = cm
modified_base        14
                     mod_base = OTHER
                     note = 2'-fluorouridine
modified_base        15
                     mod_base = gm
modified_base        16
                     mod_base = OTHER
                     note = 2'-fluoroadenosine
modified_base        17
                     mod_base = OTHER
                     note = 2'-O-methyladenosine
modified_base        18
                     mod_base = OTHER
                     note = 2'-fluorouridine
modified_base        19
                     mod_base = cm
modified_base        20
```

```
                        mod_base = OTHER
                        note = 2'-fluorocytidine
modified_base           20^21
                        mod_base = OTHER
                        note = phosphorothioate linkage
modified_base           21
                        mod_base = cm
source                  1..21
                        mol_type = other RNA
                        organism = synthetic construct
SEQUENCE: 77
ttgaaaccag atctgaatcc c                                              21

SEQ ID NO: 78           moltype = RNA   length = 21
FEATURE                 Location/Qualifiers
modified_base           1
                        mod_base = OTHER
                        note = 5 -cyclopropyl phosphonate-2 -O-methyladenosine
modified_base           1^2
                        mod_base = OTHER
                        note = phosphorothioate linkage
modified_base           2
                        mod_base = OTHER
                        note = 2'-fluorouridine
modified_base           2^3
                        mod_base = OTHER
                        note = phosphorothioate linkage
modified_base           3
                        mod_base = um
modified_base           3^4
                        mod_base = OTHER
                        note = phosphorothioate linkage
modified_base           4
                        mod_base = OTHER
                        note = 2'-fluorouridine
modified_base           5
                        mod_base = cm
modified_base           6
                        mod_base = OTHER
                        note = 2'-fluoroadenosine
modified_base           7
                        mod_base = cm
modified_base           8
                        mod_base = OTHER
                        note = 2'-fluoroguanosine
modified_base           9
                        mod_base = gm
modified_base           10
                        mod_base = OTHER
                        note = 2'-fluoroadenosine
modified_base           11
                        mod_base = OTHER
                        note = 2'-O-methyladenosine
modified_base           12
                        mod_base = OTHER
                        note = 2'-fluoroguanosine
modified_base           13
                        mod_base = OTHER
                        note = 2'-O-methyladenosine
modified_base           14
                        mod_base = OTHER
                        note = 2'-fluoroadenosine
modified_base           15
                        mod_base = cm
modified_base           16
                        mod_base = OTHER
                        note = 2'-fluoroadenosine
modified_base           17
                        mod_base = OTHER
                        note = 2'-O-methyladenosine
modified_base           18
                        mod_base = OTHER
                        note = 2'-fluoroguanosine
modified_base           19
                        mod_base = gm
modified_base           20
                        mod_base = OTHER
                        note = 2'-fluoroguanosine
modified_base           20^21
```

```
                        mod_base = OTHER
                        note = phosphorothioate linkage
modified_base           21
                        mod_base = cm
source                  1..21
                        mol_type = other RNA
                        organism = synthetic construct
SEQUENCE: 78
atttcacgga agaacaaggg c                                              21

SEQ ID NO: 79           moltype = RNA   length = 21
FEATURE                 Location/Qualifiers
modified_base           1
                        mod_base = OTHER
                        note = 5'-cyclopropyl phosphonate-2'-O-methyladenosine
modified_base           1^2
                        mod_base = OTHER
                        note = phosphorothioate linkage
modified_base           2
                        mod_base = OTHER
                        note = 2'-fluorouridine
modified_base           2^3
                        mod_base = OTHER
                        note = phosphorothioate linkage
modified_base           3
                        mod_base = gm
modified_base           3^4
                        mod_base = OTHER
                        note = phosphorothioate linkage
modified_base           4
                        mod_base = OTHER
                        note = 2'-fluorouridine
modified_base           5
                        mod_base = OTHER
                        note = 2'-O-methyladenosine
modified_base           6
                        mod_base = OTHER
                        note = 2'-fluoroadenosine
modified_base           7
                        mod_base = cm
modified_base           8
                        mod_base = OTHER
                        note = 2'-fluorouridine
modified_base           9
                        mod_base = cm
modified_base           10
                        mod_base = OTHER
                        note = 2'-fluorouridine
modified_base           11
                        mod_base = OTHER
                        note = 2'-O-methyladenosine
modified_base           12
                        mod_base = OTHER
                        note = 2'-fluoroadenosine
modified_base           13
                        mod_base = um
modified_base           14
                        mod_base = OTHER
                        note = 2'-fluorocytidine
modified_base           15
                        mod_base = cm
modified_base           16
                        mod_base = OTHER
                        note = 2'-fluoroadenosine
modified_base           17
                        mod_base = gm
modified_base           18
                        mod_base = OTHER
                        note = 2'-fluoroguanosine
modified_base           19
                        mod_base = um
modified_base           20
                        mod_base = OTHER
                        note = 2'-fluorouridine
modified_base           20^21
                        mod_base = OTHER
                        note = phosphorothioate linkage
modified_base           21
                        mod_base = um
```

```
source              1..21
                    mol_type = other RNA
                    organism = synthetic construct
SEQUENCE: 79
atgtaactct aatccaggtt t                                          21

SEQ ID NO: 80       moltype = RNA   length = 21
FEATURE             Location/Qualifiers
modified_base       1
                    mod_base = OTHER
                    note = 5 -cyclopropyl phosphonate-2 -O-methyladenosine
modified_base       1^2
                    mod_base = OTHER
                    note = phosphorothioate linkage
modified_base       2
                    mod_base = OTHER
                    note = 2'-fluorouridine
modified_base       2^3
                    mod_base = OTHER
                    note = phosphorothioate linkage
modified_base       3
                    mod_base = OTHER
                    note = 2'-O-methyladenosine
modified_base       3^4
                    mod_base = OTHER
                    note = phosphorothioate linkage
modified_base       4
                    mod_base = OTHER
                    note = 2'-fluorouridine
modified_base       5
                    mod_base = cm
modified_base       6
                    mod_base = OTHER
                    note = 2'-fluorouridine
modified_base       7
                    mod_base = cm
modified_base       8
                    mod_base = OTHER
                    note = 2'-fluorouridine
modified_base       9
                    mod_base = gm
modified_base       10
                    mod_base = OTHER
                    note = 2'-fluoroadenosine
modified_base       11
                    mod_base = OTHER
                    note = 2'-O-methyladenosine
modified_base       12
                    mod_base = OTHER
                    note = 2'-fluorocytidine
modified_base       13
                    mod_base = um
modified_base       14
                    mod_base = OTHER
                    note = 2'-fluoroadenosine
modified_base       15
                    mod_base = OTHER
                    note = 2'-O-methyladenosine
modified_base       16
                    mod_base = OTHER
                    note = 2'-fluorouridine
modified_base       17
                    mod_base = cm
modified_base       18
                    mod_base = OTHER
                    note = 2'-fluoroadenosine
modified_base       19
                    mod_base = um
modified_base       20
                    mod_base = OTHER
                    note = 2'-fluorocytidine
modified_base       20^21
                    mod_base = OTHER
                    note = phosphorothioate linkage
modified_base       21
                    mod_base = cm
source              1..21
                    mol_type = other RNA
                    organism = synthetic construct
```

```
SEQUENCE: 80
atatctctga actaatcatc c                                               21

SEQ ID NO: 81           moltype = RNA  length = 21
FEATURE                 Location/Qualifiers
modified_base           1
                        mod_base = um
modified_base           1^2
                        mod_base = OTHER
                        note = phosphorothioate linkage
modified_base           2
                        mod_base = OTHER
                        note = 2'-fluoroadenosine
modified_base           2^3
                        mod_base = OTHER
                        note = phosphorothioate linkage
modified_base           3
                        mod_base = gm
modified_base           3^4
                        mod_base = OTHER
                        note = phosphorothioate linkage
modified_base           4
                        mod_base = OTHER
                        note = 2'-O-methyladenosine
modified_base           5
                        mod_base = OTHER
                        note = 2'-O-methyladenosine
modified_base           6
                        mod_base = um
modified_base           7
                        mod_base = um
modified_base           8
                        mod_base = um
modified_base           9
                        mod_base = cm
modified_base           10
                        mod_base = OTHER
                        note = 2'-O-methyladenosine
modified_base           11
                        mod_base = cm
modified_base           12
                        mod_base = OTHER
                        note = 2'-fluoroguanosine
modified_base           13
                        mod_base = gm
modified_base           14
                        mod_base = OTHER
                        note = 2'-fluoroadenosine
modified_base           15
                        mod_base = OTHER
                        note = 2'-O-methyladenosine
modified_base           16
                        mod_base = OTHER
                        note = 2'-fluoroguanosine
modified_base           17
                        mod_base = OTHER
                        note = 2'-O-methyladenosine
modified_base           18
                        mod_base = OTHER
                        note = 2'-O-methyladenosine
modified_base           19
                        mod_base = cm
modified_base           20
                        mod_base = OTHER
                        note = 2'-O-methyladenosine
modified_base           20^21
                        mod_base = OTHER
                        note = phosphorothioate linkage
modified_base           21
                        mod_base = gm
source                  1..21
                        mol_type = other RNA
                        organism = synthetic construct
SEQUENCE: 81
tagaatttca cggaagaaca g                                               21

SEQ ID NO: 82           moltype = RNA  length = 21
FEATURE                 Location/Qualifiers
modified_base           1
```

```
modified_base                        mod_base = um
                         1^2
                                     mod_base = OTHER
                                     note = phosphorothioate linkage
modified_base            2
                                     mod_base = OTHER
                                     note = 2'-fluoroadenosine
modified_base            2^3
                                     mod_base = OTHER
                                     note = phosphorothioate linkage
modified_base            3
                                     mod_base = OTHER
                                     note = 2'-fluoroguanosine
modified_base            3^4
                                     mod_base = OTHER
                                     note = phosphorothioate linkage
modified_base            4
                                     mod_base = OTHER
                                     note = 2'-fluoroadenosine
modified_base            5
                                     mod_base = OTHER
                                     note = 2'-O-methyladenosine
modified_base            6
                                     mod_base = um
modified_base            7
                                     mod_base = um
modified_base            8
                                     mod_base = um
modified_base            9
                                     mod_base = cm
modified_base            10
                                     mod_base = OTHER
                                     note = 2'-O-methyladenosine
modified_base            11
                                     mod_base = cm
modified_base            12
                                     mod_base = OTHER
                                     note = 2'-fluoroguanosine
modified_base            13
                                     mod_base = gm
modified_base            14
                                     mod_base = OTHER
                                     note = 2'-fluoroadenosine
modified_base            15
                                     mod_base = OTHER
                                     note = 2'-O-methyladenosine
modified_base            16
                                     mod_base = OTHER
                                     note = 2'-fluoroguanosine
modified_base            17
                                     mod_base = OTHER
                                     note = 2'-O-methyladenosine
modified_base            18
                                     mod_base = OTHER
                                     note = 2'-O-methyladenosine
modified_base            19
                                     mod_base = cm
modified_base            20
                                     mod_base = OTHER
                                     note = 2'-O-methyladenosine
modified_base            20^21
                                     mod_base = OTHER
                                     note = phosphorothioate linkage
modified_base            21
                                     mod_base = gm
source                   1..21
                                     mol_type = other RNA
                                     organism = synthetic construct
SEQUENCE: 82
tagaatttca cggaagaaca g                                                 21

SEQ ID NO: 83            moltype = RNA   length = 21
FEATURE                  Location/Qualifiers
modified_base            1
                                     mod_base = um
modified_base            1^2
                                     mod_base = OTHER
                                     note = phosphorothioate linkage
modified_base            2
```

```
                        mod_base = OTHER
                        note = 2'-fluorouridine
modified_base           2^3
                        mod_base = OTHER
                        note = phosphorothioate linkage
modified_base           3
                        mod_base = cm
modified_base           3^4
                        mod_base = OTHER
                        note = phosphorothioate linkage
modified_base           4
                        mod_base = um
modified_base           5
                        mod_base = gm
modified_base           6
                        mod_base = OTHER
                        note = 2'-O-methyladenosine
modified_base           7
                        mod_base = OTHER
                        note = 2'-O-methyladenosine
modified_base           8
                        mod_base = cm
modified_base           9
                        mod_base = um
modified_base           10
                        mod_base = OTHER
                        note = 2'-O-methyladenosine
modified_base           11
                        mod_base = OTHER
                        note = 2'-O-methyladenosine
modified_base           12
                        mod_base = OTHER
                        note = 2'-fluorouridine
modified_base           13
                        mod_base = cm
modified_base           14
                        mod_base = OTHER
                        note = 2'-fluoroadenosine
modified_base           15
                        mod_base = um
modified_base           16
                        mod_base = OTHER
                        note = 2'-fluorocytidine
modified_base           17
                        mod_base = cm
modified_base           18
                        mod_base = OTHER
                        note = 2'-O-methyladenosine
modified_base           19
                        mod_base = gm
modified_base           20
                        mod_base = gm
modified_base           20^21
                        mod_base = OTHER
                        note = phosphorothioate linkage
modified_base           21
                        mod_base = OTHER
                        note = 2'-O-methyladenosine
source                  1..21
                        mol_type = other RNA
                        organism = synthetic construct
SEQUENCE: 83
ttctgaacta atcatccagg a                                          21

SEQ ID NO: 84           moltype = RNA  length = 21
FEATURE                 Location/Qualifiers
modified_base           1
                        mod_base = OTHER
                        note = 5'-cyclopropyl phosphonate-2'-O-methyluridine
modified_base           1^2
                        mod_base = OTHER
                        note = phosphorothioate linkage
modified_base           2
                        mod_base = OTHER
                        note = 2'-fluoroadenosine
modified_base           2^3
                        mod_base = OTHER
                        note = phosphorothioate linkage
modified_base           3
```

```
                        mod_base = OTHER
                        note = 2'-fluoroguanosine
modified_base           3^4
                        mod_base = OTHER
                        note = phosphorothioate linkage
modified_base           4
                        mod_base = OTHER
                        note = 2'-fluoroadenosine
modified_base           5
                        mod_base = OTHER
                        note = 2'-O-methyladenosine
modified_base           6
                        mod_base = um
modified_base           7
                        mod_base = um
modified_base           8
                        mod_base = um
modified_base           9
                        mod_base = cm
modified_base           10
                        mod_base = OTHER
                        note = 2'-O-methyladenosine
modified_base           11
                        mod_base = cm
modified_base           12
                        mod_base = OTHER
                        note = 2'-fluoroguanosine
modified_base           13
                        mod_base = gm
modified_base           14
                        mod_base = OTHER
                        note = 2'-fluoroadenosine
modified_base           15
                        mod_base = OTHER
                        note = 2'-O-methyladenosine
modified_base           16
                        mod_base = OTHER
                        note = 2'-fluoroguanosine
modified_base           17
                        mod_base = OTHER
                        note = 2'-O-methyladenosine
modified_base           18
                        mod_base = OTHER
                        note = 2'-O-methyladenosine
modified_base           19
                        mod_base = cm
modified_base           20
                        mod_base = OTHER
                        note = 2'-O-methyladenosine
modified_base           20^21
                        mod_base = OTHER
                        note = phosphorothioate linkage
modified_base           21
                        mod_base = gm
source                  1..21
                        mol_type = other RNA
                        organism = synthetic construct
SEQUENCE: 84
tagaatttca cggaagaaca g                                                 21

SEQ ID NO: 85           moltype = RNA  length = 21
FEATURE                 Location/Qualifiers
modified_base           1
                        mod_base = um
modified_base           1^2
                        mod_base = OTHER
                        note = phosphorothioate linkage
modified_base           2
                        mod_base = OTHER
                        note = 2'-fluoroadenosine
modified_base           2^3
                        mod_base = OTHER
                        note = phosphorothioate linkage
modified_base           3
                        mod_base = OTHER
                        note = 2'-fluoroguanosine
modified_base           3^4
                        mod_base = OTHER
                        note = phosphorothioate linkage
```

```
modified_base         4
                      mod_base = OTHER
                      note = 2'-fluoroadenosine
modified_base         5
                      mod_base = OTHER
                      note = 2'-O-methyladenosine
modified_base         6
                      mod_base = um
modified_base         7
                      mod_base = um
modified_base         8
                      mod_base = um
modified_base         9
                      mod_base = cm
modified_base         10
                      mod_base = OTHER
                      note = 2'-O-methyladenosine
modified_base         11
                      mod_base = cm
modified_base         12
                      mod_base = OTHER
                      note = 2'-fluoroguanosine
modified_base         13
                      mod_base = gm
modified_base         14
                      mod_base = OTHER
                      note = 2'-fluoroadenosine
modified_base         15
                      mod_base = OTHER
                      note = 2'-O-methyladenosine
modified_base         16
                      mod_base = OTHER
                      note = 2'-fluoroguanosine
modified_base         17
                      mod_base = OTHER
                      note = 2'-O-methyladenosine
modified_base         18
                      mod_base = OTHER
                      note = 2'-O-methyladenosine
modified_base         19
                      mod_base = cm
modified_base         20
                      mod_base = OTHER
                      note = 2'-O-methyladenosine
modified_base         20^21
                      mod_base = OTHER
                      note = phosphorothioate linkage
modified_base         21
                      mod_base = cm
source                1..21
                      mol_type = other RNA
                      organism = synthetic construct
SEQUENCE: 85
tagaatttca cggaagaaca c                                                  21

SEQ ID NO: 86         moltype = RNA   length = 21
FEATURE               Location/Qualifiers
modified_base         1
                      mod_base = OTHER
                      note = 5 -cyclopropyl phosphonate-2 -O-methyluridine
modified_base         1^2
                      mod_base = OTHER
                      note = phosphorothioate linkage
modified_base         2
                      mod_base = OTHER
                      note = 2'-fluoroadenosine
modified_base         2^3
                      mod_base = OTHER
                      note = phosphorothioate linkage
modified_base         3
                      mod_base = OTHER
                      note = 2'-fluoroguanosine
modified_base         3^4
                      mod_base = OTHER
                      note = phosphorothioate linkage
modified_base         4
                      mod_base = OTHER
                      note = 2'-fluoroadenosine
modified_base         5
```

```
                          mod_base = OTHER
                          note = 2'-O-methyladenosine
modified_base             6
                          mod_base = um
modified_base             7
                          mod_base = um
modified_base             8
                          mod_base = um
modified_base             9
                          mod_base = cm
modified_base             10
                          mod_base = OTHER
                          note = 2'-O-methyladenosine
modified_base             11
                          mod_base = cm
modified_base             12
                          mod_base = OTHER
                          note = 2'-fluoroguanosine
modified_base             13
                          mod_base = gm
modified_base             14
                          mod_base = OTHER
                          note = 2'-fluoroadenosine
modified_base             15
                          mod_base = OTHER
                          note = 2'-O-methyladenosine
modified_base             16
                          mod_base = OTHER
                          note = 2'-fluoroguanosine
modified_base             17
                          mod_base = OTHER
                          note = 2'-O-methyladenosine
modified_base             18
                          mod_base = OTHER
                          note = 2'-O-methyladenosine
modified_base             19
                          mod_base = cm
modified_base             20
                          mod_base = OTHER
                          note = 2'-O-methyladenosine
modified_base             20^21
                          mod_base = OTHER
                          note = phosphorothioate linkage
modified_base             21
                          mod_base = cm
source                    1..21
                          mol_type = other RNA
                          organism = synthetic construct
SEQUENCE: 86
tagaatttca cggaagaaca c                                              21

SEQ ID NO: 87            moltype = DNA  length = 21
FEATURE                  Location/Qualifiers
modified_base             1
                          mod_base = OTHER
                          note = 5-cyclopropyl phosphonate-2-O-methyluridine
modified_base             1^2
                          mod_base = OTHER
                          note = phosphorothioate linkage
modified_base             2
                          mod_base = OTHER
                          note = 2'-fluorouridine
modified_base             2^3
                          mod_base = OTHER
                          note = phosphorothioate linkage
modified_base             3
                          mod_base = gm
modified_base             3^4
                          mod_base = OTHER
                          note = phosphorothioate linkage
modified_base             4
                          mod_base = OTHER
                          note = 2'-fluoroadenosine
modified_base             5
                          mod_base = OTHER
                          note = 2'-O-methyladenosine
modified_base             6
                          mod_base = OTHER
                          note = 2'-fluoroadenosine
```

```
modified_base              7
                           mod_base = cm
modified_base              8
                           mod_base = OTHER
                           note = 2'-fluorocytidine
modified_base              9
                           mod_base = OTHER
                           note = 2'-O-methyladenosine
modified_base              10
                           mod_base = OTHER
                           note = 2'-fluoroguanosine
modified_base              11
                           mod_base = OTHER
                           note = 2'-O-methyladenosine
modified_base              12
                           mod_base = OTHER
                           note = 2'-fluorouridine
modified_base              13
                           mod_base = cm
modified_base              14
                           mod_base = OTHER
                           note = 2'-fluorouridine
modified_base              15
                           mod_base = gm
modified_base              16
                           mod_base = OTHER
                           note = 2'-fluoroadenosine
modified_base              17
                           mod_base = OTHER
                           note = 2'-O-methyladenosine
modified_base              18
                           mod_base = OTHER
                           note = 2'-fluorouridine
modified_base              19
                           mod_base = cm
modified_base              20
                           mod_base = OTHER
                           note = 2'-fluorocytidine
modified_base              20^21
                           mod_base = OTHER
                           note = phosphorothioate linkage
modified_base              21
                           mod_base = cm
source                     1..21
                           mol_type = other DNA
                           organism = synthetic construct
SEQUENCE: 87
ttgaaaccag atctgaatcc c                                              21

SEQ ID NO: 88              moltype = RNA  length = 21
FEATURE                    Location/Qualifiers
modified_base              1
                           mod_base = um
modified_base              1^2
                           mod_base = OTHER
                           note = phosphorothioate linkage
modified_base              2
                           mod_base = OTHER
                           note = 2'-fluorouridine
modified_base              2^3
                           mod_base = OTHER
                           note = phosphorothioate linkage
modified_base              3
                           mod_base = gm
modified_base              3^4
                           mod_base = OTHER
                           note = phosphorothioate linkage
modified_base              4
                           mod_base = OTHER
                           note = 2'-O-methyladenosine
modified_base              5
                           mod_base = OTHER
                           note = 2'-O-methyladenosine
modified_base              6
                           mod_base = OTHER
                           note = 2'-O-methyladenosine
modified_base              7
                           mod_base = cm
modified_base              8
```

```
                        mod_base = cm
modified_base           9
                        mod_base = OTHER
                        note = 2'-O-methyladenosine
modified_base           10
                        mod_base = gm
modified_base           11
                        mod_base = OTHER
                        note = 2'-O-methyladenosine
modified_base           12
                        mod_base = OTHER
                        note = 2'-fluorouridine
modified_base           13
                        mod_base = cm
modified_base           14
                        mod_base = OTHER
                        note = 2'-fluorouridine
modified_base           15
                        mod_base = gm
modified_base           16
                        mod_base = OTHER
                        note = 2'-fluoroadenosine
modified_base           17
                        mod_base = OTHER
                        note = 2'-O-methyladenosine
modified_base           18
                        mod_base = um
modified_base           19
                        mod_base = cm
modified_base           20
                        mod_base = cm
modified_base           20^21
                        mod_base = OTHER
                        note = phosphorothioate linkage
modified_base           21
                        mod_base = cm
source                  1..21
                        mol_type = other RNA
                        organism = synthetic construct
SEQUENCE: 88
ttgaaaccag atctgaatcc c                                           21

SEQ ID NO: 89           moltype = RNA  length = 21
FEATURE                 Location/Qualifiers
modified_base           1
                        mod_base = OTHER
                        note = 5-cyclopropyl phosphonate-2-O-methyluridine
modified_base           1^2
                        mod_base = OTHER
                        note = phosphorothioate linkage
modified_base           2
                        mod_base = OTHER
                        note = 2'-fluorouridine
modified_base           2^3
                        mod_base = OTHER
                        note = phosphorothioate linkage
modified_base           3
                        mod_base = gm
modified_base           3^4
                        mod_base = OTHER
                        note = phosphorothioate linkage
modified_base           4
                        mod_base = OTHER
                        note = 2'-O-methyladenosine
modified_base           5
                        mod_base = OTHER
                        note = 2'-O-methyladenosine
modified_base           6
                        mod_base = OTHER
                        note = 2'-O-methyladenosine
modified_base           7
                        mod_base = cm
modified_base           8
                        mod_base = cm
modified_base           9
                        mod_base = OTHER
                        note = 2'-O-methyladenosine
modified_base           10
                        mod_base = gm
```

|                | -continued |
|---|---|
| modified_base | 11<br>mod_base = OTHER<br>note = 2'-O-methyladenosine |
| modified_base | 12<br>mod_base = OTHER<br>note = 2'-fluorouridine |
| modified_base | 13<br>mod_base = cm |
| modified_base | 14<br>mod_base = OTHER<br>note = 2'-fluorouridine |
| modified_base | 15<br>mod_base = gm |
| modified_base | 16<br>mod_base = OTHER<br>note = 2'-fluoroadenosine |
| modified_base | 17<br>mod_base = OTHER<br>note = 2'-O-methyladenosine |
| modified_base | 18<br>mod_base = um |
| modified_base | 19<br>mod_base = cm |
| modified_base | 20<br>mod_base = cm |
| modified_base | 20^21<br>mod_base = OTHER<br>note = phosphorothioate linkage |
| modified_base | 21<br>mod_base = cm |
| source | 1..21<br>mol_type = other RNA<br>organism = synthetic construct |

SEQUENCE: 89
ttgaaaccag atctgaatcc c                               21

| SEQ ID NO: 90<br>FEATURE | moltype = RNA length = 21<br>Location/Qualifiers |
|---|---|
| modified_base | 1<br>mod_base = um |
| modified_base | 1^2<br>mod_base = OTHER<br>note = phosphorothioate linkage |
| modified_base | 2<br>mod_base = OTHER<br>note = 2'-fluorouridine |
| modified_base | 2^3<br>mod_base = OTHER<br>note = phosphorothioate linkage |
| modified_base | 3<br>mod_base = gm |
| modified_base | 3^4<br>mod_base = OTHER<br>note = phosphorothioate linkage |
| modified_base | 4<br>mod_base = OTHER<br>note = 2'-O-methyladenosine |
| modified_base | 5<br>mod_base = OTHER<br>note = 2'-O-methyladenosine |
| modified_base | 6<br>mod_base = OTHER<br>note = 2'-O-methyladenosine |
| modified_base | 7<br>mod_base = cm |
| modified_base | 8<br>mod_base = OTHER<br>note = 2'-fluorocytidine |
| modified_base | 9<br>mod_base = OTHER<br>note = 2'-O-methyladenosine |
| modified_base | 10<br>mod_base = OTHER<br>note = 2'-fluoroguanosine |
| modified_base | 11<br>mod_base = OTHER<br>note = 2'-O-methyladenosine |
| modified_base | 12<br>mod_base = OTHER |

```
                          note = 2'-fluorouridine
modified_base             13
                          mod_base = cm
modified_base             14
                          mod_base = OTHER
                          note = 2'-fluorouridine
modified_base             15
                          mod_base = gm
modified_base             16
                          mod_base = OTHER
                          note = 2'-fluoroadenosine
modified_base             17
                          mod_base = OTHER
                          note = 2'-O-methyladenosine
modified_base             18
                          mod_base = um
modified_base             19
                          mod_base = cm
modified_base             20
                          mod_base = cm
modified_base             20^21
                          mod_base = OTHER
                          note = phosphorothioate linkage
modified_base             21
                          mod_base = cm
source                    1..21
                          mol_type = other RNA
                          organism = synthetic construct
SEQUENCE: 90
ttgaaaccag atctgaatcc c                                               21

SEQ ID NO: 91             moltype = RNA  length = 21
FEATURE                   Location/Qualifiers
modified_base             1
                          mod_base = OTHER
                          note = 5-cyclopropyl phosphonate-2'-O-methyluridine
modified_base             1^2
                          mod_base = OTHER
                          note = phosphorothioate linkage
modified_base             2
                          mod_base = OTHER
                          note = 2'-fluorouridine
modified_base             2^3
                          mod_base = OTHER
                          note = phosphorothioate linkage
modified_base             3
                          mod_base = gm
modified_base             3^4
                          mod_base = OTHER
                          note = phosphorothioate linkage
modified_base             4
                          mod_base = OTHER
                          note = 2'-O-methyladenosine
modified_base             5
                          mod_base = OTHER
                          note = 2'-O-methyladenosine
modified_base             6
                          mod_base = OTHER
                          note = 2'-O-methyladenosine
modified_base             7
                          mod_base = cm
modified_base             8
                          mod_base = OTHER
                          note = 2'-fluorocytidine
modified_base             9
                          mod_base = OTHER
                          note = 2'-O-methyladenosine
modified_base             10
                          mod_base = OTHER
                          note = 2'-fluoroguanosine
modified_base             11
                          mod_base = OTHER
                          note = 2'-O-methyladenosine
modified_base             12
                          mod_base = OTHER
                          note = 2'-fluorouridine
modified_base             13
                          mod_base = cm
modified_base             14
```

```
                        mod_base = OTHER
                        note = 2'-fluorouridine
modified_base           15
                        mod_base = gm
modified_base           16
                        mod_base = OTHER
                        note = 2'-fluoroadenosine
modified_base           17
                        mod_base = OTHER
                        note = 2'-O-methyladenosine
modified_base           18
                        mod_base = um
modified_base           19
                        mod_base = cm
modified_base           20
                        mod_base = cm
modified_base           20^21
                        mod_base = OTHER
                        note = phosphorothioate linkage
modified_base           21
                        mod_base = cm
source                  1..21
                        mol_type = other RNA
                        organism = synthetic construct
SEQUENCE: 91
ttgaaaccag atctgaatcc c                                           21

SEQ ID NO: 92           moltype = RNA   length = 21
FEATURE                 Location/Qualifiers
modified_base           1
                        mod_base = OTHER
                        note = 5'-cyclopropyl phosphonate-2'-O-methyluridine
modified_base           1^2
                        mod_base = OTHER
                        note = phosphorothioate linkage
modified_base           2
                        mod_base = OTHER
                        note = 2'-fluorouridine
modified_base           2^3
                        mod_base = OTHER
                        note = phosphorothioate linkage
modified_base           3
                        mod_base = cm
modified_base           3^4
                        mod_base = OTHER
                        note = phosphorothioate linkage
modified_base           4
                        mod_base = um
modified_base           5
                        mod_base = gm
modified_base           6
                        mod_base = OTHER
                        note = 2'-O-methyladenosine
modified_base           7
                        mod_base = OTHER
                        note = 2'-O-methyladenosine
modified_base           8
                        mod_base = cm
modified_base           9
                        mod_base = um
modified_base           10
                        mod_base = OTHER
                        note = 2'-O-methyladenosine
modified_base           11
                        mod_base = OTHER
                        note = 2'-O-methyladenosine
modified_base           12
                        mod_base = OTHER
                        note = 2'-fluorouridine
modified_base           13
                        mod_base = cm
modified_base           14
                        mod_base = OTHER
                        note = 2'-fluoroadenosine
modified_base           15
                        mod_base = um
modified_base           16
                        mod_base = OTHER
                        note = 2'-fluorocytidine
```

```
modified_base      17
                   mod_base = cm
modified_base      18
                   mod_base = OTHER
                   note = 2'-O-methyladenosine
modified_base      19
                   mod_base = gm
modified_base      20
                   mod_base = gm
modified_base      20^21
                   mod_base = OTHER
                   note = phosphorothioate linkage
modified_base      21
                   mod_base = OTHER
                   note = 2'-O-methyladenosine
source             1..21
                   mol_type = other RNA
                   organism = synthetic construct
SEQUENCE: 92
ttctgaacta atcatccagg a                                              21

SEQ ID NO: 93      moltype = RNA  length = 21
FEATURE            Location/Qualifiers
modified_base      1
                   mod_base = OTHER
                   note = 5-cyclopropyl phosphonate-2-O-methyluridine
modified_base      1^2
                   mod_base = OTHER
                   note = phosphorothioate linkage
modified_base      2
                   mod_base = OTHER
                   note = 2'-fluoroadenosine
modified_base      2^3
                   mod_base = OTHER
                   note = phosphorothioate linkage
modified_base      3
                   mod_base = gm
modified_base      3^4
                   mod_base = OTHER
                   note = phosphorothioate linkage
modified_base      4
                   mod_base = OTHER
                   note = 2'-O-methyladenosine
modified_base      5
                   mod_base = OTHER
                   note = 2'-O-methyladenosine
modified_base      6
                   mod_base = um
modified_base      7
                   mod_base = um
modified_base      8
                   mod_base = um
modified_base      9
                   mod_base = cm
modified_base      10
                   mod_base = OTHER
                   note = 2'-O-methyladenosine
modified_base      11
                   mod_base = cm
modified_base      12
                   mod_base = OTHER
                   note = 2'-fluoroguanosine
modified_base      13
                   mod_base = gm
modified_base      14
                   mod_base = OTHER
                   note = 2'-fluoroadenosine
modified_base      15
                   mod_base = OTHER
                   note = 2'-O-methyladenosine
modified_base      16
                   mod_base = OTHER
                   note = 2'-fluoroguanosine
modified_base      17
                   mod_base = OTHER
                   note = 2'-O-methyladenosine
modified_base      18
                   mod_base = OTHER
                   note = 2'-O-methyladenosine
```

```
modified_base       19
                    mod_base = cm
modified_base       20
                    mod_base = OTHER
                    note = 2'-O-methyladenosine
modified_base       20^21
                    mod_base = OTHER
                    note = phosphorothioate linkage
modified_base       21
                    mod_base = gm
source              1..21
                    mol_type = other RNA
                    organism = synthetic construct
SEQUENCE: 93
tagaatttca cggaagaaca g                                           21

SEQ ID NO: 94       moltype = RNA  length = 21
FEATURE             Location/Qualifiers
modified_base       1
                    mod_base = um
modified_base       1^2
                    mod_base = OTHER
                    note = phosphorothioate linkage
modified_base       2
                    mod_base = OTHER
                    note = 2'-fluoroadenosine
modified_base       2^3
                    mod_base = OTHER
                    note = phosphorothioate linkage
modified_base       3
                    mod_base = gm
modified_base       3^4
                    mod_base = OTHER
                    note = phosphorothioate linkage
modified_base       4
                    mod_base = OTHER
                    note = 2'-O-methyladenosine
modified_base       5
                    mod_base = OTHER
                    note = 2'-O-methyladenosine
modified_base       6
                    mod_base = um
modified_base       7
                    mod_base = um
modified_base       8
                    mod_base = um
modified_base       9
                    mod_base = cm
modified_base       10
                    mod_base = OTHER
                    note = 2'-O-methyladenosine
modified_base       11
                    mod_base = cm
modified_base       12
                    mod_base = OTHER
                    note = 2'-fluoroguanosine
modified_base       13
                    mod_base = gm
modified_base       14
                    mod_base = OTHER
                    note = 2'-fluoroadenosine
modified_base       15
                    mod_base = OTHER
                    note = 2'-O-methyladenosine
modified_base       16
                    mod_base = OTHER
                    note = 2'-fluoroguanosine
modified_base       17
                    mod_base = OTHER
                    note = 2'-O-methyladenosine
modified_base       18
                    mod_base = OTHER
                    note = 2'-O-methyladenosine
modified_base       19
                    mod_base = cm
modified_base       20
                    mod_base = OTHER
                    note = 2'-O-methyladenosine
modified_base       20^21
```

```
                        mod_base = OTHER
                        note = phosphorothioate linkage
modified_base           21
                        mod_base = cm
source                  1..21
                        mol_type = other RNA
                        organism = synthetic construct
SEQUENCE: 94
tagaatttca cggaagaaca c                                              21

SEQ ID NO: 95           moltype = RNA   length = 21
FEATURE                 Location/Qualifiers
modified_base           1
                        mod_base = OTHER
                        note = 5´-cyclopropyl phosphonate-2´-O-methyluridine
modified_base           1^2
                        mod_base = OTHER
                        note = phosphorothioate linkage
modified_base           2
                        mod_base = OTHER
                        note = 2´-fluoroadenosine
modified_base           2^3
                        mod_base = OTHER
                        note = phosphorothioate linkage
modified_base           3
                        mod_base = gm
modified_base           3^4
                        mod_base = OTHER
                        note = phosphorothioate linkage
modified_base           4
                        mod_base = OTHER
                        note = 2´-O-methyladenosine
modified_base           5
                        mod_base = OTHER
                        note = 2´-O-methyladenosine
modified_base           6
                        mod_base = um
modified_base           7
                        mod_base = um
modified_base           8
                        mod_base = um
modified_base           9
                        mod_base = cm
modified_base           10
                        mod_base = OTHER
                        note = 2´-O-methyladenosine
modified_base           11
                        mod_base = cm
modified_base           12
                        mod_base = OTHER
                        note = 2´-fluoroguanosine
modified_base           13
                        mod_base = gm
modified_base           14
                        mod_base = OTHER
                        note = 2´-fluoroadenosine
modified_base           15
                        mod_base = OTHER
                        note = 2´-O-methyladenosine
modified_base           16
                        mod_base = OTHER
                        note = 2´-fluoroguanosine
modified_base           17
                        mod_base = OTHER
                        note = 2´-O-methyladenosine
modified_base           18
                        mod_base = OTHER
                        note = 2´-O-methyladenosine
modified_base           19
                        mod_base = cm
modified_base           20
                        mod_base = OTHER
                        note = 2´-O-methyladenosine
modified_base           20^21
                        mod_base = OTHER
                        note = phosphorothioate linkage
modified_base           21
                        mod_base = cm
source                  1..21
```

|  |  |
|---|---|
|  | mol_type = other RNA |
|  | organism = synthetic construct |
| SEQUENCE: 95 | |
| tagaatttca cggaagaaca c | 21 |
| | |
| SEQ ID NO: 96 | moltype = RNA  length = 21 |
| FEATURE | Location/Qualifiers |
| modified_base | 1 |
|  | mod_base = um |
| modified_base | 1^2 |
|  | mod_base = OTHER |
|  | note = phosphorothioate linkage |
| modified_base | 2 |
|  | mod_base = OTHER |
|  | note = 2'-fluoroguanosine |
| modified_base | 2^3 |
|  | mod_base = OTHER |
|  | note = phosphorothioate linkage |
| modified_base | 3 |
|  | mod_base = OTHER |
|  | note = 2'-O-methyladenosine |
| modified_base | 3^4 |
|  | mod_base = OTHER |
|  | note = phosphorothioate linkage |
| modified_base | 4 |
|  | mod_base = OTHER |
|  | note = 2'-O-methyladenosine |
| modified_base | 5 |
|  | mod_base = OTHER |
|  | note = 2'-O-methyladenosine |
| modified_base | 6 |
|  | mod_base = cm |
| modified_base | 7 |
|  | mod_base = cm |
| modified_base | 8 |
|  | mod_base = OTHER |
|  | note = 2'-O-methyladenosine |
| modified_base | 9 |
|  | mod_base = gm |
| modified_base | 10 |
|  | mod_base = OTHER |
|  | note = 2'-O-methyladenosine |
| modified_base | 11 |
|  | mod_base = um |
| modified_base | 12 |
|  | mod_base = OTHER |
|  | note = 2'-fluorocytidine |
| modified_base | 13 |
|  | mod_base = um |
| modified_base | 14 |
|  | mod_base = OTHER |
|  | note = 2'-fluoroguanosine |
| modified_base | 15 |
|  | mod_base = OTHER |
|  | note = 2'-O-methyladenosine |
| modified_base | 16 |
|  | mod_base = OTHER |
|  | note = 2'-fluoroadenosine |
| modified_base | 17 |
|  | mod_base = um |
| modified_base | 18 |
|  | mod_base = cm |
| modified_base | 19 |
|  | mod_base = cm |
| modified_base | 20 |
|  | mod_base = um |
| modified_base | 20^21 |
|  | mod_base = OTHER |
|  | note = phosphorothioate linkage |
| modified_base | 21 |
|  | mod_base = gm |
| source | 1..21 |
|  | mol_type = other RNA |
|  | organism = synthetic construct |
| SEQUENCE: 96 | |
| tgaaaccaga tctgaatcct g | 21 |
| | |
| SEQ ID NO: 97 | moltype = RNA  length = 21 |
| FEATURE | Location/Qualifiers |

| | |
|---|---|
| modified_base | 1<br>mod_base = OTHER<br>note = 5-cyclopropyl phosphonate-2-O-methyluridine |
| modified_base | 1^2<br>mod_base = OTHER<br>note = phosphorothioate linkage |
| modified_base | 2<br>mod_base = OTHER<br>note = 2'-fluoroguanosine |
| modified_base | 2^3<br>mod_base = OTHER<br>note = phosphorothioate linkage |
| modified_base | 3<br>mod_base = OTHER<br>note = 2'-O-methyladenosine |
| modified_base | 3^4<br>mod_base = OTHER<br>note = phosphorothioate linkage |
| modified_base | 4<br>mod_base = OTHER<br>note = 2'-O-methyladenosine |
| modified_base | 5<br>mod_base = OTHER<br>note = 2'-O-methyladenosine |
| modified_base | 6<br>mod_base = cm |
| modified_base | 7<br>mod_base = cm |
| modified_base | 8<br>mod_base = OTHER<br>note = 2'-O-methyladenosine |
| modified_base | 9<br>mod_base = gm |
| modified_base | 10<br>mod_base = OTHER<br>note = 2'-O-methyladenosine |
| modified_base | 11<br>mod_base = um |
| modified_base | 12<br>mod_base = OTHER<br>note = 2'-fluorocytidine |
| modified_base | 13<br>mod_base = um |
| modified_base | 14<br>mod_base = OTHER<br>note = 2'-fluoroguanosine |
| modified_base | 15<br>mod_base = OTHER<br>note = 2'-O-methyladenosine |
| modified_base | 16<br>mod_base = OTHER<br>note = 2'-fluoroadenosine |
| modified_base | 17<br>mod_base = um |
| modified_base | 18<br>mod_base = cm |
| modified_base | 19<br>mod_base = cm |
| modified_base | 20<br>mod_base = um |
| modified_base | 20^21<br>mod_base = OTHER<br>note = phosphorothioate linkage |
| modified_base | 21<br>mod_base = gm |
| source | 1..21<br>mol_type = other RNA<br>organism = synthetic construct |
| SEQUENCE: 97 | |
| tgaaaccaga tctgaatcct g | 21 |
| SEQ ID NO: 98<br>FEATURE | moltype = RNA  length = 21<br>Location/Qualifiers |
| modified_base | 1<br>mod_base = um |
| modified_base | 1^2<br>mod_base = OTHER<br>note = phosphorothioate linkage |
| modified_base | 2 |

```
                    mod_base = OTHER
                    note = 2'-fluoroguanosine
modified_base       2^3
                    mod_base = OTHER
                    note = phosphorothioate linkage
modified_base       3
                    mod_base = OTHER
                    note = 2'-O-methyladenosine
modified_base       3^4
                    mod_base = OTHER
                    note = phosphorothioate linkage
modified_base       4
                    mod_base = OTHER
                    note = 2'-fluoroadenosine
modified_base       5
                    mod_base = OTHER
                    note = 2'-O-methyladenosine
modified_base       6
                    mod_base = cm
modified_base       7
                    mod_base = cm
modified_base       8
                    mod_base = OTHER
                    note = 2'-O-methyladenosine
modified_base       9
                    mod_base = gm
modified_base       10
                    mod_base = OTHER
                    note = 2'-O-methyladenosine
modified_base       11
                    mod_base = um
modified_base       12
                    mod_base = OTHER
                    note = 2'-fluorocytidine
modified_base       13
                    mod_base = um
modified_base       14
                    mod_base = OTHER
                    note = 2'-fluoroguanosine
modified_base       15
                    mod_base = OTHER
                    note = 2'-O-methyladenosine
modified_base       16
                    mod_base = OTHER
                    note = 2'-fluoroadenosine
modified_base       17
                    mod_base = um
modified_base       18
                    mod_base = cm
modified_base       19
                    mod_base = cm
modified_base       20
                    mod_base = um
modified_base       20^21
                    mod_base = OTHER
                    note = phosphorothioate linkage
modified_base       21
                    mod_base = gm
source              1..21
                    mol_type = other RNA
                    organism = synthetic construct
SEQUENCE: 98
tgaaaccaga tctgaatcct g                                              21

SEQ ID NO: 99       moltype = RNA  length = 21
FEATURE             Location/Qualifiers
modified_base       1
                    mod_base = OTHER
                    note = 5 -cyclopropyl phosphonate-2 -O-methyluridine
modified_base       1^2
                    mod_base = OTHER
                    note = phosphorothioate linkage
modified_base       2
                    mod_base = OTHER
                    note = 2'-fluoroguanosine
modified_base       2^3
                    mod_base = OTHER
                    note = phosphorothioate linkage
modified_base       3
```

```
                        mod_base = OTHER
                        note = 2'-O-methyladenosine
modified_base           3^4
                        mod_base = OTHER
                        note = phosphorothioate linkage
modified_base           4
                        mod_base = OTHER
                        note = 2'-fluoroadenosine
modified_base           5
                        mod_base = OTHER
                        note = 2'-O-methyladenosine
modified_base           6
                        mod_base = cm
modified_base           7
                        mod_base = cm
modified_base           8
                        mod_base = OTHER
                        note = 2'-O-methyladenosine
modified_base           9
                        mod_base = gm
modified_base           10
                        mod_base = OTHER
                        note = 2'-O-methyladenosine
modified_base           11
                        mod_base = um
modified_base           12
                        mod_base = OTHER
                        note = 2'-fluorocytidine
modified_base           13
                        mod_base = um
modified_base           14
                        mod_base = OTHER
                        note = 2'-fluoroguanosine
modified_base           15
                        mod_base = OTHER
                        note = 2'-O-methyladenosine
modified_base           16
                        mod_base = OTHER
                        note = 2'-fluoroadenosine
modified_base           17
                        mod_base = um
modified_base           18
                        mod_base = cm
modified_base           19
                        mod_base = cm
modified_base           20
                        mod_base = um
modified_base           20^21
                        mod_base = OTHER
                        note = phosphorothioate linkage
modified_base           21
                        mod_base = gm
source                  1..21
                        mol_type = other RNA
                        organism = synthetic construct
SEQUENCE: 99
tgaaaccaga tctgaatcct g                                              21

SEQ ID NO: 100          moltype = RNA   length = 21
FEATURE                 Location/Qualifiers
modified_base           1
                        mod_base = OTHER
                        note = 5 -cyclopropyl phosphonate-2 -O-methyluridine
modified_base           1^2
                        mod_base = OTHER
                        note = phosphorothioate linkage
modified_base           2
                        mod_base = OTHER
                        note = 2'-fluoroadenosine
modified_base           2^3
                        mod_base = OTHER
                        note = phosphorothioate linkage
modified_base           3
                        mod_base = gm
modified_base           3^4
                        mod_base = OTHER
                        note = phosphorothioate linkage
modified_base           4
                        mod_base = OTHER
```

```
                    note = 2'-fluoroadenosine
modified_base       5
                    mod_base = OTHER
                    note = 2'-O-methyladenosine
modified_base       6
                    mod_base = um
modified_base       7
                    mod_base = um
modified_base       8
                    mod_base = um
modified_base       9
                    mod_base = cm
modified_base       10
                    mod_base = OTHER
                    note = 2'-O-methyladenosine
modified_base       11
                    mod_base = cm
modified_base       12
                    mod_base = OTHER
                    note = 2'-fluoroguanosine
modified_base       13
                    mod_base = gm
modified_base       14
                    mod_base = OTHER
                    note = 2'-fluoroadenosine
modified_base       15
                    mod_base = OTHER
                    note = 2'-O-methyladenosine
modified_base       16
                    mod_base = OTHER
                    note = 2'-fluoroguanosine
modified_base       17
                    mod_base = OTHER
                    note = 2'-O-methyladenosine
modified_base       18
                    mod_base = OTHER
                    note = 2'-O-methyladenosine
modified_base       19
                    mod_base = cm
modified_base       20
                    mod_base = OTHER
                    note = 2'-O-methyladenosine
modified_base       20^21
                    mod_base = OTHER
                    note = phosphorothioate linkage
modified_base       21
                    mod_base = gm
source              1..21
                    mol_type = other RNA
                    organism = synthetic construct
SEQUENCE: 100
tagaatttca cggaagaaca g                                               21

SEQ ID NO: 101      moltype = RNA  length = 21
FEATURE             Location/Qualifiers
modified_base       1
                    mod_base = OTHER
                    note = 5 -cyclopropyl phosphonate-2 -O-methyluridine
modified_base       1^2
                    mod_base = OTHER
                    note = phosphorothioate linkage
modified_base       2
                    mod_base = OTHER
                    note = 2'-fluoroadenosine
modified_base       2^3
                    mod_base = OTHER
                    note = phosphorothioate linkage
modified_base       3
                    mod_base = OTHER
                    note = 2'-fluoroguanosine
modified_base       3^4
                    mod_base = OTHER
                    note = phosphorothioate linkage
modified_base       4
                    mod_base = OTHER
                    note = 2'-O-methyladenosine
modified_base       5
                    mod_base = OTHER
                    note = 2'-O-methyladenosine
```

```
modified_base              6
                           mod_base = um
modified_base              7
                           mod_base = um
modified_base              8
                           mod_base = um
modified_base              9
                           mod_base = cm
modified_base              10
                           mod_base = OTHER
                           note = 2'-O-methyladenosine
modified_base              11
                           mod_base = cm
modified_base              12
                           mod_base = OTHER
                           note = 2'-fluoroguanosine
modified_base              13
                           mod_base = gm
modified_base              14
                           mod_base = OTHER
                           note = 2'-fluoroadenosine
modified_base              15
                           mod_base = OTHER
                           note = 2'-O-methyladenosine
modified_base              16
                           mod_base = OTHER
                           note = 2'-fluoroguanosine
modified_base              17
                           mod_base = OTHER
                           note = 2'-O-methyladenosine
modified_base              18
                           mod_base = OTHER
                           note = 2'-O-methyladenosine
modified_base              19
                           mod_base = cm
modified_base              20
                           mod_base = OTHER
                           note = 2'-O-methyladenosine
modified_base              20^21
                           mod_base = OTHER
                           note = phosphorothioate linkage
modified_base              21
                           mod_base = gm
source                     1..21
                           mol_type = other RNA
                           organism = synthetic construct
SEQUENCE: 101
tagaatttca cggaagaaca g                                              21

SEQ ID NO: 102             moltype = RNA  length = 22
FEATURE                    Location/Qualifiers
modified_base              1
                           mod_base = cm
modified_base              2
                           mod_base = OTHER
                           note = 2'-O-methyladenosine
modified_base              3
                           mod_base = gm
modified_base              4
                           mod_base = gm
modified_base              5
                           mod_base = OTHER
                           note = 2'-O-methyladenosine
modified_base              6
                           mod_base = um
modified_base              7
                           mod_base = um
modified_base              8
                           mod_base = cm
modified_base              9
                           mod_base = OTHER
                           note = 2'-fluoroadenosine
modified_base              10
                           mod_base = OTHER
                           note = 2'-fluoroguanosine
modified_base              11
                           mod_base = OTHER
                           note = 2'-fluoroadenosine
modified_base              12
```

|  |  |
|---|---|
|  | mod_base = um |
| modified_base | 13 |
|  | mod_base = cm |
| modified_base | 14 |
|  | mod_base = um |
| modified_base | 15 |
|  | mod_base = gm |
| modified_base | 16 |
|  | mod_base = gm |
| modified_base | 17 |
|  | mod_base = um |
| modified_base | 18 |
|  | mod_base = um |
| modified_base | 19 |
|  | mod_base = um |
| modified_base | 20 |
|  | mod_base = cm |
| modified_base | 21 |
|  | mod_base = OTHER |
|  | note = 2'-O-methyladenosine |
| modified_base | 22 |
|  | mod_base = OTHER |
|  | note = 2 -deoxythymidine |
| source | 1..22 |
|  | mol_type = other RNA |
|  | organism = synthetic construct |
| SEQUENCE: 102 |  |
| caggattcag atctggtttc at | 22 |
| SEQ ID NO: 103 | moltype = RNA   length = 22 |
| FEATURE | Location/Qualifiers |
| modified_base | 1 |
|  | mod_base = OTHER |
|  | note = 2'-O-methyladenosine |
| modified_base | 2 |
|  | mod_base = gm |
| modified_base | 3 |
|  | mod_base = gm |
| modified_base | 4 |
|  | mod_base = OTHER |
|  | note = 2'-O-methyladenosine |
| modified_base | 5 |
|  | mod_base = um |
| modified_base | 6 |
|  | mod_base = um |
| modified_base | 7 |
|  | mod_base = cm |
| modified_base | 8 |
|  | mod_base = OTHER |
|  | note = 2'-O-methyladenosine |
| modified_base | 9 |
|  | mod_base = OTHER |
|  | note = 2'-fluoroguanosine |
| modified_base | 10 |
|  | mod_base = OTHER |
|  | note = 2'-fluoroadenosine |
| modified_base | 11 |
|  | mod_base = OTHER |
|  | note = 2'-fluorouridine |
| modified_base | 12 |
|  | mod_base = cm |
| modified_base | 13 |
|  | mod_base = um |
| modified_base | 14 |
|  | mod_base = gm |
| modified_base | 15 |
|  | mod_base = gm |
| modified_base | 16 |
|  | mod_base = um |
| modified_base | 17 |
|  | mod_base = um |
| modified_base | 18 |
|  | mod_base = um |
| modified_base | 19 |
|  | mod_base = cm |
| modified_base | 20 |
|  | mod_base = OTHER |
|  | note = 2'-O-methyladenosine |
| modified_base | 21 |

```
                        mod_base = OTHER
                        note = 2'-O-methyladenosine
modified_base           22
                        mod_base = OTHER
                        note = 2-deoxythymidine
source                  1..22
                        mol_type = other RNA
                        organism = synthetic construct
SEQUENCE: 103
aggattcaga tctggtttca at                                                   22

SEQ ID NO: 104          moltype = RNA  length = 22
FEATURE                 Location/Qualifiers
modified_base           1
                        mod_base = cm
modified_base           2
                        mod_base = um
modified_base           3
                        mod_base = gm
modified_base           4
                        mod_base = um
modified_base           5
                        mod_base = um
modified_base           6
                        mod_base = cm
modified_base           7
                        mod_base = um
modified_base           8
                        mod_base = um
modified_base           9
                        mod_base = OTHER
                        note = 2'-fluorocytidine
modified_base           10
                        mod_base = OTHER
                        note = 2'-fluorocytidine
modified_base           11
                        mod_base = OTHER
                        note = 2'-fluoroguanosine
modified_base           12
                        mod_base = um
modified_base           13
                        mod_base = gm
modified_base           14
                        mod_base = OTHER
                        note = 2'-O-methyladenosine
modified_base           15
                        mod_base = OTHER
                        note = 2'-O-methyladenosine
modified_base           16
                        mod_base = OTHER
                        note = 2'-O-methyladenosine
modified_base           17
                        mod_base = um
modified_base           18
                        mod_base = um
modified_base           19
                        mod_base = cm
modified_base           20
                        mod_base = um
modified_base           21
                        mod_base = OTHER
                        note = 2'-O-methyladenosine
modified_base           22
                        mod_base = OTHER
                        note = 2-deoxythymidine
source                  1..22
                        mol_type = other RNA
                        organism = synthetic construct
SEQUENCE: 104
ctgttcttcc gtgaaattct at                                                   22

SEQ ID NO: 105          moltype = RNA  length = 22
FEATURE                 Location/Qualifiers
modified_base           1
                        mod_base = um
modified_base           2
                        mod_base = cm
modified_base           3
                        mod_base = cm
```

```
modified_base        4
                     mod_base = um
modified_base        5
                     mod_base = gm
modified_base        6
                     mod_base = gm
modified_base        7
                     mod_base = OTHER
                     note = 2'-O-methyladenosine
modified_base        8
                     mod_base = um
modified_base        9
                     mod_base = OTHER
                     note = 2'-fluoroguanosine
modified_base        10
                     mod_base = OTHER
                     note = 2'-fluoroadenosine
modified_base        11
                     mod_base = OTHER
                     note = 2'-fluorouridine
modified_base        12
                     mod_base = um
modified_base        13
                     mod_base = OTHER
                     note = 2'-O-methyladenosine
modified_base        14
                     mod_base = gm
modified_base        15
                     mod_base = um
modified_base        16
                     mod_base = um
modified_base        17
                     mod_base = cm
modified_base        18
                     mod_base = OTHER
                     note = 2'-O-methyladenosine
modified_base        19
                     mod_base = gm
modified_base        20
                     mod_base = OTHER
                     note = 2'-O-methyladenosine
modified_base        21
                     mod_base = OTHER
                     note = 2'-O-methyladenosine
modified_base        22
                     mod_base = OTHER
                     note = 2-deoxythymidine
source               1..22
                     mol_type = other RNA
                     organism = synthetic construct
SEQUENCE: 105
tcctggatga ttagttcaga at                                              22

SEQ ID NO: 106       moltype = RNA  length = 22
FEATURE              Location/Qualifiers
modified_base        1
                     mod_base = gm
modified_base        2
                     mod_base = cm
modified_base        3
                     mod_base = cm
modified_base        4
                     mod_base = cm
modified_base        5
                     mod_base = um
modified_base        6
                     mod_base = um
modified_base        7
                     mod_base = gm
modified_base        8
                     mod_base = um
modified_base        9
                     mod_base = OTHER
                     note = 2'-fluorouridine
modified_base        10
                     mod_base = OTHER
                     note = 2'-fluorocytidine
modified_base        11
                     mod_base = OTHER
```

```
                        note = 2'-fluorouridine
modified_base           12
                        mod_base = um
modified_base           13
                        mod_base = cm
modified_base           14
                        mod_base = cm
modified_base           15
                        mod_base = gm
modified_base           16
                        mod_base = um
modified_base           17
                        mod_base = gm
modified_base           18
                        mod_base = OTHER
                        note = 2'-O-methyladenosine
modified_base           19
                        mod_base = OTHER
                        note = 2'-O-methyladenosine
modified_base           20
                        mod_base = OTHER
                        note = 2'-O-methyladenosine
modified_base           21
                        mod_base = um
modified_base           22
                        mod_base = OTHER
                        note = 2 -deoxythymidine
source                  1..22
                        mol_type = other RNA
                        organism = synthetic construct
SEQUENCE: 106
gcccttgttc ttccgtgaaa tt                                                  22

SEQ ID NO: 107          moltype = RNA  length = 22
FEATURE                 Location/Qualifiers
modified_base           1
                        mod_base = OTHER
                        note = 2-aminoadenine
modified_base           2
                        mod_base = OTHER
                        note = 2'-O-methyladenosine
modified_base           3
                        mod_base = OTHER
                        note = 2'-O-methyladenosine
modified_base           4
                        mod_base = cm
modified_base           5
                        mod_base = cm
modified_base           6
                        mod_base = um
modified_base           7
                        mod_base = gm
modified_base           8
                        mod_base = gm
modified_base           9
                        mod_base = OTHER
                        note = 2'-fluoroadenosine
modified_base           10
                        mod_base = OTHER
                        note = 2'-fluorouridine
modified_base           11
                        mod_base = OTHER
                        note = 2'-fluorouridine
modified_base           12
                        mod_base = OTHER
                        note = 2'-O-methyladenosine
modified_base           13
                        mod_base = gm
modified_base           14
                        mod_base = OTHER
                        note = 2'-O-methyladenosine
modified_base           15
                        mod_base = gm
modified_base           16
                        mod_base = um
modified_base           17
                        mod_base = um
modified_base           18
                        mod_base = OTHER
```

```
                        note = 2'-O-methyladenosine
modified_base           19
                        mod_base = cm
modified_base           20
                        mod_base = OTHER
                        note = 2'-O-methyladenosine
modified_base           21
                        mod_base = um
modified_base           22
                        mod_base = OTHER
                        note = 2 -deoxythymidine
source                  1..22
                        mol_type = other RNA
                        organism = synthetic construct
SEQUENCE: 107
aaacctggat tagagttaca tt                                              22

SEQ ID NO: 108          moltype = RNA   length = 22
FEATURE                 Location/Qualifiers
modified_base           1
                        mod_base = gm
modified_base           2
                        mod_base = gm
modified_base           3
                        mod_base = OTHER
                        note = 2'-O-methyladenosine
modified_base           4
                        mod_base = um
modified_base           5
                        mod_base = gm
modified_base           6
                        mod_base = OTHER
                        note = 2'-O-methyladenosine
modified_base           7
                        mod_base = um
modified_base           8
                        mod_base = um
modified_base           9
                        mod_base = OTHER
                        note = 2'-fluoroadenosine
modified_base           10
                        mod_base = OTHER
                        note = 2'-fluoroguanosine
modified_base           11
                        mod_base = OTHER
                        note = 2'-fluorouridine
modified_base           12
                        mod_base = um
modified_base           13
                        mod_base = cm
modified_base           14
                        mod_base = OTHER
                        note = 2'-O-methyladenosine
modified_base           15
                        mod_base = gm
modified_base           16
                        mod_base = OTHER
                        note = 2'-O-methyladenosine
modified_base           17
                        mod_base = gm
modified_base           18
                        mod_base = OTHER
                        note = 2'-O-methyladenosine
modified_base           19
                        mod_base = um
modified_base           20
                        mod_base = OTHER
                        note = 2'-O-methyladenosine
modified_base           21
                        mod_base = um
modified_base           22
                        mod_base = OTHER
                        note = 2 -deoxythymidine
source                  1..22
                        mol_type = other RNA
                        organism = synthetic construct
SEQUENCE: 108
ggatgattag ttcagagata tt                                              22
```

| | |
|---|---|
| SEQ ID NO: 109 | moltype = RNA length = 22 |
| FEATURE | Location/Qualifiers |
| modified_base | 1 |
| | mod_base = gm |
| modified_base | 2 |
| | mod_base = um |
| modified_base | 3 |
| | mod_base = gm |
| modified_base | 4 |
| | mod_base = um |
| modified_base | 5 |
| | mod_base = um |
| modified_base | 6 |
| | mod_base = cm |
| modified_base | 7 |
| | mod_base = um |
| modified_base | 8 |
| | mod_base = um |
| modified_base | 9 |
| | mod_base = OTHER |
| | note = 2'-fluorocytidine |
| modified_base | 10 |
| | mod_base = OTHER |
| | note = 2'-fluorocytidine |
| modified_base | 11 |
| | mod_base = OTHER |
| | note = 2'-fluoroguanosine |
| modified_base | 12 |
| | mod_base = um |
| modified_base | 13 |
| | mod_base = gm |
| modified_base | 14 |
| | mod_base = OTHER |
| | note = 2'-O-methyladenosine |
| modified_base | 15 |
| | mod_base = OTHER |
| | note = 2'-O-methyladenosine |
| modified_base | 16 |
| | mod_base = OTHER |
| | note = 2'-O-methyladenosine |
| modified_base | 17 |
| | mod_base = um |
| modified_base | 18 |
| | mod_base = um |
| modified_base | 19 |
| | mod_base = cm |
| modified_base | 20 |
| | mod_base = um |
| modified_base | 21 |
| | mod_base = OTHER |
| | note = 2'-O-methyladenosine |
| modified_base | 22 |
| | mod_base = OTHER |
| | note = 2-deoxythymidine |
| source | 1..22 |
| | mol_type = other RNA |
| | organism = synthetic construct |
| SEQUENCE: 109 | |
| gtgttcttcc gtgaaattct at | 22 |
| | |
| SEQ ID NO: 110 | moltype = RNA length = 22 |
| FEATURE | Location/Qualifiers |
| modified_base | 1 |
| | mod_base = gm |
| modified_base | 2 |
| | mod_base = um |
| modified_base | 3 |
| | mod_base = gm |
| modified_base | 4 |
| | mod_base = um |
| modified_base | 5 |
| | mod_base = um |
| modified_base | 6 |
| | mod_base = cm |
| modified_base | 7 |
| | mod_base = OTHER |
| | note = 2'-fluorouridine |
| modified_base | 8 |
| | mod_base = um |

| | |
|---|---|
| modified_base | 9<br>mod_base = OTHER<br>note = 2'-fluorocytidine |
| modified_base | 10<br>mod_base = cm |
| modified_base | 11<br>mod_base = OTHER<br>note = 2'-fluoroguanosine |
| modified_base | 12<br>mod_base = um |
| modified_base | 13<br>mod_base = gm |
| modified_base | 14<br>mod_base = OTHER<br>note = 2'-O-methyladenosine |
| modified_base | 15<br>mod_base = OTHER<br>note = 2'-O-methyladenosine |
| modified_base | 16<br>mod_base = OTHER<br>note = 2'-O-methyladenosine |
| modified_base | 17<br>mod_base = um |
| modified_base | 18<br>mod_base = um |
| modified_base | 19<br>mod_base = cm |
| modified_base | 20<br>mod_base = um |
| modified_base | 21<br>mod_base = OTHER<br>note = 2'-O-methyladenosine |
| modified_base | 22<br>mod_base = OTHER<br>note = 2 -deoxythymidine |
| source | 1..22<br>mol_type = other RNA<br>organism = synthetic construct |

SEQUENCE: 110
gtgttcttcc gtgaaattct at 22

| | |
|---|---|
| SEQ ID NO: 111 | moltype = RNA  length = 22 |
| FEATURE | Location/Qualifiers |
| modified_base | 1<br>mod_base = gm |
| modified_base | 2<br>mod_base = gm |
| modified_base | 3<br>mod_base = gm |
| modified_base | 4<br>mod_base = OTHER<br>note = 2'-O-methyladenosine |
| modified_base | 5<br>mod_base = um |
| modified_base | 6<br>mod_base = um |
| modified_base | 7<br>mod_base = cm |
| modified_base | 8<br>mod_base = OTHER<br>note = 2'-O-methyladenosine |
| modified_base | 9<br>mod_base = OTHER<br>note = 2'-fluoroguanosine |
| modified_base | 10<br>mod_base = OTHER<br>note = 2'-fluoroadenosine |
| modified_base | 11<br>mod_base = OTHER<br>note = 2'-fluorouridine |
| modified_base | 12<br>mod_base = cm |
| modified_base | 13<br>mod_base = um |
| modified_base | 14<br>mod_base = gm |
| modified_base | 15<br>mod_base = gm |
| modified_base | 16 |

|  |  |
|---|---|
| modified_base | mod_base = um<br>17 |
| modified_base | mod_base = um<br>18 |
| modified_base | mod_base = um<br>19 |
| modified_base | mod_base = cm<br>20 |
| modified_base | mod_base = OTHER<br>note = 2'-O-methyladenosine<br>21 |
| modified_base | mod_base = OTHER<br>note = 2'-O-methyladenosine<br>22 |
| source | mod_base = OTHER<br>note = 2 -deoxythymidine<br>1..22<br>mol_type = other RNA<br>organism = synthetic construct |

SEQUENCE: 111
gggattcaga tctggtttca at                        22

| SEQ ID NO: 112<br>FEATURE | moltype = RNA   length = 22<br>Location/Qualifiers |
|---|---|
| modified_base | 1<br>mod_base = OTHER<br>note = 2-aminoadenine |
| modified_base | 2<br>mod_base = gm |
| modified_base | 3<br>mod_base = gm |
| modified_base | 4<br>mod_base = OTHER<br>note = 2'-O-methyladenosine |
| modified_base | 5<br>mod_base = um |
| modified_base | 6<br>mod_base = um |
| modified_base | 7<br>mod_base = cm |
| modified_base | 8<br>mod_base = OTHER<br>note = 2'-O-methyladenosine |
| modified_base | 9<br>mod_base = OTHER<br>note = 2'-fluoroguanosine |
| modified_base | 10<br>mod_base = OTHER<br>note = 2'-fluoroadenosine |
| modified_base | 11<br>mod_base = OTHER<br>note = 2'-fluorouridine |
| modified_base | 12<br>mod_base = cm |
| modified_base | 13<br>mod_base = um |
| modified_base | 14<br>mod_base = gm |
| modified_base | 15<br>mod_base = gm |
| modified_base | 16<br>mod_base = um |
| modified_base | 17<br>mod_base = um |
| modified_base | 18<br>mod_base = um |
| modified_base | 19<br>mod_base = cm |
| modified_base | 20<br>mod_base = OTHER<br>note = 2'-O-methyladenosine |
| modified_base | 21<br>mod_base = OTHER<br>note = 2'-O-methyladenosine |
| modified_base | 22<br>mod_base = OTHER<br>note = 2 -deoxythymidine |
| source | 1..22<br>mol_type = other RNA |

```
                        organism = synthetic construct
SEQUENCE: 112
aggattcaga tctggtttca at                                             22

SEQ ID NO: 113          moltype = RNA   length = 22
FEATURE                 Location/Qualifiers
modified_base           1
                        mod_base = gm
modified_base           2
                        mod_base = gm
modified_base           3
                        mod_base = gm
modified_base           4
                        mod_base = OTHER
                        note = 2'-O-methyladenosine
modified_base           5
                        mod_base = um
modified_base           6
                        mod_base = um
modified_base           7
                        mod_base = cm
modified_base           8
                        mod_base = OTHER
                        note = 2'-O-methyladenosine
modified_base           9
                        mod_base = OTHER
                        note = 2'-fluoroguanosine
modified_base           10
                        mod_base = OTHER
                        note = 2'-O-methyladenosine
modified_base           11
                        mod_base = OTHER
                        note = 2'-fluorouridine
modified_base           12
                        mod_base = cm
modified_base           13
                        mod_base = um
modified_base           14
                        mod_base = gm
modified_base           15
                        mod_base = gm
modified_base           16
                        mod_base = um
modified_base           17
                        mod_base = um
modified_base           18
                        mod_base = um
modified_base           19
                        mod_base = cm
modified_base           20
                        mod_base = OTHER
                        note = 2'-O-methyladenosine
modified_base           21
                        mod_base = OTHER
                        note = 2'-O-methyladenosine
modified_base           22
                        mod_base = OTHER
                        note = 2'-deoxythymidine
source                  1..22
                        mol_type = other RNA
                        organism = synthetic construct
SEQUENCE: 113
gggattcaga tctggtttca at                                             22

SEQ ID NO: 114          moltype = RNA   length = 22
FEATURE                 Location/Qualifiers
modified_base           1
                        mod_base = gm
modified_base           2
                        mod_base = gm
modified_base           3
                        mod_base = gm
modified_base           4
                        mod_base = OTHER
                        note = 2'-O-methyladenosine
modified_base           5
                        mod_base = um
modified_base           6
                        mod_base = um
```

| | |
|---|---|
| modified_base | 7<br>mod_base = cm |
| modified_base | 8<br>mod_base = OTHER<br>note = 2'-O-methyladenosine |
| modified_base | 9<br>mod_base = OTHER<br>note = 2'-fluoroguanosine |
| modified_base | 10<br>mod_base = OTHER<br>note = 2'-O-methyladenosine |
| modified_base | 11<br>mod_base = OTHER<br>note = 2'-fluorouridine |
| modified_base | 12<br>mod_base = OTHER<br>note = 2'-fluorocytidine |
| modified_base | 13<br>mod_base = um |
| modified_base | 14<br>mod_base = gm |
| modified_base | 15<br>mod_base = gm |
| modified_base | 16<br>mod_base = um |
| modified_base | 17<br>mod_base = um |
| modified_base | 18<br>mod_base = um |
| modified_base | 19<br>mod_base = cm |
| modified_base | 20<br>mod_base = OTHER<br>note = 2'-O-methyladenosine |
| modified_base | 21<br>mod_base = OTHER<br>note = 2'-O-methyladenosine |
| modified_base | 22<br>mod_base = OTHER<br>note = 2 -deoxythymidine |
| source | 1..22<br>mol_type = other RNA<br>organism = synthetic construct |

SEQUENCE: 114
gggattcaga tctggtttca at                                              22

| | |
|---|---|
| SEQ ID NO: 115<br>FEATURE | moltype = RNA   length = 22<br>Location/Qualifiers |
| modified_base | 1<br>mod_base = cm |
| modified_base | 2<br>mod_base = OTHER<br>note = 2'-O-methyladenosine |
| modified_base | 3<br>mod_base = gm |
| modified_base | 4<br>mod_base = gm |
| modified_base | 5<br>mod_base = OTHER<br>note = 2'-O-methyladenosine |
| modified_base | 6<br>mod_base = um |
| modified_base | 7<br>mod_base = um |
| modified_base | 8<br>mod_base = cm |
| modified_base | 9<br>mod_base = OTHER<br>note = 2'-fluoroadenosine |
| modified_base | 10<br>mod_base = OTHER<br>note = 2'-fluoroguanosine |
| modified_base | 11<br>mod_base = OTHER<br>note = 2'-fluoroadenosine |
| modified_base | 12<br>mod_base = um |
| modified_base | 13<br>mod_base = cm |

```
modified_base      14
                   mod_base = um
modified_base      15
                   mod_base = gm
modified_base      16
                   mod_base = OTHER
                   note = 2-O-methylinosine
modified_base      17
                   mod_base = um
modified_base      18
                   mod_base = um
modified_base      19
                   mod_base = um
modified_base      20
                   mod_base = cm
modified_base      21
                   mod_base = OTHER
                   note = 2'-O-methyladenosine
modified_base      22
                   mod_base = OTHER
                   note = 2-deoxythymidine
source             1..22
                   mol_type = other RNA
                   organism = synthetic construct
SEQUENCE: 115
caggattcag atctgntttc at                                      22

SEQ ID NO: 116     moltype = RNA   length = 22
FEATURE            Location/Qualifiers
modified_base      1
                   mod_base = cm
modified_base      2
                   mod_base = um
modified_base      3
                   mod_base = gm
modified_base      4
                   mod_base = um
modified_base      5
                   mod_base = um
modified_base      6
                   mod_base = cm
modified_base      7
                   mod_base = um
modified_base      8
                   mod_base = um
modified_base      9
                   mod_base = OTHER
                   note = 2'-fluorocytidine
modified_base      10
                   mod_base = cm
modified_base      11
                   mod_base = OTHER
                   note = 2'-fluoroguanosine
modified_base      12
                   mod_base = um
modified_base      13
                   mod_base = OTHER
                   note = 2'-fluoroguanosine
modified_base      14
                   mod_base = OTHER
                   note = 2'-O-methyladenosine
modified_base      15
                   mod_base = OTHER
                   note = 2'-O-methyladenosine
modified_base      16
                   mod_base = OTHER
                   note = 2'-O-methyladenosine
modified_base      17
                   mod_base = um
modified_base      18
                   mod_base = um
modified_base      19
                   mod_base = cm
modified_base      20
                   mod_base = um
modified_base      21
                   mod_base = OTHER
                   note = 2'-O-methyladenosine
modified_base      22
```

-continued

|  |  |  |
|---|---|---|
|  | mod_base = OTHER | |
|  | note = 2-deoxythymidine | |
| source | 1..22 | |
|  | mol_type = other RNA | |
|  | organism = synthetic construct | |
| SEQUENCE: 116 | | |
| ctgttcttcc gtgaaattct at | | 22 |
| | | |
| SEQ ID NO: 117 | moltype = RNA   length = 21 | |
| FEATURE | Location/Qualifiers | |
| modified_base | 1 | |
|  | mod_base = cm | |
| modified_base | 2 | |
|  | mod_base = OTHER | |
|  | note = 2'-O-methyladenosine | |
| modified_base | 3 | |
|  | mod_base = gm | |
| modified_base | 4 | |
|  | mod_base = gm | |
| modified_base | 5 | |
|  | mod_base = OTHER | |
|  | note = 2'-O-methyladenosine | |
| modified_base | 6 | |
|  | mod_base = um | |
| modified_base | 7 | |
|  | mod_base = um | |
| modified_base | 8 | |
|  | mod_base = cm | |
| modified_base | 9 | |
|  | mod_base = OTHER | |
|  | note = 2'-fluoroadenosine | |
| modified_base | 10 | |
|  | mod_base = OTHER | |
|  | note = 2'-fluoroguanosine | |
| modified_base | 11 | |
|  | mod_base = OTHER | |
|  | note = 2'-fluoroadenosine | |
| modified_base | 12 | |
|  | mod_base = um | |
| modified_base | 13 | |
|  | mod_base = cm | |
| modified_base | 14 | |
|  | mod_base = um | |
| modified_base | 15 | |
|  | mod_base = gm | |
| modified_base | 16 | |
|  | mod_base = gm | |
| modified_base | 17 | |
|  | mod_base = um | |
| modified_base | 18 | |
|  | mod_base = um | |
| modified_base | 19 | |
|  | mod_base = um | |
| modified_base | 20 | |
|  | mod_base = cm | |
| modified_base | 21 | |
|  | mod_base = OTHER | |
|  | note = 2'-O-methyladenosine | |
| source | 1..21 | |
|  | mol_type = other RNA | |
|  | organism = synthetic construct | |
| SEQUENCE: 117 | | |
| caggattcag atctggtttc a | | 21 |
| | | |
| SEQ ID NO: 118 | moltype = RNA   length = 21 | |
| FEATURE | Location/Qualifiers | |
| modified_base | 1 | |
|  | mod_base = OTHER | |
|  | note = 2'-O-methyladenosine | |
| modified_base | 2 | |
|  | mod_base = gm | |
| modified_base | 3 | |
|  | mod_base = gm | |
| modified_base | 4 | |
|  | mod_base = OTHER | |
|  | note = 2'-O-methyladenosine | |
| modified_base | 5 | |
|  | mod_base = um | |
| modified_base | 6 | |

```
                            mod_base = um
modified_base    7
                            mod_base = cm
modified_base    8
                            mod_base = OTHER
                            note = 2'-O-methyladenosine
modified_base    9
                            mod_base = OTHER
                            note = 2'-fluoroguanosine
modified_base    10
                            mod_base = OTHER
                            note = 2'-fluoroadenosine
modified_base    11
                            mod_base = OTHER
                            note = 2'-fluorouridine
modified_base    12
                            mod_base = cm
modified_base    13
                            mod_base = um
modified_base    14
                            mod_base = gm
modified_base    15
                            mod_base = gm
modified_base    16
                            mod_base = um
modified_base    17
                            mod_base = um
modified_base    18
                            mod_base = um
modified_base    19
                            mod_base = cm
modified_base    20
                            mod_base = OTHER
                            note = 2'-O-methyladenosine
modified_base    21
                            mod_base = OTHER
                            note = 2'-O-methyladenosine
source           1..21
                            mol_type = other RNA
                            organism = synthetic construct
SEQUENCE: 118
aggattcaga tctggtttca a                                              21

SEQ ID NO: 119           moltype = RNA   length = 21
FEATURE                  Location/Qualifiers
modified_base    1
                            mod_base = cm
modified_base    2
                            mod_base = um
modified_base    3
                            mod_base = gm
modified_base    4
                            mod_base = um
modified_base    5
                            mod_base = um
modified_base    6
                            mod_base = cm
modified_base    7
                            mod_base = um
modified_base    8
                            mod_base = um
modified_base    9
                            mod_base = OTHER
                            note = 2'-fluorocytidine
modified_base    10
                            mod_base = OTHER
                            note = 2'-fluorocytidine
modified_base    11
                            mod_base = OTHER
                            note = 2'-fluoroguanosine
modified_base    12
                            mod_base = um
modified_base    13
                            mod_base = gm
modified_base    14
                            mod_base = OTHER
                            note = 2'-O-methyladenosine
modified_base    15
                            mod_base = OTHER
```

```
                    note = 2'-O-methyladenosine
modified_base       16
                    mod_base = OTHER
                    note = 2'-O-methyladenosine
modified_base       17
                    mod_base = um
modified_base       18
                    mod_base = um
modified_base       19
                    mod_base = cm
modified_base       20
                    mod_base = um
modified_base       21
                    mod_base = OTHER
                    note = 2'-O-methyladenosine
source              1..21
                    mol_type = other RNA
                    organism = synthetic construct
SEQUENCE: 119
ctgttcttcc gtgaaattct a                                        21

SEQ ID NO: 120      moltype = RNA  length = 21
FEATURE             Location/Qualifiers
modified_base       1
                    mod_base = um
modified_base       2
                    mod_base = cm
modified_base       3
                    mod_base = cm
modified_base       4
                    mod_base = um
modified_base       5
                    mod_base = gm
modified_base       6
                    mod_base = gm
modified_base       7
                    mod_base = OTHER
                    note = 2'-O-methyladenosine
modified_base       8
                    mod_base = um
modified_base       9
                    mod_base = OTHER
                    note = 2'-fluoroguanosine
modified_base       10
                    mod_base = OTHER
                    note = 2'-fluoroadenosine
modified_base       11
                    mod_base = OTHER
                    note = 2'-fluorouridine
modified_base       12
                    mod_base = um
modified_base       13
                    mod_base = OTHER
                    note = 2'-O-methyladenosine
modified_base       14
                    mod_base = gm
modified_base       15
                    mod_base = um
modified_base       16
                    mod_base = um
modified_base       17
                    mod_base = cm
modified_base       18
                    mod_base = OTHER
                    note = 2'-O-methyladenosine
modified_base       19
                    mod_base = gm
modified_base       20
                    mod_base = OTHER
                    note = 2'-O-methyladenosine
modified_base       21
                    mod_base = OTHER
                    note = 2'-O-methyladenosine
source              1..21
                    mol_type = other RNA
                    organism = synthetic construct
SEQUENCE: 120
tcctggatga ttagttcaga a                                        21
```

| | | |
|---|---|---|
| SEQ ID NO: 121 | moltype = RNA length = 21 | |
| FEATURE | Location/Qualifiers | |
| modified_base | 1 | |
| | mod_base = gm | |
| modified_base | 2 | |
| | mod_base = cm | |
| modified_base | 3 | |
| | mod_base = cm | |
| modified_base | 4 | |
| | mod_base = cm | |
| modified_base | 5 | |
| | mod_base = um | |
| modified_base | 6 | |
| | mod_base = um | |
| modified_base | 7 | |
| | mod_base = gm | |
| modified_base | 8 | |
| | mod_base = um | |
| modified_base | 9 | |
| | mod_base = OTHER | |
| | note = 2'-fluorouridine | |
| modified_base | 10 | |
| | mod_base = OTHER | |
| | note = 2'-fluorocytidine | |
| modified_base | 11 | |
| | mod_base = OTHER | |
| | note = 2'-fluorouridine | |
| modified_base | 12 | |
| | mod_base = um | |
| modified_base | 13 | |
| | mod_base = cm | |
| modified_base | 14 | |
| | mod_base = cm | |
| modified_base | 15 | |
| | mod_base = gm | |
| modified_base | 16 | |
| | mod_base = um | |
| modified_base | 17 | |
| | mod_base = gm | |
| modified_base | 18 | |
| | mod_base = OTHER | |
| | note = 2'-O-methyladenosine | |
| modified_base | 19 | |
| | mod_base = OTHER | |
| | note = 2'-O-methyladenosine | |
| modified_base | 20 | |
| | mod_base = OTHER | |
| | note = 2'-O-methyladenosine | |
| modified_base | 21 | |
| | mod_base = um | |
| source | 1..21 | |
| | mol_type = other RNA | |
| | organism = synthetic construct | |
| SEQUENCE: 121 | | |
| gcccttgttc ttccgtgaaa t | | 21 |
| | | |
| SEQ ID NO: 122 | moltype = RNA length = 21 | |
| FEATURE | Location/Qualifiers | |
| modified_base | 1 | |
| | mod_base = OTHER | |
| | note = 2-aminoadenine | |
| modified_base | 2 | |
| | mod_base = OTHER | |
| | note = 2'-O-methyladenosine | |
| modified_base | 3 | |
| | mod_base = OTHER | |
| | note = 2'-O-methyladenosine | |
| modified_base | 4 | |
| | mod_base = cm | |
| modified_base | 5 | |
| | mod_base = cm | |
| modified_base | 6 | |
| | mod_base = um | |
| modified_base | 7 | |
| | mod_base = gm | |
| modified_base | 8 | |
| | mod_base = gm | |
| modified_base | 9 | |
| | mod_base = OTHER | |

```
                        note = 2'-fluoroadenosine
modified_base           10
                        mod_base = OTHER
                        note = 2'-fluorouridine
modified_base           11
                        mod_base = OTHER
                        note = 2'-fluorouridine
modified_base           12
                        mod_base = OTHER
                        note = 2'-O-methyladenosine
modified_base           13
                        mod_base = gm
modified_base           14
                        mod_base = OTHER
                        note = 2'-O-methyladenosine
modified_base           15
                        mod_base = gm
modified_base           16
                        mod_base = um
modified_base           17
                        mod_base = um
modified_base           18
                        mod_base = OTHER
                        note = 2'-O-methyladenosine
modified_base           19
                        mod_base = cm
modified_base           20
                        mod_base = OTHER
                        note = 2'-O-methyladenosine
modified_base           21
                        mod_base = um
source                  1..21
                        mol_type = other RNA
                        organism = synthetic construct
SEQUENCE: 122
aaacctggat tagagttaca t                                          21

SEQ ID NO: 123          moltype = RNA  length = 21
FEATURE                 Location/Qualifiers
modified_base           1
                        mod_base = gm
modified_base           2
                        mod_base = gm
modified_base           3
                        mod_base = OTHER
                        note = 2'-O-methyladenosine
modified_base           4
                        mod_base = um
modified_base           5
                        mod_base = gm
modified_base           6
                        mod_base = OTHER
                        note = 2'-O-methyladenosine
modified_base           7
                        mod_base = um
modified_base           8
                        mod_base = um
modified_base           9
                        mod_base = OTHER
                        note = 2'-fluoroadenosine
modified_base           10
                        mod_base = OTHER
                        note = 2'-fluoroguanosine
modified_base           11
                        mod_base = OTHER
                        note = 2'-fluorouridine
modified_base           12
                        mod_base = um
modified_base           13
                        mod_base = cm
modified_base           14
                        mod_base = OTHER
                        note = 2'-O-methyladenosine
modified_base           15
                        mod_base = gm
modified_base           16
                        mod_base = OTHER
                        note = 2'-O-methyladenosine
modified_base           17
```

```
                        mod_base = gm
modified_base           18
                        mod_base = OTHER
                        note = 2'-O-methyladenosine
modified_base           19
                        mod_base = um
modified_base           20
                        mod_base = OTHER
                        note = 2'-O-methyladenosine
modified_base           21
                        mod_base = um
source                  1..21
                        mol_type = other RNA
                        organism = synthetic construct
SEQUENCE: 123
ggatgattag ttcagagata t                                              21

SEQ ID NO: 124          moltype = RNA   length = 21
FEATURE                 Location/Qualifiers
modified_base           1
                        mod_base = gm
modified_base           2
                        mod_base = um
modified_base           3
                        mod_base = gm
modified_base           4
                        mod_base = um
modified_base           5
                        mod_base = um
modified_base           6
                        mod_base = cm
modified_base           7
                        mod_base = um
modified_base           8
                        mod_base = um
modified_base           9
                        mod_base = OTHER
                        note = 2'-fluorocytidine
modified_base           10
                        mod_base = OTHER
                        note = 2'-fluorocytidine
modified_base           11
                        mod_base = OTHER
                        note = 2'-fluoroguanosine
modified_base           12
                        mod_base = um
modified_base           13
                        mod_base = gm
modified_base           14
                        mod_base = OTHER
                        note = 2'-O-methyladenosine
modified_base           15
                        mod_base = OTHER
                        note = 2'-O-methyladenosine
modified_base           16
                        mod_base = OTHER
                        note = 2'-O-methyladenosine
modified_base           17
                        mod_base = um
modified_base           18
                        mod_base = um
modified_base           19
                        mod_base = cm
modified_base           20
                        mod_base = um
modified_base           21
                        mod_base = OTHER
                        note = 2'-O-methyladenosine
source                  1..21
                        mol_type = other RNA
                        organism = synthetic construct
SEQUENCE: 124
gtgttcttcc gtgaaattct a                                              21

SEQ ID NO: 125          moltype = RNA   length = 21
FEATURE                 Location/Qualifiers
modified_base           1
                        mod_base = gm
modified_base           2
```

```
                                mod_base = um
modified_base                   3
                                mod_base = gm
modified_base                   4
                                mod_base = um
modified_base                   5
                                mod_base = um
modified_base                   6
                                mod_base = cm
modified_base                   7
                                mod_base = OTHER
                                note = 2'-fluorouridine
modified_base                   8
                                mod_base = um
modified_base                   9
                                mod_base = OTHER
                                note = 2'-fluorocytidine
modified_base                   10
                                mod_base = cm
modified_base                   11
                                mod_base = OTHER
                                note = 2'-fluoroguanosine
modified_base                   12
                                mod_base = um
modified_base                   13
                                mod_base = gm
modified_base                   14
                                mod_base = OTHER
                                note = 2'-O-methyladenosine
modified_base                   15
                                mod_base = OTHER
                                note = 2'-O-methyladenosine
modified_base                   16
                                mod_base = OTHER
                                note = 2'-O-methyladenosine
modified_base                   17
                                mod_base = um
modified_base                   18
                                mod_base = um
modified_base                   19
                                mod_base = cm
modified_base                   20
                                mod_base = um
modified_base                   21
                                mod_base = OTHER
                                note = 2'-O-methyladenosine
source                          1..21
                                mol_type = other RNA
                                organism = synthetic construct
SEQUENCE: 125
gtgttcttcc gtgaaattct a                                                     21

SEQ ID NO: 126           moltype = RNA   length = 21
FEATURE                  Location/Qualifiers
modified_base                   1
                                mod_base = gm
modified_base                   2
                                mod_base = gm
modified_base                   3
                                mod_base = gm
modified_base                   4
                                mod_base = OTHER
                                note = 2'-O-methyladenosine
modified_base                   5
                                mod_base = um
modified_base                   6
                                mod_base = um
modified_base                   7
                                mod_base = cm
modified_base                   8
                                mod_base = OTHER
                                note = 2'-O-methyladenosine
modified_base                   9
                                mod_base = OTHER
                                note = 2'-fluoroguanosine
modified_base                   10
                                mod_base = OTHER
                                note = 2'-fluoroadenosine
modified_base                   11
```

```
                        mod_base = OTHER
                        note = 2'-fluorouridine
modified_base           12
                        mod_base = cm
modified_base           13
                        mod_base = um
modified_base           14
                        mod_base = gm
modified_base           15
                        mod_base = gm
modified_base           16
                        mod_base = um
modified_base           17
                        mod_base = um
modified_base           18
                        mod_base = um
modified_base           19
                        mod_base = cm
modified_base           20
                        mod_base = OTHER
                        note = 2'-O-methyladenosine
modified_base           21
                        mod_base = OTHER
                        note = 2'-O-methyladenosine
source                  1..21
                        mol_type = other RNA
                        organism = synthetic construct
SEQUENCE: 126
gggattcaga tctggtttca a                                              21

SEQ ID NO: 127          moltype = RNA   length = 21
FEATURE                 Location/Qualifiers
modified_base           1
                        mod_base = OTHER
                        note = 2-aminoadenine
modified_base           2
                        mod_base = gm
modified_base           3
                        mod_base = gm
modified_base           4
                        mod_base = OTHER
                        note = 2'-O-methyladenosine
modified_base           5
                        mod_base = um
modified_base           6
                        mod_base = um
modified_base           7
                        mod_base = cm
modified_base           8
                        mod_base = OTHER
                        note = 2'-O-methyladenosine
modified_base           9
                        mod_base = OTHER
                        note = 2'-fluoroguanosine
modified_base           10
                        mod_base = OTHER
                        note = 2'-fluoroadenosine
modified_base           11
                        mod_base = OTHER
                        note = 2'-fluorouridine
modified_base           12
                        mod_base = cm
modified_base           13
                        mod_base = um
modified_base           14
                        mod_base = gm
modified_base           15
                        mod_base = gm
modified_base           16
                        mod_base = um
modified_base           17
                        mod_base = um
modified_base           18
                        mod_base = um
modified_base           19
                        mod_base = cm
modified_base           20
                        mod_base = OTHER
                        note = 2'-O-methyladenosine
```

```
modified_base              21
                           mod_base = OTHER
                           note = 2'-O-methyladenosine
source                     1..21
                           mol_type = other RNA
                           organism = synthetic construct
SEQUENCE: 127
aggattcaga tctggtttca a                                              21

SEQ ID NO: 128             moltype = RNA  length = 21
FEATURE                    Location/Qualifiers
modified_base              1
                           mod_base = gm
modified_base              2
                           mod_base = gm
modified_base              3
                           mod_base = gm
modified_base              4
                           mod_base = OTHER
                           note = 2'-O-methyladenosine
modified_base              5
                           mod_base = um
modified_base              6
                           mod_base = um
modified_base              7
                           mod_base = cm
modified_base              8
                           mod_base = OTHER
                           note = 2'-O-methyladenosine
modified_base              9
                           mod_base = OTHER
                           note = 2'-fluoroguanosine
modified_base              10
                           mod_base = OTHER
                           note = 2'-O-methyladenosine
modified_base              11
                           mod_base = OTHER
                           note = 2'-fluorouridine
modified_base              12
                           mod_base = cm
modified_base              13
                           mod_base = um
modified_base              14
                           mod_base = gm
modified_base              15
                           mod_base = gm
modified_base              16
                           mod_base = um
modified_base              17
                           mod_base = um
modified_base              18
                           mod_base = um
modified_base              19
                           mod_base = cm
modified_base              20
                           mod_base = OTHER
                           note = 2'-O-methyladenosine
modified_base              21
                           mod_base = OTHER
                           note = 2'-O-methyladenosine
source                     1..21
                           mol_type = other RNA
                           organism = synthetic construct
SEQUENCE: 128
gggattcaga tctggtttca a                                              21

SEQ ID NO: 129             moltype = RNA  length = 21
FEATURE                    Location/Qualifiers
modified_base              1
                           mod_base = gm
modified_base              2
                           mod_base = gm
modified_base              3
                           mod_base = gm
modified_base              4
                           mod_base = OTHER
                           note = 2'-O-methyladenosine
modified_base              5
                           mod_base = um
```

```
modified_base           6
                        mod_base = um
modified_base           7
                        mod_base = cm
modified_base           8
                        mod_base = OTHER
                        note = 2'-O-methyladenosine
modified_base           9
                        mod_base = OTHER
                        note = 2'-fluoroguanosine
modified_base           10
                        mod_base = OTHER
                        note = 2'-O-methyladenosine
modified_base           11
                        mod_base = OTHER
                        note = 2'-fluorouridine
modified_base           12
                        mod_base = OTHER
                        note = 2'-fluorocytidine
modified_base           13
                        mod_base = um
modified_base           14
                        mod_base = gm
modified_base           15
                        mod_base = gm
modified_base           16
                        mod_base = um
modified_base           17
                        mod_base = um
modified_base           18
                        mod_base = um
modified_base           19
                        mod_base = cm
modified_base           20
                        mod_base = OTHER
                        note = 2'-O-methyladenosine
modified_base           21
                        mod_base = OTHER
                        note = 2'-O-methyladenosine
source                  1..21
                        mol_type = other RNA
                        organism = synthetic construct
SEQUENCE: 129
gggattcaga tctggtttca a                                           21

SEQ ID NO: 130          moltype = RNA  length = 21
FEATURE                 Location/Qualifiers
modified_base           1
                        mod_base = cm
modified_base           2
                        mod_base = OTHER
                        note = 2'-O-methyladenosine
modified_base           3
                        mod_base = gm
modified_base           4
                        mod_base = gm
modified_base           5
                        mod_base = OTHER
                        note = 2'-O-methyladenosine
modified_base           6
                        mod_base = um
modified_base           7
                        mod_base = um
modified_base           8
                        mod_base = cm
modified_base           9
                        mod_base = OTHER
                        note = 2'-fluoroadenosine
modified_base           10
                        mod_base = OTHER
                        note = 2'-fluoroguanosine
modified_base           11
                        mod_base = OTHER
                        note = 2'-fluoroadenosine
modified_base           12
                        mod_base = um
modified_base           13
                        mod_base = cm
modified_base           14
```

```
                        mod_base = um
modified_base           15
                        mod_base = gm
modified_base           16
                        mod_base = OTHER
                        note = 2-O-methylinosine
modified_base           17
                        mod_base = um
modified_base           18
                        mod_base = um
modified_base           19
                        mod_base = um
modified_base           20
                        mod_base = cm
modified_base           21
                        mod_base = OTHER
                        note = 2'-O-methyladenosine
source                  1..21
                        mol_type = other RNA
                        organism = synthetic construct
SEQUENCE: 130
caggattcag atctgntttc a                                              21

SEQ ID NO: 131          moltype = RNA  length = 21
FEATURE                 Location/Qualifiers
modified_base           1
                        mod_base = cm
modified_base           2
                        mod_base = um
modified_base           3
                        mod_base = gm
modified_base           4
                        mod_base = um
modified_base           5
                        mod_base = um
modified_base           6
                        mod_base = cm
modified_base           7
                        mod_base = um
modified_base           8
                        mod_base = um
modified_base           9
                        mod_base = OTHER
                        note = 2'-fluorocytidine
modified_base           10
                        mod_base = cm
modified_base           11
                        mod_base = OTHER
                        note = 2'-fluoroguanosine
modified_base           12
                        mod_base = um
modified_base           13
                        mod_base = OTHER
                        note = 2'-fluoroguanosine
modified_base           14
                        mod_base = OTHER
                        note = 2'-O-methyladenosine
modified_base           15
                        mod_base = OTHER
                        note = 2'-O-methyladenosine
modified_base           16
                        mod_base = OTHER
                        note = 2'-O-methyladenosine
modified_base           17
                        mod_base = um
modified_base           18
                        mod_base = um
modified_base           19
                        mod_base = cm
modified_base           20
                        mod_base = um
modified_base           21
                        mod_base = OTHER
                        note = 2'-O-methyladenosine
source                  1..21
                        mol_type = other RNA
                        organism = synthetic construct
SEQUENCE: 131
ctgttcttcc gtgaaattct a                                              21
```

| | | |
|---|---|---|
| SEQ ID NO: 132 | moltype = RNA length = 21 | |
| FEATURE | Location/Qualifiers | |
| modified_base | 1 | |
| | mod_base = cm | |
| modified_base | 2 | |
| | mod_base = OTHER | |
| | note = 2'-O-methyladenosine | |
| modified_base | 3 | |
| | mod_base = gm | |
| modified_base | 4 | |
| | mod_base = gm | |
| modified_base | 5 | |
| | mod_base = OTHER | |
| | note = 2'-O-methyladenosine | |
| modified_base | 6 | |
| | mod_base = um | |
| modified_base | 7 | |
| | mod_base = um | |
| modified_base | 8 | |
| | mod_base = cm | |
| modified_base | 9 | |
| | mod_base = OTHER | |
| | note = 2'-fluoroadenosine | |
| modified_base | 10 | |
| | mod_base = OTHER | |
| | note = 2'-fluoroguanosine | |
| modified_base | 11 | |
| | mod_base = OTHER | |
| | note = 2'-fluoroadenosine | |
| modified_base | 12 | |
| | mod_base = um | |
| modified_base | 13 | |
| | mod_base = cm | |
| modified_base | 14 | |
| | mod_base = um | |
| modified_base | 15 | |
| | mod_base = gm | |
| modified_base | 16 | |
| | mod_base = gm | |
| modified_base | 17 | |
| | mod_base = um | |
| modified_base | 18 | |
| | mod_base = um | |
| modified_base | 19 | |
| | mod_base = um | |
| modified_base | 20 | |
| | mod_base = cm | |
| modified_base | 21 | |
| | mod_base = OTHER | |
| | note = 2'-O-methyladenosine | |
| source | 1..21 | |
| | mol_type = other RNA | |
| | organism = synthetic construct | |
| SEQUENCE: 132 | | |
| caggattcag atctggtttc a | | 21 |
| SEQ ID NO: 133 | moltype = RNA length = 21 | |
| FEATURE | Location/Qualifiers | |
| modified_base | 1 | |
| | mod_base = OTHER | |
| | note = 2'-O-methyladenosine | |
| modified_base | 2 | |
| | mod_base = gm | |
| modified_base | 3 | |
| | mod_base = gm | |
| modified_base | 4 | |
| | mod_base = OTHER | |
| | note = 2'-O-methyladenosine | |
| modified_base | 5 | |
| | mod_base = um | |
| modified_base | 6 | |
| | mod_base = um | |
| modified_base | 7 | |
| | mod_base = cm | |
| modified_base | 8 | |
| | mod_base = OTHER | |
| | note = 2'-O-methyladenosine | |
| modified_base | 9 | |

```
                       mod_base = OTHER
                       note = 2'-fluoroguanosine
modified_base          10
                       mod_base = OTHER
                       note = 2'-fluoroadenosine
modified_base          11
                       mod_base = OTHER
                       note = 2'-fluorouridine
modified_base          12
                       mod_base = cm
modified_base          13
                       mod_base = um
modified_base          14
                       mod_base = gm
modified_base          15
                       mod_base = gm
modified_base          16
                       mod_base = um
modified_base          17
                       mod_base = um
modified_base          18
                       mod_base = um
modified_base          19
                       mod_base = cm
modified_base          20
                       mod_base = OTHER
                       note = 2'-O-methyladenosine
modified_base          21
                       mod_base = OTHER
                       note = 2'-O-methyladenosine
source                 1..21
                       mol_type = other RNA
                       organism = synthetic construct
SEQUENCE: 133
aggattcaga tctggtttca a                                              21

SEQ ID NO: 134         moltype = RNA   length = 21
FEATURE                Location/Qualifiers
modified_base          1
                       mod_base = cm
modified_base          2
                       mod_base = um
modified_base          3
                       mod_base = gm
modified_base          4
                       mod_base = um
modified_base          5
                       mod_base = um
modified_base          6
                       mod_base = cm
modified_base          7
                       mod_base = um
modified_base          8
                       mod_base = um
modified_base          9
                       mod_base = OTHER
                       note = 2'-fluorocytidine
modified_base          10
                       mod_base = OTHER
                       note = 2'-fluorocytidine
modified_base          11
                       mod_base = OTHER
                       note = 2'-fluoroguanosine
modified_base          12
                       mod_base = um
modified_base          13
                       mod_base = gm
modified_base          14
                       mod_base = OTHER
                       note = 2'-O-methyladenosine
modified_base          15
                       mod_base = OTHER
                       note = 2'-O-methyladenosine
modified_base          16
                       mod_base = OTHER
                       note = 2'-O-methyladenosine
modified_base          17
                       mod_base = um
modified_base          18
```

```
                        mod_base = um
modified_base           19
                        mod_base = cm
modified_base           20
                        mod_base = um
modified_base           21
                        mod_base = OTHER
                        note = 2'-O-methyladenosine
source                  1..21
                        mol_type = other RNA
                        organism = synthetic construct
SEQUENCE: 134
ctgttcttcc gtgaaattct a                                            21

SEQ ID NO: 135          moltype = RNA  length = 21
FEATURE                 Location/Qualifiers
modified_base           1
                        mod_base = um
modified_base           2
                        mod_base = cm
modified_base           3
                        mod_base = cm
modified_base           4
                        mod_base = um
modified_base           5
                        mod_base = gm
modified_base           6
                        mod_base = gm
modified_base           7
                        mod_base = OTHER
                        note = 2'-O-methyladenosine
modified_base           8
                        mod_base = um
modified_base           9
                        mod_base = OTHER
                        note = 2'-fluoroguanosine
modified_base           10
                        mod_base = OTHER
                        note = 2'-fluoroadenosine
modified_base           11
                        mod_base = OTHER
                        note = 2'-fluorouridine
modified_base           12
                        mod_base = um
modified_base           13
                        mod_base = OTHER
                        note = 2'-O-methyladenosine
modified_base           14
                        mod_base = gm
modified_base           15
                        mod_base = um
modified_base           16
                        mod_base = um
modified_base           17
                        mod_base = cm
modified_base           18
                        mod_base = OTHER
                        note = 2'-O-methyladenosine
modified_base           19
                        mod_base = gm
modified_base           20
                        mod_base = OTHER
                        note = 2'-O-methyladenosine
modified_base           21
                        mod_base = OTHER
                        note = 2'-O-methyladenosine
source                  1..21
                        mol_type = other RNA
                        organism = synthetic construct
SEQUENCE: 135
tcctggatga ttagttcaga a                                            21

SEQ ID NO: 136          moltype = RNA  length = 21
FEATURE                 Location/Qualifiers
modified_base           1
                        mod_base = gm
modified_base           2
                        mod_base = cm
modified_base           3
```

```
                           mod_base = cm
modified_base              4
                           mod_base = cm
modified_base              5
                           mod_base = um
modified_base              6
                           mod_base = um
modified_base              7
                           mod_base = gm
modified_base              8
                           mod_base = um
modified_base              9
                           mod_base = OTHER
                           note = 2'-fluorouridine
modified_base              10
                           mod_base = OTHER
                           note = 2'-fluorocytidine
modified_base              11
                           mod_base = OTHER
                           note = 2'-fluorouridine
modified_base              12
                           mod_base = um
modified_base              13
                           mod_base = cm
modified_base              14
                           mod_base = cm
modified_base              15
                           mod_base = gm
modified_base              16
                           mod_base = um
modified_base              17
                           mod_base = gm
modified_base              18
                           mod_base = OTHER
                           note = 2'-O-methyladenosine
modified_base              19
                           mod_base = OTHER
                           note = 2'-O-methyladenosine
modified_base              20
                           mod_base = OTHER
                           note = 2'-O-methyladenosine
modified_base              21
                           mod_base = um
source                     1..21
                           mol_type = other RNA
                           organism = synthetic construct
SEQUENCE: 136
gcccttgttc ttccgtgaaa t                                                    21

SEQ ID NO: 137             moltype = RNA   length = 21
FEATURE                    Location/Qualifiers
modified_base              1
                           mod_base = OTHER
                           note = 2-aminoadenine
modified_base              2
                           mod_base = OTHER
                           note = 2'-O-methyladenosine
modified_base              3
                           mod_base = OTHER
                           note = 2'-O-methyladenosine
modified_base              4
                           mod_base = cm
modified_base              5
                           mod_base = cm
modified_base              6
                           mod_base = um
modified_base              7
                           mod_base = gm
modified_base              8
                           mod_base = gm
modified_base              9
                           mod_base = OTHER
                           note = 2'-fluoroadenosine
modified_base              10
                           mod_base = OTHER
                           note = 2'-fluorouridine
modified_base              11
                           mod_base = OTHER
                           note = 2'-fluorouridine
```

```
modified_base        12
                     mod_base = OTHER
                     note = 2'-O-methyladenosine
modified_base        13
                     mod_base = gm
modified_base        14
                     mod_base = OTHER
                     note = 2'-O-methyladenosine
modified_base        15
                     mod_base = gm
modified_base        16
                     mod_base = um
modified_base        17
                     mod_base = um
modified_base        18
                     mod_base = OTHER
                     note = 2'-O-methyladenosine
modified_base        19
                     mod_base = cm
modified_base        20
                     mod_base = OTHER
                     note = 2'-O-methyladenosine
modified_base        21
                     mod_base = um
source               1..21
                     mol_type = other RNA
                     organism = synthetic construct
SEQUENCE: 137
aaacctggat tagagttaca t                                              21

SEQ ID NO: 138       moltype = RNA  length = 21
FEATURE              Location/Qualifiers
modified_base        1
                     mod_base = gm
modified_base        2
                     mod_base = gm
modified_base        3
                     mod_base = OTHER
                     note = 2'-O-methyladenosine
modified_base        4
                     mod_base = um
modified_base        5
                     mod_base = gm
modified_base        6
                     mod_base = OTHER
                     note = 2'-O-methyladenosine
modified_base        7
                     mod_base = um
modified_base        8
                     mod_base = um
modified_base        9
                     mod_base = OTHER
                     note = 2'-fluoroadenosine
modified_base        10
                     mod_base = OTHER
                     note = 2'-fluoroguanosine
modified_base        11
                     mod_base = OTHER
                     note = 2'-fluorouridine
modified_base        12
                     mod_base = um
modified_base        13
                     mod_base = cm
modified_base        14
                     mod_base = OTHER
                     note = 2'-O-methyladenosine
modified_base        15
                     mod_base = gm
modified_base        16
                     mod_base = OTHER
                     note = 2'-O-methyladenosine
modified_base        17
                     mod_base = gm
modified_base        18
                     mod_base = OTHER
                     note = 2'-O-methyladenosine
modified_base        19
                     mod_base = um
modified_base        20
```

```
                              mod_base = OTHER
                              note = 2'-O-methyladenosine
modified_base             21
                              mod_base = um
source                    1..21
                              mol_type = other RNA
                              organism = synthetic construct
SEQUENCE: 138
ggatgattag ttcagagata t                                          21

SEQ ID NO: 139            moltype = RNA  length = 21
FEATURE                   Location/Qualifiers
modified_base             1
                              mod_base = gm
modified_base             2
                              mod_base = um
modified_base             3
                              mod_base = gm
modified_base             4
                              mod_base = um
modified_base             5
                              mod_base = um
modified_base             6
                              mod_base = cm
modified_base             7
                              mod_base = um
modified_base             8
                              mod_base = um
modified_base             9
                              mod_base = OTHER
                              note = 2'-fluorocytidine
modified_base             10
                              mod_base = OTHER
                              note = 2'-fluorocytidine
modified_base             11
                              mod_base = OTHER
                              note = 2'-fluoroguanosine
modified_base             12
                              mod_base = um
modified_base             13
                              mod_base = gm
modified_base             14
                              mod_base = OTHER
                              note = 2'-O-methyladenosine
modified_base             15
                              mod_base = OTHER
                              note = 2'-O-methyladenosine
modified_base             16
                              mod_base = OTHER
                              note = 2'-O-methyladenosine
modified_base             17
                              mod_base = um
modified_base             18
                              mod_base = um
modified_base             19
                              mod_base = cm
modified_base             20
                              mod_base = um
modified_base             21
                              mod_base = OTHER
                              note = 2'-O-methyladenosine
source                    1..21
                              mol_type = other RNA
                              organism = synthetic construct
SEQUENCE: 139
gtgttcttcc gtgaaattct a                                          21

SEQ ID NO: 140            moltype = RNA  length = 21
FEATURE                   Location/Qualifiers
modified_base             1
                              mod_base = gm
modified_base             2
                              mod_base = um
modified_base             3
                              mod_base = gm
modified_base             4
                              mod_base = um
modified_base             5
                              mod_base = um
```

```
modified_base         6
                      mod_base = cm
modified_base         7
                      mod_base = OTHER
                      note = 2'-fluorouridine
modified_base         8
                      mod_base = um
modified_base         9
                      mod_base = OTHER
                      note = 2'-fluorocytidine
modified_base         10
                      mod_base = cm
modified_base         11
                      mod_base = OTHER
                      note = 2'-fluoroguanosine
modified_base         12
                      mod_base = um
modified_base         13
                      mod_base = gm
modified_base         14
                      mod_base = OTHER
                      note = 2'-O-methyladenosine
modified_base         15
                      mod_base = OTHER
                      note = 2'-O-methyladenosine
modified_base         16
                      mod_base = OTHER
                      note = 2'-O-methyladenosine
modified_base         17
                      mod_base = um
modified_base         18
                      mod_base = um
modified_base         19
                      mod_base = cm
modified_base         20
                      mod_base = um
modified_base         21
                      mod_base = OTHER
                      note = 2'-O-methyladenosine
source                1..21
                      mol_type = other RNA
                      organism = synthetic construct
SEQUENCE: 140
gtgttcttcc gtgaaattct a                                         21

SEQ ID NO: 141        moltype = RNA  length = 21
FEATURE               Location/Qualifiers
modified_base         1
                      mod_base = gm
modified_base         2
                      mod_base = gm
modified_base         3
                      mod_base = gm
modified_base         4
                      mod_base = OTHER
                      note = 2'-O-methyladenosine
modified_base         5
                      mod_base = um
modified_base         6
                      mod_base = um
modified_base         7
                      mod_base = cm
modified_base         8
                      mod_base = OTHER
                      note = 2'-O-methyladenosine
modified_base         9
                      mod_base = OTHER
                      note = 2'-fluoroguanosine
modified_base         10
                      mod_base = OTHER
                      note = 2'-fluoroadenosine
modified_base         11
                      mod_base = OTHER
                      note = 2'-fluorouridine
modified_base         12
                      mod_base = cm
modified_base         13
                      mod_base = um
modified_base         14
```

```
                        mod_base = gm
modified_base           15
                        mod_base = gm
modified_base           16
                        mod_base = um
modified_base           17
                        mod_base = um
modified_base           18
                        mod_base = um
modified_base           19
                        mod_base = cm
modified_base           20
                        mod_base = OTHER
                        note = 2'-O-methyladenosine
modified_base           21
                        mod_base = OTHER
                        note = 2'-O-methyladenosine
source                  1..21
                        mol_type = other RNA
                        organism = synthetic construct
SEQUENCE: 141
gggattcaga tctggtttca a                                               21

SEQ ID NO: 142          moltype = RNA  length = 21
FEATURE                 Location/Qualifiers
modified_base           1
                        mod_base = OTHER
                        note = 2-aminoadenine
modified_base           2
                        mod_base = gm
modified_base           3
                        mod_base = gm
modified_base           4
                        mod_base = OTHER
                        note = 2'-O-methyladenosine
modified_base           5
                        mod_base = um
modified_base           6
                        mod_base = um
modified_base           7
                        mod_base = cm
modified_base           8
                        mod_base = OTHER
                        note = 2'-O-methyladenosine
modified_base           9
                        mod_base = OTHER
                        note = 2'-fluoroguanosine
modified_base           10
                        mod_base = OTHER
                        note = 2'-fluoroadenosine
modified_base           11
                        mod_base = OTHER
                        note = 2'-fluorouridine
modified_base           12
                        mod_base = cm
modified_base           13
                        mod_base = um
modified_base           14
                        mod_base = gm
modified_base           15
                        mod_base = gm
modified_base           16
                        mod_base = um
modified_base           17
                        mod_base = um
modified_base           18
                        mod_base = um
modified_base           19
                        mod_base = cm
modified_base           20
                        mod_base = OTHER
                        note = 2'-O-methyladenosine
modified_base           21
                        mod_base = OTHER
                        note = 2'-O-methyladenosine
source                  1..21
                        mol_type = other RNA
                        organism = synthetic construct
SEQUENCE: 142
```
aggattcaga tctggtttca a                                              21

SEQ ID NO: 143          moltype = RNA   length = 21
FEATURE                 Location/Qualifiers
modified_base           1
                        mod_base = gm
modified_base           2
                        mod_base = gm
modified_base           3
                        mod_base = gm
modified_base           4
                        mod_base = OTHER
                        note = 2'-O-methyladenosine
modified_base           5
                        mod_base = um
modified_base           6
                        mod_base = um
modified_base           7
                        mod_base = cm
modified_base           8
                        mod_base = OTHER
                        note = 2'-O-methyladenosine
modified_base           9
                        mod_base = OTHER
                        note = 2'-fluoroguanosine
modified_base           10
                        mod_base = OTHER
                        note = 2'-O-methyladenosine
modified_base           11
                        mod_base = OTHER
                        note = 2'-fluorouridine
modified_base           12
                        mod_base = cm
modified_base           13
                        mod_base = um
modified_base           14
                        mod_base = gm
modified_base           15
                        mod_base = gm
modified_base           16
                        mod_base = um
modified_base           17
                        mod_base = um
modified_base           18
                        mod_base = um
modified_base           19
                        mod_base = cm
modified_base           20
                        mod_base = OTHER
                        note = 2'-O-methyladenosine
modified_base           21
                        mod_base = OTHER
                        note = 2'-O-methyladenosine
source                  1..21
                        mol_type = other RNA
                        organism = synthetic construct
SEQUENCE: 143
gggattcaga tctggtttca a                                              21

SEQ ID NO: 144          moltype = RNA   length = 21
FEATURE                 Location/Qualifiers
modified_base           1
                        mod_base = gm
modified_base           2
                        mod_base = gm
modified_base           3
                        mod_base = gm
modified_base           4
                        mod_base = OTHER
                        note = 2'-O-methyladenosine
modified_base           5
                        mod_base = um
modified_base           6
                        mod_base = um
modified_base           7
                        mod_base = cm
modified_base           8
                        mod_base = OTHER
                        note = 2'-O-methyladenosine

```
modified_base      9
                   mod_base = OTHER
                   note = 2'-fluoroguanosine
modified_base      10
                   mod_base = OTHER
                   note = 2'-O-methyladenosine
modified_base      11
                   mod_base = OTHER
                   note = 2'-fluorouridine
modified_base      12
                   mod_base = OTHER
                   note = 2'-fluorocytidine
modified_base      13
                   mod_base = um
modified_base      14
                   mod_base = gm
modified_base      15
                   mod_base = gm
modified_base      16
                   mod_base = um
modified_base      17
                   mod_base = um
modified_base      18
                   mod_base = um
modified_base      19
                   mod_base = cm
modified_base      20
                   mod_base = OTHER
                   note = 2'-O-methyladenosine
modified_base      21
                   mod_base = OTHER
                   note = 2'-O-methyladenosine
source             1..21
                   mol_type = other RNA
                   organism = synthetic construct
SEQUENCE: 144
gggattcaga tctggtttca a                                          21

SEQ ID NO: 145     moltype = RNA   length = 21
FEATURE            Location/Qualifiers
modified_base      1
                   mod_base = cm
modified_base      2
                   mod_base = OTHER
                   note = 2'-O-methyladenosine
modified_base      3
                   mod_base = gm
modified_base      4
                   mod_base = gm
modified_base      5
                   mod_base = OTHER
                   note = 2'-O-methyladenosine
modified_base      6
                   mod_base = um
modified_base      7
                   mod_base = um
modified_base      8
                   mod_base = cm
modified_base      9
                   mod_base = OTHER
                   note = 2'-fluoroadenosine
modified_base      10
                   mod_base = OTHER
                   note = 2'-fluoroguanosine
modified_base      11
                   mod_base = OTHER
                   note = 2'-fluoroadenosine
modified_base      12
                   mod_base = um
modified_base      13
                   mod_base = cm
modified_base      14
                   mod_base = um
modified_base      15
                   mod_base = gm
modified_base      16
                   mod_base = OTHER
                   note = 2 -O-methylinosine
modified_base      17
```

|                | mod_base = um |
|---|---|
| modified_base | 18 |
|                | mod_base = um |
| modified_base | 19 |
|                | mod_base = um |
| modified_base | 20 |
|                | mod_base = cm |
| modified_base | 21 |
|                | mod_base = OTHER |
|                | note = 2'-O-methyladenosine |
| source | 1..21 |
|                | mol_type = other RNA |
|                | organism = synthetic construct |
| SEQUENCE: 145 | | caggattcag atctgntttc a                                   21

| SEQ ID NO: 146 | moltype = RNA   length = 21 |
|---|---|
| FEATURE | Location/Qualifiers |
| modified_base | 1 |
|                | mod_base = cm |
| modified_base | 2 |
|                | mod_base = um |
| modified_base | 3 |
|                | mod_base = gm |
| modified_base | 4 |
|                | mod_base = um |
| modified_base | 5 |
|                | mod_base = um |
| modified_base | 6 |
|                | mod_base = cm |
| modified_base | 7 |
|                | mod_base = um |
| modified_base | 8 |
|                | mod_base = um |
| modified_base | 9 |
|                | mod_base = OTHER |
|                | note = 2'-fluorocytidine |
| modified_base | 10 |
|                | mod_base = cm |
| modified_base | 11 |
|                | mod_base = OTHER |
|                | note = 2'-fluoroguanosine |
| modified_base | 12 |
|                | mod_base = um |
| modified_base | 13 |
|                | mod_base = OTHER |
|                | note = 2'-fluoroguanosine |
| modified_base | 14 |
|                | mod_base = OTHER |
|                | note = 2'-O-methyladenosine |
| modified_base | 15 |
|                | mod_base = OTHER |
|                | note = 2'-O-methyladenosine |
| modified_base | 16 |
|                | mod_base = OTHER |
|                | note = 2'-O-methyladenosine |
| modified_base | 17 |
|                | mod_base = um |
| modified_base | 18 |
|                | mod_base = um |
| modified_base | 19 |
|                | mod_base = cm |
| modified_base | 20 |
|                | mod_base = um |
| modified_base | 21 |
|                | mod_base = OTHER |
|                | note = 2'-O-methyladenosine |
| source | 1..21 |
|                | mol_type = other RNA |
|                | organism = synthetic construct |
| SEQUENCE: 146 | | ctgttcttcc gtgaaattct a                                   21

| SEQ ID NO: 147 | moltype = RNA   length = 21 |
|---|---|
| FEATURE | Location/Qualifiers |
| modified_base | 1 |
|                | mod_base = cm |
| modified_base | 2 |
|                | mod_base = OTHER |

|                | | |
|---|---|---|
| | | note = 2'-O-methyladenosine |
| modified_base | 3 | |
| | | mod_base = gm |
| modified_base | 4 | |
| | | mod_base = gm |
| modified_base | 5 | |
| | | mod_base = OTHER |
| | | note = 2'-O-methyladenosine |
| modified_base | 6 | |
| | | mod_base = um |
| modified_base | 7 | |
| | | mod_base = um |
| modified_base | 8 | |
| | | mod_base = cm |
| modified_base | 9 | |
| | | mod_base = OTHER |
| | | note = 2'-fluoroadenosine |
| modified_base | 10 | |
| | | mod_base = OTHER |
| | | note = 2'-fluoroguanosine |
| modified_base | 11 | |
| | | mod_base = OTHER |
| | | note = 2'-fluoroadenosine |
| modified_base | 12 | |
| | | mod_base = um |
| modified_base | 13 | |
| | | mod_base = cm |
| modified_base | 14 | |
| | | mod_base = um |
| modified_base | 15 | |
| | | mod_base = gm |
| modified_base | 16 | |
| | | mod_base = gm |
| modified_base | 17 | |
| | | mod_base = um |
| modified_base | 18 | |
| | | mod_base = um |
| modified_base | 19 | |
| | | mod_base = um |
| modified_base | 20 | |
| | | mod_base = cm |
| modified_base | 21 | |
| | | mod_base = OTHER |
| | | note = 2'-O-methyladenosine |
| source | 1..21 | |
| | | mol_type = other RNA |
| | | organism = synthetic construct |
| SEQUENCE: 147 | | |
| caggattcag atctggtttc a | | 21 |
| SEQ ID NO: 148 | moltype = RNA length = 21 | |
| FEATURE | Location/Qualifiers | |
| modified_base | 1 | |
| | | mod_base = OTHER |
| | | note = 2'-O-methyladenosine |
| modified_base | 2 | |
| | | mod_base = gm |
| modified_base | 3 | |
| | | mod_base = gm |
| modified_base | 4 | |
| | | mod_base = OTHER |
| | | note = 2'-O-methyladenosine |
| modified_base | 5 | |
| | | mod_base = um |
| modified_base | 6 | |
| | | mod_base = um |
| modified_base | 7 | |
| | | mod_base = cm |
| modified_base | 8 | |
| | | mod_base = OTHER |
| | | note = 2'-O-methyladenosine |
| modified_base | 9 | |
| | | mod_base = OTHER |
| | | note = 2'-fluoroguanosine |
| modified_base | 10 | |
| | | mod_base = OTHER |
| | | note = 2'-fluoroadenosine |
| modified_base | 11 | |
| | | mod_base = OTHER |

|  |  |
|---|---|
|  | note = 2'-fluorouridine |
| modified_base | 12 |
|  | mod_base = cm |
| modified_base | 13 |
|  | mod_base = um |
| modified_base | 14 |
|  | mod_base = gm |
| modified_base | 15 |
|  | mod_base = gm |
| modified_base | 16 |
|  | mod_base = um |
| modified_base | 17 |
|  | mod_base = um |
| modified_base | 18 |
|  | mod_base = um |
| modified_base | 19 |
|  | mod_base = cm |
| modified_base | 20 |
|  | mod_base = OTHER |
|  | note = 2'-O-methyladenosine |
| modified_base | 21 |
|  | mod_base = OTHER |
|  | note = 2'-O-methyladenosine |
| source | 1..21 |
|  | mol_type = other RNA |
|  | organism = synthetic construct |
| SEQUENCE: 148 |  |
| aggattcaga tctggtttca a | 21 |
| SEQ ID NO: 149 | moltype = RNA  length = 21 |
| FEATURE | Location/Qualifiers |
| modified_base | 1 |
|  | mod_base = cm |
| modified_base | 2 |
|  | mod_base = um |
| modified_base | 3 |
|  | mod_base = gm |
| modified_base | 4 |
|  | mod_base = um |
| modified_base | 5 |
|  | mod_base = um |
| modified_base | 6 |
|  | mod_base = cm |
| modified_base | 7 |
|  | mod_base = um |
| modified_base | 8 |
|  | mod_base = um |
| modified_base | 9 |
|  | mod_base = OTHER |
|  | note = 2'-fluorocytidine |
| modified_base | 10 |
|  | mod_base = OTHER |
|  | note = 2'-fluorocytidine |
| modified_base | 11 |
|  | mod_base = OTHER |
|  | note = 2'-fluoroguanosine |
| modified_base | 12 |
|  | mod_base = um |
| modified_base | 13 |
|  | mod_base = gm |
| modified_base | 14 |
|  | mod_base = OTHER |
|  | note = 2'-O-methyladenosine |
| modified_base | 15 |
|  | mod_base = OTHER |
|  | note = 2'-O-methyladenosine |
| modified_base | 16 |
|  | mod_base = OTHER |
|  | note = 2'-O-methyladenosine |
| modified_base | 17 |
|  | mod_base = um |
| modified_base | 18 |
|  | mod_base = um |
| modified_base | 19 |
|  | mod_base = cm |
| modified_base | 20 |
|  | mod_base = um |
| modified_base | 21 |
|  | mod_base = OTHER |

```
                        note = 2'-O-methyladenosine
source                  1..21
                        mol_type = other RNA
                        organism = synthetic construct
SEQUENCE: 149
ctgttcttcc gtgaaattct a                                          21

SEQ ID NO: 150          moltype = RNA  length = 21
FEATURE                 Location/Qualifiers
modified_base           1
                        mod_base = um
modified_base           2
                        mod_base = cm
modified_base           3
                        mod_base = cm
modified_base           4
                        mod_base = um
modified_base           5
                        mod_base = gm
modified_base           6
                        mod_base = gm
modified_base           7
                        mod_base = OTHER
                        note = 2'-O-methyladenosine
modified_base           8
                        mod_base = um
modified_base           9
                        mod_base = OTHER
                        note = 2'-fluoroguanosine
modified_base           10
                        mod_base = OTHER
                        note = 2'-fluoroadenosine
modified_base           11
                        mod_base = OTHER
                        note = 2'-fluorouridine
modified_base           12
                        mod_base = um
modified_base           13
                        mod_base = OTHER
                        note = 2'-O-methyladenosine
modified_base           14
                        mod_base = gm
modified_base           15
                        mod_base = um
modified_base           16
                        mod_base = um
modified_base           17
                        mod_base = cm
modified_base           18
                        mod_base = OTHER
                        note = 2'-O-methyladenosine
modified_base           19
                        mod_base = gm
modified_base           20
                        mod_base = OTHER
                        note = 2'-O-methyladenosine
modified_base           21
                        mod_base = OTHER
                        note = 2'-O-methyladenosine
source                  1..21
                        mol_type = other RNA
                        organism = synthetic construct
SEQUENCE: 150
tcctggatga ttagttcaga a                                          21

SEQ ID NO: 151          moltype = RNA  length = 21
FEATURE                 Location/Qualifiers
modified_base           1
                        mod_base = gm
modified_base           2
                        mod_base = cm
modified_base           3
                        mod_base = cm
modified_base           4
                        mod_base = cm
modified_base           5
                        mod_base = um
modified_base           6
                        mod_base = um
```

```
modified_base    7
                 mod_base = gm
modified_base    8
                 mod_base = um
modified_base    9
                 mod_base = OTHER
                 note = 2'-fluorouridine
modified_base    10
                 mod_base = OTHER
                 note = 2'-fluorocytidine
modified_base    11
                 mod_base = OTHER
                 note = 2'-fluorouridine
modified_base    12
                 mod_base = um
modified_base    13
                 mod_base = cm
modified_base    14
                 mod_base = cm
modified_base    15
                 mod_base = gm
modified_base    16
                 mod_base = um
modified_base    17
                 mod_base = gm
modified_base    18
                 mod_base = OTHER
                 note = 2'-O-methyladenosine
modified_base    19
                 mod_base = OTHER
                 note = 2'-O-methyladenosine
modified_base    20
                 mod_base = OTHER
                 note = 2'-O-methyladenosine
modified_base    21
                 mod_base = um
source           1..21
                 mol_type = other RNA
                 organism = synthetic construct
SEQUENCE: 151
gcccttgttc ttccgtgaaa t                                            21

SEQ ID NO: 152   moltype = RNA   length = 21
FEATURE          Location/Qualifiers
modified_base    1
                 mod_base = OTHER
                 note = 2-aminoadenine
modified_base    2
                 mod_base = OTHER
                 note = 2'-O-methyladenosine
modified_base    3
                 mod_base = OTHER
                 note = 2'-O-methyladenosine
modified_base    4
                 mod_base = cm
modified_base    5
                 mod_base = cm
modified_base    6
                 mod_base = um
modified_base    7
                 mod_base = gm
modified_base    8
                 mod_base = gm
modified_base    9
                 mod_base = OTHER
                 note = 2'-fluoroadenosine
modified_base    10
                 mod_base = OTHER
                 note = 2'-fluorouridine
modified_base    11
                 mod_base = OTHER
                 note = 2'-fluorouridine
modified_base    12
                 mod_base = OTHER
                 note = 2'-O-methyladenosine
modified_base    13
                 mod_base = gm
modified_base    14
                 mod_base = OTHER
```

```
                        note = 2'-O-methyladenosine
modified_base           15
                        mod_base = gm
modified_base           16
                        mod_base = um
modified_base           17
                        mod_base = um
modified_base           18
                        mod_base = OTHER
                        note = 2'-O-methyladenosine
modified_base           19
                        mod_base = cm
modified_base           20
                        mod_base = OTHER
                        note = 2'-O-methyladenosine
modified_base           21
                        mod_base = um
source                  1..21
                        mol_type = other RNA
                        organism = synthetic construct
SEQUENCE: 152
aaacctggat tagagttaca t                                           21

SEQ ID NO: 153          moltype = RNA  length = 21
FEATURE                 Location/Qualifiers
modified_base           1
                        mod_base = gm
modified_base           2
                        mod_base = gm
modified_base           3
                        mod_base = OTHER
                        note = 2'-O-methyladenosine
modified_base           4
                        mod_base = um
modified_base           5
                        mod_base = gm
modified_base           6
                        mod_base = OTHER
                        note = 2'-O-methyladenosine
modified_base           7
                        mod_base = um
modified_base           8
                        mod_base = um
modified_base           9
                        mod_base = OTHER
                        note = 2'-fluoroadenosine
modified_base           10
                        mod_base = OTHER
                        note = 2'-fluoroguanosine
modified_base           11
                        mod_base = OTHER
                        note = 2'-fluorouridine
modified_base           12
                        mod_base = um
modified_base           13
                        mod_base = cm
modified_base           14
                        mod_base = OTHER
                        note = 2'-O-methyladenosine
modified_base           15
                        mod_base = gm
modified_base           16
                        mod_base = OTHER
                        note = 2'-O-methyladenosine
modified_base           17
                        mod_base = gm
modified_base           18
                        mod_base = OTHER
                        note = 2'-O-methyladenosine
modified_base           19
                        mod_base = um
modified_base           20
                        mod_base = OTHER
                        note = 2'-O-methyladenosine
modified_base           21
                        mod_base = um
source                  1..21
                        mol_type = other RNA
                        organism = synthetic construct
```

-continued

```
SEQUENCE: 153
ggatgattag ttcagagata t                                              21

SEQ ID NO: 154         moltype = RNA  length = 21
FEATURE                Location/Qualifiers
modified_base          1
                       mod_base = gm
modified_base          2
                       mod_base = um
modified_base          3
                       mod_base = gm
modified_base          4
                       mod_base = um
modified_base          5
                       mod_base = um
modified_base          6
                       mod_base = cm
modified_base          7
                       mod_base = um
modified_base          8
                       mod_base = um
modified_base          9
                       mod_base = OTHER
                       note = 2'-fluorocytidine
modified_base          10
                       mod_base = OTHER
                       note = 2'-fluorocytidine
modified_base          11
                       mod_base = OTHER
                       note = 2'-fluoroguanosine
modified_base          12
                       mod_base = um
modified_base          13
                       mod_base = gm
modified_base          14
                       mod_base = OTHER
                       note = 2'-O-methyladenosine
modified_base          15
                       mod_base = OTHER
                       note = 2'-O-methyladenosine
modified_base          16
                       mod_base = OTHER
                       note = 2'-O-methyladenosine
modified_base          17
                       mod_base = um
modified_base          18
                       mod_base = um
modified_base          19
                       mod_base = cm
modified_base          20
                       mod_base = um
modified_base          21
                       mod_base = OTHER
                       note = 2'-O-methyladenosine
source                 1..21
                       mol_type = other RNA
                       organism = synthetic construct
SEQUENCE: 154
gtgttcttcc gtgaaattct a                                              21

SEQ ID NO: 155         moltype = RNA  length = 21
FEATURE                Location/Qualifiers
modified_base          1
                       mod_base = gm
modified_base          2
                       mod_base = um
modified_base          3
                       mod_base = gm
modified_base          4
                       mod_base = um
modified_base          5
                       mod_base = um
modified_base          6
                       mod_base = cm
modified_base          7
                       mod_base = OTHER
                       note = 2'-fluorouridine
modified_base          8
                       mod_base = um
```

| | | |
|---|---|---|
| modified_base | 9 | |
| | mod_base = OTHER | |
| | note = 2'-fluorocytidine | |
| modified_base | 10 | |
| | mod_base = cm | |
| modified_base | 11 | |
| | mod_base = OTHER | |
| | note = 2'-fluoroguanosine | |
| modified_base | 12 | |
| | mod_base = um | |
| modified_base | 13 | |
| | mod_base = gm | |
| modified_base | 14 | |
| | mod_base = OTHER | |
| | note = 2'-O-methyladenosine | |
| modified_base | 15 | |
| | mod_base = OTHER | |
| | note = 2'-O-methyladenosine | |
| modified_base | 16 | |
| | mod_base = OTHER | |
| | note = 2'-O-methyladenosine | |
| modified_base | 17 | |
| | mod_base = um | |
| modified_base | 18 | |
| | mod_base = um | |
| modified_base | 19 | |
| | mod_base = cm | |
| modified_base | 20 | |
| | mod_base = um | |
| modified_base | 21 | |
| | mod_base = OTHER | |
| | note = 2'-O-methyladenosine | |
| source | 1..21 | |
| | mol_type = other RNA | |
| | organism = synthetic construct | |
| SEQUENCE: 155 | | |
| gtgttcttcc gtgaaattct a | | 21 |
| | | |
| SEQ ID NO: 156 | moltype = RNA  length = 21 | |
| FEATURE | Location/Qualifiers | |
| modified_base | 1 | |
| | mod_base = gm | |
| modified_base | 2 | |
| | mod_base = gm | |
| modified_base | 3 | |
| | mod_base = gm | |
| modified_base | 4 | |
| | mod_base = OTHER | |
| | note = 2'-O-methyladenosine | |
| modified_base | 5 | |
| | mod_base = um | |
| modified_base | 6 | |
| | mod_base = um | |
| modified_base | 7 | |
| | mod_base = cm | |
| modified_base | 8 | |
| | mod_base = OTHER | |
| | note = 2'-O-methyladenosine | |
| modified_base | 9 | |
| | mod_base = OTHER | |
| | note = 2'-fluoroguanosine | |
| modified_base | 10 | |
| | mod_base = OTHER | |
| | note = 2'-fluoroadenosine | |
| modified_base | 11 | |
| | mod_base = OTHER | |
| | note = 2'-fluorouridine | |
| modified_base | 12 | |
| | mod_base = cm | |
| modified_base | 13 | |
| | mod_base = um | |
| modified_base | 14 | |
| | mod_base = gm | |
| modified_base | 15 | |
| | mod_base = gm | |
| modified_base | 16 | |
| | mod_base = um | |
| modified_base | 17 | |
| | mod_base = um | |

```
modified_base          18
                       mod_base = um
modified_base          19
                       mod_base = cm
modified_base          20
                       mod_base = OTHER
                       note = 2'-O-methyladenosine
modified_base          21
                       mod_base = OTHER
                       note = 2'-O-methyladenosine
source                 1..21
                       mol_type = other RNA
                       organism = synthetic construct
SEQUENCE: 156
gggattcaga tctggtttca a                                              21

SEQ ID NO: 157         moltype = RNA  length = 21
FEATURE                Location/Qualifiers
modified_base          1
                       mod_base = OTHER
                       note = 2-aminoadenine
modified_base          2
                       mod_base = gm
modified_base          3
                       mod_base = gm
modified_base          4
                       mod_base = OTHER
                       note = 2'-O-methyladenosine
modified_base          5
                       mod_base = um
modified_base          6
                       mod_base = um
modified_base          7
                       mod_base = cm
modified_base          8
                       mod_base = OTHER
                       note = 2'-O-methyladenosine
modified_base          9
                       mod_base = OTHER
                       note = 2'-fluoroguanosine
modified_base          10
                       mod_base = OTHER
                       note = 2'-fluoroadenosine
modified_base          11
                       mod_base = OTHER
                       note = 2'-fluorouridine
modified_base          12
                       mod_base = cm
modified_base          13
                       mod_base = um
modified_base          14
                       mod_base = gm
modified_base          15
                       mod_base = gm
modified_base          16
                       mod_base = um
modified_base          17
                       mod_base = um
modified_base          18
                       mod_base = um
modified_base          19
                       mod_base = cm
modified_base          20
                       mod_base = OTHER
                       note = 2'-O-methyladenosine
modified_base          21
                       mod_base = OTHER
                       note = 2'-O-methyladenosine
source                 1..21
                       mol_type = other RNA
                       organism = synthetic construct
SEQUENCE: 157
aggattcaga tctggtttca a                                              21

SEQ ID NO: 158         moltype = RNA  length = 21
FEATURE                Location/Qualifiers
modified_base          1
                       mod_base = gm
modified_base          2
```

```
                        mod_base = gm
modified_base           3
                        mod_base = gm
modified_base           4
                        mod_base = OTHER
                        note = 2'-O-methyladenosine
modified_base           5
                        mod_base = um
modified_base           6
                        mod_base = um
modified_base           7
                        mod_base = cm
modified_base           8
                        mod_base = OTHER
                        note = 2'-O-methyladenosine
modified_base           9
                        mod_base = OTHER
                        note = 2'-fluoroguanosine
modified_base           10
                        mod_base = OTHER
                        note = 2'-O-methyladenosine
modified_base           11
                        mod_base = OTHER
                        note = 2'-fluorouridine
modified_base           12
                        mod_base = cm
modified_base           13
                        mod_base = um
modified_base           14
                        mod_base = gm
modified_base           15
                        mod_base = gm
modified_base           16
                        mod_base = um
modified_base           17
                        mod_base = um
modified_base           18
                        mod_base = um
modified_base           19
                        mod_base = cm
modified_base           20
                        mod_base = OTHER
                        note = 2'-O-methyladenosine
modified_base           21
                        mod_base = OTHER
                        note = 2'-O-methyladenosine
source                  1..21
                        mol_type = other RNA
                        organism = synthetic construct
SEQUENCE: 158
gggattcaga tctggtttca a                                                   21

SEQ ID NO: 159          moltype = RNA   length = 21
FEATURE                 Location/Qualifiers
modified_base           1
                        mod_base = gm
modified_base           2
                        mod_base = gm
modified_base           3
                        mod_base = gm
modified_base           4
                        mod_base = OTHER
                        note = 2'-O-methyladenosine
modified_base           5
                        mod_base = um
modified_base           6
                        mod_base = um
modified_base           7
                        mod_base = cm
modified_base           8
                        mod_base = OTHER
                        note = 2'-O-methyladenosine
modified_base           9
                        mod_base = OTHER
                        note = 2'-fluoroguanosine
modified_base           10
                        mod_base = OTHER
                        note = 2'-O-methyladenosine
modified_base           11
```

```
                        mod_base = OTHER
                        note = 2'-fluorouridine
modified_base           12
                        mod_base = OTHER
                        note = 2'-fluorocytidine
modified_base           13
                        mod_base = um
modified_base           14
                        mod_base = gm
modified_base           15
                        mod_base = gm
modified_base           16
                        mod_base = um
modified_base           17
                        mod_base = um
modified_base           18
                        mod_base = um
modified_base           19
                        mod_base = cm
modified_base           20
                        mod_base = OTHER
                        note = 2'-O-methyladenosine
modified_base           21
                        mod_base = OTHER
                        note = 2'-O-methyladenosine
source                  1..21
                        mol_type = other RNA
                        organism = synthetic construct
SEQUENCE: 159
gggattcaga tctggtttca a                                           21

SEQ ID NO: 160          moltype = RNA  length = 21
FEATURE                 Location/Qualifiers
modified_base           1
                        mod_base = cm
modified_base           2
                        mod_base = OTHER
                        note = 2'-O-methyladenosine
modified_base           3
                        mod_base = gm
modified_base           4
                        mod_base = gm
modified_base           5
                        mod_base = OTHER
                        note = 2'-O-methyladenosine
modified_base           6
                        mod_base = um
modified_base           7
                        mod_base = um
modified_base           8
                        mod_base = cm
modified_base           9
                        mod_base = OTHER
                        note = 2'-fluoroadenosine
modified_base           10
                        mod_base = OTHER
                        note = 2'-fluoroguanosine
modified_base           11
                        mod_base = OTHER
                        note = 2'-fluoroadenosine
modified_base           12
                        mod_base = um
modified_base           13
                        mod_base = cm
modified_base           14
                        mod_base = um
modified_base           15
                        mod_base = gm
modified_base           16
                        mod_base = OTHER
                        note = 2 -O-methylinosine
modified_base           17
                        mod_base = um
modified_base           18
                        mod_base = um
modified_base           19
                        mod_base = um
modified_base           20
                        mod_base = cm
```

```
modified_base        21
                     mod_base = OTHER
                     note = 2'-O-methyladenosine
source               1..21
                     mol_type = other RNA
                     organism = synthetic construct
SEQUENCE: 160
caggattcag atctgntttc a                                              21

SEQ ID NO: 161       moltype = RNA  length = 21
FEATURE              Location/Qualifiers
modified_base        1
                     mod_base = cm
modified_base        2
                     mod_base = um
modified_base        3
                     mod_base = gm
modified_base        4
                     mod_base = um
modified_base        5
                     mod_base = um
modified_base        6
                     mod_base = cm
modified_base        7
                     mod_base = um
modified_base        8
                     mod_base = um
modified_base        9
                     mod_base = OTHER
                     note = 2'-fluorocytidine
modified_base        10
                     mod_base = cm
modified_base        11
                     mod_base = OTHER
                     note = 2'-fluoroguanosine
modified_base        12
                     mod_base = um
modified_base        13
                     mod_base = OTHER
                     note = 2'-fluoroguanosine
modified_base        14
                     mod_base = OTHER
                     note = 2'-O-methyladenosine
modified_base        15
                     mod_base = OTHER
                     note = 2'-O-methyladenosine
modified_base        16
                     mod_base = OTHER
                     note = 2'-O-methyladenosine
modified_base        17
                     mod_base = um
modified_base        18
                     mod_base = um
modified_base        19
                     mod_base = cm
modified_base        20
                     mod_base = um
modified_base        21
                     mod_base = OTHER
                     note = 2'-O-methyladenosine
source               1..21
                     mol_type = other RNA
                     organism = synthetic construct
SEQUENCE: 161
ctgttcttcc gtgaaattct a                                              21

SEQ ID NO: 162       moltype = RNA  length = 21
FEATURE              Location/Qualifiers
source               1..21
                     mol_type = other RNA
                     organism = synthetic construct
SEQUENCE: 162
tgaaaccaga tctgaatcct g                                              21

SEQ ID NO: 163       moltype = RNA  length = 21
FEATURE              Location/Qualifiers
source               1..21
                     mol_type = other RNA
                     organism = synthetic construct
```

```
SEQUENCE: 163
ttgaaaccag atctgaatcc t                                                   21

SEQ ID NO: 164          moltype = RNA   length = 21
FEATURE                 Location/Qualifiers
source                  1..21
                        mol_type = other RNA
                        organism = synthetic construct
SEQUENCE: 164
tagaatttca cggaagaaca g                                                   21

SEQ ID NO: 165          moltype = RNA   length = 21
FEATURE                 Location/Qualifiers
source                  1..21
                        mol_type = other RNA
                        organism = synthetic construct
SEQUENCE: 165
ttctgaacta atcatccagg a                                                   21

SEQ ID NO: 166          moltype = RNA   length = 21
FEATURE                 Location/Qualifiers
source                  1..21
                        mol_type = other RNA
                        organism = synthetic construct
SEQUENCE: 166
atttcacgga agaacaaggg c                                                   21

SEQ ID NO: 167          moltype = RNA   length = 21
FEATURE                 Location/Qualifiers
source                  1..21
                        mol_type = other RNA
                        organism = synthetic construct
SEQUENCE: 167
atgtaactct aatccaggtt t                                                   21

SEQ ID NO: 168          moltype = RNA   length = 21
FEATURE                 Location/Qualifiers
source                  1..21
                        mol_type = other RNA
                        organism = synthetic construct
SEQUENCE: 168
atatctctga actaatcatc c                                                   21

SEQ ID NO: 169          moltype = RNA   length = 21
FEATURE                 Location/Qualifiers
source                  1..21
                        mol_type = other RNA
                        organism = synthetic construct
SEQUENCE: 169
ttgaaaccag atctgaatcc c                                                   21

SEQ ID NO: 170          moltype = RNA   length = 21
FEATURE                 Location/Qualifiers
source                  1..21
                        mol_type = other RNA
                        organism = synthetic construct
SEQUENCE: 170
tagaatttca cggaagaaca c                                                   21

SEQ ID NO: 171          moltype = DNA   length = 22
FEATURE                 Location/Qualifiers
source                  1..22
                        mol_type = other DNA
                        organism = synthetic construct
SEQUENCE: 171
caggattcag atctggtttc at                                                  22

SEQ ID NO: 172          moltype = DNA   length = 22
FEATURE                 Location/Qualifiers
source                  1..22
                        mol_type = other DNA
                        organism = synthetic construct
SEQUENCE: 172
aggattcaga tctggtttca at                                                  22

SEQ ID NO: 173          moltype = DNA   length = 22
FEATURE                 Location/Qualifiers
source                  1..22
                        mol_type = other DNA
```

```
                    organism = synthetic construct
SEQUENCE: 173
ctgttcttcc gtgaaattct at                                                  22

SEQ ID NO: 174          moltype = DNA   length = 22
FEATURE                 Location/Qualifiers
source                  1..22
                        mol_type = other DNA
                        organism = synthetic construct
SEQUENCE: 174
tcctggatga ttagttcaga at                                                  22

SEQ ID NO: 175          moltype = DNA   length = 22
FEATURE                 Location/Qualifiers
source                  1..22
                        mol_type = other DNA
                        organism = synthetic construct
SEQUENCE: 175
gcccttgttc ttccgtgaaa tt                                                  22

SEQ ID NO: 176          moltype = DNA   length = 22
FEATURE                 Location/Qualifiers
modified_base           1
                        mod_base = OTHER
                        note = 2-aminoadenine
source                  1..22
                        mol_type = other DNA
                        organism = synthetic construct
SEQUENCE: 176
naacctggat tagagttaca tt                                                  22

SEQ ID NO: 177          moltype = DNA   length = 22
FEATURE                 Location/Qualifiers
source                  1..22
                        mol_type = other DNA
                        organism = synthetic construct
SEQUENCE: 177
ggatgattag ttcagagata tt                                                  22

SEQ ID NO: 178          moltype = DNA   length = 22
FEATURE                 Location/Qualifiers
source                  1..22
                        mol_type = other DNA
                        organism = synthetic construct
SEQUENCE: 178
gtgttcttcc gtgaaattct at                                                  22

SEQ ID NO: 179          moltype = DNA   length = 22
FEATURE                 Location/Qualifiers
source                  1..22
                        mol_type = other DNA
                        organism = synthetic construct
SEQUENCE: 179
gggattcaga tctggtttca at                                                  22

SEQ ID NO: 180          moltype = DNA   length = 22
FEATURE                 Location/Qualifiers
modified_base           16
                        mod_base = i
source                  1..22
                        mol_type = other DNA
                        organism = synthetic construct
SEQUENCE: 180
caggattcag atctgntttc at                                                  22

SEQ ID NO: 181          moltype = RNA   length = 21
FEATURE                 Location/Qualifiers
source                  1..21
                        mol_type = other RNA
                        organism = synthetic construct
SEQUENCE: 181
caggattcag atctggtttc a                                                   21

SEQ ID NO: 182          moltype = RNA   length = 21
FEATURE                 Location/Qualifiers
source                  1..21
                        mol_type = other RNA
                        organism = synthetic construct
SEQUENCE: 182
```

```
aggattcaga tctggtttca a                                              21

SEQ ID NO: 183         moltype = RNA   length = 21
FEATURE                Location/Qualifiers
source                 1..21
                       mol_type = other RNA
                       organism = synthetic construct
SEQUENCE: 183
ctgttcttcc gtgaaattct a                                              21

SEQ ID NO: 184         moltype = RNA   length = 21
FEATURE                Location/Qualifiers
source                 1..21
                       mol_type = other RNA
                       organism = synthetic construct
SEQUENCE: 184
tcctggatga ttagttcaga a                                              21

SEQ ID NO: 185         moltype = RNA   length = 21
FEATURE                Location/Qualifiers
source                 1..21
                       mol_type = other RNA
                       organism = synthetic construct
SEQUENCE: 185
gcccttgttc ttccgtgaaa t                                              21

SEQ ID NO: 186         moltype = RNA   length = 21
FEATURE                Location/Qualifiers
source                 1..21
                       mol_type = other RNA
                       organism = synthetic construct
SEQUENCE: 186
aaacctggat tagagttaca t                                              21

SEQ ID NO: 187         moltype = RNA   length = 21
FEATURE                Location/Qualifiers
source                 1..21
                       mol_type = other RNA
                       organism = synthetic construct
SEQUENCE: 187
ggatgattag ttcagagata t                                              21

SEQ ID NO: 188         moltype = RNA   length = 21
FEATURE                Location/Qualifiers
source                 1..21
                       mol_type = other RNA
                       organism = synthetic construct
SEQUENCE: 188
gtgttcttcc gtgaaattct a                                              21

SEQ ID NO: 189         moltype = RNA   length = 21
FEATURE                Location/Qualifiers
source                 1..21
                       mol_type = other RNA
                       organism = synthetic construct
SEQUENCE: 189
gggattcaga tctggtttca a                                              21

SEQ ID NO: 190         moltype = RNA   length = 21
FEATURE                Location/Qualifiers
modified_base          16
                       mod_base = i
source                 1..21
                       mol_type = other RNA
                       organism = synthetic construct
SEQUENCE: 190
caggattcag atctgntttc a                                              21

SEQ ID NO: 191         moltype = RNA   length = 21
FEATURE                Location/Qualifiers
modified_base          1
                       mod_base = cm
modified_base          2
                       mod_base = OTHER
                       note = 2'-O-methyladenosine
modified_base          3
                       mod_base = gm
modified_base          4
                       mod_base = gm
```

| | |
|---|---|
| modified_base | 5<br>mod_base = OTHER<br>note = 2'-O-methyladenosine |
| modified_base | 6<br>mod_base = um |
| modified_base | 7<br>mod_base = um |
| modified_base | 8<br>mod_base = cm |
| modified_base | 9<br>mod_base = OTHER<br>note = 2'-fluoroadenosine |
| modified_base | 10<br>mod_base = OTHER<br>note = 2'-fluoroguanosine |
| modified_base | 11<br>mod_base = OTHER<br>note = 2'-fluoroadenosine |
| modified_base | 12<br>mod_base = um |
| modified_base | 13<br>mod_base = cm |
| modified_base | 14<br>mod_base = um |
| modified_base | 15<br>mod_base = gm |
| modified_base | 16<br>mod_base = gm |
| modified_base | 17<br>mod_base = um |
| modified_base | 18<br>mod_base = um |
| modified_base | 19<br>mod_base = um |
| modified_base | 20<br>mod_base = cm |
| modified_base | 21<br>mod_base = OTHER<br>note = 2'-O-methyladenosine |
| source | 1..21<br>mol_type = other RNA<br>organism = synthetic construct |

SEQUENCE: 191
caggattcag atctggtttc a                                                 21

| | |
|---|---|
| SEQ ID NO: 192 | moltype = RNA  length = 21 |
| FEATURE | Location/Qualifiers |
| modified_base | 1<br>mod_base = OTHER<br>note = 2'-O-methyladenosine |
| modified_base | 2<br>mod_base = gm |
| modified_base | 3<br>mod_base = gm |
| modified_base | 4<br>mod_base = OTHER<br>note = 2'-O-methyladenosine |
| modified_base | 5<br>mod_base = um |
| modified_base | 6<br>mod_base = um |
| modified_base | 7<br>mod_base = cm |
| modified_base | 8<br>mod_base = OTHER<br>note = 2'-O-methyladenosine |
| modified_base | 9<br>mod_base = OTHER<br>note = 2'-fluoroguanosine |
| modified_base | 10<br>mod_base = OTHER<br>note = 2'-fluoroadenosine |
| modified_base | 11<br>mod_base = OTHER<br>note = 2'-fluorouridine |
| modified_base | 12<br>mod_base = cm |
| modified_base | 13<br>mod_base = um |

-continued

```
modified_base      14
                   mod_base = gm
modified_base      15
                   mod_base = gm
modified_base      16
                   mod_base = um
modified_base      17
                   mod_base = um
modified_base      18
                   mod_base = um
modified_base      19
                   mod_base = cm
modified_base      20
                   mod_base = OTHER
                   note = 2'-O-methyladenosine
modified_base      21
                   mod_base = OTHER
                   note = 2'-O-methyladenosine
source             1..21
                   mol_type = other RNA
                   organism = synthetic construct
SEQUENCE: 192
aggattcaga tctggtttca a                                      21

SEQ ID NO: 193     moltype = RNA  length = 21
FEATURE            Location/Qualifiers
modified_base      1
                   mod_base = cm
modified_base      2
                   mod_base = um
modified_base      3
                   mod_base = gm
modified_base      4
                   mod_base = um
modified_base      5
                   mod_base = um
modified_base      6
                   mod_base = cm
modified_base      7
                   mod_base = um
modified_base      8
                   mod_base = um
modified_base      9
                   mod_base = OTHER
                   note = 2'-fluorocytidine
modified_base      10
                   mod_base = OTHER
                   note = 2'-fluorocytidine
modified_base      11
                   mod_base = OTHER
                   note = 2'-fluoroguanosine
modified_base      12
                   mod_base = um
modified_base      13
                   mod_base = gm
modified_base      14
                   mod_base = OTHER
                   note = 2'-O-methyladenosine
modified_base      15
                   mod_base = OTHER
                   note = 2'-O-methyladenosine
modified_base      16
                   mod_base = OTHER
                   note = 2'-O-methyladenosine
modified_base      17
                   mod_base = um
modified_base      18
                   mod_base = um
modified_base      19
                   mod_base = cm
modified_base      20
                   mod_base = um
modified_base      21
                   mod_base = OTHER
                   note = 2'-O-methyladenosine
source             1..21
                   mol_type = other RNA
                   organism = synthetic construct
SEQUENCE: 193
```
ctgttcttcc gtgaaattct a                                                    21

SEQ ID NO: 194          moltype = RNA   length = 21
FEATURE                 Location/Qualifiers
modified_base           1
                        mod_base = um
modified_base           2
                        mod_base = cm
modified_base           3
                        mod_base = cm
modified_base           4
                        mod_base = um
modified_base           5
                        mod_base = gm
modified_base           6
                        mod_base = gm
modified_base           7
                        mod_base = OTHER
                        note = 2'-O-methyladenosine
modified_base           8
                        mod_base = um
modified_base           9
                        mod_base = OTHER
                        note = 2'-fluoroguanosine
modified_base           10
                        mod_base = OTHER
                        note = 2'-fluoroadenosine
modified_base           11
                        mod_base = OTHER
                        note = 2'-fluorouridine
modified_base           12
                        mod_base = um
modified_base           13
                        mod_base = OTHER
                        note = 2'-O-methyladenosine
modified_base           14
                        mod_base = gm
modified_base           15
                        mod_base = um
modified_base           16
                        mod_base = um
modified_base           17
                        mod_base = cm
modified_base           18
                        mod_base = OTHER
                        note = 2'-O-methyladenosine
modified_base           19
                        mod_base = gm
modified_base           20
                        mod_base = OTHER
                        note = 2'-O-methyladenosine
modified_base           21
                        mod_base = OTHER
                        note = 2'-O-methyladenosine
source                  1..21
                        mol_type = other RNA
                        organism = synthetic construct
SEQUENCE: 194
tcctggatga ttagttcaga a                                                    21

SEQ ID NO: 195          moltype = RNA   length = 21
FEATURE                 Location/Qualifiers
modified_base           1
                        mod_base = gm
modified_base           2
                        mod_base = cm
modified_base           3
                        mod_base = cm
modified_base           4
                        mod_base = cm
modified_base           5
                        mod_base = um
modified_base           6
                        mod_base = um
modified_base           7
                        mod_base = gm
modified_base           8
                        mod_base = um
modified_base           9

-continued

```
                        mod_base = OTHER
                        note = 2'-fluorouridine
modified_base           10
                        mod_base = OTHER
                        note = 2'-fluorocytidine
modified_base           11
                        mod_base = OTHER
                        note = 2'-fluorouridine
modified_base           12
                        mod_base = um
modified_base           13
                        mod_base = cm
modified_base           14
                        mod_base = cm
modified_base           15
                        mod_base = gm
modified_base           16
                        mod_base = um
modified_base           17
                        mod_base = gm
modified_base           18
                        mod_base = OTHER
                        note = 2'-O-methyladenosine
modified_base           19
                        mod_base = OTHER
                        note = 2'-O-methyladenosine
modified_base           20
                        mod_base = OTHER
                        note = 2'-O-methyladenosine
modified_base           21
                        mod_base = um
source                  1..21
                        mol_type = other RNA
                        organism = synthetic construct
SEQUENCE: 195
gcccttgttc ttccgtgaaa t                                                  21

SEQ ID NO: 196          moltype = RNA   length = 21
FEATURE                 Location/Qualifiers
modified_base           1
                        mod_base = OTHER
                        note = 2-aminoadenine
modified_base           2
                        mod_base = OTHER
                        note = 2'-O-methyladenosine
modified_base           3
                        mod_base = OTHER
                        note = 2'-O-methyladenosine
modified_base           4
                        mod_base = cm
modified_base           5
                        mod_base = cm
modified_base           6
                        mod_base = um
modified_base           7
                        mod_base = gm
modified_base           8
                        mod_base = gm
modified_base           9
                        mod_base = OTHER
                        note = 2'-fluoroadenosine
modified_base           10
                        mod_base = OTHER
                        note = 2'-fluorouridine
modified_base           11
                        mod_base = OTHER
                        note = 2'-fluorouridine
modified_base           12
                        mod_base = OTHER
                        note = 2'-O-methyladenosine
modified_base           13
                        mod_base = gm
modified_base           14
                        mod_base = OTHER
                        note = 2'-O-methyladenosine
modified_base           15
                        mod_base = gm
modified_base           16
                        mod_base = um
```

| | | |
|---|---|---|
| modified_base | 17 | |
| | mod_base = um | |
| modified_base | 18 | |
| | mod_base = OTHER | |
| | note = 2'-O-methyladenosine | |
| modified_base | 19 | |
| | mod_base = cm | |
| modified_base | 20 | |
| | mod_base = OTHER | |
| | note = 2'-O-methyladenosine | |
| modified_base | 21 | |
| | mod_base = um | |
| source | 1..21 | |
| | mol_type = other RNA | |
| | organism = synthetic construct | |
| SEQUENCE: 196 | | |
| aaacctggat tagagttaca t | | 21 |
| | | |
| SEQ ID NO: 197 | moltype = RNA length = 21 | |
| FEATURE | Location/Qualifiers | |
| modified_base | 1 | |
| | mod_base = gm | |
| modified_base | 2 | |
| | mod_base = gm | |
| modified_base | 3 | |
| | mod_base = OTHER | |
| | note = 2'-O-methyladenosine | |
| modified_base | 4 | |
| | mod_base = um | |
| modified_base | 5 | |
| | mod_base = gm | |
| modified_base | 6 | |
| | mod_base = OTHER | |
| | note = 2'-O-methyladenosine | |
| modified_base | 7 | |
| | mod_base = um | |
| modified_base | 8 | |
| | mod_base = um | |
| modified_base | 9 | |
| | mod_base = OTHER | |
| | note = 2'-fluoroadenosine | |
| modified_base | 10 | |
| | mod_base = OTHER | |
| | note = 2'-fluoroguanosine | |
| modified_base | 11 | |
| | mod_base = OTHER | |
| | note = 2'-fluorouridine | |
| modified_base | 12 | |
| | mod_base = um | |
| modified_base | 13 | |
| | mod_base = cm | |
| modified_base | 14 | |
| | mod_base = OTHER | |
| | note = 2'-O-methyladenosine | |
| modified_base | 15 | |
| | mod_base = gm | |
| modified_base | 16 | |
| | mod_base = OTHER | |
| | note = 2'-O-methyladenosine | |
| modified_base | 17 | |
| | mod_base = gm | |
| modified_base | 18 | |
| | mod_base = OTHER | |
| | note = 2'-O-methyladenosine | |
| modified_base | 19 | |
| | mod_base = um | |
| modified_base | 20 | |
| | mod_base = OTHER | |
| | note = 2'-O-methyladenosine | |
| modified_base | 21 | |
| | mod_base = um | |
| source | 1..21 | |
| | mol_type = other RNA | |
| | organism = synthetic construct | |
| SEQUENCE: 197 | | |
| ggatgattag ttcagagata t | | 21 |
| | | |
| SEQ ID NO: 198 | moltype = RNA length = 21 | |
| FEATURE | Location/Qualifiers | |

| | | |
|---|---|---|
| modified_base | 1 | |
| | mod_base = gm | |
| modified_base | 2 | |
| | mod_base = um | |
| modified_base | 3 | |
| | mod_base = gm | |
| modified_base | 4 | |
| | mod_base = um | |
| modified_base | 5 | |
| | mod_base = um | |
| modified_base | 6 | |
| | mod_base = cm | |
| modified_base | 7 | |
| | mod_base = um | |
| modified_base | 8 | |
| | mod_base = um | |
| modified_base | 9 | |
| | mod_base = OTHER | |
| | note = 2'-fluorocytidine | |
| modified_base | 10 | |
| | mod_base = OTHER | |
| | note = 2'-fluorocytidine | |
| modified_base | 11 | |
| | mod_base = OTHER | |
| | note = 2'-fluoroguanosine | |
| modified_base | 12 | |
| | mod_base = um | |
| modified_base | 13 | |
| | mod_base = gm | |
| modified_base | 14 | |
| | mod_base = OTHER | |
| | note = 2'-O-methyladenosine | |
| modified_base | 15 | |
| | mod_base = OTHER | |
| | note = 2'-O-methyladenosine | |
| modified_base | 16 | |
| | mod_base = OTHER | |
| | note = 2'-O-methyladenosine | |
| modified_base | 17 | |
| | mod_base = um | |
| modified_base | 18 | |
| | mod_base = um | |
| modified_base | 19 | |
| | mod_base = cm | |
| modified_base | 20 | |
| | mod_base = um | |
| modified_base | 21 | |
| | mod_base = OTHER | |
| | note = 2'-O-methyladenosine | |
| source | 1..21 | |
| | mol_type = other RNA | |
| | organism = synthetic construct | |
| SEQUENCE: 198 | | |
| gtgttcttcc gtgaaattct a | | 21 |
| SEQ ID NO: 199 | moltype = RNA  length = 21 | |
| FEATURE | Location/Qualifiers | |
| modified_base | 1 | |
| | mod_base = gm | |
| modified_base | 2 | |
| | mod_base = um | |
| modified_base | 3 | |
| | mod_base = gm | |
| modified_base | 4 | |
| | mod_base = um | |
| modified_base | 5 | |
| | mod_base = um | |
| modified_base | 6 | |
| | mod_base = cm | |
| modified_base | 7 | |
| | mod_base = OTHER | |
| | note = 2'-fluorouridine | |
| modified_base | 8 | |
| | mod_base = um | |
| modified_base | 9 | |
| | mod_base = OTHER | |
| | note = 2'-fluorocytidine | |
| modified_base | 10 | |
| | mod_base = cm | |

```
modified_base      11
                   mod_base = OTHER
                   note = 2'-fluoroguanosine
modified_base      12
                   mod_base = um
modified_base      13
                   mod_base = gm
modified_base      14
                   mod_base = OTHER
                   note = 2'-O-methyladenosine
modified_base      15
                   mod_base = OTHER
                   note = 2'-O-methyladenosine
modified_base      16
                   mod_base = OTHER
                   note = 2'-O-methyladenosine
modified_base      17
                   mod_base = um
modified_base      18
                   mod_base = um
modified_base      19
                   mod_base = cm
modified_base      20
                   mod_base = um
modified_base      21
                   mod_base = OTHER
                   note = 2'-O-methyladenosine
source             1..21
                   mol_type = other RNA
                   organism = synthetic construct
SEQUENCE: 199
gtgttcttcc gtgaaattct a                                         21

SEQ ID NO: 200     moltype = RNA   length = 21
FEATURE            Location/Qualifiers
modified_base      1
                   mod_base = gm
modified_base      2
                   mod_base = gm
modified_base      3
                   mod_base = gm
modified_base      4
                   mod_base = OTHER
                   note = 2'-O-methyladenosine
modified_base      5
                   mod_base = um
modified_base      6
                   mod_base = um
modified_base      7
                   mod_base = cm
modified_base      8
                   mod_base = OTHER
                   note = 2'-O-methyladenosine
modified_base      9
                   mod_base = OTHER
                   note = 2'-fluoroguanosine
modified_base      10
                   mod_base = OTHER
                   note = 2'-fluoroadenosine
modified_base      11
                   mod_base = OTHER
                   note = 2'-fluorouridine
modified_base      12
                   mod_base = cm
modified_base      13
                   mod_base = um
modified_base      14
                   mod_base = gm
modified_base      15
                   mod_base = gm
modified_base      16
                   mod_base = um
modified_base      17
                   mod_base = um
modified_base      18
                   mod_base = um
modified_base      19
                   mod_base = cm
modified_base      20
```

```
                        mod_base = OTHER
                        note = 2'-O-methyladenosine
modified_base           21
                        mod_base = OTHER
                        note = 2'-O-methyladenosine
source                  1..21
                        mol_type = other RNA
                        organism = synthetic construct
SEQUENCE: 200
gggattcaga tctggtttca a                                                    21

SEQ ID NO: 201          moltype = RNA  length = 21
FEATURE                 Location/Qualifiers
modified_base           1
                        mod_base = OTHER
                        note = 2-aminoadenine
modified_base           2
                        mod_base = gm
modified_base           3
                        mod_base = gm
modified_base           4
                        mod_base = OTHER
                        note = 2'-O-methyladenosine
modified_base           5
                        mod_base = um
modified_base           6
                        mod_base = um
modified_base           7
                        mod_base = cm
modified_base           8
                        mod_base = OTHER
                        note = 2'-O-methyladenosine
modified_base           9
                        mod_base = OTHER
                        note = 2'-fluoroguanosine
modified_base           10
                        mod_base = OTHER
                        note = 2'-fluoroadenosine
modified_base           11
                        mod_base = OTHER
                        note = 2'-fluorouridine
modified_base           12
                        mod_base = cm
modified_base           13
                        mod_base = um
modified_base           14
                        mod_base = gm
modified_base           15
                        mod_base = gm
modified_base           16
                        mod_base = um
modified_base           17
                        mod_base = um
modified_base           18
                        mod_base = um
modified_base           19
                        mod_base = cm
modified_base           20
                        mod_base = OTHER
                        note = 2'-O-methyladenosine
modified_base           21
                        mod_base = OTHER
                        note = 2'-O-methyladenosine
source                  1..21
                        mol_type = other RNA
                        organism = synthetic construct
SEQUENCE: 201
aggattcaga tctggtttca a                                                    21

SEQ ID NO: 202          moltype = RNA  length = 21
FEATURE                 Location/Qualifiers
modified_base           1
                        mod_base = gm
modified_base           2
                        mod_base = gm
modified_base           3
                        mod_base = gm
modified_base           4
                        mod_base = OTHER
```

```
                        note = 2'-O-methyladenosine
modified_base           5
                        mod_base = um
modified_base           6
                        mod_base = um
modified_base           7
                        mod_base = cm
modified_base           8
                        mod_base = OTHER
                        note = 2'-O-methyladenosine
modified_base           9
                        mod_base = OTHER
                        note = 2'-fluoroguanosine
modified_base           10
                        mod_base = OTHER
                        note = 2'-O-methyladenosine
modified_base           11
                        mod_base = OTHER
                        note = 2'-fluorouridine
modified_base           12
                        mod_base = cm
modified_base           13
                        mod_base = um
modified_base           14
                        mod_base = gm
modified_base           15
                        mod_base = gm
modified_base           16
                        mod_base = um
modified_base           17
                        mod_base = um
modified_base           18
                        mod_base = um
modified_base           19
                        mod_base = cm
modified_base           20
                        mod_base = OTHER
                        note = 2'-O-methyladenosine
modified_base           21
                        mod_base = OTHER
                        note = 2'-O-methyladenosine
source                  1..21
                        mol_type = other RNA
                        organism = synthetic construct
SEQUENCE: 202
gggattcaga tctggtttca a                                                  21

SEQ ID NO: 203          moltype = RNA   length = 21
FEATURE                 Location/Qualifiers
modified_base           1
                        mod_base = gm
modified_base           2
                        mod_base = gm
modified_base           3
                        mod_base = gm
modified_base           4
                        mod_base = OTHER
                        note = 2'-O-methyladenosine
modified_base           5
                        mod_base = um
modified_base           6
                        mod_base = um
modified_base           7
                        mod_base = cm
modified_base           8
                        mod_base = OTHER
                        note = 2'-O-methyladenosine
modified_base           9
                        mod_base = OTHER
                        note = 2'-fluoroguanosine
modified_base           10
                        mod_base = OTHER
                        note = 2'-O-methyladenosine
modified_base           11
                        mod_base = OTHER
                        note = 2'-fluorouridine
modified_base           12
                        mod_base = OTHER
                        note = 2'-fluorocytidine
```

```
                       -continued modified_base          13
                       mod_base = um
modified_base          14
                       mod_base = gm
modified_base          15
                       mod_base = gm
modified_base          16
                       mod_base = um
modified_base          17
                       mod_base = um
modified_base          18
                       mod_base = um
modified_base          19
                       mod_base = cm
modified_base          20
                       mod_base = OTHER
                       note = 2'-O-methyladenosine
modified_base          21
                       mod_base = OTHER
                       note = 2'-O-methyladenosine
source                 1..21
                       mol_type = other RNA
                       organism = synthetic construct
SEQUENCE: 203
gggattcaga tctggtttca a                                            21

SEQ ID NO: 204         moltype = RNA  length = 21
FEATURE                Location/Qualifiers
modified_base          1
                       mod_base = cm
modified_base          2
                       mod_base = OTHER
                       note = 2'-O-methyladenosine
modified_base          3
                       mod_base = gm
modified_base          4
                       mod_base = gm
modified_base          5
                       mod_base = OTHER
                       note = 2'-O-methyladenosine
modified_base          6
                       mod_base = um
modified_base          7
                       mod_base = um
modified_base          8
                       mod_base = cm
modified_base          9
                       mod_base = OTHER
                       note = 2'-fluoroadenosine
modified_base          10
                       mod_base = OTHER
                       note = 2'-fluoroguanosine
modified_base          11
                       mod_base = OTHER
                       note = 2'-fluoroadenosine
modified_base          12
                       mod_base = um
modified_base          13
                       mod_base = cm
modified_base          14
                       mod_base = um
modified_base          15
                       mod_base = gm
modified_base          16
                       mod_base = OTHER
                       note = 2 -O-methylinosine
modified_base          17
                       mod_base = um
modified_base          18
                       mod_base = um
modified_base          19
                       mod_base = um
modified_base          20
                       mod_base = cm
modified_base          21
                       mod_base = OTHER
                       note = 2'-O-methyladenosine
source                 1..21
                       mol_type = other RNA
```

```
                        organism = synthetic construct
SEQUENCE: 204
caggattcag atctgntttc a                                                  21

SEQ ID NO: 205          moltype = RNA  length = 21
FEATURE                 Location/Qualifiers
modified_base           1
                        mod_base = cm
modified_base           2
                        mod_base = um
modified_base           3
                        mod_base = gm
modified_base           4
                        mod_base = um
modified_base           5
                        mod_base = um
modified_base           6
                        mod_base = cm
modified_base           7
                        mod_base = um
modified_base           8
                        mod_base = um
modified_base           9
                        mod_base = OTHER
                        note = 2'-fluorocytidine
modified_base           10
                        mod_base = cm
modified_base           11
                        mod_base = OTHER
                        note = 2'-fluoroguanosine
modified_base           12
                        mod_base = um
modified_base           13
                        mod_base = OTHER
                        note = 2'-fluoroguanosine
modified_base           14
                        mod_base = OTHER
                        note = 2'-O-methyladenosine
modified_base           15
                        mod_base = OTHER
                        note = 2'-O-methyladenosine
modified_base           16
                        mod_base = OTHER
                        note = 2'-O-methyladenosine
modified_base           17
                        mod_base = um
modified_base           18
                        mod_base = um
modified_base           19
                        mod_base = cm
modified_base           20
                        mod_base = um
modified_base           21
                        mod_base = OTHER
                        note = 2'-O-methyladenosine
source                  1..21
                        mol_type = other RNA
                        organism = synthetic construct
SEQUENCE: 205
ctgttcttcc gtgaaattct a                                                  21

SEQ ID NO: 206          moltype = RNA  length = 21
FEATURE                 Location/Qualifiers
modified_base           1
                        mod_base = cm
modified_base           2
                        mod_base = OTHER
                        note = 2'-O-methyladenosine
modified_base           3
                        mod_base = gm
modified_base           4
                        mod_base = gm
modified_base           5
                        mod_base = OTHER
                        note = 2'-O-methyladenosine
modified_base           6
                        mod_base = um
modified_base           7
                        mod_base = um
```

|     |     |
| --- | --- |
| modified_base | 8<br>mod_base = cm |
| modified_base | 9<br>mod_base = OTHER<br>note = 2'-fluoroadenosine |
| modified_base | 10<br>mod_base = OTHER<br>note = 2'-fluoroguanosine |
| modified_base | 11<br>mod_base = OTHER<br>note = 2'-fluoroadenosine |
| modified_base | 12<br>mod_base = um |
| modified_base | 13<br>mod_base = cm |
| modified_base | 14<br>mod_base = um |
| modified_base | 15<br>mod_base = gm |
| modified_base | 16<br>mod_base = gm |
| modified_base | 17<br>mod_base = um |
| modified_base | 18<br>mod_base = um |
| modified_base | 19<br>mod_base = um |
| modified_base | 20<br>mod_base = cm |
| modified_base | 21<br>mod_base = OTHER<br>note = 2'-O-methyladenosine |
| source | 1..21<br>mol_type = other RNA<br>organism = synthetic construct |

SEQUENCE: 206
caggattcag atctggtttc a                                            21

| | |
| --- | --- |
| SEQ ID NO: 207 | moltype = RNA   length = 21 |
| FEATURE | Location/Qualifiers |
| modified_base | 1<br>mod_base = OTHER<br>note = 2'-O-methyladenosine |
| modified_base | 2<br>mod_base = gm |
| modified_base | 3<br>mod_base = gm |
| modified_base | 4<br>mod_base = OTHER<br>note = 2'-O-methyladenosine |
| modified_base | 5<br>mod_base = um |
| modified_base | 6<br>mod_base = um |
| modified_base | 7<br>mod_base = cm |
| modified_base | 8<br>mod_base = OTHER<br>note = 2'-O-methyladenosine |
| modified_base | 9<br>mod_base = OTHER<br>note = 2'-fluoroguanosine |
| modified_base | 10<br>mod_base = OTHER<br>note = 2'-fluoroadenosine |
| modified_base | 11<br>mod_base = OTHER<br>note = 2'-fluorouridine |
| modified_base | 12<br>mod_base = cm |
| modified_base | 13<br>mod_base = um |
| modified_base | 14<br>mod_base = gm |
| modified_base | 15<br>mod_base = gm |
| modified_base | 16<br>mod_base = um |
| modified_base | 17 |

| | | |
|---|---|---|
| modified_base | | mod_base = um |
| | 18 | |
| modified_base | | mod_base = um |
| | 19 | |
| modified_base | | mod_base = cm |
| | 20 | |
| modified_base | | mod_base = OTHER |
| | | note = 2'-O-methyladenosine |
| | 21 | |
| modified_base | | mod_base = OTHER |
| | | note = 2'-O-methyladenosine |
| source | 1..21 | |
| | | mol_type = other RNA |
| | | organism = synthetic construct |
| SEQUENCE: 207 | | |
| aggattcaga tctggtttca a | | 21 |

| | | |
|---|---|---|
| SEQ ID NO: 208 | moltype = RNA length = 21 | |
| FEATURE | Location/Qualifiers | |
| modified_base | 1 | |
| | | mod_base = cm |
| modified_base | 2 | |
| | | mod_base = um |
| modified_base | 3 | |
| | | mod_base = gm |
| modified_base | 4 | |
| | | mod_base = um |
| modified_base | 5 | |
| | | mod_base = um |
| modified_base | 6 | |
| | | mod_base = cm |
| modified_base | 7 | |
| | | mod_base = um |
| modified_base | 8 | |
| | | mod_base = um |
| modified_base | 9 | |
| | | mod_base = OTHER |
| | | note = 2'-fluorocytidine |
| modified_base | 10 | |
| | | mod_base = OTHER |
| | | note = 2'-fluorocytidine |
| modified_base | 11 | |
| | | mod_base = OTHER |
| | | note = 2'-fluoroguanosine |
| modified_base | 12 | |
| | | mod_base = um |
| modified_base | 13 | |
| | | mod_base = gm |
| modified_base | 14 | |
| | | mod_base = OTHER |
| | | note = 2'-O-methyladenosine |
| modified_base | 15 | |
| | | mod_base = OTHER |
| | | note = 2'-O-methyladenosine |
| modified_base | 16 | |
| | | mod_base = OTHER |
| | | note = 2'-O-methyladenosine |
| modified_base | 17 | |
| | | mod_base = um |
| modified_base | 18 | |
| | | mod_base = um |
| modified_base | 19 | |
| | | mod_base = cm |
| modified_base | 20 | |
| | | mod_base = um |
| modified_base | 21 | |
| | | mod_base = OTHER |
| | | note = 2'-O-methyladenosine |
| source | 1..21 | |
| | | mol_type = other RNA |
| | | organism = synthetic construct |
| SEQUENCE: 208 | | |
| ctgttcttcc gtgaaattct a | | 21 |

| | | |
|---|---|---|
| SEQ ID NO: 209 | moltype = RNA length = 21 | |
| FEATURE | Location/Qualifiers | |
| modified_base | 1 | |
| | | mod_base = um |
| modified_base | 2 | |

|                | mod_base = cm |
| --- | --- |
| modified_base | 3 |
|                | mod_base = cm |
| modified_base | 4 |
|                | mod_base = um |
| modified_base | 5 |
|                | mod_base = gm |
| modified_base | 6 |
|                | mod_base = gm |
| modified_base | 7 |
|                | mod_base = OTHER |
|                | note = 2'-O-methyladenosine |
| modified_base | 8 |
|                | mod_base = um |
| modified_base | 9 |
|                | mod_base = OTHER |
|                | note = 2'-fluoroguanosine |
| modified_base | 10 |
|                | mod_base = OTHER |
|                | note = 2'-fluoroadenosine |
| modified_base | 11 |
|                | mod_base = OTHER |
|                | note = 2'-fluorouridine |
| modified_base | 12 |
|                | mod_base = um |
| modified_base | 13 |
|                | mod_base = OTHER |
|                | note = 2'-O-methyladenosine |
| modified_base | 14 |
|                | mod_base = gm |
| modified_base | 15 |
|                | mod_base = um |
| modified_base | 16 |
|                | mod_base = um |
| modified_base | 17 |
|                | mod_base = cm |
| modified_base | 18 |
|                | mod_base = OTHER |
|                | note = 2'-O-methyladenosine |
| modified_base | 19 |
|                | mod_base = gm |
| modified_base | 20 |
|                | mod_base = OTHER |
|                | note = 2'-O-methyladenosine |
| modified_base | 21 |
|                | mod_base = OTHER |
|                | note = 2'-O-methyladenosine |
| source | 1..21 |
|                | mol_type = other RNA |
|                | organism = synthetic construct |
| SEQUENCE: 209 | |
| tcctggatga ttagttcaga a | 21 |
| SEQ ID NO: 210 | moltype = RNA  length = 21 |
| FEATURE | Location/Qualifiers |
| modified_base | 1 |
|                | mod_base = gm |
| modified_base | 2 |
|                | mod_base = cm |
| modified_base | 3 |
|                | mod_base = cm |
| modified_base | 4 |
|                | mod_base = cm |
| modified_base | 5 |
|                | mod_base = um |
| modified_base | 6 |
|                | mod_base = um |
| modified_base | 7 |
|                | mod_base = gm |
| modified_base | 8 |
|                | mod_base = um |
| modified_base | 9 |
|                | mod_base = OTHER |
|                | note = 2'-fluorouridine |
| modified_base | 10 |
|                | mod_base = OTHER |
|                | note = 2'-fluorocytidine |
| modified_base | 11 |
|                | mod_base = OTHER |

```
                              note = 2'-fluorouridine
modified_base                 12
                              mod_base = um
modified_base                 13
                              mod_base = cm
modified_base                 14
                              mod_base = cm
modified_base                 15
                              mod_base = gm
modified_base                 16
                              mod_base = um
modified_base                 17
                              mod_base = gm
modified_base                 18
                              mod_base = OTHER
                              note = 2'-O-methyladenosine
modified_base                 19
                              mod_base = OTHER
                              note = 2'-O-methyladenosine
modified_base                 20
                              mod_base = OTHER
                              note = 2'-O-methyladenosine
modified_base                 21
                              mod_base = um
source                        1..21
                              mol_type = other RNA
                              organism = synthetic construct
SEQUENCE: 210
gcccttgttc ttccgtgaaa t                                          21

SEQ ID NO: 211           moltype = RNA   length = 21
FEATURE                  Location/Qualifiers
modified_base                 1
                              mod_base = OTHER
                              note = 2-aminoadenine
modified_base                 2
                              mod_base = OTHER
                              note = 2'-O-methyladenosine
modified_base                 3
                              mod_base = OTHER
                              note = 2'-O-methyladenosine
modified_base                 4
                              mod_base = cm
modified_base                 5
                              mod_base = cm
modified_base                 6
                              mod_base = um
modified_base                 7
                              mod_base = gm
modified_base                 8
                              mod_base = gm
modified_base                 9
                              mod_base = OTHER
                              note = 2'-fluoroadenosine
modified_base                 10
                              mod_base = OTHER
                              note = 2'-fluorouridine
modified_base                 11
                              mod_base = OTHER
                              note = 2'-fluorouridine
modified_base                 12
                              mod_base = OTHER
                              note = 2'-O-methyladenosine
modified_base                 13
                              mod_base = gm
modified_base                 14
                              mod_base = OTHER
                              note = 2'-O-methyladenosine
modified_base                 15
                              mod_base = gm
modified_base                 16
                              mod_base = um
modified_base                 17
                              mod_base = um
modified_base                 18
                              mod_base = OTHER
                              note = 2'-O-methyladenosine
modified_base                 19
                              mod_base = cm
```

```
modified_base          20
                       mod_base = OTHER
                       note = 2'-O-methyladenosine
modified_base          21
                       mod_base = um
source                 1..21
                       mol_type = other RNA
                       organism = synthetic construct
SEQUENCE: 211
aaacctggat tagagttaca t                                              21

SEQ ID NO: 212         moltype = RNA  length = 21
FEATURE                Location/Qualifiers
modified_base          1
                       mod_base = gm
modified_base          2
                       mod_base = gm
modified_base          3
                       mod_base = OTHER
                       note = 2'-O-methyladenosine
modified_base          4
                       mod_base = um
modified_base          5
                       mod_base = gm
modified_base          6
                       mod_base = OTHER
                       note = 2'-O-methyladenosine
modified_base          7
                       mod_base = um
modified_base          8
                       mod_base = um
modified_base          9
                       mod_base = OTHER
                       note = 2'-fluoroadenosine
modified_base          10
                       mod_base = OTHER
                       note = 2'-fluoroguanosine
modified_base          11
                       mod_base = OTHER
                       note = 2'-fluorouridine
modified_base          12
                       mod_base = um
modified_base          13
                       mod_base = cm
modified_base          14
                       mod_base = OTHER
                       note = 2'-O-methyladenosine
modified_base          15
                       mod_base = gm
modified_base          16
                       mod_base = OTHER
                       note = 2'-O-methyladenosine
modified_base          17
                       mod_base = gm
modified_base          18
                       mod_base = OTHER
                       note = 2'-O-methyladenosine
modified_base          19
                       mod_base = um
modified_base          20
                       mod_base = OTHER
                       note = 2'-O-methyladenosine
modified_base          21
                       mod_base = um
source                 1..21
                       mol_type = other RNA
                       organism = synthetic construct
SEQUENCE: 212
ggatgattag ttcagagata t                                              21

SEQ ID NO: 213         moltype = RNA  length = 21
FEATURE                Location/Qualifiers
modified_base          1
                       mod_base = gm
modified_base          2
                       mod_base = um
modified_base          3
                       mod_base = gm
modified_base          4
```

```
                         mod_base = um
modified_base    5
                         mod_base = um
modified_base    6
                         mod_base = cm
modified_base    7
                         mod_base = um
modified_base    8
                         mod_base = um
modified_base    9
                         mod_base = OTHER
                         note = 2'-fluorocytidine
modified_base   10
                         mod_base = OTHER
                         note = 2'-fluorocytidine
modified_base   11
                         mod_base = OTHER
                         note = 2'-fluoroguanosine
modified_base   12
                         mod_base = um
modified_base   13
                         mod_base = gm
modified_base   14
                         mod_base = OTHER
                         note = 2'-O-methyladenosine
modified_base   15
                         mod_base = OTHER
                         note = 2'-O-methyladenosine
modified_base   16
                         mod_base = OTHER
                         note = 2'-O-methyladenosine
modified_base   17
                         mod_base = um
modified_base   18
                         mod_base = um
modified_base   19
                         mod_base = cm
modified_base   20
                         mod_base = um
modified_base   21
                         mod_base = OTHER
                         note = 2'-O-methyladenosine
source           1..21
                         mol_type = other RNA
                         organism = synthetic construct
SEQUENCE: 213
gtgttcttcc gtgaaattct a                                              21

SEQ ID NO: 214           moltype = RNA   length = 21
FEATURE                  Location/Qualifiers
modified_base    1
                         mod_base = gm
modified_base    2
                         mod_base = um
modified_base    3
                         mod_base = gm
modified_base    4
                         mod_base = um
modified_base    5
                         mod_base = um
modified_base    6
                         mod_base = cm
modified_base    7
                         mod_base = OTHER
                         note = 2'-fluorouridine
modified_base    8
                         mod_base = um
modified_base    9
                         mod_base = OTHER
                         note = 2'-fluorocytidine
modified_base   10
                         mod_base = cm
modified_base   11
                         mod_base = OTHER
                         note = 2'-fluoroguanosine
modified_base   12
                         mod_base = um
modified_base   13
                         mod_base = gm
```

```
modified_base          14
                       mod_base = OTHER
                       note = 2'-O-methyladenosine
modified_base          15
                       mod_base = OTHER
                       note = 2'-O-methyladenosine
modified_base          16
                       mod_base = OTHER
                       note = 2'-O-methyladenosine
modified_base          17
                       mod_base = um
modified_base          18
                       mod_base = um
modified_base          19
                       mod_base = cm
modified_base          20
                       mod_base = um
modified_base          21
                       mod_base = OTHER
                       note = 2'-O-methyladenosine
source                 1..21
                       mol_type = other RNA
                       organism = synthetic construct
SEQUENCE: 214
gtgttcttcc gtgaaattct a                                       21

SEQ ID NO: 215         moltype = RNA   length = 21
FEATURE                Location/Qualifiers
modified_base          1
                       mod_base = gm
modified_base          2
                       mod_base = gm
modified_base          3
                       mod_base = gm
modified_base          4
                       mod_base = OTHER
                       note = 2'-O-methyladenosine
modified_base          5
                       mod_base = um
modified_base          6
                       mod_base = um
modified_base          7
                       mod_base = cm
modified_base          8
                       mod_base = OTHER
                       note = 2'-O-methyladenosine
modified_base          9
                       mod_base = OTHER
                       note = 2'-fluoroguanosine
modified_base          10
                       mod_base = OTHER
                       note = 2'-fluoroadenosine
modified_base          11
                       mod_base = OTHER
                       note = 2'-fluorouridine
modified_base          12
                       mod_base = cm
modified_base          13
                       mod_base = um
modified_base          14
                       mod_base = gm
modified_base          15
                       mod_base = gm
modified_base          16
                       mod_base = um
modified_base          17
                       mod_base = um
modified_base          18
                       mod_base = um
modified_base          19
                       mod_base = cm
modified_base          20
                       mod_base = OTHER
                       note = 2'-O-methyladenosine
modified_base          21
                       mod_base = OTHER
                       note = 2'-O-methyladenosine
source                 1..21
                       mol_type = other RNA
```

```
                        organism = synthetic construct
SEQUENCE: 215
gggattcaga tctggtttca a                                              21

SEQ ID NO: 216          moltype = RNA  length = 21
FEATURE                 Location/Qualifiers
modified_base           1
                        mod_base = OTHER
                        note = 2-aminoadenine
modified_base           2
                        mod_base = gm
modified_base           3
                        mod_base = gm
modified_base           4
                        mod_base = OTHER
                        note = 2'-O-methyladenosine
modified_base           5
                        mod_base = um
modified_base           6
                        mod_base = um
modified_base           7
                        mod_base = cm
modified_base           8
                        mod_base = OTHER
                        note = 2'-O-methyladenosine
modified_base           9
                        mod_base = OTHER
                        note = 2'-fluoroguanosine
modified_base           10
                        mod_base = OTHER
                        note = 2'-fluoroadenosine
modified_base           11
                        mod_base = OTHER
                        note = 2'-fluorouridine
modified_base           12
                        mod_base = cm
modified_base           13
                        mod_base = um
modified_base           14
                        mod_base = gm
modified_base           15
                        mod_base = gm
modified_base           16
                        mod_base = um
modified_base           17
                        mod_base = um
modified_base           18
                        mod_base = um
modified_base           19
                        mod_base = cm
modified_base           20
                        mod_base = OTHER
                        note = 2'-O-methyladenosine
modified_base           21
                        mod_base = OTHER
                        note = 2'-O-methyladenosine
source                  1..21
                        mol_type = other RNA
                        organism = synthetic construct
SEQUENCE: 216
aggattcaga tctggtttca a                                              21

SEQ ID NO: 217          moltype = RNA  length = 21
FEATURE                 Location/Qualifiers
modified_base           1
                        mod_base = gm
modified_base           2
                        mod_base = gm
modified_base           3
                        mod_base = gm
modified_base           4
                        mod_base = OTHER
                        note = 2'-O-methyladenosine
modified_base           5
                        mod_base = um
modified_base           6
                        mod_base = um
modified_base           7
                        mod_base = cm
```

-continued

```
modified_base          8
                       mod_base = OTHER
                       note = 2'-O-methyladenosine
modified_base          9
                       mod_base = OTHER
                       note = 2'-fluoroguanosine
modified_base          10
                       mod_base = OTHER
                       note = 2'-O-methyladenosine
modified_base          11
                       mod_base = OTHER
                       note = 2'-fluorouridine
modified_base          12
                       mod_base = cm
modified_base          13
                       mod_base = um
modified_base          14
                       mod_base = gm
modified_base          15
                       mod_base = gm
modified_base          16
                       mod_base = um
modified_base          17
                       mod_base = um
modified_base          18
                       mod_base = um
modified_base          19
                       mod_base = cm
modified_base          20
                       mod_base = OTHER
                       note = 2'-O-methyladenosine
modified_base          21
                       mod_base = OTHER
                       note = 2'-O-methyladenosine
source                 1..21
                       mol_type = other RNA
                       organism = synthetic construct
SEQUENCE: 217
gggattcaga tctggtttca a                                                   21

SEQ ID NO: 218         moltype = RNA  length = 21
FEATURE                Location/Qualifiers
modified_base          1
                       mod_base = gm
modified_base          2
                       mod_base = gm
modified_base          3
                       mod_base = gm
modified_base          4
                       mod_base = OTHER
                       note = 2'-O-methyladenosine
modified_base          5
                       mod_base = um
modified_base          6
                       mod_base = um
modified_base          7
                       mod_base = cm
modified_base          8
                       mod_base = OTHER
                       note = 2'-O-methyladenosine
modified_base          9
                       mod_base = OTHER
                       note = 2'-fluoroguanosine
modified_base          10
                       mod_base = OTHER
                       note = 2'-O-methyladenosine
modified_base          11
                       mod_base = OTHER
                       note = 2'-fluorouridine
modified_base          12
                       mod_base = OTHER
                       note = 2'-fluorocytidine
modified_base          13
                       mod_base = um
modified_base          14
                       mod_base = gm
modified_base          15
                       mod_base = gm
modified_base          16
```

```
                        mod_base = um
modified_base           17
                        mod_base = um
modified_base           18
                        mod_base = um
modified_base           19
                        mod_base = cm
modified_base           20
                        mod_base = OTHER
                        note = 2'-O-methyladenosine
modified_base           21
                        mod_base = OTHER
                        note = 2'-O-methyladenosine
source                  1..21
                        mol_type = other RNA
                        organism = synthetic construct
SEQUENCE: 218
gggattcaga tctggtttca a                                              21

SEQ ID NO: 219          moltype = RNA  length = 21
FEATURE                 Location/Qualifiers
modified_base           1
                        mod_base = cm
modified_base           2
                        mod_base = OTHER
                        note = 2'-O-methyladenosine
modified_base           3
                        mod_base = gm
modified_base           4
                        mod_base = gm
modified_base           5
                        mod_base = OTHER
                        note = 2'-O-methyladenosine
modified_base           6
                        mod_base = um
modified_base           7
                        mod_base = um
modified_base           8
                        mod_base = cm
modified_base           9
                        mod_base = OTHER
                        note = 2'-fluoroadenosine
modified_base           10
                        mod_base = OTHER
                        note = 2'-fluoroguanosine
modified_base           11
                        mod_base = OTHER
                        note = 2'-fluoroadenosine
modified_base           12
                        mod_base = um
modified_base           13
                        mod_base = cm
modified_base           14
                        mod_base = um
modified_base           15
                        mod_base = gm
modified_base           16
                        mod_base = OTHER
                        note = 2 -O-methylinosine
modified_base           17
                        mod_base = um
modified_base           18
                        mod_base = um
modified_base           19
                        mod_base = um
modified_base           20
                        mod_base = cm
modified_base           21
                        mod_base = OTHER
                        note = 2'-O-methyladenosine
source                  1..21
                        mol_type = other RNA
                        organism = synthetic construct
SEQUENCE: 219
caggattcag atctgntttc a                                              21

SEQ ID NO: 220          moltype = RNA  length = 21
FEATURE                 Location/Qualifiers
modified_base           1
```

|   |   |
|---|---|
| modified_base | mod_base = cm<br>2 |
| modified_base | mod_base = um<br>3 |
| modified_base | mod_base = gm<br>4 |
| modified_base | mod_base = um<br>5 |
| modified_base | mod_base = um<br>6 |
| modified_base | mod_base = cm<br>7 |
| modified_base | mod_base = um<br>8 |
| modified_base | mod_base = um<br>9 |
| modified_base | mod_base = OTHER<br>note = 2'-fluorocytidine<br>10 |
| modified_base | mod_base = cm<br>11 |
| modified_base | mod_base = OTHER<br>note = 2'-fluoroguanosine<br>12 |
| modified_base | mod_base = um<br>13 |
| modified_base | mod_base = OTHER<br>note = 2'-fluoroguanosine<br>14 |
| modified_base | mod_base = OTHER<br>note = 2'-O-methyladenosine<br>15 |
| modified_base | mod_base = OTHER<br>note = 2'-O-methyladenosine<br>16 |
| modified_base | mod_base = OTHER<br>note = 2'-O-methyladenosine<br>17 |
| modified_base | mod_base = um<br>18 |
| modified_base | mod_base = um<br>19 |
| modified_base | mod_base = cm<br>20 |
| modified_base | mod_base = um<br>21 |
| modified_base | mod_base = OTHER<br>note = 2'-O-methyladenosine |
| source | 1..21<br>mol_type = other RNA<br>organism = synthetic construct |

SEQUENCE: 220
ctgttcttcc gtgaaattct a                                           21

| SEQ ID NO: 221 | moltype = RNA  length = 21 |
|---|---|
| FEATURE | Location/Qualifiers |
| modified_base | 1 |
|   | mod_base = cm |
| modified_base | 2 |
|   | mod_base = um |
| modified_base | 3 |
|   | mod_base = gm |
| modified_base | 4 |
|   | mod_base = um |
| modified_base | 5 |
|   | mod_base = um |
| modified_base | 6 |
|   | mod_base = cm |
| modified_base | 7 |
|   | mod_base = um |
| modified_base | 8 |
|   | mod_base = um |
| modified_base | 9 |
|   | mod_base = OTHER<br>note = 2'-fluorocytidine |
| modified_base | 10 |
|   | mod_base = OTHER<br>note = 2'-fluorocytidine |
| modified_base | 11 |

|                |                                      |    |
|----------------|--------------------------------------|----|
|                | mod_base = OTHER                     |    |
|                | note = 2'-fluoroguanosine            |    |
| modified_base  | 12                                   |    |
|                | mod_base = um                        |    |
| modified_base  | 13                                   |    |
|                | mod_base = gm                        |    |
| modified_base  | 14                                   |    |
|                | mod_base = OTHER                     |    |
|                | note = 2'-O-methyladenosine          |    |
| modified_base  | 15                                   |    |
|                | mod_base = OTHER                     |    |
|                | note = 2'-O-methyladenosine          |    |
| modified_base  | 16                                   |    |
|                | mod_base = OTHER                     |    |
|                | note = 2'-O-methyladenosine          |    |
| modified_base  | 17                                   |    |
|                | mod_base = um                        |    |
| modified_base  | 18                                   |    |
|                | mod_base = um                        |    |
| modified_base  | 19                                   |    |
|                | mod_base = cm                        |    |
| modified_base  | 20                                   |    |
|                | mod_base = um                        |    |
| modified_base  | 21                                   |    |
|                | mod_base = OTHER                     |    |
|                | note = 2'-O-methyladenosine          |    |
| source         | 1..21                                |    |
|                | mol_type = other RNA                 |    |
|                | organism = synthetic construct       |    |
| SEQUENCE: 221  |                                      |    |
| ctgttcttcc gtgaaattct a               |                    | 21 |

| SEQ ID NO: 222 | moltype = RNA  length = 21           |    |
|----------------|--------------------------------------|----|
| FEATURE        | Location/Qualifiers                  |    |
| modified_base  | 1                                    |    |
|                | mod_base = cm                        |    |
| modified_base  | 2                                    |    |
|                | mod_base = OTHER                     |    |
|                | note = 2'-O-methyladenosine          |    |
| modified_base  | 3                                    |    |
|                | mod_base = gm                        |    |
| modified_base  | 4                                    |    |
|                | mod_base = gm                        |    |
| modified_base  | 5                                    |    |
|                | mod_base = OTHER                     |    |
|                | note = 2'-O-methyladenosine          |    |
| modified_base  | 6                                    |    |
|                | mod_base = um                        |    |
| modified_base  | 7                                    |    |
|                | mod_base = um                        |    |
| modified_base  | 8                                    |    |
|                | mod_base = cm                        |    |
| modified_base  | 9                                    |    |
|                | mod_base = OTHER                     |    |
|                | note = 2'-fluoroadenosine            |    |
| modified_base  | 10                                   |    |
|                | mod_base = OTHER                     |    |
|                | note = 2'-fluoroguanosine            |    |
| modified_base  | 11                                   |    |
|                | mod_base = OTHER                     |    |
|                | note = 2'-fluoroadenosine            |    |
| modified_base  | 12                                   |    |
|                | mod_base = um                        |    |
| modified_base  | 13                                   |    |
|                | mod_base = cm                        |    |
| modified_base  | 14                                   |    |
|                | mod_base = um                        |    |
| modified_base  | 15                                   |    |
|                | mod_base = gm                        |    |
| modified_base  | 16                                   |    |
|                | mod_base = gm                        |    |
| modified_base  | 17                                   |    |
|                | mod_base = um                        |    |
| modified_base  | 18                                   |    |
|                | mod_base = um                        |    |
| modified_base  | 19                                   |    |
|                | mod_base = um                        |    |
| modified_base  | 20                                   |    |
|                | mod_base = cm                        |    |

| | | |
|---|---|---|
| modified_base | 21 | |
| | mod_base = OTHER | |
| | note = 2'-O-methyladenosine | |
| source | 1..21 | |
| | mol_type = other RNA | |
| | organism = synthetic construct | |
| SEQUENCE: 222 | | |
| caggattcag atctggtttc a | | 21 |
| | | |
| SEQ ID NO: 223 | moltype = RNA  length = 21 | |
| FEATURE | Location/Qualifiers | |
| modified_base | 1 | |
| | mod_base = cm | |
| modified_base | 2 | |
| | mod_base = um | |
| modified_base | 3 | |
| | mod_base = gm | |
| modified_base | 4 | |
| | mod_base = um | |
| modified_base | 5 | |
| | mod_base = um | |
| modified_base | 6 | |
| | mod_base = cm | |
| modified_base | 7 | |
| | mod_base = um | |
| modified_base | 8 | |
| | mod_base = um | |
| modified_base | 9 | |
| | mod_base = OTHER | |
| | note = 2'-fluorocytidine | |
| modified_base | 10 | |
| | mod_base = OTHER | |
| | note = 2'-fluorocytidine | |
| modified_base | 11 | |
| | mod_base = OTHER | |
| | note = 2'-fluoroguanosine | |
| modified_base | 12 | |
| | mod_base = um | |
| modified_base | 13 | |
| | mod_base = gm | |
| modified_base | 14 | |
| | mod_base = OTHER | |
| | note = 2'-O-methyladenosine | |
| modified_base | 15 | |
| | mod_base = OTHER | |
| | note = 2'-O-methyladenosine | |
| modified_base | 16 | |
| | mod_base = OTHER | |
| | note = 2'-O-methyladenosine | |
| modified_base | 17 | |
| | mod_base = um | |
| modified_base | 18 | |
| | mod_base = um | |
| modified_base | 19 | |
| | mod_base = cm | |
| modified_base | 20 | |
| | mod_base = um | |
| modified_base | 21 | |
| | mod_base = OTHER | |
| | note = 2'-O-methyladenosine | |
| source | 1..21 | |
| | mol_type = other RNA | |
| | organism = synthetic construct | |
| SEQUENCE: 223 | | |
| ctgttcttcc gtgaaattct a | | 21 |
| | | |
| SEQ ID NO: 224 | moltype = RNA  length = 21 | |
| FEATURE | Location/Qualifiers | |
| modified_base | 1 | |
| | mod_base = cm | |
| modified_base | 2 | |
| | mod_base = OTHER | |
| | note = 2'-O-methyladenosine | |
| modified_base | 3 | |
| | mod_base = gm | |
| modified_base | 4 | |
| | mod_base = gm | |
| modified_base | 5 | |
| | mod_base = OTHER | |

|                | |
|---|---|
| modified_base  | 6<br>mod_base = um |
| modified_base  | 7<br>mod_base = um |
| modified_base  | 8<br>mod_base = cm |
| modified_base  | 9<br>mod_base = OTHER<br>note = 2'-fluoroadenosine |
| modified_base  | 10<br>mod_base = OTHER<br>note = 2'-fluoroguanosine |
| modified_base  | 11<br>mod_base = OTHER<br>note = 2'-fluoroadenosine |
| modified_base  | 12<br>mod_base = um |
| modified_base  | 13<br>mod_base = cm |
| modified_base  | 14<br>mod_base = um |
| modified_base  | 15<br>mod_base = gm |
| modified_base  | 16<br>mod_base = gm |
| modified_base  | 17<br>mod_base = um |
| modified_base  | 18<br>mod_base = um |
| modified_base  | 19<br>mod_base = um |
| modified_base  | 20<br>mod_base = cm |
| modified_base  | 21<br>mod_base = OTHER<br>note = 2'-O-methyladenosine |
| source         | 1..21<br>mol_type = other RNA<br>organism = synthetic construct |
| SEQUENCE: 224 | |
| caggattcag atctggtttc a | 21 |
| SEQ ID NO: 225<br>FEATURE | moltype = RNA   length = 21<br>Location/Qualifiers |
| modified_base | 1<br>mod_base = OTHER<br>note = 2'-O-methyladenosine |
| modified_base | 2<br>mod_base = gm |
| modified_base | 3<br>mod_base = gm |
| modified_base | 4<br>mod_base = OTHER<br>note = 2'-O-methyladenosine |
| modified_base | 5<br>mod_base = um |
| modified_base | 6<br>mod_base = um |
| modified_base | 7<br>mod_base = cm |
| modified_base | 8<br>mod_base = OTHER<br>note = 2'-O-methyladenosine |
| modified_base | 9<br>mod_base = OTHER<br>note = 2'-fluoroguanosine |
| modified_base | 10<br>mod_base = OTHER<br>note = 2'-fluoroadenosine |
| modified_base | 11<br>mod_base = OTHER<br>note = 2'-fluorouridine |
| modified_base | 12<br>mod_base = cm |
| modified_base | 13<br>mod_base = um |
| modified_base | 14<br>mod_base = gm |

| | | |
|---|---|---|
| modified_base | 15 | |
| | mod_base = gm | |
| modified_base | 16 | |
| | mod_base = um | |
| modified_base | 17 | |
| | mod_base = um | |
| modified_base | 18 | |
| | mod_base = um | |
| modified_base | 19 | |
| | mod_base = cm | |
| modified_base | 20 | |
| | mod_base = OTHER | |
| | note = 2'-O-methyladenosine | |
| modified_base | 21 | |
| | mod_base = OTHER | |
| | note = 2'-O-methyladenosine | |
| source | 1..21 | |
| | mol_type = other RNA | |
| | organism = synthetic construct | |
| SEQUENCE: 225 | | |
| aggattcaga tctggtttca a | | 21 |
| | | |
| SEQ ID NO: 226 | moltype = RNA  length = 21 | |
| FEATURE | Location/Qualifiers | |
| modified_base | 1 | |
| | mod_base = um | |
| modified_base | 2 | |
| | mod_base = cm | |
| modified_base | 3 | |
| | mod_base = cm | |
| modified_base | 4 | |
| | mod_base = um | |
| modified_base | 5 | |
| | mod_base = gm | |
| modified_base | 6 | |
| | mod_base = gm | |
| modified_base | 7 | |
| | mod_base = OTHER | |
| | note = 2'-O-methyladenosine | |
| modified_base | 8 | |
| | mod_base = um | |
| modified_base | 9 | |
| | mod_base = OTHER | |
| | note = 2'-fluoroguanosine | |
| modified_base | 10 | |
| | mod_base = OTHER | |
| | note = 2'-fluoroadenosine | |
| modified_base | 11 | |
| | mod_base = OTHER | |
| | note = 2'-fluorouridine | |
| modified_base | 12 | |
| | mod_base = um | |
| modified_base | 13 | |
| | mod_base = OTHER | |
| | note = 2'-O-methyladenosine | |
| modified_base | 14 | |
| | mod_base = gm | |
| modified_base | 15 | |
| | mod_base = um | |
| modified_base | 16 | |
| | mod_base = um | |
| modified_base | 17 | |
| | mod_base = cm | |
| modified_base | 18 | |
| | mod_base = OTHER | |
| | note = 2'-O-methyladenosine | |
| modified_base | 19 | |
| | mod_base = gm | |
| modified_base | 20 | |
| | mod_base = OTHER | |
| | note = 2'-O-methyladenosine | |
| modified_base | 21 | |
| | mod_base = OTHER | |
| | note = 2'-O-methyladenosine | |
| source | 1..21 | |
| | mol_type = other RNA | |
| | organism = synthetic construct | |
| SEQUENCE: 226 | | |
| tcctggatga ttagttcaga a | | 21 |

-continued

| | |
|---|---|
| SEQ ID NO: 227 | moltype = RNA   length = 21 |
| FEATURE | Location/Qualifiers |
| modified_base | 1 |
| | mod_base = OTHER |
| | note = 2-aminoadenine |
| modified_base | 2 |
| | mod_base = OTHER |
| | note = 2'-O-methyladenosine |
| modified_base | 3 |
| | mod_base = OTHER |
| | note = 2'-O-methyladenosine |
| modified_base | 4 |
| | mod_base = cm |
| modified_base | 5 |
| | mod_base = cm |
| modified_base | 6 |
| | mod_base = um |
| modified_base | 7 |
| | mod_base = gm |
| modified_base | 8 |
| | mod_base = gm |
| modified_base | 9 |
| | mod_base = OTHER |
| | note = 2'-fluoroadenosine |
| modified_base | 10 |
| | mod_base = OTHER |
| | note = 2'-fluorouridine |
| modified_base | 11 |
| | mod_base = OTHER |
| | note = 2'-fluorouridine |
| modified_base | 12 |
| | mod_base = OTHER |
| | note = 2'-O-methyladenosine |
| modified_base | 13 |
| | mod_base = gm |
| modified_base | 14 |
| | mod_base = OTHER |
| | note = 2'-O-methyladenosine |
| modified_base | 15 |
| | mod_base = gm |
| modified_base | 16 |
| | mod_base = um |
| modified_base | 17 |
| | mod_base = um |
| modified_base | 18 |
| | mod_base = OTHER |
| | note = 2'-O-methyladenosine |
| modified_base | 19 |
| | mod_base = cm |
| modified_base | 20 |
| | mod_base = OTHER |
| | note = 2'-O-methyladenosine |
| modified_base | 21 |
| | mod_base = um |
| source | 1..21 |
| | mol_type = other RNA |
| | organism = synthetic construct |
| SEQUENCE: 227 | |
| aaacctggat tagagttaca t | 21 |

| | |
|---|---|
| SEQ ID NO: 228 | moltype = RNA   length = 21 |
| FEATURE | Location/Qualifiers |
| modified_base | 1 |
| | mod_base = gm |
| modified_base | 2 |
| | mod_base = um |
| modified_base | 3 |
| | mod_base = gm |
| modified_base | 4 |
| | mod_base = um |
| modified_base | 5 |
| | mod_base = um |
| modified_base | 6 |
| | mod_base = cm |
| modified_base | 7 |
| | mod_base = um |
| modified_base | 8 |
| | mod_base = um |

| | | |
|---|---|---|
| modified_base | 9 | |
| | mod_base = OTHER | |
| | note = 2'-fluorocytidine | |
| modified_base | 10 | |
| | mod_base = OTHER | |
| | note = 2'-fluorocytidine | |
| modified_base | 11 | |
| | mod_base = OTHER | |
| | note = 2'-fluoroguanosine | |
| modified_base | 12 | |
| | mod_base = um | |
| modified_base | 13 | |
| | mod_base = gm | |
| modified_base | 14 | |
| | mod_base = OTHER | |
| | note = 2'-O-methyladenosine | |
| modified_base | 15 | |
| | mod_base = OTHER | |
| | note = 2'-O-methyladenosine | |
| modified_base | 16 | |
| | mod_base = OTHER | |
| | note = 2'-O-methyladenosine | |
| modified_base | 17 | |
| | mod_base = um | |
| modified_base | 18 | |
| | mod_base = um | |
| modified_base | 19 | |
| | mod_base = cm | |
| modified_base | 20 | |
| | mod_base = um | |
| modified_base | 21 | |
| | mod_base = OTHER | |
| | note = 2'-O-methyladenosine | |
| source | 1..21 | |
| | mol_type = other RNA | |
| | organism = synthetic construct | |

SEQUENCE: 228
gtgttcttcc gtgaaattct a                                          21

| | | |
|---|---|---|
| SEQ ID NO: 229 | moltype = RNA  length = 21 | |
| FEATURE | Location/Qualifiers | |
| modified_base | 1 | |
| | mod_base = gm | |
| modified_base | 2 | |
| | mod_base = um | |
| modified_base | 3 | |
| | mod_base = gm | |
| modified_base | 4 | |
| | mod_base = um | |
| modified_base | 5 | |
| | mod_base = um | |
| modified_base | 6 | |
| | mod_base = cm | |
| modified_base | 7 | |
| | mod_base = OTHER | |
| | note = 2'-fluorouridine | |
| modified_base | 8 | |
| | mod_base = um | |
| modified_base | 9 | |
| | mod_base = OTHER | |
| | note = 2'-fluorocytidine | |
| modified_base | 10 | |
| | mod_base = cm | |
| modified_base | 11 | |
| | mod_base = OTHER | |
| | note = 2'-fluoroguanosine | |
| modified_base | 12 | |
| | mod_base = um | |
| modified_base | 13 | |
| | mod_base = gm | |
| modified_base | 14 | |
| | mod_base = OTHER | |
| | note = 2'-O-methyladenosine | |
| modified_base | 15 | |
| | mod_base = OTHER | |
| | note = 2'-O-methyladenosine | |
| modified_base | 16 | |
| | mod_base = OTHER | |
| | note = 2'-O-methyladenosine | |

```
modified_base        17
                     mod_base = um
modified_base        18
                     mod_base = um
modified_base        19
                     mod_base = cm
modified_base        20
                     mod_base = um
modified_base        21
                     mod_base = OTHER
                     note = 2'-O-methyladenosine
source               1..21
                     mol_type = other RNA
                     organism = synthetic construct
SEQUENCE: 229
gtgttcttcc gtgaaattct a                                              21

SEQ ID NO: 230       moltype = RNA   length = 21
FEATURE              Location/Qualifiers
modified_base        1
                     mod_base = gm
modified_base        2
                     mod_base = cm
modified_base        3
                     mod_base = cm
modified_base        4
                     mod_base = cm
modified_base        5
                     mod_base = um
modified_base        6
                     mod_base = um
modified_base        7
                     mod_base = gm
modified_base        8
                     mod_base = um
modified_base        9
                     mod_base = OTHER
                     note = 2'-fluorouridine
modified_base        10
                     mod_base = OTHER
                     note = 2'-fluorocytidine
modified_base        11
                     mod_base = OTHER
                     note = 2'-fluorouridine
modified_base        12
                     mod_base = um
modified_base        13
                     mod_base = cm
modified_base        14
                     mod_base = cm
modified_base        15
                     mod_base = gm
modified_base        16
                     mod_base = um
modified_base        17
                     mod_base = gm
modified_base        18
                     mod_base = OTHER
                     note = 2'-O-methyladenosine
modified_base        19
                     mod_base = OTHER
                     note = 2'-O-methyladenosine
modified_base        20
                     mod_base = OTHER
                     note = 2'-O-methyladenosine
modified_base        21
                     mod_base = um
source               1..21
                     mol_type = other RNA
                     organism = synthetic construct
SEQUENCE: 230
gcccttgttc ttccgtgaaa t                                              21

SEQ ID NO: 231       moltype = RNA   length = 21
FEATURE              Location/Qualifiers
modified_base        1
                     mod_base = gm
modified_base        2
                     mod_base = gm
```

```
modified_base          3
                       mod_base = OTHER
                       note = 2'-O-methyladenosine
modified_base          4
                       mod_base = um
modified_base          5
                       mod_base = gm
modified_base          6
                       mod_base = OTHER
                       note = 2'-O-methyladenosine
modified_base          7
                       mod_base = um
modified_base          8
                       mod_base = um
modified_base          9
                       mod_base = OTHER
                       note = 2'-fluoroadenosine
modified_base          10
                       mod_base = OTHER
                       note = 2'-fluoroguanosine
modified_base          11
                       mod_base = OTHER
                       note = 2'-fluorouridine
modified_base          12
                       mod_base = um
modified_base          13
                       mod_base = cm
modified_base          14
                       mod_base = OTHER
                       note = 2'-O-methyladenosine
modified_base          15
                       mod_base = gm
modified_base          16
                       mod_base = OTHER
                       note = 2'-O-methyladenosine
modified_base          17
                       mod_base = gm
modified_base          18
                       mod_base = OTHER
                       note = 2'-O-methyladenosine
modified_base          19
                       mod_base = um
modified_base          20
                       mod_base = OTHER
                       note = 2'-O-methyladenosine
modified_base          21
                       mod_base = um
source                 1..21
                       mol_type = other RNA
                       organism = synthetic construct
SEQUENCE: 231
ggatgattag ttcagagata t                                           21

SEQ ID NO: 232         moltype = RNA   length = 21
FEATURE                Location/Qualifiers
modified_base          1
                       mod_base = gm
modified_base          2
                       mod_base = gm
modified_base          3
                       mod_base = gm
modified_base          4
                       mod_base = OTHER
                       note = 2'-O-methyladenosine
modified_base          5
                       mod_base = um
modified_base          6
                       mod_base = um
modified_base          7
                       mod_base = cm
modified_base          8
                       mod_base = OTHER
                       note = 2'-O-methyladenosine
modified_base          9
                       mod_base = OTHER
                       note = 2'-fluoroguanosine
modified_base          10
                       mod_base = OTHER
                       note = 2'-fluoroadenosine
```

| | |
|---|---|
| modified_base | 11<br>mod_base = OTHER<br>note = 2'-fluorouridine |
| modified_base | 12<br>mod_base = cm |
| modified_base | 13<br>mod_base = um |
| modified_base | 14<br>mod_base = gm |
| modified_base | 15<br>mod_base = gm |
| modified_base | 16<br>mod_base = um |
| modified_base | 17<br>mod_base = um |
| modified_base | 18<br>mod_base = um |
| modified_base | 19<br>mod_base = cm |
| modified_base | 20<br>mod_base = OTHER<br>note = 2'-O-methyladenosine |
| modified_base | 21<br>mod_base = OTHER<br>note = 2'-O-methyladenosine |
| source | 1..21<br>mol_type = other RNA<br>organism = synthetic construct |

SEQUENCE: 232
gggattcaga tctggtttca a                                       21

| | |
|---|---|
| SEQ ID NO: 233 | moltype = RNA   length = 21 |
| FEATURE | Location/Qualifiers |
| modified_base | 1<br>mod_base = gm |
| modified_base | 2<br>mod_base = gm |
| modified_base | 3<br>mod_base = gm |
| modified_base | 4<br>mod_base = OTHER<br>note = 2'-O-methyladenosine |
| modified_base | 5<br>mod_base = um |
| modified_base | 6<br>mod_base = um |
| modified_base | 7<br>mod_base = cm |
| modified_base | 8<br>mod_base = OTHER<br>note = 2'-O-methyladenosine |
| modified_base | 9<br>mod_base = OTHER<br>note = 2'-fluoroguanosine |
| modified_base | 10<br>mod_base = OTHER<br>note = 2'-O-methyladenosine |
| modified_base | 11<br>mod_base = OTHER<br>note = 2'-fluorouridine |
| modified_base | 12<br>mod_base = cm |
| modified_base | 13<br>mod_base = um |
| modified_base | 14<br>mod_base = gm |
| modified_base | 15<br>mod_base = gm |
| modified_base | 16<br>mod_base = um |
| modified_base | 17<br>mod_base = um |
| modified_base | 18<br>mod_base = um |
| modified_base | 19<br>mod_base = cm |
| modified_base | 20<br>mod_base = OTHER<br>note = 2'-O-methyladenosine |

```
modified_base         21
                      mod_base = OTHER
                      note = 2'-O-methyladenosine
source                1..21
                      mol_type = other RNA
                      organism = synthetic construct
SEQUENCE: 233
gggattcaga tctggtttca a                                              21

SEQ ID NO: 234        moltype = RNA   length = 21
FEATURE               Location/Qualifiers
modified_base         1
                      mod_base = gm
modified_base         2
                      mod_base = gm
modified_base         3
                      mod_base = gm
modified_base         4
                      mod_base = OTHER
                      note = 2'-O-methyladenosine
modified_base         5
                      mod_base = um
modified_base         6
                      mod_base = um
modified_base         7
                      mod_base = cm
modified_base         8
                      mod_base = OTHER
                      note = 2'-O-methyladenosine
modified_base         9
                      mod_base = OTHER
                      note = 2'-fluoroguanosine
modified_base         10
                      mod_base = OTHER
                      note = 2'-O-methyladenosine
modified_base         11
                      mod_base = OTHER
                      note = 2'-fluorouridine
modified_base         12
                      mod_base = OTHER
                      note = 2'-fluorocytidine
modified_base         13
                      mod_base = um
modified_base         14
                      mod_base = gm
modified_base         15
                      mod_base = gm
modified_base         16
                      mod_base = um
modified_base         17
                      mod_base = um
modified_base         18
                      mod_base = um
modified_base         19
                      mod_base = cm
modified_base         20
                      mod_base = OTHER
                      note = 2'-O-methyladenosine
modified_base         21
                      mod_base = OTHER
                      note = 2'-O-methyladenosine
source                1..21
                      mol_type = other RNA
                      organism = synthetic construct
SEQUENCE: 234
gggattcaga tctggtttca a                                              21

SEQ ID NO: 235        moltype = RNA   length = 21
FEATURE               Location/Qualifiers
modified_base         1
                      mod_base = cm
modified_base         2
                      mod_base = um
modified_base         3
                      mod_base = gm
modified_base         4
                      mod_base = um
modified_base         5
                      mod_base = um
```

```
modified_base         6
                      mod_base = cm
modified_base         7
                      mod_base = um
modified_base         8
                      mod_base = um
modified_base         9
                      mod_base = OTHER
                      note = 2'-fluorocytidine
modified_base         10
                      mod_base = OTHER
                      note = 2'-fluorocytidine
modified_base         11
                      mod_base = OTHER
                      note = 2'-fluoroguanosine
modified_base         12
                      mod_base = um
modified_base         13
                      mod_base = gm
modified_base         14
                      mod_base = OTHER
                      note = 2'-O-methyladenosine
modified_base         15
                      mod_base = OTHER
                      note = 2'-O-methyladenosine
modified_base         16
                      mod_base = OTHER
                      note = 2'-O-methyladenosine
modified_base         17
                      mod_base = um
modified_base         18
                      mod_base = um
modified_base         19
                      mod_base = cm
modified_base         20
                      mod_base = um
modified_base         21
                      mod_base = OTHER
                      note = 2'-O-methyladenosine
source                1..21
                      mol_type = other RNA
                      organism = synthetic construct
SEQUENCE: 235
ctgttcttcc gtgaaattct a                                              21

SEQ ID NO: 236        moltype = RNA  length = 21
FEATURE               Location/Qualifiers
modified_base         1
                      mod_base = cm
modified_base         2
                      mod_base = OTHER
                      note = 2'-O-methyladenosine
modified_base         3
                      mod_base = gm
modified_base         4
                      mod_base = gm
modified_base         5
                      mod_base = OTHER
                      note = 2'-O-methyladenosine
modified_base         6
                      mod_base = um
modified_base         7
                      mod_base = um
modified_base         8
                      mod_base = cm
modified_base         9
                      mod_base = OTHER
                      note = 2'-fluoroadenosine
modified_base         10
                      mod_base = OTHER
                      note = 2'-fluoroguanosine
modified_base         11
                      mod_base = OTHER
                      note = 2'-fluoroadenosine
modified_base         12
                      mod_base = um
modified_base         13
                      mod_base = cm
modified_base         14
```

```
                        mod_base = um
modified_base           15
                        mod_base = gm
modified_base           16
                        mod_base = gm
modified_base           17
                        mod_base = um
modified_base           18
                        mod_base = um
modified_base           19
                        mod_base = um
modified_base           20
                        mod_base = cm
modified_base           21
                        mod_base = OTHER
                        note = 2'-O-methyladenosine
source                  1..21
                        mol_type = other RNA
                        organism = synthetic construct
SEQUENCE: 236
caggattcag atctggtttc a                                              21

SEQ ID NO: 237          moltype = RNA  length = 21
FEATURE                 Location/Qualifiers
modified_base           1
                        mod_base = cm
modified_base           2
                        mod_base = OTHER
                        note = 2'-O-methyladenosine
modified_base           3
                        mod_base = gm
modified_base           4
                        mod_base = gm
modified_base           5
                        mod_base = OTHER
                        note = 2'-O-methyladenosine
modified_base           6
                        mod_base = um
modified_base           7
                        mod_base = um
modified_base           8
                        mod_base = cm
modified_base           9
                        mod_base = OTHER
                        note = 2'-fluoroadenosine
modified_base           10
                        mod_base = OTHER
                        note = 2'-fluoroguanosine
modified_base           11
                        mod_base = OTHER
                        note = 2'-fluoroadenosine
modified_base           12
                        mod_base = um
modified_base           13
                        mod_base = cm
modified_base           14
                        mod_base = um
modified_base           15
                        mod_base = gm
modified_base           16
                        mod_base = gm
modified_base           17
                        mod_base = um
modified_base           18
                        mod_base = um
modified_base           19
                        mod_base = um
modified_base           20
                        mod_base = cm
modified_base           21
                        mod_base = OTHER
                        note = 2'-O-methyladenosine
source                  1..21
                        mol_type = other RNA
                        organism = synthetic construct
SEQUENCE: 237
caggattcag atctggtttc a                                              21

SEQ ID NO: 238          moltype = RNA  length = 22
```

-continued

```
FEATURE                 Location/Qualifiers
modified_base           5..6
                        mod_base = OTHER
                        note = thymine
modified_base           11
                        mod_base = OTHER
                        note = thymine
modified_base           13
                        mod_base = OTHER
                        note = thymine
modified_base           16..18
                        mod_base = OTHER
                        note = thymine
modified_base           22
                        mod_base = OTHER
                        note = thymine
modified_base           1
                        mod_base = OTHER
                        note = 2-aminoadenine
source                  1..22
                        mol_type = other RNA
                        organism = synthetic construct
SEQUENCE: 238
nggattcaga tctggtttca at                                               22

SEQ ID NO: 239          moltype = RNA   length = 21
FEATURE                 Location/Qualifiers
modified_base           1
                        mod_base = OTHER
                        note = 2-aminoadenine
source                  1..21
                        mol_type = other RNA
                        organism = synthetic construct
modified_base           5..6
                        mod_base = OTHER
                        note = thymine
modified_base           11
                        mod_base = OTHER
                        note = thymine
modified_base           13
                        mod_base = OTHER
                        note = thymine
modified_base           16..18
                        mod_base = OTHER
                        note = thymine
SEQUENCE: 239
nggattcaga tctggtttca a                                                21

SEQ ID NO: 240          moltype =   length =
SEQUENCE: 240
000

SEQ ID NO: 241          moltype =   length =
SEQUENCE: 241
000

SEQ ID NO: 242          moltype =   length =
SEQUENCE: 242
000

SEQ ID NO: 243          moltype =   length =
SEQUENCE: 243
000

SEQ ID NO: 244          moltype = RNA   length = 21
FEATURE                 Location/Qualifiers
modified_base           1
                        mod_base = OTHER
                        note = 2-aminoadenine
```

```
                     modified_base        2
                                          mod_base = gm
                     modified_base        3
                                          mod_base = gm
                     modified_base        4
                                          mod_base = OTHER
                                          note = 2'-O-methyladenosine
                     modified_base        5
                                          mod_base = um
                     modified_base        6
                                          mod_base = um
                     modified_base        7
                                          mod_base = cm
                     modified_base        8
                                          mod_base = OTHER
                                          note = 2'-O-methyladenosine
                     modified_base        9
                                          mod_base = OTHER
                                          note = 2'-fluoroguanosine
                     modified_base        10
                                          mod_base = OTHER
                                          note = 2'-fluoroadenosine
                     modified_base        11
                                          mod_base = OTHER
                                          note = 2'-fluorouridine
                     modified_base        12
                                          mod_base = cm
                     modified_base        13
                                          mod_base = um
                     modified_base        14
                                          mod_base = gm
                     modified_base        15
                                          mod_base = gm
                     modified_base        16
                                          mod_base = um
                     modified_base        17
                                          mod_base = um
                     modified_base        18
                                          mod_base = um
                     modified_base        19
                                          mod_base = cm
                     modified_base        20
                                          mod_base = OTHER
                                          note = 2'-O-methyladenosine
                     modified_base        21
                                          mod_base = OTHER
                                          note = 2'-O-methyladenosine
                     source               1..21
                                          mol_type = other RNA
                                          organism = synthetic construct
SEQUENCE: 244
aggattcaga tctggtttca a                                                   21

SEQ ID NO: 245       moltype = RNA  length = 21
FEATURE              Location/Qualifiers
                     modified_base        1
                                          mod_base = OTHER
                                          note = 2-aminoadenine
                     modified_base        2
                                          mod_base = gm
                     modified_base        3
                                          mod_base = gm
                     modified_base        4
                                          mod_base = OTHER
                                          note = 2'-O-methyladenosine
                     modified_base        5
                                          mod_base = um
                     modified_base        6
                                          mod_base = um
                     modified_base        7
                                          mod_base = cm
                     modified_base        8
                                          mod_base = OTHER
                                          note = 2'-O-methyladenosine
                     modified_base        9
                                          mod_base = OTHER
                                          note = 2'-fluoroguanosine
                     modified_base        10
                                          mod_base = OTHER
```

```
                        note = 2'-fluoroadenosine
modified_base           11
                        mod_base = OTHER
                        note = 2'-fluorouridine
modified_base           12
                        mod_base = cm
modified_base           13
                        mod_base = um
modified_base           14
                        mod_base = gm
modified_base           15
                        mod_base = gm
modified_base           16
                        mod_base = um
modified_base           17
                        mod_base = um
modified_base           18
                        mod_base = um
modified_base           19
                        mod_base = cm
modified_base           20
                        mod_base = OTHER
                        note = 2'-O-methyladenosine
modified_base           21
                        mod_base = OTHER
                        note = 2'-O-methyladenosine
source                  1..21
                        mol_type = other RNA
                        organism = synthetic construct
SEQUENCE: 245
aggattcaga tctggtttca a                                           21
```

RNAI AGENTS FOR INHIBITING EXPRESSION OF DUX4, COMPOSITIONS THEREOF, AND METHODS OF USE

CROSS REFERENCE TO RELATED APPLICATIONS

This application is a continuation application under 35 U. S.C. 111(a) of PCT Application No. PCT/US2021/049871, filed on Sep. 10, 2021, which claims the benefit of priority of U.S. Provisional Patent Application Ser. No. 63/077,272, filed on Sep. 11, 2020, and U.S. Provisional Patent Application Ser. No. 63/214,742, filed on Jun. 24, 2021, the contents of each of which are incorporated herein by reference in their entirety.

SEQUENCE LISTING

This application contains a Sequence Listing which has been submitted in XML format and is hereby incorporated by reference in its entirety. The XML copy is named 30679-US1_ST26_SeqListing.xml, created Mar. 3, 2023, and is 1609 kb in size.

FIELD OF THE INVENTION

The present disclosure relates to RNA interference (RNAi) agents, e.g., double stranded RNAi agents, for inhibition of double homeobox 4 (DUX4) gene expression, compositions that include DUX4 RNAi agents, and methods of use thereof.

BACKGROUND

DUX4 is a transcription factor normally expressed during embryogenesis containing two homeobox domains whose partial gene is located within the D4Z4 macrosatellite repeat array on chromosome 4. It is normally heavily epigenetically repressed via methylation in all tissues except testis and has no known physiological function in adult skeletal muscle. Under conditions where DUX4 is hypomethylated and derepressed in skeletal muscle, DUX4 can be expressed and can activate the transcription of germline genes, immunemediators, retrotransposons, endogenous retrovirus elements, and pericentromeric satellite HSATII sequences which can promote the misexpression of non-physiological transcripts, long noncoding RNAs, or antisense transcripts that ultimately cause intracellular and extracellular signaling cascades resulting in muscle degeneration. It is the expression of DUX4 that causes the muscle pathology and weakness responsible for the common symptoms of Facioscapulohuneral Muscular Dystrophy (FSHD), the most common adult myopathy affecting 1 in 15,000 to 1 in 20,000 adults.

FSHD onset is relatively late, with typical diagnoses occurring at 20 to 30 years of age, and progression is slow, with muscle weakness severity increasing over years to decades. FSHD patients commonly experience asymmetric muscle weakness and loss of mass in the muscles of the face, back, upper arms, abdominal core, hip girdle, and legs resulting in a significantly reduced quality of life. Both major forms of FSH4D, referred to as FSHD1 and FSHD2, are caused by permissive expression of DUX4. FSHD1 occurs when the D4Z4 macrosatellite repeat array is fewer than 11 copies in length. The short length of the array results in insufficient methylation and epigenetic repression and permits DUX4 to be sporadically expressed in myonuclei which leads to the aforementioned myotoxic signaling cascades. FSHD2 is caused by loss of function mutations in the structural maintenance of the chromosomes hinge domain 1 (SMCHD1) gene responsible, in part, for methylating and repressing the D4Z4 macrosatellite repeat array. Reduced SMCHD1 activity results in epigenetic de-repression and expression of DUX4.

As DUX4 is not normally expressed in adult skeletal muscle, has no known normal physiological function in skeletal muscle, and, when expressed, results in a gain of function myotoxicity, it is a difficult target for most modalities such as small molecule chemical compounds or antibodies. Currently, there is no effective treatment to reverse or prevent the myotoxic effects of DUX4 expression in skeletal muscle. There exists a need for a therapeutic capable of inhibiting DUX4 expression and preventing, halting, and/or reversing the DUX4 expression-related muscle degeneration, muscle mass loss, and muscle weakness associated with FSHD.

SUMMARY

There is a need for novel RNA interference (RNAi) agents (also herein referred to as RNAi agent, RNAi trigger, or trigger), e.g., double stranded RNAi agents, that are able to selectively and efficiently inhibit the expression of a double homeobox 4 (DUX4) gene, particularly in vivo. Further, there exists a need for compositions of novel DUX4-specific RNAi agents for the treatment of diseases or disorders, such as Facioscapulohumeral Muscular Dystrophy (FSHD), that can be ameliorated at least in part by a reduction in DUX4 protein levels.

In general, the present disclosure features DUX4 RNAi agents, compositions that include such RNAi agents, and methods for inhibiting expression of a DUX4 gene in vitro and/or in vivo using the RNAi agents and compositions that include the RNAi agents described herein. The DUX4 RNAi agents described herein are able to selectively and efficiently decrease, inhibit, or silence expression of a DUX4 gene.

The described DUX4 RNAi agents can be used in methods for therapeutic treatment (including preventative, intervention, or prophylactic treatment) of symptoms and diseases such as FSHD, including the most common forms of FSHD1 and FSHD2, which are both caused by permissive expression of DUX4. The methods disclosed herein include the administration of one or more DUX4 RNAi agents to a subject, e.g., a human or animal subject, using any suitable methods known in the art, such as for example, subcutaneous (SQ) injection, intramuscular injection, or intravenous (IV) administration.

In one aspect, the disclosure features RNAi agents for inhibiting expression of a DUX4 gene, wherein the RNAi agent includes a sense strand (also referred to as a passenger strand) and an antisense strand (also referred to as a guide strand). The sense strand and the antisense strand can be partially, substantially, or fully complementary to each other. The length of the RNAi agent sense strands described herein each can be 15 to 49 nucleotides in length. The length of the RNAi agent antisense strands described herein each can be 17 to 49 nucleotides in length. In some embodiments, the sense and antisense strands are independently 17 to 26 nucleotides in length. The sense and antisense strands can be either the same length or different lengths. In some embodiments, the sense and antisense strands are independently 21 to 26 nucleotides in length. In some embodiments, the sense and antisense strands are independently 21 to 24 nucleotides in length. In some embodiments, both the sense strand and the antisense strand are 21 nucleotides in length. In some embodiments, the antisense strands are independently 17, 18, 19, 20, 21, 22, 23, 24, 25, 26, 27, 28, 29, or 30 nucleotides in length. In some embodiments, the sense strands are independently 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nucleotides in length. The RNAi agents described herein, upon delivery to a cell expressing DUX4 such as a skeletal muscle cell (a skeletal myofiber), inhibit the expression of one or more DUX4 gene transcripts in vivo and/or in vitro.

The DUX4 RNAi agents disclosed herein target a double homeobox 4 (DUX4) gene (see, e.g., SEQ ID NO:1 & SEQ ID NO:2, *Homo sapiens* transcript variant 2). In some embodiments, the RNAi agents disclosed herein target a portion of a DUX4 gene having the sequence of any of the sequences disclosed in Table 1.

In another aspect, the disclosure features pharmaceutical compositions that include one or more of the disclosed DUX4 RNAi agents that are able to selectively and efficiently decrease expression of a DUX4 gene. The pharmaceutical compositions that include one or more DUX4 RNAi agents described herein can be administered to a subject, such as a human or animal subject, for the treatment (including intervention or prophylactic treatment or inhibition) of symptoms and diseases that can be ameliorated at least in part by a reduction in DUX4 protein levels. The pharmaceutical compositions described herein include an RNAi agent capable of inhibiting the expression of a DUX4 gene and at least one pharmaceutically acceptable excipient.

Examples of DUX4 RNAi agent sense strands and antisense strands that can be used in a DUX4 RNAi agent are provided in Tables 3 and Tables 4.1, 4.2, 4.3, 4.4, 4.5, 4.6, and Table 5.4. Examples of DUX4 RNAi agent duplexes are provided in Tables 5.1, 5.2, 5.3, and 5.4. Examples of 19-nucleotide core stretch sequences that may consist of or may be included in the sense strands and antisense strands of certain DUX4 RNAi agents disclosed herein, are provided in Table 2.

One aspect described herein is an RNAi agent for inhibiting expression of a DUX4 gene comprising:
  (i) an antisense strand comprising at least 17 contiguous nucleotides differing by 0 or 1 nucleotides from any one of the sequences provided in Table 3 or Table 5.4; and
  (ii) a sense strand comprising a nucleotide sequence that is at least partially complementary to the antisense strand.

In another aspect described herein is an RNAi agent for inhibiting expression of a DUX4 gene comprising:
  (i) an antisense strand comprising at least 17 contiguous nucleotides differing by 0 or 1 nucleotides from any one of the sequences provided in Table 3 or Table 5.4;
  (ii) a sense strand comprising a nucleotide sequence that is at least partially complementary to the antisense strand;
  (iii) a targeting ligand linked to the sense strand that has affinity for skeletal muscle cells and/or a receptor present on skeletal muscle cells; and
  (iv) a PK/PD modulator linked to the sense strand.

In yet a further aspect described herein is an RNAi agent for inhibiting expression of a DUX4 gene comprising:
  (i) an antisense strand comprising at least 17 contiguous nucleotides differing by 0 or 1 nucleotides from any one of the sequences provided in Table 3 or Table 5.4;
  (ii) a sense strand comprising a nucleotide sequence that is at least partially complementary to the antisense strand;
  (iii) a targeting ligand linked to the sense strand that has affinity for skeletal muscle cells and/or a receptor present on skeletal muscle cells wherein the targeting ligand is linked to the 5' terminal end of the sense strand; and
  (iv) a PK/PD modulator linked to the 3' terminal end of the sense strand.

In another aspect described herein is an RNAi agent for inhibiting expression of a DUX4 gene comprising:
  (i) an antisense strand comprising at least 17 contiguous nucleotides differing by 0 or 1 nucleotides from any one of the sequences provided in Table 3 or Table 5.4;
  (ii) a sense strand comprising a nucleotide sequence that is at least partially complementary to the antisense strand;
  (iii) a targeting ligand that comprises a chemical structure represented in Table 6.2 or 6.3 herein, wherein the targeting ligand is linked to the 5' terminal end of the sense strand; and
  (iv) a PK/PD modulator that comprises a chemical structure represented in Table 6.5 or 6.7 herein, wherein the PK/PD modulator is linked to the 3' terminal end of the sense strand.

In another aspect, the disclosure features methods for delivering DUX4 RNAi agents to skeletal muscle cells in a subject, such as a mammal, e.g., a human subject, in vivo. Also described herein are compositions for use in such methods.

The one or more DUX4 RNAi agents can be delivered to target cells or tissues using any oligonucleotide delivery technology known in the art. In some embodiments, a DUX4 RNAi agent is delivered to cells or tissues by covalently linking the RNAi agent to a targeting group. In some embodiments, the targeting group can include a cell receptor ligand. A targeting group can be linked to the 3' or 5' end of a sense strand or an antisense strand of a DUX4 RNAi agent. In some embodiments, a targeting group is linked to the 3' or 5' end of the sense strand. In some embodiments, a targeting group is linked to the 5' end of the sense strand. In some embodiments, a targeting group is linked internally to a nucleotide on the sense strand and/or the antisense strand of the RNAi agent. In some embodiments, a targeting group is linked to the RNAi agent via a linker. Example targeting ligands that have affinity for skeletal muscle cells and/or receptors present on skeletal muscle cells (e.g., integrin alpha-v-beta-6 (αvβ6)), are shown in Table 6.2 and 6.3 herein. The synthesis and conjugation of certain targeting ligands suitable for use with the DUX4 RNAi agents disclosed herein are shown in Example 1.

In some embodiments, the DUX4 RNAi agents disclosed herein that are conjugated to targeting groups or targeting ligands that direct the RNAi agent to skeletal muscle cells, whereby the RNAi agents can be selectively internalized either through receptor-mediated endocytosis or by other means.

In another aspect, the disclosure features methods for inhibiting DUX4 gene expression in a subject, the methods including administering to the subject an amount of a DUX4 RNAi agent capable of inhibiting the expression of a DUX4 gene, wherein the DUX4 RNAi agent comprises a sense strand and an antisense strand, and wherein the antisense strand includes the sequence of any one of the antisense strand nucleotide sequences in Table 2, Table 3, or Table 5.4.

In a further aspect, the disclosure features methods of treatment (including prophylactic, intervention, or preventative treatment) of diseases or symptoms that can be ameliorated at least in part by a reduction in DUX4 protein levels, the methods comprising administering to a subject in need thereof a DUX4 RNAi agent that includes an antisense strand comprising the sequence of any of the sequences in Table 2, Table 3, or Table 5.4. Pharmaceutical compositions for use in such methods are also described.

In some embodiments, a DUX4 RNAi agent is linked to one or more linking groups or other non-nucleotide groups or compounds, such as pharmacokinetic/pharmacodynamic (PK/PD) modulators. PK/PD modulators can increase circulation time of the conjugated drug and/or increase the activity of the RNAi agent through improved cell receptor binding, improved cellular uptake, and/or other means. Examples of PK/PD modulators suitable for use with the DUX4 RNAi agents disclosed herein can be found in Table 6.5 and 6.7, herein.

In some embodiments, a DUX4 RNAi agent is conjugated to a targeting group, a linking group, a PK/PD modulator, and/or another non-nucleotide group. In some embodiments, a DUX4 RNAi agent is conjugated to a targeting group and a PK/PD modulator.

The use of DUX4 RNAi agents provides methods for therapeutic (including prophylactic or intervention) treatment of diseases or disorders that can be ameliorated at least in part by a reduction in DUX4 protein levels. Described herein are compositions for delivery of DUX4 RNAi agents to skeletal muscle cells to a subject. In some embodiments, the DUX4 RNAi agents disclosed herein are able to reduce DUX4 gene expression in paraspinal, facial, torso, abdominal, and limb muscle tissues of the subject, for example, in the triceps, biceps, quadriceps, pectoralis, gastrocnemius, soleus, masseter, EDL (extensor digitorum longus), TA (Tibialis anterior), trapezius, and/or diaphragm, of the subject.

In some embodiments, methods for the treatment (including prophylactic or intervention treatment) of a pathological state mediated at least in part by DUX4 expression, such as FSHD, are disclosed herein, wherein the methods include administering to a subject a therapeutically effective amount of an RNAi agent that includes a sense strand comprising the sequence of any of the sequences in Table 2, Table 4.1, Table 4.2, Table 4.3, Table 4.4, Table 4.5, Table 4.6, or Table 5.4.

In some embodiments, methods for the treatment (including prophylactic or intervention treatment) of a pathological state mediated at least in part by DUX4 expression are disclosed herein, wherein the methods include administering to a subject a therapeutically effective amount of a DUX4 RNAi agent that includes a sense strand comprising the sequence of any of the sequences in Table 4.1, 4.2, 4.3, 4.4, 4.5, 4.6, or 5.4 herein, and an antisense strand comprising the sequence of any of the sequences in Table 3.

In some embodiments, methods of inhibiting expression of a DUX4 gene are disclosed herein, wherein the methods include administering to a subject a DUX4 RNAi agent that includes a sense strand consisting of the nucleobase sequence of any of the sequences in Table 4.1, 4.2, 4.3, 4.4, 4.5, 4.6, or 5.4 herein, and the antisense strand consisting of the nucleobase sequence of any of the sequences in Table 3 or Table 5.4. In other embodiments, disclosed herein are methods of inhibiting expression of a DUX4 gene, wherein the methods include administering to a subject a DUX4 RNAi agent that includes a sense strand consisting of the modified sequence of any of the modified sequences in Table 4.1, 4.2, 4.3, 4.4, 4.5, 4.6, or Table 5.4 herein, and the antisense strand consisting of the modified sequence of any of the modified sequences in Table 3 or Table 5.4.

In some embodiments, a DUX4 RNAi agent disclosed herein includes an antisense strand that consists of, consists essentially of, or comprises a nucleobase sequence differing by 0 or 1 nucleobases from the nucleotide sequence (5'→3') selected from the group consisting of:

UAGAAUUUCACGGAAGAACAG; (SEQ ID NO: 164)

UGAAACCAGAUCUGAAUCCUG; (SEQ ID NO: 162)

UUGAAACCAGAUCUGAAUCCU; (SEQ ID NO: 163)
and

UUGAAACCAGAUCUGAAUCCC. (SEQ ID NO: 169)

In some embodiments, a DUX4 RNAi agent disclosed herein includes an antisense strand that consists of, consists essentially of, or comprises a nucleotide sequence differing by no more than 1 nucleotide from the nucleotide sequence (5'→3') selected from the group consisting of:

UAGAAUUUCACGGAAGAACAG; (SEQ ID NO: 164)

UGAAACCAGAUCUGAAUCCUG; (SEQ ID NO: 162)

UUGAAACCAGAUCUGAAUCCU; (SEQ ID NO: 163)
and

UUGAAACCAGAUCUGAAUCCC; (SEQ ID NO: 169)

wherein all or substantially all of the nucleotides are modified nucleotides.

In some embodiments, a DUX4 RNAi agent disclosed herein includes an antisense strand that consists of, consists essentially of, or comprises a nucleobase sequence differing by 0 or 1 nucleobases from the nucleotide sequence (5'→3') selected from the group consisting of:

UAGAAUUUCACGGAAGAACAG; (SEQ ID NO: 164)

UGAAACCAGAUCUGAAUCCUG; (SEQ ID NO: 162)

UUGAAACCAGAUCUGAAUCCU; (SEQ ID NO: 163)
and

UUGAAACCAGAUCUGAAUCCC; (SEQ ID NO: 169)

wherein the respective sequence above is located at positions 1-21 (5'→3') of the antisense strand.

In some embodiments, a DUX4 RNAi agent disclosed herein includes an antisense strand that consists of, consists essentially of, or comprises a modified nucleotide sequence differing by no more than 1 nucleotide from the nucleotide sequence (5'→3') selected from the group consisting of:

usAfsGfsAfauuucacGfgAfaGfaacasg; (SEQ ID NO: 82)

cPrpusAfsGfsAfauuucacGfgAfaGfaacasg; (SEQ ID NO: 84)

-continued

```
                                                (SEQ ID NO: 100)
cPrpusAfsgsAfauuucacGfgAfaGfaacasg;

(SEQ ID NO: 101)
cPrpusAfsGfsaauuucacGfgAfaGfaacasg;

(SEQ ID NO: 97)
cPrpusGfsasaaccagauCfuGfaAfuccusg;

(SEQ ID NO: 99)
cPrpusGfsasAfaccagauCfuGfaAfuccusg;

(SEQ ID NO: 75)
cPrpusGfsasAfaCfcAfgAfuCfuGfaAfuCfcUfsg;

(SEQ ID NO: 96)
usGfsasaaccagauCfuGfaAfuccusg;

(SEQ ID NO: 76)
cPrpusUfsgsAfaAfcCfaGfaUfcUfgAfaUfcCfsu;

(SEQ ID NO: 89)
cPrpusUfsgsaaaccagaUfcUfgAfauccsc;

(SEQ ID NO: 87)
cPrpusUfsgsAfaAfcCfaGfaUfcUfgAfaUfcCfsc;
``` wherein a, c, g, and u represent 2′-O-methyl adenosine, cytidine, guanosine, and uridine, respectively; Af, Cf, Gf, and Uf represent 2′-fluoro adenosine, cytidine, guanosine, and uridine, respectively; cPrpu represents a 5′-cyclopropyl phosphonate-2′-O-methyl uridine; and s represents a phosphorothioate linkage; and wherein the sense strand is at least substantially complementary to the antisense strand. As the person of ordinary skill in the art would clearly understand, the inclusion of a phosphorothioate linkage as shown in the modified nucleotide sequences disclosed herein replaces the phosphodiester linkage typically present in oligonucleotides.

In some embodiments, a DUX4 RNAi agent disclosed herein includes:

(i) an antisense strand that consists of, consists essentially of, or comprises the modified nucleotide sequence (5′→3′) usAfsGfsAfauuucacGfgAfaGfaacasg (SEQ ID NO:82), and a sense strand that consists of, consists essentially of, or comprises the modified nucleotide sequence (5′→3′) cuguucuuCfCfGfugaaauucua (SEQ ID NO:149);

(ii) an antisense strand that consists of, consists essentially of, or comprises the modified nucleotide sequence (5′→3′) cPrpusAfsGfsAfauuucacGfgAfaGfaacasg (SEQ ID NO:84), and a sense strand that consists of, consists essentially of, or comprises the modified nucleotide sequence (5′→3′) cuguucuuCfCfGfugaaauucua (SEQ ID NO:149);

(iii) an antisense strand that consists of, consists essentially of, or comprises the modified nucleotide sequence (5′→3′) cPrpusAfsgsAfauuucacGfgAfaGfaacasg (SEQ ID NO:100), and a sense strand that consists of, consists essentially of, or comprises the modified nucleotide sequence (5′→3′) cuguucuuCfCfGfugaaauucua (SEQ ID NO:149);

(iv) an antisense strand that consists of, consists essentially of, or comprises the modified nucleotide sequence (5′→3′) cPrpusAfsGfsaauuucacGfgAfaGfaacasg (SEQ ID NO:101), and a sense strand that consists of, consists essentially of, or comprises the modified nucleotide sequence (5′→3′) cuguucuuCfCfGfugaaauucua (SEQ ID NO:149);

(v) an antisense strand that consists of, consists essentially of, or comprises the modified nucleotide sequence (5′→3′) cPrpusGfsasaaccagauCfuGfaAfuccusg (SEQ ID NO:97), and a sense strand that consists of, consists essentially of, or comprises the modified nucleotide sequence (5′→3′) caggauucAfGfAfucugguuuca (SEQ ID NO:147);

(vi) an antisense strand that consists of, consists essentially of, or comprises the modified nucleotide sequence (5′→3′) cPrpusGfsasAfaccagauCfuGfaAfuccusg (SEQ ID NO:99), and a sense strand that consists of, consists essentially of, or comprises the modified nucleotide sequence (5′→3′) caggauucAfGfAfucugguuuca (SEQ ID NO:147);

(vii) an antisense strand that consists of, consists essentially of, or comprises the modified nucleotide sequence (5′→3′) cPrpusGfsasAfaCfcAfgAfuCfuGfaAfuCfcUfsg (SEQ ID NO:75), and a sense strand that consists of, consists essentially of, or comprises the modified nucleotide sequence (5′→3′) caggauucAfGfAfucugguuuca (SEQ ID NO:147);

(viii) an antisense strand that consists of, consists essentially of, or comprises the modified nucleotide sequence (5′→3′) usGfsasaaccagauCfuGfaAfuccusg (SEQ ID NO:96), and a sense strand that consists of, consists essentially of, or comprises the modified nucleotide sequence (5′→3′) caggauucAfGfAfucugguuuca (SEQ ID NO:147);

(ix) an antisense strand that consists of, consists essentially of, or comprises the modified nucleotide sequence (5′→3′) cPrpusUfsgsAfaAfcCfaGfaUfcUfgAfaUfcCfsu (SEQ ID NO:76), and a sense strand that consists of, consists essentially of, or comprises the modified nucleotide sequence (5′→3′) aggauucaGfAfJfcugguuucaa (SEQ ID NO:148);

(x) an antisense strand that consists of, consists essentially of, or comprises the modified nucleotide sequence (5′→3′) cPrpusUfsgsaaaccagaUfcUfgAfauccsc (SEQ ID NO:89), and a sense strand that consists of, consists essentially of, or comprises the modified nucleotide sequence (5′→3′) gggauucaGfAfLJfcugguuucaa (SEQ ID NO:156); or (xi) an antisense strand that consists of, consists essentially of, or comprises the modified nucleotide sequence (5′→3′) cPrpusUfsgsAfaAfcCfaGfaUfcUfgAfaUfcCfsc (SEQ ID NO:87), and a sense strand that consists of, consists essentially of, or comprises the modified nucleotide sequence (5′→3′) gggauucaGfaUfCfugguuucaa (SEQ ID NO:159);

wherein a, c, g, and u represent 2′-O-methyl adenosine, cytidine, guanosine, and uridine, respectively; Af, Cf, Gf, and Uf represent 2′-fluoro adenosine, cytidine, guanosine, and uridine, respectively; cPrpu represents a 5′-cyclopropyl phosphonate-2′-O-methyl uridine; and s represents a phosphorothioate linkage.

In some embodiments, a DUX4 RNAi agent disclosed herein includes:

(xii) an antisense strand that consists of, consists essentially of, or comprises the modified nucleotide sequence (5′→3′) usAfsGfsAfauuucacGfgAfaGfaacasg (SEQ ID NO:82), and a sense strand that consists of, consists essentially of, or comprises the modified nucleotide sequence (5′→3′) cuguucuuCfCfGfugaaauucua (SEQ ID NO:149);

(xiii) an antisense strand that consists of, consists essentially of, or comprises the modified nucleotide sequence (5′→3′) cPrpusAfsGfsAfauuucacGfgAfaGfaacasg (SEQ ID NO:84), and a sense strand that consists of, consists essentially of, or comprises the modified nucleotide sequence (5'→3') cuguuc-uuCfCfGfugaaauucua (SEQ ID NO:149);

(xiv) an antisense strand that consists of, consists essentially of, or comprises the modified nucleotide sequence (5'→3') cPrpusAfsgsAfauuucacGfgAf-aGfaacasg (SEQ ID NO:100), and a sense strand that consists of, consists essentially of, or comprises the modified nucleotide sequence (5'→3') cuguuc-uuCfCfGfugaaauucua (SEQ ID NO:149);

(xv) an antisense strand that consists of, consists essentially of, or comprises the modified nucleotide sequence (5'→3') cPrpusAfsGfsaauuucacGfgAf-aGfaacasg (SEQ ID NO:101), and a sense strand that consists of, consists essentially of, or comprises the modified nucleotide sequence (5'→3') cuguuc-uuCfCfGfugaaauucua (SEQ ID NO:149);

(xvi) an antisense strand that consists of, consists essentially of, or comprises the modified nucleotide sequence (5'→3') cPrpusGfsasaaccagauCfuGfaAfuc-cusg (SEQ ID NO:97), and a sense strand that consists of, consists essentially of, or comprises the modified nucleotide sequence (5'→3') caggauucAfGfAfucug-guuuca (SEQ ID NO:147);

(xvii) an antisense strand that consists of, consists essentially of, or comprises the modified nucleotide sequence (5'→3') cPrpusGfsasAfaccagauCfuGfaAfuc-cusg (SEQ ID NO:99), and a sense strand that consists of, consists essentially of, or comprises the modified nucleotide sequence (5'→3') caggauucAfGfAfucug-guuuca (SEQ ID NO:147);

(xviii) an antisense strand that consists of, consists essentially of, or comprises the modified nucleotide sequence (5'→3') cPrpusGfsasAfaCfcAfgA-fuCfuGfaAfuCfcUfsg (SEQ ID NO:75), and a sense strand that consists of, consists essentially of, or comprises the modified nucleotide sequence (5'→3') cag-gauucAfGfAfucugguuuca (SEQ ID NO:147);

(xix) an antisense strand that consists of, consists essentially of, or comprises the modified nucleotide sequence (5'→3') usGfsasaaccagauCfuGfaAfuccusg (SEQ ID NO:96), and a sense strand that consists of, consists essentially of, or comprises the modified nucleotide sequence (5'→3') caggauucAfGfAfucug-guuuca (SEQ ID NO:147);

(xx) an antisense strand that consists of, consists essentially of, or comprises the modified nucleotide sequence (5'→3') cPrpusUfsgsAfaAfcCfaGfaUf-cUfgAfaUfcCfsu (SEQ ID NO:76), and a sense strand that consists of, consists essentially of, or comprises the modified nucleotide sequence (5'→3') aggauucaGfAfJfcugguuucaa (SEQ ID NO:148);

(xxi) an antisense strand that consists of, consists essentially of, or comprises the modified nucleotide sequence (5'→3') cPrpusUfsgsaaaccagaUfcUfgAfau-ccsc (SEQ ID NO:89), and a sense strand that consists of, consists essentially of, or comprises the modified nucleotide sequence (5'→3') gggauucaGfAfLJfcug-guuucaa (SEQ ID NO:156); or (xxii) an antisense strand that consists of, consists essentially of, or comprises the modified nucleotide sequence (5'→3') cPrpusUfsgsAfaAfcCfaGfaUf-cUfgAfaUfcCfsc (SEQ ID NO:87), and a sense strand that consists of, consists essentially of, or comprises the modified nucleotide sequence (5'→3') gggauucaGfaUfCfugguuucaa (SEQ ID NO:159);

wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; cPrpu represents a 5'-cyclopropyl phosphonate-2'-O-methyl uridine; s represents a phosphorothioate linkage; and wherein the respective sense strand further includes an inverted abasic residue at the 3' terminal end of the nucleotide sequence and at the 5' terminal end of the nucleotide sequence; and the sense strand also includes a targeting ligand that is covalently linked to the inverted abasic residue at the 5' terminal end of the sense strand, wherein the targeting ligand has affinity for skeletal muscle cells and/or a receptor present on skeletal muscle cells, and wherein the sense strand further includes a PK/PD modulator that is covalently linked to the inverted abasic residue at the 3' terminal end of the sense strand.

In some embodiments, a DUX4 RNAi agent disclosed herein includes an antisense strand that consists of, consists essentially of, or comprises a nucleotide sequence that differs by 0 or 1 nucleotides from one of the following nucleotide sequences (5'→3'):

```
                                      (SEQ ID NO: 164)
         UAGAAUUUCACGGAAGAACAG;

(SEQ ID NO: 162)
         UGAAACCAGAUCUGAAUCCUG;

(SEQ ID NO: 163)
         UUGAAACCAGAUCUGAAUCCU;
         and (SEQ ID NO: 169)
         UUGAAACCAGAUCUGAAUCCC;
``` wherein the DUX4 RNAi agent further includes a sense strand that is at least partially complementary to the antisense strand; and wherein all or substantially all of the nucleotides on both the antisense strand and the sense strand are modified nucleotides.

In some embodiments, a DUX4 RNAi agent disclosed herein includes an antisense strand that consists of, consists essentially of, or comprises a nucleotide sequence that differs by 0 or 1 nucleotides from one of the following nucleotide sequences (5'→3'):

```
                                      (SEQ ID NO: 164)
         UAGAAUUUCACGGAAGAACAG;

(SEQ ID NO: 162)
         UGAAACCAGAUCUGAAUCCUG;

(SEQ ID NO: 163)
         UUGAAACCAGAUCUGAAUCCU;
         and (SEQ ID NO: 169)
         UUGAAACCAGAUCUGAAUCCC;
``` wherein the DUX4 RNAi agent further includes a sense strand that is at least partially complementary to the antisense strand; wherein all or substantially all of the nucleotides on both the antisense strand and the sense strand are modified nucleotides; and wherein the sense strand further includes an inverted abasic residue at both the 3' terminal end of the nucleotide sequence and at the 5' terminal end of the nucleotide sequence, and the sense strand also includes a targeting ligand at the 5' terminal end of the sense strand that is covalently linked to the inverted abasic residue, wherein the targeting ligand has affinity for skeletal muscle cells and/or a receptor present on skeletal muscle cells.

In some embodiments, a DUX4 RNAi agent disclosed herein includes an antisense strand that consists of, consists essentially of, or comprises a nucleotide sequence that differs by 0 or 1 nucleotides from one of the following nucleotide sequences (5'→3'):

```
                                    (SEQ ID NO: 164)
UAGAAUUUCACGGAAGAACAG;

(SEQ ID NO: 162)
UGAAACCAGAUCUGAAUCCUG;

(SEQ ID NO: 163)
UUGAAACCAGAUCUGAAUCCU;
and (SEQ ID NO: 169)
UUGAAACCAGAUCUGAAUCCC;
``` wherein the DUX4 RNAi agent further includes a sense strand that is at least partially complementary to the antisense strand; wherein all or substantially all of the nucleotides on both the antisense strand and the sense strand are modified nucleotides; and wherein the sense strand further includes an inverted abasic residue at both the 3' terminal end of the nucleotide sequence and at the 5' terminal end of the nucleotide sequence, and the sense strand also includes a targeting ligand that is covalently linked to the 5' terminal end, wherein the targeting ligand has affinity for skeletal muscle cells and/or a receptor present on skeletal muscle cells, and the sense strand further includes a PK/PD modulator that is covalently linked to the inverted abasic residue at the 3' terminal end; and wherein the respective antisense strand sequence is located at positions 1-21 of the antisense strand.

In some embodiments, a DUX4 RNAi agent disclosed herein includes an antisense strand and a sense strand, wherein the antisense strand and the sense strand consist of, consist essentially of, or comprise nucleotide sequences that differ by 0 or 1 nucleotides from one of the following nucleotide sequence (5'→3') pairs:

```
                                    (SEQ ID NO: 164)
UAGAAUUUCACGGAAGAACAG;
and (SEQ ID NO: 183)
CUGUUCUUCCGUGAAAUUCUA;
or (SEQ ID NO: 162)
UGAAACCAGAUCUGAAUCCUG;
and (SEQ ID NO: 181)
CAGGAUUCAGAUCUGGUUUCA;
or (SEQ ID NO: 163)
UUGAAACCAGAUCUGAAUCCU;
and (SEQ ID NO: 182)
AGGAUUCAGAUCUGGUUUCAA;
or (SEQ ID NO: 169)
UUGAAACCAGAUCUGAAUCCC;
and (SEQ ID NO: 189)
GGGAUUCAGAUCUGGUUUCAA;
``` wherein all or substantially all of the nucleotides on both the antisense strand and the sense strand are modified nucleotides.

In some embodiments, a DUX4 RNAi agent disclosed herein includes an antisense strand and a sense strand, wherein the antisense strand and the sense strand consist of, consist essentially of, or comprise nucleotide sequences that differ by 0 or 1 nucleotides from one of the following nucleotide sequences 5'→3' airs:

```
                                    (SEQ ID NO: 164)
UAGAAUUUCACGGAAGAACAG;
and (SEQ ID NO: 183)
CUGUUCUUCCGUGAAAUUCUA;
or (SEQ ID NO: 162)
UGAAACCAGAUCUGAAUCCUG;
and (SEQ ID NO: 181)
CAGGAUUCAGAUCUGGUUUCA;
or (SEQ ID NO: 163)
UUGAAACCAGAUCUGAAUCCU;
and (SEQ ID NO: 182)
AGGAUUCAGAUCUGGUUUCAA;
or (SEQ ID NO: 169)
UUGAAACCAGAUCUGAAUCCC;
and (SEQ ID NO: 189)
GGGAUUCAGAUCUGGUUUCAA;
``` wherein all or substantially all of the nucleotides on both the antisense strand and the sense strand are modified nucleotides; and wherein the sense strand further includes inverted abasic residues at the 3' terminal end and at the 5' terminal end of the respective nucleotide sequence, and wherein the sense strand also includes a targeting ligand that is covalently linked to the inverted abasic residue at the 5' terminal end, wherein the targeting ligand has affinity for skeletal muscle cells and/or a receptor present on skeletal muscle cells, and wherein the sense strand also includes a PK/PD modulator covalently linked t the inverted abasic residue at the 3' terminal end.

In some embodiments, a DUX4 RNAi agent disclosed herein includes an antisense strand that consists of, consists essentially of, or comprises a modified nucleotide sequence that differs by 0 or 1 nucleotides from one of the following nucleotide sequences (5'→3'):

```
                                    (SEQ ID NO: 82)
usAfsGfsAfauuucacGfgAfaGfaacasg;

(SEQ ID NO: 84)
cPrpusAfsGfsAfauuucacGfgAfaGfaacasg;

(SEQ ID NO: 100)
cPrpusAfsgsAfauuucacGfgAfaGfaacasg;
```

-continued (SEQ ID NO: 101)
cPrpusAfsGfsaauuucacGfgAfaGfaacasg;

(SEQ ID NO: 97)
cPrpusGfsasaaccagauCfuGfaAfuccusg;

(SEQ ID NO: 99)
cPrpusGfsasAfaccagauCfuGfaAfuccusg;

(SEQ ID NO: 75)
cPrpusGfsasAfaCfcAfgAfuCfuGfaAfuCfcUfsg;

(SEQ ID NO: 96)
usGfsasaaccagauCfuGfaAfuccusg;

(SEQ ID NO: 76)
cPrpusUfsgsAfaAfcCfaGfaUfcUfgAfaUfcCfsu;

(SEQ ID NO: 89)
cPrpusUfsgsaaaccagaUfcUfgAfauccsc;

(SEQ ID NO: 87)
cPrpusUfsgsAfaAfcCfaGfaUfcUfgAfaUfcCfsc;

wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; cPrpu represents a 5'-cyclopropyl phosphonate-2'-O-methyl uridine; and s represents a phosphorothioate linkage; and wherein the DUX4 RNAi agent further includes the sense strand that is at least partially complementary to the antisense strand; and wherein all or substantially all of the nucleotides on the sense strand are modified nucleotides.

In some embodiments, a DUX4 RNAi agent disclosed herein includes an antisense strand that consists of, consists essentially of, or comprises a modified nucleotide sequence that differs by 0 or 1 nucleotides from one of the following nucleotide sequences (5'->3'):

(SEQ ID NO: 82)
usAfsGfsAfauuucacGfgAfaGfaacasg;

(SEQ ID NO: 84)
cPrpusAfsGfsAfauuucacGfgAfaGfaacasg;

(SEQ ID NO: 100)
cPrpusAfsgsAfauuucacGfgAfaGfaacasg;

(SEQ ID NO: 101)
cPrpusAfsGfsaauuucacGfgAfaGfaacasg;

(SEQ ID NO: 97)
cPrpusGfsasaaccagauCfuGfaAfuccusg;

(SEQ ID NO: 99)
cPrpusGfsasAfaccagauCfuGfaAfuccusg;

(SEQ ID NO: 75)
cPrpusGfsasAfaCfcAfgAfuCfuGfaAfuCfcUfsg;

(SEQ ID NO: 96)
usGfsasaaccagauCfuGfaAfuccusg;

(SEQ ID NO: 76)
cPrpusUfsgsAfaAfcCfaGfaUfcUfgAfaUfcCfsu;

(SEQ ID NO: 89)
cPrpusUfsgsaaaccagaUfcUfgAfauccsc;

(SEQ ID NO: 87)
cPrpusUfsgsAfaAfcCfaGfaUfcUfgAfaUfcCfsc;

wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; cPrpu represents a 5'-cyclopropyl phosphonate-2'-O-methyl uridine; and s represents a phosphorothioate linkage; and wherein the DUX4 RNAi agent further includes the sense strand that is at least partially complementary to the antisense strand; and wherein all or substantially all of the nucleotides on the sense strand are modified nucleotides; and wherein the sense strand further includes inverted abasic residues at the 3' terminal end of the nucleotide sequence and at the 5' terminal end of the nucleotide sequence, and the sense strand also includes a targeting ligand that is covalently linked to the inverted abasic residue at the 5' terminal end, wherein the targeting ligand has affinity for skeletal muscle cells and/or a receptor present on skeletal muscle cells, and wherein the sense strand also includes a PK/PD modulator that is covalently linked to the inverted abasic residue at the 3' terminal end.

In some embodiments, a DUX4 RNAi agent disclosed herein includes an antisense strand and a sense strand that consists of, consists essentially of, or comprises modified nucleotide sequences that differs by 0 or 1 nucleotides from one of the following nucleotide sequence pairs (5'→3'):

(SEQ ID NO: 82)
usAfsGfsAfauuucacGfgAfaGfaacasg;
and (SEQ ID NO: 149)
cuguucuuCfCfGfugaaauucua;

(SEQ ID NO: 84)
cPrpusAfsGfsAfauuucacGfgAfaGfaacasg
and (SEQ ID NO: 149)
cuguucuuCfCfGfugaaauucua;

(SEQ ID NO: 100)
cPrpusAfsgsAfauuucacGfgAfaGfaacasg
and (SEQ ID NO: 149)
cuguucuuCfCfGfugaaauucua;

(SEQ ID NO: 101)
cPrpusAfsGfsaauuucacGfgAfaGfaacasg
and (SEQ ID NO: 149)
cuguucuuCfCfGfugaaauucua;
or (SEQ ID NO: 97)
cPrpusGfsasaaccagauCfuGfaAfuccusg
and (SEQ ID NO: 147)
caggauucAfGfAfucugguuuca;

(SEQ ID NO: 99)
cPrpusGfsasAfaccagauCfuGfaAfuccusg
and (SEQ ID NO: 147)
caggauucAfGfAfucugguuuca;

(SEQ ID NO: 75)
cPrpusGfsasAfaCfcAfgAfuCfuGfaAfuCfcUfsg
and (SEQ ID NO: 147)
caggauucAfGfAfucugguuuca;

(SEQ ID NO: 96)
usGfsasaaccagauCfuGfaAfuccusg
and (SEQ ID NO: 147)
caggauucAfGfAfucugguuuca;

(SEQ ID NO: 76)
cPrpusUfsgsAfaAfcCfaGfaUfcUfgAfaUfcCfsu
and (SEQ ID NO: 148)
aggauucaGfAfUfcugguuucaa;

(SEQ ID NO: 89)
cPrpusUfsgsaaaccagaUfcUfgAfauccsc
and (SEQ ID NO: 156)
gggauucaGfAfUfcugguuucaa;

(SEQ ID NO: 87)
cPrpusUfsgsAfaAfcCfaGfaUfcUfgAfaUfcCfsc
and (SEQ ID NO: 159)
gggauucaGfaUfCfugguuucaa;

wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; cPrpu represents a 5'-cyclopropyl phosphonate-2'-O-methyl uridine; and s represents a phosphorothioate linkage.

In some embodiments, a DUX4 RNAi agent disclosed herein includes an antisense strand and a sense strand that consists of, consists essentially of, or comprises one of the following nucleotide sequence pairs (5'→3'):

(SEQ ID NO: 82)
usAfsGfsAfauuucacGfgAfaGfaacasg;
and (SEQ ID NO: 149)
cuguucuuCfCfGfugaaauucua;

(SEQ ID NO: 84)
cPrpusAfsGfsAfauuucacGfgAfaGfaacasg
and (SEQ ID NO: 149)
cuguucuuCfCfGfugaaauucua;

(SEQ ID NO: 100)
cPrpusAfsgsAfauuucacGfgAfaGfaacasg
and (SEQ ID NO: 149)
cuguucuuCfCfGfugaaauucua;

(SEQ ID NO: 101)
cPrpusAfsGfsaauuucacGfgAfaGfaacasg
and (SEQ ID NO: 149)
cuguucuuCfCfGfugaaauucua;
or (SEQ ID NO: 97)
cPrpusGfsasaaccagauCfuGfaAfuccusg
and (SEQ ID NO: 147)
caggauucAfGfAfucugguuuca;

(SEQ ID NO: 99)
cPrpusGfsasAfaccagauCfuGfaAfuccusg
and (SEQ ID NO: 147)
caggauucAfGfAfucugguuuca;

(SEQ ID NO: 75)
cPrpusGfsasAfaCfcAfgAfuCfuGfaAfuCfcUfsg
and (SEQ ID NO: 147)
caggauucAfGfAfucugguuuca;

(SEQ ID NO: 96)
usGfsasaaccagauCfuGfaAfuccusg
and (SEQ ID NO: 147)
caggauucAfGfAfucugguuuca;

(SEQ ID NO: 76)
cPrpusUfsgsAfaAfcCfaGfaUfcUfgAfaUfcCfsu
and (SEQ ID NO: 148)
aggauucaGfAfUfcugguuucaa;

(SEQ ID NO: 89)
cPrpusUfsgsaaaccagaUfcUfgAfauccsc
and (SEQ ID NO: 156)
gggauucaGfAfUfcugguuucaa;

(SEQ ID NO: 87)
cPrpusUfsgsAfaAfcCfaGfaUfcUfgAfaUfcCfsc
and (SEQ ID NO: 159)
gggauucaGfaUfCfugguuucaa;

wherein a, c, g, and u represent 2'-O-methyl adenosine, cytidine, guanosine, and uridine, respectively; Af, Cf, Gf, and Uf represent 2'-fluoro adenosine, cytidine, guanosine, and uridine, respectively; cPrpu represents a 5'-cyclopropyl phosphonate-2'-O-methyl uridine; s represents a phosphorothioate linkage; and wherein the sense strand further includes an inverted abasic residue at the 3' terminal end of the nucleotide sequence and at the 5' terminal end of the nucleotide sequence, and the sense strand also includes a targeting ligand that is covalently linked to the inverted abasic residue at the 5' terminal end, wherein the targeting ligand has affinity for skeletal muscle cells and/or a receptor present on skeletal muscle cells, and wherein the sense strand further includes a PK/PD modulator that is covalently linked to the inverted abasic residue at the 3' terminal end.

In some embodiments, a DUX4 RNAi agent disclosed herein includes an antisense strand that includes a nucleobase sequence that differs by 0 or 1 nucleobases from the nucleotide sequences selected from the group consisting of (5'→3'):

(SEQ ID NO: 22)
UAGAAUUUCACGGAAGAAC;

(SEQ ID NO: 10)
UGAAACCAGAUCUGAAUCC;
and (SEQ ID NO: 14)
UUGAAACCAGAUCUGAAUC;

wherein all or substantially all of the nucleotides are modified nucleotides.

In some embodiments, a DUX4 RNAi agent disclosed herein includes an antisense strand that includes a nucleobase sequence that differs by 0 or 1 nucleobases from the nucleotide sequences selected from the group consisting of (5'→3'):

UAGAAUUUCACGGAAGAAC; (SEQ ID NO: 22)

UGAAACCAGAUCUGAAUCC; (SEQ ID NO: 10)
and

UUGAAACCAGAUCUGAAUC; (SEQ ID NO: 14)

wherein all or substantially all of the nucleotides are modified nucleotides, and wherein the respective sequence is located at nucleotide positions 1-19 (5'→3') of the antisense strand.

In some embodiments, a DUX4 RNAi agent disclosed herein includes an antisense strand and a sense strand that each include a nucleobase sequences that differs by 0 or 1 nucleobases from the nucleotide sequence pairs selected from the group consisting of (5'→3'):

UAGAAUUUCACGGAAGAAC (SEQ ID NO: 22)
and

GUUCUUCCGUGAAAUUCUA; (SEQ ID NO: 50)

UGAAACCAGAUCUGAAUCC (SEQ ID NO: 10)
and

GGAUUCAGAUCUGGUUUCA; (SEQ ID NO: 38)
and

UUGAAACCAGAUCUGAAUC (SEQ ID NO: 14)
and

GAUUCAGAUCUGGUUUCAA; (SEQ ID NO: 42)

and
wherein all or substantially all of the nucleotides are modified nucleotides.

As used herein, the terms "oligonucleotide" and "polynucleotide" mean a polymer of linked nucleosides each of which can be independently modified or unmodified.

As used herein, an "RNAi agent" (also referred to as an "RNAi trigger") means a composition that contains an RNA or RNA-like (e.g., chemically modified RNA) oligonucleotide molecule that is capable of degrading or inhibiting (e.g., degrades or inhibits under appropriate conditions) translation of messenger RNA (mRNA) transcripts of a target mRNA in a sequence specific manner. As used herein, RNAi agents may operate through the RNA interference mechanism (i.e., inducing RNA interference through interaction with the RNA interference pathway machinery (RNA-induced silencing complex or RISC) of mammalian cells), or by any alternative mechanism(s) or pathway(s). While it is believed that RNAi agents, as that term is used herein, operate primarily through the RNA interference mechanism, the disclosed RNAi agents are not bound by or limited to any particular pathway or mechanism of action. RNAi agents disclosed herein are comprised of a sense strand and an antisense strand, and include, but are not limited to: short (or small) interfering RNAs (siRNAs), double stranded RNAs (dsRNA), micro RNAs (miRNAs), short hairpin RNAs (shRNA), and dicer substrates. The antisense strand of the RNAi agents described herein is at least partially complementary to the mRNA being targeted (i.e. DUX4 mRNA). RNAi agents can include one or more modified nucleotides and/or one or more non-phosphodiester linkages.

As used herein, the terms "silence," "reduce," "inhibit," "down-regulate," or "knockdown" when referring to expression of a given gene, mean that the expression of the gene, as measured by the level of RNA transcribed from the gene or the level of polypeptide, protein, or protein subunit translated from the mRNA in a cell, group of cells, tissue, organ, or subject in which the gene is transcribed, is reduced when the cell, group of cells, tissue, organ, or subject is treated with the RNAi agents described herein as compared to a second cell, group of cells, tissue, organ, or subject that has not or have not been so treated.

As used herein, the terms "sequence" and "nucleotide sequence" mean a succession or order of nucleobases or nucleotides, described with a succession of letters using standard nomenclature.

As used herein, a "base," "nucleotide base," or "nucleobase," is a heterocyclic pyrimidine or purine compound that is a component of a nucleotide, and includes the primary purine bases adenine and guanine, and the primary pyrimidine bases cytosine, thymine, and uracil. A nucleobase may further be modified to include, without limitation, universal bases, hydrophobic bases, promiscuous bases, size-expanded bases, and fluorinated bases. (See, e.g., Modified Nucleosides in Biochemistry, Biotechnology and Medicine, Herdewijn, P. ed. Wiley-VCH, 2008). The synthesis of such modified nucleobases (including phosphoramidite compounds that include modified nucleobases) is known in the art.

As used herein, the term "nucleotide" has the same meaning as commonly understood in the art, and thus refers to a glycoside comprising a sugar moiety, a base moiety and a covalently linked group (linkage group), such as a phosphate or phosphorothioate internucleoside linkage group, and covers both naturally occurring nucleotides, such as DNA or RNA, and non-naturally occurring nucleotides comprising modified sugar and/or base moieties, which are also referred to as nucleotide analogs or modified nucleotides herein. Herein, a single nucleotide can be referred to as a monomer or unit.

As used herein, and unless otherwise indicated, the term "complementary," when used to describe a first nucleobase or nucleotide sequence (e.g., RNAi agent sense strand or targeted mRNA) in relation to a second nucleobase or nucleotide sequence (e.g., RNAi agent antisense strand or a single-stranded antisense oligonucleotide), means the ability of an oligonucleotide or polynucleotide including the first nucleotide sequence to hybridize (form base pair hydrogen bonds under mammalian physiological conditions (or otherwise suitable in vivo or in vitro conditions)) and form a duplex or double helical structure under certain standard conditions with an oligonucleotide that includes the second nucleotide sequence. The person of ordinary skill in the art would be able to select the set of conditions most appropriate for a hybridization test. Complementary sequences include Watson-Crick base pairs or non-Watson-Crick base pairs and include natural or modified nucleotides or nucleotide mimics, at least to the extent that the above hybridization requirements are fulfilled. Sequence identity or complementarity is independent of modification. For example, a and Af, as defined herein, are complementary to U (or T) and identical to A for the purposes of determining identity or complementarity.

As used herein, "perfectly complementary" or "fully complementary" means that in a hybridized pair of nucleobase or nucleotide sequence molecules, all (100%) of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, "partially complementary" means that in a hybridized pair of nucleobase or nucleotide sequence molecules, at least 70%, but not all, of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, "substantially complementary" means that in a hybridized pair of nucleobase or nucleotide sequence molecules, at least 85%, but not all, of the bases in a contiguous sequence of a first oligonucleotide will hybridize with the same number of bases in a contiguous sequence of a second oligonucleotide. The contiguous sequence may comprise all or a part of a first or second nucleotide sequence.

As used herein, the terms "complementary," "fully complementary," "partially complementary," and "substantially complementary" are used with respect to the nucleobase or nucleotide matching between the sense strand and the antisense strand of an RNAi agent, or between the antisense strand of an RNAi agent and a sequence of a DUX4 mRNA.

As used herein, the term "substantially identical" or "substantial identity," as applied to a nucleic acid sequence means the nucleotide sequence (or a portion of a nucleotide sequence) has at least about 85% sequence identity or more, e.g., at least 90%, at least 95%, or at least 99% identity, compared to a reference sequence. Percentage of sequence identity is determined by comparing two optimally aligned sequences over a comparison window. The percentage is calculated by determining the number of positions at which the same type of nucleic acid base occurs in both sequences to yield the number of matched positions, dividing the number of matched positions by the total number of positions in the window of comparison and multiplying the result by 100 to yield the percentage of sequence identity. The inventions disclosed herein encompass nucleotide sequences substantially identical to those disclosed herein.

As used herein, the terms "individual", "patient" and "subject", are used interchangeably to refer to a member of any animal species including, but not limited to, birds, humans and other primates, and other mammals including commercially relevant mammals or animal models such as mice, rats, monkeys, cattle, pigs, horses, sheep, cats, and dogs. Preferably, the subject is a human.

As used herein, the terms "treat," "treatment," and the like, mean the methods or steps taken to provide relief from or alleviation of the number, severity, and/or frequency of one or more symptoms of a disease in a subject. As used herein, "treat" and "treatment" may include the prevention, management, prophylactic or intervention treatment, and/or inhibition or reduction of the number, severity, and/or frequency of one or more symptoms of a disease in a subject.

As used herein, the phrase "introducing into a cell," when referring to an RNAi agent, means functionally delivering the RNAi agent into a cell. The phrase "functional delivery," means delivering the RNAi agent to the cell in a manner that enables the RNAi agent to have the expected biological activity, e.g., sequence-specific inhibition of gene expression.

Unless stated otherwise, use of the ⸂ symbol as used herein means that any group or groups may be linked thereto that is in accordance with the scope of the inventions described herein.

As used herein, the term "isomers" refers to compounds that have identical molecular formulae, but that differ in the nature or the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images are termed "enantiomers," or sometimes optical isomers. A carbon atom bonded to four non-identical substituents is termed a "chiral center."

As used herein, unless specifically identified in a structure as having a particular conformation, for each structure in which asymmetric centers are present and thus give rise to enantiomers, diastereomers, or other stereoisomeric configurations, each structure disclosed herein is intended to represent all such possible isomers, including their optically pure and racemic forms. For example, the structures disclosed herein are intended to cover mixtures of diastereomers as well as single stereoisomers.

As used in a claim herein, the phrase "consisting of" excludes any element, step, or ingredient not specified in the claim. When used in a claim herein, the phrase "consisting essentially of" limits the scope of a claim to the specified materials or steps and those that do not materially affect the basic and novel characteristic(s) of the claimed invention.

The person of ordinary skill in the art would readily understand and appreciate that the compounds and compositions disclosed herein may have certain atoms (e.g., N, O, or S atoms) in a protonated or deprotonated state, depending upon the environment in which the compound or composition is placed. Accordingly, as used herein, the structures disclosed herein envisage that certain functional groups, such as, for example, OH, SH, or NH, may be protonated or deprotonated. The disclosure herein is intended to cover the disclosed compounds and compositions regardless of their state of protonation based on the environment (such as pH), as would be readily understood by the person of ordinary skill in the art. Correspondingly, compounds described herein with labile protons or basic atoms should also be understood to represent salt forms of the corresponding compound. Compounds described herein may be in a free acid, free base, or salt form. Pharmaceutically acceptable salts of the compounds described herein should be understood to be within the scope of the invention. A typical pharmaceutically acceptable salt of the disclosed DUX4 RNAi agents is in the form of a sodium salt.

As used herein, the term "linked" or "conjugated" when referring to the connection between two compounds or molecules means that two compounds or molecules are joined by a covalent bond. Unless stated, the terms "linked" and "conjugated" as used herein may refer to the connection between a first compound and a second compound either with or without any intervening atoms or groups of atoms.

As used herein, the term "including" is used to herein mean, and is used interchangeably with, the phrase "including but not limited to." The term "or" is used herein to mean, and is used interchangeably with, the term "and/or," unless the context clearly indicates otherwise.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Where a value is explicitly recited, it is to be understood that values which are about the same quantity or amount as the recited value are also within the scope of the disclosure. Where a combination is disclosed, each sub-combination of the elements of that combination is also specifically disclosed and is within the scope of the disclosure. Conversely, where different elements or groups of elements are individually disclosed, combinations thereof are also disclosed. Where any element of a disclosure is disclosed as having a plurality of alternatives, examples of that disclosure in which each alternative is excluded singly or in any combination with the other alternatives are also hereby disclosed; more than one element of a disclosure can have such exclusions, and all combinations of elements having such exclusions are hereby disclosed.

Other objects, features, aspects, and advantages of the invention will be apparent from the following detailed description, accompanying figures, and from the claims.

BRIEF DESCRIPTION OF THE DRAWINGS

FIG. 15A. Schematic diagram of the modified sense and antisense strands of the DUX4 RNAi agent conjugate having the structure of AC000232 (see, e.g., Table 5.4), having an avb6-SM45b targeting ligand linked via an L4 linker to the ($NH_2$-$C_6$) linking group at the 5' end of the sense strand, and having a PK/PD modulator with the structure of LP1b linked via the C6-SS-C6 linker at the 3' end of the sense strand. (See, e.g., Examples 1 and 3 herein).

Figure 1:
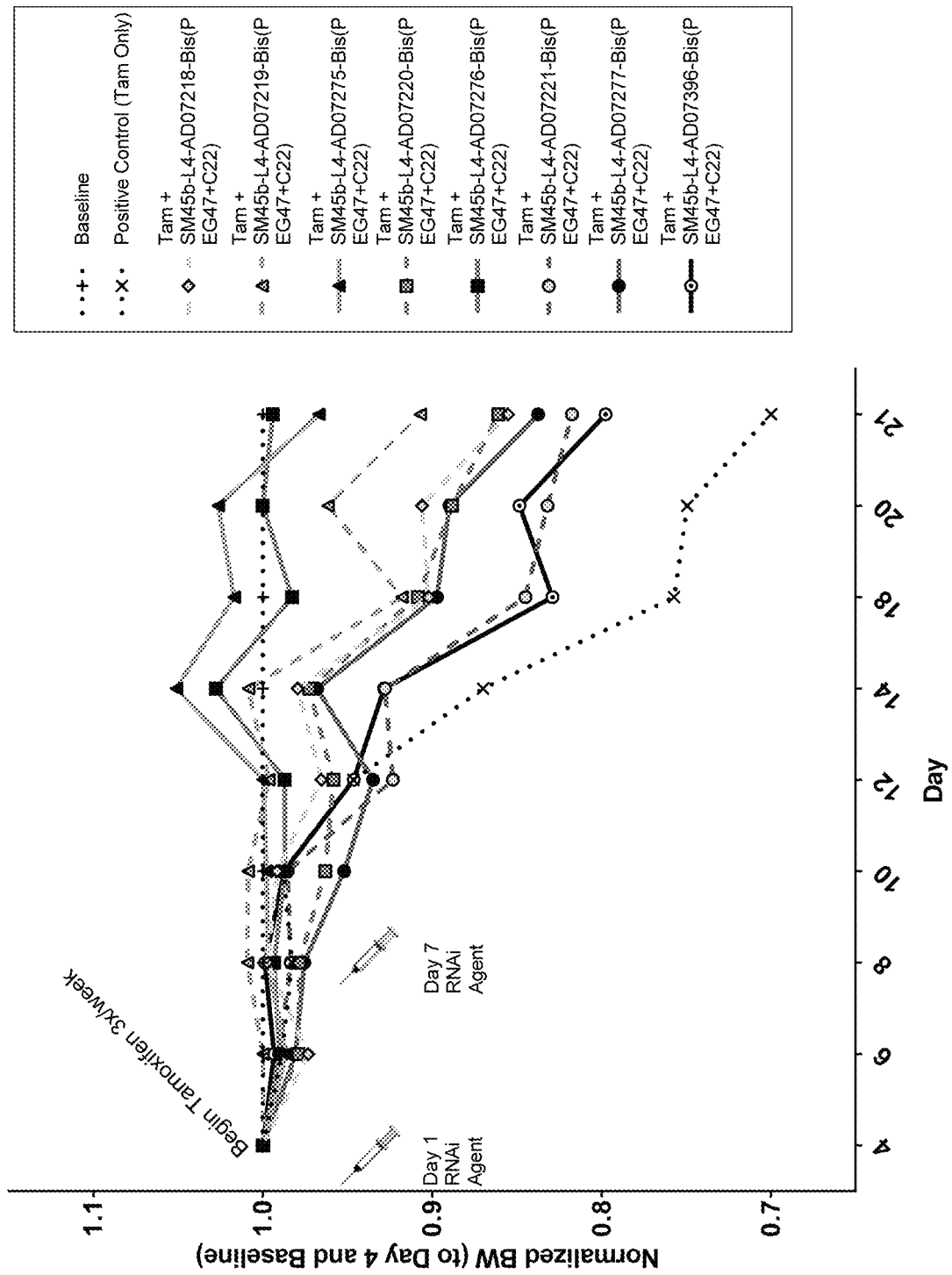
FIG. 1. Graph depicting mean bodyweights of FSHD-like model mice, as more fully described in Example 3.

The following abbreviations are used in FIGS. 15A to 15I: a, c, g, and u are 2'-O-methyl modified nucleotides; Af, Cf, Gf, and Uf are 2'-fluoro modified nucleotides; o is a phosphodiester linkage; s is a phosphorothioate linkage; invAb is an inverted abasic residue (see, e.g., Table 6.1); cPrpu is a 5'-cyclopropyl phosphonate-2'-O-methyluridine modified nucleotide (see, e.g., Table 6.1); avb6-SM45b is the small molecule targeting ligand of SM45b (see, e.g., Table 6.3); -L4- is the linker having the structure as described in Example 3; avb6-pep1 is the avb6 peptide 1 targeting ligand (see, e.g., Table 6.3); -C6-S- is the linking group as shown in Table 6.1; (NH—C6) is the linking group as shown in Table 6.1; and LP1b, LP29b, and LP38b are, each respectively, the PK/PD modulators having the structures as described in Table 6.7 herein. (See also, Examples 1 and 3 herein).

Figures 15A, 15B, 15C:
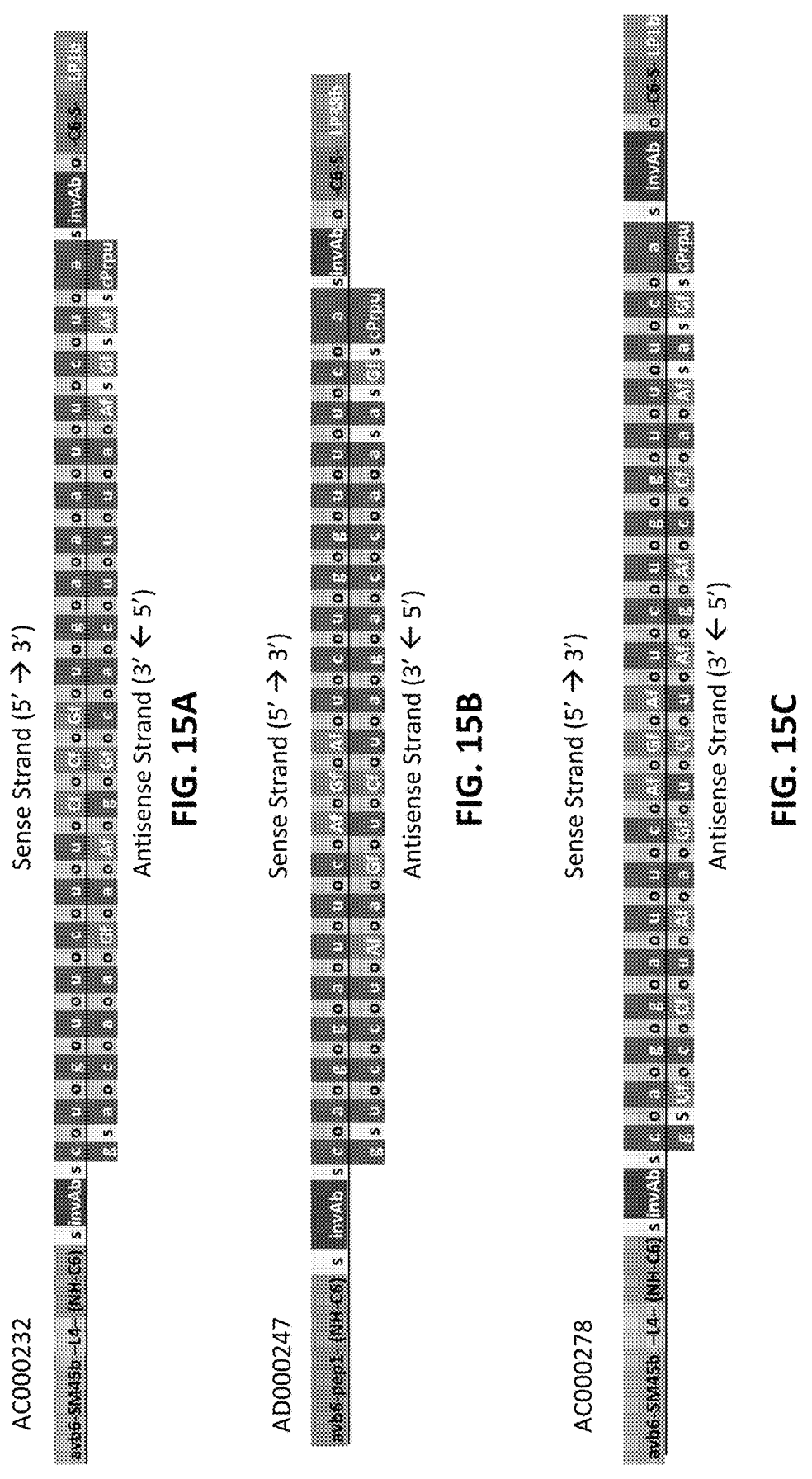

FIG. 15B. Schematic diagram of the modified sense and antisense strands of the DUX4 RNAi agent conjugate having the structure of AC000247 (see, e.g., Table 5.4), shown having an avb6-peptide 1 targeting ligand linked to the ($NH_2$-$C_6$) linking group at the 5' end of the sense strand, and with the PK/PD modulator having the structure of LP38b linked to the C6-SS-C6 linker at the 3' end of the sense strand (See, e.g., Examples 1 and 3 herein).

FIG. 15C. Schematic diagram of the modified sense and antisense strands of the DUX4 RNAi agent conjugate having the structure of AC000278 (see, e.g., Table 5.4), having an avb6-SM45b targeting ligand linked via an L4 linker to the ($NH_2$-$C_6$) linking group at the 5' end of the sense strand, and having a PK/PD modulator with the structure of LP1b linked via the C6-SS-C6 linker at the 3' end of the sense strand. (See, e.g., Examples 1 and 3 herein).

Figures 15D, 15E, 15F:
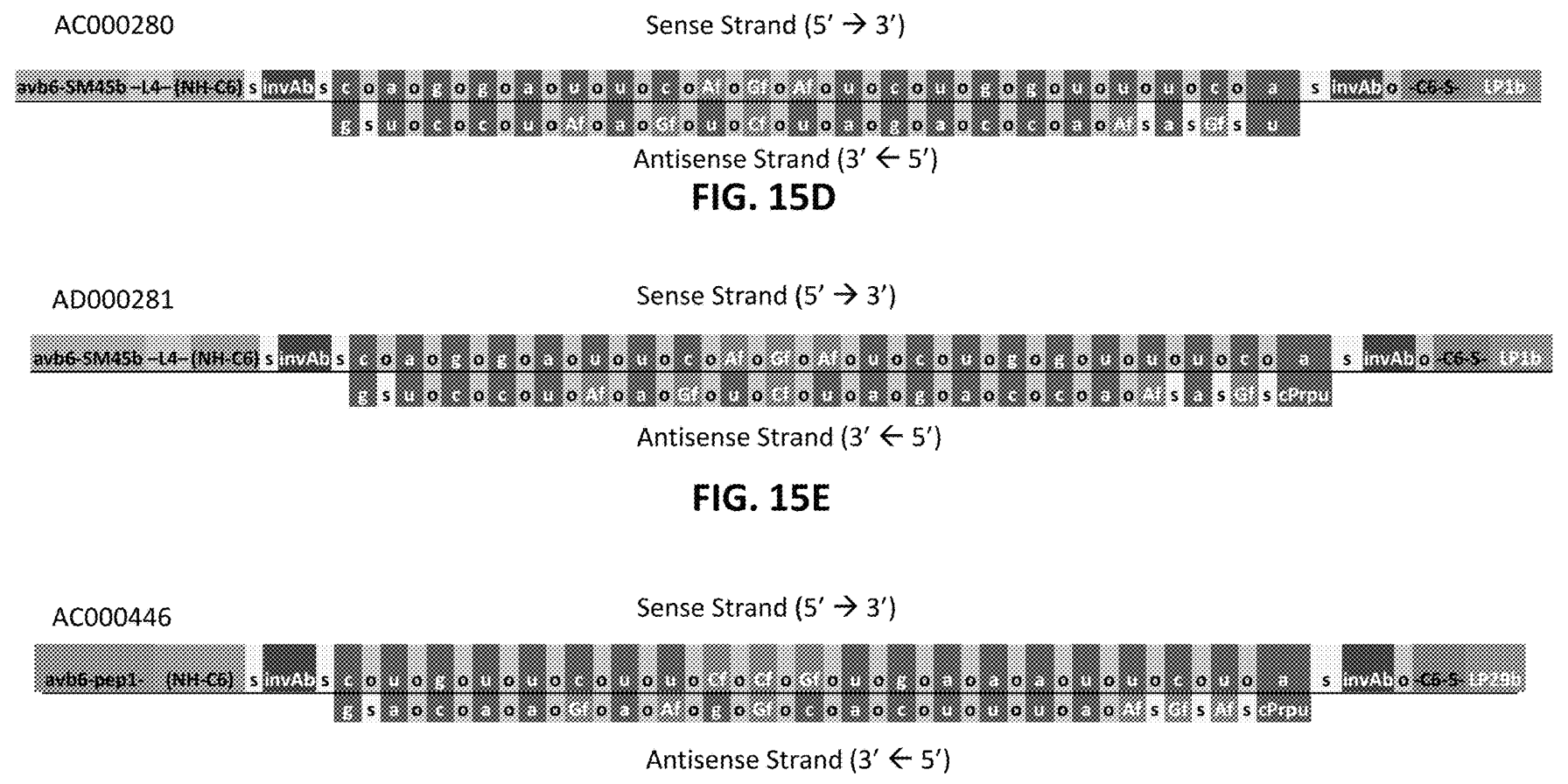

FIG. 15D. Schematic diagram of the modified sense and antisense strands of the DUX4 RNAi agent conjugate having the structure of AC0000280 (see, e.g., Table 5.4), having an avb6-SM45b targeting ligand linked via an L4 linker to the ($NH_2$-$C_6$) linking group at the 5' end of the sense strand, and having a PK/PD modulator with the structure of LP1b linked via the C6-SS-C6 linker at the 3' end of the sense strand. (See, e.g., Examples 1 and 3 herein)

FIG. 15E. Schematic diagram of the modified sense and antisense strands of the DUX4 RNAi agent conjugate having the structure of AC0000281 (see, e.g., Table 5.4), having an avb6-SM45b targeting ligand linked via an L4 linker to the ($NH_2$-$C_6$) linking group at the 5' end of the sense strand, and having a PK/PD modulator with the structure of LP1b linked via the C6-SS-C6 linker at the 3' end of the sense strand. (See, e.g., Examples 1 and 3 herein)

FIG. 15F. Schematic diagram of the modified sense and antisense strands of the DUX4 RNAi agent conjugate having the structure of AC000446 (see, e.g., Table 5.4), shown having an avb6-peptide 1 targeting ligand linked to the ($NH_2$-$C_6$) linking group at the 5' end of the sense strand, and with the PK/PD modulator having the structure of LP29b linked to the C6-SS-C6 linker at the 3' end of the sense strand (See, e.g., Examples 1 and 3 herein).

Figures 15G, 15H, 15I:
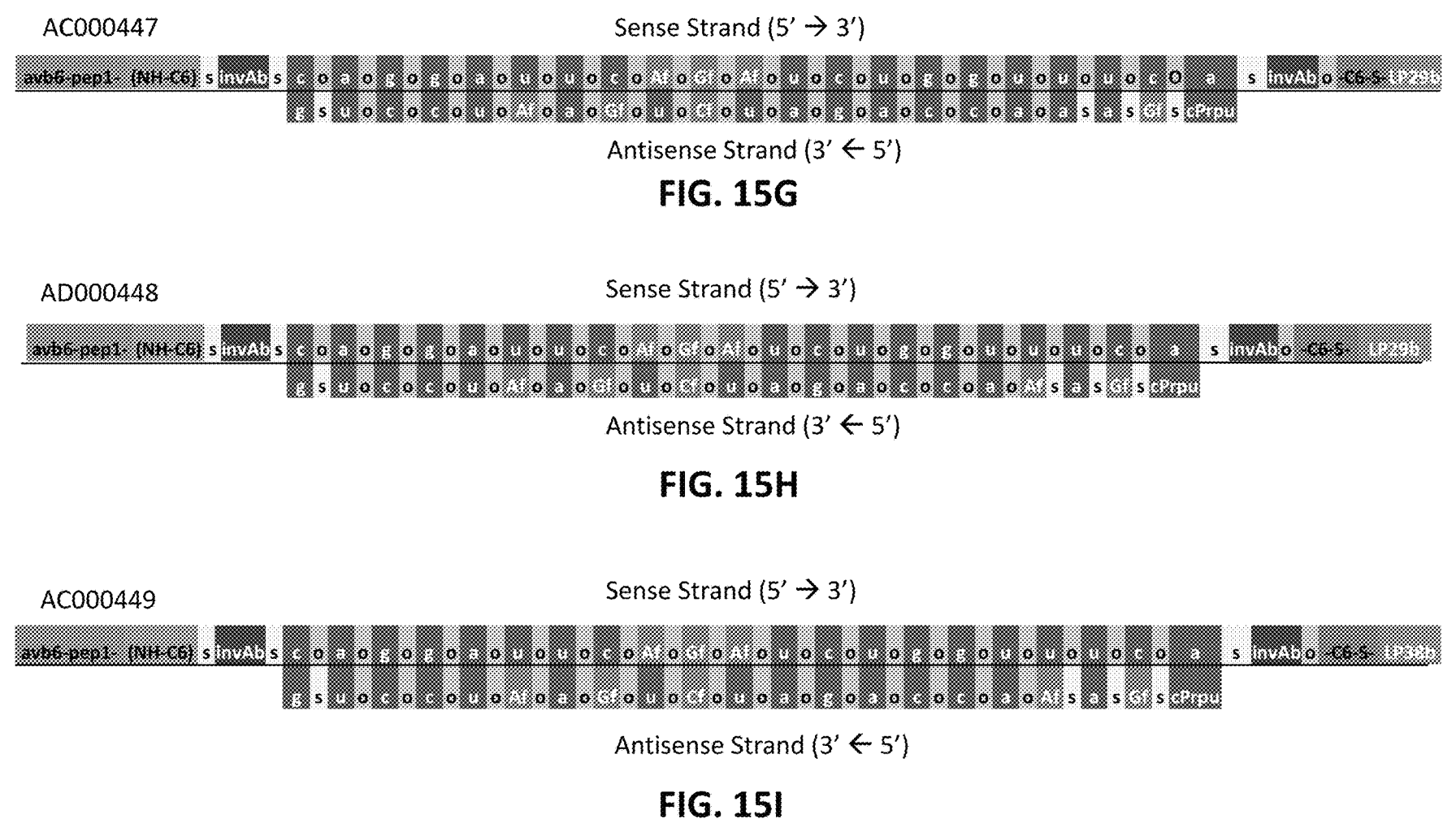

FIG. 15G. Schematic diagram of the modified sense and antisense strands of the DUX4 RNAi agent conjugate having the structure of AC000447 (see, e.g., Table 5.4), shown having an avb6-peptide 1 targeting ligand linked to the ($NH_2$-$C_6$) linking group at the 5' end of the sense strand, and with the PK/PD modulator having the structure of LP29b linked to the C6-SS-C6 linker at the 3' end of the sense strand (See, e.g., Examples 1 and 3 herein).

FIG. 15H. Schematic diagram of the modified sense and antisense strands of the DUX4 RNAi agent conjugate having the structure of AC000448 (see, e.g., Table 5.4), shown having an avb6-peptide 1 targeting ligand linked to the ($NH_2$-$C_6$) linking group at the 5' end of the sense strand, and with the PK/PD modulator having the structure of LP29b linked to the C6-SS-C6 linker at the 3' end of the sense strand (See, e.g., Examples 1 and 3 herein).

FIG. 15I. Schematic diagram of the modified sense and antisense strands of the DUX4 RNAi agent conjugate having the structure of AC000449 (see, e.g., Table 5.4), shown having an avb6-peptide 1 targeting ligand linked to the ($NH_2$-$C_6$) linking group at the 5' end of the sense strand, and with the PK/PD modulator having the structure of LP28b linked to the C6-SS-C6 linker at the 3' end of the sense strand (See, e.g., Examples 1 and 3 herein).

FIG. 16A through FIG. 16E. Chemical structure representation of DUX4 RNAi agent conjugate of AC000446 (see, e.g., Table 5.4), shown in a free acid form.

FIG. 17A through FIG. 17E. Chemical structure representation of DUX4 RNAi agent conjugate having the structure of AC0000446 (see, e.g., Table 5.4), shown in a sodium salt form.

FIG. 18A through FIG. 18E. Chemical structure representation of DUX4 RNAi agent conjugate of AC000448 (see, e.g., Table 5.4), shown in a free acid form.

FIG. 19A through FIG. 19E. Chemical structure representation of DUX4 RNAi agent conjugate having the structure of AC0000448 (see, e.g., Table 5.4), shown in a sodium salt form.

FIG. 20A through FIG. 20E. Chemical structure representation of DUX4 RNAi agent conjugate of AC000449 (see, e.g., Table 5.4), shown in a free acid form.

FIG. 21A through FIG. 21E. Chemical structure representation of DUX4 RNAi agent conjugate having the structure of AC0000449 (see, e.g., Table 5.4), shown in a sodium salt form.

DETAILED DESCRIPTION

Described herein are RNAi agents for inhibiting expression of a DUX4 gene (referred to herein as DUX4 RNAi agents or DUX4 RNAi triggers). Each DUX4 RNAi agent comprises a sense strand and an antisense strand. The sense strand can be 15 to 49 nucleotides in length. The antisense strand each can be 17 to 49 nucleotides in length. The sense and antisense strands can be either the same length or they can be different lengths. In some embodiments, the sense and antisense strands are each independently 17 to 27 nucleotides in length. In some embodiments, the sense and antisense strands are each independently 19-21 nucleotides in length. In some embodiments, both the sense and antisense strands are each 21-26 nucleotides in length. In some embodiments, the sense and antisense strands are each 21-24 nucleotides in length. In some embodiments, the sense strand is about 19 nucleotides in length while the antisense strand is about 21 nucleotides in length. In some embodiments, the sense strand is about 21 nucleotides in length while the antisense strand is about 23 nucleotides in length. In some embodiments, a sense strand is 23 nucleotides in length and an antisense strand is 21 nucleotides in length. In some embodiments, both the sense and antisense strands are each 21 nucleotides in length. In some embodiments, the RNAi agent sense strands are 15, 16, 17, 18, 19, 20, 21, 22, 23, 24, 25, 26, 27, 28, 29, 30, 31, 32, 33, 34, 35, 36, 36, 38, 39, 40, 41, 42, 43, 44, 45, 46, 47, 48, or 49 nucleotides in length. In some embodiments, the RNAi agent antisense strands are 17, 18, 19, 20, 21, 22, 23, 24, 25, 26, 27, 28, 29, or 30 nucleotides in length. In some embodiments, a double-stranded RNAi agent has a duplex length of about 15, 16, 17, 18, 19, 20, 21, 22, 23 or 24 nucleotides.

Examples of nucleotide sequences used in forming DUX4 RNAi agents are provided in Tables 2, 3, 4.1, 4.2, 4.3, 4.4, 4.5, 4.6, and 5.4. Examples of RNAi agent duplexes, that include the sense strand and antisense strand sequences in Tables 2, 3, 4.1, 4.2, 4.3, 4.4, 4.5, 4.6, are shown in Tables 5.1, 5.2, 5.3, and 5.4.

In some embodiments, the region of perfect, substantial, or partial complementarity between the sense strand and the antisense strand (sometimes referred to the "duplex region") is 12-26 (e.g., 12, 13, 14, 15, 16, 17, 18, 19, 20, 21, 22, 23, 24, 25, or 26) nucleotides in length and occurs at or near the 5' end of the antisense strand (e.g., this region may be separated from the 5' end of the antisense strand by 0, 1, 2, 3, or 4 nucleotides that are not perfectly, substantially, or partially complementary).

A sense strand of the DUX4 RNAi agents described herein includes at least 12 consecutive nucleotides that have at least 85% identity to a core stretch sequence (also referred to herein as a "core stretch" or "core sequence") of the same number of nucleotides in a DUX4 mRNA. In some embodiments, a sense strand core stretch sequence is 100% (perfectly) complementary or at least about 85% (substantially) complementary to a core stretch sequence in the antisense strand, and thus the sense strand core stretch sequence is typically perfectly identical or at least about 85% identical to a nucleotide sequence of the same length (sometimes referred to, e.g., as a target sequence) present in the DUX4 mRNA target. In some embodiments, this sense strand core stretch is 12, 13, 14, 15, 16, 17, 18, 19, 20, 21, 22, or 23 nucleotides in length. In some embodiments, this sense strand core stretch is 17 nucleotides in length. In some embodiments, this sense strand core stretch is 19 nucleotides in length. In some embodiments, this sense strand core stretch is 21 nucleotides in length.

An antisense strand of a DUX4 RNAi agent described herein includes at least 17 consecutive nucleotides that have at least 85% complementarity to a core stretch of the same number of nucleotides in a DUX4 mRNA, and in some embodiments, to a core stretch of the same number of nucleotides in the corresponding sense strand. In some embodiments, an antisense strand core stretch is 100% (perfectly) complementary or at least about 85% (substantially) complementary to a nucleotide sequence (e.g., target sequence) of the same length present in the DUX4 mRNA target. In some embodiments, this antisense strand core stretch is 17, 18, 19, 20, 21, 22, or 23 nucleotides in length. In some embodiments, this antisense strand core stretch is 19 nucleotides in length. In some embodiments, this antisense strand core stretch is 17 nucleotides in length. In some embodiments, this antisense strand core stretch is 21 nucleotides in length. In some embodiments, this antisense strand core stretch is 23 nucleotides in length. A sense strand core stretch sequence can be the same length as a corresponding antisense core sequence or it can be a different length.

The DUX4 RNAi agent sense and antisense strands anneal to form a duplex. A sense strand and an antisense strand of a DUX4 RNAi agent can be partially, substantially, or fully complementary to each other. Within the complementary duplex region, the sense strand core stretch sequence is at least 85% complementary or 100% complementary to the antisense core stretch sequence. In some embodiments, the sense strand core stretch sequence contains a sequence of at least 16, at least 17, at least 18, at least 19, at least 20, at least 21, at least 22, or at least 23 nucleotides that is at least 85% or 100% complementary to a corresponding 16, 17, 18, 19, 20, 21, 22, or 23 nucleotide sequence of the antisense strand core stretch sequence (i.e., the sense and antisense core stretch sequences of a DUX4 RNAi agent have a region of at least 16, at least 17, at least 18, at least 19, at least 20, at least 21, at least 22, or at least 23 nucleotides that is at least 85% base paired or 100% base paired.)

In some embodiments, the antisense strand of a DUX4 RNAi agent disclosed herein differs by 0, 1, 2, or 3 nucleotides from any of the antisense strand sequences in Table 2, Table 3, or Table 5.4.

In some embodiments, the sense strand of a DUX4 RNAi agent disclosed herein differs by 0, 1, 2, or 3 nucleotides from any of the sense strand sequences in Table 2 or Table 4.1, or Table 4.2, or Table 4.3, or Table 4.4, or Table 4.5, Table 4.6, or Table 5.4.

In some embodiments, the sense strand and/or the antisense strand can optionally and independently contain an additional 1, 2, 3, 4, 5, or 6 nucleotides (extension) at the 3' end, the 5' end, or both the 3' and 5' ends of the core stretch sequences. The antisense strand additional nucleotides, if present, may or may not be complementary to the corresponding sequence in the DUX4 mRNA. The sense strand additional nucleotides, if present, may or may not be identical to the corresponding sequence in the DUX4 mRNA. The antisense strand additional nucleotides, if present, may or may not be complementary to the corresponding sense strand's additional nucleotides, if present.

As used herein, an extension comprises 1, 2, 3, 4, 5, or 6 nucleotides at the 5' and/or 3' end of the sense strand core stretch sequence and/or antisense strand core stretch sequence. The extension nucleotides on a sense strand may or may not be complementary to nucleotides, either core stretch sequence nucleotides or extension nucleotides, in the corresponding antisense strand. Conversely, the extension nucleotides on an antisense strand may or may not be complementary to nucleotides, either core stretch nucleotides or extension nucleotides, in the corresponding sense strand. In some embodiments, both the sense strand and the antisense strand of an RNAi agent contain 3' and 5' extensions. In some embodiments, one or more of the 3' extension nucleotides of one strand base pairs with one or more 5' extension nucleotides of the other strand. In other embodiments, one or more of 3' extension nucleotides of one strand do not base pair with one or more 5' extension nucleotides of the other strand. In some embodiments, a DUX4 RNAi agent has an antisense strand having a 3' extension and a sense strand having a 5' extension. In some embodiments, the extension nucleotide(s) are unpaired and form an overhang. As used herein, an "overhang" refers to a stretch of one or more unpaired nucleotides located at a terminal end of either the sense strand or the antisense strand that does not form part of the hybridized or duplexed portion of an RNAi agent disclosed herein.

In some embodiments, a DUX4 RNAi agent comprises an antisense strand having a 3' extension of 1, 2, 3, 4, 5, or 6 nucleotides in length. In other embodiments, a DUX4 RNAi agent comprises an antisense strand having a 3' extension of 1, 2, or 3 nucleotides in length. In some embodiments, one or more of the antisense strand extension nucleotides comprise nucleotides that are complementary to the corresponding DUX4 mRNA sequence. In some embodiments, one or more of the antisense strand extension nucleotides comprise nucleotides that are not complementary to the corresponding DUX4 mRNA sequence.

In some embodiments, a DUX4 RNAi agent comprises a sense strand having a 3' extension of 1, 2, 3, 4, or 5 nucleotides in length. In some embodiments, one or more of the sense strand extension nucleotides comprises adenosine, uracil, or thymidine nucleotides, AT dinucleotide, or nucleotides that correspond to or are the identical to nucleotides in the DUX4 mRNA sequence. In some embodiments, the 3' sense strand extension includes or consists of one of the following sequences, but is not limited to: T, UT, TT, UU, UUT, TTT, or TTTT (each listed 5' to 3').

A sense strand can have a 3' extension and/or a 5' extension. In some embodiments, a DUX4 RNAi agent comprises a sense strand having a 5' extension of 1, 2, 3, 4, 5, or 6 nucleotides in length. In some embodiments, one or more of the sense strand extension nucleotides comprise nucleotides that correspond to or are identical to nucleotides in the DUX4 mRNA sequence. In some embodiments, the sense strand 5' extension is one of the following sequences, but is not limited to: CA, AUAGGC, AUAGG, AUAG, AUA, A, AA, AC, GCA, GGCA, GGC, UAUCA, UAUC, UCA, UAU, U, UU (each listed 5' to 3').

Examples of sequences used in forming DUX4 RNAi agents are provided in Tables 2, 3, and 4.1, 4.2, 4.3, 4.4, 4.5, 4.6, and 5.4. In some embodiments, a DUX4 RNAi agent antisense strand includes a sequence of any of the sequences in Tables 2 or 3. In certain embodiments, a DUX4 RNAi agent antisense strand comprises or consists of any one of the modified sequences in Table 3 or Table 5.4. In some embodiments, a DUX4 RNAi agent antisense strand includes the sequence of nucleotides (from 5' end→3' end) 1-17, 2-15, 2-17, 1-18, 2-18, 1-19, 2-19, 1-20, 2-20, 1-21, or 2-21, of any of the sequences in Tables 2, 3, or 5.4. In some embodiments, a DUX4 RNAi agent sense strand includes the sequence of any of the sequences in Tables 2 or 4. In some embodiments, a DUX4 RNAi agent sense strand includes the sequence of nucleotides (from 5' end→3' end) 1-18, 1-19, 1-20, 1-21, 2-19, 2-20, 2-21, 3-20, 3-21, or 4-21 of any of the sequences in Tables 2, 4.1, 4.2, 4.3, 4.4, 4.5, 4.6, or 5.4. In certain embodiments, a DUX4 RNAi agent sense strand comprises or consists of a modified sequence of any one of the modified sequences in Table 4.1, Table 4.2, Table 4.3, Table 4.4, Table 4.5, Table 4.6, or Table 5.4.

In some embodiments, the sense and antisense strands of the RNAi agents described herein contain the same number of nucleotides. In some embodiments, the sense and antisense strands of the RNAi agents described herein contain different numbers of nucleotides. In some embodiments, the sense strand 5' end and the antisense strand 3' end of an RNAi agent form a blunt end. In some embodiments, the sense strand 3' end and the antisense strand 5' end of an RNAi agent form a blunt end. In some embodiments, both ends of an RNAi agent form blunt ends. In some embodiments, neither end of an RNAi agent is blunt-ended. As used herein a "blunt end" refers to an end of a double stranded RNAi agent in which the terminal nucleotides of the two annealed strands are complementary (form a complementary base-pair).

In some embodiments, the sense strand 5' end and the antisense strand 3' end of an RNAi agent form a frayed end. In some embodiments, the sense strand 3' end and the antisense strand 5' end of an RNAi agent form a frayed end. In some embodiments, both ends of an RNAi agent form a frayed end. In some embodiments, neither end of an RNAi agent is a frayed end. As used herein a frayed end refers to an end of a double stranded RNAi agent in which the terminal nucleotides of the two annealed strands from a pair (i.e., do not form an overhang) but are not complementary (i.e. form a non-complementary pair). In some embodiments, one or more unpaired nucleotides at the end of one strand of a double stranded RNAi agent form an overhang. The unpaired nucleotides may be on the sense strand or the antisense strand, creating either 3' or 5' overhangs. In some embodiments, the RNAi agent contains: a blunt end and a frayed end, a blunt end and 5' overhang end, a blunt end and a 3' overhang end, a frayed end and a 5' overhang end, a frayed end and a 3' overhang end, two 5' overhang ends, two 3' overhang ends, a 5' overhang end and a 3' overhang end, two frayed ends, or two blunt ends. Typically, when present, overhangs are located at the 3' terminal ends of the sense strand, the antisense strand, or both the sense strand and the antisense strand.

The DUX4 RNAi agents disclosed herein may also be comprised of one or more modified nucleotides. In some embodiments, substantially all of the nucleotides of the sense strand and substantially all of the nucleotides of the antisense strand of the DUX4 RNAi agent are modified nucleotides. The DUX4 RNAi agents disclosed herein may further be comprised of one or more modified internucleoside linkages, e.g., one or more phosphorothioate or phosphorodithioates linkages. In some embodiments, a DUX4 RNAi agent contains one or more modified nucleotides and one or more modified internucleoside linkages. In some embodiments, a 2'-modified nucleotide is combined with modified internucleoside linkage.

In some embodiments, a DUX4 RNAi agent is prepared or provided as a salt, mixed salt, or a free-acid. In some embodiments, a DUX4 RNAi agent is prepared as a sodium salt. Such forms that are well known in the art are within the scope of the inventions disclosed herein.

Modified Nucleotides

Modified nucleotides, when used in various oligonucleotide constructs, can preserve activity of the compound in cells while at the same time increasing the serum stability of these compounds, and can also minimize the possibility of activating interferon activity in humans upon administering of the oligonucleotide construct.

In some embodiments, a DUX4 RNAi agent contains one or more modified nucleotides. As used herein, a "modified nucleotide" is a nucleotide other than a ribonucleotide (2'-hydroxyl nucleotide). In some embodiments, at least 50% (e.g., at least 60%, at least 70%, at least 80%, at least 90%, at least 95%, at least 97%, at least 98%, at least 99%, or 100%) of the nucleotides are modified nucleotides. As used herein, modified nucleotides can include, but are not limited to, deoxyribonucleotides, nucleotide mimics, abasic nucleotides, 2'-modified nucleotides, inverted nucleotides, modified nucleobase-comprising nucleotides, bridged nucleotides, peptide nucleic acids (PNAs), 2',3'-seco nucleotide mimics (unlocked nucleobase analogues), locked nucleotides, 3'-O-methoxy (2' internucleoside linked) nucleotides, 2'-F-Arabino nucleotides, 5'-Methyl, 2'-fluoro nucleotides, morpholino nucleotides, vinyl phosphonate-containing nucleotides, and cyclopropyl phosphonate-containing nucleotides. 2'-modified nucleotides (i.e., a nucleotide with a group other than a hydroxyl group at the 2' position of the five-membered sugar ring) include, but are not limited to, 2'-O-methyl nucleotides (also referred to as 2'-methoxy nucleotides), 2'-fluoro nucleotides (also referred to herein as 2'-deoxy-2'-fluoro nucleotides), 2'-deoxy nucleotides, 2'-methoxyethyl (2'-O-(2-methoxylethyl)) nucleotides (also referred to as 2'-MOE), 2'-amino nucleotides, and 2'-alkyl nucleotides. It is not necessary for all positions in a given compound to be uniformly modified. Conversely, more than one modification can be incorporated in a single DUX4 RNAi agent or even in a single nucleotide thereof. The DUX4 RNAi agent sense strands and antisense strands can be synthesized and/or modified by methods known in the art. Modification at one nucleotide is independent of modification at another nucleotide. Various modified nucleotides are well known and described in the art.

Modified nucleobases include synthetic and natural nucleobases, such as 5-substituted pyrimidines, 6-azapyrimidines and N-2, N-6 and 0-6 substituted purines, (e.g., 2-aminopropyladenine, 5-propynyluracil, or 5-propynylcytosine), 5-methylcytosine (5-me-C), 5-hydroxymethyl cytosine, xanthine, 2-aminoadenine, 6-alkyl (e.g., 6-methyl, 6-ethyl, 6-isopropyl, or 6-n-butyl) derivatives of adenine and guanine, 2-alkyl (e.g., 2-methyl, 2-ethyl, 2-isopropyl, or 2-n-butyl) and other alkyl derivatives of adenine and guanine, 2-thiouracil, 2-thiothymine, 2-thiocytosine, 5-halouracil, cytosine, 5-propynyl uracil, 5-propynyl cytosine, 6-azo uracil, 6-azo cytosine, 6-azo thymine, 5-uracil (pseudouracil), 4-thiouracil, 8-halo, 8-amino, 8-sulfhydryl, 8-thioalkyl, 8-hydroxyl and other 8-substituted adenines and guanines, 5-halo (e.g., 5-bromo), 5-trifluoromethyl, and other 5-substituted uracils and cytosines, 7-methylguanine and 7-methyladenine, 8-azaguanine and 8-azaadenine, 7-deazaguanine, 7-deazaadenine, 3-deazaguanine, and 3-deazaadenine.

In some embodiments, the 5' and/or 3' end of the antisense strand can include abasic residues (Ab), which can also be referred to as an "abasic site" or "abasic nucleotide." An abasic residue (Ab) is a nucleotide or nucleoside that lacks a nucleobase at the 1' position of the sugar moiety. In some embodiments, an abasic residue can be placed internally in a nucleotide sequence. In some embodiments, Ab or AbAb can be added to the 3' end of the antisense strand. In some embodiments, the 5' end of the sense strand can include one or more additional abasic residues (e.g., (Ab) or (AbAb)). In some embodiments, UUAb, UAb, or Ab are added to the 3' end of the sense strand. In some embodiments, an abasic (deoxyribose) residue can be replaced with a ribitol (abasic ribose) residue.

In some embodiments, all or substantially all of the nucleotides of an RNAi agent are modified nucleotides. As used herein, an RNAi agent wherein substantially all of the nucleotides present are modified nucleotides is an RNAi agent having four or fewer (i.e., 0, 1, 2, 3, or 4) nucleotides in both the sense strand and the antisense strand being ribonucleotides (i.e., unmodified). As used herein, a sense strand wherein substantially all of the nucleotides present are modified nucleotides is a sense strand having two or fewer (i.e., 0, 1, or 2) nucleotides in the sense strand being unmodified ribonucleotides. As used herein, an antisense sense strand wherein substantially all of the nucleotides present are modified nucleotides is an antisense strand having two or fewer (i.e., 0, 1, or 2) nucleotides in the sense strand being unmodified ribonucleotides. In some embodiments, one or more nucleotides of an RNAi agent is an unmodified ribonucleotide. Chemical structures for certain modified nucleotides are set forth in Table 6.1 herein.

Modified Internucleoside Linkages

In some embodiments, one or more nucleotides of a DUX4 RNAi agent are linked by non-standard linkages or backbones (i.e., modified internucleoside linkages or modified backbones). Modified internucleoside linkages or backbones include, but are not limited to, phosphorothioate groups (represented herein as a lower case "s"), chiral phosphorothioates, thiophosphates, phosphorodithioates, phosphotriesters, aminoalkyl-phosphotriesters, diphosphorothioates, alkyl phosphonates (e.g., methyl phosphonates or 3'-alkylene phosphonates), chiral phosphonates, phosphinates, phosphoramidates (e.g., 3'-amino phosphoramidate, aminoalkylphosphoramidates, or thionophosphoramidates), thionoalkyl-phosphonates, thionoalkylphosphotriesters, morpholino linkages, boranophosphates having normal 3'-5' linkages, 2'-5' linked analogs of boranophosphates, or boranophosphates having inverted polarity wherein the adjacent pairs of nucleoside units are linked 3'-5' to 5'-3' or 2'-5' to 5'-2'. In some embodiments, a modified internucleoside linkage or backbone lacks a phosphorus atom. Modified internucleoside linkages lacking a phosphorus atom include, but are not limited to, short chain alkyl or cycloalkyl inter-sugar linkages, mixed heteroatom and alkyl or cycloalkyl inter-sugar linkages, or one or more short chain heteroatomic or heterocyclic inter-sugar linkages. In some embodiments, modified internucleoside backbones include, but are not limited to, siloxane backbones, sulfide backbones, sulfoxide backbones, sulfone backbones, formacetyl and thioformacetyl backbones, methylene formacetyl and thioformacetyl backbones, alkene-containing backbones, sulfamate backbones, methyleneimino and methylenehydrazino backbones, sulfonate and sulfonamide backbones, amide backbones, and other backbones having mixed N, O, S, and $CH_2$ components.

In some embodiments, a sense strand of a DUX4 RNAi agent can contain 1, 2, 3, 4, 5, or 6 phosphorothioate linkages, an antisense strand of a DUX4 RNAi agent can contain 1, 2, 3, 4, 5, or 6 phosphorothioate linkages, or both the sense strand and the antisense strand independently can contain 1, 2, 3, 4, 5, or 6 phosphorothioate linkages. In some embodiments, a sense strand of a DUX4 RNAi agent can contain 1, 2, 3, or 4 phosphorothioate linkages, an antisense strand of a DUX4 RNAi agent can contain 1, 2, 3, or 4 phosphorothioate linkages, or both the sense strand and the antisense strand independently can contain 1, 2, 3, or 4 phosphorothioate linkages.

In some embodiments, a DUX4 RNAi agent sense strand contains at least two phosphorothioate internucleoside linkages. In some embodiments, the phosphorothioate internucleoside linkages are between the nucleotides at positions 1-3 from the 3' end of the sense strand. In some embodiments, one phosphorothioate internucleoside linkage is at the 5' end of the sense strand nucleotide sequence, and another phosphorothioate linkage is at the 3' end of the sense strand nucleotide sequence. In some embodiments, two phosphorothioate internucleoside linkage are located at the 5' end of the sense strand, and another phosphorothioate linkage is at the 3' end of the sense strand. In some embodiments, the sense strand does not include any phosphorothioate internucleoside linkages between the nucleotides, but contains one, two, or three phosphorothioate linkages between the terminal nucleotides on both the 5' and 3' ends and the optionally present inverted abasic residue terminal caps. In some embodiments, the targeting ligand is linked to the sense strand via a phosphorothioate linkage.

In some embodiments, a DUX4 RNAi agent antisense strand contains four phosphorothioate internucleoside linkages. In some embodiments, the four phosphorothioate internucleoside linkages are between the nucleotides at positions 1-3 from the 5' end of the antisense strand and between the nucleotides at positions 19-21, 20-22, 21-23, 22-24, 23-25, or 24-26 from the 5' end. In some embodiments, three phosphorothioate internucleoside linkages are located between positions 1-4 from the 5' end of the antisense strand, and a fourth phosphorothioate internucleoside linkage is located between positions 20-21 from the 5' end of the antisense strand. In some embodiments, a DUX4 RNAi agent contains at least three or four phosphorothioate internucleoside linkages in the antisense strand.

Capping Residues or Moieties

In some embodiments, the sense strand may include one or more capping residues or moieties, sometimes referred to in the art as a "cap," a "terminal cap," or a "capping residue." As used herein, a "capping residue" is a non-nucleotide compound or other moiety that can be incorporated at one or more termini of a nucleotide sequence of an RNAi agent disclosed herein. A capping residue can provide the RNAi agent, in some instances, with certain beneficial properties, such as, for example, protection against exonuclease degradation. In some embodiments, inverted abasic residues (invAb) (also referred to in the art as "inverted abasic sites") are added as capping residues (see Table 6.1). (See, e.g., F. Czauderna, Nucleic Acids Res., 2003, 31(11), 2705-16; U.S. Pat. No. 5,998,203). Capping residues are generally known in the art, and include, for example, inverted abasic residues as well as carbon chains such as a terminal $C_3H_7$ (propyl), $C_6H_{13}$ (hexyl), or $C_{12}H_{25}$ (dodecyl) groups. In some embodiments, a capping residue is present at either the 5' terminal end, the 3' terminal end, or both the 5' and 3' terminal ends of the sense strand. In some embodiments, the 5' end and/or the 3' end of the sense strand may include more than one inverted abasic deoxyribose moiety as a capping residue.

In some embodiments, one or more inverted abasic residues (invAb) are added to the 3' end of the sense strand. In some embodiments, one or more inverted abasic residues (invAb) are added to the 5' end of the sense strand. In some embodiments, one or more inverted abasic residues or inverted abasic sites are inserted between the targeting ligand and the nucleotide sequence of the sense strand of the RNAi agent. In some embodiments, one or more inverted abasic residues or inverted abasic sites are inserted between the PK/PD modulator and the nucleotide sequence of the sense strand of the RNAi agent. In some embodiments, the inclusion of one or more inverted abasic residues or inverted abasic sites at or near the terminal end or terminal ends of the sense strand of an RNAi agent allows for enhanced activity or other desired properties of an RNAi agent.

In some embodiments, one or more inverted abasic residues (invAb) are added to the 5' end of the sense strand. In some embodiments, one or more inverted abasic residues can be inserted between the targeting ligand and the nucleotide sequence of the sense strand of the RNAi agent. The inverted abasic residues may be linked via phosphate, phosphorothioate (e.g., shown herein as (invAb)s)), or other internucleoside linkages. In some embodiments, the inclusion of one or more inverted abasic residues at or near the terminal end or terminal ends of the sense strand of an RNAi agent may allow for enhanced activity or other desired properties of an RNAi agent. In some embodiments, an inverted abasic (deoxyribose) residue can be replaced with an inverted ribitol (abasic ribose) residue. In some embodiments, the 3' end of the antisense strand core stretch sequence, or the 3' end of the antisense strand sequence, may include an inverted abasic residue. Chemical structures for inverted abasic deoxyribose residues are shown in Table 6.1 below.

DUX4 RNAi Agents

The DUX4 RNAi agent embodiments disclosed herein were designed to target specific positions on a DUX4 gene (i.e., specific positions on a DUX4 gene transcript). As defined herein, an antisense strand sequence is designed to target a DUX4 gene at a specific position on the gene when the 5' terminal nucleobase of the antisense strand is aligned with a position that is 21 nucleotides downstream (towards the 3' end) from the position on the gene when base pairing to the gene. For example, as illustrated in Tables 1 and 2 herein, an antisense strand sequence designed to target a DUX4 gene at position 408 requires that when base pairing to the gene, the 5' terminal nucleobase of the antisense strand is aligned with position 428 of the DUX4 gene.

As provided herein, for the specific embodiments disclosed herein, a DUX4 RNAi agent does not require that the nucleobase at position 1 (5'->3') of the antisense strand be complementary to the gene, provided that there is at least 85% complementarity (e.g., at least 85, 86, 87, 88, 89, 90, 91, 92, 93, 94, 95, 96, 97, 98, 99, or 100% complementarity) of the antisense strand and the gene across a core stretch sequence of at least 16 consecutive nucleotides. For example, for a DUX4 RNAi agent disclosed herein that is designed to target position 408 of a DUX4 gene, the 5' terminal nucleobase of the antisense strand of the of the DUX4 RNAi agent must be aligned with position 428 of the gene; however, the 5' terminal nucleobase of the antisense strand may be, but is not required to be, complementary to position 428 of a DUX4 gene, provided that there is at least 85% complementarity (e.g., at least 85, 86, 87, 88, 89, 90, 91, 92, 93, 94, 95, 96, 97, 98, 99, or 100% complementarity) of the antisense strand and the gene across a core stretch sequence of at least 16 consecutive nucleotides. As shown by, among other things, the various examples disclosed herein, the specific site of binding of the gene by the antisense strand of the DUX4 RNAi agent (e.g., whether the DUX4 RNAi agent is designed to target a DUX4 gene at position 408, at position 1437, or at some other position) is important to the level of inhibition achieved by the DUX4 RNAi agent.

In some embodiments, the DUX4 RNAi agents disclosed herein target a DUX4 gene at or near the positions of the DUX4 sequence shown in Table 1. In some embodiments, the antisense strand of a DUX4 RNAi agent disclosed herein includes a core stretch sequence that is fully, substantially, or at least partially complementary to a target DUX4 19-mer sequence disclosed in Table 1.

TABLE 1

DUX4 19-mer mRNA Target Sequences (taken from *homo sapiens* double homeobox 4, transcript variant 2, GenBank NM_001293798.2)

| SEQ ID No. | DUX4 19-mer Target Sequences (5' → 3') | Corresponding Positions of Sequence on SEQ ID NO: 1 | Targeted Gene Position (as referred to herein) |
| --- | --- | --- | --- |
| 3 | GGAUUCAGAUCUGGUUUCA | 408-428 | 408 |
| 4 | GAUUCAGAUCUGGUUUCAA | 409-429 | 409 |
| 5 | CCUUGUUCUUCCGUGAAAU | 1433-1453 | 1433 |
| 6 | GUUCUUCCGUGAAAUUCUA | 1437-1457 | 1437 |
| 7 | ACCUGGAUUAGAGUUACAU | 1496-1516 | 1496 |
| 8 | CUGGAUGAUUAGUUCAGAA | 1518-1538 | 1518 |
| 9 | AUGAUUAGUUCAGAGAUAU | 1522-1542 | 1522 |

In some embodiments, a DUX4 RNAi agent includes an antisense strand wherein position 19 of the antisense strand (5'→3') is capable of forming a base pair with position 1 of a 19-mer target sequence disclosed in Table 1. In some embodiments, a DUX4 RNAi agent includes an antisense strand wherein position 1 of the antisense strand (5'→3') is capable of forming a base pair with position 19 of a 19-mer target sequence disclosed in Table 1.

In some embodiments, a DUX4 RNAi agent includes an antisense strand wherein position 2 of the antisense strand (5'→3') is capable of forming a base pair with position 18 of a 19-mer target sequence disclosed in Table 1. In some embodiments, a DUX4 RNAi agent includes an antisense strand wherein positions 2 through 18 of the antisense strand (5'→3') are capable of forming base pairs with each of the respective complementary bases located at positions 18 through 2 of the 19-mer target sequence disclosed in Table 1.

For the RNAi agents disclosed herein, the nucleotide at position 1 of the antisense strand (from 5' end→3' end) can be perfectly complementary to the DUX4 gene, or can be non-complementary to the DUX4 gene. In some embodiments, the nucleotide at position 1 of the antisense strand (from 5' end→3' end) is a U, A, or dT. In some embodiments, the nucleotide at position 1 of the antisense strand (from 5' end→3' end) forms an A:U or U:A base pair with the sense strand.

In some embodiments, a DUX4 RNAi agent antisense strand comprises the sequence of nucleotides (from 5' end→3' end) 2-18 or 2-19 of any of the antisense strand sequences in Table 2, Table 3, or Table 5.4. In some embodiments, a DUX4 RNAi sense strand comprises the sequence of nucleotides (from 5' end→3' end) 1-17, 1-18, or 2-18 of any of the sense strand sequences in Table 2 or Tables 4.1, 4.2, 4.3, 4.4, 4.5, 4.6 or 5.4.

In some embodiments, a DUX4 RNAi agent is comprised of (i) an antisense strand comprising the sequence of nucleotides (from 5' end→3' end) 2-18 or 2-19 of any of the antisense strand sequences in Table 2 or Table 3, and (ii) a sense strand comprising the sequence of nucleotides (from 5' end→3' end) 1-17 or 1-18 of any of the sense strand sequences in Table 2 or Tables 4.1, 4.2, 4.3, 4.4, 4.5, 4.6 or 5.4.

In some embodiments, the DUX4 RNAi agents include core 19-mer nucleotide sequences shown in the following Table 2.

TABLE 2

DUX4 RNAi Agent Antisense Strand and Sense Strand
Core Stretch Base Sequences (N = any nucleobase)

| SEQ ID NO:. | Antisense Strand Base Sequence (5' → 3') (Shown as an Unmodified Nucleotide Sequence) | SEQ ID NO:. | Sense Strand Base Sequence (5' → 3') (Shown as an Unmodified Nucleotide Sequence) | Corresponding Positions of Identified Sequence on SEQ ID NO: 1 | Targeted Gene Position |
|---|---|---|---|---|---|
| 10 | UGAAACCAGAUCUGAAUCC | 38 | GGAUUCAGAUCUGGUUUCA | 410-428 | 408 |
| 11 | AGAAACCAGAUCUGAAUCC | 39 | GGAUUCAGAUCUGGUUUCU | 410-428 | 408 |
| 12 | NGAAACCAGAUCUGAAUCC | 40 | GGAUUCAGAUCUGGUUUCN | 410-428 | 408 |
| 13 | NGAAACCAGAUCUGAAUCN | 41 | NGAUUCAGAUCUGGUUUCN | 410-428 | 408 |
| 14 | UUGAAACCAGAUCUGAAUC | 42 | GAUUCAGAUCUGGUUUCAA | 411-429 | 409 |
| 15 | AUGAAACCAGAUCUGAAUC | 43 | GAUUCAGAUCUGGUUUCAU | 411-429 | 409 |
| 16 | NUGAAACCAGAUCUGAAUC | 44 | GAUUCAGAUCUGGUUUCAN | 411-429 | 409 |
| 17 | NUGAAACCAGAUCUGAAUN | 45 | NAUUCAGAUCUGGUUUCAN | 411-429 | 409 |
| 18 | AUUUCACGGAAGAACAAGG | 46 | CCUUGUUCUUCCGUGAAAU | 1435-1453 | 1433 |
| 19 | UUUUCACGGAAGAACAAGG | 47 | CCUUGUUCUUCCGUGAAAA | 1435-1453 | 1433 |
| 20 | NUUUCACGGAAGAACAAGG | 48 | CCUUGUUCUUCCGUGAAAN | 1435-1453 | 1433 |
| 21 | NUUUCACGGAAGAACAAGN | 49 | NCUUGUUCUUCCGUGAAAN | 1435-1453 | 1433 |
| 22 | UAGAAUUUCACGGAAGAAC | 50 | GUUCUUCCGUGAAAUUCUA | 1439-1457 | 1437 |
| 23 | AAGAAUUUCACGGAAGAAC | 51 | GUUCUUCCGUGAAAUUCUU | 1439-1457 | 1437 |
| 24 | NAGAAUUUCACGGAAGAAC | 52 | GUUCUUCCGUGAAAUUCUN | 1439-1457 | 1437 |
| 25 | NAGAAUUUCACGGAAGAAN | 53 | NUUCUUCCGUGAAAUUCUN | 1439-1457 | 1437 |
| 26 | AUGUAACUCUAAUCCAGGU | 54 | ACCUGGAUUAGAGUUACAU | 1498-1516 | 1496 |
| 27 | UUGUAACUCUAAUCCAGGU | 55 | ACCUGGAUUAGAGUUACAA | 1498-1516 | 1496 |
| 28 | NUGUAACUCUAAUCCAGGU | 56 | ACCUGGAUUAGAGUUACAN | 1498-1516 | 1496 |
| 29 | NUGUAACUCUAAUCCAGGN | 57 | NCCUGGAUUAGAGUUACAN | 1498-1516 | 1496 |
| 30 | UUCUGAACUAAUCAUCCAG | 58 | CUGGAUGAUUAGUUCAGAA | 1520-1538 | 1518 |
| 31 | AUCUGAACUAAUCAUCCAG | 59 | CUGGAUGAUUAGUUCAGAU | 1520-1538 | 1518 |
| 32 | NUCUGAACUAAUCAUCCAG | 60 | CUGGAUGAUUAGUUCAGAN | 1520-1538 | 1518 |
| 33 | NUCUGAACUAAUCAUCCAN | 61 | NUGGAUGAUUAGUUCAGAN | 1520-1538 | 1518 |
| 34 | AUAUCUCUGAACUAAUCAU | 62 | AUGAUUAGUUCAGAGAUAU | 1524-1542 | 1522 |
| 35 | UUAUCUCUGAACUAAUCAU | 63 | AUGAUUAGUUCAGAGAUAA | 1524-1542 | 1522 |
| 36 | NUAUCUCUGAACUAAUCAU | 64 | AUGAUUAGUUCAGAGAUAN | 1524-1542 | 1522 |
| 37 | NUAUCUCUGAACUAAUCAN | 65 | NUGAUUAGUUCAGAGAUAN | 1524-1542 | 1522 |

The DUX4 RNAi agent sense strands and antisense strands that comprise or consist of the nucleotide sequences in Table 2 can be modified nucleotides or unmodified nucleotides. In some embodiments, the DUX4 RNAi agents having the sense and antisense strand sequences that comprise or consist of any of the nucleotide sequences in Table 2 are all or substantially all modified nucleotides.

In some embodiments, the antisense strand of a DUX4 RNAi agent disclosed herein differs by 0, 1, 2, or 3 nucleotides from any of the antisense strand sequences in Table 2. In some embodiments, the sense strand of a DUX4 RNAi agent disclosed herein differs by 0, 1, 2, or 3 nucleotides from any of the sense strand sequences in Table 2.

As used herein, each N listed in a sequence disclosed in Table 2 may be independently selected from any and all nucleobases (including those found on both modified and unmodified nucleotides). In some embodiments, an N nucleotide listed in a sequence disclosed in Table 2 has a nucleobase that is complementary to the N nucleotide at the corresponding position on the other strand. In some embodiments, an N nucleotide listed in a sequence disclosed in Table 2 has a nucleobase that is not complementary to the N nucleotide at the corresponding position on the other strand. In some embodiments, an N nucleotide listed in a sequence disclosed in Table 2 has a nucleobase that is the same as the N nucleotide at the corresponding position on the other strand. In some embodiments, an N nucleotide listed in a sequence disclosed in Table 2 has a nucleobase that is different from the N nucleotide at the corresponding position on the other strand.

Certain modified DUX4 RNAi agent sense and antisense strands are provided in Table 3 and Tables 4.1, 4.2, 4.3, 4.4, 4.5, 4.6, and 5.4. Modified DUX4 RNAi agent antisense strands, as well as their underlying unmodified nucleobase sequences, are provided in Table 3. Modified DUX4 RNAi agent sense strands, as well as their underlying unmodified nucleobase sequences, are provided in Tables 4.1, 4.2, 4.3, 4.4, 4.5, 4.6 and 5.4. In forming DUX4 RNAi agents, each of the nucleotides in each of the underlying base sequences listed in Tables 3 and Tables 4.1, 4.2, 4.3, 4.4, 4.5, 4.6, and 5.4, as well as in Table 2, above, can be a modified nucleotide.

The DUX4 RNAi agents described herein are formed by annealing an antisense strand with a sense strand. A sense strand containing a sequence listed in Table 2 or Tables 4.1, 4.2, 4.3, 4.4, 4.5, 4.6, or 5.4 can be hybridized to any antisense strand containing a sequence listed in Table 2, Table 3, or Table 5.4 provided the two sequences have a region of at least 85% complementarity over a contiguous 16, 17, 18, 19, 20, or 21 nucleotide sequence.

In some embodiments, a DUX4 RNAi agent antisense strand comprises a nucleotide sequence of any of the sequences in Table 2, Table 3, or Table 5.4.

In some embodiments, a DUX4 RNAi agent comprises or consists of a duplex having the nucleobase sequences of the sense strand and the antisense strand of any of the sequences in Table 2, Table 3, or Tables 4.1, 4.2, 4.3, 4.4, 4.5, 4.6, or 5.4.

Examples of antisense strands containing modified nucleotides are provided in Table 3. Examples of sense strands containing modified nucleotides are provided in Tables 4.1, 4.2, 4.3, 4.4, 4.5, 4.6, and 5.4.

As used in Tables 3 and Tables 4.1, 4.2, 4.3, 4.4, 4.5, 4.6, and 5.4 the following notations are used to indicate modified nucleotides, targeting groups, and linking groups:

A=adenosine-3'-phosphate
C=cytidine-3'-phosphate
G=guanosine-3'-phosphate
U=uridine-3'-phosphate
I=inosine-3'-phosphate
a=2'-O-methyladenosine-3'-phosphate
as=2'-O-methyladenosine-3'-phosphorothioate
c=2'-O-methylcytidine-3'-phosphate
cs=2'-O-methylcytidine-3'-phosphorothioate
g=2'-O-methylguanosine-3'-phosphate
gs=2'-O-methylguanosine-3'-phosphorothioate
i=2'-O-methylinosine-3'-phosphate
is=2'-O-methylinosine-3'-phosphorothioate
t=2'-O-methyl-5-methyluridine-3'-phosphate
ts=2'-O-methyl-5-methyluridine-3'-phosphorothioate
u=2'-O-methyluridine-3'-phosphate
us=2'-O-methyluridine-3'-phosphorothioate
Af=2'-fluoroadenosine-3'-phosphate
Afs=2'-fluoroadenosine-3'-phosporothioate
Cf=2'-fluorocytidine-3'-phosphate
Cfs=2'-fluorocytidine-3'-phosphorothioate
Gf=2'-fluoroguanosine-3'-phosphate
Gfs=2'-fluoroguanosine-3'-phosphorothioate
Tf=2'-fluoro-5'-methyluridine-3'-phosphate
Tfs=2'-fluoro-5'-methyluridine-3'-phosphorothioate
Uf=2'-fluorouridine-3'-phosphate
Ufs=2'-fluorouridine-3'-phosphorothioate
dT=2'-deoxythymidine-3'-phosphate
$A_{UNA}$=2',3'-seco-adenosine-3'-phosphate
$A_{UNAS}$=2',3'-seco-adenosine-3'-phosphorothioate
$C_{UNA}$=2',3'-seco-cytidine-3'-phosphate
$C_{UNAS}$=2',3'-seco-cytidine-3'-phosphorothioate
$G_{UNA}$=2',3'-seco-guanosine-3'-phosphate
$G_{UNAS}$=2',3'-seco-guanosine-3'-phosphorothioate
$U_{UNA}$=2',3'-seco-uridine-3'-phosphate
$U_{UNAS}$=2',3'-seco-uridine-3'-phosphorothioate
a_2N=see Table 6.1
a_2Ns=see Table 6.1
(invAb)=inverted abasic deoxyribonucleotide-5'-phosphate, see Table 6.1
(invAb)s=inverted abasic deoxyribonucleotide-5'-phosphorothioate, see Table 6.1
s=phosphorothioate linkage
p=terminal phosphate (as synthesized)
vpdN=vinyl phosphonate deoxyribonucleotide
cPrpa=5'-cyclopropyl phosphonate-2'-O-methyladenosine-3'-phosphate (see Table 6.1)
cPrpas=5'-cyclopropyl phosphonate-2'-O-methyladenosine-3'-phosphorothioate (see Table 6.1)
cPrpu=5'-cyclopropyl phosphonate-2'-O-methyluridine-3'-phosphate (see Table 6.1)
cPrpus=5'-cyclopropyl phosphonate-2'-O-methyluridine-3'-phosphorothioate (see Table 6.1)
aAlk=2'-O-propargyladenosine-3'-phosphate, see Table 6.1
aAlks=2'-O-propargyladenosine-3'-phosphorothioate, see Table 6.1
cAlk=2'-O-propargylcytidine-3'-phosphate, see Table 6.1
cAlks=2'-O-propargylcytidine-3'-phosphorothioate, see Table 6.1
gAlk=2'-O-propargylguanosine-3'-phosphate, see Table 6.1
gAlks=2'-O-propargylguanosine-3'-phosphorothioate, see Table 6.1
tAlk=2'-O-propargyl-5-methyluridine-3'-phosphate, see Table 6.1
tAlks=2'-O-propargyl-5-methyluridine-3'-phosphorothioate, see Table 6.1
uAlk=2'-O-propargyluridine-3'-phosphate, see Table 6.1
uAlks=2'-O-propargyluridine-3'-phosphorothioate, see Table 6.1
(Alk-SS-C6)=see Table 6.1
(C6-SS-Alk)=see Table 6.1
(C6-SS-C6)=see Table 6.1
(6-SS-6)=see Table 6.1
(C6-SS-Alk-Me)=see Table 6.1
(NH2-C6)=see Table 6.1
(Alk-cyHex)=see Table 6.1
(Alk-cyHex)s=see Table 6.1

As the person of ordinary skill in the art would readily understand, unless otherwise indicated by the sequence (such as, for example, by a phosphorothioate linkage "s"), when present in an oligonucleotide, the nucleotide monomers are mutually linked by 5'-3'-phosphodiester bonds. As the person of ordinary skill in the art would clearly understand, the inclusion of a phosphorothioate linkage as shown in the modified nucleotide sequences disclosed herein replaces the phosphodiester linkage typically present in oligonucleotides. Further, the person of ordinary skill in the art would readily understand that the terminal nucleotide at the 3' end of a given oligonucleotide sequence would typically have a hydroxyl (—OH) group at the respective 3′ position of the given monomer instead of a phosphate moiety ex vivo. Moreover, as the person of ordinary skill would readily understand and appreciate, while the phosphorothioate chemical structures depicted herein typically show the anion on the sulfur atom, the inventions disclosed herein encompass all phosphorothioate tautomers (e.g., where the sulfur atom has a double-bond and the anion is on an oxygen atom). Unless expressly indicated otherwise herein, such understandings of the person of ordinary skill in the art are used when describing the DUX4 RNAi agents and compositions of DUX4 RNAi agents disclosed herein.

Certain examples of targeting groups and linking groups used with the DUX4 RNAi agents disclosed herein are included in the chemical structures provided below in Table 6.1. Each sense strand and/or antisense strand can have any targeting groups or linking groups listed herein, as well as other targeting or linking groups, conjugated to the 5′ and/or 3′ end of the sequence.

TABLE 3

DUX4 RNAi Agent Antisense Strand Sequences

| Antisense Strand ID | Modified Antisense Strand (5′ → 3′) | SEQ ID NO: | Underlying Base Sequence (5′ → 3′) (Shown as an Unmodified Nucleotide Sequence) | SEQ ID NO: |
|---|---|---|---|---|
| AM09247-AS | usGfsasAfaCfcAfgAfuCfuGfaAfuCfcUfsg | 66 | UGAAACCAGAUCUGAAUCCUG | 162 |
| AM09250-AS | usUfsgsAfaAfcCfaGfaUfcUfgAfaUfcCfsu | 67 | UUGAAACCAGAUCUGAAUCCU | 163 |
| AM09252-AS | usAfsgsAfaUfuUfcAfcGfgAfaGfaAfcAfsg | 68 | UAGAAUUUCACGGAAGAACAG | 164 |
| AM09260-AS | usUfscsUfgAfaCfuAfaUfcAfuCfcAfgGfsa | 69 | UUCUGAACUAAUCAUCCAGGA | 165 |
| AM10009-AS | asUfsusUfcAfcGfgAfaGfaAfcAfaGfgGfsc | 70 | AUUUCACGGAAGAACAAGGGC | 166 |
| AM10019-AS | asUfsgsUfaAfcUfcUfaAfuCfcAfgGfuUfsu | 71 | AUGUAACUCUAAUCCAGGUUU | 167 |
| AM10023-AS | asUfsasUfcUfcUfgAfaCfuAfaUfcAfuCfsc | 72 | AUAUCUCUGAACUAAUCAUCC | 168 |
| AM10026-AS | cPrpusAfsgsAfaUfuUfcAfcGfgAfaGfaAfcAfsg | 73 | UAGAAUUUCACGGAAGAACAG | 164 |
| AM10028-AS | cPrpusUfscsUfgAfaCfuAfaUfcAfuCfcAfgGfsa | 74 | UUCUGAACUAAUCAUCCAGGA | 165 |
| AM10029-AS | cPrpusGfsasAfaCfcAfgAfuCfuGfaAfuCfcUfsg | 75 | UGAAACCAGAUCUGAAUCCUG | 162 |
| AM10030-AS | cPrpusUfsgsAfaAfcCfaGfaUfcUfgAfaUfcCfsu | 76 | UUGAAACCAGAUCUGAAUCCU | 163 |
| AM10159-AS | usUfsgsAfaAfcCfaGfaUfcUfgAfaUfcCfsc | 77 | UUGAAACCAGAUCUGAAUCCC | 169 |
| AM10195-AS | cPrpasUfsusUfcAfcGfgAfaGfaAfcAfaGfgGfsc | 78 | AUUUCACGGAAGAACAAGGGC | 166 |
| AM10197-AS | cPrpasUfsgsUfaAfcUfcUfaAfuCfcAfgGfuUfsu | 79 | AUGUAACUCUAAUCCAGGUUU | 167 |
| AM10199-AS | cPrpasUfsasUfcUfcUfgAfaCfuAfaUfcAfuCfsc | 80 | AUAUCUCUGAACUAAUCAUCC | 168 |
| AM10251-AS | usAfsgsaauuucacGfgAfaGfaacasg | 81 | UAGAAUUUCACGGAAGAACAG | 164 |
| AM10252-AS | usAfsGfsAfauuucacGfgAfaGfaacasg | 82 | UAGAAUUUCACGGAAGAACAG | 164 |
| AM10260-AS | usUfscsugaacuaaUfcAfuCfcaggsa | 83 | UUCUGAACUAAUCAUCCAGGA | 165 |
| AM10378-AS | cPrpusAfsGfsAfauuucacGfgAfaGfaacasg | 84 | UAGAAUUUCACGGAAGAACAG | 164 |
| AM10380-AS | usAfsGfsAfauuucacGfgAfaGfaacasc | 85 | UAGAAUUUCACGGAAGAACAC | 170 |
| AM10381-AS | cPrpusAfsGfsAfauuucacGfgAfaGfaacasc | 86 | UAGAAUUUCACGGAAGAACAC | 170 |
| AM10464-AS | cPrpusUfsgsAfaAfcCfaGfaUfcUfgAfaUfcCfsc | 87 | UUGAAACCAGAUCUGAAUCCC | 169 |
| AM10564-AS | usUfsgsaaaccagaUfcUfgAfauccsc | 88 | UUGAAACCAGAUCUGAAUCCC | 169 |
| AM10565-AS | cPrpusUfsgsaaaccagaUfcUfgAfauccsc | 89 | UUGAAACCAGAUCUGAAUCCC | 169 |
| AM10566-AS | usUfsgsaaacCfaGfaUfcUfgAfauccsc | 90 | UUGAAACCAGAUCUGAAUCCC | 169 |
| AM10567-AS | cPrpusUfsgsaaacCfaGfaUfcUfgAfauccsc | 91 | UUGAAACCAGAUCUGAAUCCC | 169 |
| AM10645-AS | cPrpusUfscsugaacuaaUfcAfuCfcaggsa | 92 | UUCUGAACUAAUCAUCCAGGA | 165 |
| AM10646-AS | cPrpusAfsgsaauuucacGfgAfaGfaacasg | 93 | UAGAAUUUCACGGAAGAACAG | 164 |
| AM10647-AS | usAfsgsaauuucacGfgAfaGfaacasc | 94 | UAGAAUUUCACGGAAGAACAC | 170 |

TABLE 3-continued

DUX4 RNAi Agent Antisense Strand Sequences

| Antisense Strand ID | Modified Antisense Strand (5' → 3') | SEQ ID NO: | Underlying Base Sequence (5' → 3') (Shown as an Unmodified Nucleotide Sequence) | SEQ ID NO: |
|---|---|---|---|---|
| AM10648-AS | cPrpusAfsgsaauuucacGfgAfaGfaacasc | 95 | UAGAAUUUCACGGAAGAACAC | 170 |
| AM10850-AS | usGfsasaaccagauCfuGfaAfuccusg | 96 | UGAAACCAGAUCUGAAUCCUG | 162 |
| AM10851-AS | cPrpusGfsasaaccagauCfuGfaAfuccusg | 97 | UGAAACCAGAUCUGAAUCCUG | 162 |
| AM10852-AS | usGfsasAfaccagauCfuGfaAfuccusg | 98 | UGAAACCAGAUCUGAAUCCUG | 162 |
| AM10853-AS | cPrpusGfsasAfaccagauCfuGfaAfuccusg | 99 | UGAAACCAGAUCUGAAUCCUG | 162 |
| AM10948-AS | cPrpusAfsgsAfauuucacGfgAfaGfaacasg | 100 | UAGAAUUUCACGGAAGAACAG | 164 |
| AM10949-AS | cPrpusAfsGfsaauuucacGfgAfaGfaacasg | 101 | UAGAAUUUCACGGAAGAACAG | 164 |

TABLE 4.1

DUX4 RNAi Agent Sense Strand Sequences

| Sense Strand ID | Modified Sense Strand (5' → 3') | SEQ ID NO: | Underlying Base Sequence (5' → 3') (Shown as an Unmodified Nucleotide Sequence) | SEQ ID NO: |
|---|---|---|---|---|
| AM09965-SS | (NH2-C6)s(invAb)scaggauucAfGfAfucugguuucas(invAb)(C6-SS-C6)dT | 102 | CAGGAUUCAGAUCUGGUUUCAT | 171 |
| AM09966-SS | (NH2-C6)s(invAb)saggauucaGfAfUfcugguuucaas(invAb)(C6-SS-C6)dT | 103 | AGGAUUCAGAUCUGGUUUCAT | 172 |
| AM09967-SS | (NH2-C6)s(invAb)scuguucuCfCfGfugaaauucuas(invAb)(C6-SS-C6)dT | 104 | CUGUUCUUCCGUGAAAUUCUAT | 173 |
| AM09968-SS | (NH2-C6)s(invAb)succuggaUfGfAfUfuaguucagaas(invAb)(C6-SS-C6)dT | 105 | UCCUGGAUGAUUAGUUCAGAAT | 174 |
| AM10194-SS | (NH2-C6)s(invAb)sgcccuuguUfCfUfuccgugaaaus(invAb)(C6-SS-C6)dT | 106 | GCCCUUGUUCUUCCGUGAAAUT | 175 |
| AM10196-SS | (NH2-C6)s(invAb)sa_2NaaccuggAfUfUfagaguuacaus(invAb)(C6-SS-C6)dT | 107 | (A2N)AACCUGGAUUAGAGUUACAUT | 176 |
| AM10198-SS | (NH2-C6)s(invAb)sggaugauuAfGfUfucagagauaus(invAb)(C6-SS-C6)dT | 108 | GGAUGAUUAGUUCAGAGAUAUT | 177 |
| AM10379-SS | (NH2-C6)s(invAb)sguguucuuCfCfGfugaaauucuas(invAb)(C6-SS-C6)dT | 109 | GUGUUCUUCCGUGAAAUUCUAT | 178 |
| AM10382-SS | (NH2-C6)s(invAb)sguguucUfuCfcGfugaaauucuas(invAb)(C6-SS-C6)dT | 110 | GUGUUCUUCCGUGAAAUUCUAT | 178 |
| AM10463-SS | (NH2-C6)s(invAb)sgggauucaGfAfUfcugguuucaas(invAb)(C6-SS-C6)dT | 111 | GGGAUUCAGAUCUGGUUUCAT | 179 |
| AM10465-SS | (NH2-C6)s(invAb)sa_2NggauucaGfAfUfcugguuucaas(invAb)(C6-SS-C6)dT | 112 | (A2N)GGAUUCAGAUCUGGUUUCAAT | 238 |
| AM10568-SS | (NH2-C6)s(invAb)sgggauucaGfaUfcugguuucaas(invAb)(C6-SS-C6)dT | 113 | GGGAUUCAGAUCUGGUUUCAT | 179 |
| AM10569-SS | (NH2-C6)s(invAb)sgggauucaGfaUfCfugguuucaas(invAb)(C6-SS-C6)dT | 114 | GGGAUUCAGAUCUGGUUUCAT | 179 |
| AM10854-SS | (NH2-C6)s(invAb)scaggauucAfGfAfucugIuuucas(invAb)(C6-SS-C6)dT | 115 | CAGGAUUCAGAUCUGIUUUCAT | 180 |
| AM10950-SS | (NH2-C6)s(invAb)scuguucuuCfcGfuGfaaauucuas(invAb)(C6-SS-C6)dT | 116 | CUGUUCUUCCGUGAAAUUCUAT | 173 |

(A2N) represents a 2-aminoadenine nucleotide;
I represents an inosine (hypoxanthine) nucleotide As shown in Table 4.1, above, the example DUX4 RNAi agent sense strand nucleotide sequences are shown to further include reactive linking groups at both the 5' terminal end and the 3' terminal end of the sense strand. For example, the DUX4 RNAi agent sense strand sequences shown in Table 4.1 above have an (NH2-C6) linking group at the 5' end of the nucleotide sequence. Similarly, the DUX4 RNAi agent nucleotide sequences shown in Table 4.1 above have a (C6-SS-C6) linking group near the 3' end of the nucleotide sequence. Such reactive linking groups are positioned to facilitate the linking of targeting ligands, targeting groups, and/or PK/PD modulators to the DUX4 RNAi agents disclosed herein. Linking or conjugation reactions are well known in the art and provide for formation of covalent linkages between two molecules or reactants. Suitable conjugation reactions for use in the scope of the inventions herein include, but are not limited to, amide coupling reaction, Michael addition reaction, hydrazone formation reaction, and click chemistry cycloaddition reaction.

In some embodiments, targeting ligands can be synthesized as a tetrafluorophenyl (TFP) ester, which react with an amino group (e.g., NH2-C6) to attach the targeting ligand to the DUX4 RNAi agents disclosed herein. In some embodiments, targeting ligands are synthesized as azides, which can be conjugated to a propargyl or DBCO group, for example, via click chemistry cycloaddition reaction.

Additionally, the nucleotide sequences shown in Table 4.1 were synthesized with a dT nucleotide at the 3' terminal end of the sense strand, followed by (3'→5') a linker (e.g., C6-SS-C6). A suitable and commercially available dT-loaded resin can be used to initiate the synthesis of the oligonucleotide strand. The (C6-SS-C6) linker can, in some embodiments, then be used facilitate the linkage to additional components, such as, for example, a PK/PD modulator or one or more targeting ligands. As described herein, the C6-SS-C6 is first reduced cleaving among other things the dT residue off the molecule, which can then facilitate the conjugation of the desired PK/PD modulator. Table 4.2 below shows the nucleotide sequences identified in Table 4.1, above, but without the inclusion of the 3' terminal dT nucleotide, as these properly reflect the sequence of the DUX4 RNAi agents disclosed herein when delivered in vivo.

Further, Table 4.3 below, shows the nucleotide sequences identified in Table 4.1, above, but without the terminal linking groups present (i.e., the nucleotide sequences with only capping groups).

TABLE 4.2

DUX4 RNAi Agent Sense Strand Sequences Shown Without 3' Terminal dT

| Sense Strand ID: | Modified Sense Strand (5' -> 3') | SEQ ID NO. | Underlying Base Sequence (5' → 3') (Shown as an Unmodified Nucleotide Sequence) | SEQ ID NO. |
|---|---|---|---|---|
| AM09965-SS | (NH2-C6)s(invAb)scaggauucAfGfAfucugguuucas(invAb)(C6-SS-C6) | 117 | CAGGAUUCAGAUCUGGUUUCA | 181 |
| AM09966-SS | (NH2-C6)s(invAb)saggauucaGfAfUfcugguuucaas(invAb)(C6-SS-C6) | 118 | AGGAUUCAGAUCUGGUUUCAA | 182 |
| AM09967-SS | (NH2-C6)s(invAb)scuguucuuCfCfGfugaaauucuas(invAb)(C6-SS-C6) | 119 | CUGUUCUUCCGUGAAAUUCUA | 183 |
| AM09968-SS | (NH2-C6)s(invAb)succuggauGfAfUfuaguucagaas(invAb)(C6-SS-C6) | 120 | UCCUGGAUGAUUAGUUCAGAA | 184 |
| AM10194-SS | (NH2-C6)s(invAb)sgcccuuguUfCfUfuccgugaaaus(invAb)(C6-SS-C6) | 121 | GCCCUUGUUCUUCCGUGAAAU | 185 |
| AM10196-SS | (NH2-C6)s(invAb)sa_2NaaccuggAfUfUfagaguuacaus(invAb)(C6-SS-C6) | 122 | ($A^{2N}$)AACCUGGAUUAGAGUUACAU | 186 |
| AM10198-SS | (NH2-C6)s(invAb)sggaugauuAfGfUfucagagauaus(invAb)(C6-SS-C6) | 123 | GGAUGAUUAGUUCAGAGAUAU | 187 |

TABLE 4.2-continued

DUX4 RNAi Agent Sense Strand Sequences Shown Without 3' Terminal dT

| Sense Strand ID: | Modified Sense Strand (5' -> 3') | SEQ ID NO. | Underlying Base Sequence (5' → 3') (Shown as an Unmodified Nucleotide Sequence) | SEQ ID NO. |
|---|---|---|---|---|
| AM10379-SS | (NH2-C6)s(invAb)sguguucuuCfCfGfugaaauucuas(invAb)(C6-SS-C6) | 124 | GUGUUCUUCCGUGAAAUUCUA | 188 |
| AM10382-SS | (NH2-C6)s(invAb)sguguucUfuCfcGfugaaauucuas(invAb)(C6-SS-C6) | 125 | GUGUUCUUCCGUGAAAUUCUA | 188 |
| AM10463-SS | (NH2-C6)s(invAb)sgggauucaGfAfUfcugguuucaas(invAb)(C6-SS-C6) | 126 | GGGAUUCAGAUCUGGUUUCAA | 189 |
| AM10465-SS | (NH2-C6)s(invAb)sa_2NggauucaGfAfUfcugguuucaas(invAb)(C6-SS-C6) | 127 | (A$^{2N}$)GGAUUCAGAUCUGGUUUCAA | 239 |
| AM10568-SS | (NH2-C6)s(invAb)sgggauucaGfaUfcugguuucaas(invAb)(C6-SS-C6) | 128 | GGGAUUCAGAUCUGGUUUCAA | 189 |
| AM10569-SS | (NH2-C6)s(invAb)sgggauucaGfaUfCfugguuucaas(invAb)(C6-SS-C6) | 129 | GGGAUUCAGAUCUGGUUUCAA | 189 |
| AM10854-SS | (NH2-C6)s(invAb)scaggauucAfGfAfucugiuuucas(invAb)(C6-SS-C6) | 130 | CAGGAUUCAGAUCUGIUUUCA | 190 |
| AM10950-SS | (NH2-C6)s(invAb)scuguucuuCfcGfuGfaaauucuas(invAb)(C6-SS-C6) | 131 | CUGUUCUUCCGUGAAAUUCUA | 183 |

(A$^{2N}$) represents a 2-aminoadenine nucleotide;
I represents an inosine (hypoxanthine) nucleotide

TABLE 4.3

DUX4 RNAi Agent Sense Strand Sequences Shown Without Terminal Linking Groups

| Sense Strand ID | Modified Sense Strand (5' → 3') | SEQ ID NO: | Underlying Base Sequence (5' → 3') (Shown as an Unmodified Nucleotide Sequence) | SEQ ID NO: |
|---|---|---|---|---|
| AM09965-SS | (invAb)scaggauucAfGfAfucugguuucas(invAb) | 132 | CAGGAUUCAGAUCUGGUUUCA | 181 |
| AM09966-SS | (invAb)saggauucaGfAfUfcugguuucaas(invAb) | 133 | AGGAUUCAGAUCUGGUUUCAA | 182 |
| AM09967-SS | (invAb)scuguucuuCfCfGfugaaauucuas(invAb) | 134 | CUGUUCUUCCGUGAAAUUCUA | 183 |

TABLE 4.3-continued

DUX4 RNAi Agent Sense Strand Sequences Shown Without Terminal Linking Groups

| Sense Strand ID | Modified Sense Strand (5' → 3') | SEQ ID NO: | Underlying Base Sequence (5' → 3') (Shown as an Unmodified Nucleotide Sequence) | SEQ ID NO: |
|---|---|---|---|---|
| AM09968-SS | (invAb)suc cuggauGfAf Ufuaguucag aas(invAb) | 135 | UCCUGGAUGA UUAGUUCAGA A | 184 |
| AM10194-SS | (invAb)sgc ccuuguUfCf Ufuccgugaa aus(invAb) | 136 | GCCCUUGUUC UUCCGUGAAA U | 185 |
| AM10196-SS | (invAb)sa_ 2NaaccuggA fUfUfagagu uacaus(inv Ab) | 137 | $(A^{2N})$AACCU GGAUUAGAGU UACAU | 186 |
| AM10198-SS | (invAb)sgg augauuAfGf Ufucagagau aus(invAb) | 138 | GGAUGAUUAG UUCAGAGAUA U | 187 |
| AM10379-SS | (invAb)sgu guucuuCfCf Gfugaaauuc uas(invAb) | 139 | GUGUUCUUCC GUGAAAUUCU A | 188 |
| AM10382-SS | (invAb)sgu guucUfuCfCf Gfugaaauuc uas(invAb) | 140 | GUGUUCUUCC GUGAAAUUCU A | 188 |
| AM10463-SS | (invAb)sgg gauucaGfAf Ufcugguuuc aas(invAb) | 141 | GGGAUUCAGA UCUGGUUUCA A | 189 |
| AM10465-SS | (invAb)sa_ 2NggauucaG fAfUfcuggu uucaas(inv Ab) | 142 | $(A^{2N})$GGAUU CAGAUCUGGU UUCAA | 239 |
| AM10568-SS | (invAb)sgg gauucaGfaU fcugguuuca as(invAb) | 143 | GGGAUUCAGA UCUGGUUUCA A | 189 |
| AM10569-SS | (invAb)sgg gauucaGfaU fCfugguuuc aas(invAb) | 144 | GGGAUUCAGA UCUGGUUUCA A | 189 |
| AM10854-SS | (invAb)sca ggauucAfGf Afucugiuuu cas(invAb) | 145 | CAGGAUUCAG AUCUGIUUUC A | 190 |
| AM10950-SS | (invAb)scu guucuuCfcG fuGfaaauuc uas(invAb) | 146 | CUGUUCUUCC GUGAAAUUCU A | 183 |

$(A^{2N})$ represents a 2-aminoadenine nucleotide;
I represents an inosine (hypoxanthine) nucleotide

TABLE 4.4

DUX4 RNAi Agent Sense Strand Sequences Shown As Modified Nucleotide Sequence Only (Without Terminal Linking Groups Or Inverted Abasic Capping Moieties)

| Sense Strand ID | Modified Sense Strand (5' → 3') | SEQ ID NO: | Underlying Base Sequence (Shown as an Unmodified Nucleotide Sequence) (5' → 3') | SEQ ID NO: |
|---|---|---|---|---|
| AM09965-SS | caggauucAf GfAfucuggu uuca | 147 | CAGGAUUCAG AUCUGGUUUC A | 181 |
| AM09966-SS | aggauucaGf AfUfcugguu ucaa | 148 | AGGAUUCAGA UCUGGUUUCA A | 182 |
| AM09967-SS | cuguucuuCf CfGfugaaaau ucua | 149 | CUGUUCUUCC GUGAAAUUCU A | 183 |
| AM09968-SS | uccuggauGf AfUfuaguuc agaa | 150 | UCCUGGAUGA UUAGUUCAGA A | 184 |
| AM10194-SS | gcccuuguUf CfUfuccgug aaau | 151 | GCCCUUGUUC UUCCGUGAAA U | 185 |
| AM10196-SS | a_2Naaccug gAfUfUfaga guuacau | 152 | $(A^{2N})$AACCU GGAUUAGAGU UACAU | 186 |
| AM10198-SS | ggaugauuAf GfUfucagag auau | 153 | GGAUGAUUAG UUCAGAGAUA U | 187 |
| AM10379-SS | guguucuuCf CfGfugaaau ucua | 154 | GUGUUCUUCC GUGAAAUUCU A | 188 |
| AM10382-SS | guguucUfuC fCfGfugaaauuc ucua | 155 | GUGUUCUUCC GUGAAAUUCU A | 188 |
| AM10463-SS | gggauucaGf AfUfcugguu ucaa | 156 | GGGAUUCAGA UCUGGUUUCA A | 189 |
| AM10465-SS | a_2Nggauuc aGfAfUfcug guuucaa | 157 | $(A^{2N})$GGAUU CAGAUCUGGU UUCAA | 239 |
| AM10568-SS | gggauucaGf aUfcugguuu caa | 158 | GGGAUUCAGA UCUGGUUUCA A | 189 |
| AM10569-SS | gggauucaGf aUfCfugguu ucaa | 159 | GGGAUUCAGA UCUGGUUUCA A | 189 |
| AM10854-SS | caggauucAf GfAfucugiu uuca | 160 | CAGGAUUCAG AUCUGIUUUC A | 190 |
| AM10950-SS | cuguucuuCf cGfuGfaaau ucua | 161 | CUGUUCUUCC GUGAAAUUCU A | 183 |

$(A^{2N})$ represents a 2-aminoadenine nucleotide;
I represents an inosine (hypoxanthine) nucleotide As discussed herein, in some embodiments, one or more targeting ligands and/or PK/PD modulators are linked or conjugated to the RNAi agent. In some embodiments, a targeting ligand (or targeting group) and/or a PK/PD modulator is linked to the 5' end of the sense strand, the 3' end of the sense strand, and/or to one or more internal nucleotides. The synthesis of the sense strand and/or the antisense strand can be designed such that reactive groups are readily available to facilitate linkage to additional components, such as a targeting ligand or PK/PD modulator. The following Table 4.5 depicts the sense strand of the DUX4 RNAi agents disclosed above in Table 4.1 after linking to one or more targeting ligands and/or PK/PD modulators (collectively, shown below, as Z). Pharmacological moieties are linked to the DUX4 RNAi agents using reactions described in Example 1, below. Following conjugation to targeting ligands, the linking groups may have the structure (NH-C6), (NH-C6)s, or (C6-S), the structure of each of which is shown in Table 6.1, below.

TABLE 4.5

DUX4 RNAi Agent Sense Strand Sequences Showing Targeting Ligand and/or PK/PD modulator Positions (Z = pharmacological moiety (e.g., targeting ligand, targeting group, and/or PK/PD modulator))

| Sense Strand ID: | Modified Sense Strand (5' → 3') | SEQ ID NO. |
|---|---|---|
| AM09965-SS | Z-(NH-C6)s(invAb)scaggauucAfGfAfucugguuucas(invAb)(C6-S)-Z | 191 |
| AM09966-SS | Z-(NH-C6)s(invAb)saggauucaGfAfUfcugguuucaas(invAb)(C6-S)-Z | 192 |
| AM09967-SS | Z-(NH-C6)s(invAb)scuguucuuCfCfGfugaaauucuas(invAb)(C6-S)-Z | 193 |
| AM09968-SS | Z-(NH-C6)s(invAb)succuggauGfAfUfuaguucagaas(invAb)(C6-S)-Z | 194 |
| AM10194-SS | Z-(NH-C6)s(invAb)sgcccuuguUfCfUfuccgugaaaus(invAb)(C6-S)-Z | 195 |
| AM10196-SS | Z-(NH-C6)s(invAb)sa_2NaaccuggAfUfUfagaguuacaus(invAb)(C6-S)-Z | 196 |
| AM10198-SS | Z-(NH-C6)s(invAb)sggaugauuAfGfUfucagagauaus(invAb)(C6-S)-Z | 197 |

TABLE 4.5-continued

DUX4 RNAi Agent Sense Strand Sequences Showing Targeting Ligand and/or PK/PD modulator Positions (Z = pharmacological moiety (e.g., targeting ligand, targeting group, and/or PK/PD modulator))

| Sense Strand ID: | Modified Sense Strand (5' → 3') | SEQ ID NO. |
|---|---|---|
| AM10379-SS | Z-(NH-C6)s(invAb)sguguucuuCfCfGfugaaauucuas(invAb)(C6-S)-Z | 198 |
| AM10382-SS | Z-(NH-C6)s(invAb)sguguucUfuCfcGfugaaauucuas(invAb)(C6-S)-Z | 199 |
| AM10463-SS | Z-(NH-C6)s(invAb)sgggauucaGfAfUfcugguuucaas(invAb)(C6-S)-Z | 200 |
| AM10465-SS | Z-(NH-C6)s(invAb)sa_2NggauucaGfAfUfcugguuucaas(invAb)(C6-S)-Z | 201 |
| AM10568-SS | Z-(NH-C6)s(invAb)sgggauucaGfaUfcugguuucaas(invAb)(C6-S)-Z | 202 |
| AM10569-SS | Z-(NH-C6)s(invAb)sgggauucaGfaUfCfugguuucaas(invAb)(C6-S)-Z | 203 |
| AM10854-SS | Z-(NH-C6)s(invAb)scaggauucAfGfAfucugiuuucas(invAb)(C6-S)-Z | 204 |
| AM10950-SS | Z-(NH-C6)s(invAb)scuguucuuCfcGfuGfaaauucuas(invAb)(C6-S)-Z | 205 |

TABLE 4.6

DUX4 RNAi Agent Sense Strand Sequences
Showing Targeting Ligand linked at
the 5' terminal end and PK/PD modulator
linked at the 3' terminal end of
the sense strand.
(TL = targeting ligand;
PK = PK/PD modulator))

| Sense Strand ID: | Modified Sense Strand (5' → 3') | SEQ ID NO. |
|---|---|---|
| AM09965-SS | TL-(NH-C6)s(inv Ab)scaggauucAfG fAfucugguuucas( invAb)(C6-S)-PK | 206 |
| AM09966-SS | TL-(NH-C6)s(inv Ab)saggauucaGfA fUfcugguuucaas( invAb)(C6-S)-PK | 207 |
| AM09967-SS | TL-(NH-C6)s(inv Ab)scuguucuuCfC fGfugaaauucuas( invAb)(C6-S)-PK | 208 |
| AM09968-SS | TL-(NH-C6)s(inv Ab)succuggauGfA fUfuaguucagaas( invAb)(C6-S)-PK | 209 |
| AM10194-SS | TL-(NH-C6)s(inv Ab)sgcccuuguUfC fUfuccgugaaaus( invAb)(C6-S)-PK | 210 |
| AM10196-SS | TL-(NH-C6)s(inv Ab)sa_2Naaccugg AfUfUfagaguuaca us(invAb)(C6-S) -PK | 211 |
| AM10198-SS | TL-(NH-C6)s(inv Ab)sggaugauuAfG fUfucagagauaus( invAb)(C6-S)-PK | 212 |
| AM10379-SS | TL-(NH-C6)s(inv Ab)sguguucuuCfC fGfugaaauucuas( invAb)(C6-S)-PK | 213 |
| AM10382-SS | TL-(NH-C6)s(inv Ab)sguguucUfuCf cGfugaaauucuas( invAb)(C6-S)-PK | 214 |
| AM10463-SS | TL-(NH-C6)s(inv Ab)sgggauucaGfA fUfcugguuucaas( invAb)(C6-S)-PK | 215 |
| AM10465-SS | TL-(NH-C6)s(inv Ab)sa_2Nggauuca GfAfUfcugguuuca as(invAb)(C6-S) -PK | 216 |
| AM10568-SS | TL-(NH-C6)s(inv Ab)sgggauucaGfa Ufcugguuucaas(i nvAb)(C6-S)-PK | 217 |
| AM10569-SS | TL-(NH-C6)s(inv Ab)sgggauucaGfa UfCfugguuucaas( invAb)(C6-S)-PK | 218 |
| AM10854-SS | TL-(NH-C6)s(inv Ab)scaggauucAfG fAfucugiuuucas( invAb)(C6-S)-PK | 219 |
| AM10950-SS | TL-(NH-C6)s(inv Ab)scuguucuuCfc GfuGfaaauucuas( invAb)(C6-S)-PK | 220 |

The DUX4 RNAi agents described herein are formed by annealing an antisense strand with a sense strand. A sense strand containing a sequence listed in Table 2 or Table 4.1, 4.2, 4.3, 4.4, 4.5, 4.6 or 5.4 can be hybridized to any antisense strand containing a sequence listed in Table 2, Table 3, or Table 5.4, provided the two sequences have a region of at least 85% complementarity over a contiguous 16, 17, 18, 19, 20, or 21 nucleotide sequence.

In some embodiments, the antisense strand of a DUX4 RNAi agent disclosed herein differs by 0, 1, 2, or 3 nucleotides from any of the antisense strand sequences in Table 3. In some embodiments, the sense strand of a DUX4 RNAi agent disclosed herein differs by 0, 1, 2, or 3 nucleotides from any of the sense strand sequences in Table 4.1, 4.2, 4.3, 4.4, 4.5, 4.6, or 5.4.

In some embodiments, a DUX4 RNAi agent antisense strand comprises a nucleotide sequence of any of the sequences in Table 2 or Table 3. In some embodiments, a DUX4 RNAi agent antisense strand comprises the sequence of nucleotides (from 5' end→3' end) 1-17, 2-17, 1-18, 2-18, 1-19, 2-19, 1-20, 2-20, 1-21, 2-21, 1-22, 2-22, 1-23, 2-23, 1-24, or 2-24 of any of the sequences in Table 2, Table 3, or Table 5.4. In certain embodiments, a DUX4 RNAi agent antisense strand comprises or consists of a modified sequence of any one of the modified sequences in Table 3.

In some embodiments, a DUX4 RNAi agent sense strand comprises the nucleotide sequence of any of the sequences in Table 2 or Table 4.1, 4.2, 4.3, 4.4, 4.5, 4.6, or 5.4. In some embodiments, a DUX4 RNAi agent sense strand comprises the sequence of nucleotides (from 5' end→3' end) 1-17, 2-17, 3-17, 4-17, 1-18, 2-18, 3-18, 4-18, 1-19, 2-19, 3-19, 4-19, 1-20, 2-20, 3-20, 4-20, 1-21, 2-21, 3-21, 4-21, 1-22, 2-22, 3-22, 4-22, 1-23, 2-23, 3-23, 4-23, 1-24, 2-24, 3-24, or 4-24 of any of the sequences in Table 2 or Table 4.1, 4.2, 4.3, 4.4, 4.5, 4.6, or 5.4. In certain embodiments, a DUX4 RNAi agent sense strand comprises or consists of a modified sequence of any one of the modified sequences in Table 4.1, 4.2, 4.3, 4.4, 4.5, 4.6, or 5.4.

For the DUX4 RNAi agents disclosed herein, the nucleotide at position 1 of the antisense strand (from 5' end→3' end) can be perfectly complementary to a DUX4 gene, or can be non-complementary to a DUX4 gene. In some embodiments, the nucleotide at position 1 of the antisense strand (from 5' end→3' end) is a U, A, or dT (or a modified version thereof). In some embodiments, the nucleotide at position 1 of the antisense strand (from 5' end→3' end) forms an A:U or U:A base pair with the sense strand.

In some embodiments, a DUX4 RNAi agent antisense strand comprises the sequence of nucleotides (from 5' end→3' end) 2-18 or 2-19 of any of the antisense strand sequences in Table 2 or Table 3. In some embodiments, a DUX4 RNAi sense strand comprises the sequence of nucleotides (from 5' end→3' end) 1-17 or 1-18 of any of the sense strand sequences in Table 2 or Table 4.1, 4.2, 4.3, 4.4, 4.5, 4.6, or 5.4.

In some embodiments, a DUX4 RNAi agent includes (i) an antisense strand comprising the sequence of nucleotides (from 5' end→3' end) 2-18 or 2-19 of any of the antisense strand sequences in Table 2 or Table 3, and (ii) a sense strand comprising the sequence of nucleotides (from 5' end→3' end) 1-17 or 1-18 of any of the sense strand sequences in Table 2 or Table 4.1, 4.2, 4.3, 4.4, 4.5, 4.6, or 5.4.

A sense strand containing a sequence listed in Table 2 or Table 4 can be hybridized to any antisense strand containing a sequence listed in Table 2 or Table 3, provided the two sequences have a region of at least 85% complementarity over a contiguous 16, 17, 18, 19, 20, or 21 nucleotide sequence. In some embodiments, the DUX4 RNAi agent has a sense strand consisting of the modified sequence of any of the modified sequences in Table 4.1, 4.2, 4.3, 4.4, 4.5, 4.6, or 5.4 and an antisense strand consisting of the modified sequence of any of the modified sequences in Table 3 or Table 5.4. Certain representative sequence pairings are exemplified by the Duplex ID Nos. shown in Table 5.1, 5.2, 5.3, and 5.4.

In some embodiments, a DUX4 RNAi agent comprises, consists of, or consists essentially of a duplex represented by any one of the Duplex ID Nos. presented herein. In some embodiments, a DUX4 RNAi agent comprises the sense strand and antisense strand nucleotide sequences of any of the duplexes represented by any of the Duplex ID Nos. presented herein. In some embodiments, a DUX4 RNAi agent comprises the sense strand and antisense strand nucleotide sequences of any of the duplexes represented by any of the Duplex ID Nos. presented herein and a targeting ligand, targeting group, and/or linking group wherein the targeting ligand, targeting group, and/or linking group is covalently linked (i.e., conjugated) to the sense strand or the antisense strand. In some embodiments, a DUX4 RNAi agent includes the sense strand and antisense strand modified nucleotide sequences of any of the Duplex ID Nos. presented herein. In some embodiments, a DUX4 RNAi agent comprises the sense strand and antisense strand modified nucleotide sequences of any of the Duplex ID Nos. presented herein and a targeting ligand, targeting group, and/or linking group, wherein the targeting ligand, targeting group, and/or linking group is covalently linked to the sense strand or the antisense strand.

In some embodiments, a DUX4 RNAi agent comprises an antisense strand and a sense strand having the nucleotide sequences of any of the antisense strand/sense strand duplexes of Table 2 or Table 5.1 (or Table 5.2, Table 5.3, or Table 5.4), and further comprises a targeting group. In some embodiments, a DUX4 RNAi agent comprises an antisense strand and a sense strand having the nucleotide sequences of any of the antisense strand/sense strand duplexes of Table 5.1 (or Table 5.2, or 5.3, or Table 5.4), and further comprises an integrin receptor ligand targeting group.

In some embodiments, a DUX4 RNAi agent comprises an antisense strand and a sense strand having the nucleotide sequences of any of the antisense strand/sense strand duplexes of Table 5.1, 5.2, 5.3, or 5.4, and comprises one or more linking groups selected from the group consisting of (NH2-C6), (C6-NH2), (C6-SS-C6), or (6-SS-6), each as defined in Table 6.1.

In some embodiments, a DUX4 RNAi agent comprises an antisense strand and a sense strand having the modified nucleotide sequence of any of the antisense strand and/or sense strand nucleotide sequences in Table 3 or Table 4.1, 4.2, 4.3, 4.4, 4.5, 4.6 or 5.4.

In some embodiments, a DUX4 RNAi agent comprises an antisense strand and a sense strand having a modified nucleotide sequence of any of the antisense strand and/or sense strand nucleotide sequences of any of the duplexes Table 5.1 (or Table 5.2, 5.3 or 5.4), and further comprises an integrin targeting group.

In some embodiments, a DUX4 RNAi agent comprises, consists of, or consists essentially of any of the duplexes of Table 5.1 (or Table 5.2, 5.3, or 5.4).

TABLE 5.1

DUX4 RNAi Agents Duplexes with Corresponding Sense and Antisense Strand ID Numbers

| Duplex ID | Antisense Strand ID | Sense Strand ID |
| --- | --- | --- |
| AD07218 | AM09247-AS | AM09965-SS |
| AD07219 | AM09250-AS | AM09966-SS |
| AD07220 | AM09252-AS | AM09967-SS |
| AD07221 | AM09260-AS | AM09968-SS |
| AD07274 | AM10029-AS | AM09965-SS |
| AD07275 | AM10030-AS | AM09966-SS |
| AD07276 | AM10026-AS | AM09967-SS |
| AD07277 | AM10028-AS | AM09968-SS |
| AD07394 | AM10009-AS | AM10194-SS |
| AD07395 | AM10195-AS | AM10194-SS |
| AD07396 | AM10019-AS | AM10196-SS |
| AD07397 | AM10197-AS | AM10196-SS |
| AD07398 | AM10023-AS | AM10198-SS |
| AD07399 | AM10199-AS | AM10198-SS |
| AD07510 | AM10252-AS | AM09967-SS |
| AD07511 | AM10378-AS | AM09967-SS |
| AD07512 | AM10380-AS | AM10379-SS |
| AD07513 | AM10381-AS | AM10379-SS |
| AD07514 | AM10380-AS | AM10382-SS |
| AD07515 | AM10381-AS | AM10382-SS |
| AD07555 | AM10159-AS | AM10463-SS |
| AD07556 | AM10464-AS | AM10463-SS |
| AD07557 | AM09250-AS | AM10465-SS |
| AD07558 | AM10030-AS | AM10465-SS |
| AD07615 | AM10564-AS | AM10463-SS |
| AD07616 | AM10565-AS | AM10463-SS |
| AD07617 | AM10566-AS | AM10463-SS |
| AD07618 | AM10567-AS | AM10463-SS |
| AD07619 | AM10464-AS | AM10568-SS |
| AD07620 | AM10464-AS | AM10569-SS |
| AD07662 | AM10260-AS | AM09968-SS |
| AD07663 | AM10645-AS | AM09968-SS |
| AD07664 | AM10251-AS | AM09967-SS |
| AD07665 | AM10646-AS | AM09967-SS |
| AD07666 | AM10647-AS | AM10379-SS |
| AD07667 | AM10648-AS | AM10379-SS |
| AD07775 | AM10850-AS | AM09965-SS |
| AD07776 | AM10851-AS | AM09965-SS |
| AD07777 | AM10852-AS | AM09965-SS |
| AD07778 | AM10853-AS | AM09965-SS |
| AD07779 | AM09247-AS | AM10854-SS |
| AD07780 | AM10029-AS | AM10854-SS |
| AD07843 | AM10948-AS | AM09967-SS |
| AD07844 | AM10949-AS | AM09967-SS |
| AD07845 | AM10949-AS | AM10950-SS |

TABLE 5.2

DUX4 RNAi Agent Duplexes with Corresponding Sense and Antisense Strand ID
Numbers and Sequence ID numbers for the modified and unmodified nucleotide sequences.

| Duplex | AS ID | AS modified SEQ ID NO: | AS unmodified SEQ ID NO: | SS ID | SS modified SEQ ID NO*: | SS unmodified SEQ ID NO: |
|---|---|---|---|---|---|---|
| AD07218 | AM09247-AS | 66 | 162 | AM09965-SS | 117 | 181 |
| AD07219 | AM09250-AS | 67 | 163 | AM09966-SS | 118 | 182 |
| AD07220 | AM09252-AS | 68 | 164 | AM09967-SS | 119 | 183 |
| AD07221 | AM09260-AS | 69 | 165 | AM09968-SS | 120 | 184 |
| AD07274 | AM10029-AS | 75 | 162 | AM09965-SS | 117 | 181 |
| AD07275 | AM10030-AS | 76 | 163 | AM09966-SS | 118 | 182 |
| AD07276 | AM10026-AS | 73 | 164 | AM09967-SS | 119 | 183 |
| AD07277 | AM10028-AS | 74 | 165 | AM09968-SS | 120 | 184 |
| AD07394 | AM10009-AS | 70 | 166 | AM10194-SS | 121 | 185 |
| AD07395 | AM10195-AS | 78 | 166 | AM10194-SS | 121 | 185 |
| AD07396 | AM10019-AS | 71 | 167 | AM10196-SS | 122 | 186 |
| AD07397 | AM10197-AS | 79 | 167 | AM10196-SS | 122 | 186 |
| AD07398 | AM10023-AS | 72 | 168 | AM10198-SS | 123 | 187 |
| AD07399 | AM10199-AS | 80 | 168 | AM10198-SS | 123 | 187 |
| AD07510 | AM10252-AS | 82 | 164 | AM09967-SS | 119 | 183 |
| AD07511 | AM10378-AS | 84 | 164 | AM09967-SS | 119 | 183 |
| AD07512 | AM10380-AS | 85 | 170 | AM10379-SS | 124 | 188 |
| AD07513 | AM10381-AS | 86 | 170 | AM10379-SS | 124 | 188 |
| AD07514 | AM10380-AS | 85 | 170 | AM10382-SS | 125 | 188 |
| AD07515 | AM10381-AS | 86 | 170 | AM10382-SS | 125 | 188 |
| AD07555 | AM10159-AS | 77 | 169 | AM10463-SS | 126 | 189 |
| AD07556 | AM10464-AS | 87 | 169 | AM10463-SS | 126 | 189 |
| AD07557 | AM09250-AS | 67 | 163 | AM10465-SS | 127 | 239 |
| AD07558 | AM10030-AS | 76 | 163 | AM10465-SS | 127 | 239 |
| AD07615 | AM10564-AS | 88 | 169 | AM10463-SS | 126 | 189 |
| AD07616 | AM10565-AS | 89 | 169 | AM10463-SS | 126 | 189 |
| AD07617 | AM10566-AS | 90 | 169 | AM10463-SS | 126 | 189 |
| AD07618 | AM10567-AS | 91 | 169 | AM10463-SS | 126 | 189 |
| AD07619 | AM10464-AS | 87 | 169 | AM10568-SS | 128 | 189 |
| AD07620 | AM10464-AS | 87 | 169 | AM10569-SS | 129 | 189 |
| AD07662 | AM10260-AS | 83 | 165 | AM09968-SS | 120 | 184 |
| AD07663 | AM10645-AS | 92 | 165 | AM09968-SS | 120 | 184 |
| AD07664 | AM10251-AS | 81 | 164 | AM09967-SS | 119 | 183 |
| AD07665 | AM10646-AS | 93 | 164 | AM09967-SS | 119 | 183 |
| AD07666 | AM10647-AS | 94 | 170 | AM10379-SS | 124 | 188 |
| AD07667 | AM10648-AS | 95 | 170 | AM10379-SS | 124 | 188 |
| AD07775 | AM10850-AS | 96 | 162 | AM09965-SS | 117 | 181 |
| AD07776 | AM10851-AS | 97 | 162 | AM09965-SS | 117 | 181 |
| AD07777 | AM10852-AS | 98 | 162 | AM09965-SS | 117 | 181 |
| AD07778 | AM10853-AS | 99 | 162 | AM09965-SS | 117 | 181 |
| AD07779 | AM09247-AS | 66 | 162 | AM10854-SS | 130 | 190 |
| AD07780 | AM10029-AS | 75 | 162 | AM10854-SS | 130 | 190 |
| AD07843 | AM10948-AS | 100 | 164 | AM09967-SS | 119 | 183 |
| AD07844 | AM10949-AS | 101 | 164 | AM09967-SS | 119 | 183 |
| AD07845 | AM10949-AS | 101 | 164 | AM10950-SS | 131 | 183 |

*Modified SS sequence is taken from Table 4.2 (shown without terminal dT added for manufacturability).

TABLE 5.3

DUX4 RNAi Agents Duplexes with
Corresponding Sense and Antisense Strand
ID Numbers Referencing Position Targeted on DUX4 Gene

| Duplex ID | Antisense Strand ID | Sense Strand ID | Targeted XHD Gene Position (Of SEQ ID NO: 1) |
|---|---|---|---|
| AD07218 | AM09247-AS | AM09965-SS | 408 |
| AD07219 | AM09250-AS | AM09966-SS | 409 |
| AD07220 | AM09252-AS | AM09967-SS | 1437 |
| AD07221 | AM09260-AS | AM09968-SS | 1518 |
| AD07274 | AM10029-AS | AM09965-SS | 408 |
| AD07275 | AM10030-AS | AM09966-SS | 409 |
| AD07276 | AM10026-AS | AM09967-SS | 1437 |
| AD07277 | AM10028-AS | AM09968-SS | 1518 |
| AD07394 | AM10009-AS | AM10194-SS | 1433 |
| AD07395 | AM10195-AS | AM10194-SS | 1433 |
| AD07396 | AM10019-AS | AM10196-SS | 1496 |
| AD07397 | AM10197-AS | AM10196-SS | 1496 |
| AD07398 | AM10023-AS | AM10198-SS | 1522 |
| AD07399 | AM10199-AS | AM10198-SS | 1522 |
| AD07510 | AM10252-AS | AM09967-SS | 1437 |
| AD07511 | AM10378-AS | AM09967-SS | 1437 |
| AD07512 | AM10380-AS | AM10379-SS | 1437 |
| AD07513 | AM10381-AS | AM10379-SS | 1437 |
| AD07514 | AM10380-AS | AM10382-SS | 1437 |
| AD07515 | AM10381-AS | AM10382-SS | 1437 |
| AD07555 | AM10159-AS | AM10463-SS | 409 |
| AD07556 | AM10464-AS | AM10463-SS | 409 |
| AD07557 | AM09250-AS | AM10465-SS | 409 |
| AD07558 | AM10030-AS | AM10465-SS | 409 |
| AD07615 | AM10564-AS | AM10463-SS | 409 |
| AD07616 | AM10565-AS | AM10463-SS | 409 |

TABLE 5.3-continued

DUX4 RNAi Agents Duplexes with Corresponding Sense and Antisense Strand ID Numbers Referencing Position Targeted on DUX4 Gene

| Duplex ID | Antisense Strand ID | Sense Strand ID | Targeted XHD Gene Position (Of SEQ ID NO: 1) |
|---|---|---|---|
| AD07617 | AM10566-AS | AM10463-SS | 409 |
| AD07618 | AM10567-AS | AM10463-SS | 409 |
| AD07619 | AM10464-AS | AM10568-SS | 409 |
| AD07620 | AM10464-AS | AM10569-SS | 409 |
| AD07662 | AM10260-AS | AM09968-SS | 1518 |
| AD07663 | AM10645-AS | AM09968-SS | 1518 |
| AD07664 | AM10251-AS | AM09967-SS | 1437 |
| AD07665 | AM10646-AS | AM09967-SS | 1437 |
| AD07666 | AM10647-AS | AM10379-SS | 1437 |
| AD07667 | AM10648-AS | AM10379-SS | 1437 |
| AD07775 | AM10850-AS | AM09965-SS | 408 |
| AD07776 | AM10851-AS | AM09965-SS | 408 |
| AD07777 | AM10852-AS | AM09965-SS | 408 |
| AD07778 | AM10853-AS | AM09965-SS | 408 |
| AD07779 | AM09247-AS | AM10854-SS | 408 |
| AD07780 | AM10029-AS | AM10854-SS | 408 |
| AD07843 | AM10948-AS | AM09967-SS | 1437 |
| AD07844 | AM10949-AS | AM09967-SS | 1437 |
| AD07845 | AM10949-AS | AM10950-SS | 1437 |

As described herein, in some embodiments, the duplexed sense strand nucleotide sequence and antisense strand nucleotide sequence can be linked to certain targeting ligands and/or PK/PD modulators. Certain exemplary targeting ligands and/or PK/PD modulators we linked as shown in the following Table 5.4, which shows fully conjugated duplexes and have an "AC" identification prefix.

TABLE 5.4

Conjugate ID Numbers With Chemically Modified Antisense and Sense Strands (including Linkers and Conjugates)

| ACID Number | Strand (SS = Sense Strand AS = Antisense strand) | Strand (Fully Modified with Conjugated Targeting Ligand) (5' → 3') | Fully Conjugated Version of AD ID Number |
|---|---|---|---|
| AC000232 | SS | αvβ6-SM45-L4-(NH-C6)s(invAb)scuguucuuCfCfGfugaaauucuas(invAb)(C6-S)-LP1b (SEQ ID NO: 221) | AD07511 |
|  | AS | cPrpusAfsGfsAfauuucacGfgAfaGfaacasg (SEQ ID NO: 84) |  |
| AC000237 | SS | αvβ6-SM45-L4-(NH-C6)s(invAb)scaggauucAfGfAfucugguuucas(invAb)(C6-S)-LP1b (SEQ ID NO: 222) | AD07776 |
|  | AS | cPrpusGfsasaaccagauCfuGfaAfuccusg (SEQ ID NO: 97) |  |
| AC000246 | SS | αvβ6-pep1-(NH-C6)s(invAb)scuguucuuCfCfGfugaaauucuas(invAb)(C6-S)-LP38b (SEQ ID NO: 223) | AD07511 |
|  | AS | cPrpusAfsGfsAfauuucacGfgAfaGfaacasg (SEQ ID NO: 84) |  |
| AC000247 | SS | αvβ6-pep1-(NH-C6)s(invAb)scaggauucAfGfAfucugguuucas(invAb)(C6-S)-LP38b (SEQ ID NO: 224) | AD07776 |
|  | AS | cPrpusGfsasaaccagauCfuGfaAfuccusg (SEQ ID NO: 97) |  |
| AC000250 | SS | αvβ6-SM45-L4-(NH-C6)s(invAb)scuguucuuCfCfGfugaaauucuas(invAb)(C6-S)-LP1b (SEQ ID NO: 221) | AD07220 |
|  | AS | usAfsgsAfaUfuUfcAfcGfgAfaGfaAfcAfsg (SEQ ID NO: 68) |  |
| AC000251 | SS | αvβ6-SM45-L4-(NH-C6)s(invAb)scaggauucAfGfAfucugguuucas(invAb)(C6-S)-LP1b (SEQ ID NO: 222) | AD07218 |
|  | AS | usGfsasAfaCfcAfgAfuCfuGfaAfuCfcUfsg (SEQ ID NO: 66) |  |
| AC000252 | SS | αvβ6-SM45-L4-(NH-C6)s(invAb)saggauucaGfAfUfcugguuucaas(invAb)(C6-S)-LP1b (SEQ ID NO: 225) | AD07219 |
|  | AS | usUfsgsAfaAfcCfaGfaUfcUfgAfaUfcCfsu (SEQ ID NO: 67) |  |

TABLE 5.4-continued

Conjugate ID Numbers With Chemically Modified Antisense and
Sense Strands (including Linkers and Conjugates)

| ACID Number | Strand (SS = Sense Strand AS = Antisense strand) | Strand (Fully Modified with Conjugated Targeting Ligand) (5' → 3') | Fully Conjugated Version of AD ID Number |
|---|---|---|---|
| AC000253 | SS | αvβ6-SM45-L4-(NH-C6)s(invAb)saggauucaGfAfUfcugguuucaas(invAb)(C6-S)-LP1b (SEQ ID NO: 225) | AD07275 |
| | AS | cPrpusUfsgsAfaAfcCfaGfaUfcUfgAfaUfcCfsu (SEQ ID NO: 76) | |
| AC000254 | SS | αvβ6-SM45-L4-(NH-C6)s(invAb)scuguucuuCfCfGfugaaauucuas(invAb)(C6-S)-LP1b (SEQ ID NO: 221) | AD07276 |
| | AS | cPrpusAfsgsAfaUfuUfcAfcGfgAfaGfaAfcAfsg (SEQ ID NO: 73) | |
| AC000255 | SS | αvβ6-SM45-L4-(NH-C6)s(invAb)succuggauGfAfUfuaguucagaas(invAb)(C6-S)-LP1b (SEQ ID NO: 226) | AD07221 |
| | AS | usUfscsUfgAfaCfuAfaUfcAfuCfcAfgGfsa (SEQ ID NO: 69) | |
| AC000256 | SS | αvβ6-SM45-L4-(NH-C6)s(invAb)succuggauGfAfUfuaguucagaas(invAb)(C6-S)-LP1b (SEQ ID NO: 226) | AD07277 |
| | AS | cPrpusUfscsUfgAfaCfuAfaUfcAfuCfcAfgGfsa (SEQ ID NO: 74) | |
| AC000257 | SS | αvβ6-SM45-L4-(NH-C6)s(invAb)sa_2NaaccuggAfUfUfagaguuacaus(invAb)(C6-S)-LP1b (SEQ ID NO: 227) | AD07396 |
| | AS | asUfsgsUfaAfcCfcUfaAfuCfcAfgGfuUfsu (SEQ ID NO: 71) | |
| AC000258 | SS | αvβ6-SM45-L4-(NH-C6)s(invAb)scuguucuuCfCfGfugaaauucuas(invAb)(C6-S)-LP1b (SEQ ID NO: 221) | AD07276 |
| | AS | cPrpusAfsgsAfaUfuUfcAfcGfgAfaGfaAfcAfsg (SEQ ID NO: 73) | |
| AC000259 | SS | αvβ6-SM45-L4-(NH-C6)s(invAb)scuguucuuCfCfGfugaaauucuas(invAb)(C6-S)-LP1b (SEQ ID NO: 221) | AD07510 |
| | AS | usAfsGfsAfauuucacGfgAfaGfaacasg (SEQ ID NO: 82) | |
| AC000260 | SS | αvβ6-SM45-L4-(NH-C6)s(invAb)sguguucuuCfCfGfugaaauucuas(invAb)(C6-S)-LP1b (SEQ ID NO: 228) | AD07512 |
| | AS | us AfsGfsAfauuucacGfgAfaGfaacasc (SEQ ID NO: 85) | |
| AC000261 | SS | αvβ6-SM45-L4-(NH-C6)s(invAb)sguguucuuCfCfGfugaaauucuas(invAb)(C6-S)-LP1b (SEQ ID NO: 228) | AD07513 |
| | AS | cPrpusAfsGfsAfauuucacGfgAfaGfaacasc (SEQ ID NO: 86) | |
| AC000262 | SS | αvβ6-SM45-L4-(NH-C6)s(invAb)sguguucUfuCfcCfgGfugaaauucuas(invAb)(C6-S)-LP1b (SEQ ID NO: 229) | AD07514 |
| | AS | usAfsGfsAfauuucacGfgAfaGfaacasc (SEQ ID NO: 85) | |
| AC000263 | SS | αvβ6-SM45-L4-(NH-C6)s(invAb)sguguucUfuCfcCfgGfugaaauucuas(invAb)(C6-S)-LP1b (SEQ ID NO: 229) | AD07515 |
| | AS | cPrpusAfsGfsAfauuucacGfgAfaGfaacasc (SEQ ID NO: 86) | |
| AC000264 | SS | αvβ6-SM45-L4-(NH-C6)s(invAb)sgcccuuguUfCfUfuccgugaaaus(invAb)(C6-S)-LP1b (SEQ ID NO: 230) | AD07394 |
| | AS | asUfsusUfcAfcGfgAfaGfaAfcAfaGfgGfsc (SEQ ID NO: 70) | |
| AC000265 | SS | αvβ6-SM45-L4-(NH-C6)s(invAb)sgcccuuguUfCfUfuccgugaaaus(invAb)(C6-S)-LP1b (SEQ ID NO: 230) | AD07395 |
| | AS | cPrpasUfsusUfcAfcGfgAfaGfaAfcAfaGfgGfsc (SEQ ID NO: 78) | |
| AC000266 | SS | αvβ6-SM45-L4-(NH-C6)s(invAb)sggaugauuAfGfUfucagagauaus(invAb)(C6-S)-LP1b (SEQ ID NO: 231) | AD07398 |
| | AS | asUfsasUfcUfcUfgAfaCfuAfaUfcAfuCfsc (SEQ ID NO: 72) | |

TABLE 5.4-continued

Conjugate ID Numbers With Chemically Modified Antisense and
Sense Strands (including Linkers and Conjugates)

| ACID Number | Strand (SS = Sense Strand AS = Antisense strand) | Strand (Fully Modified with Conjugated Targeting Ligand) (5' → 3') | Fully Conjugated Version of AD ID Number |
|---|---|---|---|
| AC000267 | SS | αvβ6-SM45-L4-(NH-C6)s(invAb)sggaugauuAfGfUfucagagauaus(invAb)(C6-S)-LP1b (SEQ ID NO: 231) | AD07399 |
|  | AS | cPrpasUfsasUfcUfcUfgAfaCfuAfaUfcAfuCfsc (SEQ ID NO: 80) |  |
| AC000268 | SS | αvβ6-SM45-L4-(NH-C6)s(invAb)sgggauucaGfAfUfcugguuucaas(invAb)(C6-S)-LP1b (SEQ ID NO: 232) | AD07555 |
|  | AS | usUfsgsAfaAfcCfaGfaUfcUfgAfaUfcCfsc (SEQ ID NO: 77) |  |
| AC000269 | SS | αvβ6-SM45-L4-(NH-C6)s(invAb)sgggauucaGfAfUfcugguuucaas(invAb)(C6-S)-LP1b (SEQ ID NO: 232) | AD07556 |
|  | AS | cPrpusUfsgsAfaAfcCfaGfaUfcUfgAfaUfcCfsc (SEQ ID NO: 87) |  |
| AC000270 | SS | αvβ6-SM45-L4-(NH-C6)s(invAb)sa_2NggauucaGfAfUfcugguuucaas(invAb)(C6-S)-LP1b (SEQ ID NO: 244) | AD07557 |
|  | AS | usUfsgsAfaAfcCfaGfaUfcUfgAfaUfcCfsu (SEQ ID NO: 67) |  |
| AC000271 | SS | αvβ6-SM45-L4-(NH-C6)s(invAb)sa_2NggauucaGfAfUfcugguuucaas(invAb)(C6-S)-LP1b (SEQ ID NO: 245) | AD07558 |
|  | AS | cPrpusUfsgsAfaAfcCfaGfaUfcUfgAfaUfcCfsu (SEQ ID NO: 76) |  |
| AC000272 | SS | αvβ6-SM45-L4-(NH-C6)s(invAb)sgggauucaGfAfUfcugguuucaas(invAb)(C6-S)-LP1b (SEQ ID NO: 232) | AD07615 |
|  | AS | us UfsgsaaaccagaUfcUfgAfauccsc (SEQ ID NO: 88) |  |
| AC000273 | SS | αvβ6-SM45-L4-(NH-C6)s(invAb)sgggauucaGfAfUfcugguuucaas(invAb)(C6-S)-LP1b (SEQ ID NO: 232) | AD07616 |
|  | AS | cPrpusUfsgsaaaccagaUfcUfgAfauccsc (SEQ ID NO: 89) |  |
| AC000274 | SS | αvβ6-SM45-L4-(NH-C6)s(invAb)sgggauucaGfAfUfcugguuucaas(invAb)(C6-S)-LP1b (SEQ ID NO: 232) | AD07617 |
|  | AS | usUfsgsaaacCfaGfaUfcUfgAfauccsc (SEQ ID NO: 90) |  |
| AC000275 | SS | αvβ6-SM45-L4-(NH-C6)s(invAb)sgggauucaGfAfUfcugguuucaas(invAb)(C6-S)-LP1b (SEQ ID NO: 232) | AD07618 |
|  | AS | cPrpusUfsgsaaacCfaGfaUfcUfgAfauccsc (SEQ ID NO: 91) |  |
| AC000276 | SS | αvβ6-SM45-L4-(NH-C6)s(invAb)sgggauucaGfaUfcugguuucaas(invAb)(C6-S)-LP1b (SEQ ID NO: 233) | AD07619 |
|  | AS | cPrpusUfsgsAfaAfcCfaGfaUfcUfgAfaUfcCfsc (SEQ ID NO: 87) |  |
| AC000277 | SS | αvβ6-SM45-L4-(NH-C6)s(invAb)sgggauucaGfaUfCfugguuucaas(invAb)(C6-S)-LP1b (SEQ ID NO: 234) | AD07620 |
|  | AS | cPrpusUfsgsAfaAfcCfaGfaUfcUfgAfaUfcCfsc (SEQ ID NO: 87) |  |
| AC000278 | SS | αvβ6-SM45-L4-(NH-C6)s(invAb)scaggauucAfGfAfucugguuucas(invAb)(C6-S)-LP1b (SEQ ID NO: 222) | AD07274 |
|  | AS | cPrpusGfsasAfaCfcAfgAfuCfuGfaAfuCfcUfsg (SEQ ID NO: 75) |  |
| AC000279 | SS | αvβ6-SM45-L4-(NH-C6)s(invAb)scaggauucAfGfAfucugguuucas(invAb)(C6-S)-LP1b (SEQ ID NO: 222) | AD07775 |
|  | AS | usGfsasaaccagauCfuGfaAfuccusg (SEQ ID NO: 96) |  |

TABLE 5.4-continued

Conjugate ID Numbers With Chemically Modified Antisense and
Sense Strands (including Linkers and Conjugates)

| ACID Number | Strand (SS = Sense Strand AS = Antisense strand) | Strand (Fully Modified with Conjugated Targeting Ligand) (5' → 3') | Fully Conjugated Version of AD ID Number |
|---|---|---|---|
| AC000280 | SS | αvβ6-SM45-L4-(NH-C6)s(invAb)scaggauucAfGfAfucugguuucas(invAb)(C6-S)-LP1b (SEQ ID NO: 222) | AD07777 |
|  | AS | usGfsasAfaccagauCfuGfaAfuccusg (SEQ ID NO: 98) |  |
| AC000281 | SS | αvβ6-SM45-L4-(NH-C6)s(invAb)scaggauucAfGfAfucugguuucas(invAb)(C6-S)-LP1b (SEQ ID NO: 222) | AD07778 |
|  | AS | cPrpusGfsasAfaccagauCfuGfaAfuccusg (SEQ ID NO: 99) |  |
| AC000282 | SS | αvβ6-SM45-L4-(NH-C6)s(invAb)scuguucuuCfCfGfugaaauucuas(invAb)(C6-S)-LP1b (SEQ ID NO: 221) | AD07843 |
|  | AS | cPrpusAfsgsAfauuucacGfgAfaGfaacasg (SEQ ID NO: 100) |  |
| AC000283 | SS | αvβ6-SM45-L4-(NH-C6)s(invAb)scuguucuuCfCfGfugaaauucuas(invAb)(C6-S)-LP1b (SEQ ID NO: 221) | AD07844 |
|  | AS | cPrpus AfsGfsaauuucacGfgAfaGfaacasg (SEQ ID NO: 101) |  |
| AC000446 | SS | αvβ6-peptide 1-(NH-C6)s(invAb)scuguucuuCfCfGfugaaauucuas(invAb)(C6-S)-LP29b (SEQ ID NO: 235) | AD07511 |
|  | AS | cPrpusAfsGfsAfauuucacGfgAfaGfaacasg (SEQ ID NO: 84) |  |
| AC000447 | SS | αvβ6-peptide 1-(NH-C6)s(invAb)scaggauucAfGfAfucugguuucas(invAb)(C6-S)-LP29b (SEQ ID NO: 236) | AD07776 |
|  | AS | cPrpusGfsasaaccagauCfuGfaAfuccusg (SEQ ID NO: 97) |  |
| AC000448 | SS | αvβ6-peptide 1-(NH-C6)s(invAb)scaggauucAfGfAfucugguuucas(invAb)(C6-S)-LP29b (SEQ ID NO: 236) | AD07778 |
|  | AS | cPrpusGfsasAfaccagauCfuGfaAfuccusg (SEQ ID NO: 99) |  |
| AC000449 | SS | αvβ6-peptide 1-(NH-C6)s(invAb)scaggauucAfGfAfucugguuucas(invAb)(C6-S)-LP38b (SEQ ID NO: 237) | AD07778 |
|  | AS | cPrpusGfsasAfaccagauCfuGfaAfuccusg (SEQ ID NO: 99) |  |

In some embodiments, a DUX4 RNAi agent is prepared or provided as a salt, mixed salt, a free-acid, or a free base. In some embodiments, a XDH RNAi agent is prepared as a pharmaceutically acceptable salt. In some embodiments, a XDH RNAi agent is prepared as a pharmaceutically acceptable sodium salt. Such forms that are well known in the art are within the scope of the inventions disclosed herein. The RNAi agents described herein, upon delivery to a cell expressing a DUX4 gene, inhibit or knockdown expression of one or more DUX4 genes in vivo and/or in vitro.

In some embodiments, described herein are compositions that include a combination or cocktail of at least two DUX4 RNAi agents having different sequences. In some embodiments, the two or more DUX4 RNAi agents are each separately and independently linked to targeting groups. In some embodiments, the two or more DUX4 RNAi agents are each linked to targeting groups that include or consist of targeting ligands. In some embodiments, the two or more DUX4 RNAi agents are each linked to targeting groups.

Targeting Groups, Linking Groups, and Delivery Vehicles

In some embodiments, a DUX4 RNAi agent contains or is conjugated to one or more non-nucleotide groups including, but not limited to, a targeting group, a linking group, a pharmacokinetic/pharmacodynamic (PK/PD) modulator, a delivery polymer, or a delivery vehicle. The non-nucleotide group can enhance targeting, delivery, or attachment of the RNAi agent. Examples of linking groups are provided in Table 6.1, and examples of targeting groups or targeting ligands are provided in Tables 6.2 and 6.3. The non-nucleotide group can be covalently linked to the 3' and/or 5' end of either the sense strand and/or the antisense strand. In some embodiments, a DUX4 RNAi agent contains a non-nucleotide group linked to the 3' and/or 5' end of the sense strand. In some embodiments, a non-nucleotide group is linked to the 5' end of a DUX4 RNAi agent sense strand. A non-nucleotide group can be linked directly or indirectly to the RNAi agent via a linker/linking group. In some embodiments, a non-nucleotide group is linked to the RNAi agent via a labile, cleavable, or reversible bond or linker.

In some embodiments, a non-nucleotide group enhances the pharmacokinetic or biodistribution properties of an RNAi agent or conjugate to which it is attached to improve cell- or tissue-specific distribution and cell-specific uptake of the conjugate. In some embodiments, a non-nucleotide group enhances endocytosis of the RNAi agent.

Targeting groups or targeting ligands enhance the pharmacokinetic or biodistribution properties of a conjugate or RNAi agent to which they are attached to improve cell-specific (including, in some cases, organ specific) distribution and cell-specific (or organ specific) uptake of the conjugate or RNAi agent. A targeting group can be monovalent, divalent, trivalent, tetravalent, or have higher valency for the target to which it is directed. Representative targeting groups include, without limitation, compounds with affinity to cell surface molecule, cell receptor ligands, hapten, antibodies, monoclonal antibodies, antibody fragments, and antibody mimics with affinity to cell surface molecules. In some embodiments, a targeting group is linked to an RNAi agent using a linker, such as a PEG linker or one, two, or three abasic and/or ribitol (abasic ribose) residues, which in some instances can serve as linkers.

The DUX4 RNAi agents described herein can be synthesized having a reactive group, such as an amino group (also referred to herein as an amine), at the 5'-terminus and/or the 3'-terminus. The reactive group can be used subsequently to attach a targeting moiety using methods typical in the art.

For example, in some embodiments, the DUX4 RNAi agents disclosed herein are synthesized having an $NH_2$-$C_6$ group (represented as ($NH_2$-$C_6$) in the modified sequences herein) at the 5'-terminus of the sense strand of the RNAi agent. The terminal amino group subsequently can be reacted to form a conjugate with, for example, a group that includes a targeting ligand. In some embodiments, the DUX4 RNAi agents disclosed herein are synthesized having one or more alkyne groups at the 5'-terminus of the sense strand of the RNAi agent. The terminal alkyne group(s) can subsequently be reacted to form a conjugate with, for example, a group that includes a targeting ligand.

In some embodiments, RNAi agents comprise a targeting group, which includes 2 or more targeting ligands. In some embodiments, a targeting group may be conjugated at the 5' or 3' end of the sense strand of an RNAi agent. In some embodiments, a targeting group may be conjugated to an internal nucleotide on an RNAi agent. In some embodiments, a targeting group may consist of two targeting ligands linked together, referred to as a "bidentate" targeting group. In some embodiments, a targeting group may consist of three targeting ligands linked together, referred to as a "tridentate" targeting group. In some embodiments, a targeting group may consist of four targeting ligands linked together, referred to as a "tetradentate" targeting group.

In some embodiments, the use of a targeting ligand facilitates cell-specific targeting to cells having desired receptors on its respective surface, and binding of the targeting ligand can facilitate entry of the therapeutic agent, such as an RNAi agent, to which it is linked, into cells such as skeletal muscle cells. Targeting ligands can be monomeric or monovalent (e.g., having a single targeting moiety) or multimeric or multivalent (e.g., having multiple targeting moieties). The targeting group can be attached to the 3' and/or 5' end of the RNAi oligonucleotide using methods known in the art.

Embodiments of the present disclosure include pharmaceutical compositions for delivering a DUX4 RNAi agent to a skeletal muscle cell in vivo. Such pharmaceutical compositions can include, for example, a DUX4 RNAi agent conjugated to a targeting group that comprises a targeting ligand.

In some embodiments, the DUX4 RNAi agents disclosed herein can reduce DUX4 gene expression in one or more of the following tissues: paraspinal, facial, torso, abdominal, and limb muscle tissues, including for example, in the triceps, biceps, quadriceps, pectoralis, gastrocnemius, soleus, masseter, EDL (extensor digitorum longus), TA (Tibialis anterior), trapezius, and/or diaphragm.

In some embodiments, a linking group is conjugated to the RNAi agent. The linking group facilitates covalent linkage of the agent to a targeting group, pharmacokinetic modulator, delivery polymer, or delivery vehicle. The linking group can be linked to the 3' and/or the 5' end of the RNAi agent sense strand or antisense strand. In some embodiments, the linking group is linked to the RNAi agent sense strand. In some embodiments, the linking group is conjugated to the 5' or 3' end of an RNAi agent sense strand. In some embodiments, a linking group is conjugated to the 5' end of an RNAi agent sense strand. Examples of linking groups, include, but are not limited to: C6-SS-C6, 6-SS-6, reactive groups such as primary amines (e.g., NH2-C6) and alkynes, alkyl groups, abasic residues/nucleotides, amino acids, tri-alkyne functionalized groups, ribitol, and/or PEG groups.

A linker or linking group is a connection between two atoms that links one chemical group (such as an RNAi agent) or segment of interest to another chemical group (such as a targeting group, pharmacokinetic modulator, or delivery polymer) or segment of interest via one or more covalent bonds. A labile linkage contains a labile bond. A linkage can optionally include a spacer that increases the distance between the two joined atoms. A spacer may further add flexibility and/or length to the linkage. Spacers include, but are not be limited to, alkyl groups, alkenyl groups, alkynyl groups, aryl groups, aralkyl groups, aralkenyl groups, and aralkynyl groups; each of which can contain one or more heteroatoms, heterocycles, amino acids, nucleotides, and saccharides. Spacer groups are well known in the art and the preceding list is not meant to limit the scope of the description.

In some embodiments, targeting groups are linked to the DUX4 RNAi agents without the use of an additional linker. In some embodiments, the targeting group is designed having a linker readily present to facilitate the linkage to a DUX4 RNAi agent. In some embodiments, when two or more RNAi agents are included in a composition, the two or more RNAi agents can be linked to their respective targeting groups using the same linkers. In some embodiments, when two or more RNAi agents are included in a composition, the two or more RNAi agents are linked to their respective targeting groups using different linkers.

Any of the DUX4 RNAi agent nucleotide sequences listed in Tables 2, 3, and 4.1, 4.2, 4.3, 4.4, 4.5, 4.6, and 5.4, whether modified or unmodified, can contain 3' and/or 5' targeting group(s), linking group(s), and/or pharmacokinetic modulator(s). Any of the DUX4 RNAi agent sequences listed in Tables 3 and 4.1, 4.2, 4.3, 4.4, 4.5, 4.6, and 5.4, or are otherwise described herein, which contain a 3' or 5' targeting group, linking group, or pharmacokinetic modulator can alternatively contain no 3' or 5' targeting group, linking group, or PK/PD modulator, or can contain a different 3' or 5' targeting group, linking group, or PK/PD modulator including, but not limited to, those depicted in Tables 6.1, 6.2, 6.3, 6.4, 6.5, 6.6 or 6.7. Any of the DUX4 RNAi agent duplexes listed in Table 5.1 (or Table 5.2, 5.3 or 5.4), whether modified or unmodified, can further comprise a targeting group, linking group, or PK/PD modulator, including, but not limited to, those depicted in Tables 6.1, 6.2, 6.3, 6.4, 6.5, 6.6, or 6.7, and in some embodiments the targeting group, linking group and/or PK/PD modulator can be attached to the 3' or 5' terminus of either the sense strand or the antisense strand of the DUX4 RNAi agent duplex.

Examples of certain modified nucleotides and linking groups are provided in Table 6.1.

TABLE 6.1

Structures Representing Various Modified Nucleotides and Linking Groups

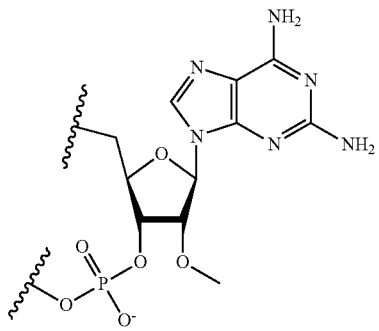
a 2N

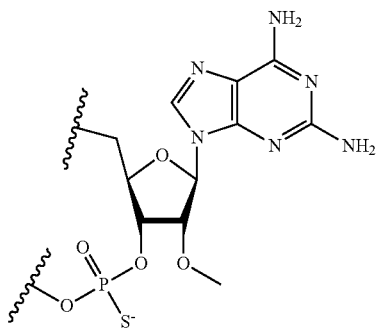
a 2Ns

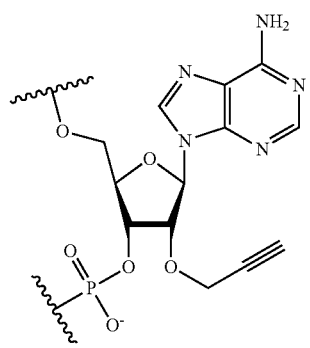
aAlk

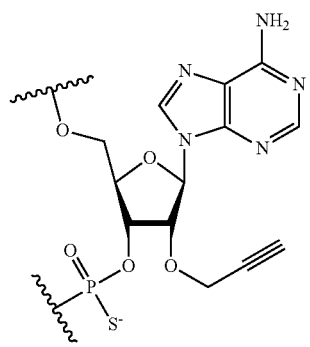
aAlks

TABLE 6.1-continued
Structures Representing Various Modified Nucleotides and Linking Groups
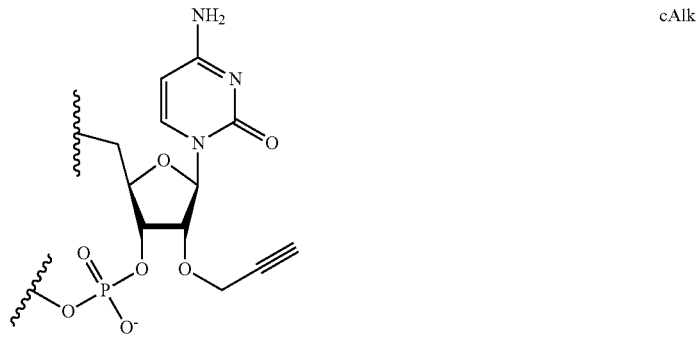
cAlk
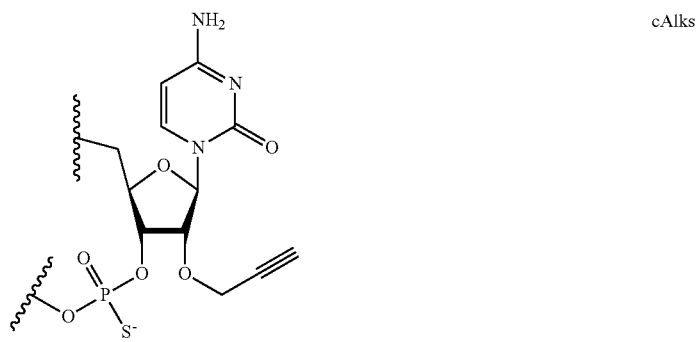
cAlks
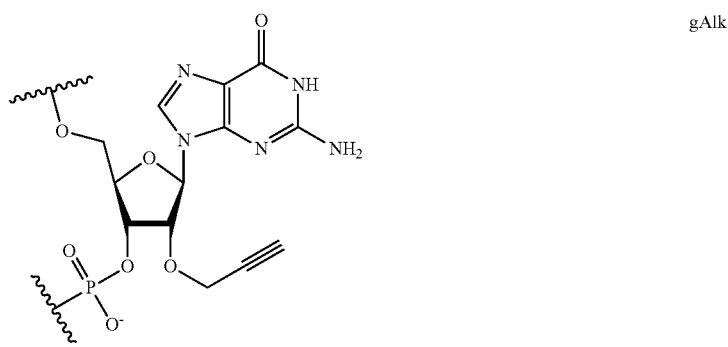
gAlk
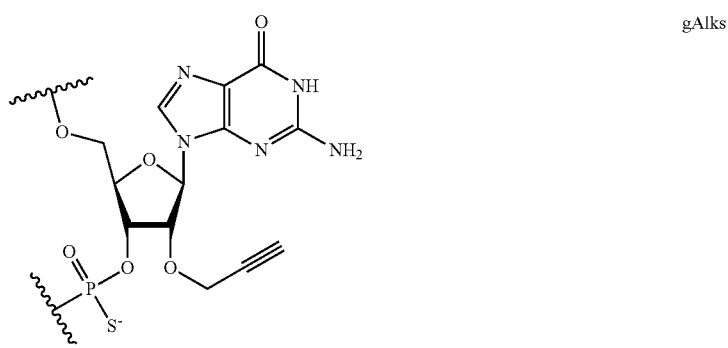
gAlks TABLE 6.1-continued
Structures Representing Various Modified Nucleotides and Linking Groups
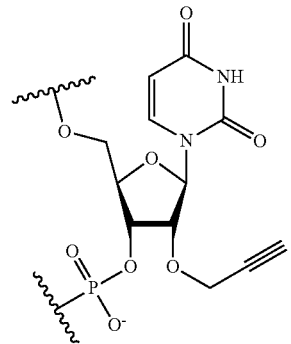
uAlk
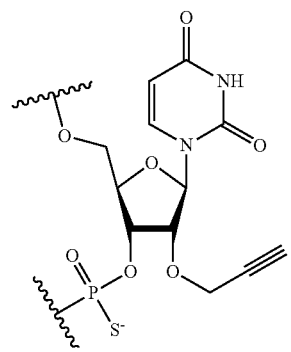
uAlks
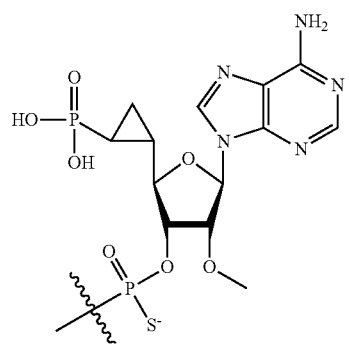
cPrpas
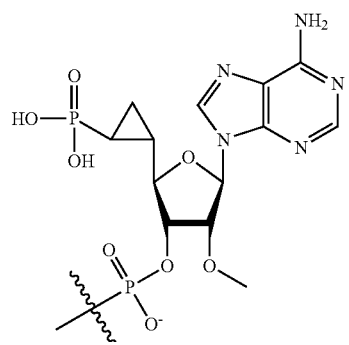
cPrpa TABLE 6.1-continued
Structures Representing Various Modified Nucleotides and Linking Groups
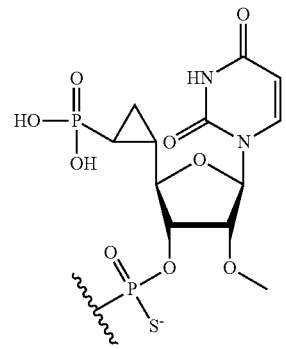
cPrpus
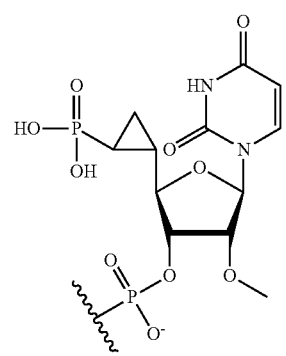
cPrpu
When positioned internally:
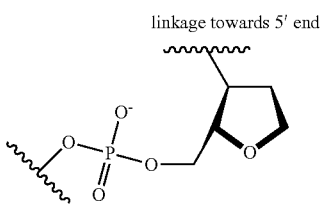
linkage towards 5′ end
linkage towards 3′ end
(invAb)
When positioned internally:
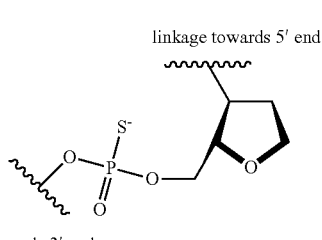
linkage towards 5′ end
linkage towards 3′ end
(invAb)s TABLE 6.1-continued Structures Representing Various Modified Nucleotides and Linking Groups When positioned at the 3' terminal end:

linkage towards 5' end

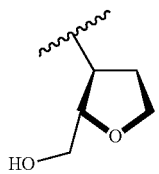

(invAb)

When positioned at the 3' terminal end of oligonucleotide:

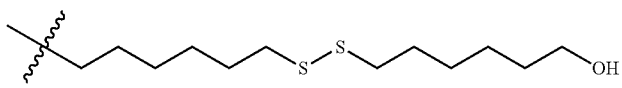 [SMILES: *CCCCCCSSCCCCCCO]

(C6-SS-C6)

When positioned internally:

linkage towards 5' end of oligonucleotide                    linkage towards 3' end of oligonucleotide

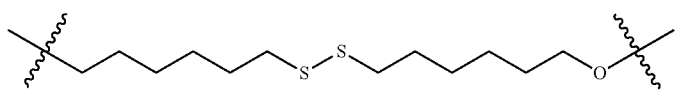

(C6-SS-C6)

linkage towards 5' end of oligonucleotide                    linkage towards 3' end of oligonucleotide

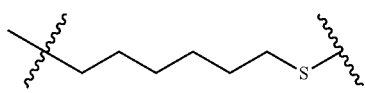

(C6-S)

When positioned at the 3' terminal end:

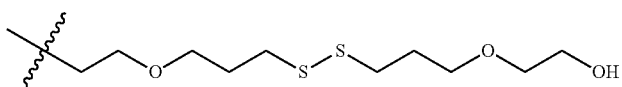 [SMILES: *CCOCCCSSCCCOCCO]

(6-SS-6)

When positioned internally in oligonucleotide:

linkage towards 5' end of oligonucleotide                    linkage towards 3' end of oligonucleotide

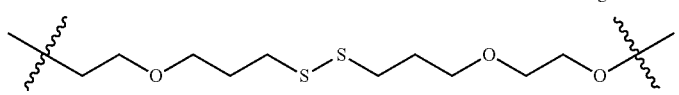

(6-SS-6)

TABLE 6.1-continued
Structures Representing Various Modified Nucleotides and Linking Groups
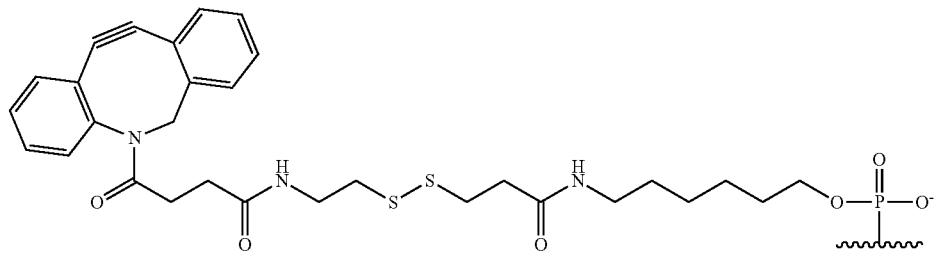 [SMILES: *P(=O)([O-])OCCCCCCNC(=O)CCSSCCNC(=O)CCC(=O)N1Cc2ccccc2C#Cc2ccccc21]
(C6-SS-Alk) or (Alk-SS-C6)
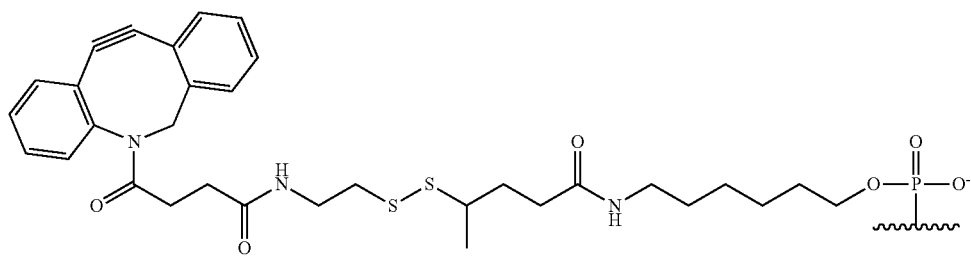 [SMILES: *P(=O)([O-])OCCCCCCNC(=O)CCC(C)SSCCNC(=O)CCC(=O)N1Cc2ccccc2C#Cc2ccccc21]
(C6-SS-Alk-Me)
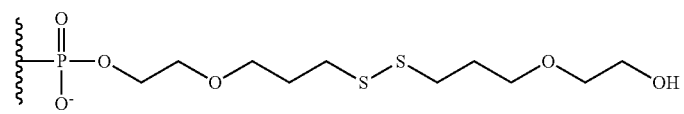 [SMILES: *P(=O)([O-])OCCOCCCSSCCCOCCO]
(PEG-C3-SS)
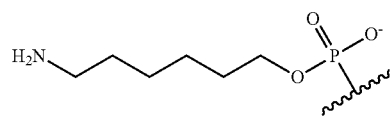 [SMILES: *P(=O)([O-])OCCCCCCN]
(NH2-C6)
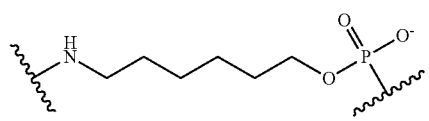
(NH-C6)
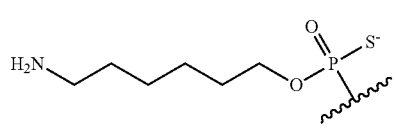 [SMILES: *P(=O)([S-])OCCCCCCN]
(NH2-C6)s
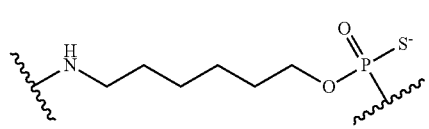 [SMILES: *NCCCCCCOP(*)(=O)[S-]]
(NH-C6)s TABLE 6.1-continued
Structures Representing Various Modified Nucleotides and Linking Groups
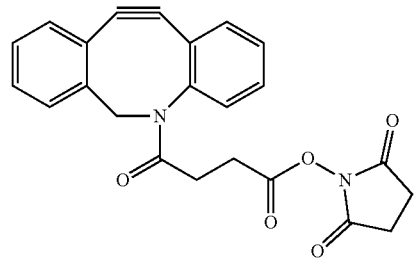 [SMILES: O=C(CCC(=O)N1Cc2ccccc2C#Cc2ccccc21)ON1C(=O)CCC1=O]
DBCO-NHS (BroadPharm® BP-22231)
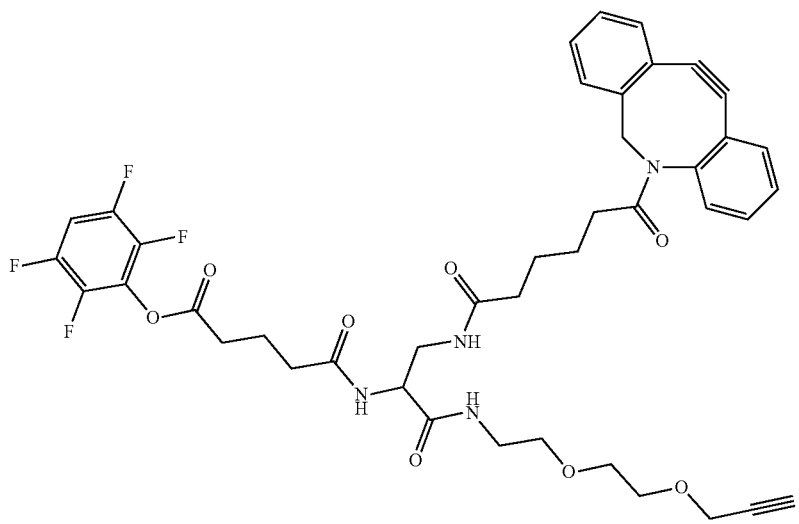 [SMILES: C#CCOCCOCCNC(=O)C(CNC(=O)CCCCC(=O)N1Cc2ccccc2C#Cc2ccccc21)NC(=O)CCCC(=O)Oc1c(F)c(F)cc(F)c1F]
Linker-1
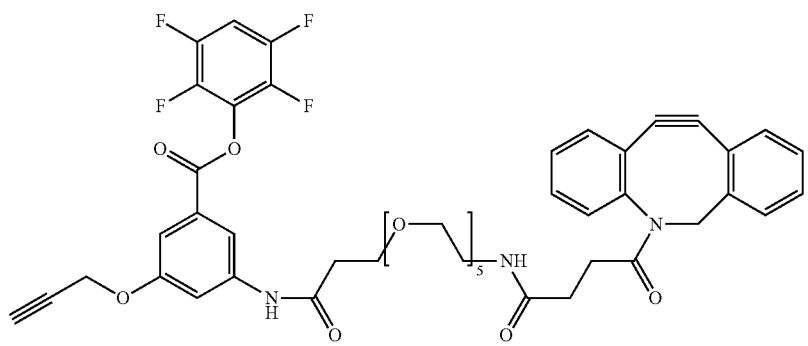
Linker-2

TABLE 6.1-continued
Structures Representing Various Modified Nucleotides and Linking Groups
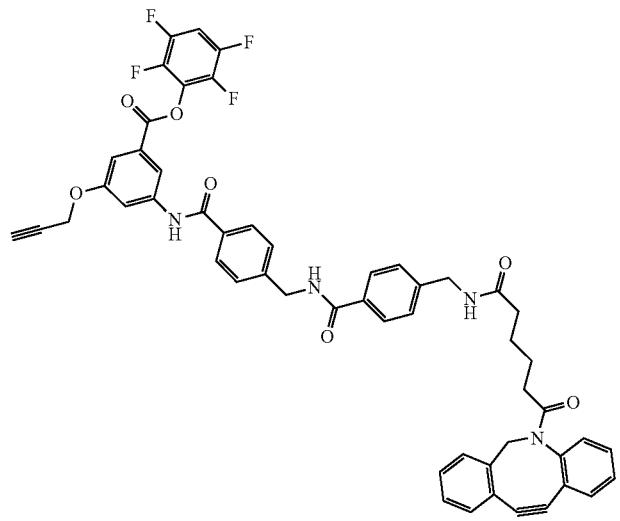 [SMILES: C#CCOc1cc(NC(=O)c2ccc(CNC(=O)c3ccc(CNC(=O)CCCCC(=O)N4Cc5ccccc5C#Cc5ccccc54)cc3)cc2)cc(C(=O)Oc2c(F)c(F)cc(F)c2F)c1]
Linker-3
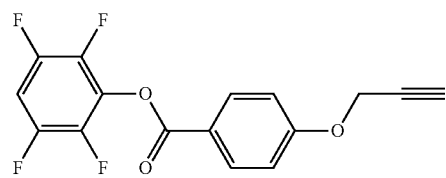 [SMILES: C#CCOc1ccc(C(=O)Oc2c(F)c(F)cc(F)c2F)cc1]
Linker-4
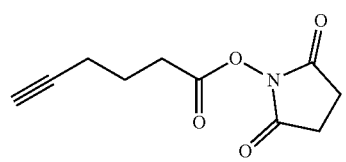
Linker-5 (Activate Scientific® AS28942)
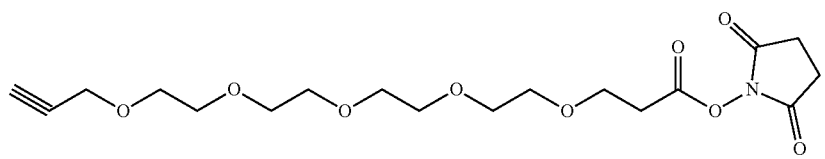 [SMILES: C#CCOCCOCCOCCOCCOCCC(=O)ON1C(=O)CCC1=O]
Linker-6 (BroadPharm® BP-20907)
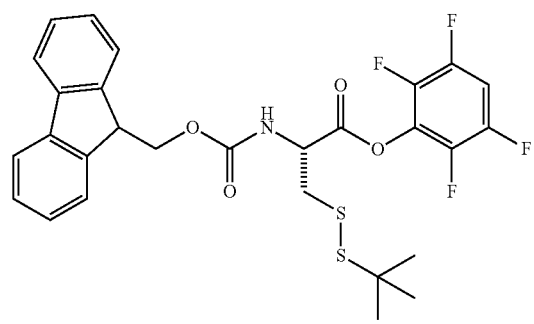 [SMILES: CC(C)(C)SSC[C@H](NC(=O)OCC1c2ccccc2-c2ccccc21)C(=O)Oc1c(F)c(F)cc(F)c1F]
Linker-7

TABLE 6.1-continued

Structures Representing Various Modified Nucleotides and Linking Groups

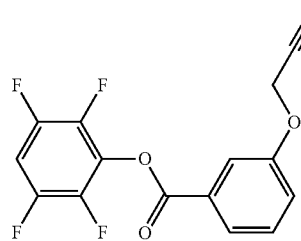

Linker-8

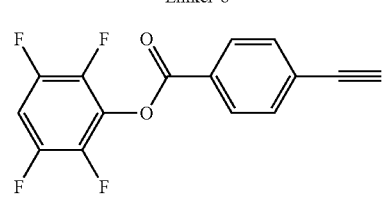

Linker-9

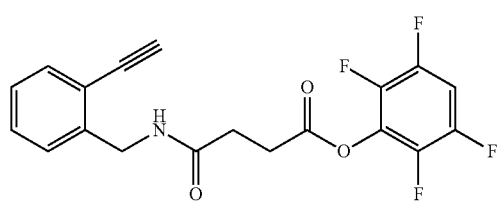 [SMILES: C#Cc1ccccc1CNC(=O)CCC(=O)Oc1c(F)c(F)cc(F)c1F]

Linker-10

Alternatively, other linking groups known in the art may be used. In many instances, linking groups can be commercially acquired or alternatively, are incorporated into commercially available nucleotide phosphoramidites.

In some embodiments, a targeting ligand is linked to the DUX4 RNAi agents disclosed herein. Examples of certain targeting ligands are provided in Table 6.2:

TABLE 6.2

Structures Representing Targeting Ligands

| Compound Number | Formula |
|---|---|
| SM40a | |

TABLE 6.2-continued

Structures Representing Targeting Ligands

| Compound Number | Formula |
| --- | --- |
| SM41a | |
| SM42a | |
| SM43a | |
| SM44a | |

TABLE 6.2-continued
Structures Representing Targeting Ligands
| Compound Number | Formula |
|---|---|
| SM45a | 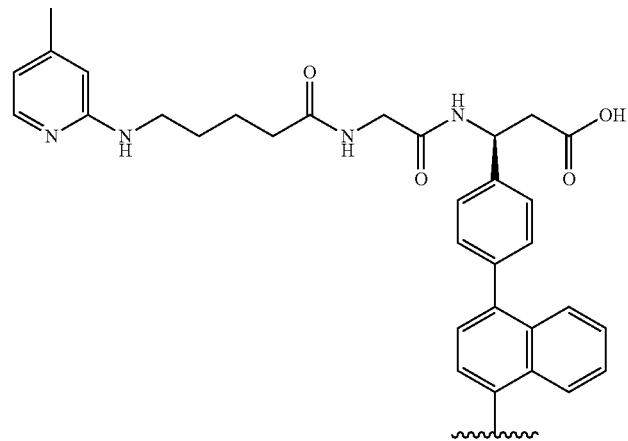 [SMILES: *c1ccc(-c2ccc([C@H](CC(=O)O)NC(=O)CNC(=O)CCCCNc3cc(C)ccn3)cc2)c2ccccc12] |
| SM46a | 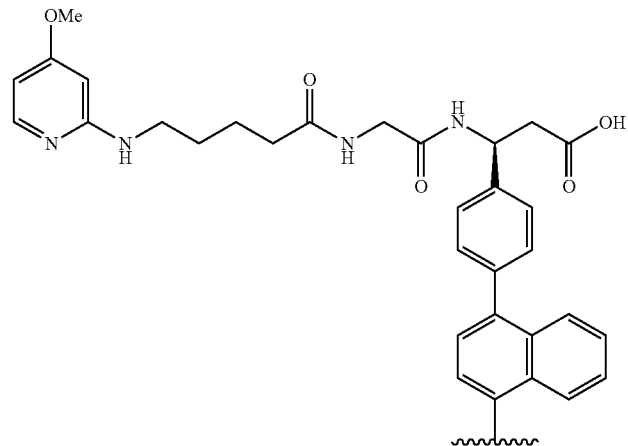 [SMILES: *c1ccc(-c2ccc([C@H](CC(=O)O)NC(=O)CNC(=O)CCCCNc3cc(OC)ccn3)cc2)c2ccccc12] |
| SM47a | 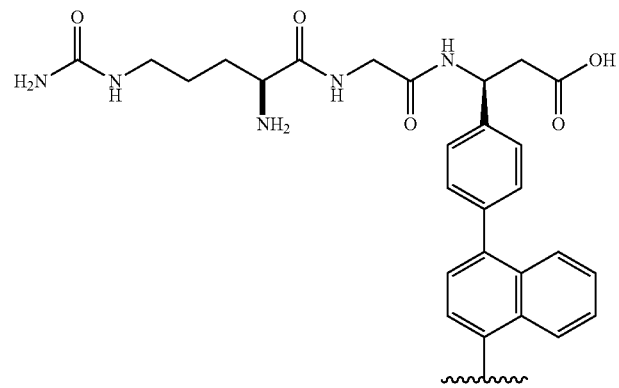 |

TABLE 6.2-continued
Structures Representing Targeting Ligands
| Compound Number | Formula |
|---|---|
| SM48a | 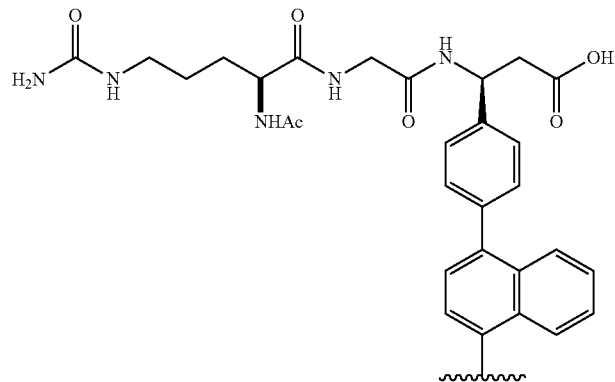 [SMILES: *c1ccc(-c2ccc([C@H](CC(=O)O)NC(=O)CNC(=O)[C@H](CCCNC(N)=O)NC(C)=O)cc2)c2ccccc12] |
| SM49a | 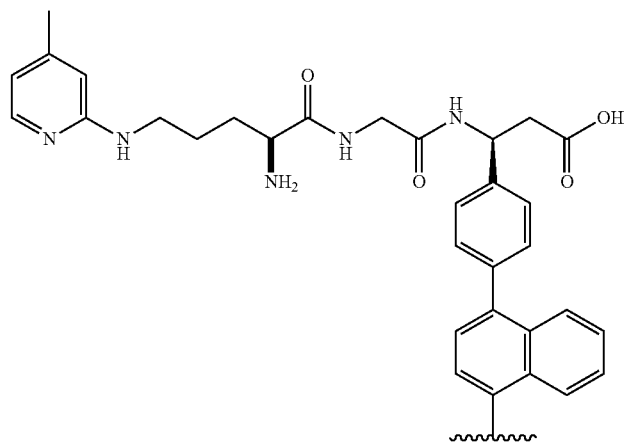 [SMILES: *c1ccc(-c2ccc([C@H](CC(=O)O)NC(=O)CNC(=O)[C@@H](N)CCCNc3cc(C)ccn3)cc2)c2ccccc12] |
| SM50a | 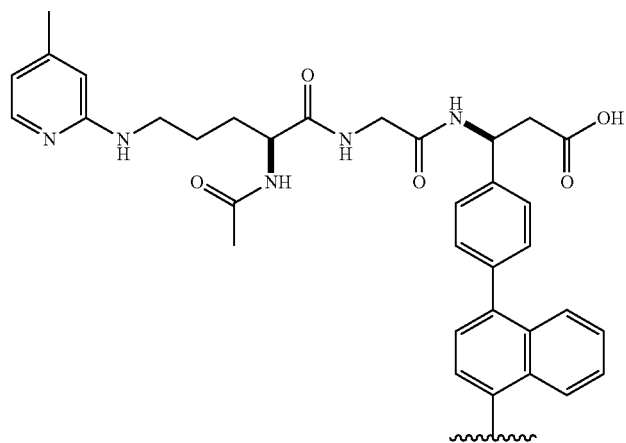 |

TABLE 6.2-continued
Structures Representing Targeting Ligands
| Compound Number | Formula |
|---|---|
| SM51a | 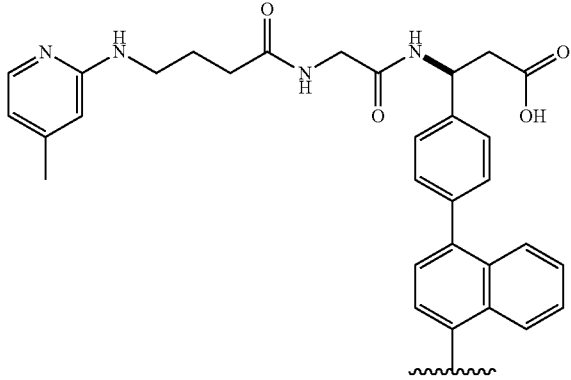 |
| SM52a | 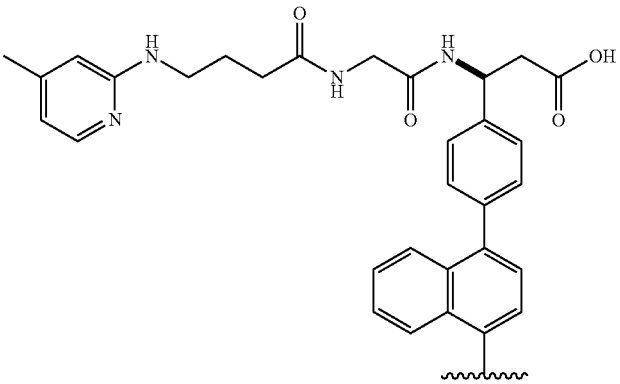 |
| SM53a | 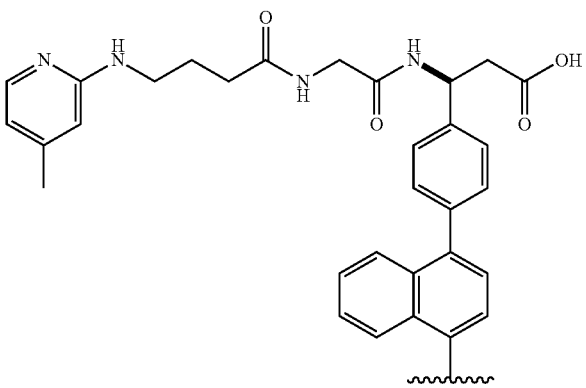 |
| SM54a | 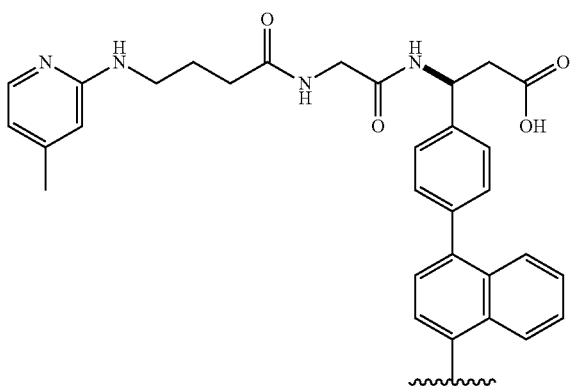 |

TABLE 6.2-continued
Structures Representing Targeting Ligands
| Compound Number | Formula |
| --- | --- |
| SM55a | 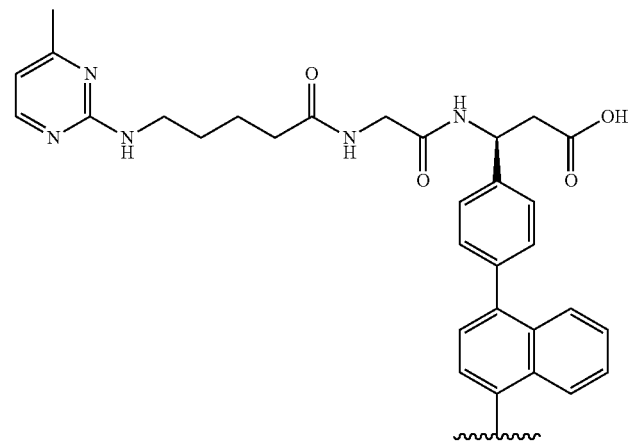 [SMILES: *c1ccc(-c2ccc([C@H](CC(=O)O)NC(=O)CNC(=O)CCCCNc3nccc(C)n3)cc2)c2ccccc12] |
| SM56a | 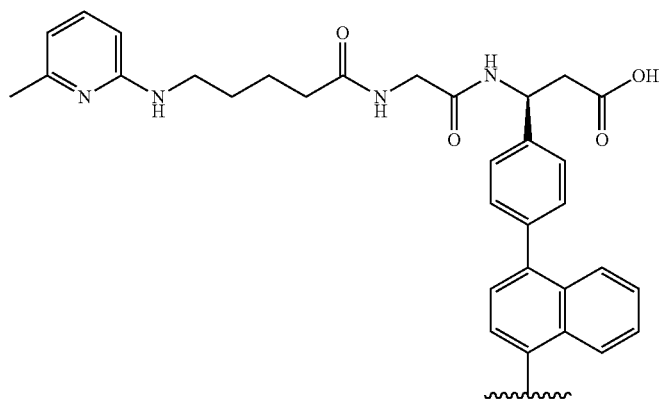 [SMILES: *c1ccc(-c2ccc([C@H](CC(=O)O)NC(=O)CNC(=O)CCCCNc3cccc(C)n3)cc2)c2ccccc12] |
| SM57a | 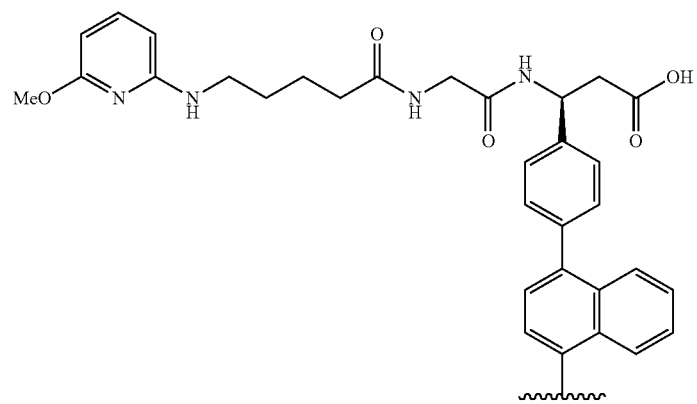 [SMILES: *c1ccc(-c2ccc([C@H](CC(=O)O)NC(=O)CNC(=O)CCCCNc3cccc(OC)n3)cc2)c2ccccc12] |

TABLE 6.2-continued
Structures Representing Targeting Ligands
| Compound Number | Formula |
|---|---|
| SM58a | 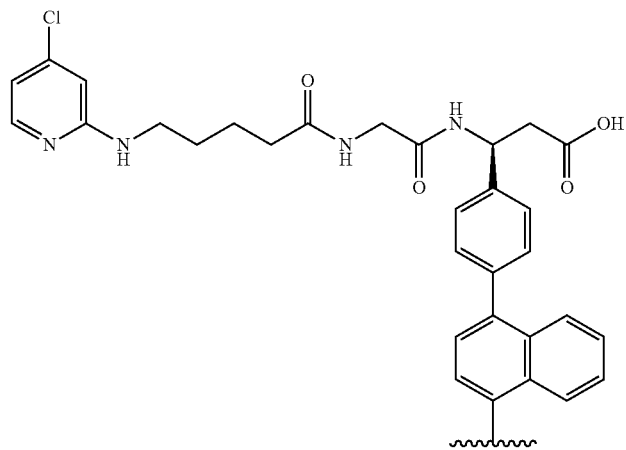 [SMILES: *c1ccc(-c2ccc([C@H](CC(=O)O)NC(=O)CNC(=O)CCCCNc3cc(F)ccn3)cc2)c2ccccc12] |
| SM59a | 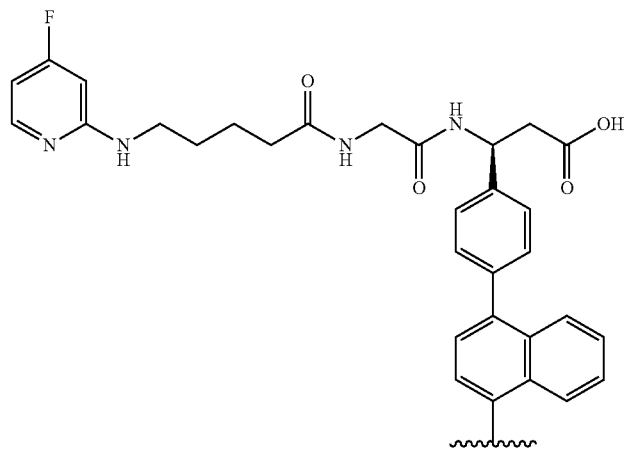 |
| SM60a | 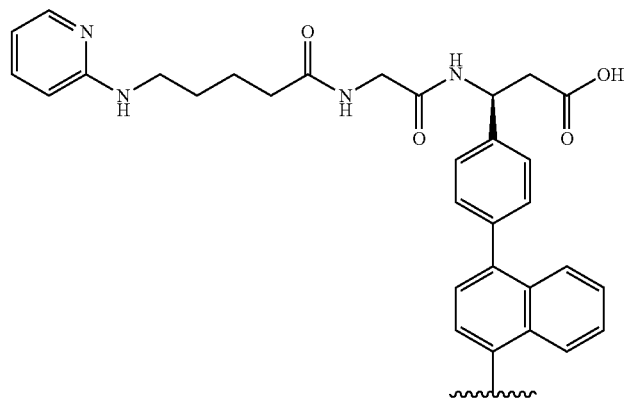 [SMILES: *c1ccc(-c2ccc([C@H](CC(=O)O)NC(=O)CNC(=O)CCCCNc3ccccn3)cc2)c2ccccc12] |

TABLE 6.2-continued

Structures Representing Targeting Ligands

| Compound Number | Formula |
| --- | --- |
| Peptide 1a | (chemical structure of peptide) | or a pharmaceutically acceptable salt thereof, wherein ⁣{ indicates the point of connection to the DUX4 RNAi agents. In some embodiments, a PEG or other linking group is incorporated between the RNAi agent and the targeting ligand.

In some embodiments, the targeting groups in Table 6.2 are synthesized with reactive groups allowing for efficient coupling of a targeting ligand that includes one or more targeting groups to the RNAi agents disclosed herein. In some embodiments, the targeting groups identified in Table 6.2 are synthesized as azides to facilitate linkage to the RNAi agent.

In some embodiments, the DUX4 RNAi agents are linked to a targeting ligand having a structure disclosed in Table 6.3:

TABLE 6.3

Example targeting ligands for combination with DUX4 RNAi agents.

| Compound Number | Formula |
| --- | --- |
| 40b | (chemical structure) |

TABLE 6.3-continued
Example targeting ligands for combination with DUX4 RNAi agents.
| Compound Number | Formula |
|---|---|
| 41b | 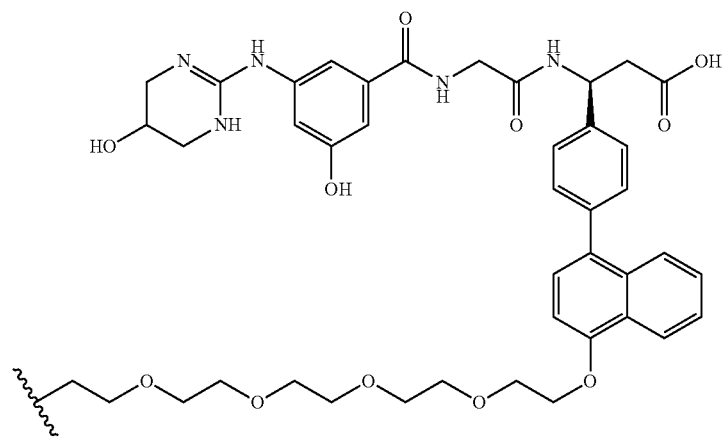 [SMILES: *CCOCCOCCOCCOCCOc1ccc(-c2ccc([C@H](CC(=O)O)NC(=O)CNC(=O)c3cc(O)cc(NC4=NCC(O)CN4)c3)cc2)c2ccccc12] |
| 42b | 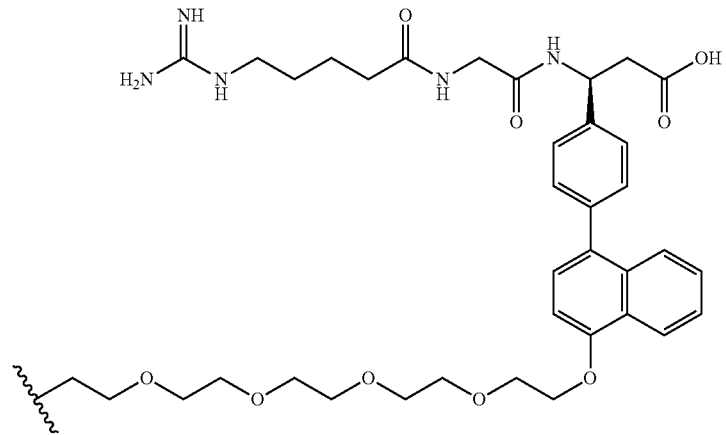 [SMILES: *CCOCCOCCOCCOCCOc1ccc(-c2ccc([C@H](CC(=O)O)NC(=O)CNC(=O)CCCCNC(=N)N)cc2)c2ccccc12] |
| 43b | 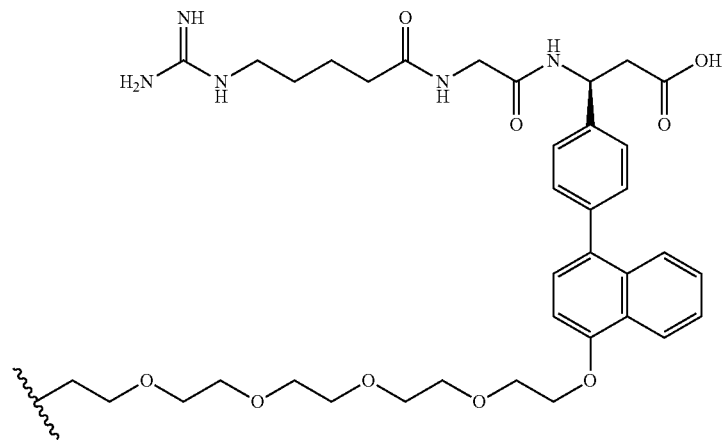 [SMILES: *CCOCCOCCOCCOCCOc1ccc(-c2ccc([C@H](CC(=O)O)NC(=O)CNC(=O)CCCCNC(=N)N)cc2)c2ccccc12] |

TABLE 6.3-continued
Example targeting ligands for combination with DUX4 RNAi agents.
| Compound Number | Formula |
|---|---|
| 44b | 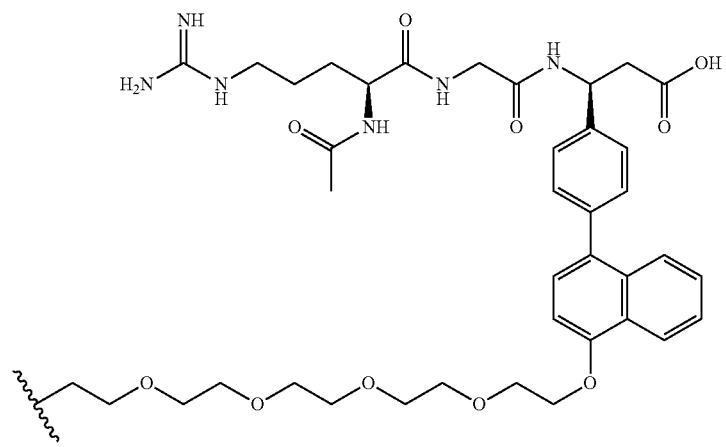 [SMILES: *CCOCCOCCOCCOCCOc1ccc(-c2ccc([C@H](CC(=O)O)NC(=O)CNC(=O)[C@H](CCCNC(=N)N)NC(C)=O)cc2)c2ccccc12] |
| 45b | 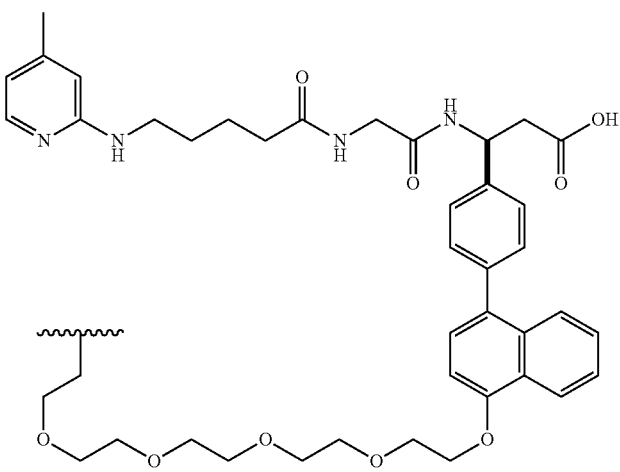 [SMILES: *CCOCCOCCOCCOCCOc1ccc(-c2ccc([C@H](CC(=O)O)NC(=O)CNC(=O)CCCCNc3cc(C)ccn3)cc2)c2ccccc12] |
| 46b | 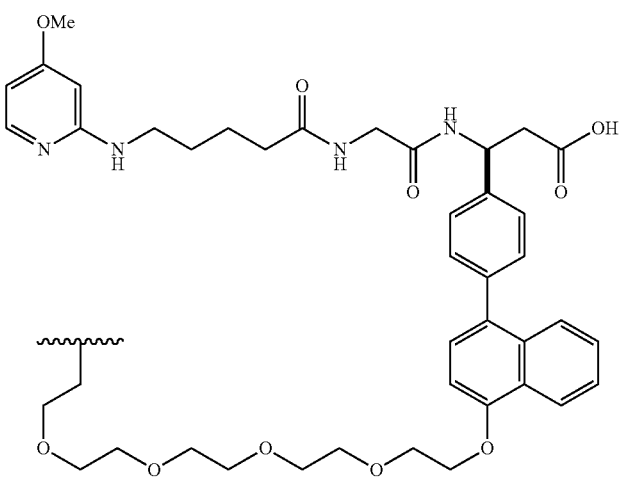 [SMILES: *CCOCCOCCOCCOCCOc1ccc(-c2ccc([C@H](CC(=O)O)NC(=O)CNC(=O)CCCCNc3cc(OC)ccn3)cc2)c2ccccc12] |

TABLE 6.3-continued
Example targeting ligands for combination with DUX4 RNAi agents.
| Compound Number | Formula |
| --- | --- |
| 47b | 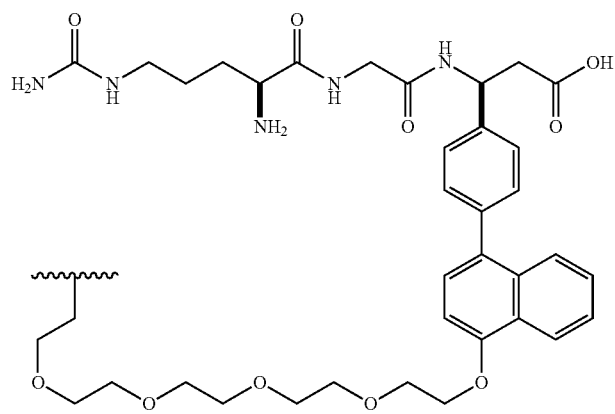 [SMILES: *CCOCCOCCOCCOCCOc1ccc(-c2ccc([C@H](CC(=O)O)NC(=O)CNC(=O)[C@@H](N)CCCNC(N)=O)cc2)c2ccccc12] |
| 48b | 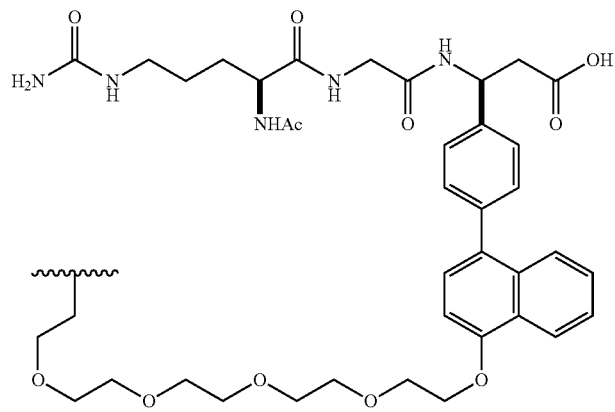 [SMILES: *CCOCCOCCOCCOCCOc1ccc(-c2ccc([C@H](CC(=O)O)NC(=O)CNC(=O)[C@H](CCCNC(N)=O)NC(C)=O)cc2)c2ccccc12] |
| 49b | 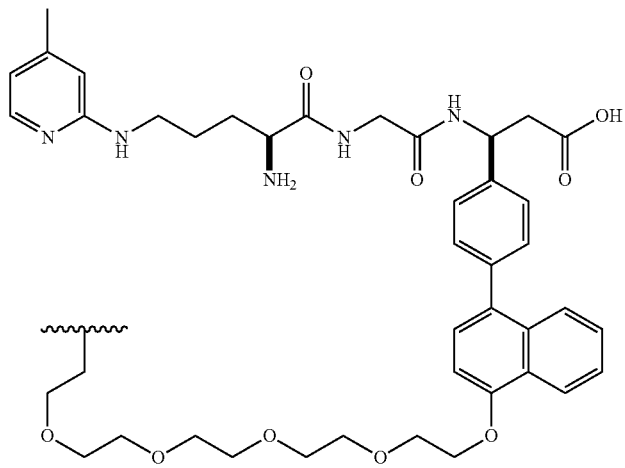 [SMILES: *CCOCCOCCOCCOCCOc1ccc(-c2ccc([C@H](CC(=O)O)NC(=O)CNC(=O)[C@@H](N)CCCNc3cc(C)ccn3)cc2)c2ccccc12] |

TABLE 6.3-continued
Example targeting ligands for combination with DUX4 RNAi agents.
| Compound Number | Formula |
|---|---|
| 50b | 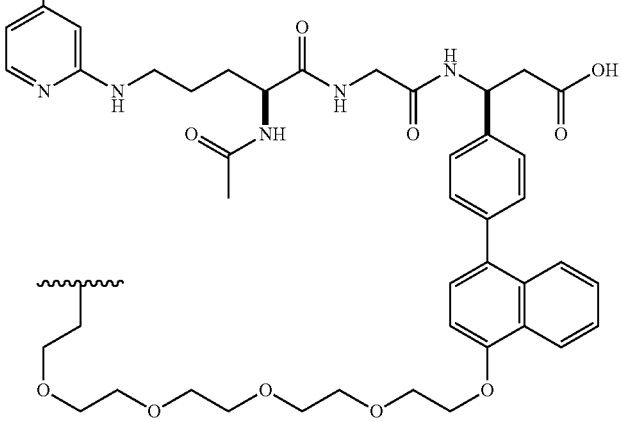 |
| 51b | 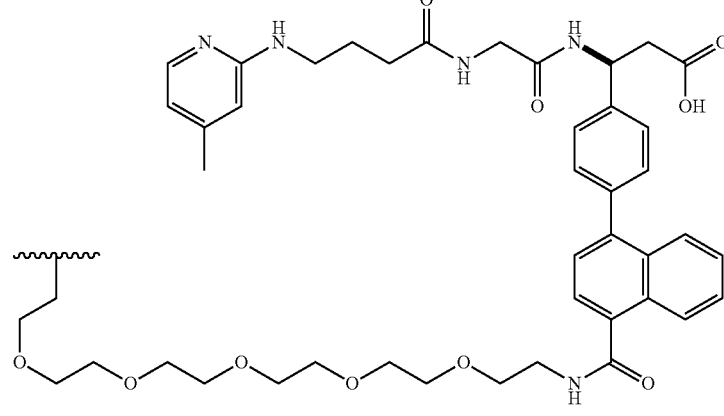 |
| 52b | 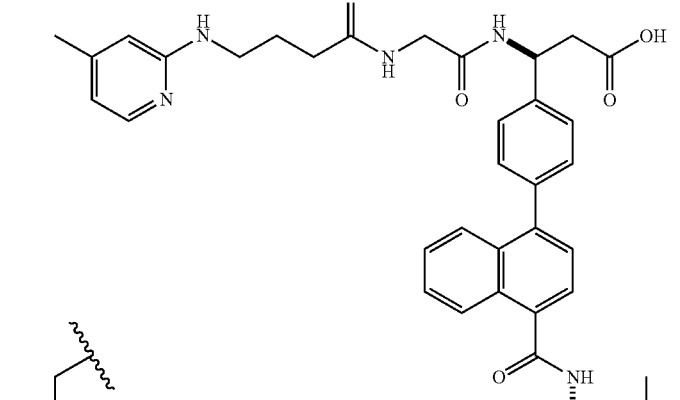 |

TABLE 6.3-continued
Example targeting ligands for combination with DUX4 RNAi agents.
| Compound Number | Formula |
|---|---|
| 53b | 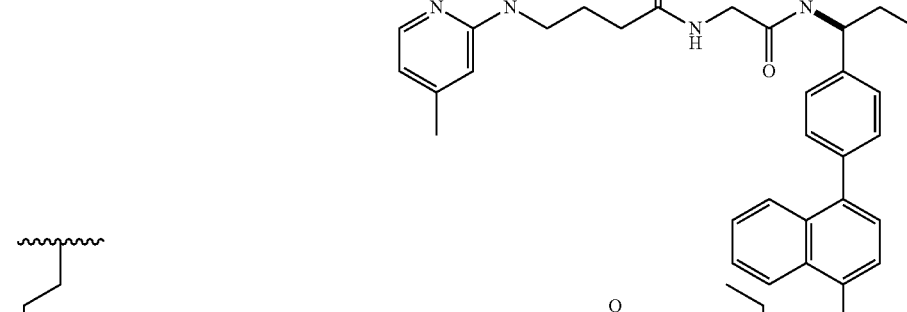 |
| 54b | 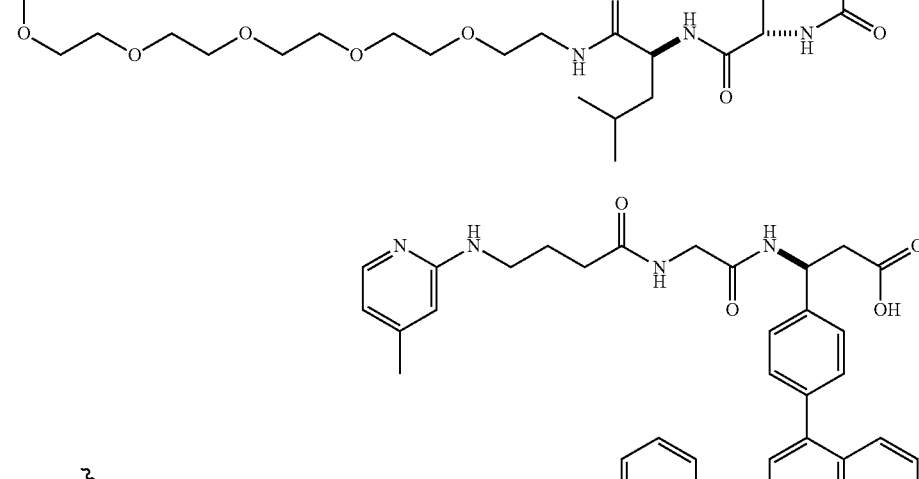 |
| 55b | 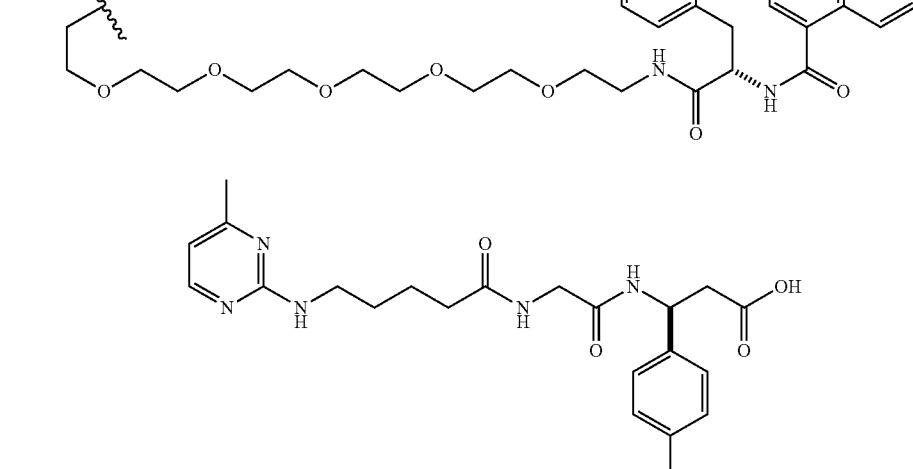 |

TABLE 6.3-continued
Example targeting ligands for combination with DUX4 RNAi agents.
| Compound Number | Formula |
|---|---|
| 56b | 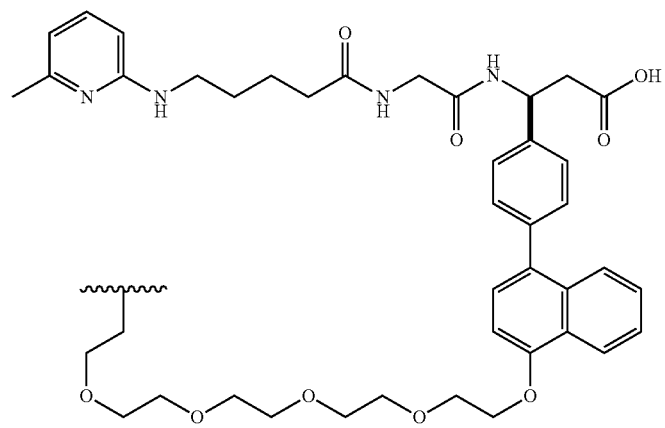 [SMILES: *CCOCCOCCOCCOCCOc1ccc(-c2ccc([C@H](CC(=O)O)NC(=O)CNC(=O)CCCCNc3cccc(C)n3)cc2)c2ccccc12] |
| 57b | 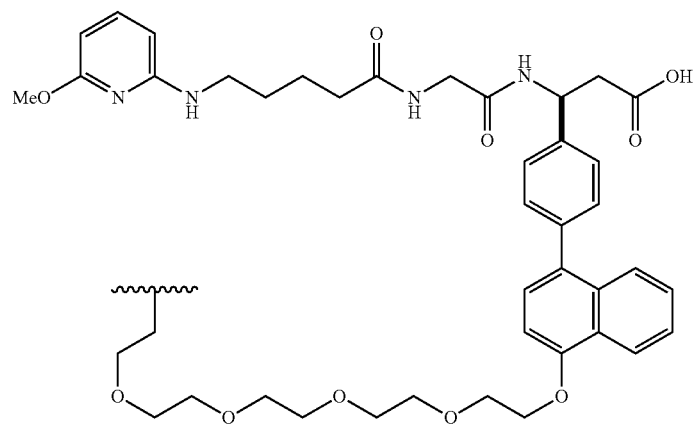 [SMILES: *CCOCCOCCOCCOCCOc1ccc(-c2ccc([C@H](CC(=O)O)NC(=O)CNC(=O)CCCCNc3cccc(OC)n3)cc2)c2ccccc12] |
| 58b | 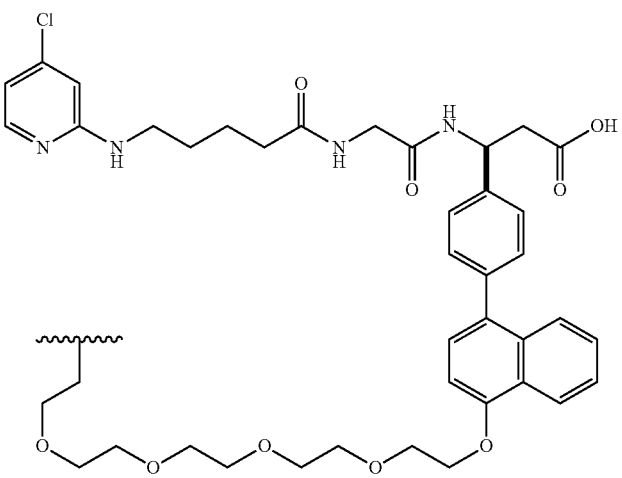 [SMILES: *CCOCCOCCOCCOCCOc1ccc(-c2ccc([C@H](CC(=O)O)NC(=O)CNC(=O)CCCCNc3cc(Cl)ccn3)cc2)c2ccccc12] |

TABLE 6.3-continued
Example targeting ligands for combination with DUX4 RNAi agents.
| Compound Number | Formula |
| --- | --- |
| 59b | 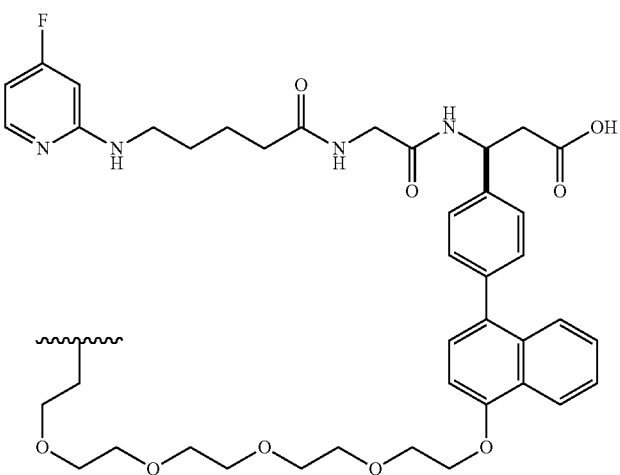 |
| 60b | 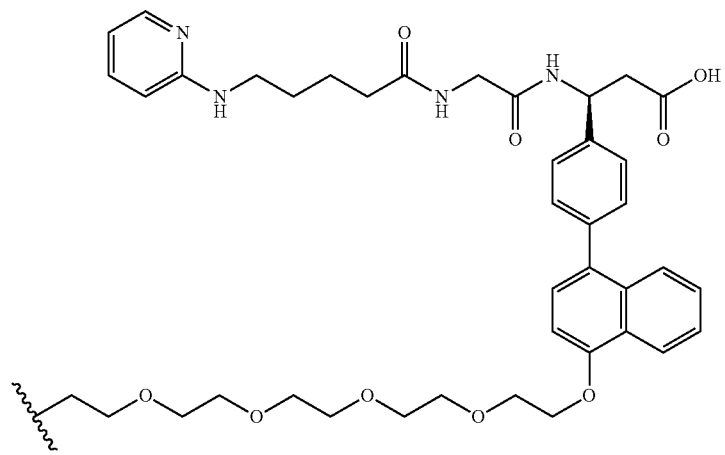 [SMILES: *CCOCCOCCOCCOCCOc1ccc(-c2ccc([C@H](CC(=O)O)NC(=O)CNC(=O)CCCCNc3ccccn3)cc2)c2ccccc12] |

TABLE 6.3-continued

Example targeting ligands for combination with DUX4 RNAi agents.

| Compound Number | Formula |
| --- | --- |
| αvβ6 Peptide 1 | 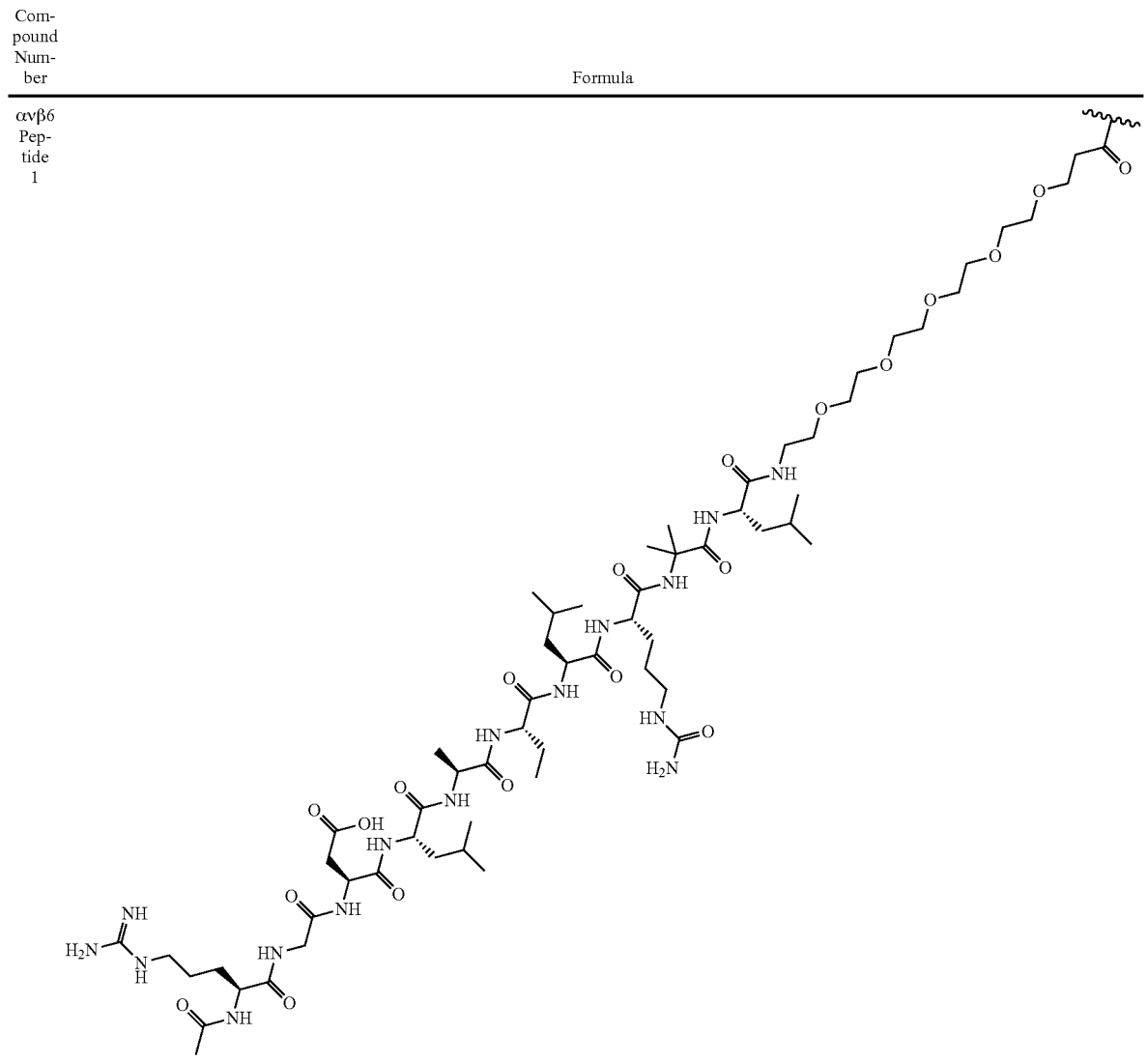 | or a pharmaceutically acceptable salt thereof, wherein ⁀ indicates the point of connection to the DUX4 RNAi agents.

In some embodiments, a delivery vehicle may be used to deliver an RNAi agent to a cell or tissue. A delivery vehicle is a compound that improves delivery of the RNAi agent to a cell or tissue. A delivery vehicle can include, or consist of, but is not limited to: a polymer, such as an amphipathic polymer, a membrane active polymer, a peptide, a melittin peptide, a melittin-like peptide (MLP), a lipid, a reversibly modified polymer or peptide, or a reversibly modified membrane active polyamine.

In some embodiments, the RNAi agents can be combined with lipids, nanoparticles, polymers, liposomes, micelles, DPCs or other delivery systems available in the art for nucleic acid delivery. The RNAi agents can also be chemically conjugated to targeting groups, lipids (including, but not limited to cholesteryl and cholesteryl derivatives), encapsulating in nanoparticles, liposomes, micelles, conjugating to polymers or DPCs (see, for example WO 2000/053722, WO 2008/022309, WO 2011/104169, and WO 2012/083185, WO 2013/032829, WO 2013/158141, each of which is incorporated herein by reference), by iontophoresis, or by incorporation into other delivery vehicles or systems available in the art such as hydrogels, cyclodextrins, biodegradable nanocapsules, bioadhesive microspheres, or proteinaceous vectors. In some embodiments the RNAi agents can be conjugated to antibodies having affinity for skeletal muscle cells. In some embodiments, the RNAi agents can be linked to targeting ligands that have affinity for skeletal muscle cells or receptors present on skeletal muscle cells.

Pharmacokinetic/Pharmacodynamic (PK/PD) Modulators

In some embodiments, the DUX4 RNAi agents disclosed herein are further or alternatively linked to one or more PK/PD modulators. Examples of certain pharmacodynamic/pharmacokinetic (PK/PD) modulators suitable for use with the RNAi agents disclosed herein are provided in Table 6.4. In Table 6.4, PK/PD modulators were acquired from commercial suppliers where indicated and were otherwise synthesized using commercially available materials:

TABLE 6.4

Exemplary PK/PD Modulator Compounds.

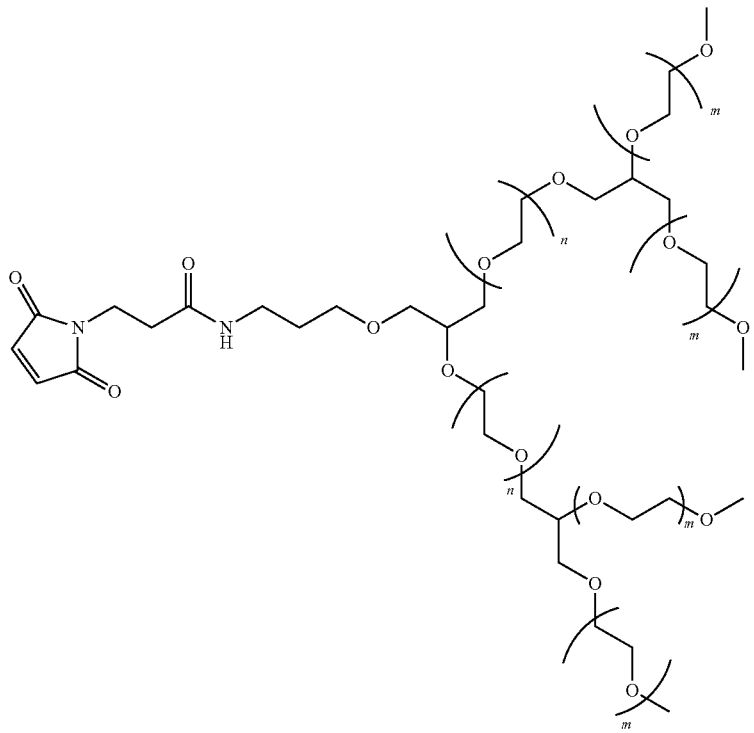

PEG40K (2x2-arm),
wherein n and m are integers, and the molecular weight of the PEG groups is about 40 kilodaltons
NOF, Sunbright ® GL4-400MA

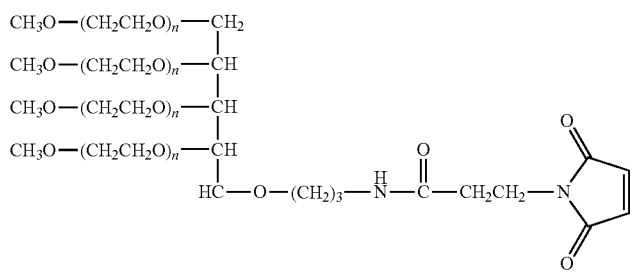

PEG40K (4-arm),
wherein n is an integer, and the molecular weight of the PEG groups is about 40 kilodaltons
NOF, Sunbright ® XY4-400MA

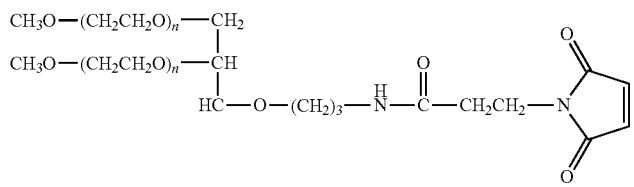

PEG40K (2-arm),
wherein n is an integer, and the molecular weight of the PEG groups is about 40 kilodaltons
NOF, Sunbright ® GL2-400MA TABLE 6.4-continued Exemplary PK/PD Modulator Compounds.

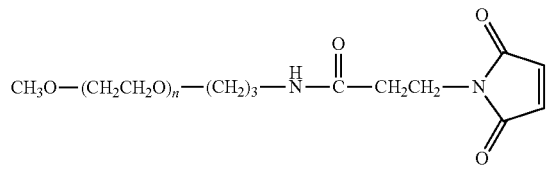

PEG40K,
wherein n is an integer, and the molecular weight of the PEG groups is about 40 kilodaltons
NOF, Sunbright ® ME-400MA

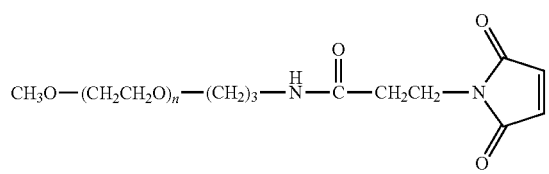

PEG10K,
wherein n is an integer, and the molecular weight of the PEG groups is about 10 kilodaltons
NOF, Sunbright ® ME-100MA

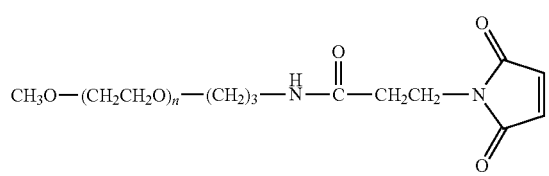

PEG5K,
wherein n is an integer, and the molecular weight of the PEG groups is about 5 kilodaltons
NOF, Sunbright ® ME-050MA

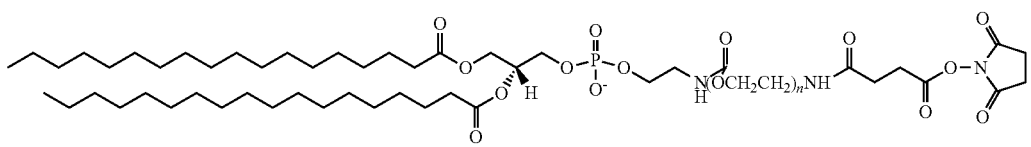

DSPE-PEG5K-NHS (Naonsoft Polymers ™ #SKU 1544)
(1,2-distearoyl-sn-glycero-3-phosphoethanolamine-N-[succinimidyl(polyethylene glycol)]),
wherein n is an integer and the molecular weight of the PEG groups is about 5 kilodaltons

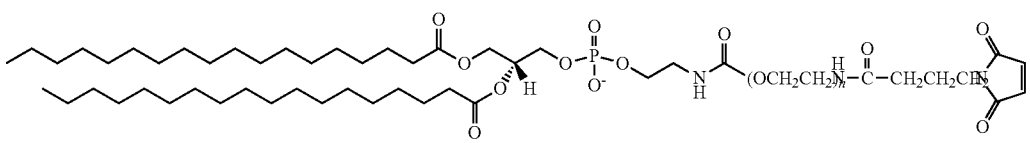

DSPE-PEG5K-MAL (Naonsoft Polymers ™ SKU #2049)
1,2-distearoyl-sn-glycero-3-phosphoethanolamine-N-[maleimide(polyethylene glycol)],
Wherein n is an integer and the molecular weight of the PEG groups is about 5 kilodaltons

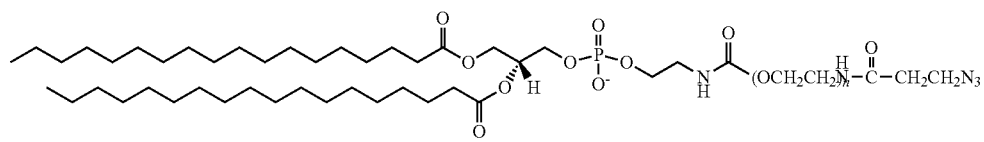

DSPE-PEG5K-N3 (Naonsoft Polymers ™ SKU #2274)
1,2-distearoyl-sn-glycero-3-phosphoethanolamine-N-[azido(polyethylene glycol)], wherein
n is an integer and the molecular weight of the PEG groups is about 5 kilodaltons TABLE 6.4-continued
Exemplary PK/PD Modulator Compounds.
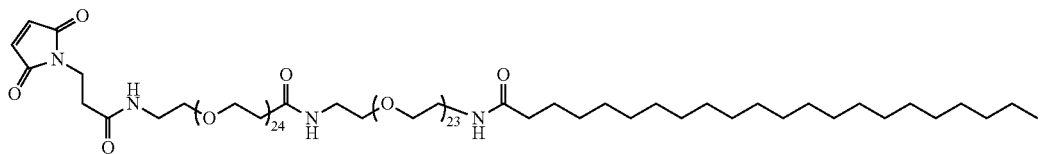
PEG47 + C22
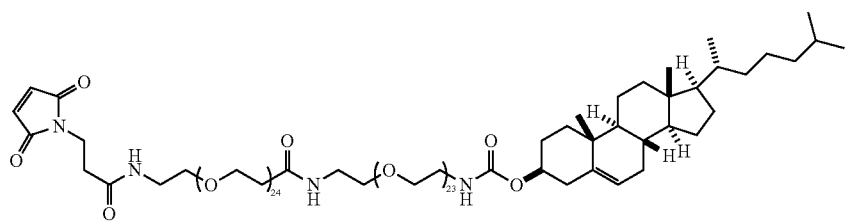
PEG47 + CLS (cholesterol)
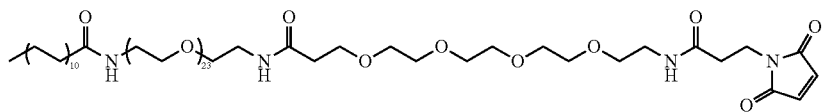
PEG23 + C22
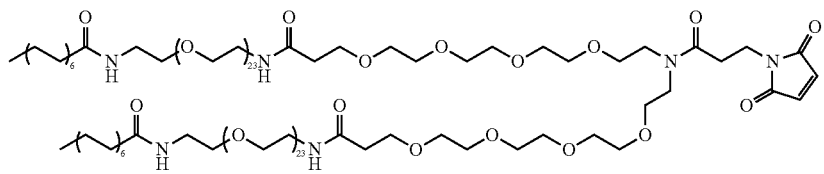
Bis(PEG23 + C14)
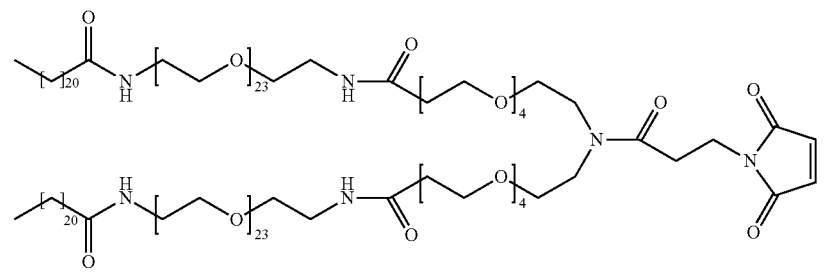
Bis(PEG23 + C22)
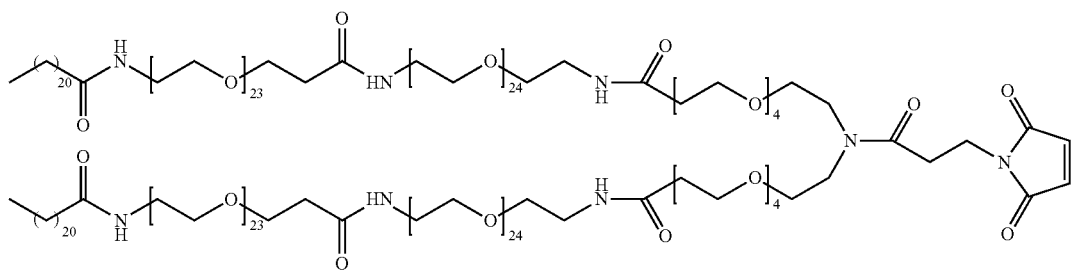
Bis(PEG47 + C22)

TABLE 6.4-continued
Exemplary PK/PD Modulator Compounds.
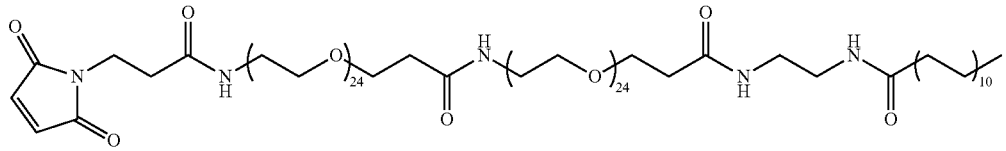
PEG48 + C22
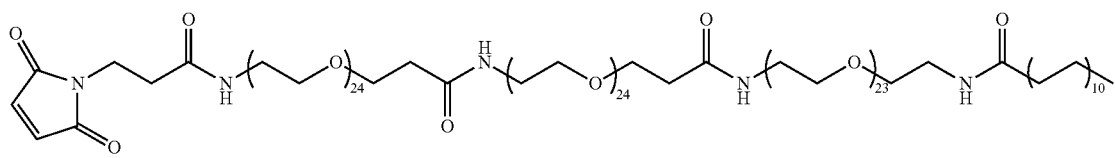
PEG71 + C22
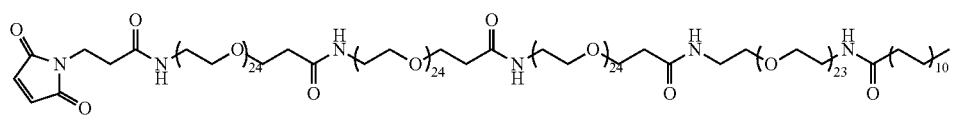
PEG95 + C22
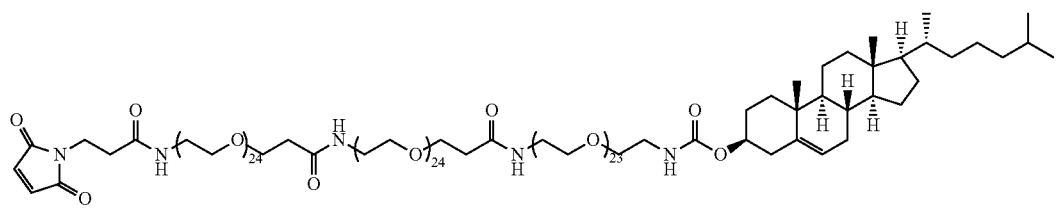
PEG71 + CLS
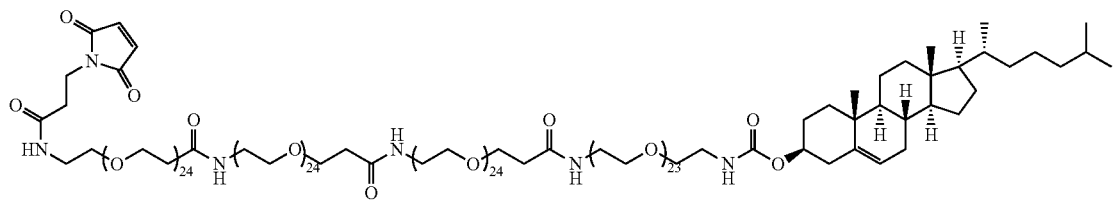
PEG95 + CLS
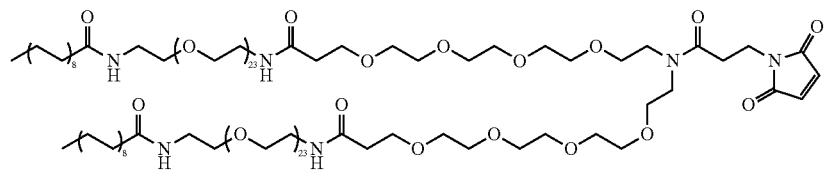
Bis(PEG23 + C18)

TABLE 6.4-continued
Exemplary PK/PD Modulator Compounds.
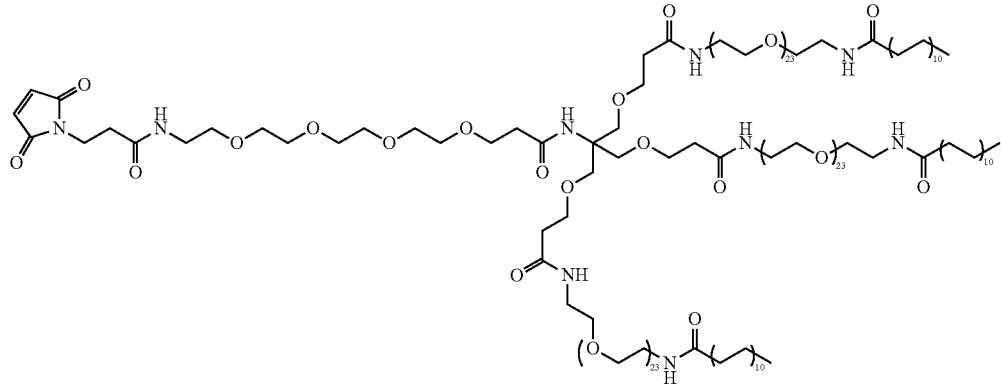
Tris(PEG23 + C22)
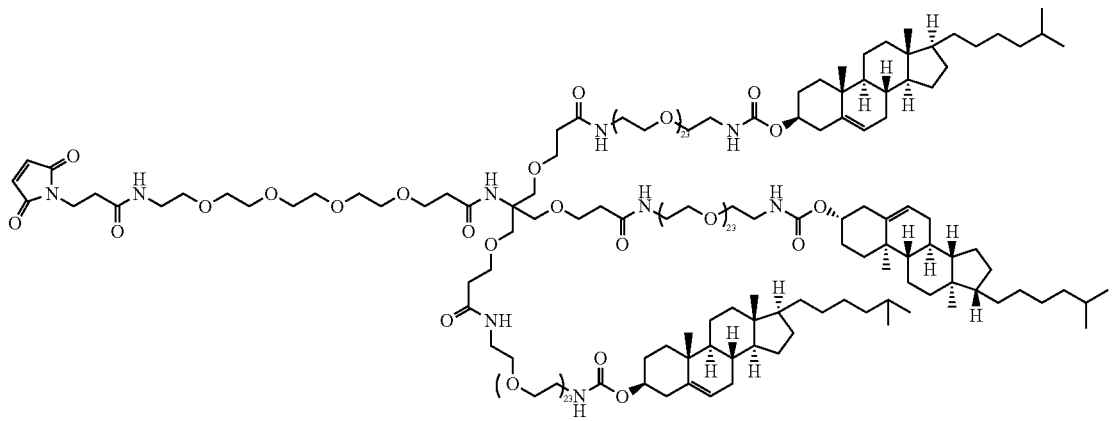
Tris(PEG23 + CLS)

TABLE 6.4-continued
Exemplary PK/PD Modulator Compounds.
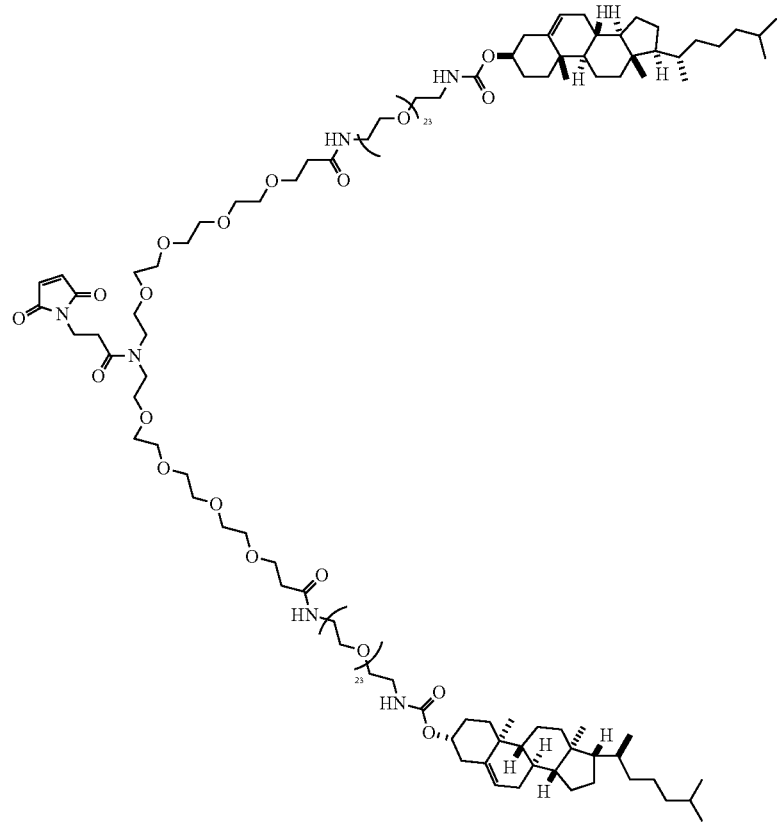
Bis(PEG23 + CLS)
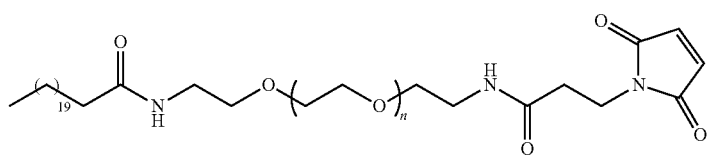
PEG5K + C22
wherein n is an integer and the molecular weight of the PEG units is about 5 kilodaltons
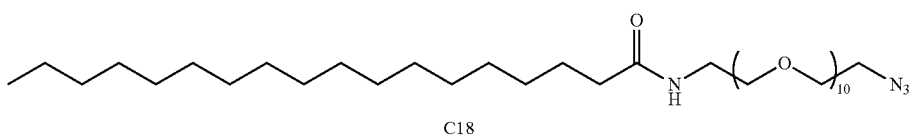
C18
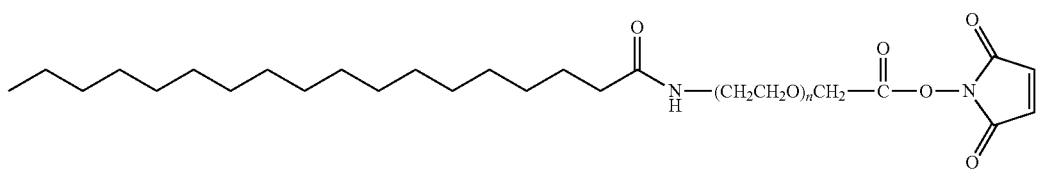
(NHS)-PEG1K + C18 (Nanosoft Polymers ™ SKU #10668-1000)
wherein n is an integer and the molecular weight of the PEG units is about 1 kilodalton TABLE 6.4-continued Exemplary PK/PD Modulator Compounds.

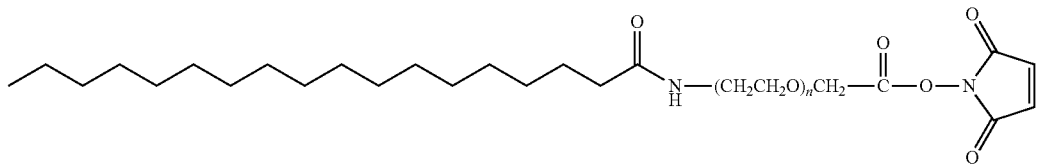

(NHS)-PEG2K + C18 (Nanosoft Polymers ™ SKU #10668-2000)
wherein n is an integer and the molecular weight of the PEG units is about 2 kilodaltons

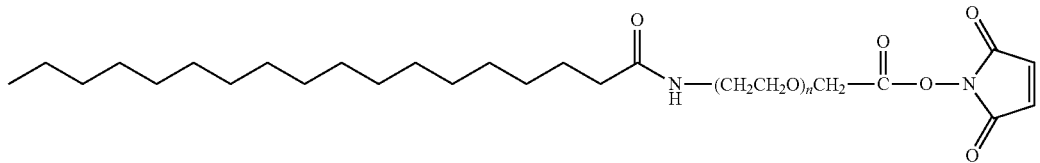

(NHS)-PEG5K + C18 (Nanosoft Polymers ™ SKU #10668-5000)
wherein n is an integer and the molecular weight of the PEG units is about 5 kilodaltons

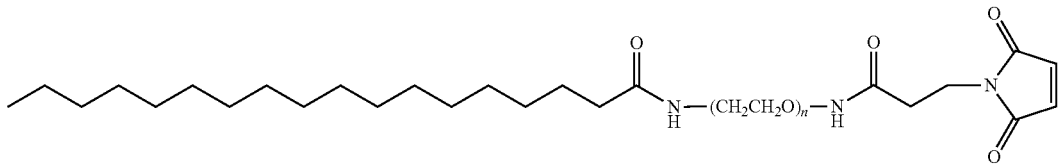

(MAL)-PEG5K + C18 (Nanosoft Polymers ™ SKU #10647)
wherein n is an integer and the molecular weight of the PEG units is about 5 kilodaltons

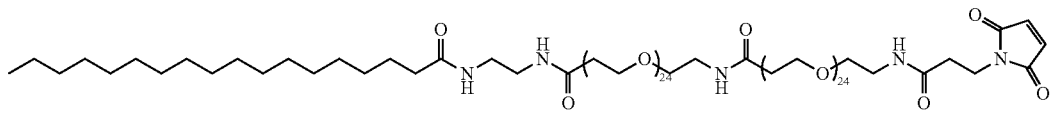

PEG48 + C18

In some embodiments, the PK/PD modulators of Table 6.4 have the following structures following conjugation to the DUX4 RNAi agents as shown in Table 6.5:

TABLE 6.5

Example PK/PD modulators conjugated to DUX4 RNAi agents.

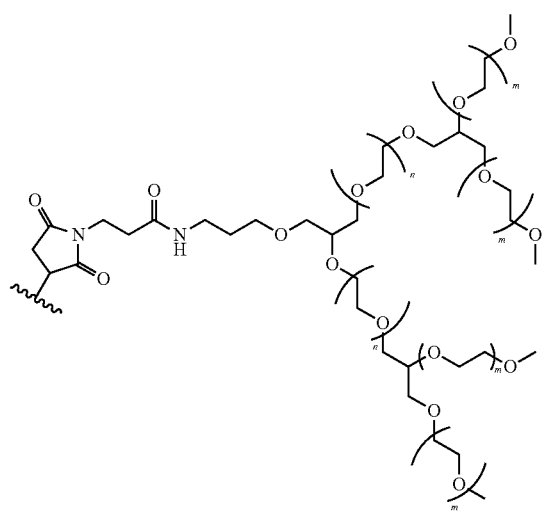

TABLE 6.5-continued

Example PK/PD modulators conjugated to DUX4 RNAi agents.

PEG40K (2x2-arm),
wherein n and m are integers, and the molecular weight of the PEG groups is about 40 kilodaltons

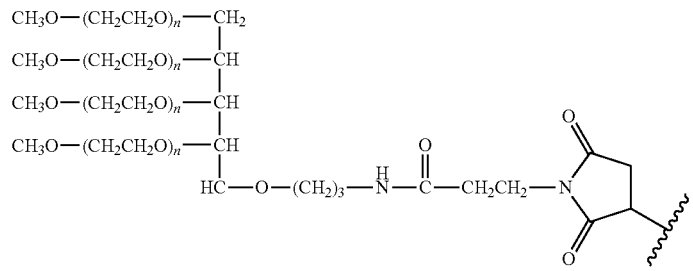

PEG40K (4-arm),
wherein n is an integer, and the molecular weight of the PEG groups is about 40 kilodaltons

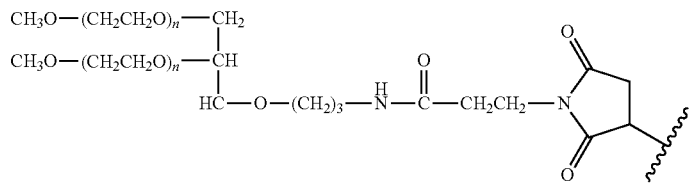

PEG40K (2-arm),
wherein n is an integer, and the molecular weight of the PEG groups is about 40 kilodaltons

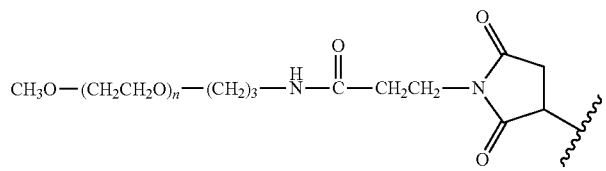

PEG40K,
wherein n is an integer, and the molecular weight of the PEG groups is about 40 kilodaltons

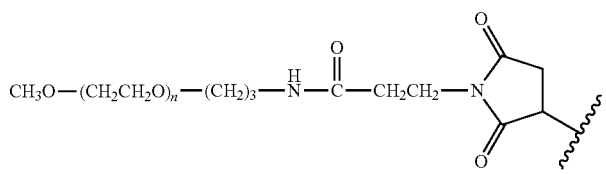

PEG10K,
wherein n is an integer, and the molecular weight of the PEG groups is about 10 kilodaltons

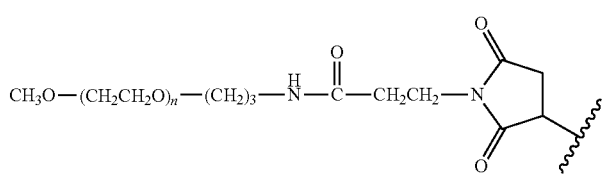

PEG5K,
wherein n is an integer, and the molecular weight of the PEG groups is about 5 kilodaltons TABLE 6.5-continued Example PK/PD modulators conjugated to DUX4 RNAi agents.

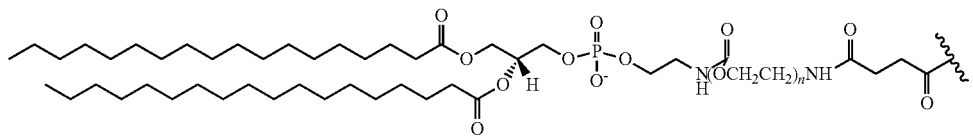

DSPE-PEG5K-NHS
wherein n is an integer and the molecular weight of the PEG groups is about 5 kilodaltons

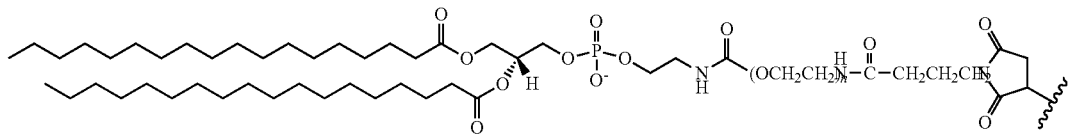

DSPE-PEG5K-MAL
Wherein n is an integer and the molecular weight of the PEG groups is about 5 kilodaltons

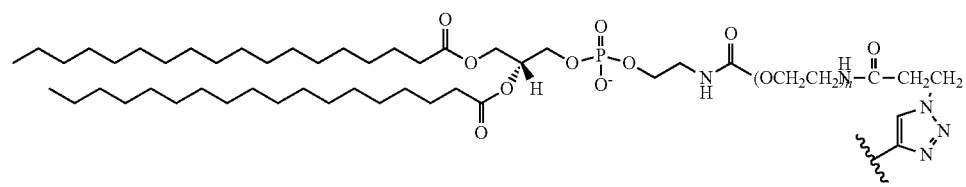

DSPE-PEG5K-N3
wherein n is an integer and the molecular weight of the PEG groups is about 5 kilodaltons

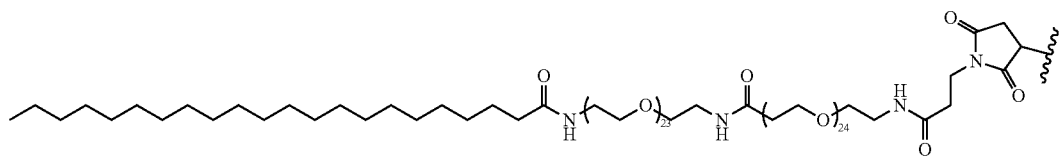

PEG47 + C22

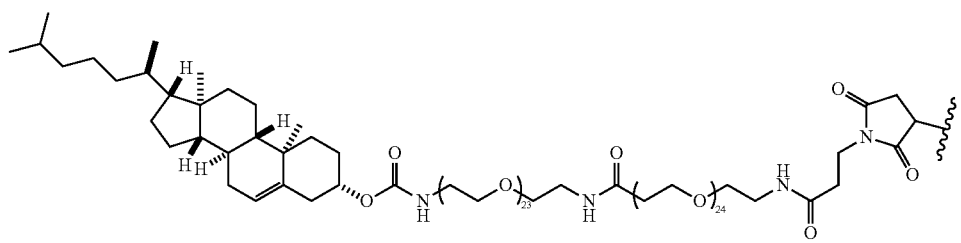

PEG47 + CLS (cholesterol)

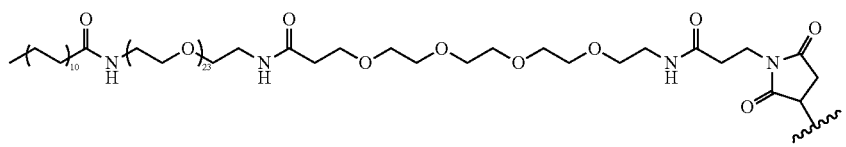

PEG23 + C22

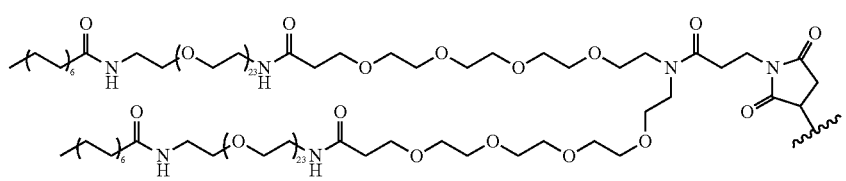

Bis(PEG23 + C14)

TABLE 6.5-continued
Example PK/PD modulators conjugated to DUX4 RNAi agents.
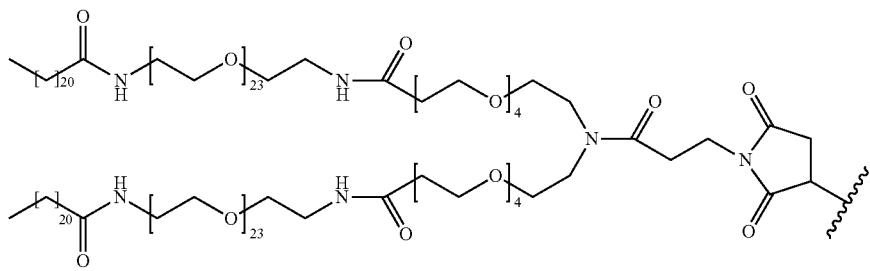
Bis(PEG23 + C22)
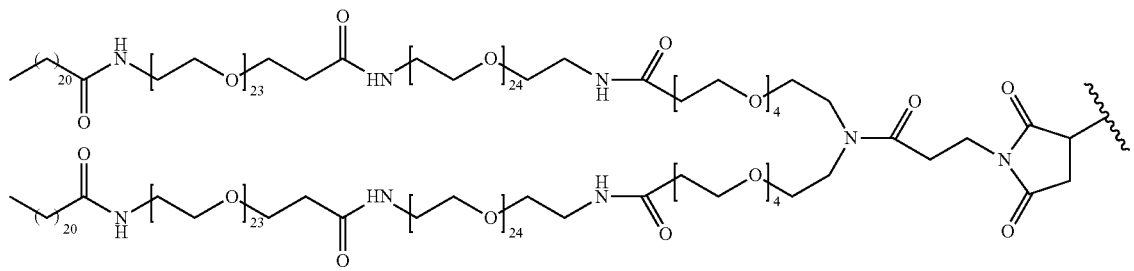
Bis(PEG47 + C22)
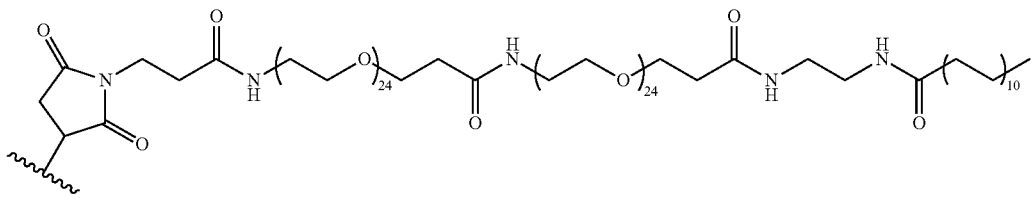
PEG48 + C22
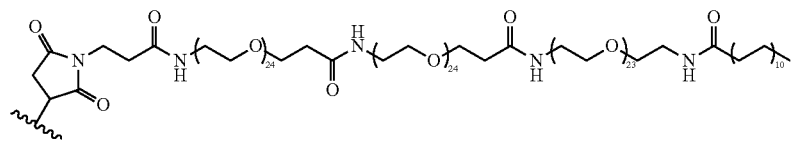
PEG71 + C22
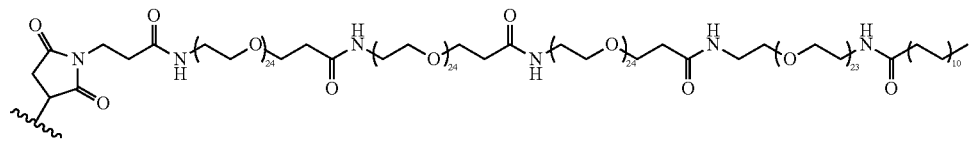
PEG95 + C22
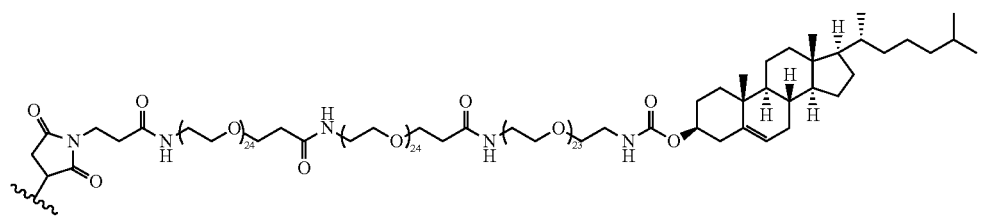
PEG71 + CLS TABLE 6.5-continued
Example PK/PD modulators conjugated to DUX4 RNAi agents.
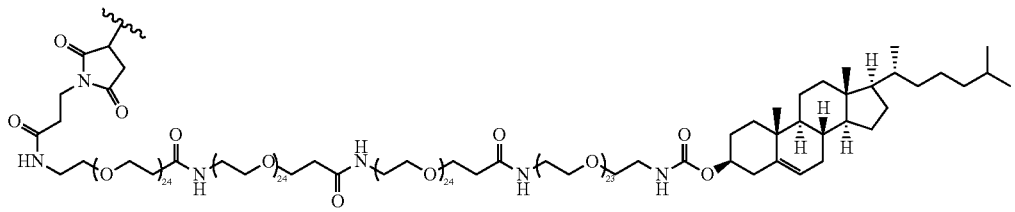
PEG95 + CLS
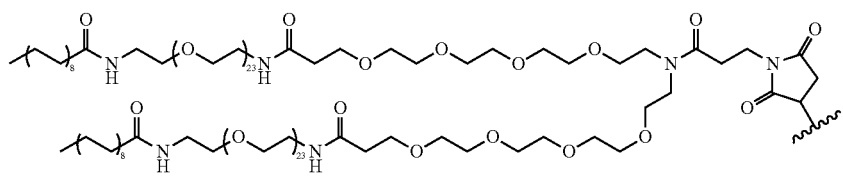
Bis(PEG23 + C18)
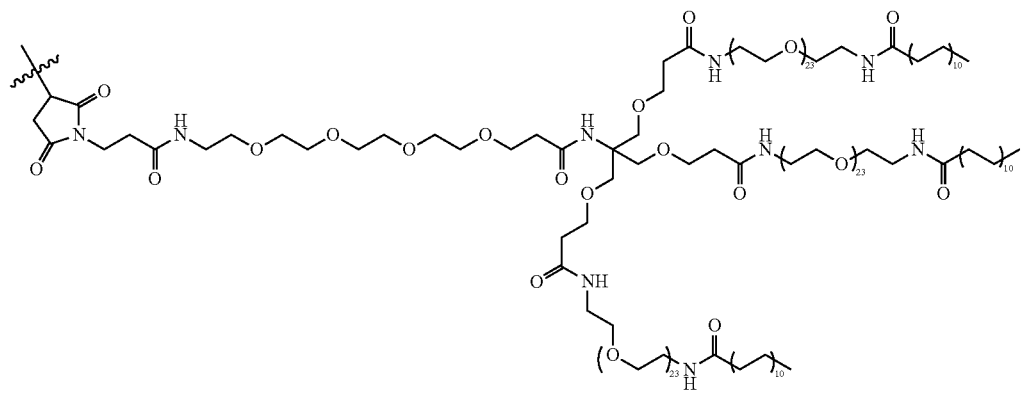
Tris(PEG23 + C22)
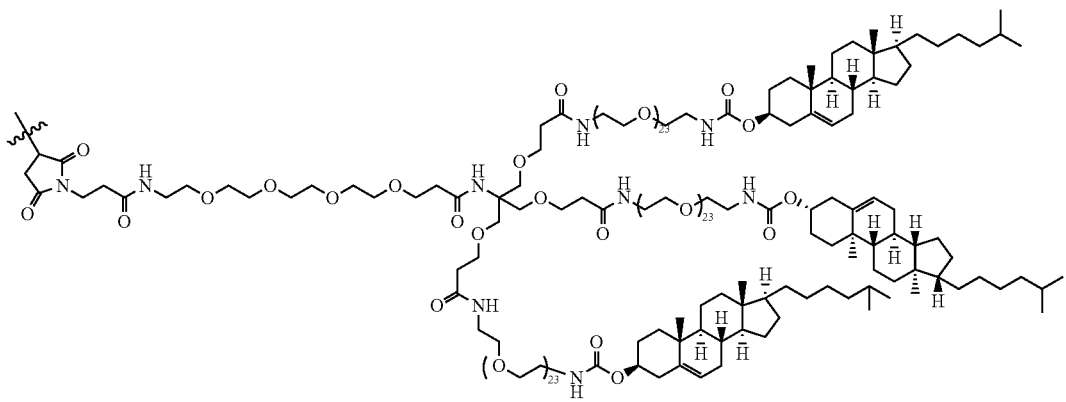
Tris(PEG23 + CLS)

TABLE 6.5-continued
Example PK/PD modulators conjugated to DUX4 RNAi agents.
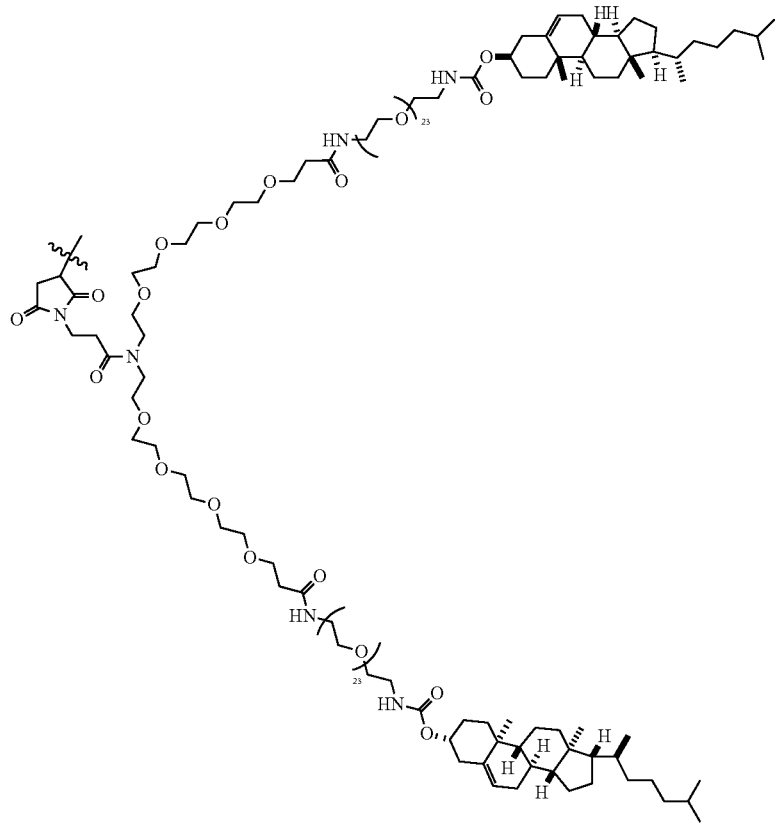
Bis(PEG23 + CLS)
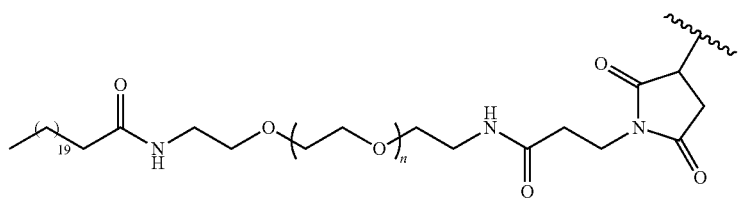
PEG5K + C22
wherein n is an integer and the molecular weight of the PEG units is about 5 kilodaltons
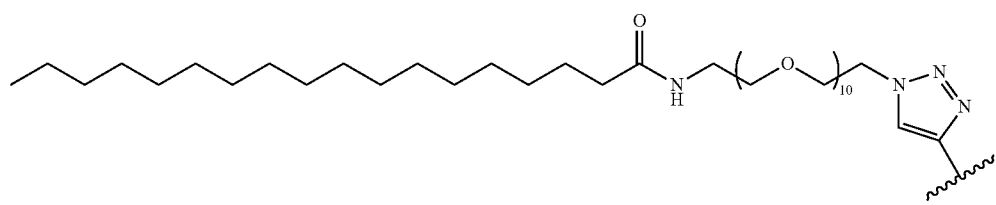
C18
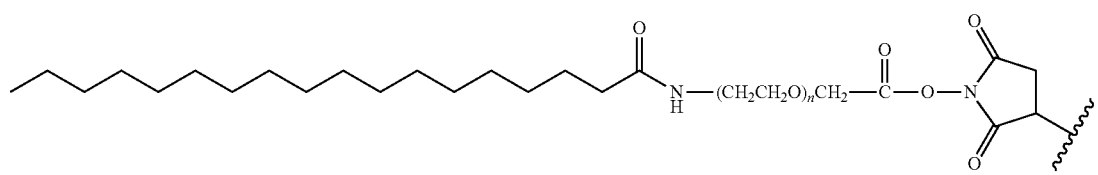
(NHS)-PEG1K + C18
wherein n is an integer and the molecular weight of the PEG units is about 1 kilodalton TABLE 6.5-continued Example PK/PD modulators conjugated to DUX4 RNAi agents.

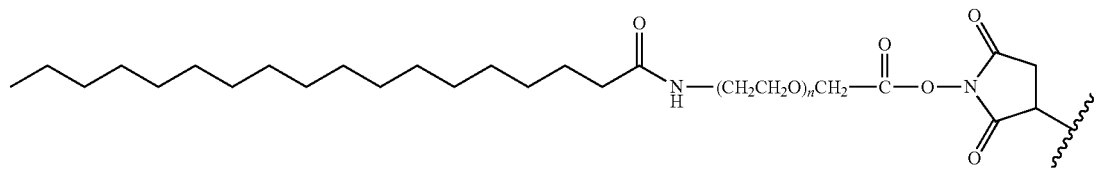

(NHS)-PEG2K + C18
wherein n is an integer and the molecular weight of the PEG units is about 2 kilodaltons

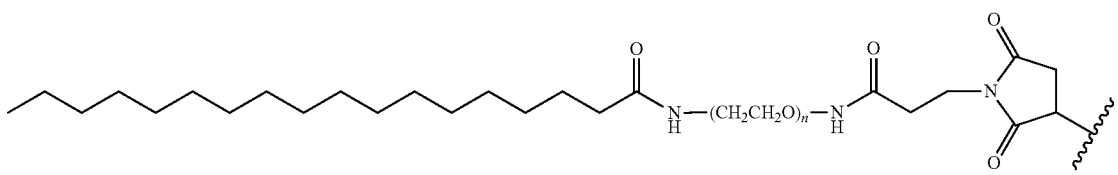

(NHS)-PEG5K + C18
wherein n is an integer and the molecular weight of the PEG units is about 5 kilodaltons

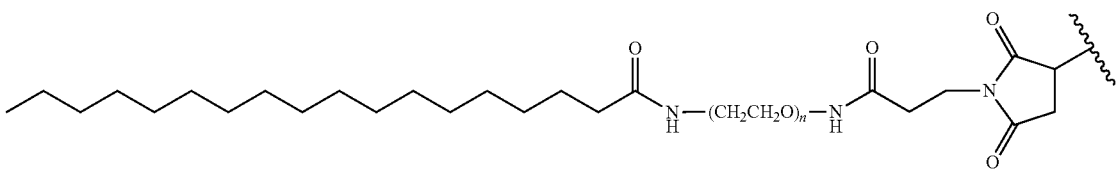

(MAL)-PEG5K + C18
wherein n is an integer and the molecular weight of the PEG units is about 5 kilodaltons

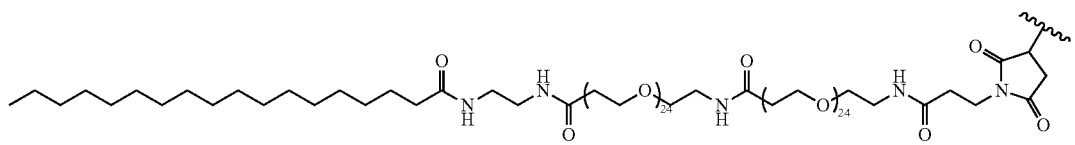

PEG48 + C18 or a pharmaceutically acceptable salt thereof, wherein ⸹ indicates the point of connection to the DUX4 RNAi agents.

In other embodiments, the PK/PD modulator that may be conjugated to the DUX4 RNAi agents described herein may be selected from the group consisting of the PK/PD modulators in Table 6.6:

TABLE 6.6

Example PK/PD modulators for conjugating to DUX4 RNAi agents (Compound number appears before structure.)

TABLE 6.6-continued
Example PK/PD modulators for conjugating to DUX4 RNAi agents (Compound number appears before structure.)
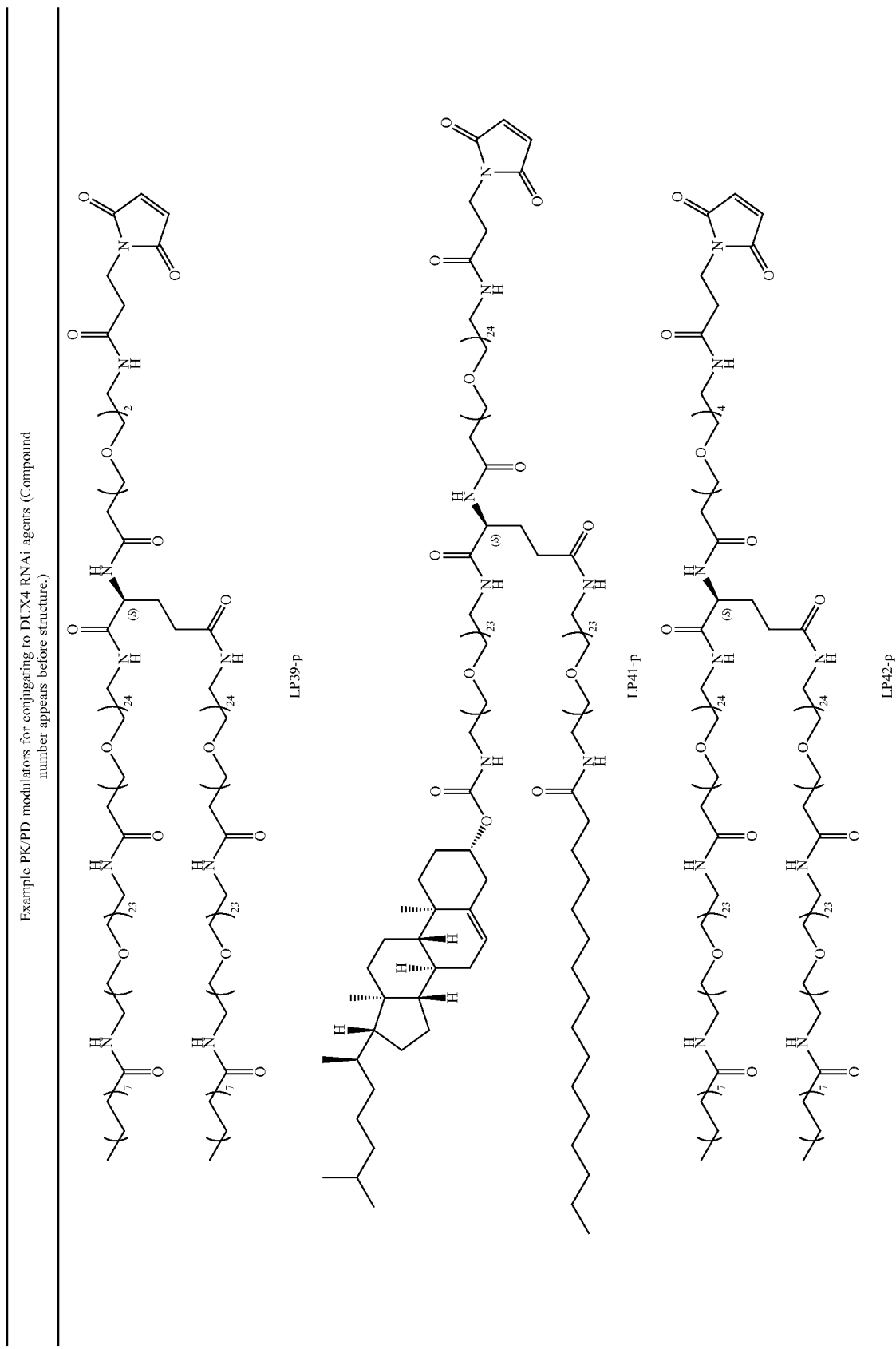

TABLE 6.6-continued
Example PK/PD modulators for conjugating to DUX4 RNAi agents (Compound number appears before structure.)
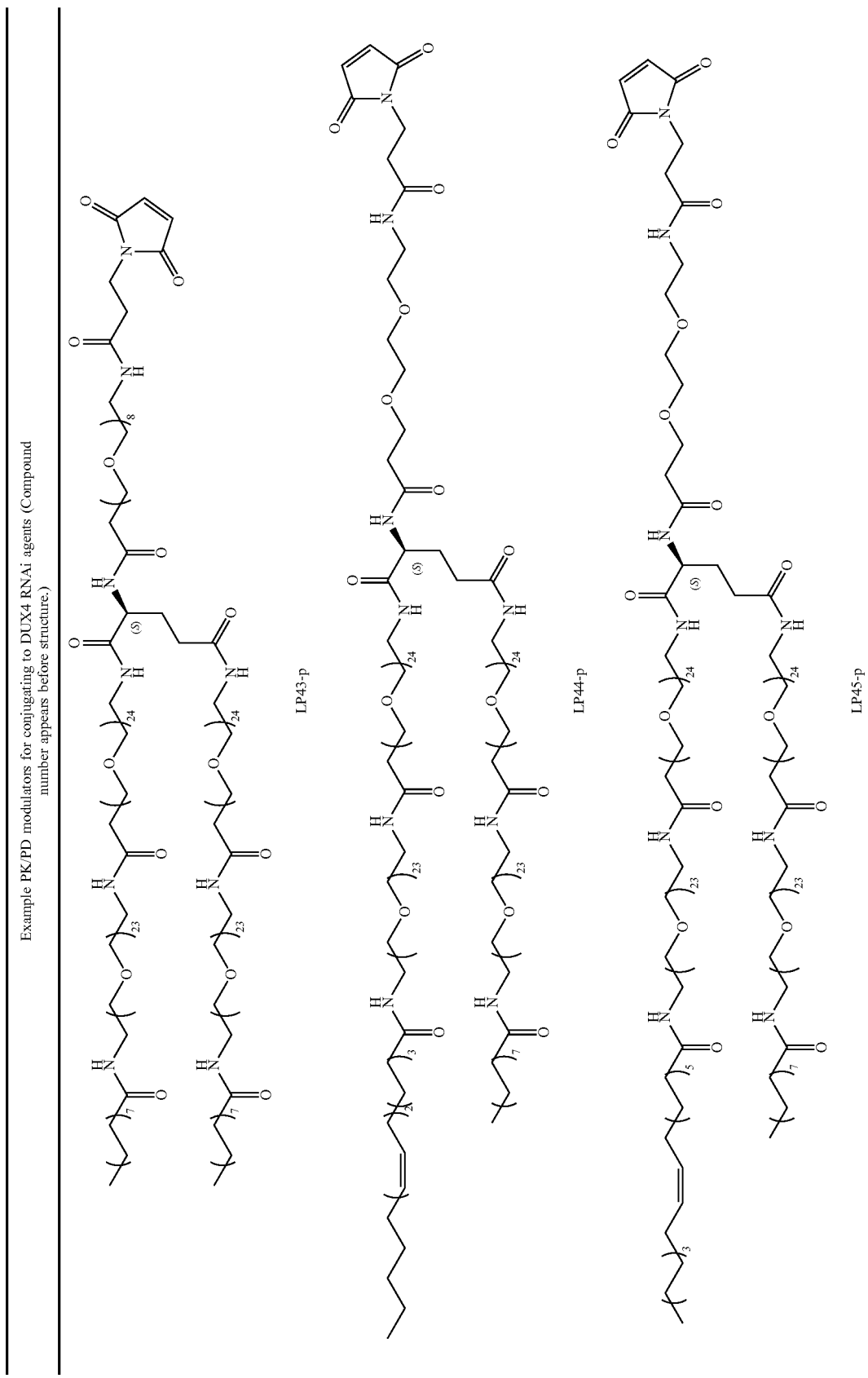
LP43-p
LP44-p
LP45-p TABLE 6.6-continued
Example PK/PD modulators for conjugating to DUX4 RNAi agents (Compound number appears before structure.)
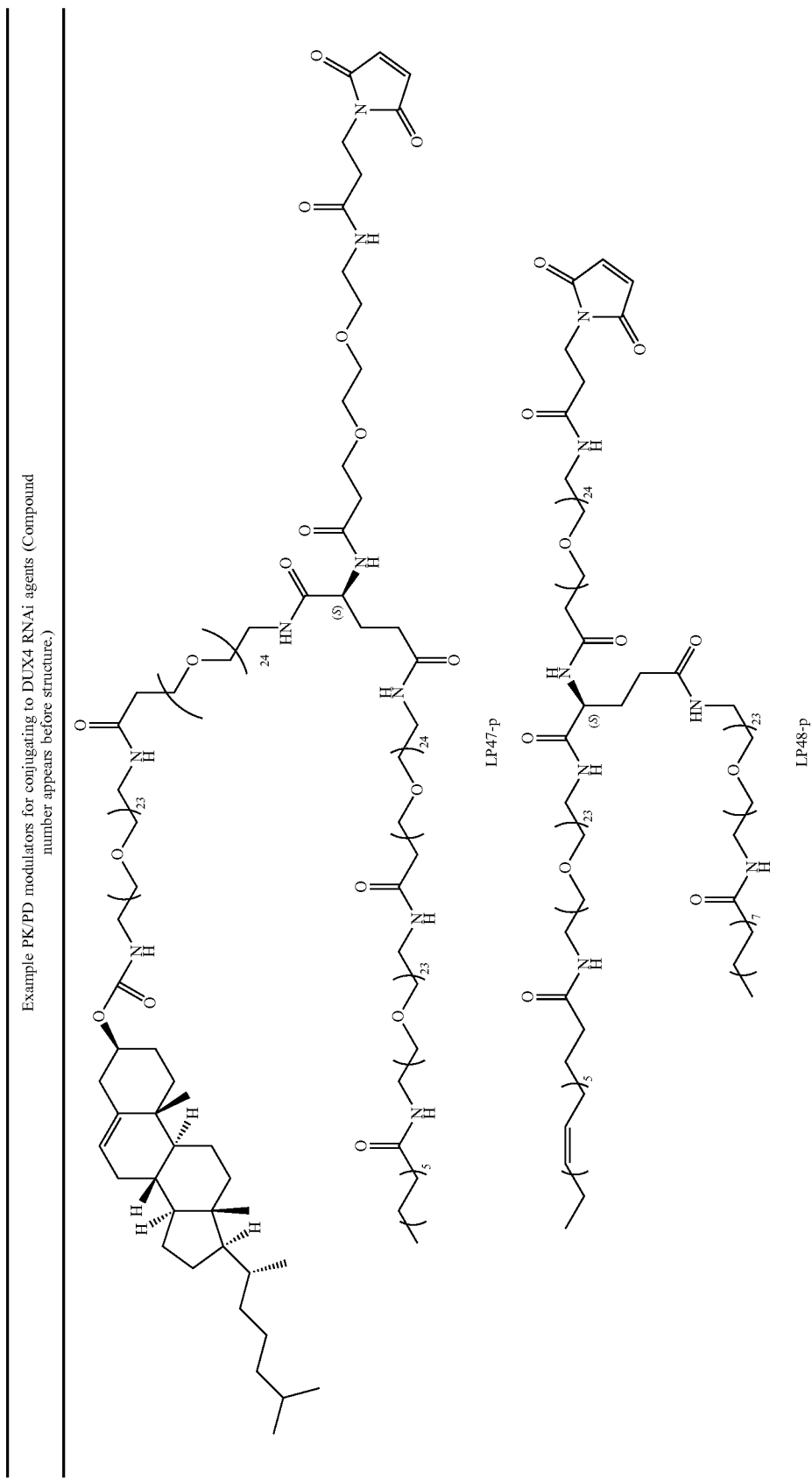

TABLE 6.6-continued
Example PK/PD modulators for conjugating to DUX4 RNAi agents (Compound number appears before structure.)
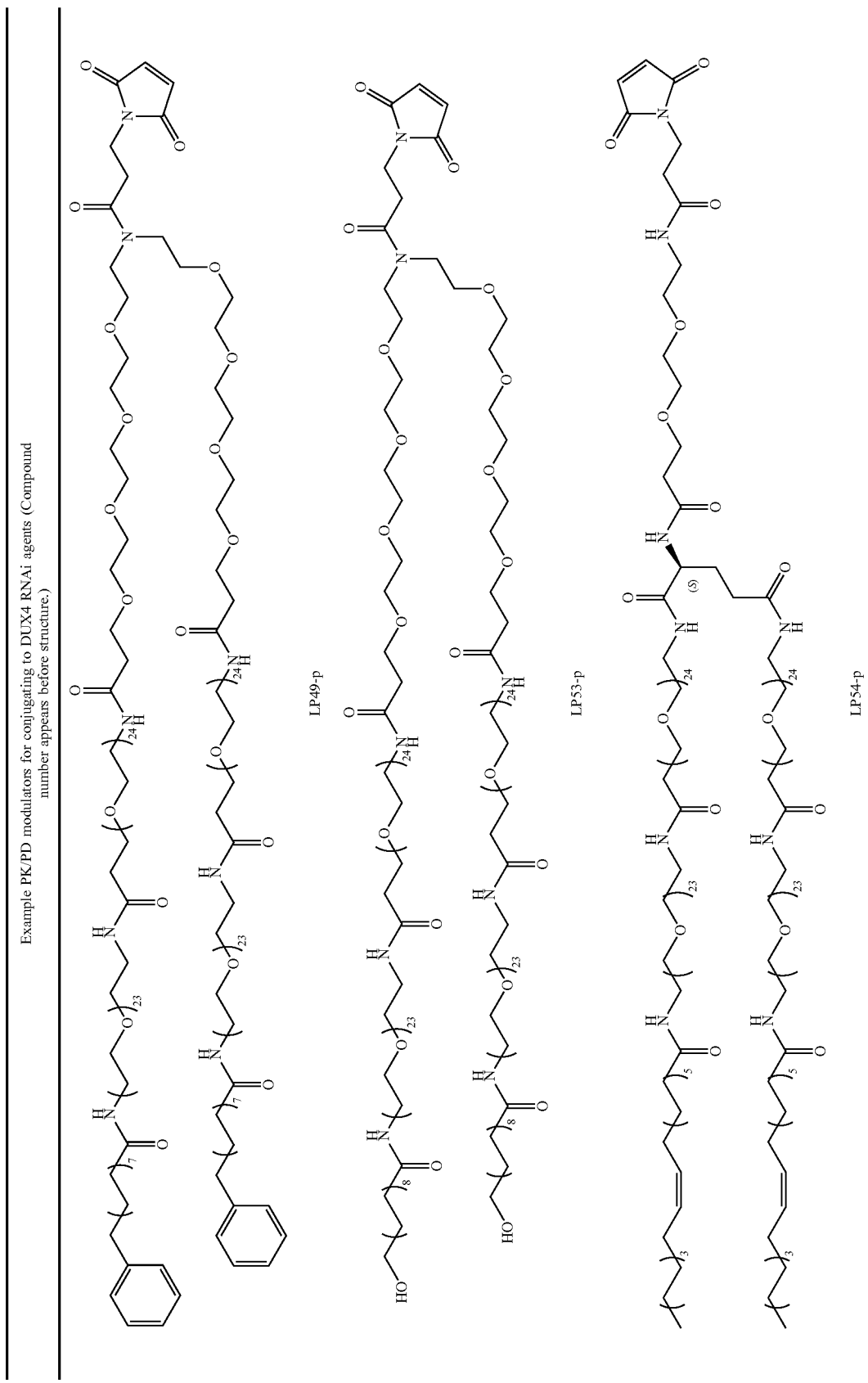
LP49-p
LP53-p
LP54-p TABLE 6.6-continued
Example PK/PD modulators for conjugating to DUX4 RNAi agents (Compound number appears before structure.)
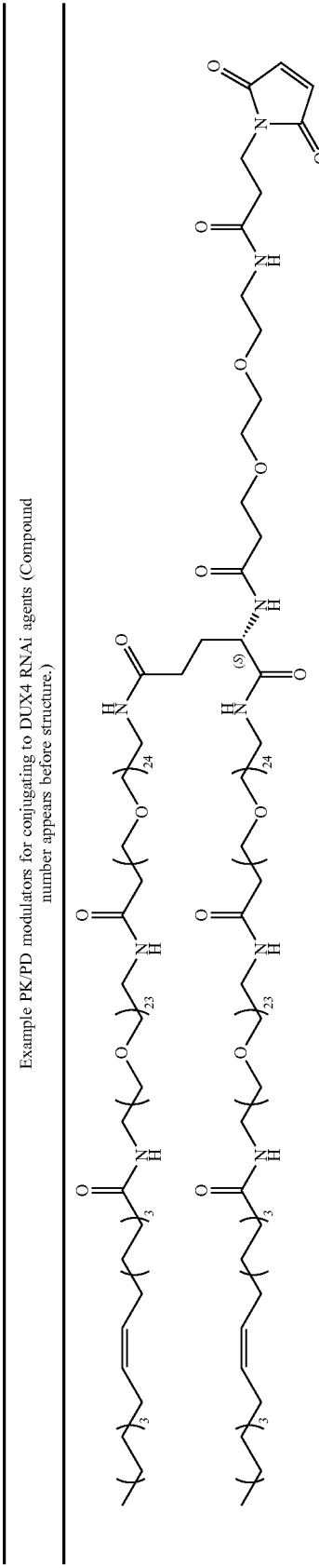
LP55-p
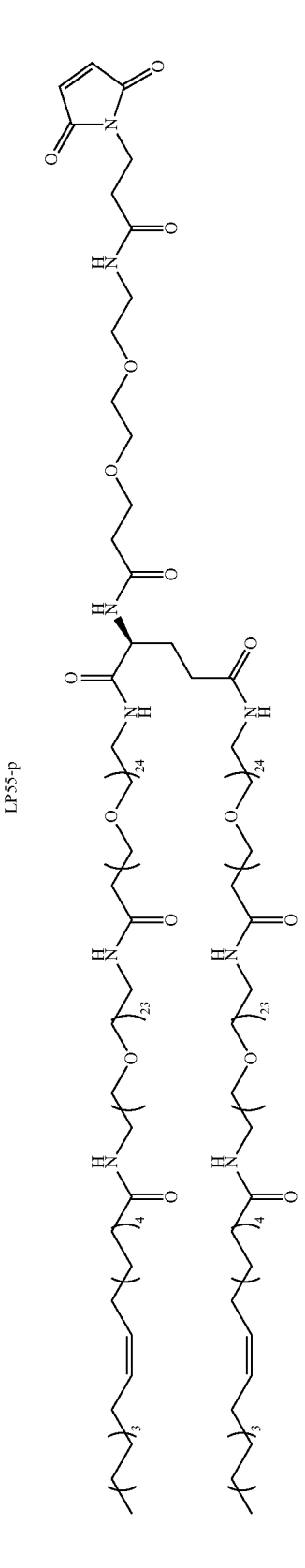
LP56-p
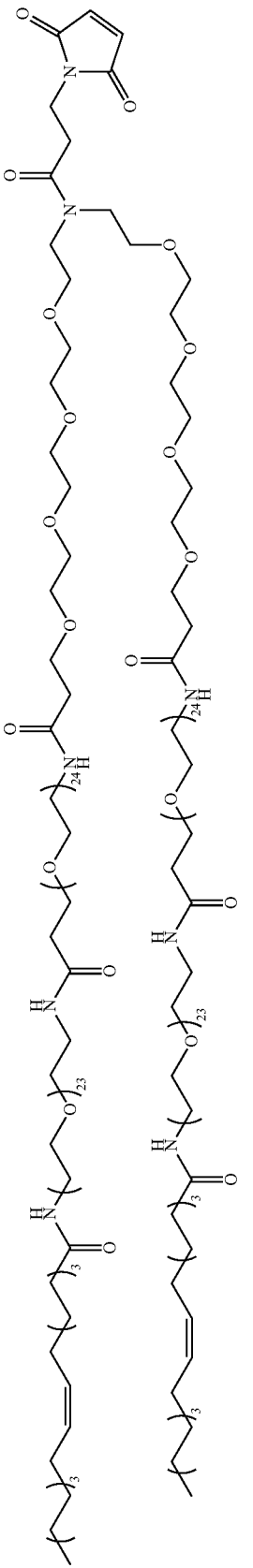
LP57-p TABLE 6.6-continued Example PK/PD modulators for conjugating to DUX4 RNAi agents (Compound number appears before structure.)

LP58-p

LP59-p

LP60-p

TABLE 6.6-continued
Example PK/PD modulators for conjugating to DUX4 RNAi agents (Compound number appears before structure.)
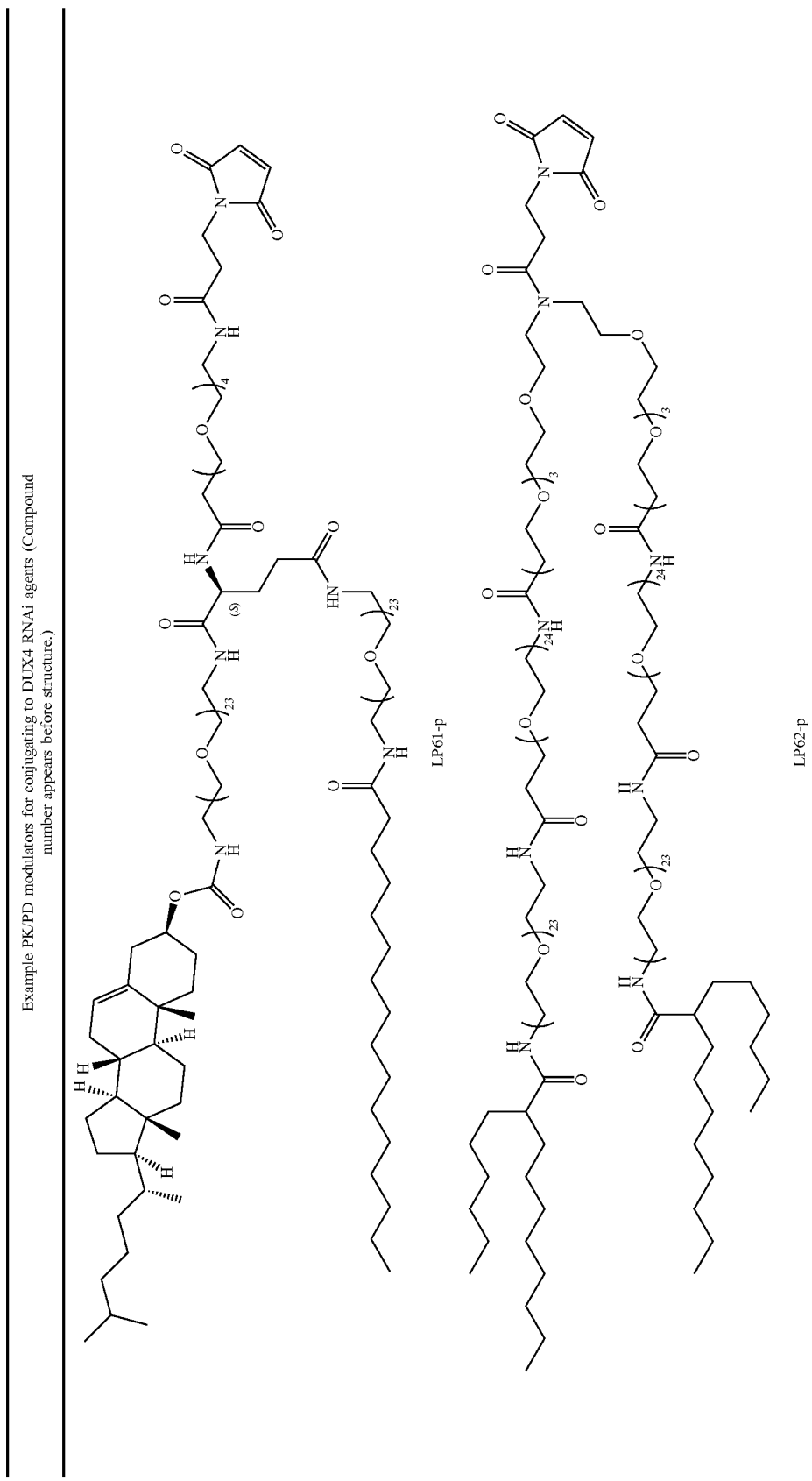

TABLE 6.6-continued
Example PK/PD modulators for conjugating to DUX4 RNAi agents (Compound number appears before structure.)
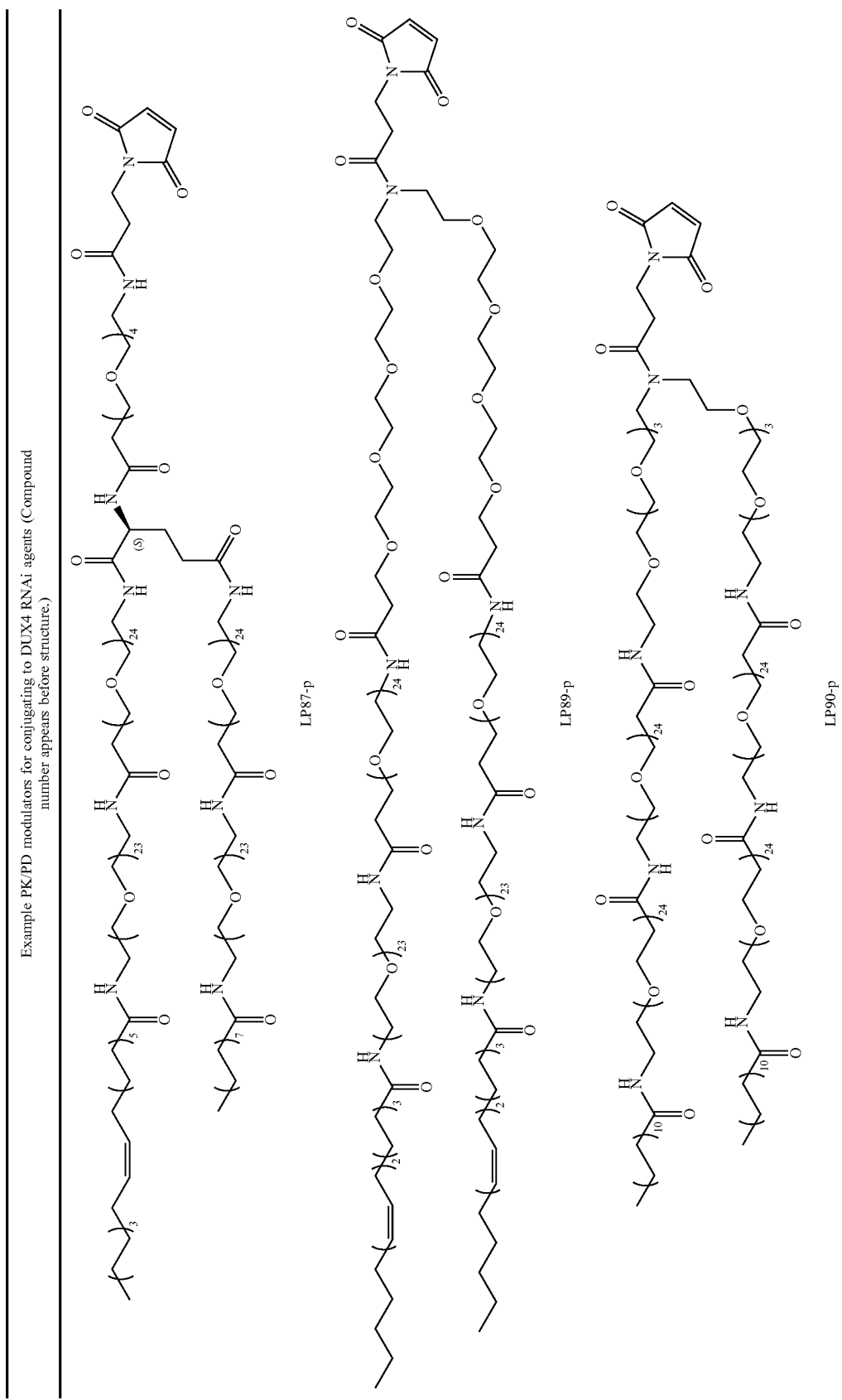
LP87-p
LP89-p
LP90-p TABLE 6.6-continued
Example PK/PD modulators for conjugating to DUX4 RNAi agents (Compound number appears before structure.)
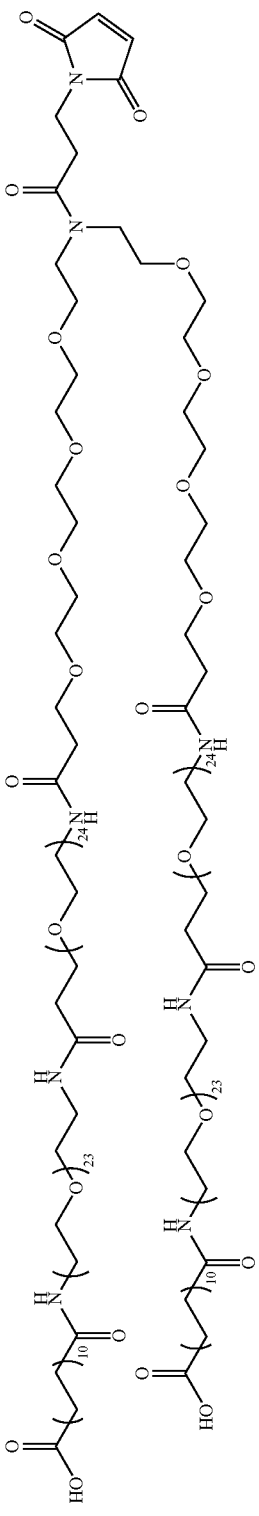
LP92-p
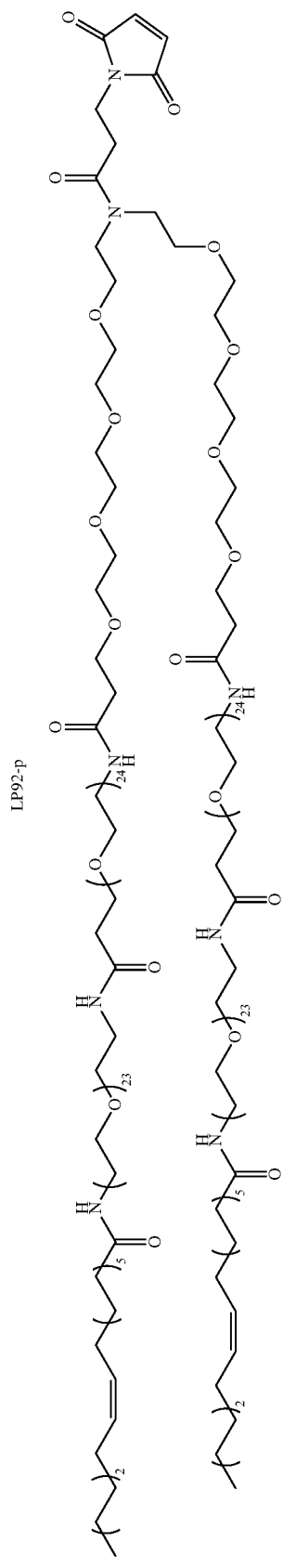
LP93-p
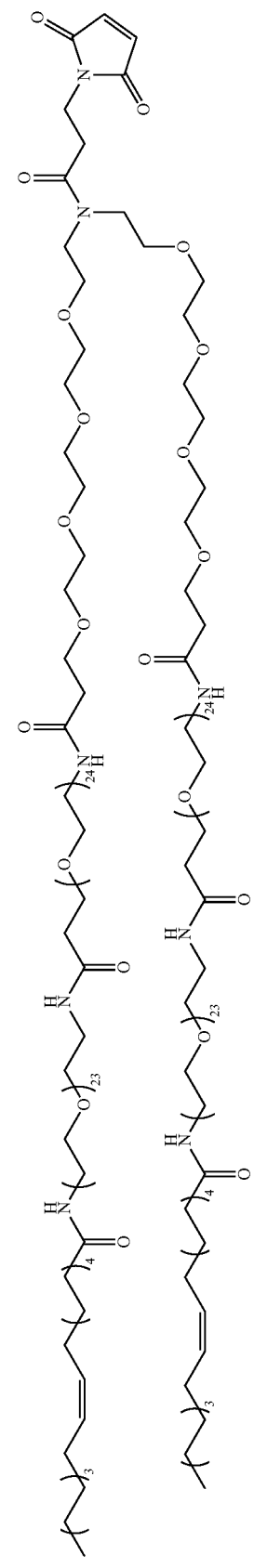
LP94-p TABLE 6.6-continued
Example PK/PD modulators for conjugating to DUX4 RNAi agents (Compound number appears before structure.)
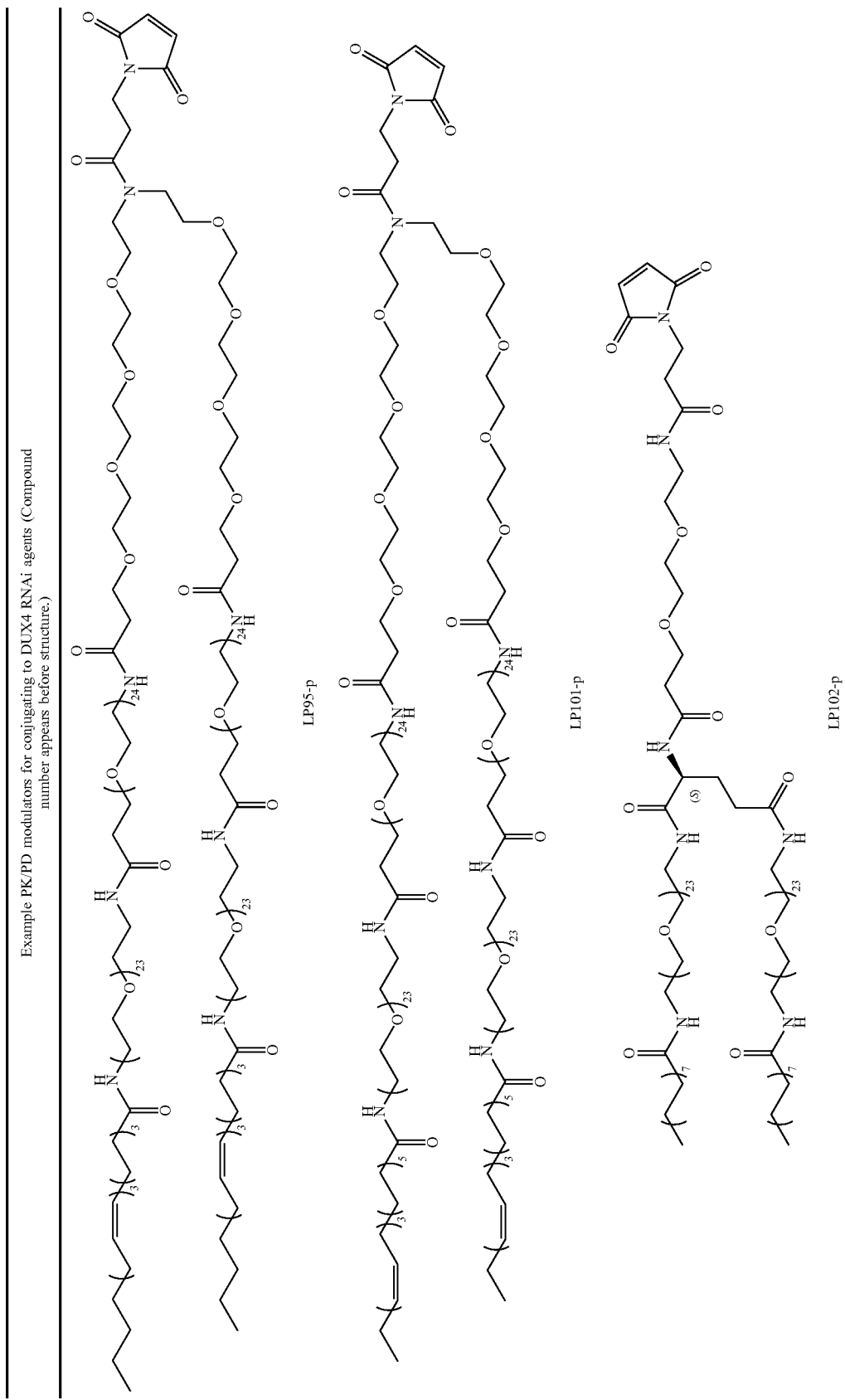

TABLE 6.6-continued
Example PK/PD modulators for conjugating to DUX4 RNAi agents (Compound number appears before structure.)
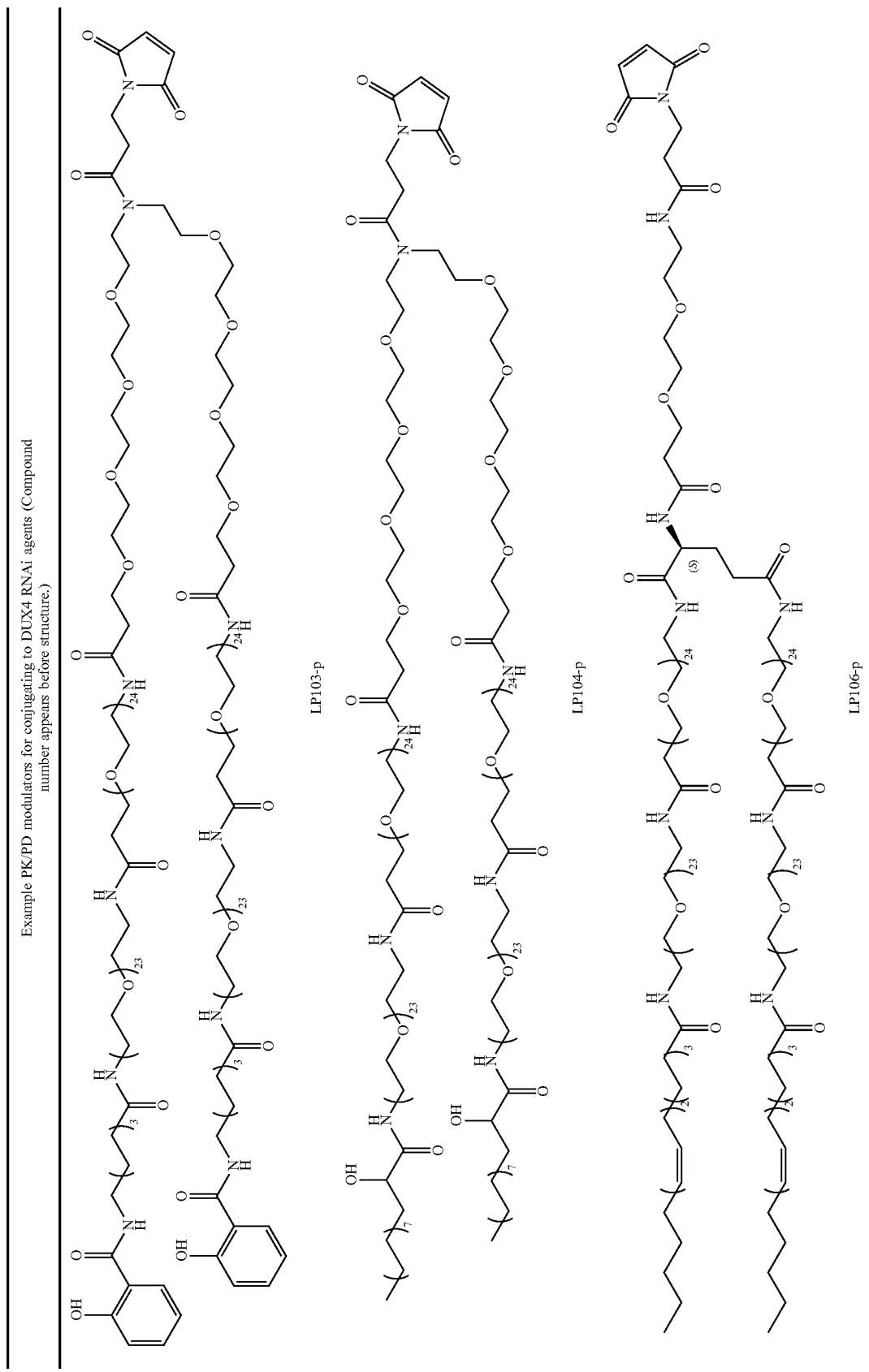

TABLE 6.6-continued
Example PK/PD modulators for conjugating to DUX4 RNAi agents (Compound number appears before structure.)
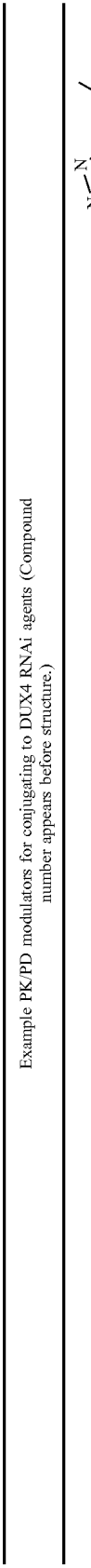
LP107-p
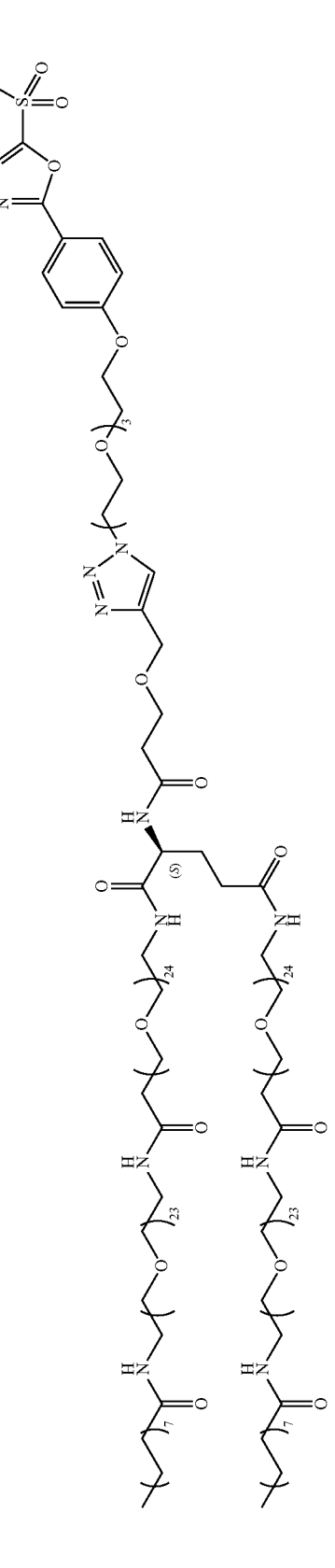
LP108-p
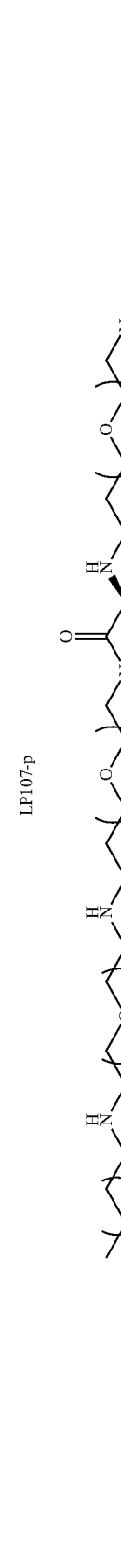
LP109-p TABLE 6.6-continued Example PK/PD modulators for conjugating to DUX4 RNAi agents (Compound number appears before structure.)

LP110-p

LP111-p

LP124-p

TABLE 6.6-continued

Example PK/PD modulators for conjugating to DUX4 RNAi agents (Compound number appears before structure.)

LP130-p

LP143-p

LP210-p

TABLE 6.6-continued
Example PK/PD modulators for conjugating to DUX4 RNAi agents (Compound number appears before structure.)
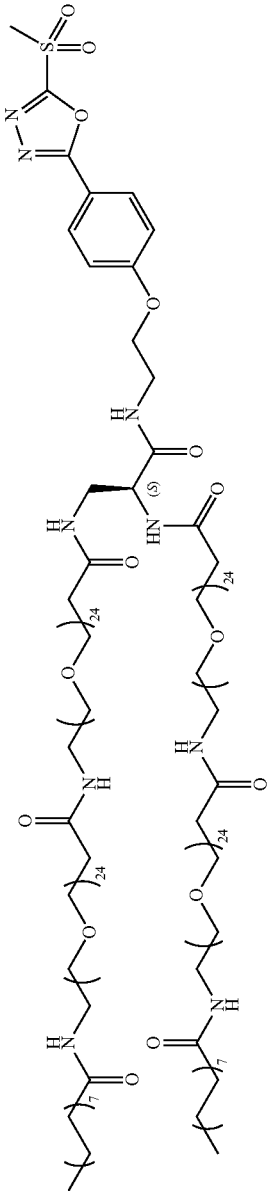
LP217-p
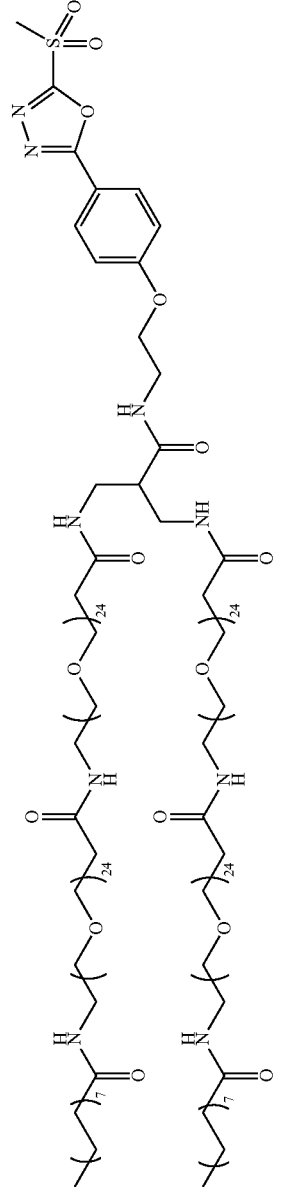
LP220-p
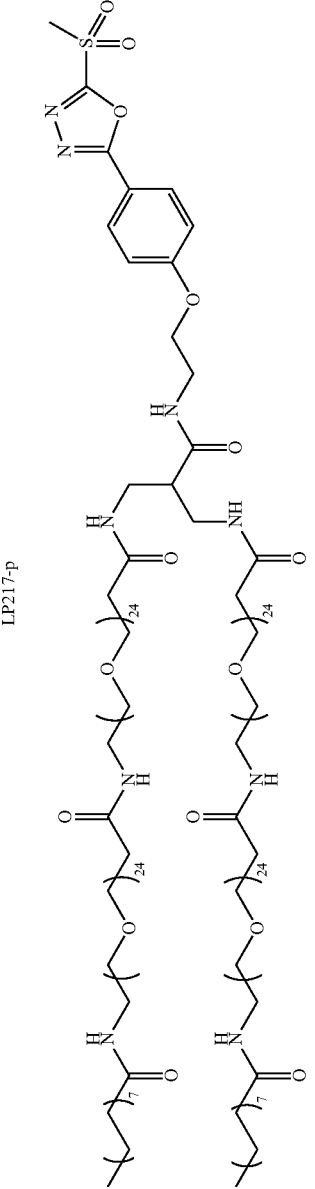
LP221-p TABLE 6.6-continued Example PK/PD modulators for conjugating to DUX4 RNAi agents (Compound number appears before structure.)

LP223-p

LP224-p

LP225-p

TABLE 6.6-continued
Example PK/PD modulators for conjugating to DUX4 RNAi agents (Compound number appears before structure.)
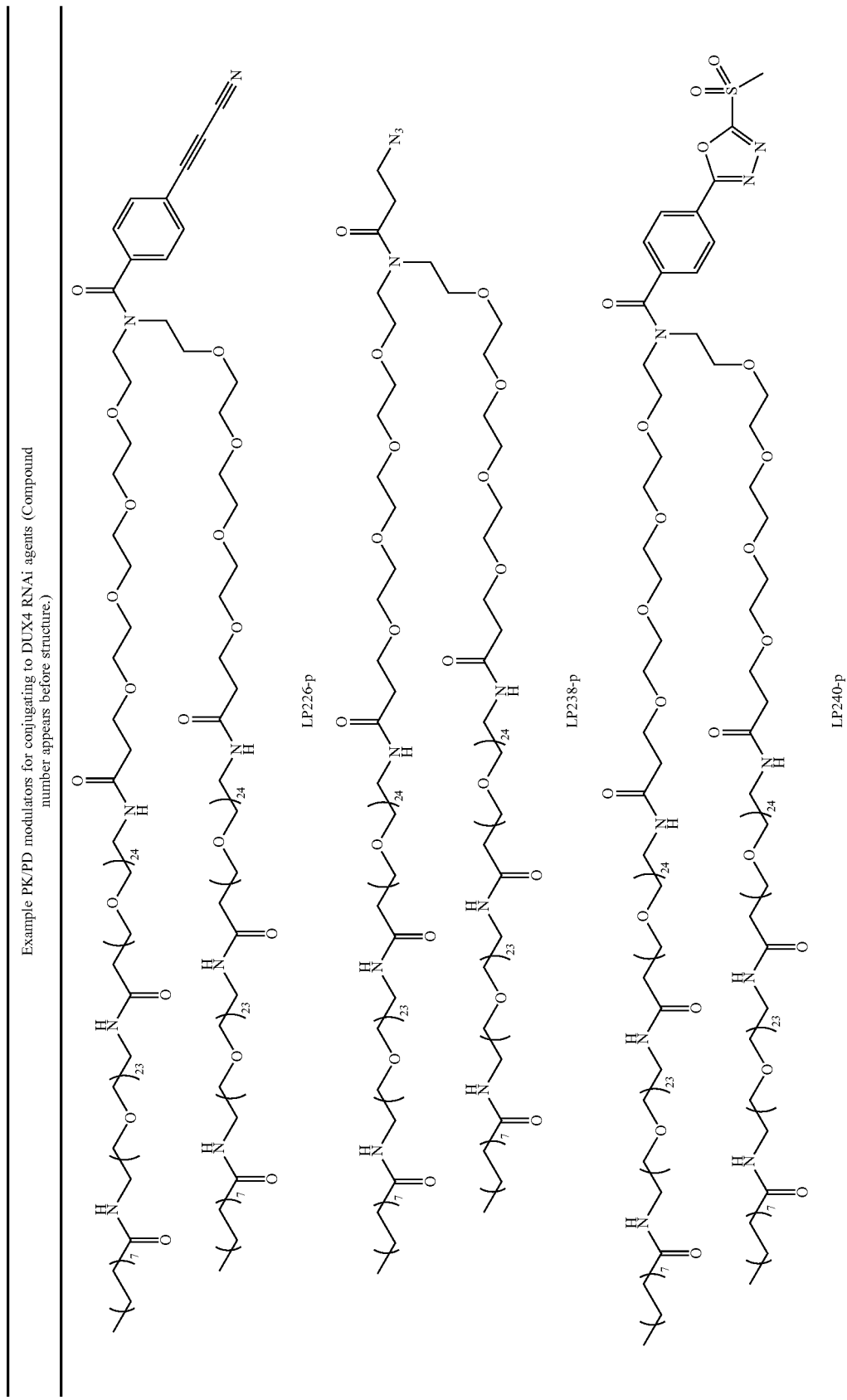

TABLE 6.6-continued

Example PK/PD modulators for conjugating to DUX4 RNAi agents (Compound number appears before structure.)

LP246-p

LP247-p

LP339-p

TABLE 6.6-continued
Example PK/PD modulators for conjugating to DUX4 RNAi agents (Compound number appears before structure.)
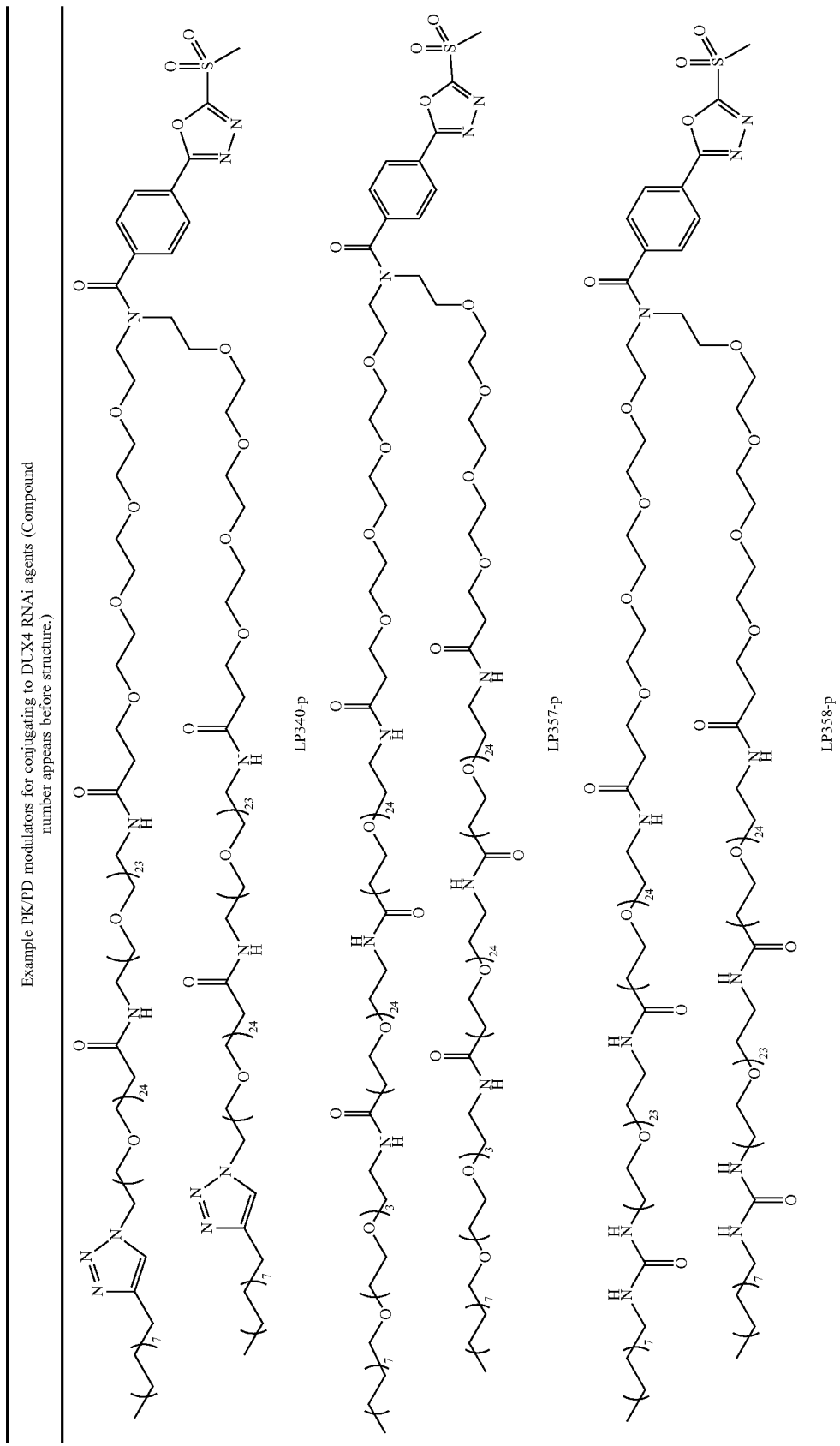

TABLE 6.6-continued
Example PK/PD modulators for conjugating to DUX4 RNAi agents (Compound number appears before structure.)
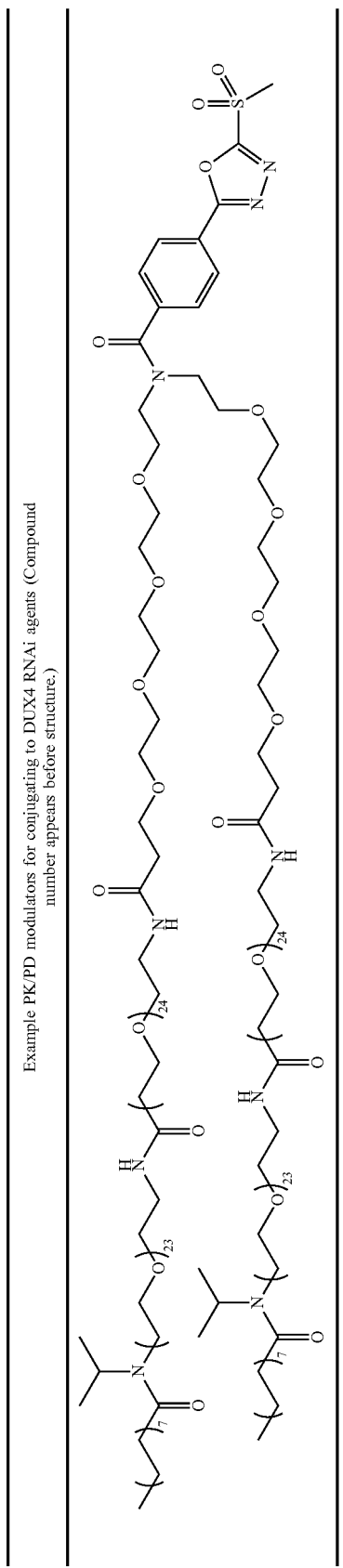

In some embodiments, the PK/PD modulators of Table 6.6 have the following structures following conjugation to the DUX4 RNAi agents as shown in Table 6.7:

TABLE 6.7
Example PK/PD modulators for use with DUX4 RNAi agents
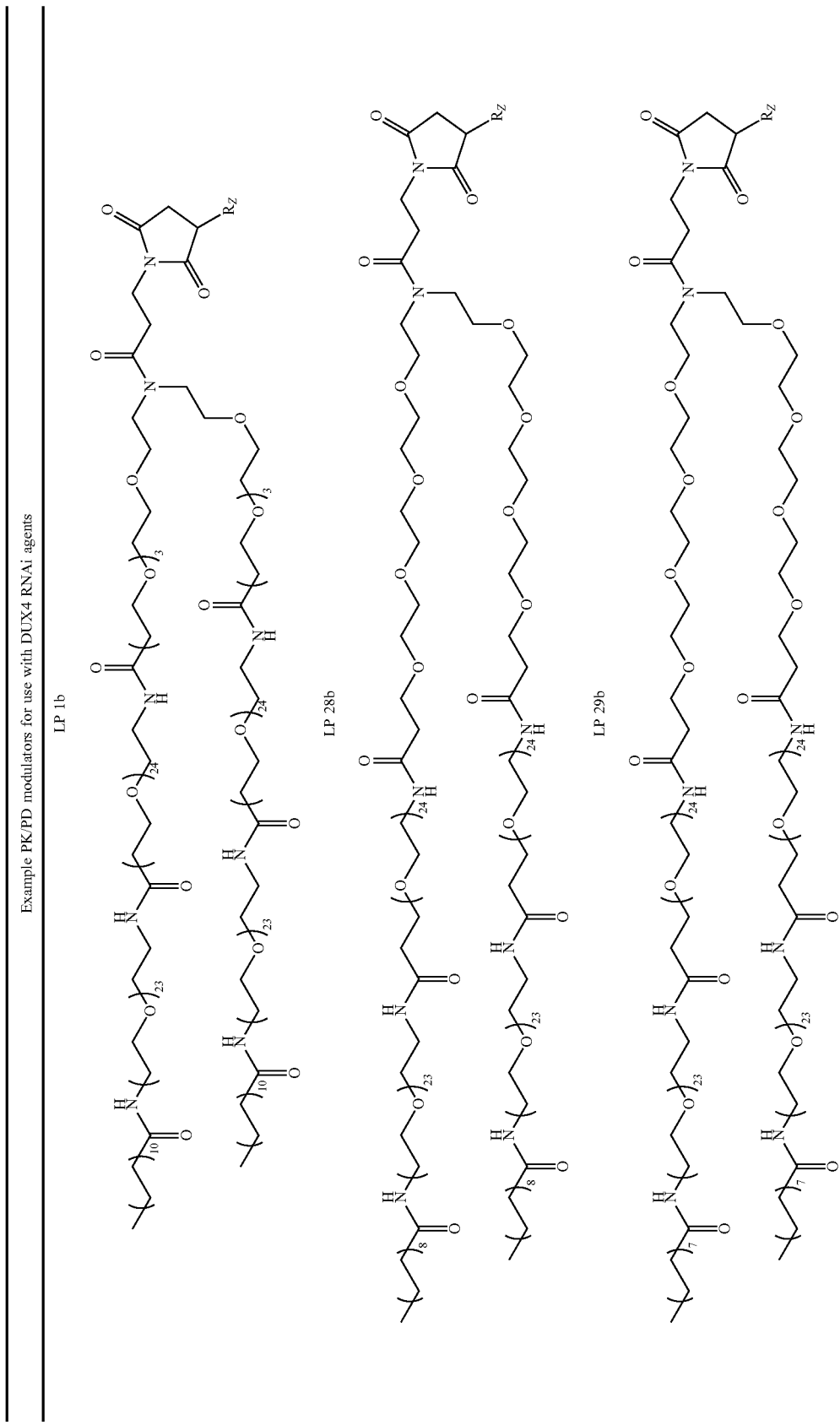

TABLE 6.7-continued
Example PK/PD modulators for use with DUX4 RNAi agents
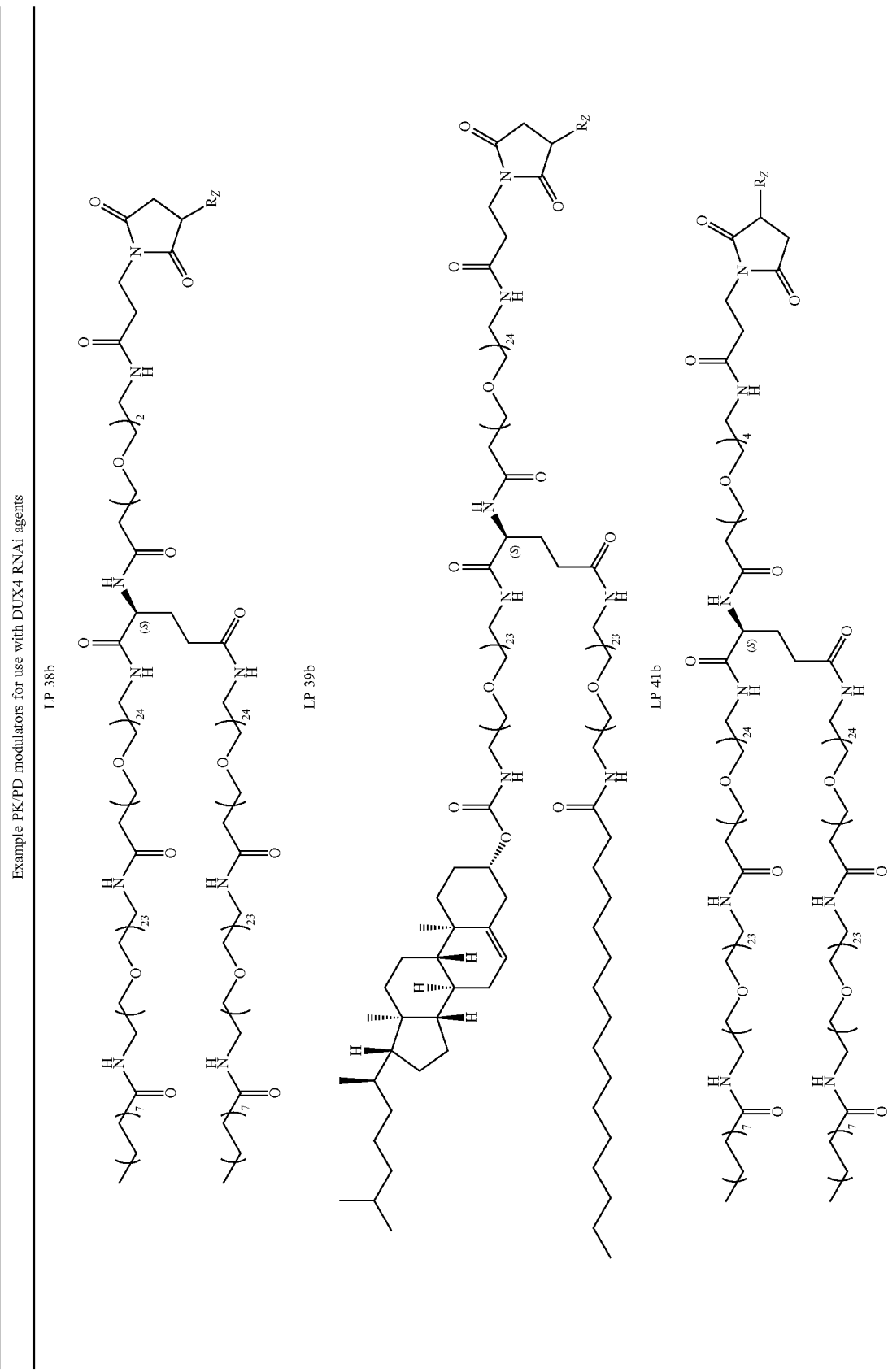

TABLE 6.7-continued
Example PK/PD modulators for use with DUX4 RNAi agents
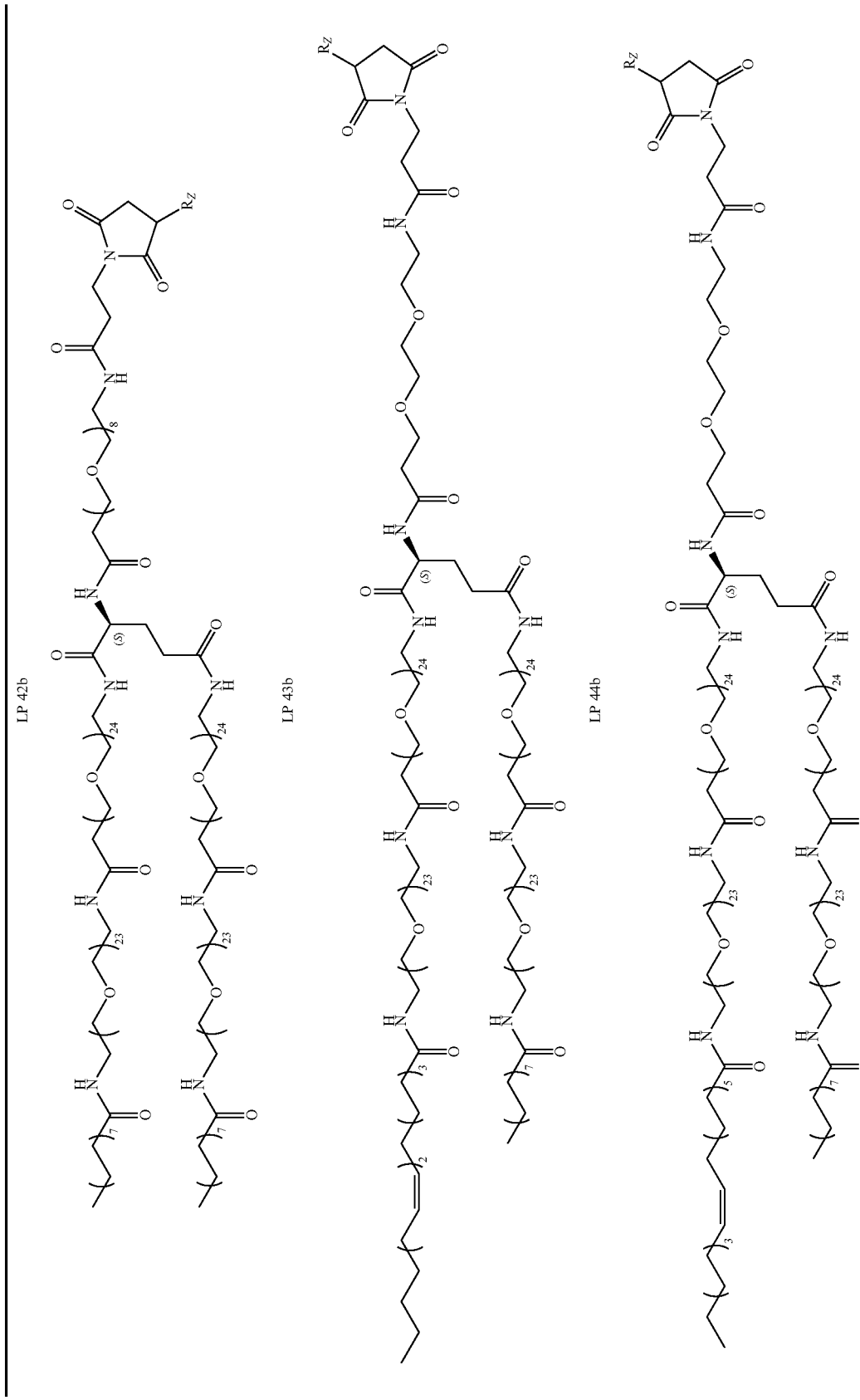
LP 42b
LP 43b
LP 44b TABLE 6.7-continued
Example PK/PD modulators for use with DUX4 RNAi agents
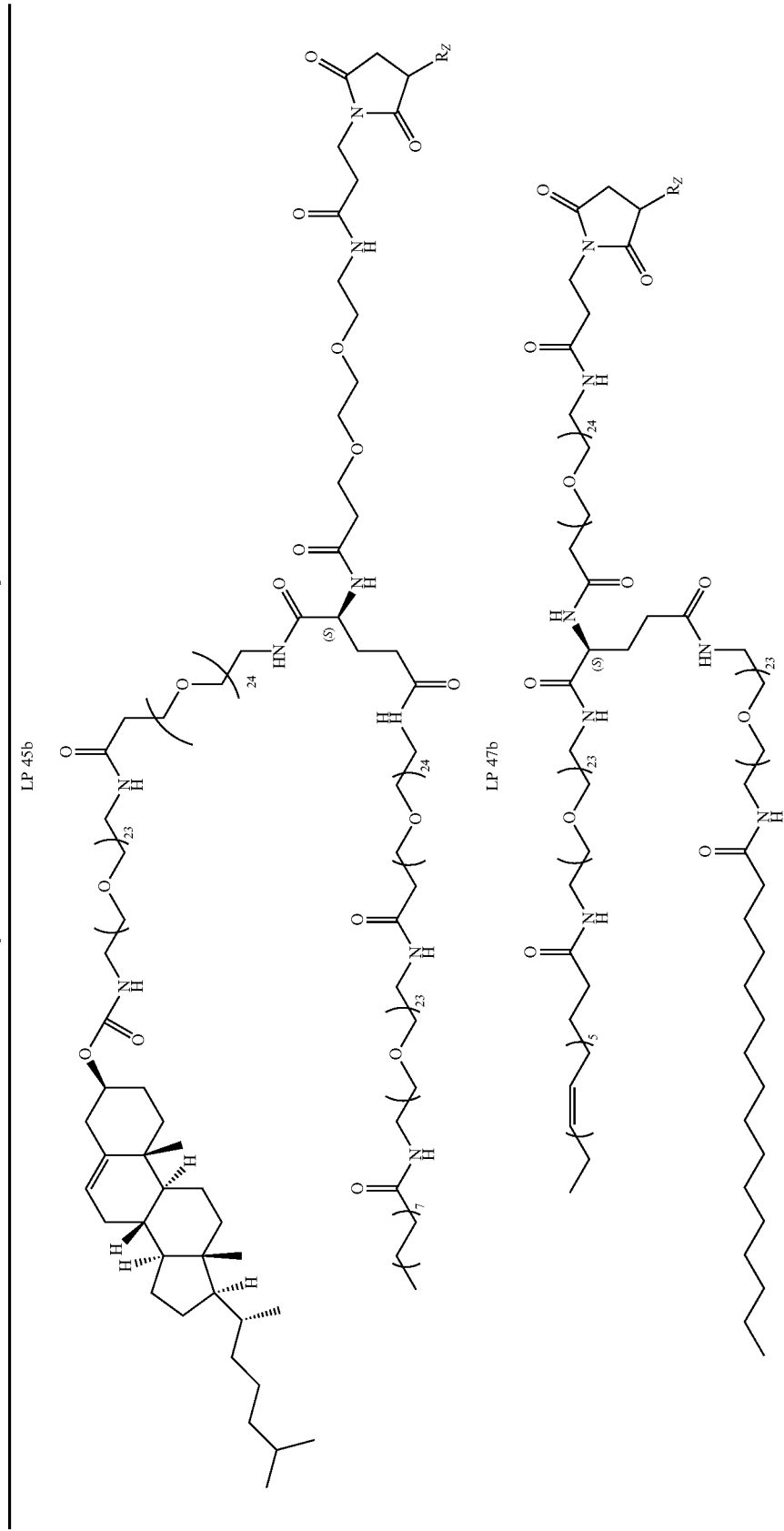
LP 45b
LP 47b TABLE 6.7-continued
Example PK/PD modulators for use with DUX4 RNAi agents
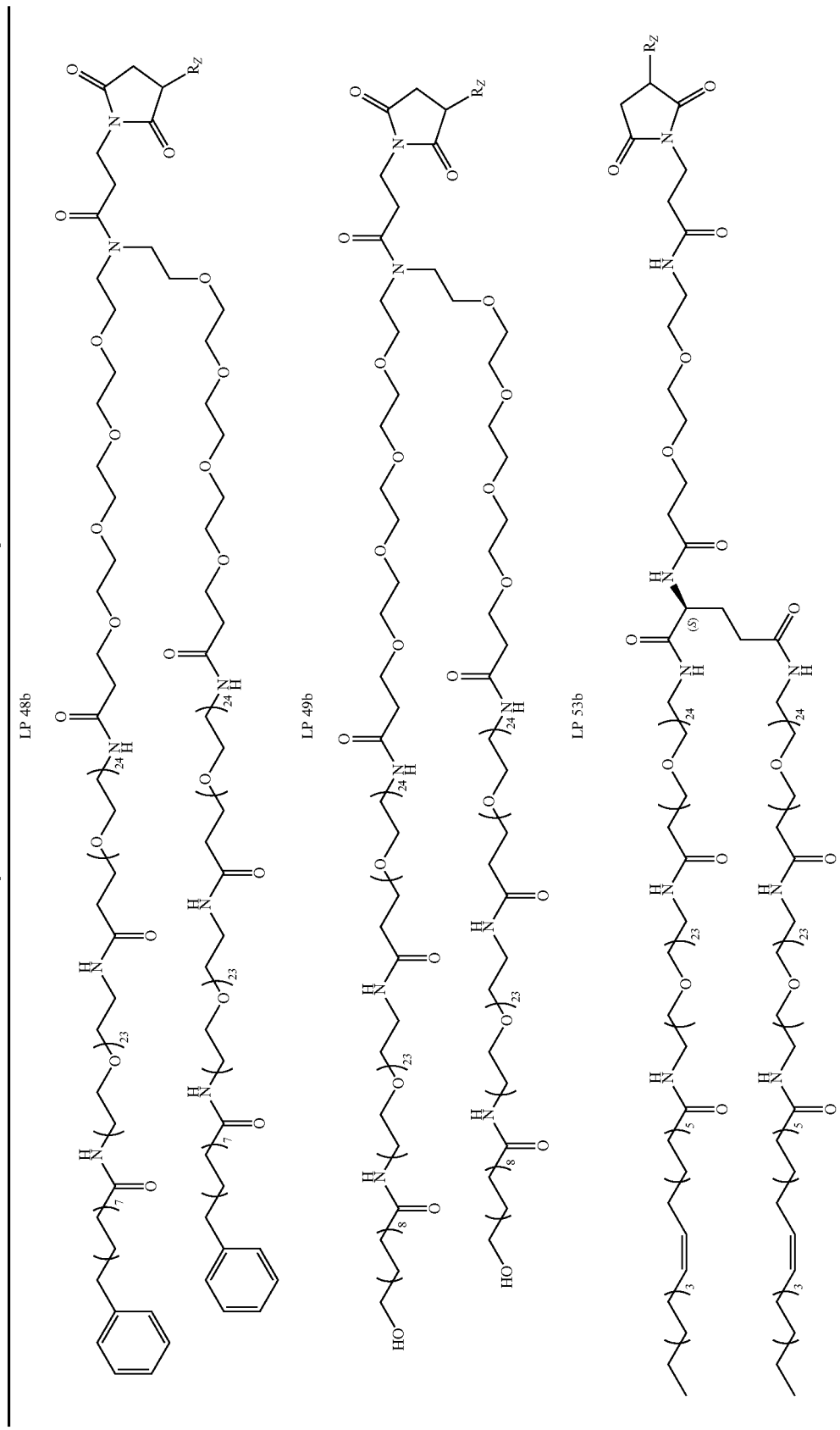
LP 48b
LP 49b
LP 53b TABLE 6.7-continued
Example PK/PD modulators for use with DUX4 RNAi agents
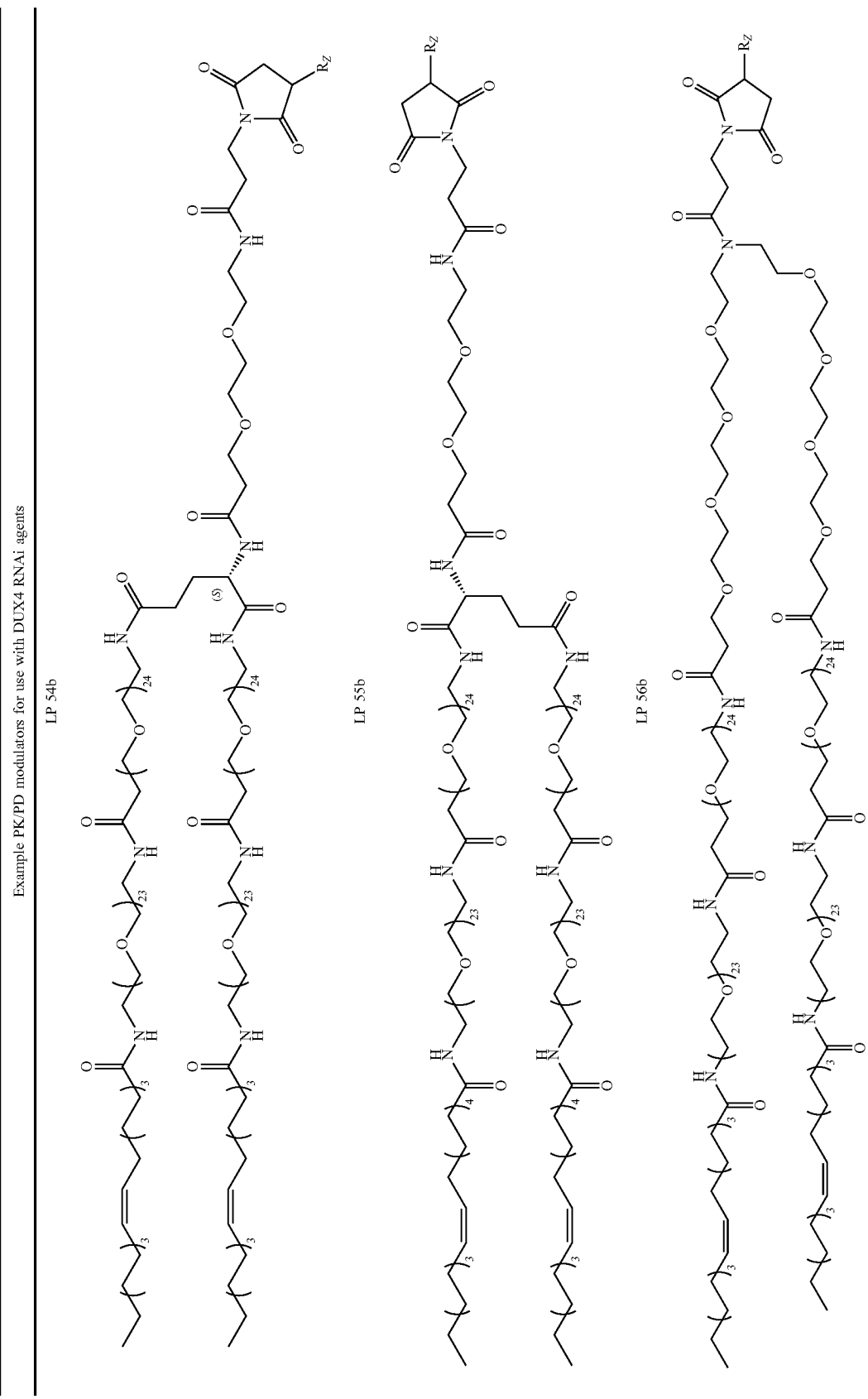
LP 54b
LP 55b
LP 56b TABLE 6.7-continued
Example PK/PD modulators for use with DUX4 RNAi agents
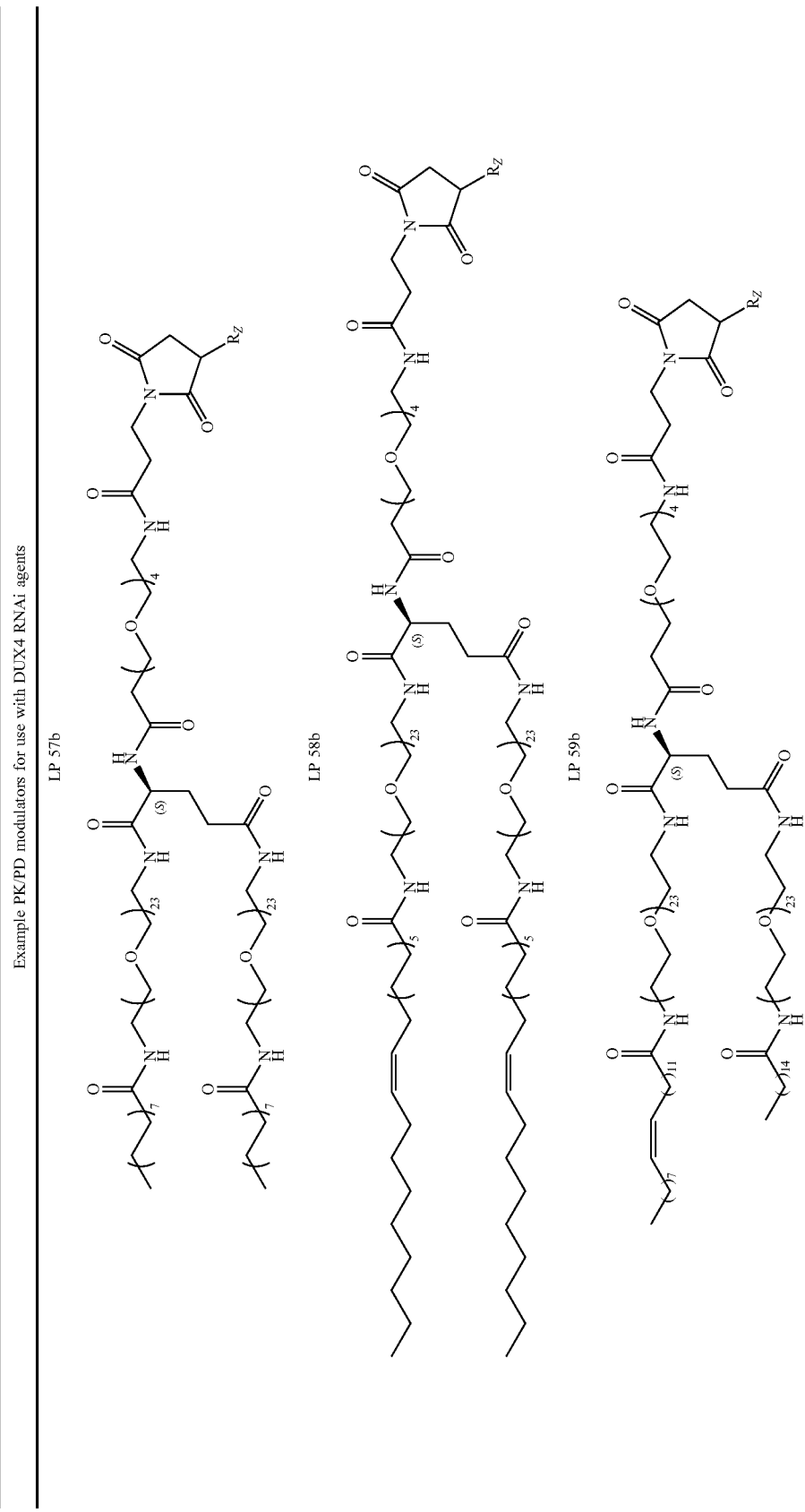
LP 57b
LP 58b
LP 59b TABLE 6.7-continued
Example PK/PD modulators for use with DUX4 RNAi agents
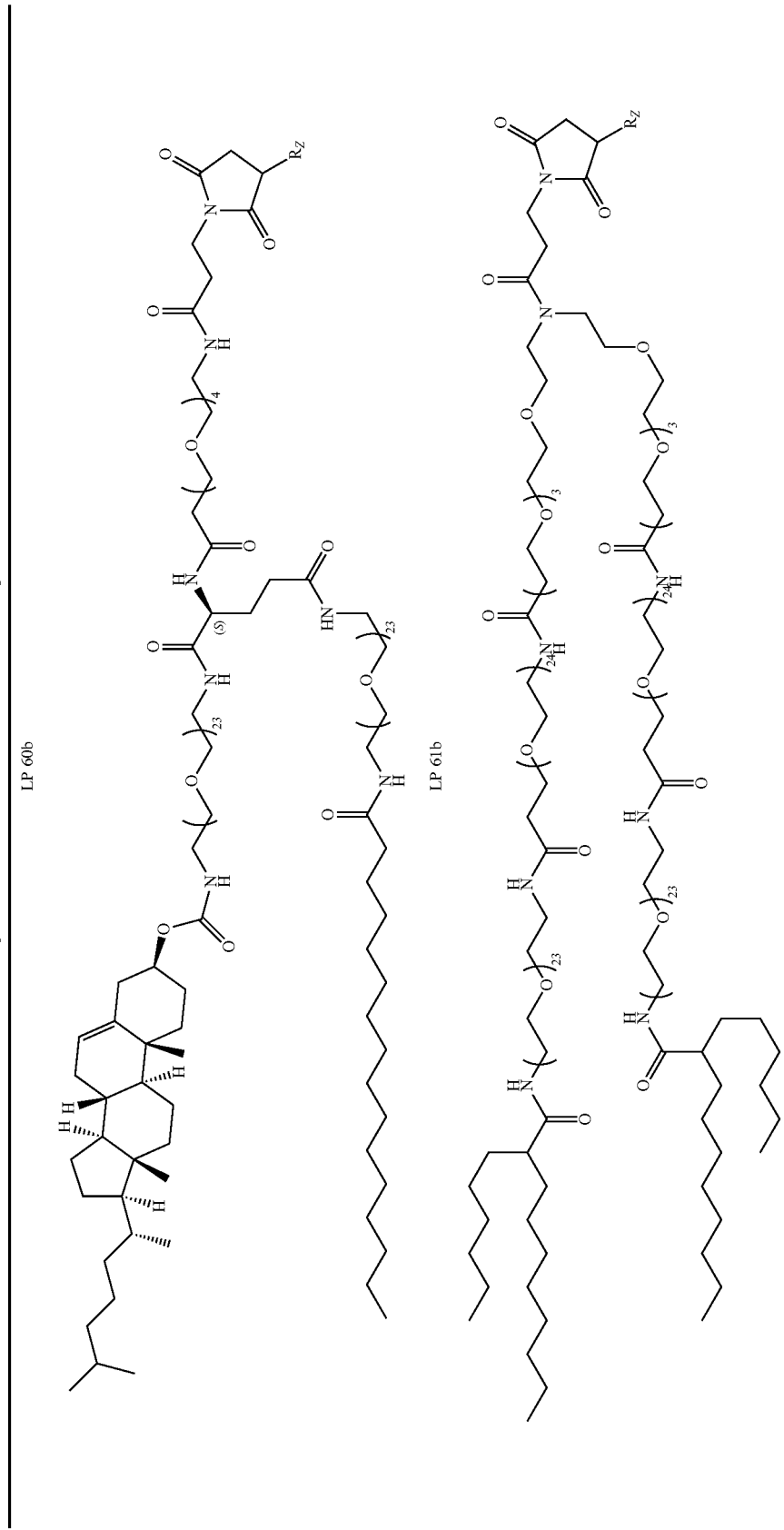
LP 60b
LP 61b TABLE 6.7-continued
Example PK/PD modulators for use with DUX4 RNAi agents
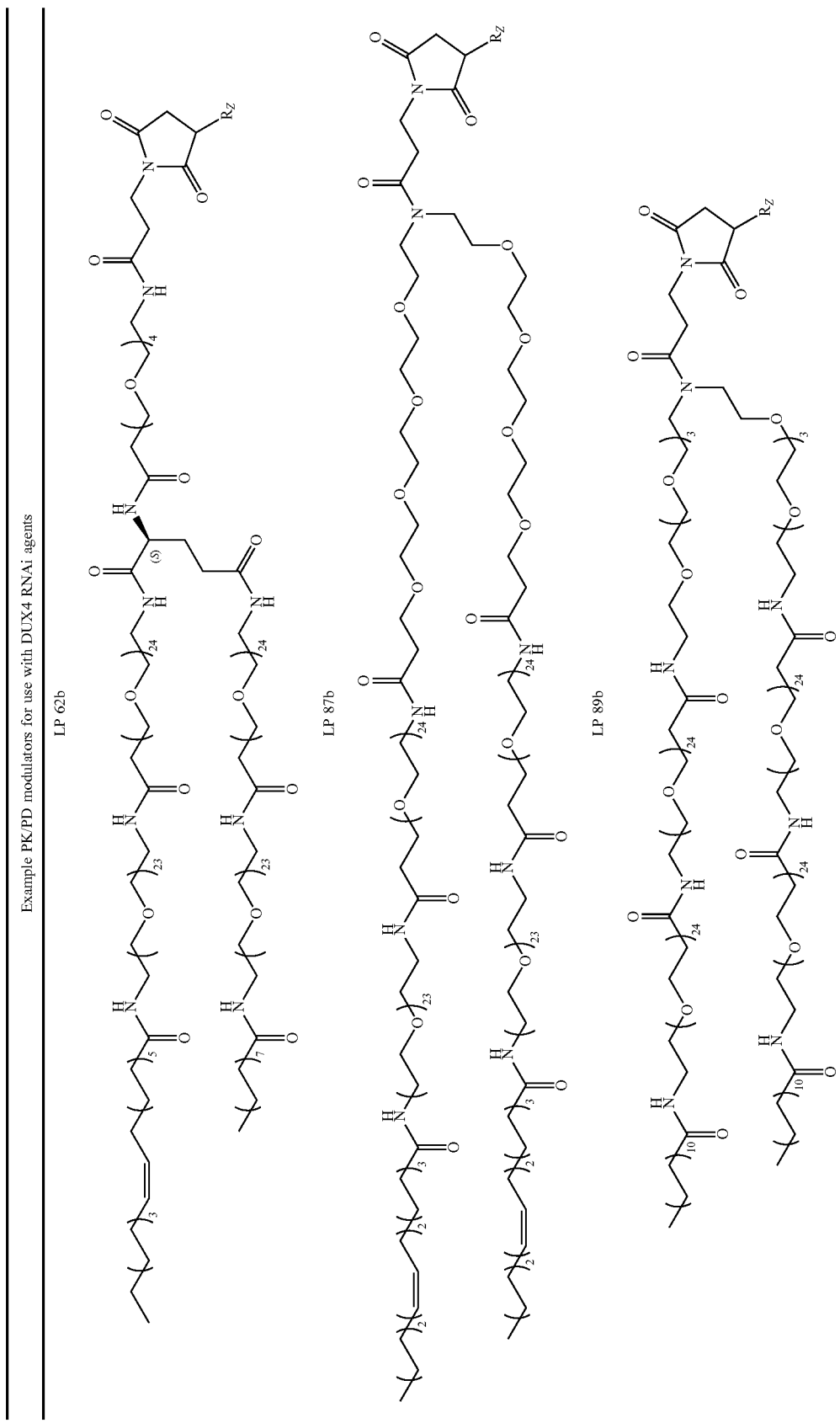
LP 62b
LP 87b
LP 89b TABLE 6.7-continued
Example PK/PD modulators for use with DUX4 RNAi agents
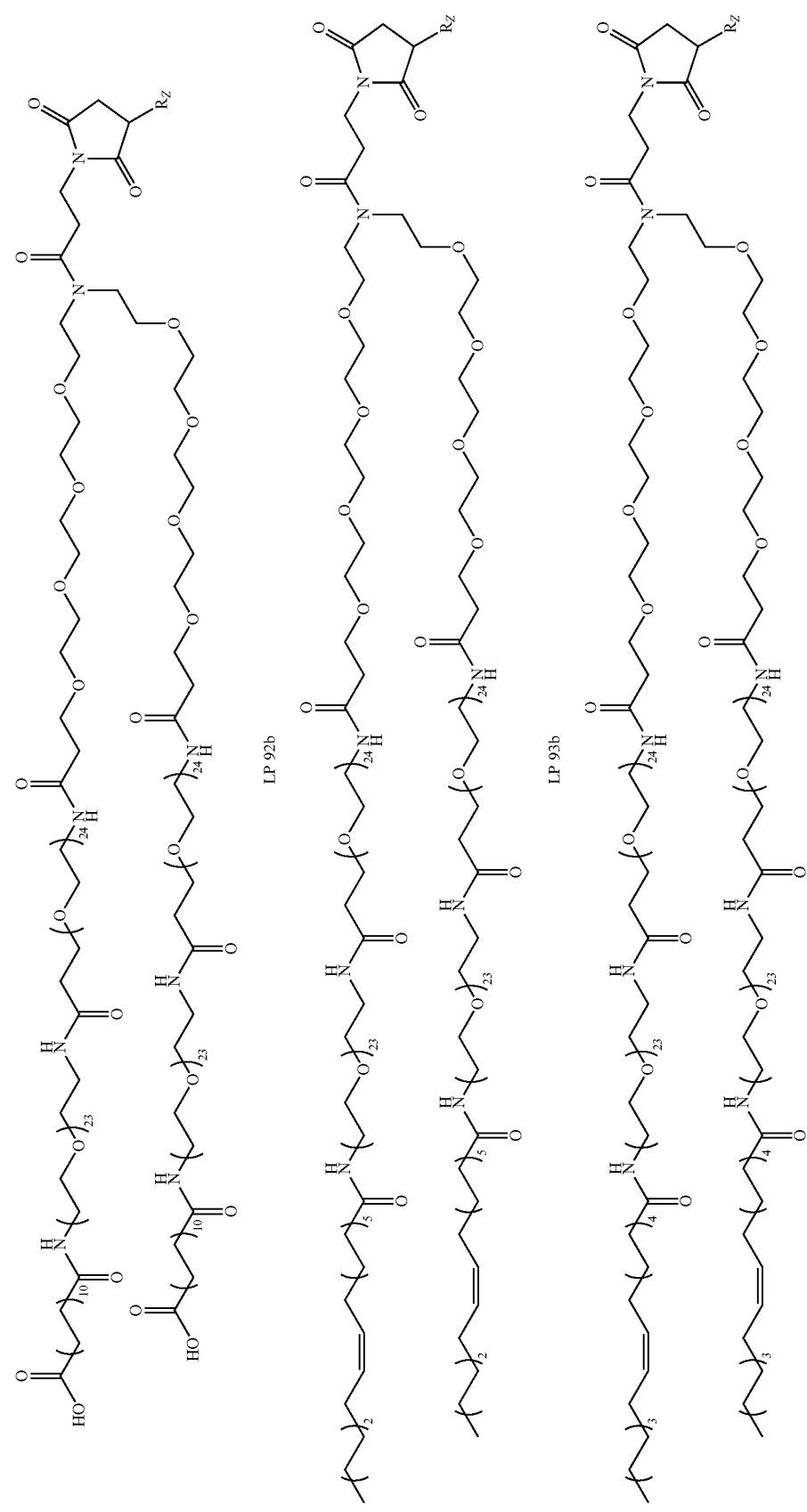
LP 90b
LP 92b
LP 93b TABLE 6.7-continued
Example PK/PD modulators for use with DUX4 RNAi agents
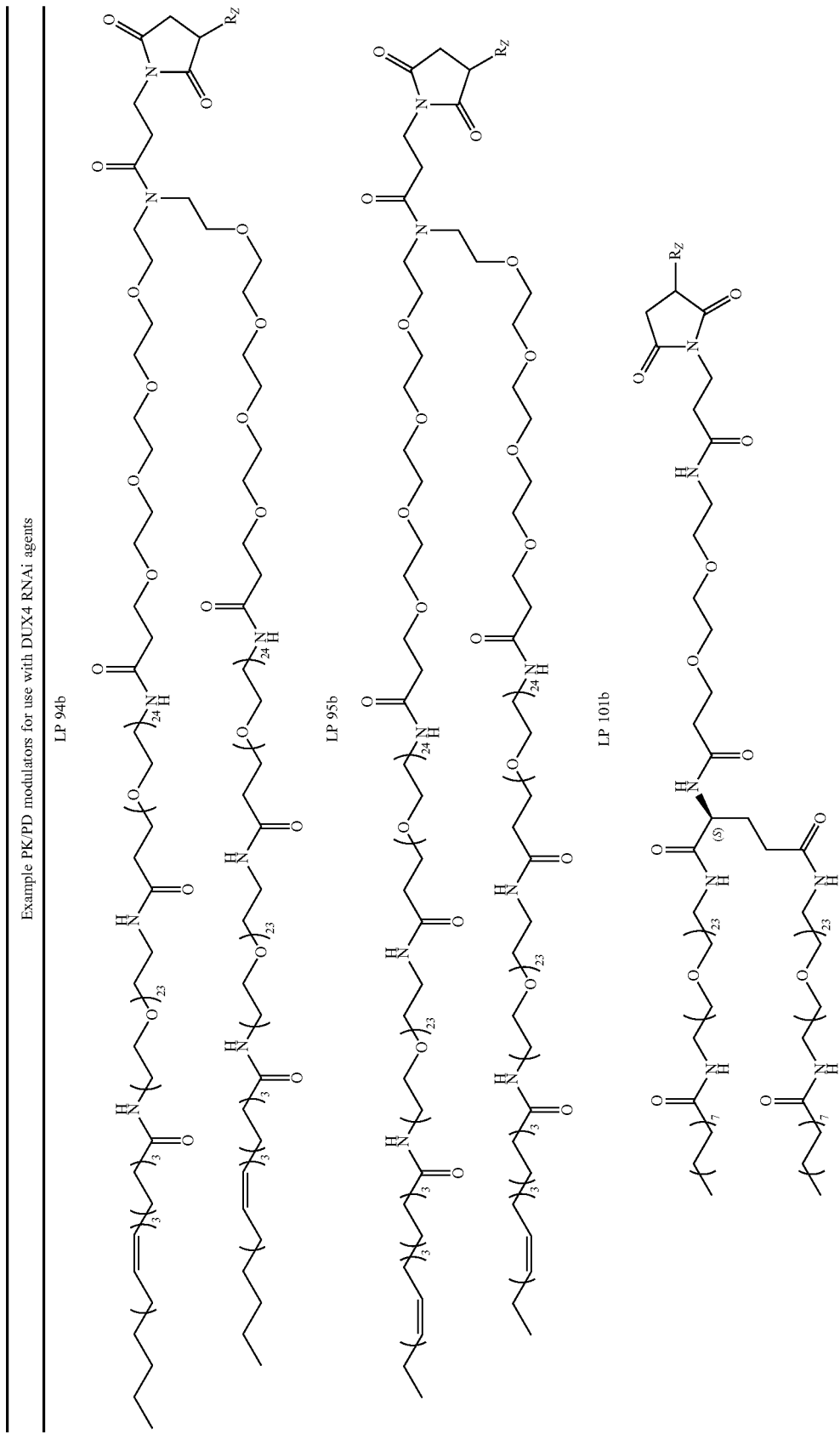
LP 94b
LP 95b
LP 101b TABLE 6.7-continued
Example PK/PD modulators for use with DUX4 RNAi agents
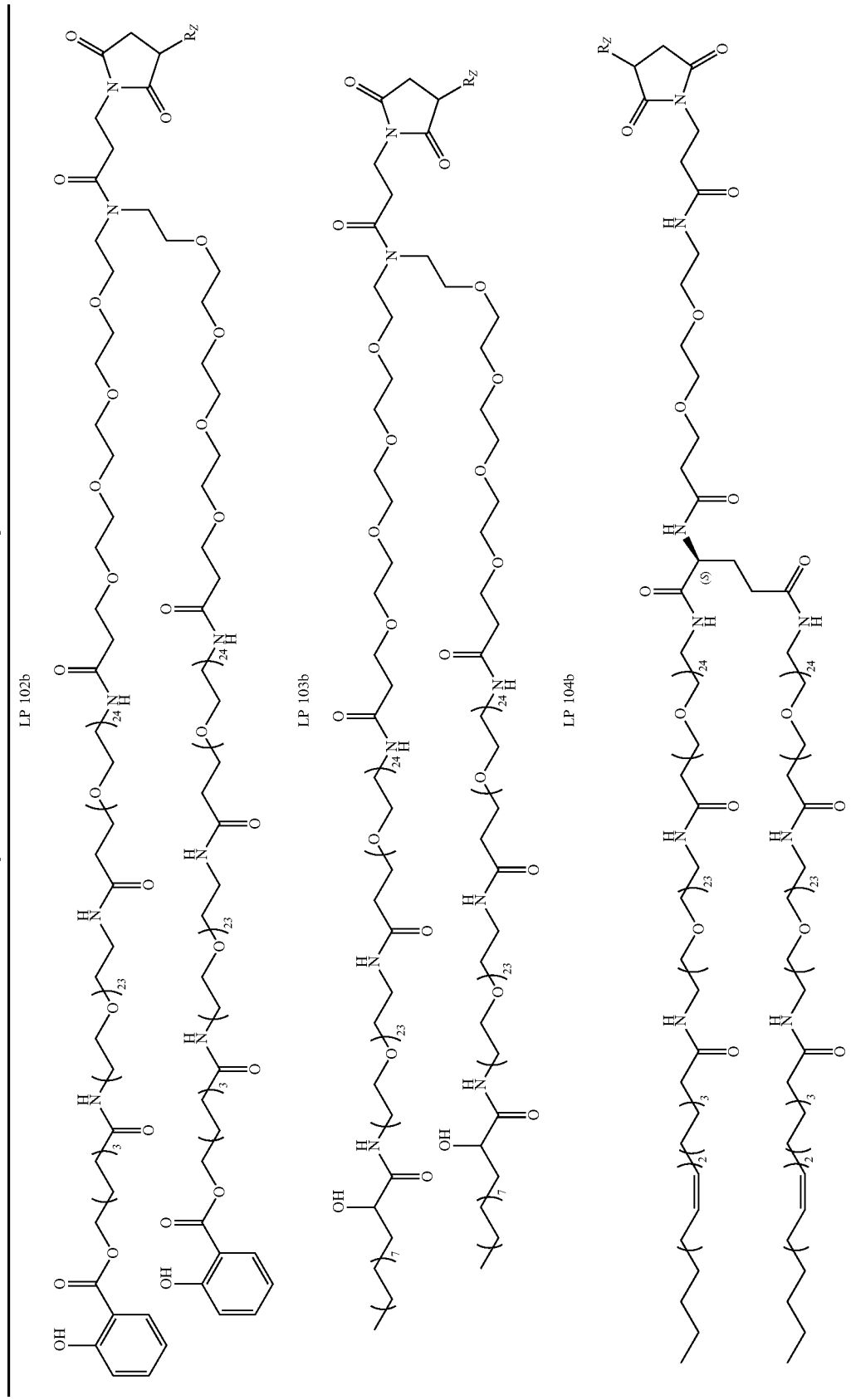
LP 102b
LP 103b
LP 104b TABLE 6.7-continued
Example PK/PD modulators for use with DUX4 RNAi agents
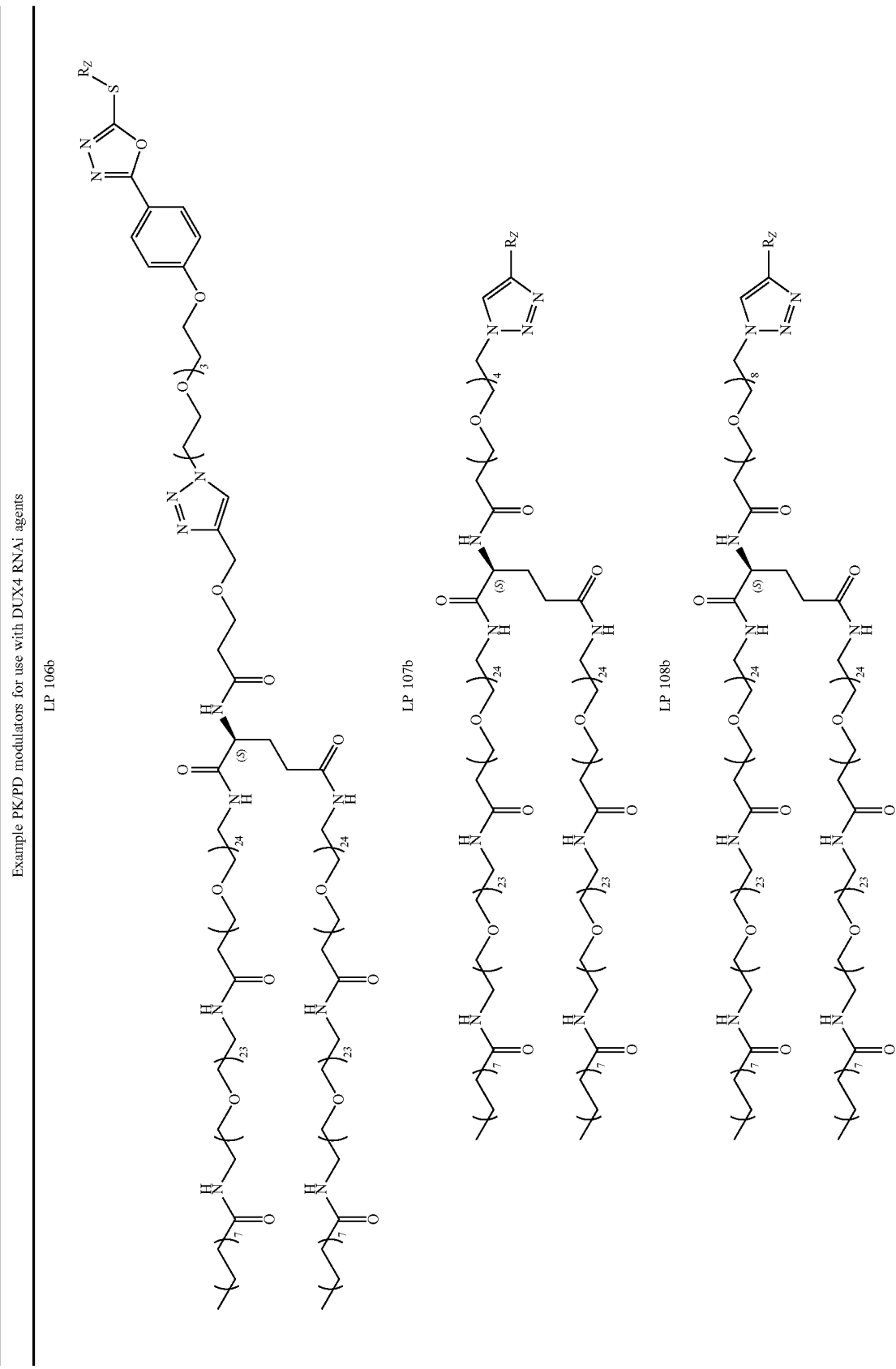
LP 106b
LP 107b
LP 108b TABLE 6.7-continued
Example PK/PD modulators for use with DUX4 RNAi agents
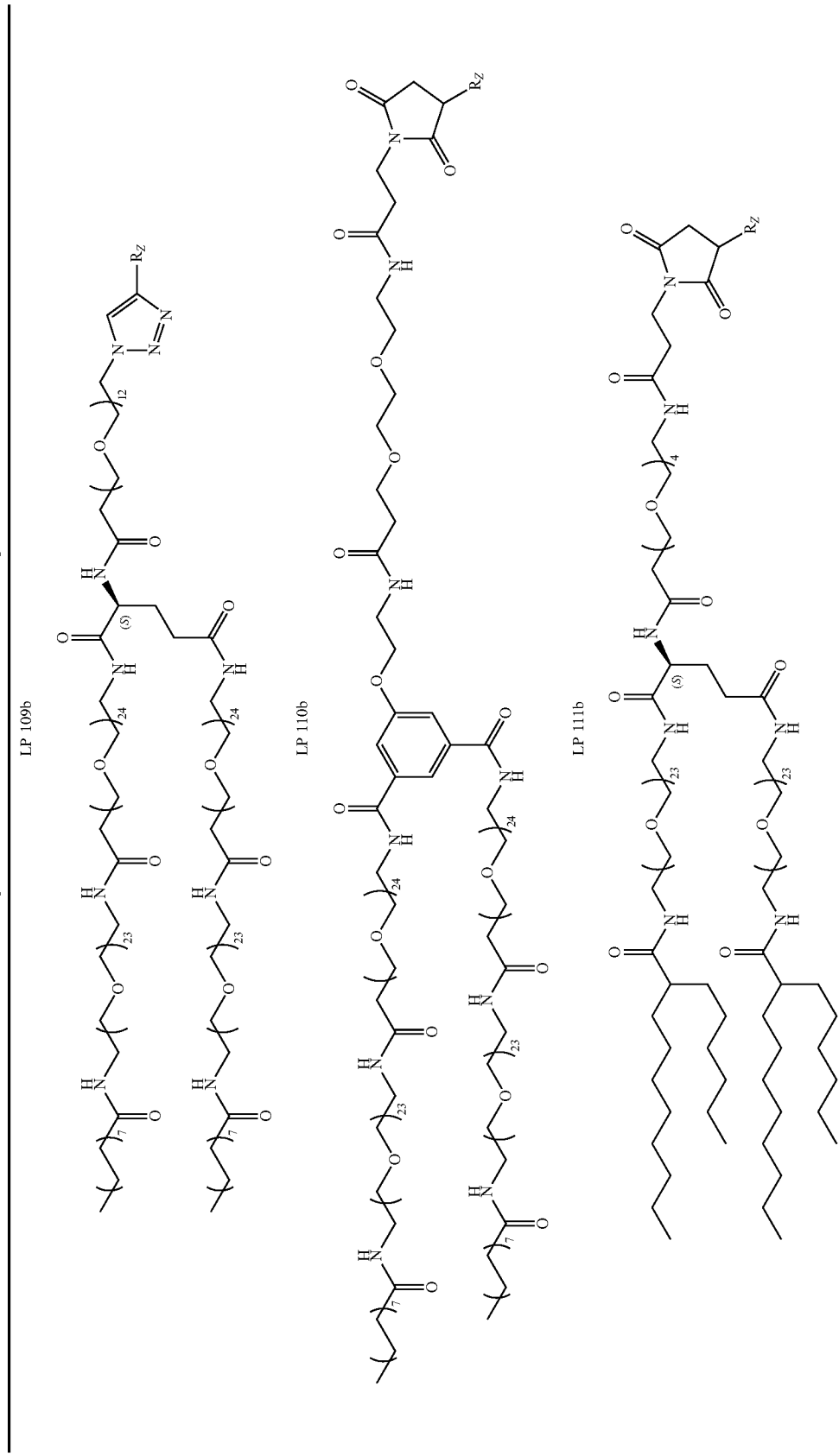

TABLE 6.7-continued
Example PK/PD modulators for use with DUX4 RNAi agents
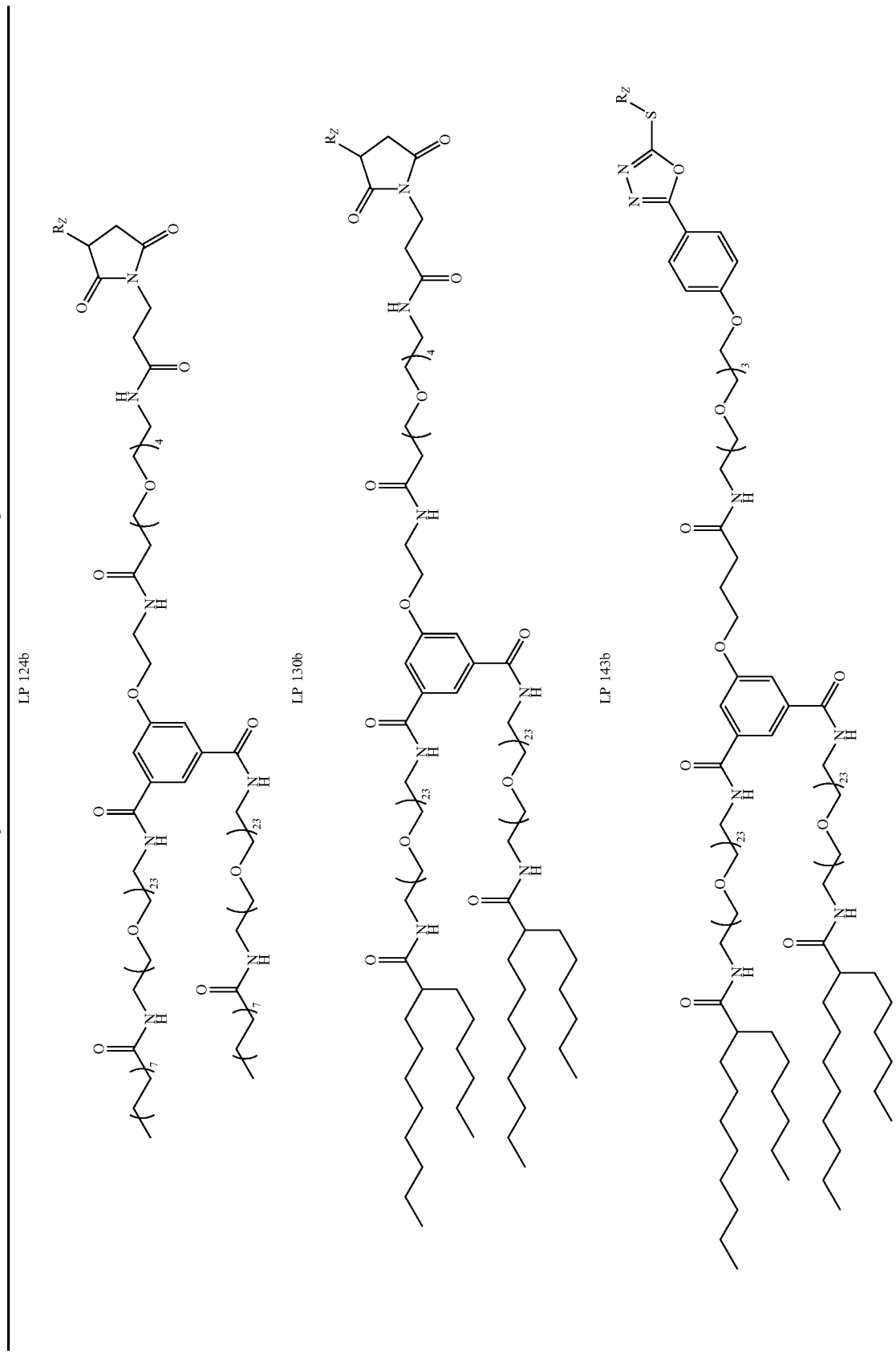
LP 124b
LP 130b
LP 143b TABLE 6.7-continued
Example PK/PD modulators for use with DUX4 RNAi agents
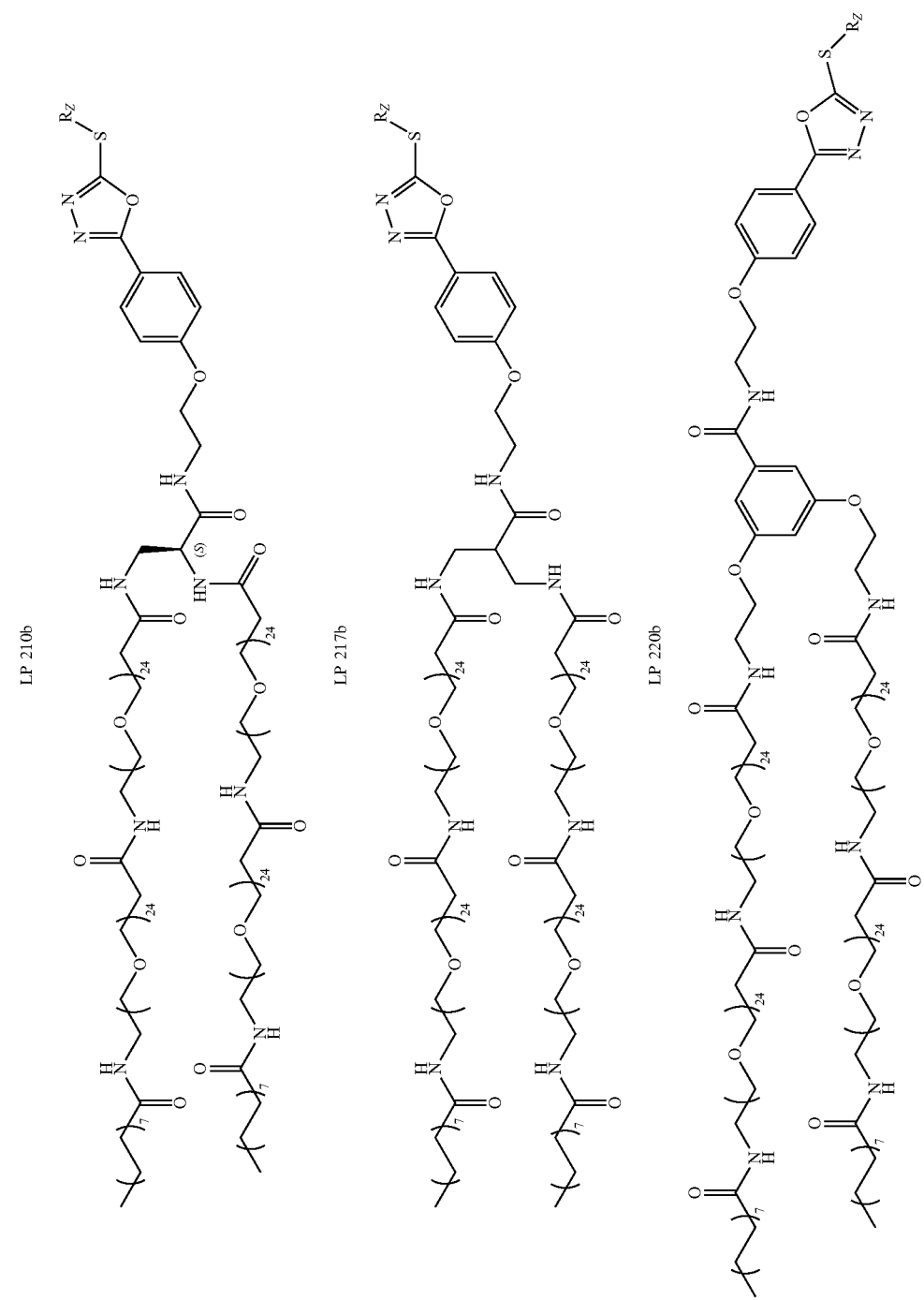
LP 210b
LP 217b
LP 220b TABLE 6.7-continued
Example PK/PD modulators for use with DUX4 RNAi agents
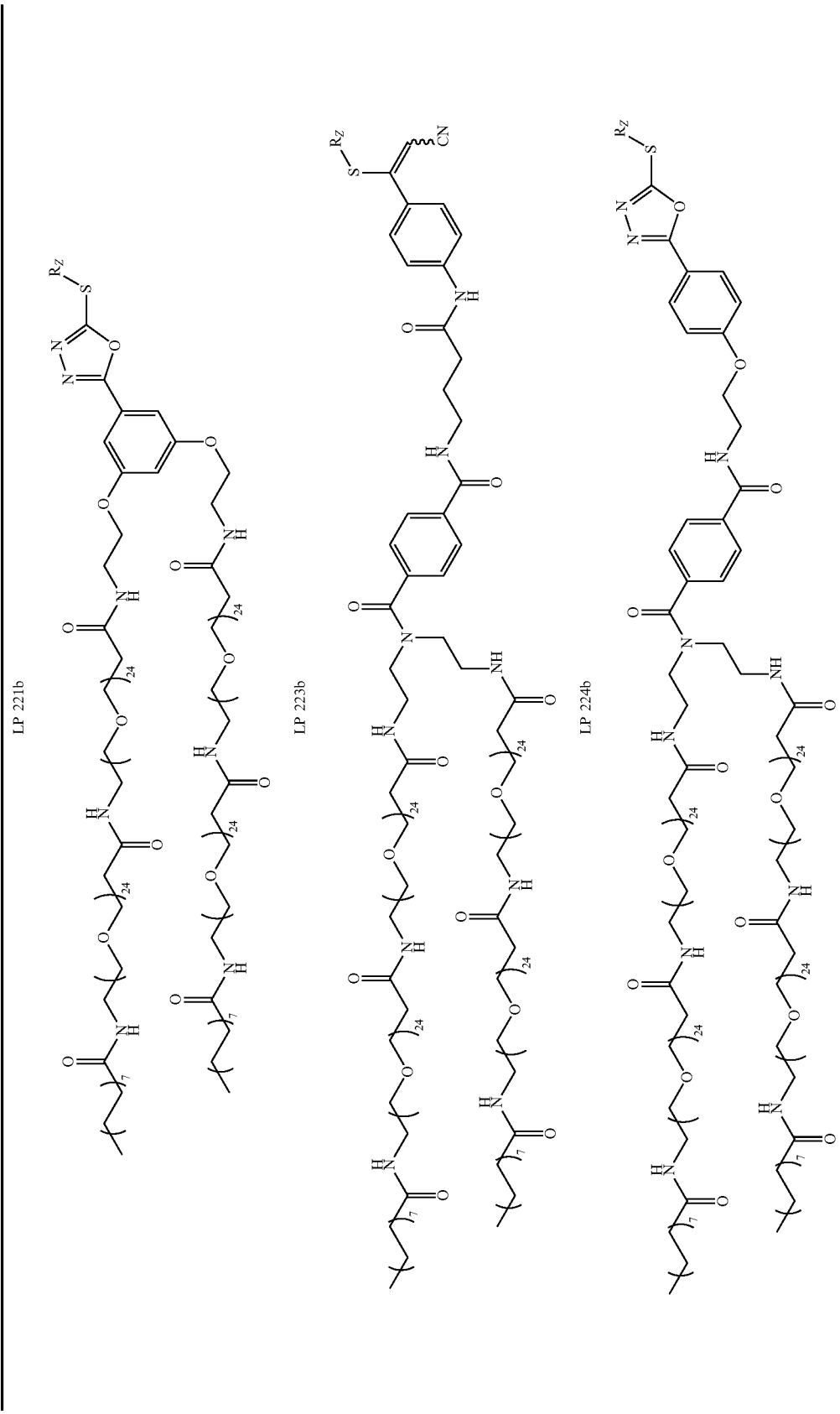
LP 221b
LP 223b
LP 224b TABLE 6.7-continued
Example PK/PD modulators for use with DUX4 RNAi agents
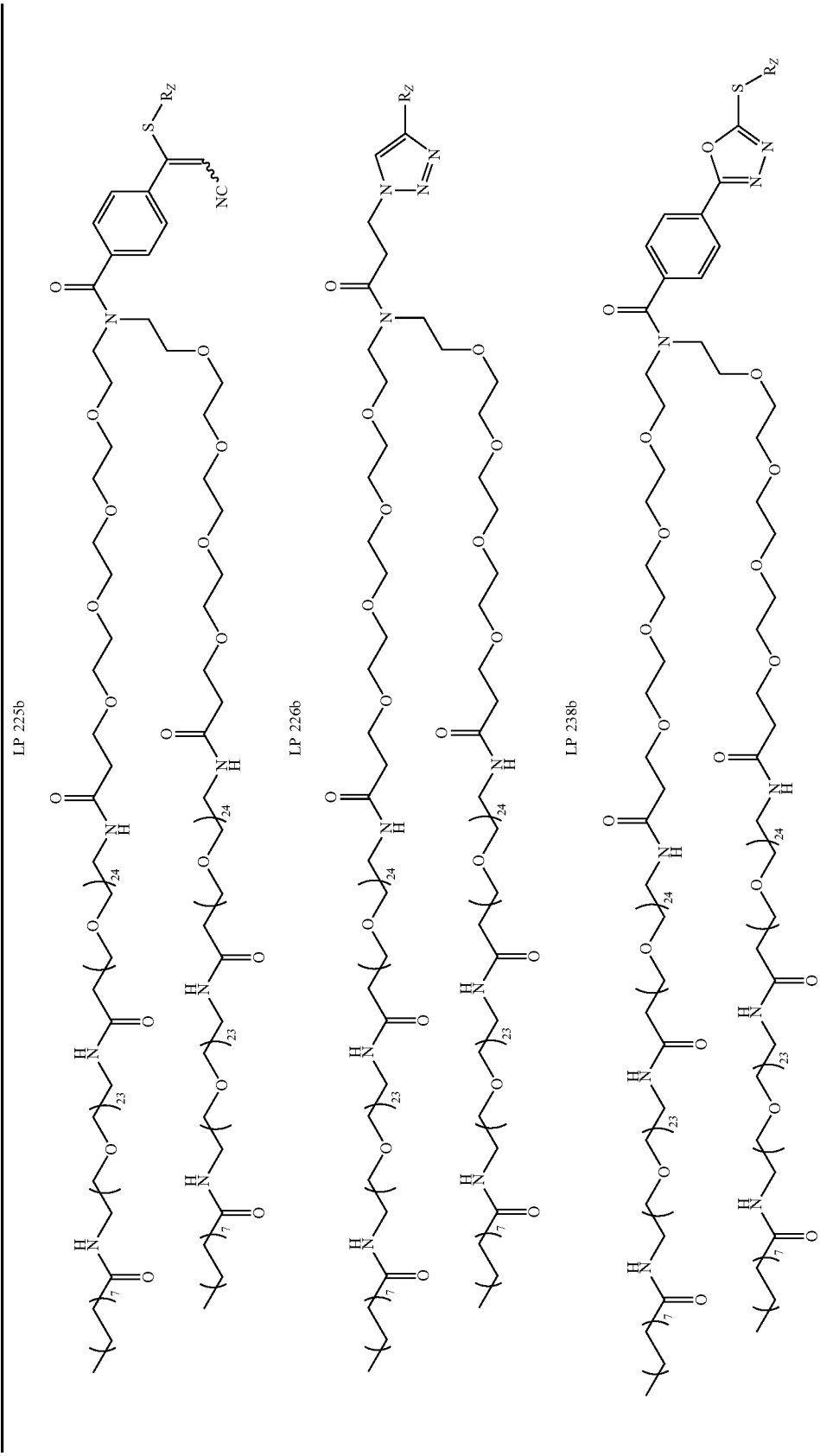
LP 225b
LP 226b
LP 238b

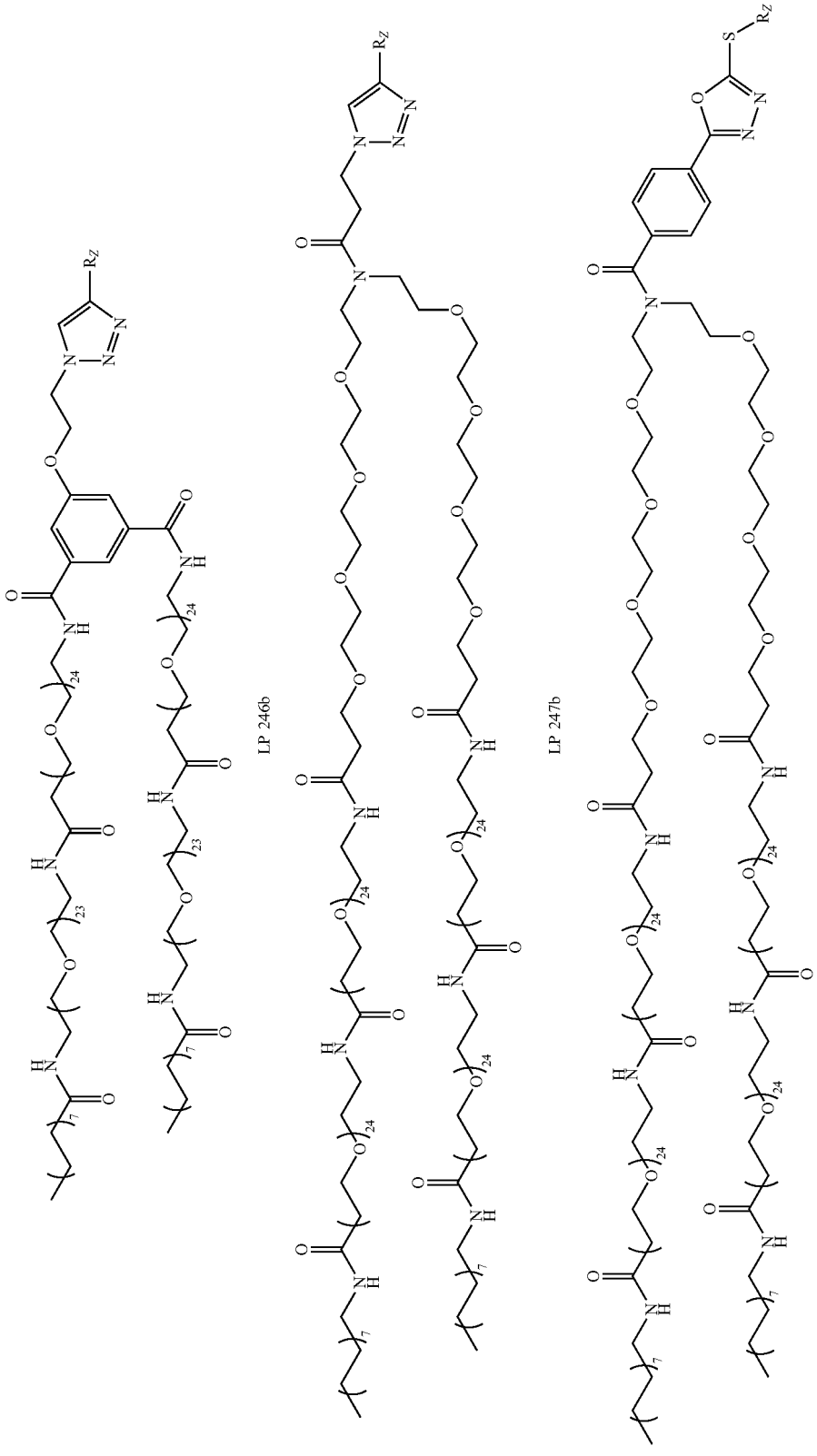
TABLE 6.7-continued
Example PK/PD modulators for use with DUX4 RNAi agents TABLE 6.7-continued
Example PK/PD modulators for use with DUX4 RNAi agents
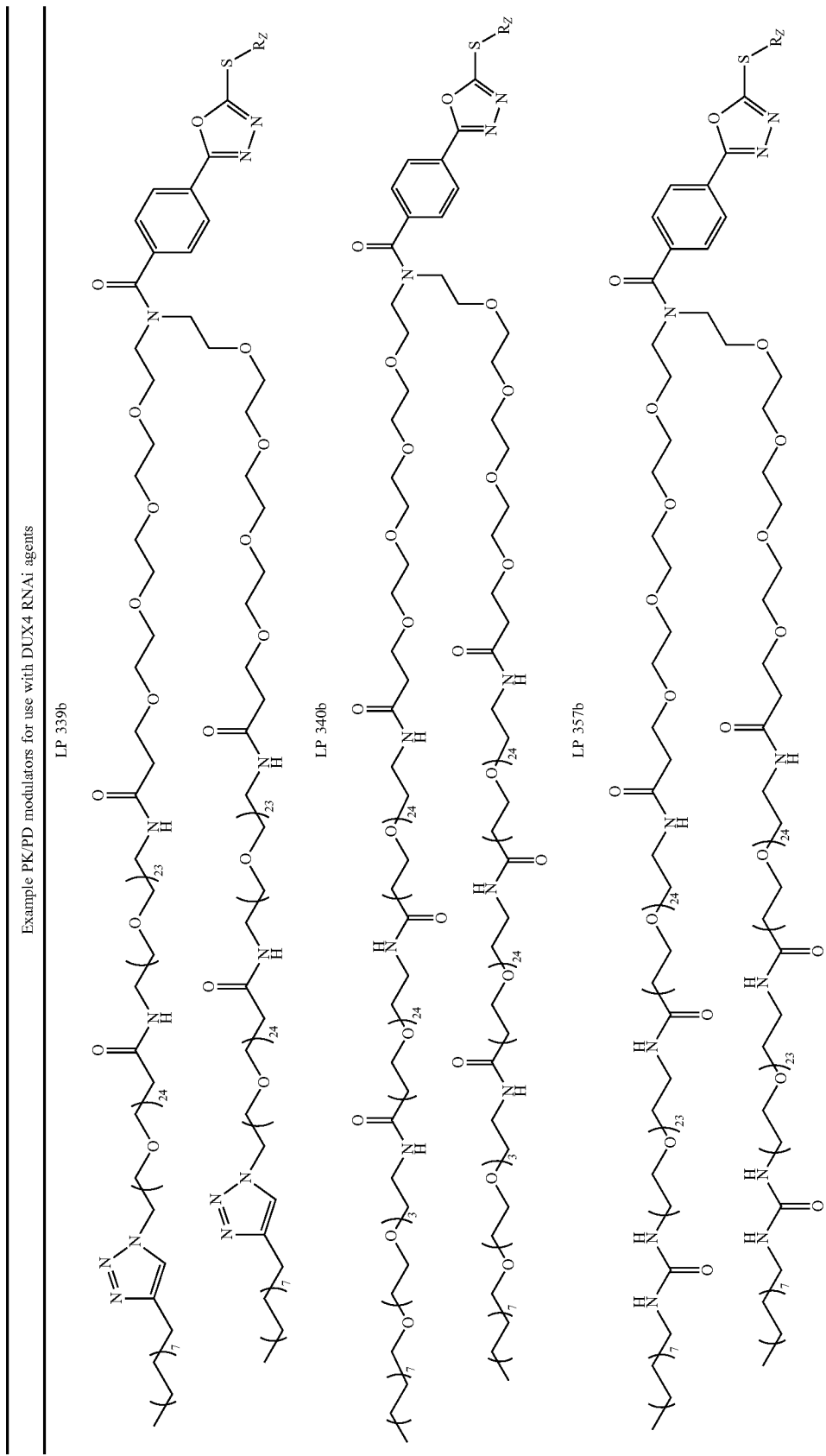
LP 339b
LP 340b
LP 357b TABLE 6.7-continued
Example PK/PD modulators for use with DUX4 RNAi agents
LP 358b
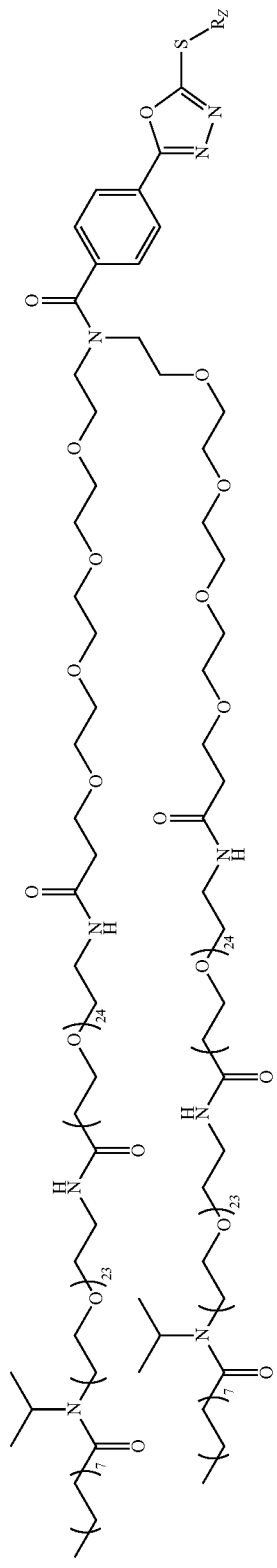

wherein $R_z$ comprises the DUX4 RNAi agent.

In some embodiments, DUX4 RNAi agents may comprise one or more PK/PD modulators. In some embodiments, the DUX4 RNAi agents disclosed herein comprise one, two, three, four, five, six, seven or more PK/PD modulators.

PK/PD modulators may be conjugated to a DUX4 RNAi agent using any known method in the art. Many PK/PD modulators, including several of those above, are commercially available. In some embodiments, such as several of the compounds shown in Table 6.4, PK/PD modulators can include a maleimide moiety and be reacted with an RNAi agent comprising a disulfide linkage to form an RNAi agent comprising a PK/PD modulator. The disulfide may be reduced, and added to a maleimide by way of a Michael-Addition reaction. An example reaction scheme is shown below:

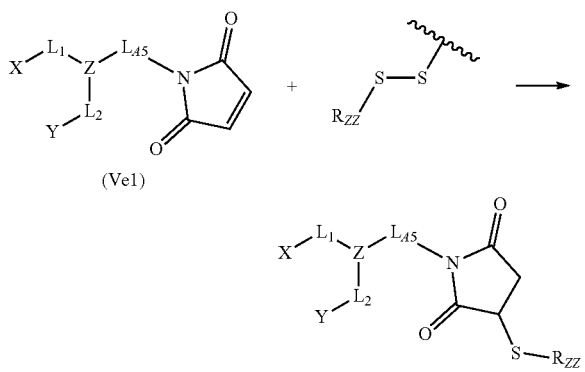

(Ve1)

wherein $R_{ZZ}$ comprises an RNAi agent, and § indicates a point of connection to any suitable group known in the art. In some instances of the reaction scheme above,

is attached to an alkyl group such as hexyl ($C_6H_{13}$).

In some embodiments, PK/PD modulator precursors may comprise a sulfone moiety and may react with a disulfide. An example reaction scheme is shown below:

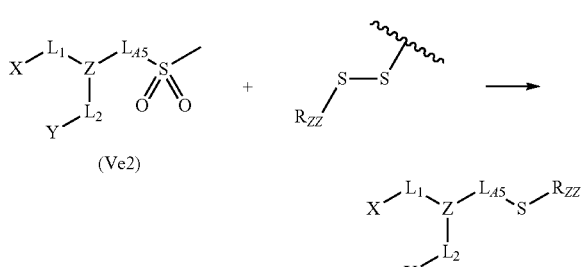

(Ve2)

wherein $R_{zz}$ comprises an RNAi agent, and § indicates a point of connection to any suitable group known in the art. In some instances of the reaction scheme above,

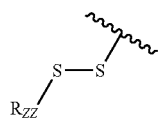

is attached to an alkyl group such as hexyl ($C_6H_{13}$).

In some embodiments, PK/PD modulator precursors may comprise an azide moiety and be reacted with an RNAi agent comprising an alkyne to form a compound comprising a PK/PD modulator conjugated to an RNAi agent according to the general reaction scheme below:

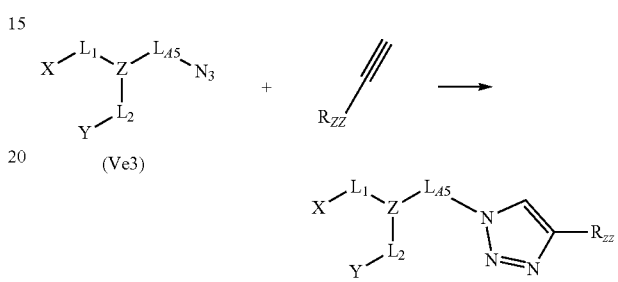

(Ve3)

wherein $R_{zz}$ comprises an RNAi agent.

In some embodiments, PK/PD modulator precursors may comprise an alkyne moiety and be reacted with an RNAi agent comprising a disulfide to form a compound comprising a PK/PD modulator conjugated to an RNAi agent according to the general reaction scheme below:

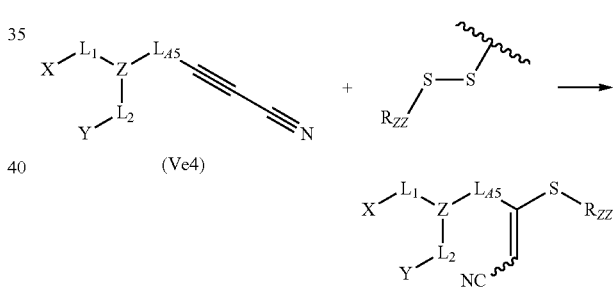

(Ve4)

wherein $R_{zz}$ comprises an RNAi agent, and § indicates a point of connection to any suitable group known in the art. In some instances of the reaction scheme above,

is attached to an alkyl group such as hexyl ($C_6H_{13}$).

In some embodiments, PK/PD modulators may be conjugated to the 5' end of the sense or antisense strand, the 3' end of the sense or antisense strand, or to an internal nucleotide of a DUX4 RNAi agent. In some embodiments, a DUX4 RNAi agent is synthesized with a disulfide-containing moiety at the 3' end of the sense strand, and a PK/PD modulator may be conjugated to the 3' end of the sense strand using the general synthetic scheme shown above.

Pharmaceutical Compositions and Formulations

The DUX4 RNAi agents disclosed herein can be prepared as pharmaceutical compositions or formulations (also referred to herein as "medicaments"). In some embodiments, pharmaceutical compositions include at least one DUX4 RNAi agent. These pharmaceutical compositions are particularly useful in the inhibition of the expression of DUX4 mRNA in a target cell, a group of cells, a tissue, or an organism. The pharmaceutical compositions can be used to treat a subject having a disease, disorder, or condition that would benefit from reduction in the level of the target mRNA, or inhibition in expression of the target gene. In some embodiments, the diseases to be treated is FSHD, including FSHD1 and FSHD2. The pharmaceutical compositions can be used to treat a subject at risk of developing a disease or disorder that would benefit from reduction of the level of the target mRNA or an inhibition in expression the target gene. In one embodiment, the method includes administering a DUX4 RNAi agent linked to a targeting ligand as described herein, to a subject to be treated. In some embodiments, one or more pharmaceutically acceptable excipients (including vehicles, carriers, diluents, and/or delivery polymers) are added to the pharmaceutical compositions that include a DUX4 RNAi agent, thereby forming a pharmaceutical formulation or medicament suitable for in vivo delivery to a subject, including a human.

In some embodiments, one or more of the described DUX4 RNAi agents are administered to a mammal in a pharmaceutically acceptable carrier or diluent. In some embodiments, the mammal is a human. The pharmaceutical compositions including one or more DUX4 RNAi agents can be administered in a number of ways depending upon whether local or systemic treatment is desired. Administration can be, but is not limited to, for example, intravenous, intraarterial, subcutaneous, intraperitoneal, subdermal (e.g., via an implanted device), and intraparenchymal administration.

The pharmaceutical compositions that include a DUX4 RNAi agent and methods disclosed herein decrease the level of the target mRNA in a cell, group of cells, group of cells, tissue, organ, or subject, including by administering to the subject a therapeutically effective amount of a herein described DUX4 RNAi agent, thereby inhibiting the expression of DUX4 mRNA in the subject. In some embodiments, the subject has been previously identified or diagnosed as having a disease or disorder that is mediated at least in part by DUX4 expression. In some embodiments, the subject has been previously identified or diagnosed as having a condition, disease, or disorder that would benefit from a reduction of DUX4 protein levels in one or more cells or tissues. In some embodiments, the subject has been previously diagnosed with having one or more skeletal muscular diseases such as FSHD, such as FSHD1 or FSHD2. In some embodiments, the subject has been suffering from symptoms associated with one or more skeletal muscle diseases.

In some embodiments, the described pharmaceutical compositions that include a DUX4 RNAi agent are used for treating or managing clinical presentations in a subject that would benefit from the inhibition of expression of DUX4. In some embodiments, a therapeutically or prophylactically effective amount of one or more of pharmaceutical compositions is administered to a subject in need of such treatment. In some embodiments, administration of any of the disclosed DUX4 RNAi agents can be used to decrease the number, severity, and/or frequency of symptoms of a disease in a subject.

The described pharmaceutical compositions that include a DUX4 RNAi agent can be used to treat at least one symptom in a subject having a disease or disorder that would benefit from reduction or inhibition in expression of DUX4 mRNA. In some embodiments, the subject is administered a therapeutically effective amount of one or more pharmaceutical compositions that include a DUX4 RNAi agent thereby treating the symptom.

The route of administration is the path by which a DUX4 RNAi agent is brought into contact with the body. In general, methods of administering drugs, oligonucleotides, and nucleic acids, for treatment of a mammal are well known in the art and can be applied to administration of the compositions described herein. The DUX4 RNAi agents disclosed herein can be administered via any suitable route in a preparation appropriately tailored to the particular route. In some embodiments, the pharmaceutical compositions can be administered by injection, for example, intravenously, intramuscularly, intracutaneously, subcutaneously, intraarticularly, or intraperitoneally, or topically.

The pharmaceutical compositions including a DUX4 RNAi agent described herein can be delivered to a cell, group of cells, tissue, or subject using oligonucleotide delivery technologies known in the art. In general, any suitable method recognized in the art for delivering a nucleic acid molecule (in vitro or in vivo) can be adapted for use with the compositions described herein. For example, delivery can be by local administration (e.g., direct injection, implantation, or topical administering), systemic administration, or subcutaneous, intravenous, intraperitoneal, or parenteral routes, including intracranial (e.g., intraventricular, intraparenchymal and intrathecal), intramuscular, transdermal, airway (aerosol), nasal, oral, rectal, or topical (including buccal and sublingual) administration. In some embodiments, the compositions are administered via subcutaneous injection, intramuscular injection, or intravenous administration.

In some embodiments, the pharmaceutical compositions described herein comprise one or more pharmaceutically acceptable excipients. The pharmaceutical compositions described herein are formulated for administration to a subject.

In some embodiments, pharmaceutical formulations that include the DUX4 RNAi agents disclosed herein suitable for SQ or IV administration can be prepared in an aqueous sodium phosphate buffer (e.g., the DUX4 RNAi agent formulated in 0.5 mM sodium phosphate monobasic, 0.5 mM sodium phosphate dibasic, in water)

As used herein, a pharmaceutical composition or medicament includes a pharmacologically effective amount of at least one of the described therapeutic compounds and one or more pharmaceutically acceptable excipients. Pharmaceutically acceptable excipients (excipients) are substances other than the Active Pharmaceutical Ingredient (API, therapeutic product, e.g., DUX4 RNAi agent) that are intentionally included in the drug delivery system. Excipients do not exert or are not intended to exert a therapeutic effect at the intended dosage. Excipients can act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, buffering agents, carriers, coating agents, colors, delivery enhancers, delivery polymers, detergents, dextran, dextrose, diluents, disintegrants, emulsifiers, extenders, fillers, flavors, glidants, humectants, lubricants, oils, polymers, preservatives, saline, salts, solvents, sugars, surfactants, suspending agents, sustained release matrices, sweeteners, thickening agents, tonicity agents, vehicles, water-repelling agents, and wetting agents.

Pharmaceutical compositions suitable for injectable use include sterile aqueous solutions (where water-soluble) or dispersions and sterile powders for the extemporaneous preparation of sterile injectable solutions or dispersion. For intravenous administration, suitable carriers include physiological saline, bacteriostatic water, Cremophor® EL™ (BASF, Parsippany, NJ) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration can be in the form of a sterile aqueous preparation of the drug that can be in microcrystalline form, for example, in the form of an aqueous microcrystalline suspension. Liposomal formulations or biodegradable polymer systems can also be used to present the drug for both intra-articular and ophthalmic administration.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

The DUX4 RNAi agents can be formulated in compositions in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the therapeutic effect to be achieved, and the limitations inherent in the art of compounding such an active compound for the treatment of individuals.

A pharmaceutical composition can contain other additional components commonly found in pharmaceutical compositions. Such additional components include, but are not limited to: anti-pruritics, astringents, local anesthetics, analgesics, antihistamines, or anti-inflammatory agents (e.g., acetaminophen, NSAIDs, diphenhydramine, etc.). It is also envisioned that cells, tissues, or isolated organs that express or comprise the herein defined RNAi agents may be used as "pharmaceutical compositions." As used herein, "pharmacologically effective amount," "therapeutically effective amount," or simply "effective amount" refers to that amount of an RNAi agent to produce a pharmacological, therapeutic, or preventive result.

In some embodiments, the methods disclosed herein further comprise the step of administering a second therapeutic or treatment in addition to administering an RNAi agent disclosed herein. In some embodiments, the second therapeutic is another DUX4 RNAi agent (e.g., a DUX4 RNAi agent that targets a different sequence within the DUX4 target). In other embodiments, the second therapeutic can be a small molecule drug, an antibody, an antibody fragment, and/or an aptamer.

Generally, an effective amount of a DUX4 RNAi agent disclosed herein will be in the range of from about 0.0001 to about 20 mg/kg of body weight/dose, e.g., from about 0.5 to about 10 mg/kg of body weight/dose. The amount administered and dosing frequency (e.g., daily, bi-weekly, weekly, monthly, quarterly, or semi-annually) will likely depend on such variables as the overall health status of the patient, the relative biological efficacy of the compound delivered, the formulation of the drug, the presence and types of excipients in the formulation, and the route of administration. Also, it is to be understood that the initial dosage administered can be increased beyond the above upper level to rapidly achieve the desired blood-level or tissue level, or the initial dosage can be smaller than the optimum.

For treatment of disease or for formation of a medicament or composition for treatment of a disease, the pharmaceutical compositions described herein including a DUX4 RNAi agent can be combined with an excipient or with a second therapeutic agent or treatment including, but not limited to: a second or other RNAi agent, a small molecule drug, an antibody, an antibody fragment, peptide, and/or an aptamer.

The described DUX4 RNAi agents, when added to pharmaceutically acceptable excipients or adjuvants, can be packaged into kits, containers, packs, or dispensers. The pharmaceutical compositions described herein can be packaged, for example, in pre-filled syringes or vials.

Methods of Treatment and Inhibition of Expression

The DUX4 RNAi agents disclosed herein can be used to treat a subject (e.g., a human or other mammal) having a disease or disorder that would benefit from administration of the RNAi agent. In some embodiments, the RNAi agents disclosed herein can be used to treat a subject (e.g., a human) that would benefit from a reduction and/or inhibition in expression of DUX4 mRNA.

In some embodiments, the RNAi agents disclosed herein can be used to treat a subject (e.g., a human) having a disease or disorder for which the subject would benefit from reduction in DUX4 protein levels, including but not limited to, for example, FSHD, including FSHD1 and FSHD2. Treatment of a subject can include therapeutic and/or prophylactic treatment. The subject is administered a therapeutically effective amount of any one or more DUX4 RNAi agents described herein. The subject can be a human, patient, or human patient. The subject may be an adult, adolescent, child, or infant. Administration of a pharmaceutical composition described herein can be to a human being or animal.

In some embodiments, the described DUX4 RNAi agents are used to treat at least one symptom mediated at least in part by DUX4 protein levels, in a subject. The subject is administered a therapeutically effective amount of any one or more of the described DUX4 RNAi agents. In some embodiments, the subject is administered a prophylactically effective amount of any one or more of the described RNAi agents, thereby treating the subject by preventing or inhibiting the at least one symptom.

In certain embodiments, the present disclosure provides methods for treatment of diseases, disorders, conditions, or pathological states mediated at least in part by DUX4 gene expression, in a patient in need thereof, wherein the methods include administering to the patient any of the DUX4 RNAi agents described herein.

In some embodiments, the DUX4 RNAi agents are used to treat or manage a clinical presentation or pathological state in a subject, wherein the clinical presentation or pathological state is mediated at least in part by DUX4 expression. The subject is administered a therapeutically effective amount of one or more of the DUX4 RNAi agents or DUX4 RNAi agent-containing compositions described herein. In some embodiments, the method comprises administering a composition comprising a DUX4 RNAi agent described herein to a subject to be treated.

In some embodiments, the gene expression level or mRNA level of a DUX4 gene in certain skeletal muscle cells of subject to whom a described DUX4 RNAi agent is administered is reduced by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or greater than 99%, relative to the subject prior to being administered the DUX4 RNAi agent or to a subject not receiving the DUX4 RNAi agent. In some embodiments, the DUX4 protein levels of a subject to whom a described DUX4 RNAi agent is administered is reduced by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or greater than 99%, relative to the subject prior to being administered the DUX4 RNAi agent or to a subject not receiving the DUX4 RNAi agent. The gene expression level, protein level, and/or mRNA level in the subject may be reduced in a cell, group of cells, tissue, and/or other fluid of the subject. In some embodiments, the DUX4 mRNA levels in certain skeletal muscle cells or skeletal muscle tissues in a subject to whom a described DUX4 RNAi agent has been administered is reduced by at least about 30%, 35%, 40%, 45%, 50%, 55%, 60%, 65%, 70%, 75%, 80%, 85%, 90%, 95%, or 98% relative to the subject prior to being administered the DUX4 RNAi agent or to a subject not receiving the DUX4 RNAi agent. In some embodiments, the level of DUX4 protein in the skeletal muscle cells and/or skeletal muscle tissue of a subject to whom a described DUX4 RNAi agent has been administered is reduced by at least about 30%, 35%, 40%, 45%, 50%, 55%, 60%, 65%, 70%, 75%, 80%, 85%, 90%, 95%, or 98% relative to the subject prior to being administered the DUX4 RNAi agent or to a subject not receiving the DUX4 RNAi agent.

As noted herein the DUX4 protein level and/or DUX4 mRNA level in the subject may be reduced in a cell, group of cells, tissue, blood, and/or other fluid (e.g., serum) of the subject, as would be understood by the person of ordinary skill in the art. For example, in some embodiments, the level of DUX4 mRNA of a subject to whom a described DUX4 RNAi agent has been administered is reduced by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or greater than 99%, relative to the subject prior to being administered the DUX4 RNAi agent or to a subject not receiving the DUX4 RNAi agent in one or more skeletal muscle cells or skeletal muscle tissues. In some embodiments, the level of DUX4 mRNA and/or DUX4 protein in a subset of skeletal muscle cells, of a subject to whom a described DUX4 RNAi agent has been administered is reduced by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or greater than 99%, relative to the subject prior to being administered the DUX4 RNAi agent or to a subject not receiving the DUX4 RNAi agent.

In some embodiments, the DUX4 RNAi agents can reduce DUX4 gene expression in one or more of the following muscle tissues: triceps, biceps, quadriceps, gastrocnemius, soleus, masseter EDL (extensor digitorum longus), TA (Tibialis anterior), trapezius, and/or diaphragm.

A reduction in gene expression, mRNA, and protein levels can be assessed by any methods known in the art. For example, the Examples set forth herein provide appropriate ways for measuring DUX4 protein levels and DUX4 mRNA levels in a subject. Reduction or decrease in DUX4 mRNA level and/or DUX4 protein levels, are collectively referred to herein as a reduction or decrease in DUX4 or inhibiting or reducing the expression of a DUX4 gene. The Examples set forth herein illustrate known methods for assessing inhibition of DUX4 gene expression.

Cells, Tissues, Organs, and Non-Human Organisms

Cells, tissues, organs, and non-human organisms that include at least one of the DUX4 RNAi agents described herein are contemplated. The cell, tissue, organ, or non-human organism is made by delivering the RNAi agent to the cell, tissue, organ, or non-human organism.

The above provided embodiments and items are now illustrated with the following, non-limiting examples.

EXAMPLES

Example 1. Synthesis of DUX4 RNAi Agents

The DUX4 RNAi agents disclosed herein were synthesized in accordance with the following:

A. Synthesis

The sense and antisense strands of the DUX4 RNAi agents were synthesized according to phosphoramidite technology on solid phase used in oligonucleotide synthesis. Depending on the scale, a MerMade96E® (Bioautomation), a MerMade12® (Bioautomation), or an OP Pilot 100 (GE Healthcare) was used. Syntheses were performed on a solid support made of controlled pore glass (CPG, 500 Å or 600 Å, obtained from Prime Synthesis, Aston, PA, USA). All RNA and 2'-modified RNA phosphoramidites were purchased from Thermo Fisher Scientific (Milwaukee, WI, USA). Specifically, the 2'-O-methyl phosphoramidites that were used included the following: (5'-O-dimethoxytrityl-N6-(benzoyl)-2'-O-methyl-adenosine-3'-O-(2-cyanoethyl-N,N-diisopropylamino) phosphoramidite, 5'-O-dimethoxy-trityl-N4-(acetyl)-2'-O-methyl-cytidine-3'-O-(2-cyanoethyl-N,N-diisopropyl-amino) phosphoramidite, (5'-O-dimethoxytrityl-N2-(isobutyryl)-2'-O-methyl-guanosine-3'-O-(2-cyanoethyl-N,N-diisopropylamino) phosphoramidite, and 5'-O-dimethoxytrityl-2'-O-methyl-uridine-3'-O-(2-cyanoethyl-N,N-diisopropylamino) phosphoramidite. The 2'-deoxy-2'-fluoro-phosphoramidites carried the same protecting groups as the 2'-O-methyl RNA amidites. 5'-dimethoxytrityl-2'-O-methyl-inosine-3'-O-(2-cyanoethyl-N,N-diisopropylamino) phosphoramidites were purchased from Glen Research (Virginia). The inverted abasic (3'-O-dimethoxytrityl-2'-deoxyribose-5'-O-(2-cyanoethyl-N,N-diisopropylamino) phosphoramidites were purchased from ChemGenes (Wilmington, MA, USA). UNA phosphoramidites include 5'-(4,4'-Dimethoxytrityl)-N6-(benzoyl)-2', 3'-seco-adenosine, 2'-benzoyl-3'-[(2-cyanoethyl)-(N,N-diisopropyl)]-phosphoramidite, 5'-(4,4'-Dimethoxytrityl)-N-acetyl-2',3'-seco-cytosine, 2'-benzoyl-3'-[(2-cyanoethyl)-(N,N-diiso-propyl)]-phosphoramidite, 5'-(4,4'-Dimethoxytrityl)-N-isobutyryl-2',3'-seco-guanosine, 2'-benzoyl-3'-[(2-cyanoethyl)-(N,N-diisopropyl)]-phosphoramidite, and 5'-(4,4'-Dimethoxy-trityl)-2',3'-seco-uridine, 2'-benzoyl-3'-[(2-cyanoethyl)-(N,N-diiso-propyl)]-phosphoramidite. The cyclopropyl phosphonate phosphoramidites were synthesized in accordance with International Patent Application Publication No. WO 2017/214112 and Erich F. Altenhafer et al., *Synthesis of a novel cyclopropyl phosphonate nucleotide as a phosphate mimic*, Chemical Communications (June 2021) (DOI:10.1039/d1cc02328d). TFA aminolink phosphoramidites were also commercially purchased (ThermoFisher).

B. Cleavage and Deprotection of Support Bound Oligomer

After finalization of the solid phase synthesis, the dried solid support was treated with a 1:1 volume solution of 40 wt. % methylamine in water and 28% to 31% ammonium hydroxide solution (Aldrich) for 1.5 hours at 30° C. The solution was evaporated and the solid residue was reconstituted in water (see below).

C. Purification

Crude oligomers were purified by anionic exchange HPLC using a TSKgel SuperQ-5PW 13 μm column and Shimadzu LC-8 system. Buffer A was 20 mM Tris, 5 mM EDTA, pH 9.0 and contained 20% Acetonitrile and buffer B was the same as buffer A with the addition of 1.5 M sodium chloride. UV traces at 260 nm were recorded. Appropriate fractions were pooled then run on size exclusion HPLC using a GE Healthcare XK 16/40 column packed with Sephadex G-25 fine with a running buffer of 100 mM ammonium bicarbonate, pH 6.7 and 20% Acetonitrile or filtered water. Alternatively, pooled fractions were desalted and exchanged into an appropriate buffer or solvent system via tangential flow filtration.

D. Annealing

Complementary strands were mixed by combining equimolar RNA solutions (sense and antisense) in 1×PBS (Phosphate-Buffered Saline, 1×, Corning, Cellgro) to form the RNAi agents. Some RNAi agents were lyophilized and stored at −15 to −25° C. Duplex concentration was determined by measuring the solution absorbance on a UV-Vis spectrometer in 1×PBS. The solution absorbance at 260 nm was then multiplied by a conversion factor and the dilution factor to determine the duplex concentration. The conversion factor used was either 0.050 mg/(mL·cm) or experimentally determined.

E. Synthesis of SM45-p for conjugation to RNAi agents; (S)-3-(4-(4-((14-azido-3,6,9,12-tetraoxatetradecyl)oxy)naphthalen-1-yl)phenyl)-3-(2-(5-((4-methylpyridin-2-yl)amino)pentanamido)acetamido) propanoic acid

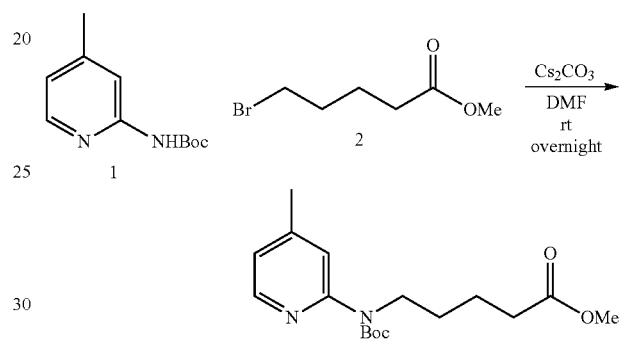

To a solution of compound 1 (0.50 g) in DMF under N₂ (g) at rt was added Cs₂CO₃ (0.94 g). Compound 2 (0.49 g) was then added slowly dropwise. The reaction was stirred overnight. Approx. 50% conversion to desired product by LC-MS was then confirmed. The reaction mixture was quenched with NaHCO₃ (10 mL). The product was extracted with EtOAc (3×15 mL) and then washed with water (3×10 mL) and brine (10 mL). The combined organic phase was dried over Na₂SO₄, filtered, and concentrated. The residue was purified by CombiFlash using silica gel as the stationary phase with a gradient of hex to EtOAc (0-70%), in which product eluted at 16% B. The product was concentrated under vacuum to provide a clear oil (0.35 g, 45.0% yield). LC-MS: calculated [M+H]+ 323.19 m/z, observed 328.38 m/z.

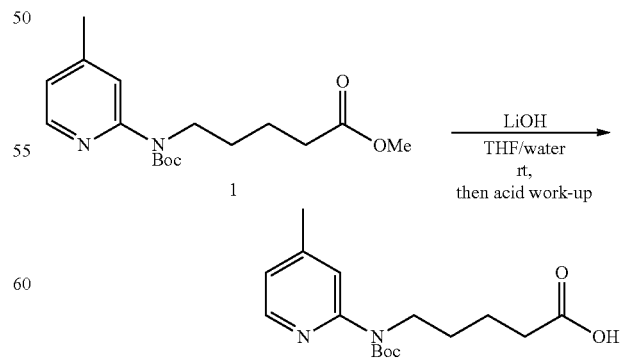

To a solution of compound 1 (0.35 g) in 1:1 THF/water was added LiOH (0.078 g) at rt under normal atmosphere. The reaction was stirred at rt until full conversion was observed by LC-MS. After 1 h, the reaction mixture was acidifed with 6 N HCl to a pH of ~3. The product was extracted with EtOAc (3×15 mL). The combined organic phase was dried over Na₂SO₄, filtered, and concentrated, providing a clear, colorless oil (0.32 g, 94.9% yield). No isolation was necessary. LC-MS: calculated [M+H]+ 309.17 m/z, observed 309.24 m/z.

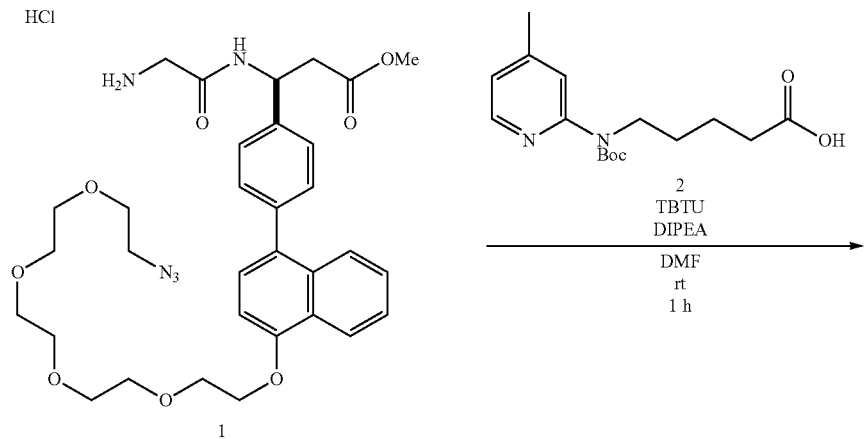

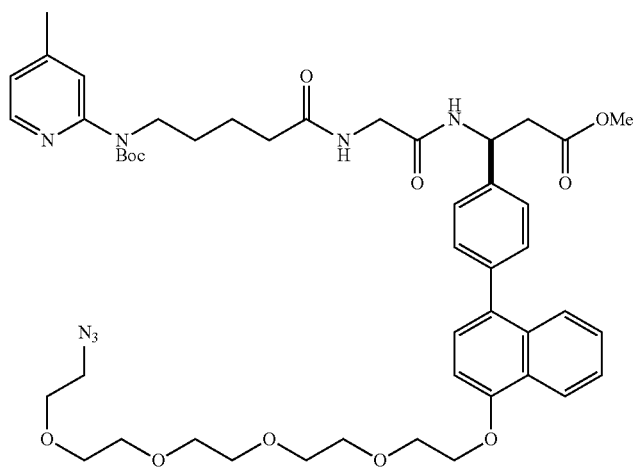

To a solution of compounds 1 (0.10 g) and 2 (0.049 g) in DMF was added TBTU (0.058 g) and then DIPEA (0.079 mL) under ambient conditions. Reaction was stirred for 1 h until full conversion was observed by LC-MS. The reaction mixture was then quenched with NaHCO₃ (10 mL). The product was extracted with EtOAc (3×15 mL) and then washed with water (3×10 mL) and brine (10 mL). The combined organic phase was dried over Na₂SO₄, filtered, and concentrated. The residue was purified by CombiFlash® using silica gel as the stationary phase with a gradient of DCM to 20% MeOH in DCM (0-70%), in which product eluted at 23% B. The product was concentrated under vacuum to provide a clear colorless oil (0.088 g, yield 63.6%.)

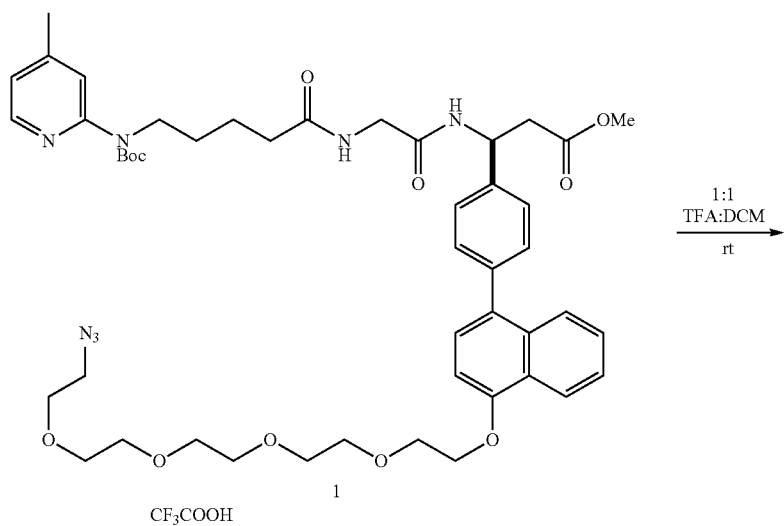

To a solution of compound 1 (0.088 g) in DCM was added TFA (0.22 mL) at rt. The reaction was stirred under ambient conditions. Reaction was stirred for 5 h until full conversion was confirmed via LC-MS. The reaction mixture was azeotroped with PhMe and concentrated under vacuum. No isolation was necessary. Concentration provided a clear colorless oil (0.10 g, yield 113%.) LC-MS: calculated [M+H]+ 814.41 m/z, observed 814.63 m/z.

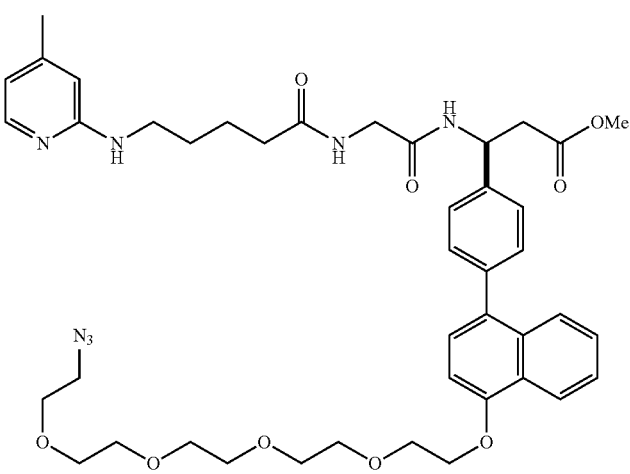

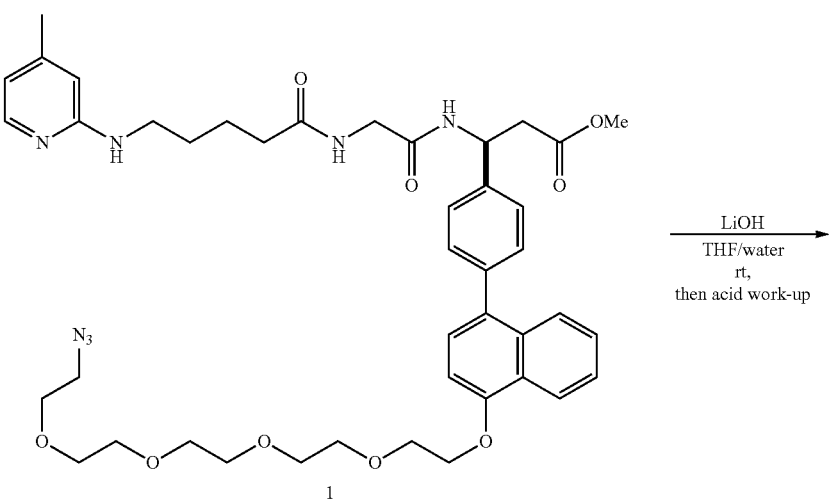

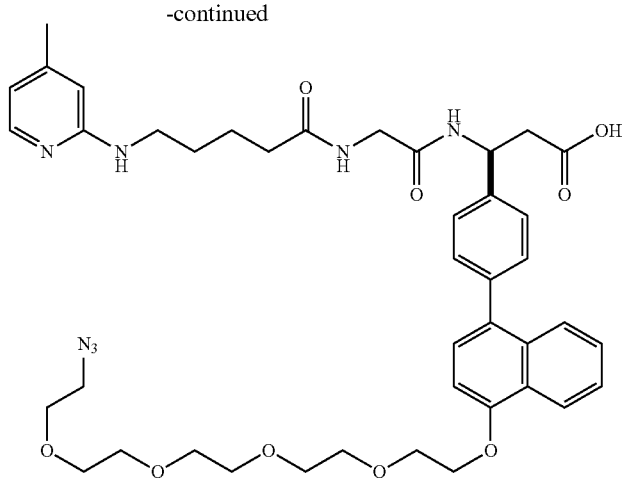

To a solution of compound 1 (0.10 g) in 1:1 THF/water was added LiOH (0.0078 g) at rt under normal atmosphere. The reaction was stirred at rt until full conversion was observed by LC-MS. After 4 h, the reaction mixture was acidified with 6 N HCl to a pH of ~3. The product was extracted with 20% CF₃CH₂OH/DCM (3×15 mL). The combined organic phase was dried over Na₂SO₄, filtered, and concentrated, providing a light yellow solid (0.104 g, yield 119%.) LC-MS: calculated [M+H]+ 800.39 m/z, observed 800.76 m/z.

F. Synthesis of Activated-Ester Skeletal Muscle Cell Receptor Peptide (αvβ6 Peptide 1) for Conjugation to RNAi Agents

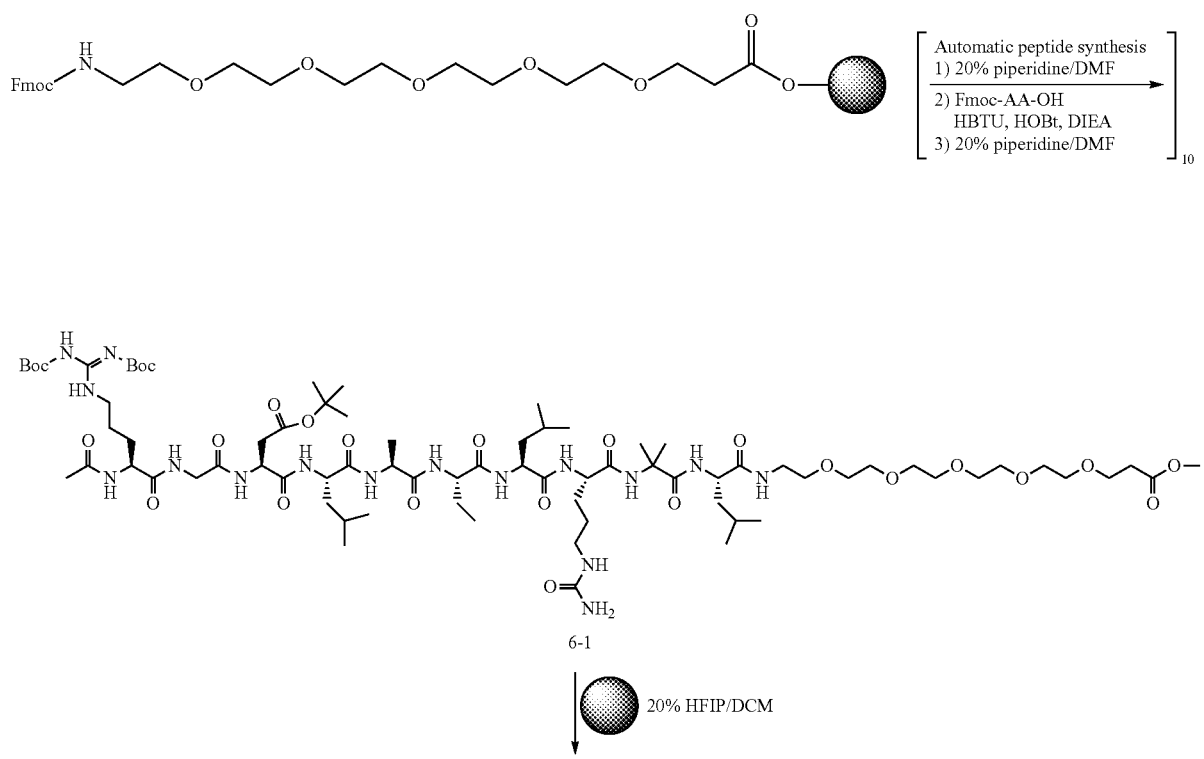

-continued

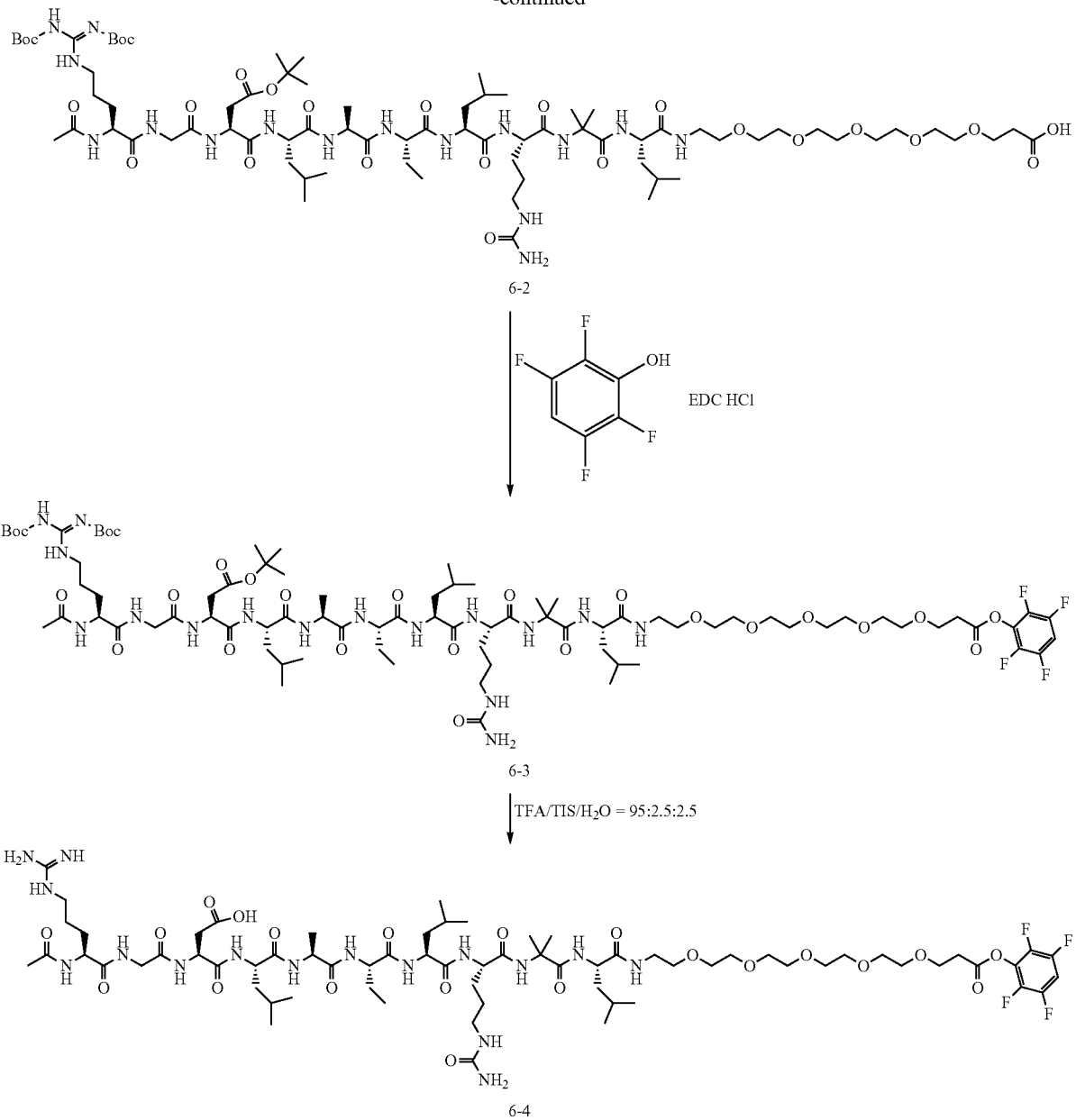

Peptide 1 was prepared by modification of Arg-Gly-Asp(tBu)-Leu-Ala-Abu-Leu-Cit-Aib-Leu-Peg$_5$-CO$_2$-2-Cl-Trt resin 1 that was obtained using general Fmoc peptide chemistry on CS Bio peptide synthesizer utilizing Fmoc-Peg$_5$-CO$_2$H preloaded 2-Cl-Trt resin on (0.79 mmol/g) at 4.1 mmol scale as described above. Following cleavage from resin the peptide 6-2 was converted into tetrafluorophenyl ester 6-3, and the crude product was used in the next step without purification.

Final deprotection was done by treatment of crude peptide 6-3 with deprotection cocktail TFA/TIS/H$_2$O=90:5:5 (80 mL) for 1.5 h. The reaction mixture was added dropwise to methyl tert-butyl ether (700 mL), and the resulting precipitate was collected by centrifugation. The pellets were washed with additional methyl tert-butyl ether (500 mL). The residue was purified by RP-HPLC (Phenomenex Gemini C18 250×50 mm, 10 micron, 60 mL/mm, 30-45% ACN gradient in water containing 0.1% TFA, approx. 1 gram of crude per run), affording 4.25 g of pure peptide 6-4.

G. Conjugation of Targeting Ligands

Either prior to or after annealing, the 5' or 3' amine functionalized sense strand is conjugated to a targeting ligand, either directly or via the use of a linker such as an alkyne functionalized linker (for example, DBCO or Linkers 1-10 as shown in Table 6.1), which can then be used to facilitate the conjugation to the targeting ligand(s).

The following generally describes the conjugation of activated ester functionalized linkers, including DBCO and Linkers 1-10, to the single strand or annealed duplex: Amine-functionalized duplex was dissolved in 90% DMSO/10% H$_2$O, at ~50-70 mg/mL. 40 equivalents triethylamine was added, followed by 3 equivalents (L4). The reaction was monitored by RP-HPLC. Once complete, the conjugate was precipitated twice in a solvent system of 1× phosphate buffered saline/acetonitrile (1:14 ratio), and dried.

i. Conjugation of Targeting Ligands to Propargyl Linkers

Either prior to or after annealing, the 5' or 3' tridentate alkyne functionalized sense strand is conjugated to the αvβ6 Integrin Ligands. The following example describes the conjugation of αvβ6 integrin ligands to the annealed duplex: Stock solutions of 0.5M Tris(3-hydroxypropyltriazolylmethyl)amine (THPTA), 0.5M of Cu(II) sulfate pentahydrate (Cu(II)SO$_4$·5 H$_2$O) and 2M solution of sodium ascorbate were prepared in deionized water. A 75 mg/mL solution in DMSO of αvβ6 integrin ligand was made. In a 1.5 mL centrifuge tube containing tri-alkyne functionalized duplex (3 mg, 75 μL, 40 mg/mL in deionized water, ~15,000 g/mol), 25 μL of 1M Hepes pH 8.5 buffer is added. After vortexing, 35 μL of DMSO was added and the solution is vortexed. αvβ6 integrin ligand was added to the reaction (6 eq/duplex, 2 eq/alkyne, ~15 μL) and the solution is vortexed. Using pH paper, pH was checked and confirmed to be pH ~8. In a separate 1.5 mL centrifuge tube, 50 μL of 0.5M THPTA was mixed with 10 uL of 0.5M Cu(II)SO$_4$·5 H$_2$O, vortexed, and incubated at room temp for 5 min. After 5 min, THPTA/Cu solution (7.2 μL, 6 eq 5:1 THPTA:Cu) was added to the reaction vial, and vortexed. Immediately afterwards, 2M ascorbate (5 μL, 50 eq per duplex, 16.7 per alkyne) was added to the reaction vial and vortexed. Once the reaction was complete (typically complete in 0.5-1 h), the reaction was immediately purified by non-denaturing anion exchange chromatography.

ii. Conjugation of Targeting Ligands to Amine-Functionalized Sense Strand

The following procedure may be used to conjugate an activated ester-functionalized targeting ligand such as αvβ6 peptide 1 to an amine functionalized RNAi agent comprising an amine, such as C6-NH2, NH2-C6, or (NH2-C$_6$)s, as shown in Table 6.1, above.

An annealed, lyophilized RNAi agent was dissolved in DMSO and 10% water (v/v %) at 25 mg/mL. Then 50-100 equivalents TEA and three equivalents of activated ester targeting ligand were added to the mixture. The reaction was allowed to stir for 1-2 hours while monitored by RP-HPLC-MS (mobile phase A: 100 mM HFIP, 14 mM TEA; mobile phase B: Acetonitrile; column: XBridge C18). After the reaction was complete, 12 mL of acetonitrile was added followed by 0.4 mL of PBS and then the mixture was centrifuged. The solid pellet was collected and dissolved in 0.4 mL of 1×PBS and then 12 mL of acetonitrile was added. The resulting pellet was collected and dried on high vacuum for 1 hour.

H. Synthesis of PK/PD Modulators

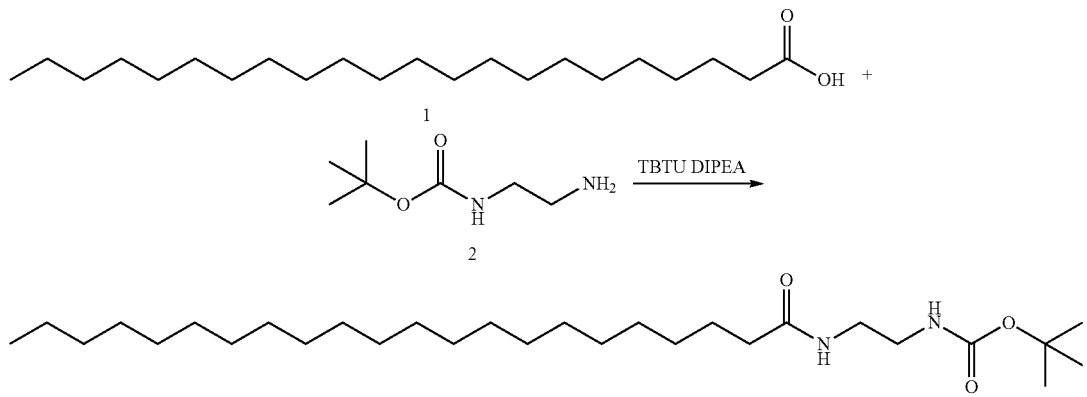

To a solution of compound 1 (350 mg, 1.027 mmol, 1.0 equiv.), compound 2 (181 mg, 1.130 mmol, 1.1 equiv.) and diisopropylethylamine (0.537 mL, 3.082 mmol, 3.0 equiv.) in anhydrous DMF (3 mL) was added TBTU (396 mg, 1.233 mmol, 1.2 equiv.) at room temperature. The reaction was kept at room temperature for 2 hrs. The reaction was quenched with saturated NaHCO$_3$ aqueous solution (20 mL) and the aqueous was extracted with dicholoromethane (3×10 mL). The organic phase was combined, dried over anhydrous Na$_2$SO$_4$, and concentrated. The product was purified by CombiFlash® and was eluted with 4-5% methanol in dichloromethane. LC-MS: calculated [M+H]+ 483.44, found 483.67.

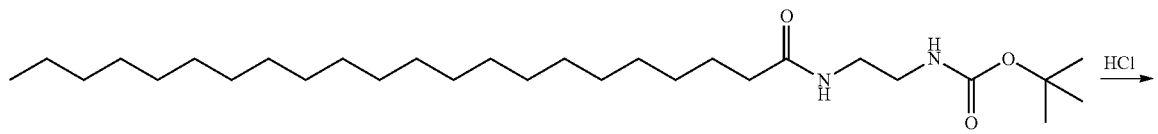

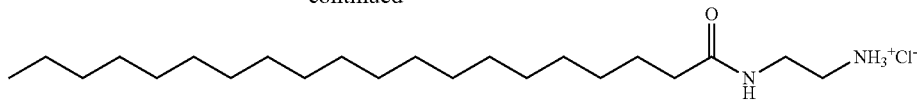

To a solution of compound 1 (290 mg, 0.600 mmol, 1.0 equiv.) in anhydrous 1,4-dioxane (1 mL) was added HCl solution in dioxane (0.751 mL, 3.003 mmol, 5.0 equiv.) at room temperature. The reaction was kept at room temperature for 3 hrs and the solvent was concentrated. The product was used directly without further purification. LC-MS: calculated [M+H]+ 383.39, found 383.57.

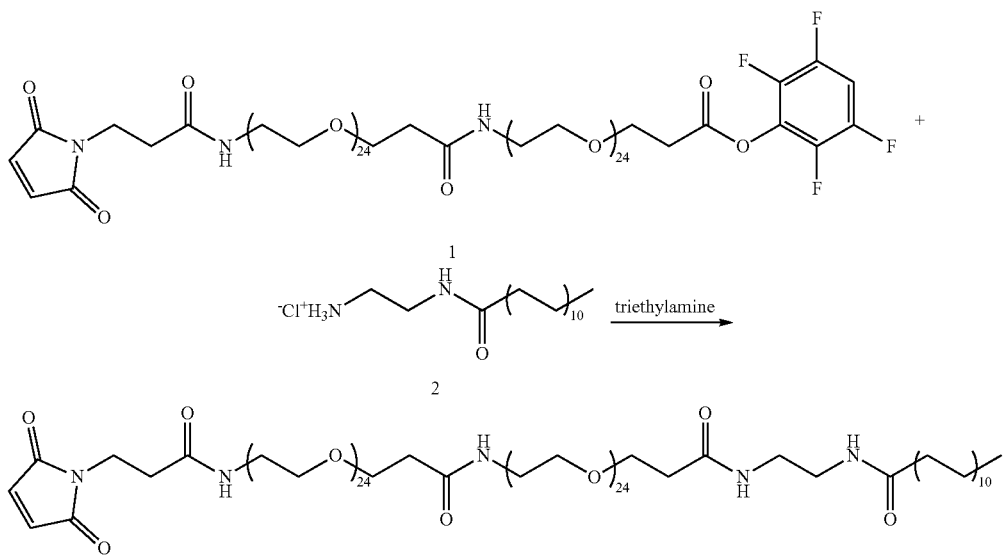

To a solution of compound 1 (83 mg, 0.0322 mmol, 1.0 equiv.) and compound 2 (13.5 mg, 0.322 mmol, 1.0 equiv.) in anhydrous DMF (2 mL) was added triethylamine (0.014 mL, 0.0967 mmol, 3.0 equiv.) at room temperature. The reaction was kept at room temperature for 3 hrs and the solvent was concentrated. The product was separated by CombiFlash and was eluted with 10-15% methanol in dicholoromethane. LC-MS: calculated [M+4H]+/4 698.18, found 698.49, calculated [M+3H]+/3 930.58, found 930.61.

Synthesis of LP29-p

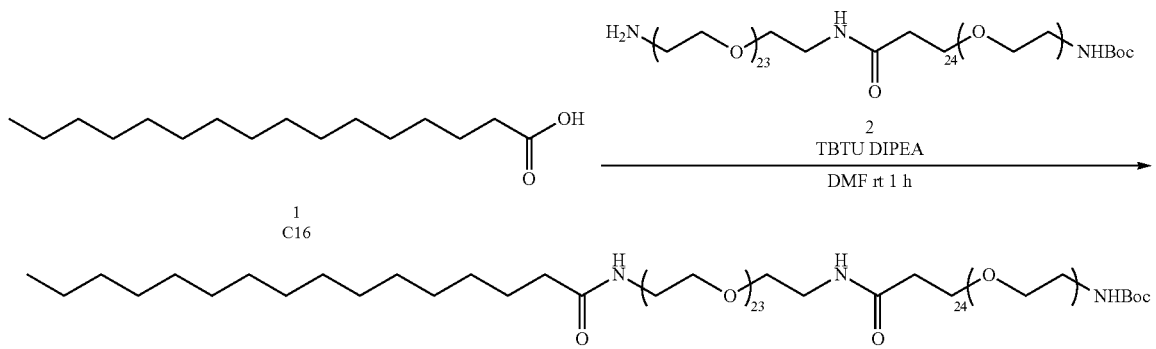

To a solution of compounds 1 (40 mg) and 2 (334 mg) in DMF was added TBTU (50.1 mg) and then DIPEA (0.082 mL) under ambient conditions. The reaction was stirred until full conversion was observed by LC-MS. The reaction mixture was then directly concentrated for isolation. The residue was purified by CombiFlash using silica gel as the stationary phase with a gradient of DCM to 20% MeOH in DCM (0-80%) over 20-30 min., in which product eluted at 71% B. The product was concentrated under vacuum to provide a white oily residue. LC-MS: calculated [M+H]+ 2539.62 m/z, observed 1288.21 (+2/2, +H$_2$O) m/z.

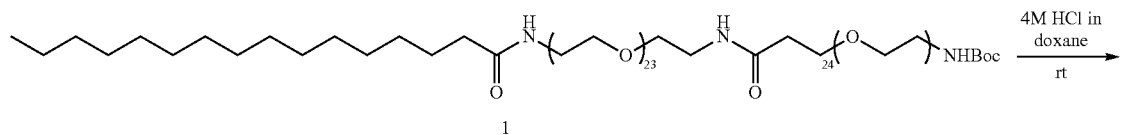

1

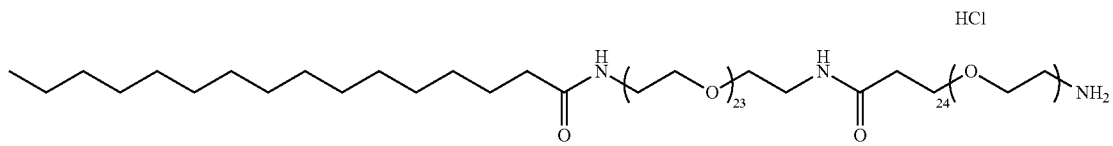

To compound 1 (147 mg) was added 4 M HCl/dioxane (21.2 mg) at room temperature. The reaction was stirred under ambient conditions. The reaction was stirred overnight until full conversion was confirmed via LC-MS. The reaction mixture was azeotroped with PhMe and concentrated under vacuum overnight to provide an oil. LC-MS: calculated [M+H]+ 2439.57 m/z, observed 611.16 (+4/4) m/z.

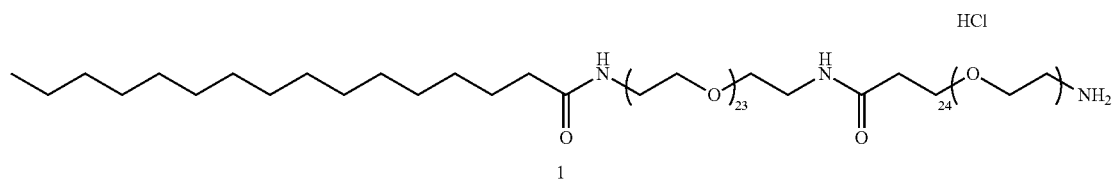

1

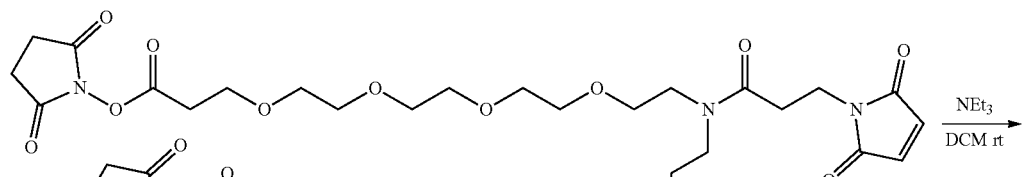

2

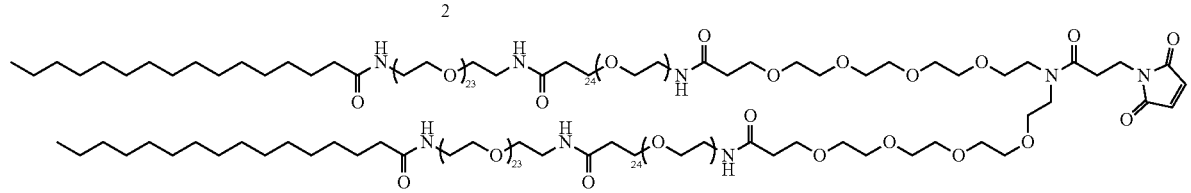

A solution of compound 1 (143 mg) and NEt3 (0.024 mL) in anh. DCM was prepared and stirred under sparging nitrogen atmosphere. Compound 2 (23.4 mg) was then added to the reaction mixture. The reaction mixture was stirred at room temperature until full conversion was observed by LC-MS.

The reaction mixture was directly concentrated for isolation. The residue was purified by CombiFlash using silica gel as the stationary phase and was eluted with a gradient of DCM to 20% MeOH in DCM (0-100% B). Product eluted at 54% B. LC-MS: calculated [M+H]+ 5506.42 m/z, observed 1854.41 (+3/3, +H$_2$O) m/z.

Synthesis of LP38-p

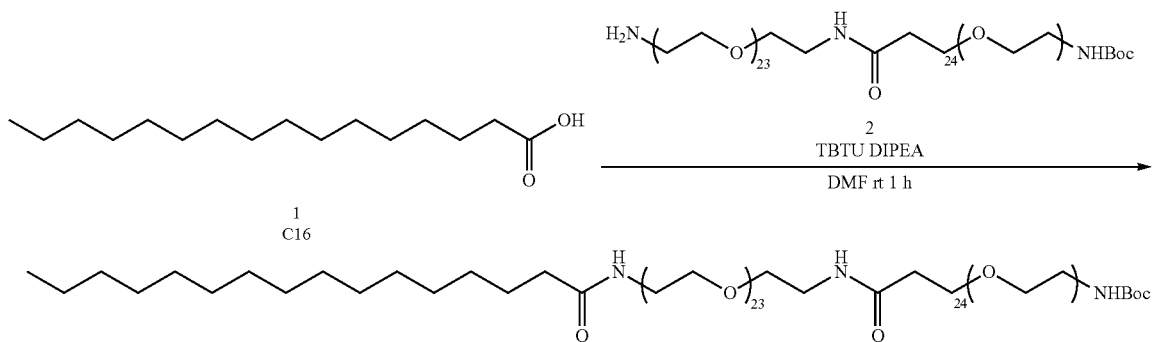

To a solution of compounds 1 (35 mg) and 2 (299 mg) in DMF was added TBTU (43.8 mg) and then DIPEA (0.071 mL) under ambient conditions. Reaction was stirred until full conversion was observed by LC-MS. The reaction mixture was then directly concentrated for isolation. The residue was purified by CombiFlash using silica gel as the stationary phase with a gradient of DCM to 20% MeOH in DCM (0-100%) over 20-30 min., in which product eluted at 56% B. The product was concentrated under vacuum to provide a white oily residue. LC-MS: calculated [M+H]+ 2539.62 m/z, observed 1288.07 (+2/2, +H2O) m/z.

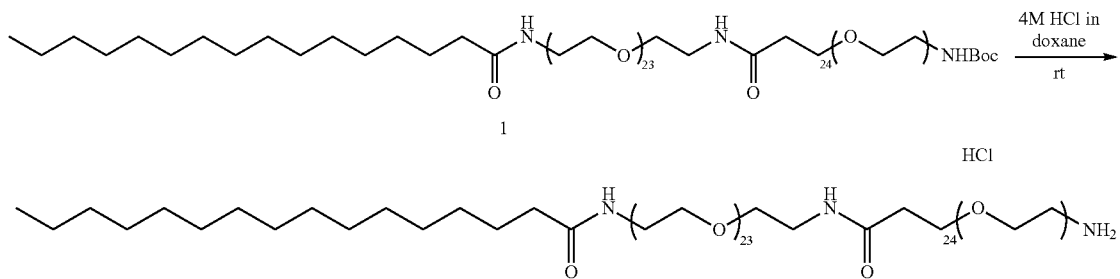

To compound 1 (186 mg) was added 4 M HCl/dioxane (26.7 mg) at room temperature. The reaction was stirred under ambient conditions. The reaction was stirred overnight until full conversion was confirmed via LC-MS. The reaction mixture was azeotroped with PhMe and concentrated under vacuum overnight to provide an oil. LC-MS: calculated [M+H]+2439.57 m/z, observed 1220.97 (+2/2) m/z.

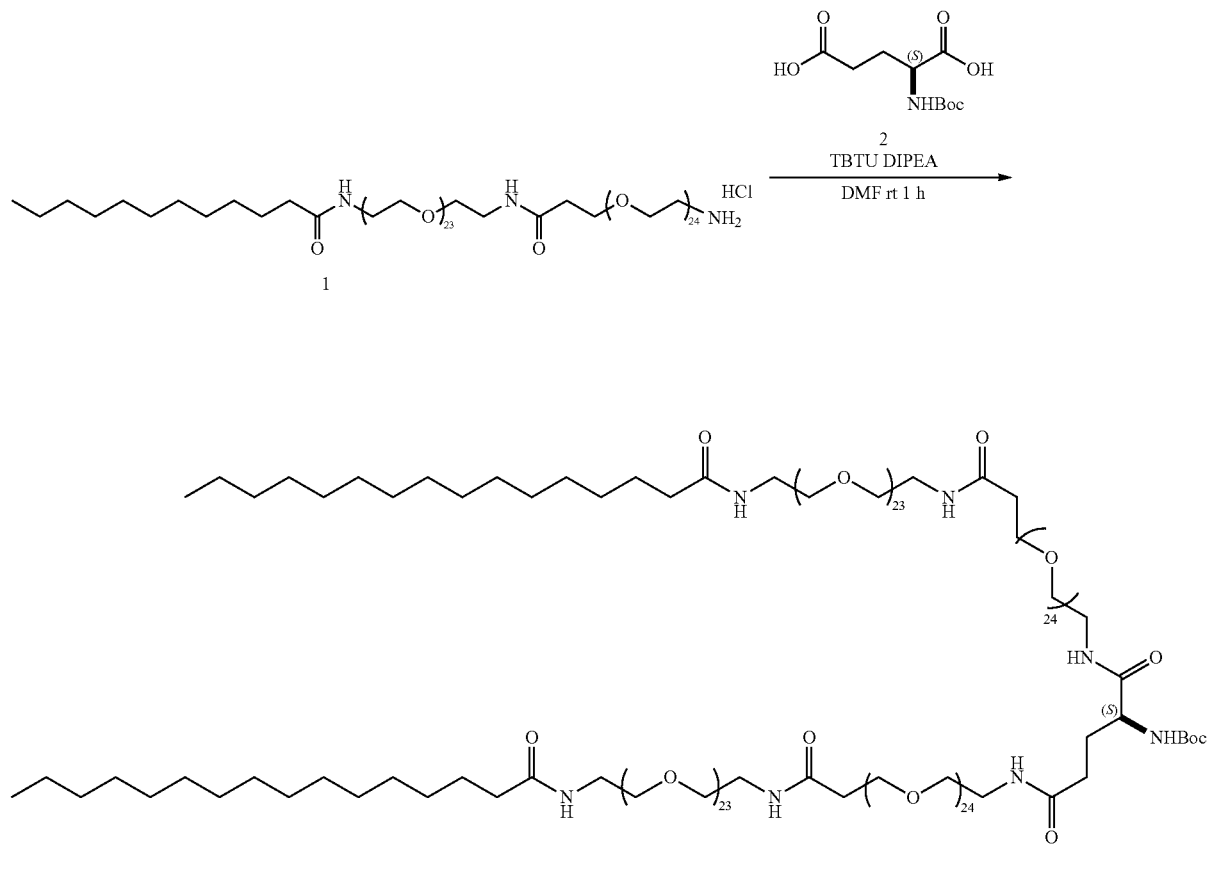

To a solution of compound 1 (181 mg), TBTU (24 mg), and DIEA (0.033 mL) in DMF was added 2 (8.7 mg) under ambient conditions. Reaction was stirred until full conversion was observed by LC-MS. The reaction mixture was then directly concentrated for isolation. The residue was purified by CombiFlash using silica gel as the stationary phase with a gradient of DCM to 20% MeOH in DCM (0-100%) over 20-30 min., in which product eluted at 65% B. The product was concentrated under vacuum to provide a white oily residue. LC-MS: calculated [M+H]+ 5089.22 m/z, observed 1036.24 (+5/5, +H2O) m/z.

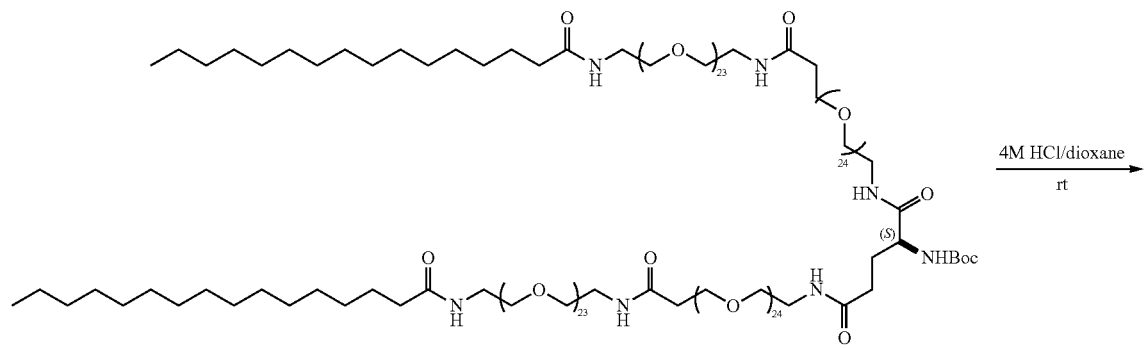

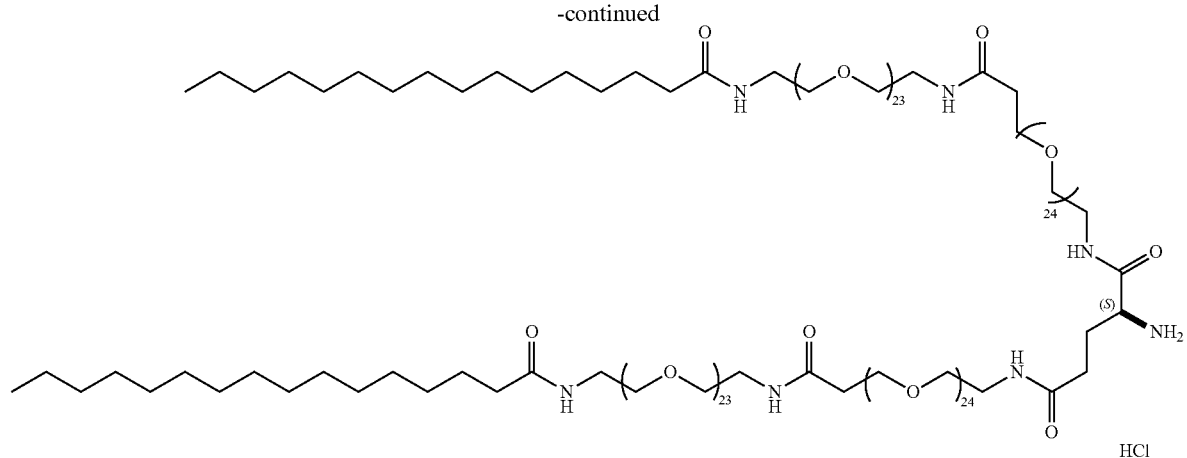

To compound 1 (130 mg) was added 4 M HCl/dioxane (9.3 mg) at rt. The reaction was stirred under ambient conditions. Reaction was stirred overnight until full conversion was confirmed via LC-MS. The reaction mixture was azeotroped with PhMe and concentrated under vacuum overnight to provide an oil. LC-MS: calculated [M+H]+ 4989.17 m/z, observed 1248.58 (+4/4) m/z.

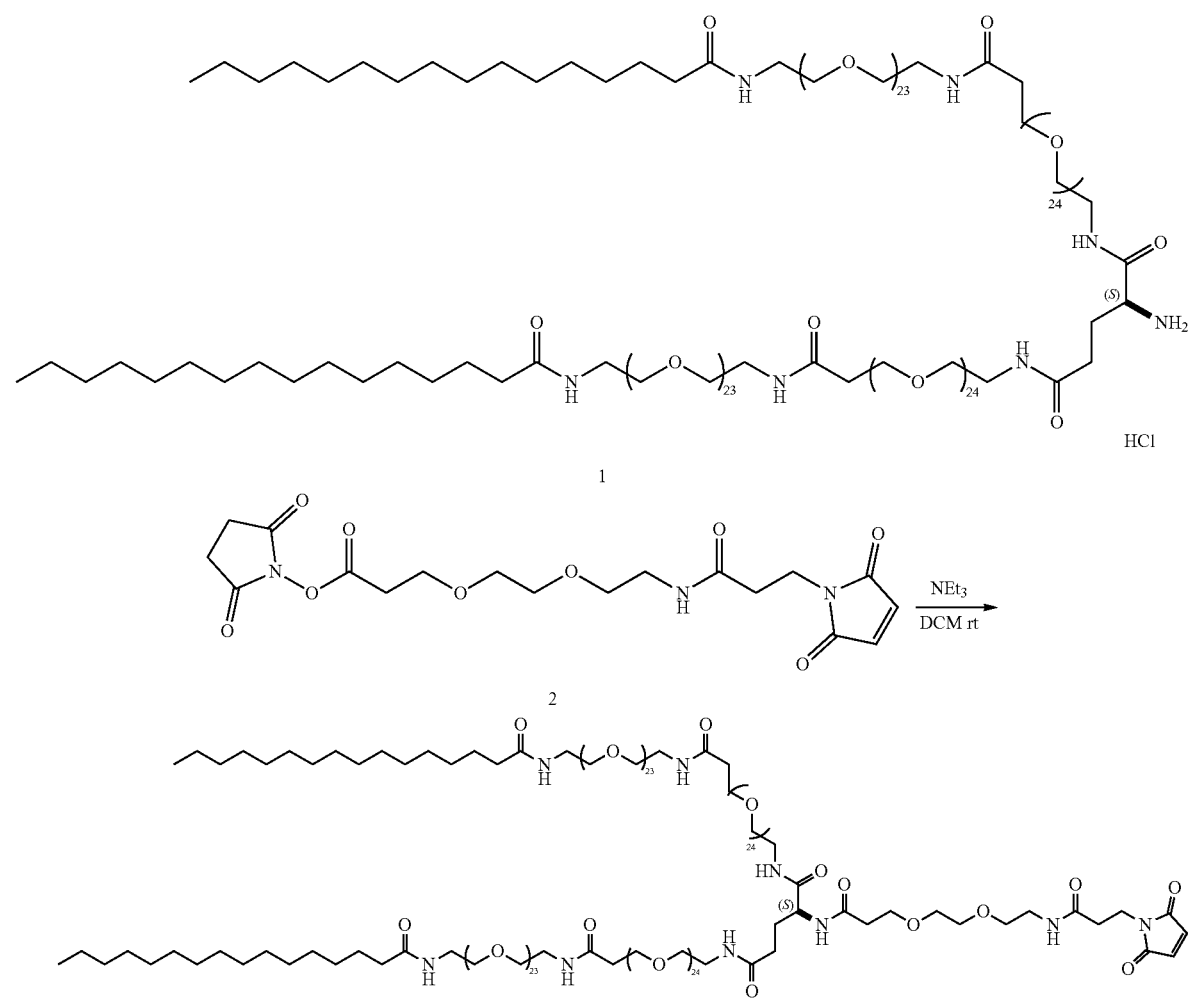

A solution of compound 1 (128 mg) and NEt₃ (0.018 mL) in anhydrous DCM under sparging N₂(g) was prepared at room temperature. Compound 2 (10.3 mg) was then added slowly. The reaction mixture was allowed to stir until full conversion was observed by LC-MS. The reaction mixture was allowed to stir until full conversion was observed by LC-MS. The reaction mixture was then directly concentrated. The residue was purified by CombiFlash using silica gel as the stationary phase with a gradient of DCM to 20% MeOH/DCM (0-100%) over 30 min., in which product eluted at 100% B. Product was concentrated to provide a white solid. LC-MS: calculated [M+H]+ 5299.28 m/z, observed 1786.62 (+3/3, +H$_2$O) m/z.

Synthesis of LP238-p

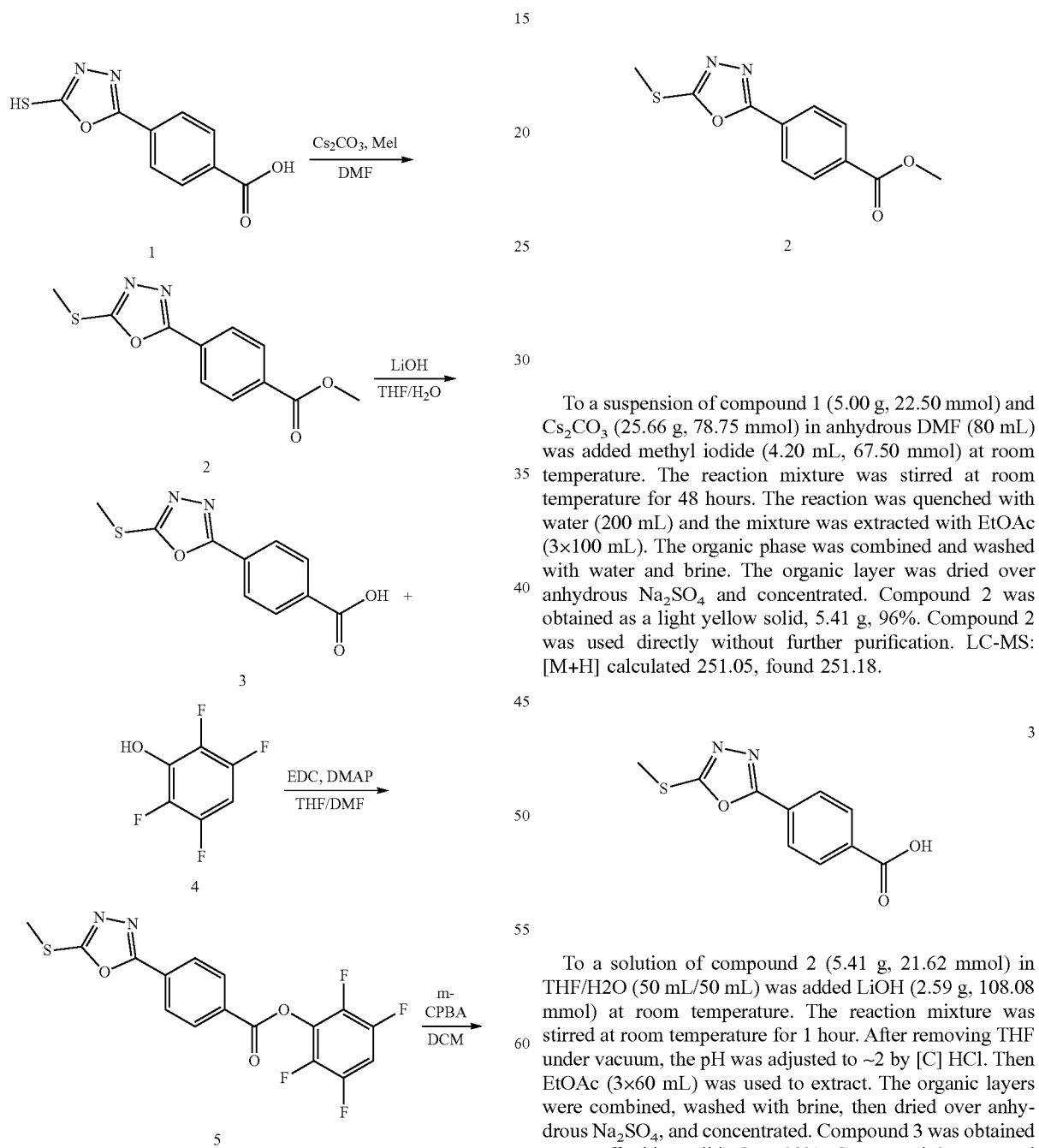

To a suspension of compound 1 (5.00 g, 22.50 mmol) and Cs$_2$CO$_3$ (25.66 g, 78.75 mmol) in anhydrous DMF (80 mL) was added methyl iodide (4.20 mL, 67.50 mmol) at room temperature. The reaction mixture was stirred at room temperature for 48 hours. The reaction was quenched with water (200 mL) and the mixture was extracted with EtOAc (3×100 mL). The organic phase was combined and washed with water and brine. The organic layer was dried over anhydrous Na$_2$SO$_4$ and concentrated. Compound 2 was obtained as a light yellow solid, 5.41 g, 96%. Compound 2 was used directly without further purification. LC-MS: [M+H] calculated 251.05, found 251.18.

To a solution of compound 2 (5.41 g, 21.62 mmol) in THF/H2O (50 mL/50 mL) was added LiOH (2.59 g, 108.08 mmol) at room temperature. The reaction mixture was stirred at room temperature for 1 hour. After removing THF under vacuum, the pH was adjusted to ~2 by [C] HCl. Then EtOAc (3×60 mL) was used to extract. The organic layers were combined, washed with brine, then dried over anhydrous Na$_2$SO$_4$, and concentrated. Compound 3 was obtained as an off-white solid, 5 g, 98%. Compound 3 was used directly without further purification. LC-MS: calculated [M+H] 237.03, found 237.26.

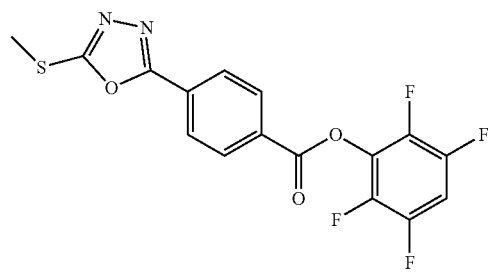

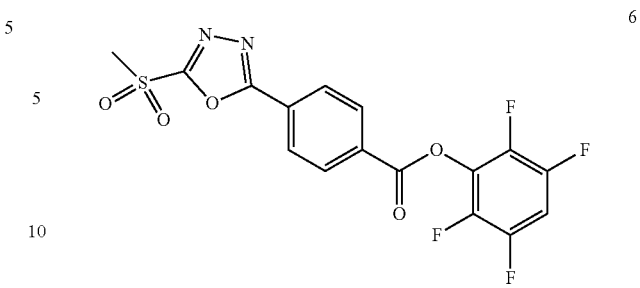

To a solution of compound 3 (5.81 g, 24.60 mmol) in THF/DMF (80 mL/20 mL) was added EDC (7.07 g, 36.90 mmol), DMAP (0.30 g, 2.46 mmol) and compound 4 (6.13 g, 36.90 mmol) at room temperature. The reaction mixture was stirred at room temperature overnight. After removing solvent under vacuum, the residue was loaded on a 120 g column and compound 5 was eluted with 0-50% EtOAc in hexanes. Compound 5 was obtained as a white solid, 9.36 g, 99%. LC-MS: calculated [M+H] 385.03, found 385.46.

To a solution of compound 5 (2.29 g, 5.96 mmol) in DCM (110 mL) was added 70% m-CPBA (5.14 g, 27.79 mmol) at 0° C. The reaction mixture was stirred at room temperature for 6 hours. Another 1.8 g m-CPBA was added at room temperature. The reaction mixture was stirred at room temperature overnight. After filtration, the solvent was removed under vacuum. The residue was recrystallized from DCM/EtOAc (50 mL/50 mL) twice. Compound 6 was obtained as white needle crystal, 1.93 g, 78%. LC-MS: calculated [M+H] 417, found 417.

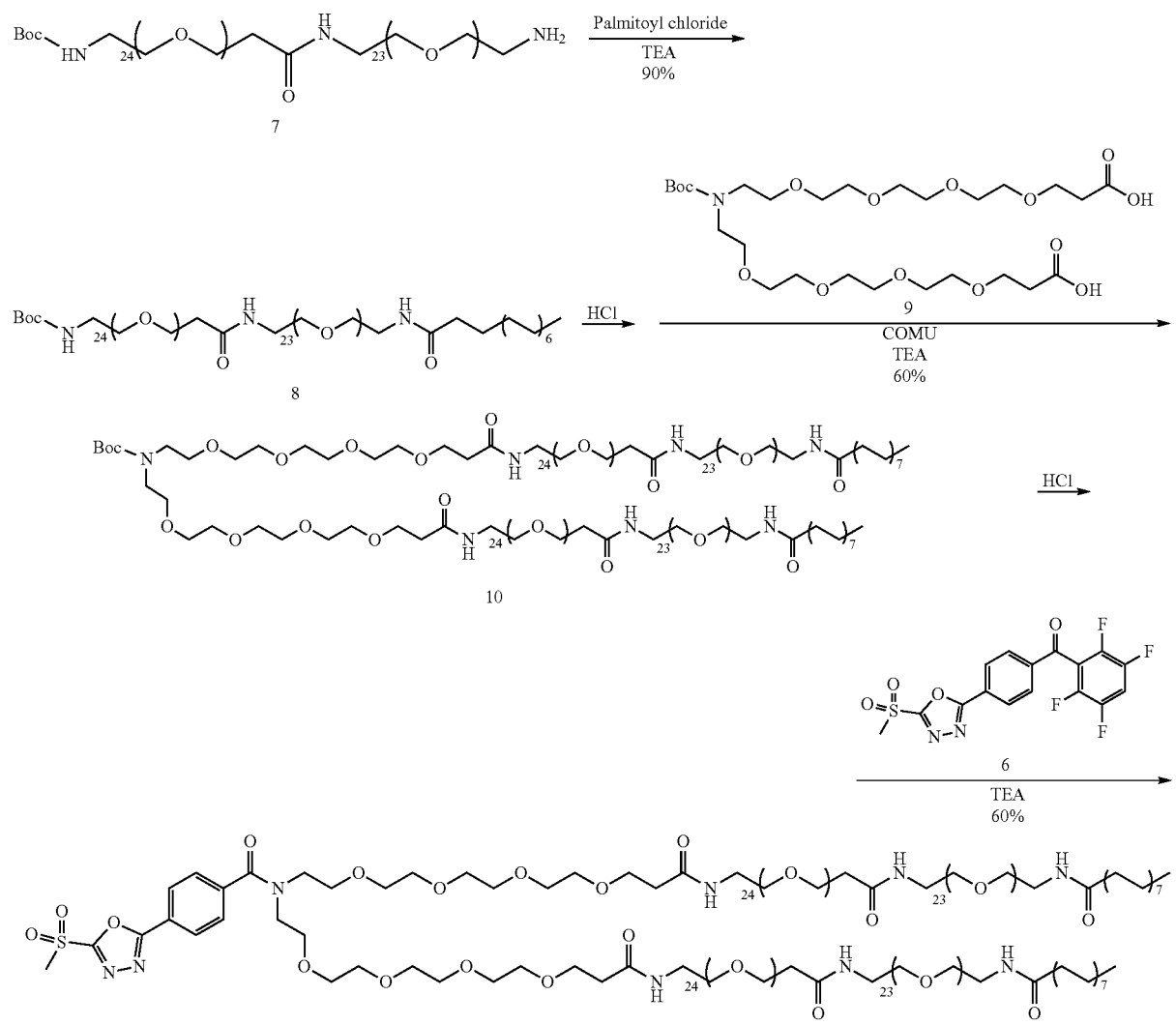

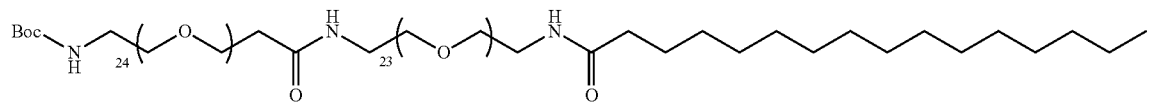

8

To a solution of compound 7 (10.00 g, 4.34 mmol) in DCM (100 mL) was added palmitoyl chloride (1.31 g, 4.78 mmol) and TEA at 0 (C. The reaction mixture was stirred at room temperature overnight and then the solvent was removed under vacuum. The residue was purified by silica-gel chromatography using 0-20% MeOH in DCM Compound 8 was obtained as a white solid, 10.0 g, 90%.

conjugation process used to link lipid PK/PD modulator precursors to the constructs set forth in the Examples depicted herein.

A. Conjugation of a Maleimide-Containing Lipid PK/PD Modulator Precursor

The following describes the general process used to link a maleimide-containing lipid PK/PD modulator precursor to

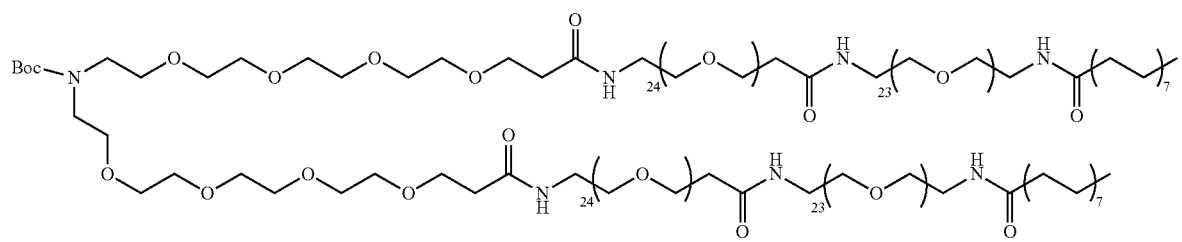

10

Compound 8 (9.56 g, 3.76 mmol) was dissolved in 25 mL 4N HCl/dioxane and stirred at room temperature for 1 hour. All solvent was removed and the residue was dried under vacuum for 2 hours. The residue was re-dissolved in 150 mL DCM and TEA was added, followed by compound 9 (1.10 g, 1.79 mmol), and COMU (1.69 g, 3.94 mmol). The reaction mixture was stirred at room temperature overnight. After a standard workup (1N HCl, Sat. bicarb, brine wash), DCM was removed. Compound 10 was purified by a 120 g column using 0-20% MeOH in DCM to obtain 5.90 g, 60%.

the (C6-SS-C6) or (6-SS-6) functionalized sense strand of an RNAi agent by undertaking a dithiothreitol reduction of disulfide followed by a thiol-Michael Addition of the respective maleimide-containing lipid PK/PD modulator precursor: In a vial, functionalized sense strand was dissolved at 50 mg/mL in sterilized water. Then 20 equivalents of each of 0.1M Hepes pH 8.5 buffer and dithiothreitol were added. The mixture was allowed to react for one hour, then the conjugate was precipitated in acetonitrile and PBS, and the solids were centrifuged into a pellet.

LP238-p

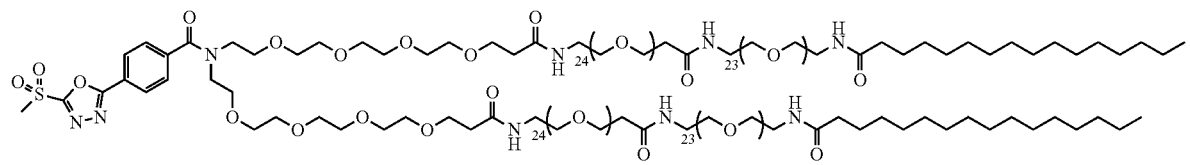

Compound 10 (4.50 g, 0.82 mmol) was dissolved in 20 mL 4N HCl/dioxane and stirred at room temperature for 1 hour. All solvent was removed and the residue was dried under vacuum for 2 hours. The residue was re-dissolved in 100 mL DCM and TEA was added, followed by compound 6 (0.69 g, 1.65 mmol). The reaction mixture was stirred at room temperature overnight. TEA was removed by a 1H HCl wash and the organic layer was concentrated. Crude LP238-p was purified by silica gel chromatography using 0-20% MeOH in DCM. 2.80 g (60%) of LP238-p was obtained as a light yellow solid.

I. Conjugation of PK/PD Modulators to RNAi Agents

Either prior to or after annealing and prior to or after conjugation of one or more targeting ligands, one or more lipid PK/PD modulator precursors can be linked to the RNAi agents disclosed herein. The following describes the general The pellet was brought up in a 70/30 mixture of DMSO/water at a solids concentration of 30 mg/mL. Then, the maleimide-containing lipid PK/PD modulator precursor was added at 1.5 equivalents. The mixture was allowed to react for 30 minutes. The product was purified on an AEX-HPLC (mobile phase A: 25 mM TRIS pH=7.2, 1 mM EDTA, 50% acetonitrile; mobile phase B: 25 mM TRIS pH=7.2, 1 mM EDTA, 500 mM NaBr, 50% acetonitrile; solid phase TSK-gel-30; 1.5 cm×10 cm.) The solvent was removed by rotary evaporator, and desalted with a 3K spin column using 2×10 mL exchanges with sterilized water. The solid product was dried using lyophilization and stored for later use.

B. Conjugation of a Sulfone-Containing Lipid PK/PD Modulator Precursor

In a vial, functionalized sense strand was dissolved at 50 mg/mL in sterilized water. Then 20 equivalents of each of 0.1M Hepes pH 8.5 buffer and dithiothreitol are added. The mixture was allowed to react for one hour, then the conjugate was precipitated in acetonitrile and PBS, and the solids were centrifuged into a pellet.

The pellet was brought up in a 70/30 mixture of DMSO/water at a solids concentration of 30 mg/mL. Then, the sulfone-containing lipid PK/PD modulator precursor was added at 1.5 equivalents. The vial was purged with $N_2$, and heated to 40° C. while stirring. The mixture was allowed to react for one hour. The product was purified on an AEX-HPLC (mobile phase A: 25 mM TRIS pH=7.2, 1 mM EDTA, 50% acetonitrile; mobile phase B: 25 mM TRIS pH=7.2, 1 mM EDTA, 500 mM NaBr, 50% acetonitrile; solid phase TSKgel-30; 1.5 cm×10 cm.) The solvent was removed by rotary evaporator, and desalted with a 3K spin column using 2×10 mL exchanges with sterilized water. The solid product was dried using lyophilization and stored for later use.

C. Conjugation of an Azide-Containing Lipid PK/PD Modulator Precursor

One molar equivalent of TG-TBTA resin loaded with Cu(I) was weighed into a glass vial. The vial was purged with $N_2$ for 15 minutes. Then, functionalized sense strand was dissolved in a separate vial in sterilized water at a concentration of 100 mg/mL. Then two equivalents of the azide-containing lipid PK/PD modulator precursor (50 mg/mL in DMF) is added to the vial. Then TEA, DMF and water are added until the final reaction conditions are 33 mM TEA, 60% DMF, and 20 mg/mL of the conjugated product. The solution was then transferred to the vial with resin via a syringe. The $N_2$ purge was removed and the vial was sealed and moved to a stir plate at 40° C. The mixture was allowed to react for 16 hours. The resin was filtered off using a 0.45 µm filter.

The product was purified using AEX purification (mobile phase A: 25 mM TRIS pH=7.2, 1 mM EDTA, 50% acetonitrile; mobile phase B: 25 mM TRIS pH=7.2, 1 mM EDTA, 500 mM NaBr, 50% acetonitrile solid phase TSKgel-30; 1.5 cm×10 cm.) The acetonitrile was removed using a rotary evaporator, and desalted with a 3K spin column using 2×10 mL exchanges with sterilized water. The solid product was dried using lyophilization and stored for later use.

D. Conjugation of an Alkyne-Containing Lipid PK/PD Modulator Precursor

The following describes the general process used to link an activated alkyne-containing lipid PK/PD modulator precursor to the (C6-SS-C6) or (6-SS-6) functionalized sense strand of an RNAi agent by undertaking a dithiothreitol reduction of disulfide followed by addition to an alkyne-containing PK/PD modulator precursor: In a vial, 10 mg of siRNA comprising the (C6-SS-C6) or (6-SS-6) functionalized sense strand was dissolved at 50 mg/mL in sterilized water. Then 20 equivalents of each of 0.1M Hepes pH 8.5 buffer and dithiothreitol (1M in sterilized water) were added. The mixture was allowed to react for one hour, then purified on XBridge BEH C4 Column using a mobile phase A of 100 mM HFIP, 14 mM, and TEA, and a mobile phase B of Acetonitrile using the following formula, wherein % B indicates the amount of mobile phase B while the remainder is mobile phase A.

| Time | % B |
|---|---|
| 0 | 3 |
| 8 | 70 |
| 10 | 90 |
| 11 | 90 |
| 11.1 | 3 |
| 13 | 3 |

The product was precipitated once by adding 12 mL of acetonitrile and 0.4 mL 1×PBS, and the resulting solid was centrifuged into a pellet. The pellet was re-dissolved in 0.4 mL 1×PBS and 12 mL of acetonitrile. The pellet was dried on high vacuum for one hour.

The pellet was brought up in a vial a 70/30 mixture of DMSO/water at a solids concentration of 30 mg/mL. Then, the alkyne-containing lipid PK/PD modulator precursor was added at 2 equivalents relative to siRNA. Then 10 equivalents of TEA was added. The vial was purged using N2, and the reaction mixture was heated to 40° C. while stirring. The mixture was allowed to react for one hour. The product was purified using anion-exchange HPLC using a TSKgel-30 packed column, 1.5 cm×10 cm, using a mobile phase A of 25 mM TRIS pH=7.2, 1 mM EDTA, 50% Acetonitrile, and a mobile phase B of 25 mM TRIS pH=7.2, 1 mM EDTA, 500 mM NaBr, 50% Acetonitrile using the following formula, wherein % B indicates the amount of mobile phase B while the remainder is mobile phase A.

| Time | % B |
|---|---|
| 4 | 10 |
| 7 | 80 |
| 10.5 | 80 |
| 11 | 10 |
| 14 | 10 |

The fractions containing the product were collected, and acetonitrile was removed using a rotary evaporator. The product was desalted with a 3K spin column, using 2×10 mL exchanges with sterilized water. The product was then dried using lyophilization and stored for later use.

J. Synthesis of Linker 4

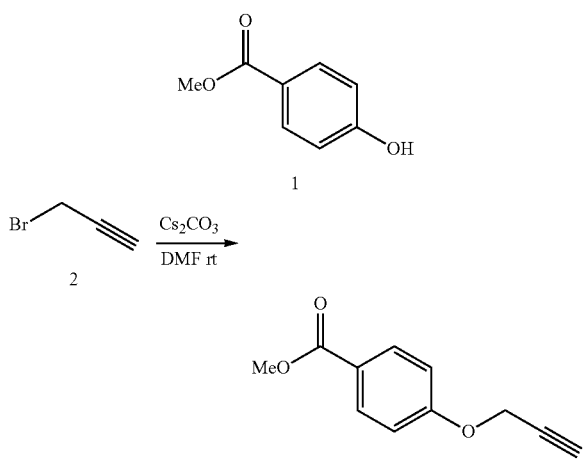

To a solution of compound 1 (3.00 g) in DMF was added $Cs_2CO_3$ (7.71 g) at rt. Compound 2 (1.85 mL) was then added slowly. Reaction was stirred overnight under $N_2$ (g). Approx. full conversion to desired product by LC-MS was then confirmed. The reaction mixture was quenched with NaHCO$_3$ (10 mL). The product was extracted with EtOAc (5×10 mL) and then washed with water (3×8 mL) and brine (8 mL). The combined organic phase was dried over Na$_2$SO$_4$, filtered, and concentrated. The residue was purified by CombiFlash using silica gel as the stationary phase with a gradient of hex to EtOAc (0-30%), in which product eluted at 14% B. The product was concentrated under vacuum to provide a white solid. LC-MS: calculated [M+H]+ 191.06 m/z, observed 191.23 m/z.

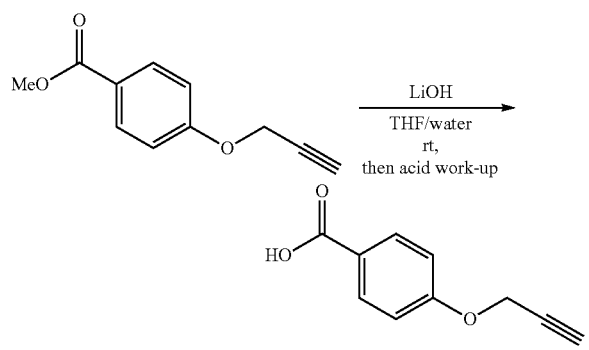

To a solution of compound 1 (2.87 g) in 1:1 THF/water was added LiOH (1.08 g) at rt under normal atmosphere. The reaction was stirred until full conversion was observed by LC-MS. Residual starting material was extracted via EtOAc, and then aqueous phase was acidified with 6 N HCl to a pH of ~3. Product crashed out as white solid and was filtered over vacuum and washed with water. Due to its wet/sticky nature, solvent was required to transfer the solid to a round bottom flask; material was transferred via MeOH and DCM. Due to poor solvation in either and the combination, material was not able to be dried over Na$_2$SO$_4$ and was correspondingly merely concentrated under vacuum to provide a white, fluffy crystalline solid. No isolation was necessary. LC-MS: calculated [M+H]+ 177.05 m/z, observed 177.19 m/z.

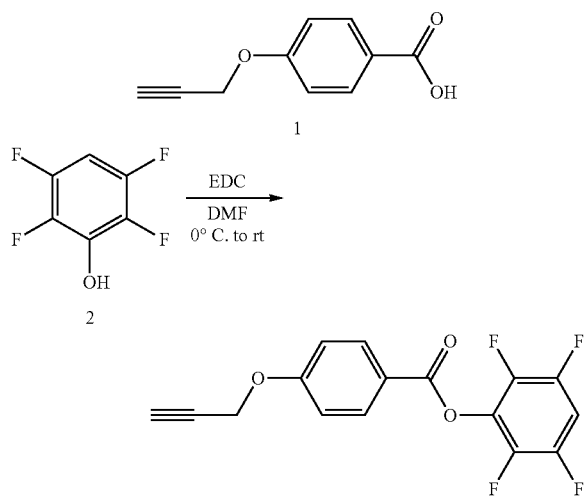

To a solution of compounds 1 (1.00 g) and 2 (1.04 g) in DMF (10.0 mL) under N$_2$(g) was added EDC (1.20 g) at rt. The reaction mixture was allowed to stir until full conversion was observed by LC-MS. Due to an inability to successfully observe product after overnight stirring, reaction mixture was quenched with NaHCO$_3$, in which crash-out followed. Precipitate was confirmed to contain starting materials via LC-MS and was filtered over vacuum, attempted to be resuspended in MeOH/DCM, and then concentrated under vacuum. Mixture was then resolvated in DMF, dried over Na$_2$SO$_4$, and filtered over vacuum, rinsing with DMF. EDC was readded to filtrate (reaction mixture), and mixture was allowed to stir overnight at rt. The reaction mixture was directly concentrated and azeotroped with MeOH and PhMe for isolation. The residue was purified by CombiFlash® using silica gel as the stationary phase and was eluted with a gradient of DCM to 20% of MeOH/DCM (0-15% B). Product eluted at 0% B to provide a white solid. LC-MS: calculated [M+H]+ 325.04 m/z, observed 325.35 m/z.

Example 2. FSHD-like Transgenic Mouse Model (FLExDUX4/HSA-MCM)

To assess DUX4 RNAi agents in vivo, a transgenic model of FSHD was used. FLExDUX4 mice (B6(Cg)-Gt(ROSA) 26Sortm1.1(DUX4*)Plj/J) were commercially acquired and crossed with HSA-MCM mice (Tg(ACTA1-cre/Esr1*) 2Kesr/J) by Jackson Laboratories (JAX) to produce homozygous offspring that express human DUX4 in skeletal muscle upon administration of tamoxifen.

FLExDUX4 Mouse Background: The FLExDUX4 mice were created using a cre-dependent one-way genetic switch (FLEx) system. Homozygote mice carrying this DUX4 conditional allele are viable and fertile. Two sets of incompatible outward facing recombination sites (loxP and lox511) flank an inverted human DUX4 sequence, including exons 1-3 and both introns. The DUX4 gene encodes several alternative mRNA splicing variants. The hereditary muscle disorder, facioscapulohumeral muscular dystrophy (FSHD) is caused by the expression of DUX4 encoded by the DUX4-full-length (DUX4-fl) mRNA isoform. As noted previously herein, the DUX4-fl mRNA, which encodes a paired homeobox domain transcription factor, is typically not expressed in healthy muscle. However, in FSHD, the rare expression of DUX4-fl (in less than 1% of muscle fibers) initiates a pathogenic cascade of events including apoptosis, differentiation defects, muscle atrophy, and susceptibility to oxidative stress. Overall, FSHD is characterized by a slowly progressing muscular dystrophy that predominantly affects the skeletal muscles of the face, scapula, and upper arms but can affect muscles of the abdomen, hip girdle, and lower legs with ~20% of patients ultimately losing ambulation.

The DUX4 promoter drives expression of a short non-pathogenic isoform (DUX4-s) and a longer cytotoxic isoform (DUX4-fl). This strain contains 4 point mutations in the 5' splicing donor sites for the two DUX4-s mRNAs, abolishing expression of the short isoforms and only generating the pathogenic DUX4-fl mRNA isoform.

Because this construct was targeted for insertion into the Gt(ROSA)26Sor locus, DUX4-fl expression is determined by which tissue(s) express Cre recombinase. When bred to mice that express Cre recombinase, the resulting offspring will have the loxP or lox511 sites recombined, resulting in the inversion of the human DUX4-fl sequence, ending in a sense orientation.

Hemizygous and homozygous mice have low level DUX4-fl expression in the absence of Cre Recombinase. These mice exhibit alopecia, and, with age, soft stool, inflammation, and muscle weakness. Homozygous are more affected, as are males compared to females.

HSA-MCM Mouse Background: HSA-MCM mice express MerCreMer double fusion protein under the control of the human ACTA1 (actin, alpha 1, skeletal muscle) promoter. Heterozygous mice are viable and fertile. Homozygotes are also viable but exhibit significantly reduced fertility. Of note, the MerCreMer double fusion protein has substantially greater Cre recombinase activity with less promiscuity compared with the CreMer single fusion protein. When HSA-MCM mice are bred with mice containing loxP-flanked sequences, tamoxifen-inducible Cre-mediated recombination results in deletion of the floxed sequences in skeletal muscles of the limbs, face/tongue, and diaphragm of the offspring.

The MerCreMer double fusion protein consists of Cre recombinase flanked on each end with a mutated murine estrogen receptor (mer) ligand binding domain (amino acids 281-599, G525R); which does not bind its natural ligand (170-estradiol) at physiological concentrations but will bind the synthetic estrogen receptor ligands 4-hydroxytamoxifen (OHT or tamoxifen) and, with lesser sensitivity, ICI 182780. Restricted to the cytoplasm, MerCreMer can only gain access to the nuclear compartment after exposure to tamoxifen.

Tamoxifen induction of DUX4 expression: Tamoxifen dissolved in corn oil (1 mg/mL) was administered via oral gavage 2 or 3 times weekly to induce increased DUX4 expression in skeletal muscle for the duration of the study (generally 18 to 31 days).

Bodyweight assessments: As increased DUX4 expression is known to result in muscle wasting and bodyweight loss in this animal model of FSHD, for the Examples disclosed herein, bodyweights were recorded throughout the duration of various studies, including on days of tamoxifen or RNAi agent administration and on the day of tissue harvest. Bodyweights were normalized to the first day of tamoxifen administration and average bodyweight of the "baseline" control group which was administered corn oil (containing no tamoxifen) and saline (containing no RNAi agent).

Gross motor coordination assessment: During the week prior to administration of tamoxifen or RNAi agents, mice were acclimated to a commercially acquired Rotarod apparatus at least 5 times. Once tamoxifen and/or RNAi agents were administered, gross motor coordination was assessed using the Rotarod apparatus at least twice weekly by taking the average of five attempts on each day of assessment.

Tissue collection: Mice were anesthetized with 3-4% isoflurane and euthanized via exsanguination. Tissues of interest intended for gene expression analysis were harvested and snap frozen in liquid nitrogen and then later stored at −80° C. Tissues of interest intended for histology were fixed in formalin then embedded in paraffin wax and stained via histochemical or immunohistochemical protocols.

Gene expression analysis: Whole frozen tissues were homogenized using a Precellys Tissue Homogenization System (Bertin) and RNA was isolated via acid guanidinium thiocyanate-phenol-chloroform extraction. Extracted RNA was used to synthesize complimentary DNA using a SuperScript™ VILO™ cDNA Synthesis Kit (Thermo) and DUX4 expression was measured using a QX200 droplet digital PCR (Bio-Rad). Wfdc3 and Myo1 g expression was measured using a QuantFlex7 qRT-PCR (Applied Biosystems) systems employing Taqman primer/probe sets (ThermoFisher) designed to detect genes of interest. Gene expression was normalized to a reference gene (e.g. Arl1) and the average of the "baseline" control group which was administered corn oil (containing no tamoxifen) and saline (containing no RNAi agent).

WAP-type four-disulfide core domain 3 (Wfdc3) expression as biomarker of DUX4 activity in mouse muscle: WAP-type four-disulfide core domain 3 is a well-documented direct murine target of overexpressed DUX4-fl protein. Gene expression of Wfdc3 is measured (using qRT-PCR as described above) and used as a biomarker of DUX4 activity in collected muscle tissue.

Myosin 1G (Myo1g) expression as biomarker of DUX4 activity in mouse muscle: Myo1g is a well-documented direct murine target of overexpressed DUX4-fl protein. Gene expression of Myo1g is measured (using qRT-PCR as described above) and used as a biomarker of DUX4 activity in collected muscle tissue The FSHD-like transgenic mouse model as described in Example 2 were used to assess DUX4 RNAi agents. DUX4 RNAi agents that included a sense strand and an antisense strand were synthesized according to phosphoramidite technology on solid phase in accordance with general procedures known in the art and commonly used in oligonucleotide synthesis, as set forth in Example 1 herein.

Example 3. In Vivo Administration of DUX4 RNAi Agents in Fshd-Like Transgenic Mice On Study Day 1, mice were injected between the skin and muscle (i.e. subcutaneous injections) into the loose skin region over the neck and shoulder area with either isotonic saline (vehicle control) or a DUX4 RNAi agent formulated in isotonic saline. Starting on day 4, an oral gavage of 100 μL/20 g mouse of either corn oil (negative control) or tamoxifen dissolved in corn oil (1 mg/mL) was administered three times per week (days 4, 6, 8, 10, 12, 15, 17, and 19) to induce increased expression of DUX4. The dosing regimen and details are set forth in the following Table:

TABLE 7

Dosing Groups for Example 3.

| Group | RNAi agent and Dose | RNAi agent Dosing Regimen | Induction Agent Administration | Induction Agent Dosing Regimen |
|---|---|---|---|---|
| 1 | Baseline (no RNAi agent, saline injection) | N/A | Corn oil (negative control) | 3 times per week starting on day 4 |
| 2 | Positive Control (no RNAi agent, saline injection) | N/A | Tamoxifen | 3 times per week starting on day 4 |

TABLE 7-continued

Dosing Groups for Example 3.

| Group | RNAi agent and Dose | RNAi agent Dosing Regimen | Induction Agent Administration | Induction Agent Dosing Regimen |
|---|---|---|---|---|
| 3 | SM45b-L4-AD07218-Bis(PEG47 + C22) | 5 mg/kg administered on days 1 and 7 | Tamoxifen | 3 times per week starting on day 4 |
| 4 | SM45b-L4-AD07219-Bis(PEG47 + C22) | 5 mg/kg administered on days 1 and 7 | Tamoxifen | 3 times per week starting on day 4 |
| 5 | SM456-L4-AD07275-Bis(PEG47 + C22) | 5 mg/kg administered on days 1 and 7 | Tamoxifen | 3 times per week starting on day 4 |
| 6 | SM45b-L4-AD07220-Bis(PEG47 + C22) | 5 mg/kg administered on days 1 and 7 | Tamoxifen | 3 times per week starting on day 4 |
| 7 | SM45b-L4-AD07276-Bis(PEG47 + C22) | 5 mg/kg administered on days 1 and 7 | Tamoxifen | 3 times per week starting on day 4 |
| 8 | SM45b-L4-AD07221-Bis(PEG47 + C22) | 5 mg/kg administered on days 1 and 7 | Tamoxifen | 3 times per week starting on day 4 |
| 9 | SM45b-L4-AD07277-Bis(PEG47 + C22) | 5 mg/kg administered on days 1 and 7 | Tamoxifen | 3 times per week starting on day 4 |
| 10 | SM45b-L4-AD07396-Bis(PEG47 + C22) | 5 mg/kg administered on days 1 and 7 | Tamoxifen | 3 times per week starting on day 4 |

The RNAi agents in Example 2 (Groups 3-10) were synthesized having nucleotide sequences directed to target the DUX4 gene (i.e., mRNA transcript), and included a functionalized amine reactive group ($NH_2$-$C_6$) at the 5' terminal end of the sense strand to facilitate conjugation to the linker L4, which may be conjugated to the targeting ligand, a small molecule having affinity for a receptor present on skeletal muscle cells (referred to herein as a "skeletal muscle cell receptor small molecule"). Procedures for conjugating the linker to the sense strand and conjugating the targeting ligand to the linker are provided in Example 1, above.

The DUX4 RNAi agents were linked to a small molecule targeting ligand SM45b having affinity for skeletal muscle cells. DUX4 RNAi agents were linked to a compound having the following chemical structure:

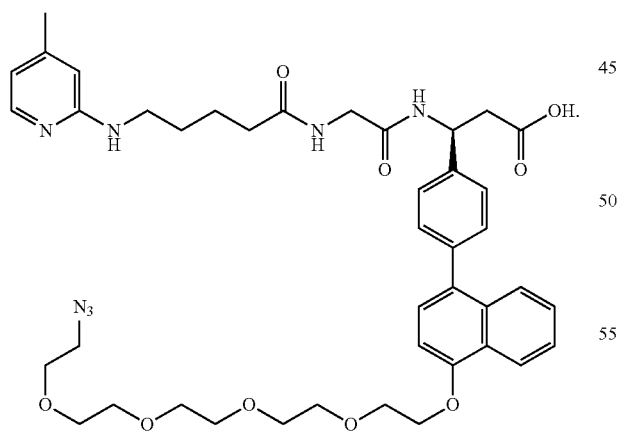

(SM45-p)

The targeting ligand SM45-p was synthesized as an azide, which allowed for convenient coupling to Linker L4. Linker L4 was originally synthesized as a tetrafluorophenyl (TFP) ester functionalized compound having the following structure:

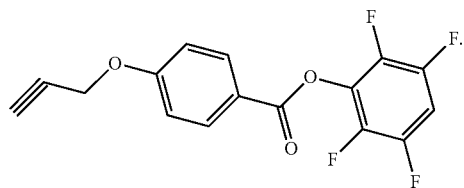

(L4)

The TFP ester reactive group was first linked to the terminal amine ($NH_2$-$C_6$) on the 5' end of the sense strand. The azide of SM45 was then coupled to the alkyne of linker (L4).

The DUX4 RNAi agents in Example 2 were further synthesized with a disulfide functional group (C6-SS-C6) at the 3' terminal end of the sense strand to facilitate conjugation to a PK/PD modulator. A Bis(PEG47+C22) moiety was attached to the 3' terminal end of the sense strand to serve as a pharmacokinetic/pharmacodynamic (PK/PD) modulator having the following structure:

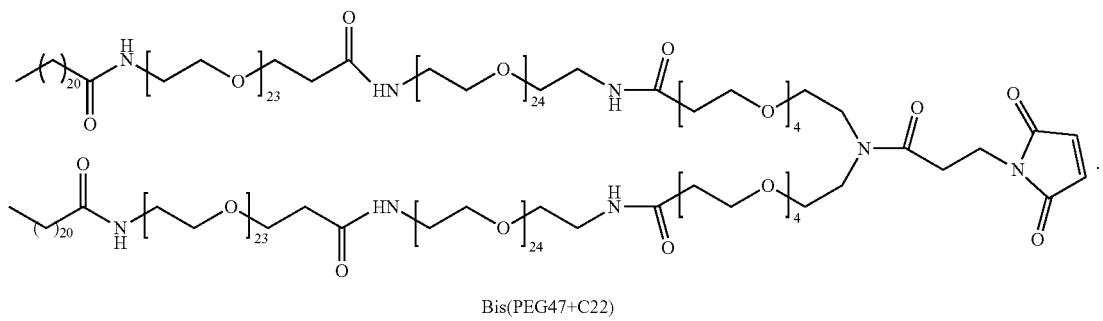

Bis(PEG47+C22)

The maleimide was linked to the 3' end of the sense strand by reducing the terminal 3' disulfide bond and performing Michael addition to the terminal 3' thiol. As described herein, a PK/PD modulator can increase circulation time of the conjugated drug and/or increase the activity of the RNAi agent through improved cell receptor binding, improved cellular uptake, and/or other means. Upon conjugation to the targeting ligand and PK/PD modulator, the DUX4 RNAi agent sense strands had the general structure as shown in Table 4.5.

The modified RNAi agent nucleotide sequences were synthesized as shown herein in Table 3, Table 4.1, Table 4.6, and Tables 5.1, Table 5.2, Table 5.3, and Table 5.4 (showing the fully modified conjugate).

Five mice were dosed in each Group (n=5), except for Group 1 where only 3 mice were dosed (n=3). On day 21, animals were sacrificed and muscles were harvested, processed, and analyzed in accordance with the procedures described in Example 2.

Average relative DUX4 expression in harvested tissue is shown in the following Tables for various muscle types:

TABLE 8.1

Average relative DUX4 expression in biceps for mice of Example 3 normalized to Baseline (Group 1).

| | Biceps Day 21 | |
|---|---|---|
| | Relative DUX4 Expression | Standard Deviation (+/−) |
| Group 1 (Baseline) | 1.000 | 0.259 |
| Group 2 (Positive Control (Tamoxifen only)) | 1.323 | 0.327 |
| Group 3 (AD07218) | 0.628 | 0.141 |
| Group 4 (AD07219) | 0.941 | 0.340 |
| Group 5 (AD07275) | 0.578 | 0.140 |
| Group 6 (AD07220) | 0.922 | 0.589 |
| Group 7 (AD07276) | 0.544 | 0.143 |
| Group 8 (AD07221) | 0.878 | 0.170 |
| Group 9 (AD07277) | 0.551 | 0.154 |
| Group 10 (AD07396) | 1.096 | 0.406 |

TABLE 8.2

Average relative DUX4 expression in diaphragm for mice of Example 3 normalized to Baseline (Group 1).

| | Diaphragm Day 21 | |
|---|---|---|
| | Relative DUX4 Expression | Standard Deviation (+/−) |
| Group 1 (Baseline) | 1.000 | 0.385 |
| Group 2 (Positive Control (Tamoxifen only)) | 1.739 | 0.686 |
| Group 3 (AD07218) | 1.227 | 0.422 |
| Group 4 (AD07219) | 1.497 | 0.694 |
| Group 5 (AD07275) | 0.806 | 0.340 |
| Group 6 (AD07220) | 1.063 | 0.241 |
| Group 7 (AD07276) | 0.636 | 0.196 |
| Group 8 (AD07221) | 0.909 | 0.404 |
| Group 9 (AD07277) | 0.891 | 0.059 |
| Group 10 (AD07396) | 1.047 | 0.545 |

TABLE 8.3

Average relative DUX4 expression in EDL (extensor digitorum longus) for mice of Example 3 normalized to Baseline (Group 1).

| | EDL Day 21 | |
|---|---|---|
| | Relative DUX4 Expression | Standard Deviation (+/−) |
| Group 1 (Baseline) | 1.000 | 0.231 |
| Group 2 (Positive Control (Tamoxifen only)) | 1.076 | 0.172 |
| Group 3 (AD07218) | 0.748 | 0.140 |
| Group 4 (AD07219) | 0.759 | 0.268 |
| Group 5 (AD07275) | 0.530 | 0.165 |
| Group 6 (AD07220) | 0.664 | 0.064 |
| Group 7 (AD07276) | 0.569 | 0.164 |
| Group 8 (AD07221) | 0.662 | 0.249 |
| Group 9 (AD07277) | 0.463 | 0.154 |
| Group 10 (AD07396) | 0.874 | 0.166 |

TABLE 8.4

Average relative DUX4 expression in gastrocnemius for mice of Example 3 normalized to Baseline (Group 1).

| | Gastrocnemius Day 21 | |
|---|---|---|
| | Relative DUX4 Expression | Standard Deviation (+/−) |
| Group 1 (Baseline) | 1.000 | 0.375 |
| Group 2 (Positive Control (Tamoxifen only)) | 1.663 | 0.509 |

TABLE 8.4-continued

Average relative DUX4 expression in gastrocnemius for mice of Example 3 normalized to Baseline (Group 1).

| | Gastrocnemius Day 21 | |
|---|---|---|
| | Relative DUX4 Expression | Standard Deviation (+/−) |
| Group 3 (AD07218) | 1.021 | 0.465 |
| Group 4 (AD07219) | 1.159 | 0.756 |
| Group 5 (AD07275) | 0.585 | 0.214 |
| Group 6 (AD07220) | 0.998 | 0.395 |
| Group 7 (AD07276) | 0.553 | 0.140 |
| Group 8 (AD07221) | 0.647 | 0.191 |
| Group 9 (AD07277) | 0.556 | 0.119 |
| Group 10 (AD07396) | 0.819 | 0.483 |

TABLE 8.5

Average relative DUX4 expression in masseter for mice of Example 3 normalized to Baseline (Group 1).

| | Masseter Day 21 | |
|---|---|---|
| | Relative DUX4 Expression | Standard Deviation (+/−) |
| Group 1 (Baseline) | 1.000 | 0.206 |
| Group 2 (Positive Control (Tamoxifen only)) | 1.585 | 0.659 |
| Group 3 (AD07218) | 1.191 | 0.375 |
| Group 4 (AD07219) | 1.325 | 0.353 |
| Group 5 (AD07275) | 0.774 | 0.357 |
| Group 6 (AD07220) | 1.161 | 0.515 |
| Group 7 (AD07276) | 0.826 | 0.153 |
| Group 8 (AD07221) | 1.219 | 1.077 |
| Group 9 (AD07277) | 1.007 | 0.217 |
| Group 10 (AD07396) | 0.976 | 0.277 |

TABLE 8.6

Average relative DUX4 expression in soleus for mice of Example 3 normalized to Baseline (Group 1).

| | Soleus Day 21 | |
|---|---|---|
| | Relative DUX4 Expression | Standard Deviation (+/−) |
| Group 1 (Baseline) | 1.000 | 0.101 |
| Group 2 (Positive Control (Tamoxifen only)) | 0.884 | 0.130 |
| Group 3 (AD07218) | 0.916 | 0.283 |
| Group 4 (AD07219) | 0.884 | 0.209 |
| Group 5 (AD07275) | 0.711 | 0.243 |
| Group 6 (AD07220) | 1.034 | 0.101 |
| Group 7 (AD07276) | 0.800 | 0.168 |
| Group 8 (AD07221) | 0.646 | 0.095 |
| Group 9 (AD07277) | 0.799 | 0.061 |
| Group 10 (AD07396) | 0.822 | 0.260 |

TABLE 8.7

Average relative DUX4 expression in TA (tibialis anterior) for mice of Example 3 normalized to Baseline (Group 1).

| | TA Day 21 | |
|---|---|---|
| | Relative DUX4 Expression | Standard Deviation (+/−) |
| Group 1 (Baseline) | 1.000 | 0.675 |
| Group 2 (Positive Control (Tamoxifen only)) | 1.121 | 0.353 |
| Group 3 (AD07218) | 0.741 | 0.122 |
| Group 4 (AD07219) | 0.874 | 0.367 |
| Group 5 (AD07275) | 0.550 | 0.304 |
| Group 6 (AD07220) | 0.819 | 0.122 |
| Group 7 (AD07276) | 0.375 | 0.196 |
| Group 8 (AD07221) | 0.636 | 0.285 |
| Group 9 (AD07277) | 0.498 | 0.083 |
| Group 10 (AD07396) | 0.805 | 0.327 |

TABLE 8.8

Average relative DUX4 expression in trapezius for mice of Example 3 normalized to Baseline (Group 1).

| | Trapezius Day 21 | |
|---|---|---|
| | Relative DUX4 Expression | Standard Deviation (+/−) |
| Group 1 (Baseline) | 1.000 | 0.624 |
| Group 2 (Positive Control (Tamoxifen only)) | 2.372 | 0.969 |
| Group 3 (AD07218) | 1.298 | 0.688 |
| Group 4 (AD07219) | 1.424 | 0.399 |
| Group 5 (AD07275) | 0.711 | 0.126 |
| Group 6 (AD07220) | 1.252 | 0.282 |
| Group 7 (AD07276) | 0.688 | 0.334 |
| Group 8 (AD07221) | 1.189 | 0.331 |
| Group 9 (AD07277) | 0.765 | 0.321 |
| Group 10 (AD07396) | 1.410 | 0.373 |

TABLE 8.9

Average relative DUX4 expression in triceps for mice of Example 3 normalized to Baseline (Group 1).

| | Triceps Day 21 | |
|---|---|---|
| | Relative DUX4 Expression | Standard Deviation (+/−) |
| Group 1 (Baseline) | 1.000 | 0.380 |
| Group 2 (Positive Control (Tamoxifen only)) | 2.812 | 0.542 |
| Group 3 (AD07218) | 1.189 | 0.445 |
| Group 4 (AD07219) | 1.240 | 0.426 |
| Group 5 (AD07275) | 0.691 | 0.133 |
| Group 6 (AD07220) | 1.302 | 0.522 |
| Group 7 (AD07276) | 0.503 | 0.101 |
| Group 8 (AD07221) | 1.150 | 0.160 |
| Group 9 (AD07277) | 0.785 | 0.271 |
| Group 10 (AD07396) | 1.322 | 0.502 |

TABLE 9.1

Average relative Wfdc3 expression in biceps for mice of Example 3 normalized to Baseline (Group 1).

| | Biceps Day 21 | | |
|---|---|---|---|
| | Relative Wfdc3 Expression | Low (error) | High (error) |
| Group 1 (Baseline) | 1.000 | 0.813 | 4.339 |
| Group 2 (Positive Control (Tamoxifen only)) | 13.361 | 1.868 | 2.172 |
| Group 3 (AD07218) | 9.383 | 4.112 | 7.319 |
| Group 4 (AD07219) | 7.677 | 2.713 | 4.195 |
| Group 5 (AD07275) | 1.678 | 0.732 | 1.298 |
| Group 6 (AD07220) | 8.267 | 1.842 | 2.370 |
| Group 7 (AD07276) | 2.320 | 0.964 | 1.650 |
| Group 8 (AD07221) | 11.011 | 2.190 | 2.733 |
| Group 9 (AD07277) | 8.878 | 1.748 | 2.177 |
| Group 10 (AD07396) | 11.367 | 1.687 | 1.980 |

As discussed herein, Wfdc3 transcript levels serve as a biomarker for DUX4 protein activity levels. Average relative Wfdc3 transcript levels in harvested tissue were similarly determined as shown in the following Tables for various muscle types:

TABLE 9.2

Average relative Wfdc3 expression in diaphragm for mice of Example 3 normalized to Baseline (Group 1).

| | Diaphragm Day 21 | | |
|---|---|---|---|
| | Relative Wfdc3 Expression | Low (error) | High (error) |
| Group 1 (Baseline) | 1.000 | 0.664 | 1.975 |
| Group 2 (Positive Control (Tamoxifen only)) | 18.199 | 3.336 | 4.085 |
| Group 3 (AD07218) | 9.174 | 2.429 | 3.304 |
| Group 4 (AD07219) | 6.604 | 3.138 | 5.978 |
| Group 5 (AD07275) | 0.495 | 0.237 | 0.457 |
| Group 6 (AD07220) | 10.531 | 2.171 | 2.734 |
| Group 7 (AD07276) | 1.563 | 0.215 | 0.249 |
| Group 8 (AD07221) | 15.696 | 3.022 | 3.743 |
| Group 9 (AD07277) | 12.060 | 3.654 | 5.243 |
| Group 10 (AD07396) | 18.914 | 3.786 | 4.733 |

TABLE 9.3

Average relative Wfdc3 expression in EDL (extensor digitorum longus) for mice of Example 3 normalized to Baseline (Group 1).

| | EDL Day 21 | | |
|---|---|---|---|
| | Relative Wfdc3 Expression | Low (error) | High (error) |
| Group 1 (Baseline) | 1.000 | 0.852 | 5.777 |
| Group 2 (Positive Control (Tamoxifen only)) | 12.724 | 1.272 | 1.413 |
| Group 3 (AD07218) | 6.344 | 1.658 | 2.244 |
| Group 4 (AD07219) | 6.694 | 0.893 | 1.031 |
| Group 5 (AD07275) | 1.080 | 0.358 | 0.535 |
| Group 6 (AD07220) | 6.976 | 1.300 | 1.597 |
| Group 7 (AD07276) | 2.512 | 0.508 | 0.638 |
| Group 8 (AD07221) | 8.875 | 1.493 | 1.795 |
| Group 9 (AD07277) | 5.914 | 1.141 | 1.414 |
| Group 10 (AD07396) | 10.992 | 1.059 | 1.172 |

TABLE 9.4

Average relative Wfdc3 expression in gastrocnemius for mice of Example 3 normalized to Baseline (Group 1).

| | Gastrocnemius Day 21 | | |
|---|---|---|---|
| | Relative Wfdc3 Expression | Low (error) | High (error) |
| Group 1 (Baseline) | 1.000 | 0.820 | 4.547 |
| Group 2 (Positive Control (Tamoxifen only)) | 8.719 | 2.368 | 3.251 |
| Group 3 (AD07218) | 4.624 | 0.429 | 0.473 |
| Group 4 (AD07219) | 5.130 | 0.952 | 1.169 |
| Group 5 (AD07275) | 0.897 | 0.290 | 0.430 |
| Group 6 (AD07220) | 6.630 | 0.606 | 0.668 |
| Group 7 (AD07276) | 2.119 | 0.424 | 0.530 |
| Group 8 (AD07221) | 8.283 | 0.689 | 0.751 |
| Group 9 (AD07277) | 5.471 | 0.892 | 1.065 |
| Group 10 (AD07396) | 8.881 | 1.075 | 1.223 |

TABLE 9.5

Average relative Wfdc3 expression in masseter for mice of Example 3 normalized to Baseline (Group 1).

| | Masseter Day 21 | | |
|---|---|---|---|
| | Relative Wfdc3 Expression | Low (error) | High (error) |
| Group 1 (Baseline) | 1.000 | 0.865 | 6.401 |
| Group 2 (Positive Control (Tamoxifen only)) | 14.978 | 3.110 | 3.926 |
| Group 3 (AD07218) | 5.741 | 0.618 | 0.693 |
| Group 4 (AD07219) | 5.675 | 1.998 | 3.083 |
| Group 5 (AD07275) | 1.333 | 0.506 | 0.815 |
| Group 6 (AD07220) | 6.550 | 2.586 | 4.274 |
| Group 7 (AD07276) | 1.952 | 0.492 | 0.659 |
| Group 8 (AD07221) | 11.286 | 3.380 | 4.824 |
| Group 9 (AD07277) | 5.732 | 1.860 | 2.754 |
| Group 10 (AD07396) | 10.845 | 2.718 | 3.627 |

TABLE 9.6

Average relative Wfdc3 expression in soleus for mice of Example 3 normalized to Baseline (Group 1).

| | Soleus Day 21 | | |
|---|---|---|---|
| | Relative Wfdc3 Expression | Low (error) | High (error) |
| Group 1 (Baseline) | 1.000 | 0.692 | 2.243 |
| Group 2 (Positive Control (Tamoxifen only)) | 13.759 | 3.999 | 5.637 |
| Group 3 (AD07218) | 11.716 | 1.296 | 1.457 |
| Group 4 (AD07219) | 14.551 | 2.494 | 3.009 |
| Group 5 (AD07275) | 7.020 | 1.053 | 1.239 |
| Group 6 (AD07220) | 13.022 | 2.046 | 2.427 |
| Group 7 (AD07276) | 8.457 | 1.391 | 1.665 |
| Group 8 (AD07221) | 12.482 | 2.060 | 2.467 |
| Group 9 (AD07277) | 11.943 | 1.119 | 1.235 |
| Group 10 (AD07396) | 14.068 | 1.580 | 1.780 |

TABLE 9.7

Average relative Wfdc3 expression in TA (tibialis anterior) for mice of Example 3 normalized to Baseline (Group 1).

| | TA Day 21 | | |
|---|---|---|---|
| | Relative Wfdc3 Expression | Low (error) | High (error) |
| Group 1 (Baseline) | 1.000 | 0.910 | 10.072 |
| Group 2 (Positive Control (Tamoxifen only)) | 15.728 | 1.743 | 1.961 |
| Group 3 (AD07218) | 6.427 | 0.572 | 0.628 |
| Group 4 (AD07219) | 6.384 | 1.762 | 2.433 |
| Group 5 (AD07275) | 0.983 | 0.425 | 0.749 |
| Group 6 (AD07220) | 8.774 | 1.905 | 2.433 |
| Group 7 (AD07276) | 2.507 | 0.466 | 0.572 |
| Group 8 (AD07221) | 11.377 | 1.958 | 2.366 |
| Group 9 (AD07277) | 7.636 | 1.613 | 2.045 |
| Group 10 (AD07396) | 11.927 | 0.841 | 0.905 |

TABLE 9.8

Average relative Wfdc3 expression in trapezius for mice of Example 3 normalized to Baseline (Group 1).

| | Trapezius Day 21 | | |
|---|---|---|---|
| | Relative Wfdc3 Expression | Low (error) | High (error) |
| Group 1 (Baseline) | 1.000 | 0.846 | 5.489 |
| Group 2 (Positive Control (Tamoxifen only)) | 13.554 | 2.388 | 2.899 |
| Group 3 (AD07218) | 4.817 | 1.669 | 2.554 |
| Group 4 (AD07219) | 3.640 | 1.035 | 1.446 |
| Group 5 (AD07275) | 0.349 | 0.180 | 0.373 |
| Group 6 (AD07220) | 5.388 | 0.974 | 1.189 |
| Group 7 (AD07276) | 0.819 | 0.292 | 0.453 |
| Group 8 (AD07221) | 9.104 | 1.209 | 1.394 |
| Group 9 (AD07277) | 5.020 | 1.571 | 2.288 |
| Group 10 (AD07396) | 10.919 | 1.398 | 1.603 |

TABLE 9.9

Average relative Wfdc3 expression in triceps for mice of Example 3 normalized to Baseline (Group 1).

| | Triceps Day 21 | | |
|---|---|---|---|
| | Relative Wfdc3 Expression | Low (error) | High (error) |
| Group 1 (Baseline) | 1.000 | 0.846 | 5.475 |
| Group 2 (Positive Control (Tamoxifen only)) | 15.243 | 1.053 | 1.131 |
| Group 3 (AD07218) | 3.624 | 1.143 | 1.671 |
| Group 4 (AD07219) | 3.323 | 1.488 | 2.694 |
| Group 5 (AD07275) | 0.334 | 0.114 | 0.173 |
| Group 6 (AD07220) | 5.235 | 0.634 | 0.721 |
| Group 7 (AD07276) | 0.965 | 0.123 | 0.141 |
| Group 8 (AD07221) | 10.811 | 2.080 | 2.575 |
| Group 9 (AD07277) | 5.284 | 1.677 | 2.456 |
| Group 10 (AD07396) | 11.046 | 2.195 | 2.740 |

Additionally, body weight measurements were taken on days 4, 6, 8, 10, 12, 14, 18, 20, and 21. Preservation of body weight can be indicative of a preventative effect. Body weights as normalized to Day 4 (pre-tamoxifen administration) and baseline are shown in FIG. 1.

For the DUX4 RNAi agents shown above, AD07218 (Group 3) included nucleotide sequences designed to inhibit a DUX4 gene (i.e., a DUX4 mRNA transcript) at position 408 of the gene; AD07219 and AD07275 (Groups 4 and 5) included nucleotide sequences designed to inhibit a DUX4 gene at position 409 of the gene; AD07220 and AD07276 (Groups 6 and 7) included nucleotide sequences designed to inhibit a DUX4 gene at position 1437 of the gene; AD07221 and AD07277 (Groups 8 and 9) included nucleotide sequences designed to inhibit a DUX4 gene at position 1518 of the gene; and AD07396 (Group 10) included nucleotide sequences designed to inhibit a DUX4 gene at position 1496 of the gene.

As the data in the tables above show, the DUX4 RNAi agents provide for a reduction in DUX4 gene expression in the FSHD-like mouse model, with the DUX4 RNAi agents targeting positions 408, 409, and 1437 in particular evidencing substantial inhibition of DUX4 gene expression. For example, as shown in Tables 8.1-8.9, the relative expression of DUX4 in Groups 3, 5, and 7 in which a DUX4 RNAi agent was administered remained well below the tamoxifen group and at or below the baseline group in all muscles indicating a preventative effect. This effect was confirmed by the prevention of dramatic increase in Wfdc3 expression in Groups 5 and 7 as shown in Tables 9.1-9.9 and in the prevention of bodyweight loss in Groups 5 and 7 (FIG. 1).

Example 4. In Vivo Administration of RNAi Agents Targeting DUX4 in FSHD-Like Transgenic Mice The FSHD-like transgenic mouse model as described in Example 2 were used to assess DUX4 RNAi agents. DUX4 RNAi agents that included a sense strand and an antisense strand were synthesized according to phosphoramidite technology on solid phase in accordance with general procedures known in the art and commonly used in oligonucleotide synthesis, as set forth in Example 1 herein.

On Study Day 1, mice were injected between the skin and muscle (i.e. subcutaneous injections) into the loose skin region over the neck and shoulder area with either isotonic saline (vehicle control) or a DUX4 RNAi agent formulated in isotonic saline. Starting on day 4, an oral gavage of 100 μL/20 g mouse of either corn oil (negative control) or tamoxifen dissolved in corn oil (1 mg/mL) was administered three times per week (i.e., days 4, 6, 8, 10, 12, 15, 17, and 19) to induce increased expression of DUX4. The dosing regimen and details are set forth in the following Table:

TABLE 10

Dosing Groups for mice of Example 4.

| Group | RNAi agent and Dose | RNAi agent Dosing Regimen | Induction Agent Administration | Induction Agent Dosing Regimen |
|---|---|---|---|---|
| 1 | Baseline (no RNAi agent, saline injection) | N/A | Corn oil (negative control) | 3 times per week starting on day 4 |
| 2 | Positive Control (no RNAi agent, saline injection) | N/A | Tamoxifen | 3 times per week starting on day 4 |
| 3 | SM45b-L4-AD07276-Bis(PEG47 + C22) | 5 mg/kg administered on days 1 and 7 | Tamoxifen | 3 times per week starting on day 4 |
| 4 | SM45b-L4-AD07510-Bis(PEG47 + C22) | 5 mg/kg administered on days 1 and 7 | Tamoxifen | 3 times per week starting on day 4 |
| 5 | SM45b-L4-AD07511-Bis(PEG47 + C22) | 5 mg/kg administered on days 1 and 7 | Tamoxifen | 3 times per week starting on day 4 |
| 6 | SM45b-L4-AD07512-Bis(PEG47 + C22) | 5 mg/kg administered on days 1 and 7 | Tamoxifen | 3 times per week starting on day 4 |
| 7 | SM45b-L4-AD07513-Bis(PEG47 + C22) | 5 mg/kg administered on days 1 and 7 | Tamoxifen | 3 times per week starting on day 4 |
| 8 | SM45b-L4-AD07514-Bis(PEG47 + C22) | 5 mg/kg administered on days 1 and 7 | Tamoxifen | 3 times per week starting on day 4 |
| 9 | SM45b-L4-AD07515-Bis(PEG47 + C22) | 5 mg/kg administered on days 1 and 7 | Tamoxifen | 3 times per week starting on day 4 |
| 10 | SM45b-L4-AD07394-Bis(PEG47 + C22) | 5 mg/kg administered on days 1 and 7 | Tamoxifen | 3 times per week starting on day 4 |
| 11 | SM45b-L4-AD07395-Bis(PEG47 + C22) | 5 mg/kg administered on days 1 and 7 | Tamoxifen | 3 times per week starting on day 4 |
| 12 | SM45b-L4-AD07398-Bis(PEG47 + C22) | 5 mg/kg administered on days 1 and 7 | Tamoxifen | 3 times per week starting on day 4 |
| 13 | SM45b-L4-AD07399-Bis(PEG47 + C22) | 5 mg/kg administered on days 1 and 7 | Tamoxifen | 3 times per week starting on day 4 |

The RNAi agents in Example 4 (Groups 3-13) were synthesized having nucleotide sequences directed to target the DUX4 gene (i.e., DUX4 mRNA transcript), and included a functionalized amine reactive group ($NH_2$-$C_6$) at the 5' terminal end of the sense strand to facilitate conjugation to the skeletal muscle cell receptor small molecule targeting ligand SM45. The targeting ligand SM45 was synthesized as an azide, which allowed for convenient coupling to Linker L4. (See, e.g., Example 3, above, for structural and related information for SM45 and L4).

The DUX4 RNAi agents in Example 2 were further synthesized with a disulfide functional group (C6-SS-C6) at the 3' terminal end of the sense strand to facilitate conjugation to the PK/PD modulator Bis(PEG47+C22). (See, e.g., Example 3, above, for structural information and related information).

The modified RNAi agent nucleotide sequences were synthetized as shown herein in Table 3, Table 4.1, Table 4.6, and Tables 5.1, Table 5.2, Table 5.3, and Table 5.4 (showing the fully modified conjugate).

Five mice were dosed in each Group (n=5), except for Group 1 where only 4 mice were dosed (n=4). On day 22, animals were sacrificed and muscles were harvested, processed, and analyzed in accordance with the procedures described in Example 2.

Figure 2:
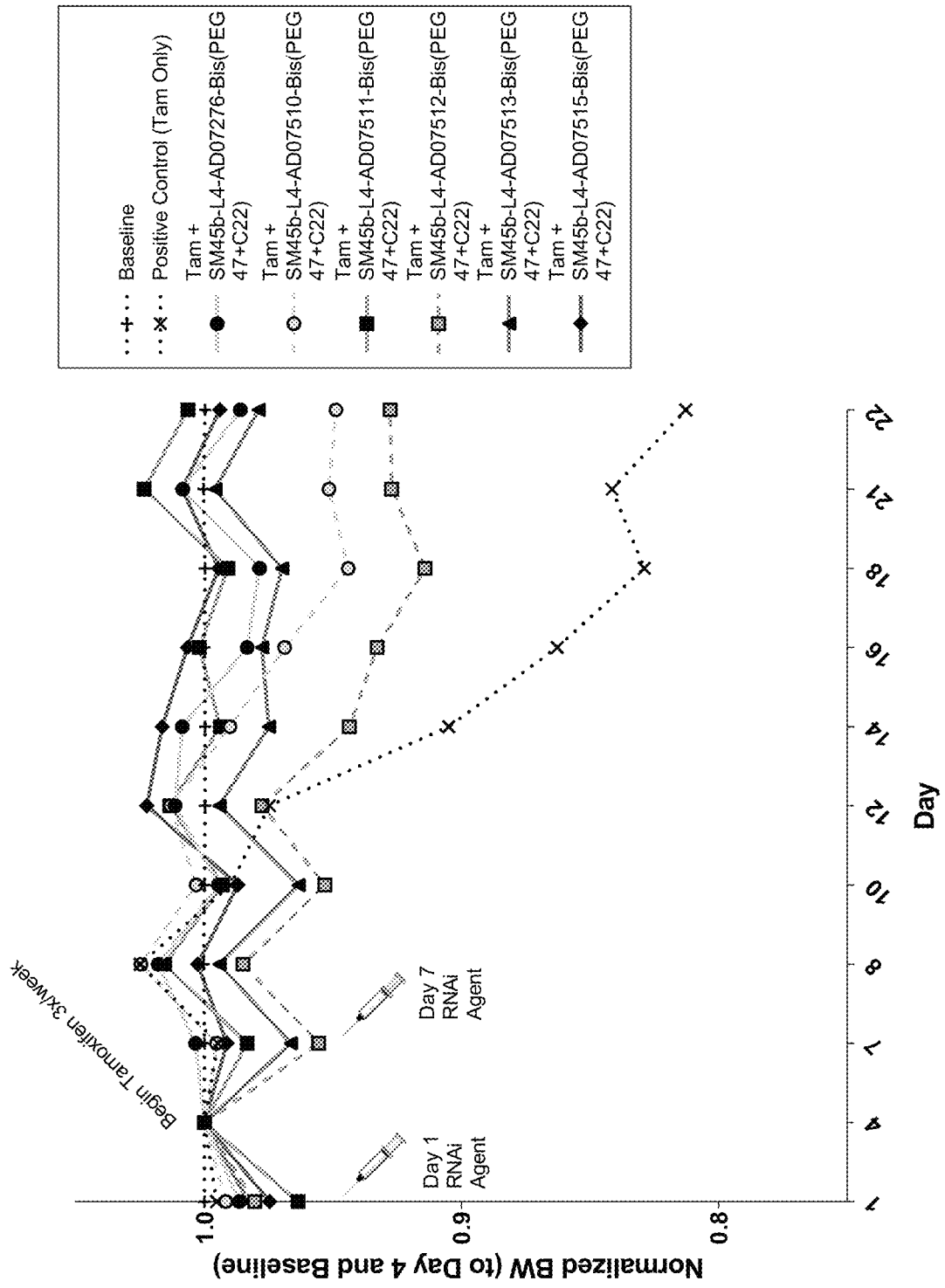
FIG. 2. Graph depicting mean bodyweights of FSHD-like model mice, as more fully described in Example 4.
Figure 3:
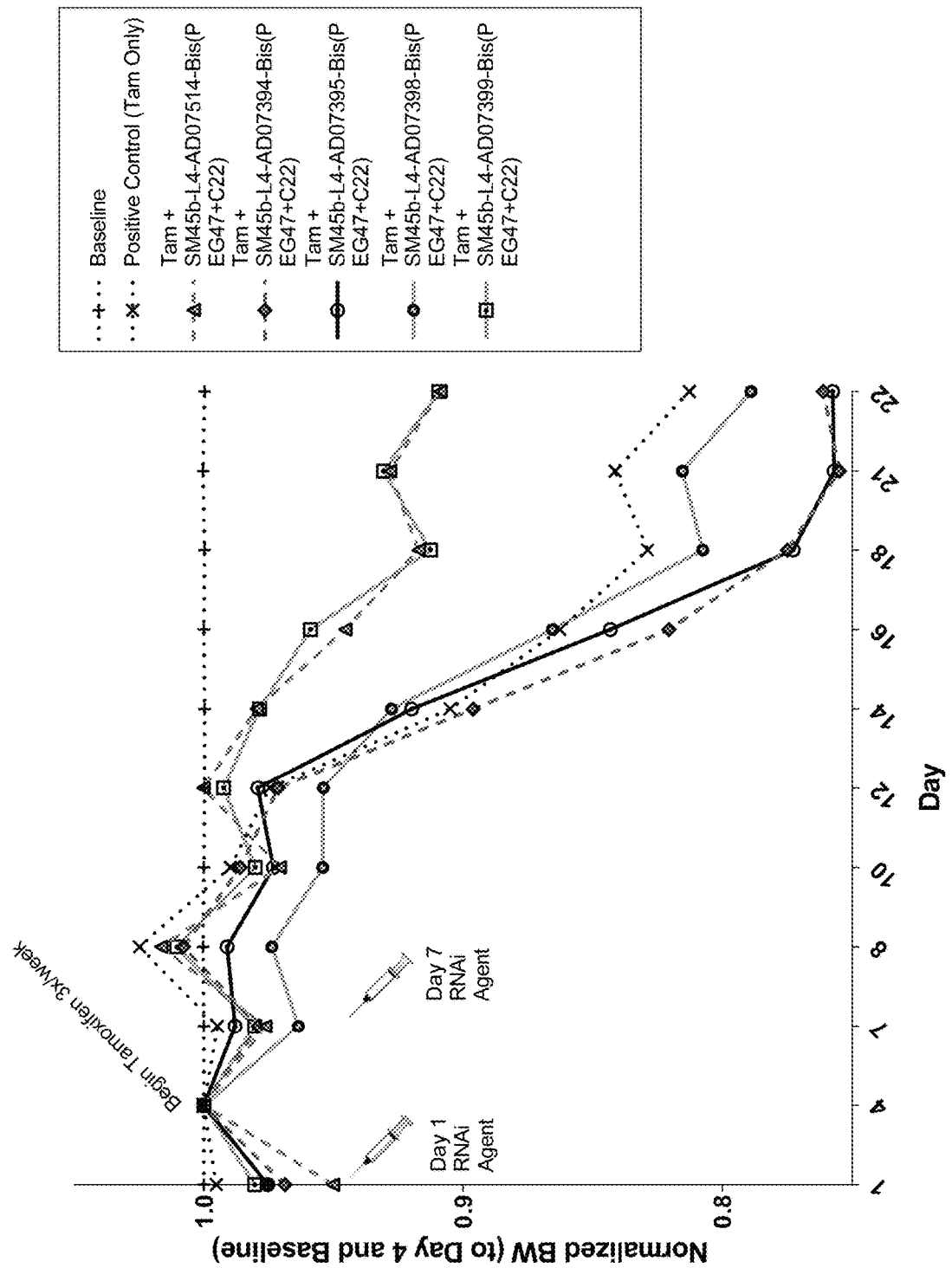
FIG. 3. Graph depicting mean bodyweights of FSHD-like model mice, as more fully described in Example 4.

Body weight measurements were taken on days 1, 4, 7, 8, 10, 12, 14, 18, 21, and 22, and as noted above preservation of body weight can be indicative of a preventative effect on muscle wasting. The RNAi agents of Group 10 (AD07394), Group 11 (AD07395), Group 12 (AD07398), and Group 13 (AD07399) did not show an acceptable preservation of bodyweight compared to the positive control (tamoxifen administration only), and thus further assessments were not made for these Groups. Additionally, while Group 8 (AD07514) and Group 13 (AD07399) both showed some preventative effect of maintaining body weight, body-weights declined more than several other RNAi agents that targeted the same position of the DUX4 gene, and thus further assessments were not made for these Groups either. Body weights as normalized to Day 4 (pre-tamoxifen administration) and baseline are shown in FIGS. 2 and 3.

Average relative DUX4 expression in harvested tissue is shown in the following Tables for various muscle types for Groups 1-7 and 9:

TABLE 11.1

Average relative DUX4 expression in biceps for mice of Example 4 normalized to Baseline (Group 1).

| | Biceps Day 22 | |
|---|---|---|
| | Relative DUX4 Expression | Standard Deviation (+/−) |
| Group 1 (Baseline) | 1.000 | 0.498 |
| Group 2 (Positive Control (Tamoxifen only)) | 1.678 | 0.299 |
| Group 3 (AD07276) | 1.016 | 0.167 |
| Group 4 (AD07510) | 0.861 | 0.345 |
| Group 5 (AD07511) | 0.819 | 0.161 |
| Group 6 (AD07512) | 1.045 | 0.509 |
| Group 7 (AD07513) | 0.716 | 0.157 |
| Group 9 (AD07515) | 0.834 | 0.430 |

TABLE 11.2

Average relative DUX4 expression in diaphragm for mice of Example 4 normalized to Baseline (Group 1).

| | Diaphragm Day 22 | |
|---|---|---|
| | Relative DUX4 Expression | Standard Deviation (+/−) |
| Group 1 (Baseline) | 1.000 | 0.226 |
| Group 2 (Positive Control (Tamoxifen only)) | 2.273 | 0.830 |

TABLE 11.2-continued

Average relative DUX4 expression in diaphragm for mice of Example 4 normalized to Baseline (Group 1).

| | Diaphragm Day 22 | |
|---|---|---|
| | Relative DUX4 Expression | Standard Deviation (+/−) |
| Group 3 (AD07276) | 1.535 | 0.519 |
| Group 4 (AD07510) | 1.096 | 0.361 |
| Group 5 (AD07511) | 0.755 | 0.158 |
| Group 6 (AD07512) | 2.129 | 0.429 |
| Group 7 (AD07513) | 1.230 | 0.440 |
| Group 9 (AD07515) | 0.757 | 0.252 |

TABLE 11.3

Average relative DUX4 expression in gastrocnemius for mice of Example 4 normalized to Baseline (Group 1).

| | Gastrocnemius Day 22 | |
|---|---|---|
| | Relative DUX4 Expression | Standard Deviation (+/−) |
| Group 1 (Baseline) | 1.000 | 0.272 |
| Group 2 (Positive Control (Tamoxifen only)) | 1.156 | 0.212 |
| Group 3 (AD07276) | 1.264 | 0.107 |
| Group 4 (AD07510) | 0.872 | 0.376 |
| Group 5 (AD07511) | 0.534 | 0.101 |
| Group 6 (AD07512) | 0.987 | 0.248 |
| Group 7 (AD07513) | 1.318 | 0.994 |
| Group 9 (AD07515) | 1.756 | 0.744 |

TABLE 11.4

Average relative DUX4 expression in masseter for mice of Example 4 normalized to Baseline (Group 1).

| | Masseter Day 22 | |
|---|---|---|
| | Relative DUX4 Expression | Standard Deviation (+/−) |
| Group 1 (Baseline) | 1.000 | 0.267 |
| Group 2 (Positive Control (Tamoxifen only)) | 0.867 | 0.165 |
| Group 3 (AD07276) | 0.500 | 0.153 |
| Group 4 (AD07510) | 0.603 | 0.215 |
| Group 5 (AD07511) | 0.449 | 0.142 |
| Group 6 (AD07512) | 0.915 | 0.236 |
| Group 7 (AD07513) | 0.438 | 0.105 |
| Group 9 (AD07515) | 0.447 | 0.094 |

TABLE 11.5

Average relative DUX4 expression in TA (tibialis anterior) for mice of Example 4 normalized to Baseline (Group 1).

| | TA Day 22 | |
|---|---|---|
| | Relative DUX4 Expression | Standard Deviation (+/−) |
| Group 1 (Baseline) | 1.000 | 0.177 |
| Group 2 (Positive Control (Tamoxifen only)) | 1.429 | 0.484 |
| Group 3 (AD07276) | 0.767 | 0.117 |
| Group 4 (AD07510) | 0.643 | 0.105 |
| Group 5 (AD07511) | 0.516 | 0.161 |

TABLE 11.5-continued

Average relative DUX4 expression in TA (tibialis anterior) for mice of Example 4 normalized to Baseline (Group 1).

| | TA Day 22 | |
|---|---|---|
| | Relative DUX4 Expression | Standard Deviation (+/−) |
| Group 6 (AD07512) | 0.775 | 0.189 |
| Group 7 (AD07513) | 0.634 | 0.207 |
| Group 9 (AD07515) | 0.618 | 0.171 |

TABLE 11.6

Average relative DUX4 expression in trapezius for mice of Example 4 normalized to Baseline (Group 1).

| | Trapezius Day 22 | |
|---|---|---|
| | Relative DUX4 Expression | Standard Deviation (+/−) |
| Group 1 (Baseline) | 1.000 | 0.306 |
| Group 2 (Positive Control (Tamoxifen only)) | 1.669 | 0.280 |
| Group 3 (AD07276) | 0.707 | 0.210 |
| Group 4 (AD07510) | 0.710 | 0.233 |
| Group 5 (AD07511) | 0.543 | 0.161 |
| Group 6 (AD07512) | 0.833 | 0.290 |
| Group 7 (AD07513) | 0.541 | 0.193 |
| Group 9 (AD07515) | 0.549 | 0.248 |

TABLE 11.7

Average relative DUX4 expression in triceps for mice of Example 4 normalized to Baseline (Group 1).

| | Triceps Day 22 | |
|---|---|---|
| | Relative DUX4 Expression | Standard Deviation (+/−) |
| Group 1 (Baseline) | 1.000 | 0.410 |
| Group 2 (Positive Control (Tamoxifen only)) | 1.679 | 0.885 |
| Group 3 (AD07276) | 0.487 | 0.081 |
| Group 4 (AD07510) | 0.480 | 0.096 |
| Group 5 (AD07511) | 0.391 | 0.118 |
| Group 6 (AD07512) | 0.550 | 0.179 |
| Group 7 (AD07513) | 0.327 | 0.120 |
| Group 9 (AD07515) | 0.287 | 0.074 |

Average relative Wfdc3 mRNA transcript levels in harvested tissue were similarly determined as shown in the following Tables for various muscle types for Groups 1-7 and 9:

TABLE 12.1

Average relative Wfdc3 expression in biceps for mice of Example 4 normalized to Baseline (Group 1).

| | Biceps Day 22 | | |
|---|---|---|---|
| | Relative Wfdc3 Expression | Low (error) | High (error) |
| Group 1 (Baseline) | 1.000 | 0.900 | 9.018 |
| Group 2 (Positive Control (Tamoxifen only)) | 16.231 | 4.505 | 6.236 |
| Group 3 (AD07276) | 4.928 | 1.787 | 2.802 |
| Group 4 (AD07510) | 9.048 | 3.580 | 5.925 |
| Group 5 (AD07511) | 1.478 | 0.415 | 0.577 |

TABLE 12.1-continued

Average relative Wfdc3 expression in biceps for mice of Example 4 normalized to Baseline (Group 1).

| | Biceps Day 22 | | |
|---|---|---|---|
| | Relative Wfdc3 Expression | Low (error) | High (error) |
| Group 6 (AD07512) | 13.042 | 2.577 | 3.212 |
| Group 7 (AD07513) | 1.922 | 0.834 | 1.475 |
| Group 9 (AD07515) | 2.589 | 1.172 | 2.141 |

TABLE 12.2

Average relative Wfdc3 expression in diaphragm for mice of Example 4 normalized to Baseline (Group 1).

| | Diaphragm Day 22 | | |
|---|---|---|---|
| | Relative Wfdc3 Expression | Low (error) | High (error) |
| Group 1 (Baseline) | 1.000 | 0.780 | 3.554 |
| Group 2 (Positive Control (Tamoxifen only)) | 17.540 | 6.624 | 10.642 |
| Group 3 (AD07276) | 1.834 | 0.986 | 2.132 |
| Group 4 (AD07510) | 7.582 | 3.337 | 5.960 |
| Group 5 (AD07511) | 0.531 | 0.164 | 0.236 |
| Group 6 (AD07512) | 10.993 | 2.761 | 3.687 |
| Group 7 (AD07513) | 0.621 | 0.297 | 0.570 |
| Group 9 (AD07515) | 1.024 | 0.319 | 0.463 |

TABLE 12.3

Average relative Wfdc3 expression in gastrocnemius for mice of Example 4 normalized to Baseline (Group 1).

| | Gastrocnemius Day 22 | | |
|---|---|---|---|
| | Relative Wfdc3 Expression | Low (error) | High (error) |
| Group 1 (Baseline) | 1.000 | 0.799 | 3.981 |
| Group 2 (Positive Control (Tamoxifen only)) | 5.449 | 1.871 | 2.849 |
| Group 3 (AD07276) | 1.455 | 0.533 | 0.842 |
| Group 4 (AD07510) | 3.452 | 0.735 | 0.934 |
| Group 5 (AD07511) | 0.461 | 0.104 | 0.135 |
| Group 6 (AD07512) | 3.895 | 0.420 | 0.470 |
| Group 7 (AD07513) | 0.590 | 0.228 | 0.371 |
| Group 9 (AD07515) | 0.712 | 0.284 | 0.472 |

TABLE 12.4

Average relative Wfdc3 expression in masseter for mice of Example 4 normalized to Baseline (Group 1).

| | Masseter Day 22 | | |
|---|---|---|---|
| | Relative Wfdc3 Expression | Low (error) | High (error) |
| Group 1 (Baseline) | 1.000 | 0.794 | 3.862 |
| Group 2 (Positive Control (Tamoxifen only)) | 7.246 | 2.966 | 5.021 |
| Group 3 (AD07276) | 1.353 | 0.595 | 1.062 |
| Group 4 (AD07510) | 3.051 | 0.834 | 1.148 |
| Group 5 (AD07511) | 0.299 | 0.093 | 0.135 |
| Group 6 (AD07512) | 3.994 | 1.011 | 1.354 |
| Group 7 (AD07513) | 0.337 | 0.152 | 0.275 |
| Group 9 (AD07515) | 0.569 | 0.154 | 0.212 |

TABLE 12.5

Average relative Wfdc3 expression in TA (tibialis anterior) for mice of Example 4 normalized to Baseline (Group 1).

| | TA Day 22 | | |
|---|---|---|---|
| | Relative Wfdc3 Expression | Low (error) | High (error) |
| Group 1 (Baseline) | 1.000 | 0.925 | 12.306 |
| Group 2 (Positive Control (Tamoxifen only)) | 18.324 | 8.692 | 16.536 |
| Group 3 (AD07276) | 2.436 | 1.027 | 1.775 |
| Group 4 (AD07510) | 5.873 | 1.830 | 2.658 |
| Group 5 (AD07511) | 0.539 | 0.235 | 0.417 |
| Group 6 (AD07512) | 7.128 | 1.095 | 1.293 |
| Group 7 (AD07513) | 0.694 | 0.314 | 0.574 |
| Group 9 (AD07515) | 1.148 | 0.481 | 0.827 |

TABLE 12.6

Average relative Wfdc3 expression in trapezius for mice of Example 4 normalized to Baseline (Group 1).

| | Trapezius Day 22 | | |
|---|---|---|---|
| | Relative Wfdc3 Expression | Low (error) | High (error) |
| Group 1 (Baseline) | 1.000 | 0.840 | 5.248 |
| Group 2 (Positive Control (Tamoxifen only)) | 8.145 | 3.444 | 5.969 |
| Group 3 (AD07276) | 0.966 | 0.529 | 1.168 |
| Group 4 (AD07510) | 3.212 | 1.085 | 1.638 |
| Group 5 (AD07511) | 0.154 | 0.052 | 0.079 |
| Group 6 (AD07512) | 4.472 | 1.194 | 1.629 |
| Group 7 (AD07513) | 0.206 | 0.101 | 0.197 |
| Group 9 (AD07515) | 0.379 | 0.157 | 0.267 |

TABLE 12.7

Average relative Wfdc3 expression in triceps for mice of Example 4 normalized to Baseline (Group 1).

| | Triceps Day 22 | | |
|---|---|---|---|
| | Relative Wfdc3 Expression | Low (error) | High (error) |
| Group 1 (Baseline) | 1.000 | 0.853 | 5.811 |
| Group 2 (Positive Control (Tamoxifen only)) | 8.594 | 3.757 | 6.675 |
| Group 3 (AD07276) | 1.115 | 0.472 | 0.820 |
| Group 4 (AD07510) | 3.253 | 0.926 | 1.295 |
| Group 5 (AD07511) | 0.326 | 0.108 | 0.161 |
| Group 6 (AD07512) | 3.948 | 0.932 | 1.219 |
| Group 7 (AD07513) | 0.451 | 0.168 | 0.268 |
| Group 9 (AD07515) | 0.590 | 0.176 | 0.251 |

For the DUX4 RNAi agents shown above, AD07276, AD07510, AD07511, AD07512, AD07513, AD07514, AD07515 (Groups 3-9) included nucleotide sequences designed to inhibit a DUX4 gene (i.e., DUX4 mRNA transcript) at position 1437 of the gene; AD07394 and AD07395 (Groups 10 and 11) included nucleotide sequences designed to inhibit a DUX4 gene at position 1433 of the gene; AD07398 and AD07399 (Groups 12 and 13) included nucleotide sequences designed to inhibit a DUX4 gene at position 1522 of the gene.

As the data in the tables above show, the DUX4 RNAi agents targeting position 1437 of the gene provide for a reduction in DUX4 gene expression in the FSHD-like mouse model. Of particular note, DUX4 gene expression levels were observed to be below baseline and Wfdc3 gene expression levels were observed to be far below baseline in 7 of 7 muscles assayed from mice administered AD07511 (see Tables 11.1-11.7 and 12.1-12.7).

Example 5. In Vivo Administration of RNAi Agents Targeting DUX4 in FSHD-Like Transgenic Mice The FSHD-like transgenic mouse model as described in Example 2 were used to assess DUX4 RNAi agents. DUX4 RNAi agents that included a sense strand and an antisense strand were synthesized according to phosphoramidite technology on solid phase in accordance with general procedures known in the art and commonly used in oligonucleotide synthesis, as set forth in Example 1 herein.

On Study Day 1, mice were injected between the skin and muscle (i.e. subcutaneous injections) into the loose skin region over the neck and shoulder area with either isotonic saline (vehicle control) or a DUX4 RNAi agent formulated in isotonic saline. Starting on day 4, an oral gavage of 100 µL/20 g mouse of either corn oil (negative control) or tamoxifen dissolved in corn oil (1 mg/mL) was administered three times per week (days 4, 6, 8, 10, 12, 15, 17, and 19) to induce increased expression of DUX4. The dosing regimen and details are set forth in the following Table:

and Tables 5.1, Table 5.2, Table 5.3, and Table 5.4 (showing the fully modified conjugate).

Five mice were dosed in each Group (n=5). On day 22, animals were sacrificed and muscles were harvested, processed, and analyzed in accordance with the procedures described in Example 2.

Figure 4:
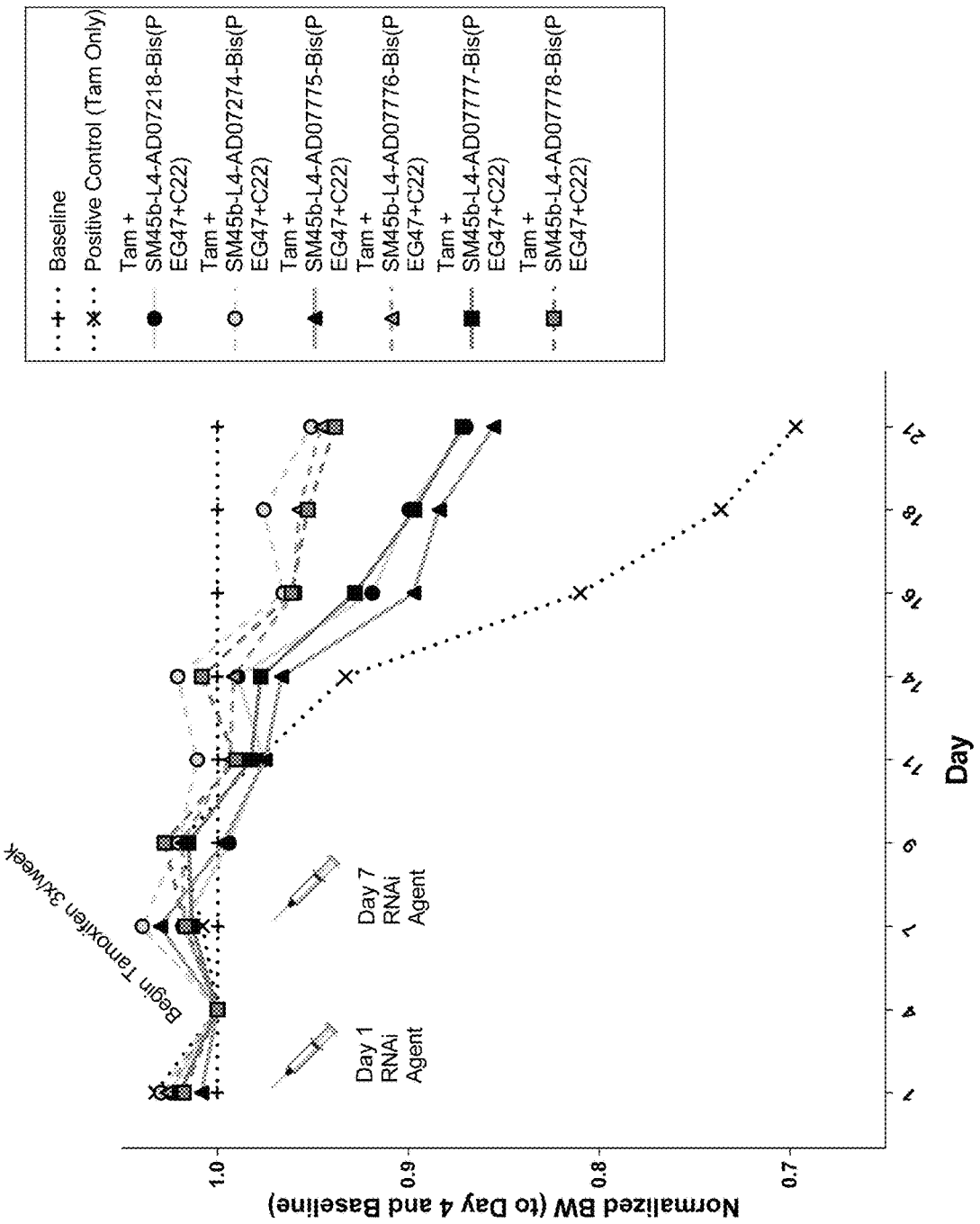
FIG. 4. Graph depicting mean bodyweights of FSHD-like model mice, as more fully described in Example 5.

Body weight measurements were taken on days 1, 4, 7, 9, 11, 14, 16, 18, and 21, and as noted above preservation of body weight can be indicative of preventative effect on muscle wasting. The RNAi agents of Group 3 (AD07218), Group 5 (AD07775), and Group 7 (AD07777), showed some preventative effect of maintaining body weight. However, the DUX4 RNAi agents of AD07274, AD07776, and AD07778 performed the best of the RNAi agents tested with respect to retaining animal body weight after administration of tamoxifen, and were subject to additional assessments. Body weights as normalized to day 4 (pre-tamoxifen administration) and baseline are shown in FIG. 4.

Average relative DUX4 expression in harvested tissue is shown in the following Tables for various muscle types for Groups 1, 2, 4, 6, and 8:

TABLE 13

Dosing Groups for mice of Example 5.

| Group | RNAi agent and Dose | RNAi agent Dosing Regimen | Induction Agent Administration | Induction Agent Dosing Regimen |
|---|---|---|---|---|
| 1 | Baseline (no RNAi agent, saline injection) | N/A | Corn oil (negative control) | 3 times per week starting on day 4 |
| 2 | Positive Control (no RNAi agent, saline injection) | N/A | Tamoxifen | 3 times per week starting on day 4 |
| 3 | SM45b-L4-AD07218-Bis(PEG47 + C22) | 5 mg/kg administered on days 1 and 7 | Tamoxifen | 3 times per week starting on day 4 |
| 4 | SM45b-L4-AD07274-Bis(PEG47 + C22) | 5 mg/kg administered on days 1 and 7 | Tamoxifen | 3 times per week starting on day 4 |
| 5 | SM45b-L4-AD07775-Bis(PEG47 + C22) | 5 mg/kg administered on days 1 and 7 | Tamoxifen | 3 times per week starting on day 4 |
| 6 | SM45b-L4-AD07776-Bis(PEG47 + C22) | 5 mg/kg administered on days 1 and 7 | Tamoxifen | 3 times per week starting on day 4 |
| 7 | SM456-L4-AD07777-Bis(PEG47 + C22) | 5 mg/kg administered on days 1 and 7 | Tamoxifen | 3 times per week starting on day 4 |
| 8 | SM45b-L4-AD07778-Bis(PEG47 + C22) | 5 mg/kg administered on days 1 and 7 | Tamoxifen | 3 times per week starting on day 4 |

The RNAi agents in Example 5 (Groups 3-8) were synthesized having nucleotide sequences directed to target the DUX4 gene, and included a functionalized amine reactive group ($NH_2$-$C_6$) at the 5' terminal end of the sense strand to facilitate conjugation to the skeletal muscle cell receptor small molecule targeting ligand SM45. The targeting ligand SM45 was synthesized as an azide, which allowed for convenient coupling to Linker L4. (See, e.g., Example 3, above, for structural and related information for SM45 and L4).

The DUX4 RNAi agents in Example 2 were further synthesized with a disulfide functional group (C6-SS-C6) at the 3' terminal end of the sense strand to facilitate conjugation to the PK/PD modulator Bis(PEG47+C22). (See, e.g., Example 3, above, for structural information and related information).

The modified RNAi agent nucleotide sequences were synthetized as shown herein in Table 3, Table 4.1, Table 4.6,

TABLE 14.1

Average relative DUX4 expression in biceps for mice of Example 5 normalized to Baseline (Group 1).

| | Biceps Day 22 | |
|---|---|---|
| | Relative DUX4 Expression | Standard Deviation (+/−) |
| Group 1 (Baseline) | 1.000 | 0.634 |
| Group 2 (Positive Control (Tamoxifen only)) | 2.414 | 0.840 |
| Group 4 (AD07274) | 0.725 | 0.353 |
| Group 6 (AD07776) | 1.092 | 0.394 |
| Group 8 (AD07778) | 1.534 | 0.738 |

TABLE 14.2

Average relative DUX4 expression in diaphragm for mice of Example 5 normalized to Baseline (Group 1).

| | Diaphragm Day 22 | |
|---|---|---|
| | Relative DUX4 Expression | Standard Deviation (+/−) |
| Group 1 (Baseline) | 1.000 | 0.504 |
| Group 2 (Positive Control (Tamoxifen only)) | 2.024 | 0.872 |
| Group 4 (AD07274) | 0.488 | 0.062 |
| Group 6 (AD07776) | 0.745 | 0.198 |
| Group 8 (AD07778) | 0.734 | 0.466 |

TABLE 14.3

Average relative DUX4 expression in gastrocnemius for mice of Example 5 normalized to Baseline (Group 1).

| | Gastrocnemius Day 22 | |
|---|---|---|
| | Relative DUX4 Expression | Standard Deviation (+/−) |
| Group 1 (Baseline) | 1.000 | 0.308 |
| Group 2 (Positive Control (Tamoxifen only)) | 2.343 | 1.059 |
| Group 4 (AD07274) | 0.643 | 0.397 |
| Group 6 (AD07776) | 0.676 | 0.310 |
| Group 8 (AD07778) | 0.634 | 0.353 |

TABLE 14.4

Average relative DUX4 expression in masseter for mice of Example 5 normalized to Baseline (Group 1).

| | Masseter Day 22 | |
|---|---|---|
| | Relative DUX4 Expression | Standard Deviation (+/−) |
| Group 1 (Baseline) | 1.000 | 0.388 |
| Group 2 (Positive Control (Tamoxifen only)) | 1.974 | 0.761 |
| Group 4 (AD07274) | 0.685 | 0.236 |
| Group 6 (AD07776) | 0.639 | 0.190 |
| Group 8 (AD07778) | 0.798 | 0.127 |

TABLE 14.5

Average relative DUX4 expression in TA (tibialis anterior) for mice of Example 5 normalized to Baseline (Group 1).

| | TA Day 22 | |
|---|---|---|
| | Relative DUX4 Expression | Standard Deviation (+/−) |
| Group 1 (Baseline) | 1.000 | 0.180 |
| Group 2 (Positive Control (Tamoxifen only)) | 1.471 | 0.503 |
| Group 4 (AD07274) | 0.623 | 0.176 |
| Group 6 (AD07776) | 0.616 | 0.123 |
| Group 8 (AD07778) | 0.768 | 0.258 |

TABLE 14.6

Average relative DUX4 expression in trapezius for mice of Example 5 normalized to Baseline (Group 1).

| | Trapezius Day 22 | |
|---|---|---|
| | Relative DUX4 Expression | Standard Deviation (+/−) |
| Group 1 (Baseline) | 1.000 | 0.216 |
| Group 2 (Positive Control (Tamoxifen only)) | 4.907 | 2.097 |
| Group 4 (AD07274) | 0.930 | 0.487 |
| Group 6 (AD07776) | 1.180 | 0.273 |
| Group 8 (AD07778) | 1.106 | 0.965 |

TABLE 14.7

Average relative DUX4 expression in triceps for mice of Example 5 normalized to Baseline (Group 1).

| | Triceps Day 22 | |
|---|---|---|
| | Relative DUX4 Expression | Standard Deviation (+/−) |
| Group 1 (Baseline) | 1.000 | 0.421 |
| Group 2 (Positive Control (Tamoxifen only)) | 2.284 | 0.888 |
| Group 4 (AD07274) | 1.004 | 0.697 |
| Group 6 (AD07776) | 0.666 | 0.346 |
| Group 8 (AD07778) | 0.768 | 0.529 |

TABLE 15.1

Average relative Wfdc3 expression in biceps for mice of Example 5 normalized to Baseline (Group 1).

| | Biceps Day 22 | | |
|---|---|---|---|
| | Relative Wfdc3 Expression | Low (error) | High (error) |
| Group 1 (Baseline) | 1.000 | 0.848 | 5.574 |
| Group 2 (Positive Control (Tamoxifen only)) | 37.917 | 4.969 | 5.718 |
| Group 4 (AD07274) | 3.269 | 1.221 | 1.948 |
| Group 6 (AD07776) | 1.017 | 0.316 | 0.459 |
| Group 8 (AD07778) | 0.940 | 0.580 | 1.518 |

Average relative Wfdc3 mRNA transcript levels in harvested tissue were similarly determined as shown in the following Tables for various muscle types for Groups 1, 2, 4, 6, and 8:

TABLE 15.2

Average relative Wfdc3 expression in diaphragm for mice of Example 5 normalized to Baseline (Group 1).

| | Diaphragm Day 22 | | |
|---|---|---|---|
| | Relative Wfdc3 Expression | Low (error) | High (error) |
| Group 1 (Baseline) | 1.000 | 0.814 | 4.371 |
| Group 2 (Positive Control (Tamoxifen only)) | 69.613 | 13.167 | 16.238 |
| Group 4 (AD07274) | 0.766 | 0.260 | 0.393 |
| Group 6 (AD07776) | 0.307 | 0.139 | 0.256 |
| Group 8 (AD07778) | 0.323 | 0.166 | 0.342 |

TABLE 15.3

Average relative Wfdc3 expression in gastrocnemius for mice of Example 5 normalized to Baseline (Group 1).

| | Gastrocnemius Day 22 | | |
|---|---|---|---|
| | Relative Wfdc3 Expression | Low (error) | High (error) |
| Group 1 (Baseline) | 1.000 | 0.807 | 4.179 |
| Group 2 (Positive Control (Tamoxifen only)) | 17.428 | 2.830 | 3.378 |
| Group 4 (AD07274) | 1.136 | 0.303 | 0.414 |
| Group 6 (AD07776) | 0.339 | 0.091 | 0.124 |
| Group 8 (AD07778) | 0.458 | 0.166 | 0.260 |

TABLE 15.4

Average relative Wfdc3 expression in masseter for mice of Example 5 normalized to Baseline (Group 1).

| | Masseter Day 22 | | |
|---|---|---|---|
| | Relative Wfdc3 Expression | Low (error) | High (error) |
| Group 1 (Baseline) | 1.000 | 0.825 | 4.715 |
| Group 2 (Positive Control (Tamoxifen only)) | 16.944 | 2.072 | 2.361 |
| Group 4 (AD07274) | 0.646 | 0.191 | 0.272 |
| Group 6 (AD07776) | 0.061 | 0.009 | 0.011 |
| Group 8 (AD07778) | 0.089 | 0.052 | 0.126 |

TABLE 15.5

Average relative Wfdc3 expression in TA (tibialis anterior) for mice of Example 5 normalized to Baseline (Group 1).

| | TA Day 22 | | |
|---|---|---|---|
| | Relative Wfdc3 Expression | Low (error) | High (error) |
| Group 1 (Baseline) | 1.000 | 0.867 | 6.517 |
| Group 2 (Positive Control (Tamoxifen only)) | 41.110 | 5.691 | 6.605 |
| Group 4 (AD07274) | 1.034 | 0.265 | 0.356 |
| Group 6 (AD07776) | 0.198 | 0.122 | 0.314 |
| Group 8 (AD07778) | 0.294 | 0.204 | 0.670 |

TABLE 15.6

Average relative Wfdc3 expression in trapezius for mice of Example 5 normalized to Baseline (Group 1).

| | Trapezius Day 22 | | |
|---|---|---|---|
| | Relative Wfdc3 Expression | Low (error) | High (error) |
| Group 1 (Baseline) | 1.000 | 0.851 | 5.697 |
| Group 2 (Positive Control (Tamoxifen only)) | 31.526 | 3.384 | 3.791 |
| Group 4 (AD07274) | 0.424 | 0.255 | 0.640 |
| Group 6 (AD07776) | 0.073 | 0.027 | 0.043 |
| Group 8 (AD07778) | 0.099 | 0.053 | 0.113 |

TABLE 15.7

Average relative Wfdc3 expression in triceps for mice of Example 5 normalized to Baseline (Group 1).

| | Triceps Day 22 | | |
|---|---|---|---|
| | Relative Wfdc3 Expression | Low (error) | High (error) |
| Group 1 (Baseline) | 1.000 | 0.774 | 3.428 |
| Group 2 (Positive Control (Tamoxifen only)) | 23.499 | 3.361 | 3.922 |
| Group 4 (AD07274) | 0.385 | 0.124 | 0.182 |
| Group 6 (AD07776) | 0.060 | 0.032 | 0.067 |
| Group 8 (AD07778) | 0.100 | 0.053 | 0.113 |

For all of the DUX4 RNAi agents shown above, the RNAi agents included nucleotide sequences designed to inhibit a DUX4 gene at position 408 of the gene. As shown herein, the DUX4 RNAi agents showed substantial reductions in relevant parameters, with AD07776 and AD07778 having particular potency in reducing DUX4 and Wfdc3 gene expression.

Example 6. In Vivo Administration of RNAi Agents Targeting DUX4 in FSHD-Like Transgenic Mice The FSHD-like transgenic mouse model as described in Example 2 were used to assess DUX4 RNAi agents. DUX4 RNAi agents that included a sense strand and an antisense strand were synthesized according to phosphoramidite technology on solid phase in accordance with general procedures known in the art and commonly used in oligonucleotide synthesis, as set forth in Example 1 herein.

On Study Day 1, mice were injected between the skin and muscle (i.e. subcutaneous injections) into the loose skin region over the neck and shoulder area with either isotonic saline (vehicle control) or a DUX4 RNAi agent formulated in isotonic saline. Starting on day 4, an oral gavage of 100 µL/20 g mouse of either corn oil (negative control) or tamoxifen dissolved in corn oil (1 mg/mL) was administered three times per week (days 4, 6, 8, 10, 12, 15, 17, and 19) to induce increased expression of DUX4. The dosing regimen and details are set forth in the following Table:

TABLE 16

Dosing Groups for mice of Example 6.

| Group | RNAi agent and Dose | RNAi agent Dosing Regimen | Induction Agent Administration | Induction Agent Dosing Regimen |
|---|---|---|---|---|
| 1 | Baseline (no RNAi agent, saline injection) | N/A | Corn oil (negative control) | 3 times per week starting on day 4 |
| 2 | Positive Control (no RNAi agent, saline injection) | N/A | Tamoxifen | 3 times per week starting on day 4 |
| 3 | SM45b-L4-AD07511-Bis(PEG47 + C22) | 1 mg/kg administered on days 1 and 7 | Tamoxifen | 3 times per week starting on day 4 |
| 4 | SM45b-L4-AD07511-Bis(PEG47 + C22) | 5 mg/kg administered on days 1 and 7 | Tamoxifen | 3 times per week starting on day 4 |
| 5 | SM45b-L4-AD07843-Bis(PEG47 + C22) | 1 mg/kg administered on days 1 and 7 | Tamoxifen | 3 times per week starting on day 4 |
| 6 | SM45b-L4-AD07843-Bis(PEG47 + C22) | 5 mg/kg administered on days 1 and 7 | Tamoxifen | 3 times per week starting on day 4 |
| 7 | SM45b-L4-AD07844-Bis(PEG47 + C22) | 1 mg/kg administered on days 1 and 7 | Tamoxifen | 3 times per week starting on day 4 |
| 8 | SM456-L4-AD07844-Bis(PEG47 + C22) | 5 mg/kg administered on days 1 and 7 | Tamoxifen | 3 times per week starting on day 4 |
| 9 | SM45b-L4-AD07776-Bis(PEG47 + C22) | 1 mg/kg administered on days 1 and 7 | Tamoxifen | 3 times per week starting on day 4 |
| 10 | SM45b-L4-AD07776-Bis(PEG47 + C22) | 5 mg/kg administered on days 1 and 7 | Tamoxifen | 3 times per week starting on day 4 |
| 11 | SM45b-L4-AD07778-Bis(PEG47 + C22) | 1 mg/kg administered on days 1 and 7 | Tamoxifen | 3 times per week starting on day 4 |
| 12 | SM45b-L4-AD07778-Bis(PEG47 + C22) | 5 mg/kg administered on days 1 and 7 | Tamoxifen | 3 times per week starting on day 4 |
| 13 | αvβ6 Peptide 1-AD07511-LP38b | 1 mg/kg administered on days 1 and 7 | Tamoxifen | 3 times per week starting on day 4 |
| 14 | αvβ6 Peptide 1-AD07511-LP38b | 1 mg/kg administered on days 1 and 7 | Tamoxifen | 3 times per week starting on day 4 |

The RNAi agents in Example 6 (Groups 3-14) were synthesized having nucleotide sequences directed to target the DUX4 gene, and included a functionalized amine reactive group ($NH_2$-$C_6$) at the 5' terminal end of the sense strand to facilitate conjugation to the respective targeting ligand.

For Groups 3-12, the targeting ligand SM45 was synthesized as an azide, which allowed for convenient coupling to Linker L4. (See, e.g., Example 3, above, for structural and related information for SM45 and L4).

For Groups 13-14, a peptide having affinity for a receptor present on skeletal muscle cells was conjugated to the sense strand of the DUX4 RNAi agent. The skeletal muscle cell receptor peptide (Peptide 1) was linked to the RNAi agent via an amide coupling reaction as described in Example 1, above at the 5' end of the sense strand. αvβ6 Peptide 1 is represented by the following structure:

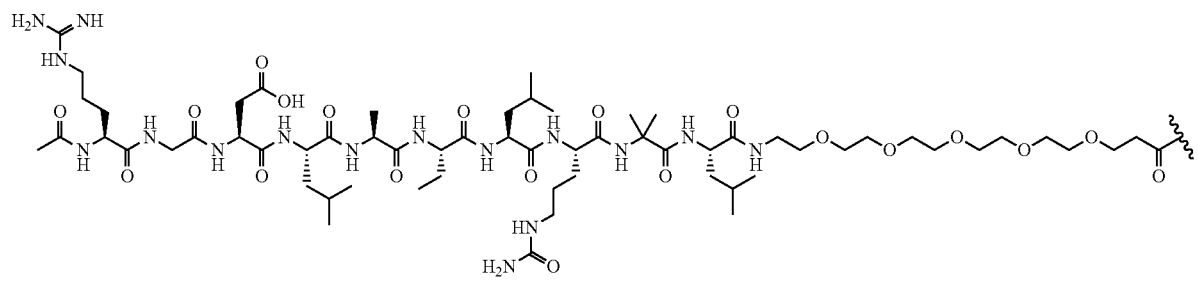 [SMILES: *C(=O)CCOCCOCCOCCOCCOCCNC(=O)[C@H](CC(C)C)NC(=O)C(C)(C)NC(=O)[C@H](CCCNC(N)=O)NC(=O)[C@H](CC(C)C)NC(=O)[C@H](CC)NC(=O)[C@H](C)NC(=O)[C@H](CC(C)C)NC(=O)[C@H](CC(=O)O)NC(=O)CNC(=O)[C@H](CCCNC(=N)N)NC(C)=O]

wherein ┆ indicates the point of connection to the RNAi agent (via the reactive amine ($NH_2$-$C_6$) linker).

The DUX4 RNAi agents in Example 6 were further synthesized with a disulfide functional group (C6-SS-C6) at the 3' terminal end of the sense strand to facilitate conjugation to a PK/PD modulator.

For Groups 3-12, a Bis(PEG47+C22) moiety was attached to the 3' terminal end of the sense strand to serve as a pharmacokinetic/pharmacodynamic (PK/PD) modulator (See, e.g., Example 3, above, for structural information and related information).

For Groups 13-14, an LP38b moiety was attached to the 3' terminal end of the sense strand to serve as a pharmacokinetic/pharmacodynamic (PK/PD) modulator having the following structure:

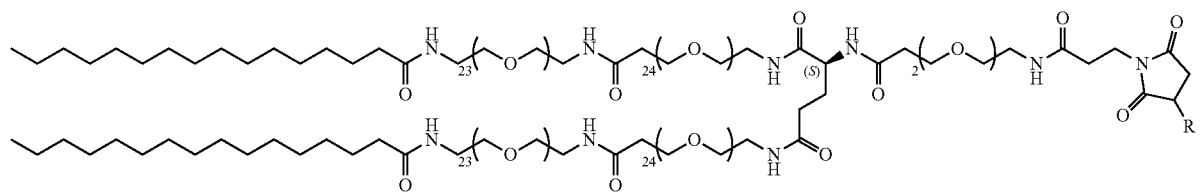

wherein R is the remainder of the RNAi agent. The maleimide was linked to the 3' end of the sense strand by reducing the terminal 3' disulfide bond and performing Michael addition to the terminal 3' thiol.

The modified RNAi agent nucleotide sequences were synthetized as shown herein in Table 3, Table 4.1, Table 4.6, and Tables 5.1, Table 5.2, Table 5.3, and Table 5.4 (showing the fully modified conjugate).

Six mice were dosed in each Group (n=6). On day 22, animals were sacrificed and muscles were harvested, processed, and analyzed in accordance with the procedures described in Example 2.

Figure 5:
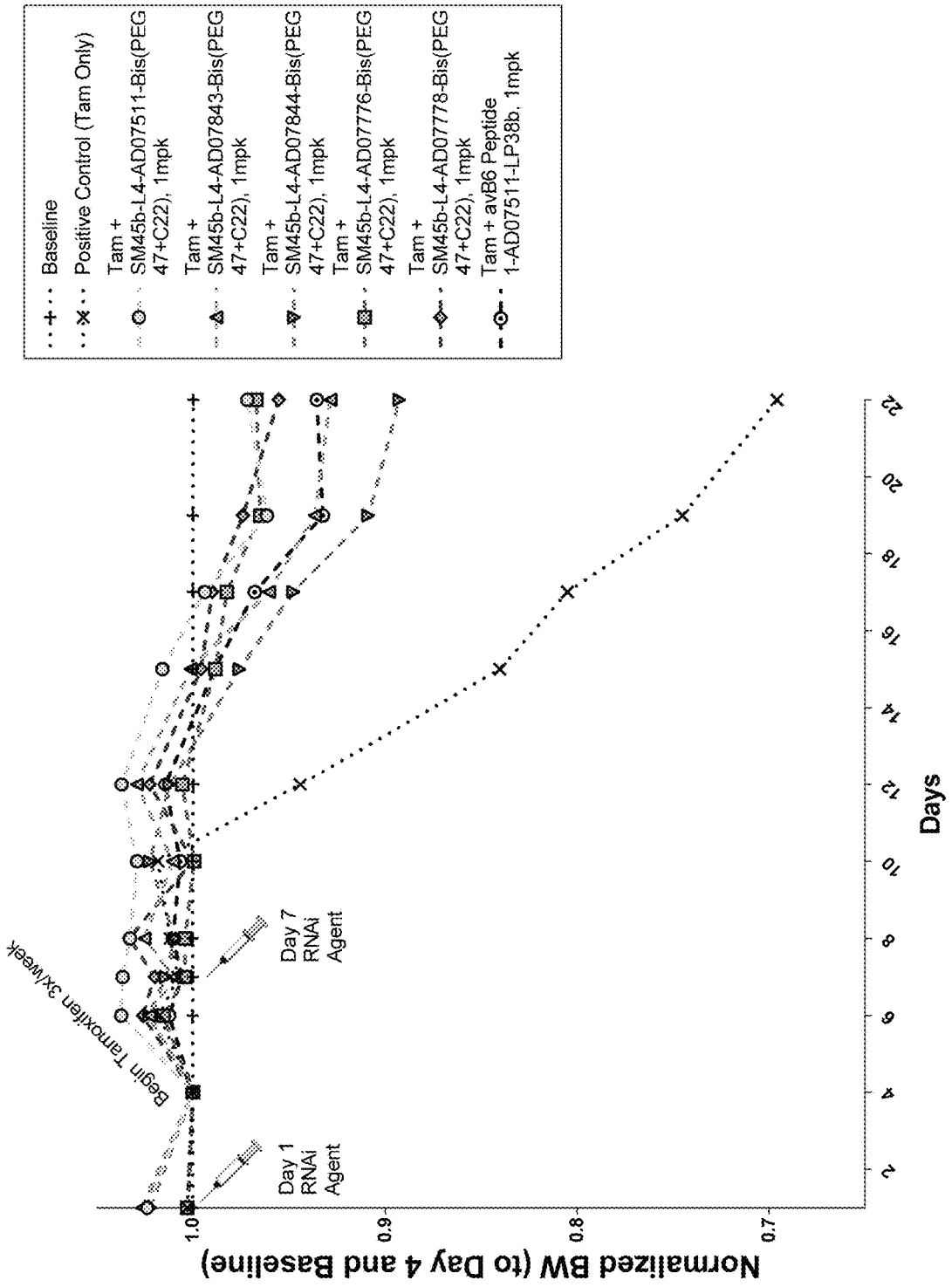
FIG. 5. Graph depicting mean bodyweights of FSHD-like model mice, as more fully described in Example 6.
Figure 6:
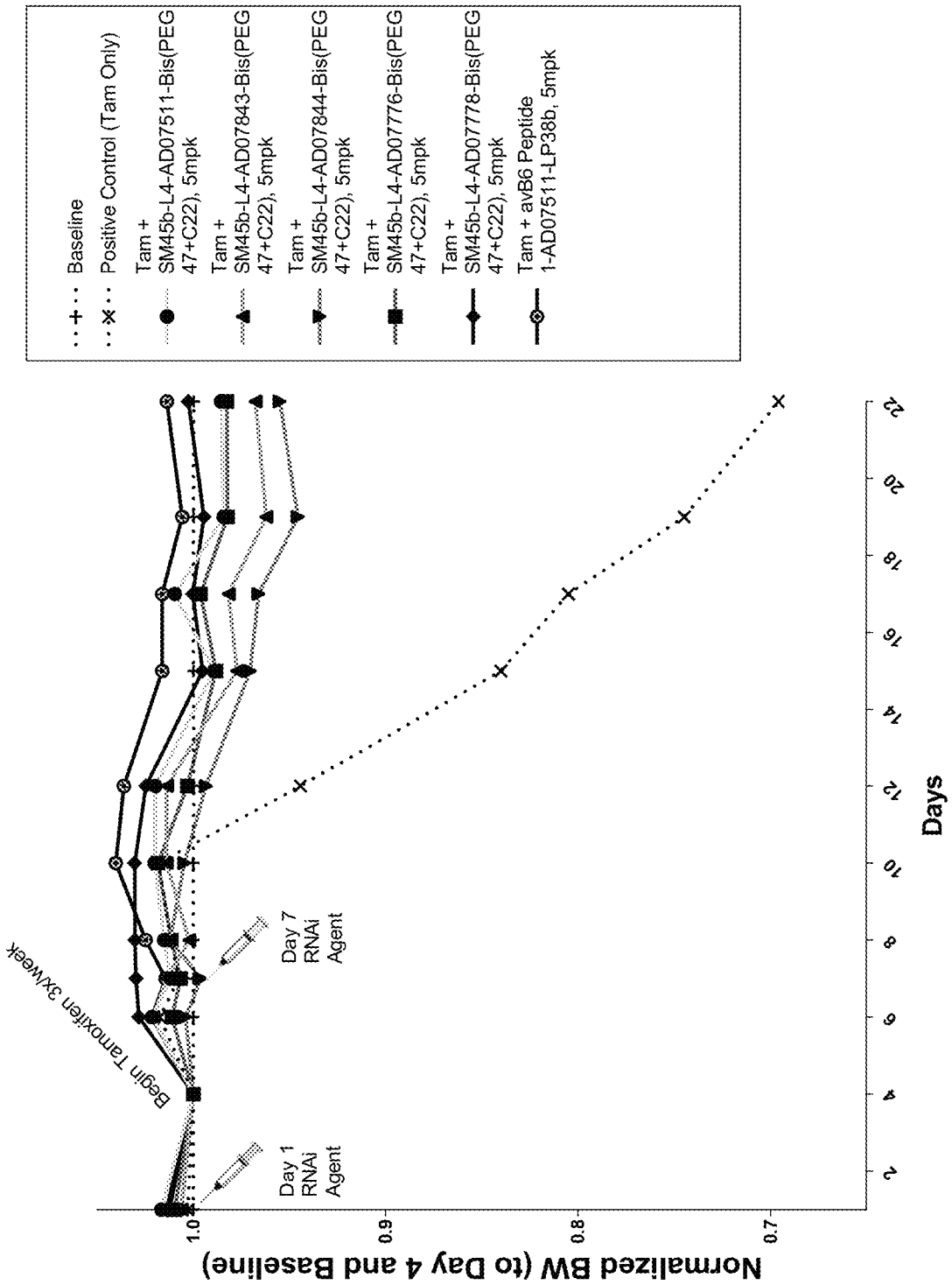
FIG. 6. Graph depicting mean bodyweights of FSHD-like model mice, as more fully described in Example 6.

Body weight measurements were taken on days 1, 4, 6, 7, 8, 10, 12, 15, 17, 19, and 22, and were normalized to Day 4 (pre-tamoxifen administration) and baseline, as shown in FIG. 5 (1 mg/kg) and FIG. 6 (5 mg/kg). Bodyweight was preserved above positive control levels in all groups treated with 1 or 5 mg/kg RNAi agent. Of particular note, animals treated with AD07511, AD07776, and AD07778 maintained bodyweight at levels equivalent to baseline. at both 1 and 5 mg/kg.

For certain Groups, average relative DUX4 expression in harvested tissue was examined, as shown in the following Tables for various muscle types:

TABLE 17.1

Average relative DUX4 expression in biceps for mice of Example 6 normalized to Baseline (Group 1).

| | Biceps Day 22 | |
|---|---|---|
| | Relative DUX4 Expression | Standard Deviation (+/−) |
| Group 1 (Baseline) | 1.000 | 0.502 |
| Group 2 (Positive Control (Tamoxifen only)) | 1.574 | 0.380 |
| Group 3 (1 mg/kg SM45b-AD07511-PK/PD) | 0.801 | 0.243 |
| Group 4 (5 mg/kg SM45b-AD07511-PK/PD) | 0.674 | 0.253 |
| Group 11 (1 mg/kg SM45b-AD07778-PK/PD) | 0.991 | 0.184 |
| Group 12 (5 mg/kg SM45b-AD07778-PK/PD) | 0.422 | 0.188 |
| Group 13 (1 mg/kg αvβ6 Peptide 1-AD07511-PK/PD) | 0.880 | 0.250 |
| Group 14 (5 mg/kg αvβ6 Peptide 1-AD07511-PK/PD) | 0.622 | 0.222 |

TABLE 17.2

Average relative DUX4 expression in biceps for mice of Example 6 normalized to Baseline (Group 1).

| | Diaphragm Day 22 | |
|---|---|---|
| | Relative DUX4 Expression | Standard Deviation (+/−) |
| Group 1 (Baseline) | 1.000 | 0.270 |
| Group 2 (Positive Control (Tamoxifen only)) | 2.025 | 0.716 |
| Group 3 (1 mg/kg SM45b-AD07511-PK/PD) | 1.045 | 0.317 |
| Group 4 (5 mg/kg SM45b-AD07511-PK/PD) | 0.857 | 0.652 |
| Group 11 (1 mg/kg SM45b-AD07778-PK/PD) | 1.090 | 0.478 |
| Group 12 (5 mg/kg SM45b-AD07778-PK/PD) | 1.067 | 0.455 |
| Group 13 (1 mg/kg αvβ6 Peptide 1-AD07511-PK/PD) | 1.087 | 0.349 |
| Group 14 (5 mg/kg αvβ6 Peptide 1-AD07511-PK/PD) | 0.709 | 0.257 |

TABLE 17.3

Average relative DUX4 expression in diaphragm for mice of Example 6 normalized to Baseline (Group 1).

| | Gastrocnemius Day 22 | |
|---|---|---|
| | Relative DUX4 Expression | Standard Deviation (+/−) |
| Group 1 (Baseline) | 1.000 | 0.202 |
| Group 2 (Positive Control (Tamoxifen only)) | 1.778 | 1.042 |
| Group 3 (1 mg/kg SM45b-AD07511-PK/PD) | 0.967 | 0.464 |
| Group 4 (5 mg/kg SM45b-AD07511-PK/PD) | 0.505 | 0.313 |
| Group 11 (1 mg/kg SM45b-AD07778-PK/PD) | 0.799 | 0.204 |
| Group 12 (5 mg/kg SM45b-AD07778-PK/PD) | 0.796 | 0.481 |
| Group 13 (1 mg/kg αvβ6 Peptide 1-AD07511-PK/PD) | 0.531 | 0.261 |
| Group 14 (5 mg/kg αvβ6 Peptide 1-AD07511-PK/PD) | 0.547 | 0.248 |

TABLE 17.4

Average relative DUX4 expression in gastrocnemius for mice of Example 6 normalized to Baseline (Group 1).

| | Masseter Day 22 | |
|---|---|---|
| | Relative DUX4 Expression | Standard Deviation (+/−) |
| Group 1 (Baseline) | 1.000 | 0.326 |
| Group 2 (Positive Control (Tamoxifen only)) | 1.376 | 0.398 |
| Group 3 (1 mg/kg SM45b-AD07511-PK/PD) | 1.124 | 0.456 |
| Group 4 (5 mg/kg SM45b-AD07511-PK/PD) | 0.842 | 0.563 |
| Group 11 (1 mg/kg SM45b-AD07778-PK/PD) | 0.962 | 0.289 |
| Group 12 (5 mg/kg SM45b-AD07778-PK/PD) | 1.039 | 0.545 |
| Group 13 (1 mg/kg αvβ6 Peptide 1-AD07511-PK/PD) | 0.829 | 0.339 |
| Group 14 (5 mg/kg αvβ6 Peptide 1-AD07511-PK/PD) | 0.578 | 0.224 |

TABLE 17.5

Average relative DUX4 expression in TA (tibialis anterior) for mice of Example 5 normalized to Baseline (Group 1).

| | TA Day 22 | |
|---|---|---|
| | Relative DUX4 Expression | Standard Deviation (+/−) |
| Group 1 (Baseline) | 1.000 | 0.434 |
| Group 2 (Positive Control (Tamoxifen only)) | 1.664 | 0.653 |
| Group 3 (1 mg/kg SM45b-AD07511-PK/PD) | 0.627 | 0.192 |
| Group 4 (5 mg/kg SM45b-AD07511-PK/PD) | 0.609 | 0.537 |
| Group 11 (1 mg/kg SM45b-AD07778-PK/PD) | 0.786 | 0.119 |
| Group 12 (5 mg/kg SM45b-AD07778-PK/PD) | 0.724 | 0.348 |
| Group 13 (1 mg/kg αvβ6 Peptide 1-AD07511-PK/PD) | 0.642 | 0.208 |
| Group 14 (5 mg/kg αvβ6 Peptide 1-AD07511-PK/PD) | 0.539 | 0.170 |

TABLE 17.6

Average relative DUX4 expression in trapezius for mice of Example 5 normalized to Baseline (Group 1).

| | Trapezius Day 22 | |
|---|---|---|
| | Relative DUX4 Expression | Standard Deviation (+/−) |
| Group 1 (Baseline) | 1.000 | 0.307 |
| Group 2 (Positive Control (Tamoxifen only)) | 2.968 | 0.377 |
| Group 3 (1 mg/kg SM45b-AD07511-PK/PD) | 1.331 | 0.190 |
| Group 4 (5 mg/kg SM45b-AD07511-PK/PD) | 0.961 | 0.803 |
| Group 11 (1 mg/kg SM45b-AD07778-PK/PD) | 1.050 | 0.306 |
| Group 12 (5 mg/kg SM45b-AD07778-PK/PD) | 1.159 | 0.382 |
| Group 13 (1 mg/kg αvβ6 Peptide 1-AD07511-PK/PD) | 0.942 | 0.387 |
| Group 14 (5 mg/kg αvβ6 Peptide 1-AD07511-PK/PD) | 1.244 | 0.337 |

TABLE 17.7

Average relative DUX4 expression in triceps for mice of Example 6 normalized to Baseline (Group 1).

| | Triceps Day 22 | |
|---|---|---|
| | Relative DUX4 Expression | Standard Deviation (+/−) |
| Group 1 (Baseline) | 1.000 | 0.207 |
| Group 2 (Positive Control (Tamoxifen only)) | 1.774 | 0.214 |
| Group 3 (1 mg/kg SM45b-AD07511-PK/PD) | 0.640 | 0.292 |
| Group 4 (5 mg/kg SM45b-AD07511-PK/PD) | 0.500 | 0.490 |
| Group 11 (1 mg/kg SM45b-AD07778-PK/PD) | 0.705 | 0.132 |
| Group 12 (5 mg/kg SM45b-AD07778-PK/PD) | 0.642 | 0.274 |
| Group 13 (1 mg/kg αvβ6 Peptide 1-AD07511-PK/PD) | 0.629 | 0.301 |
| Group 14 (5 mg/kg αvβ6 Peptide 1-AD07511-PK/PD) | 0.523 | 0.215 |

To further illustrate inhibition levels, the data in Tables 17.1 through 17.7 above were compared solely to the positive control (tamoxifen only) group, to show the % of DUX4 knockdown or reduction (not relative expression) for the various Groups:

TABLE 18.1

Percentage of DUX4 knockdown in biceps for mice of Example 6 compared to Positive Control (Tamoxifen Only) (Group 2).

| Biceps Day 22 | % Knockdown DUX4 |
|---|---|
| Group 3 (1 mg/kg SM45b-AD07511-PK/PD) | 0.491 |
| Group 4 (5 mg/kg SM45b-AD07511-PK/PD) | 0.572 |
| Group 11 (1 mg/kg SM45b-AD07778-PK/PD) | 0.370 |
| Group 12 (5 mg/kg SM45b-AD07778-PK/PD) | 0.732 |
| Group 13 (1 mg/kg αvβ6 Peptide 1-AD07511-PK/PD) | 0.441 |
| Group 14 (5 mg/kg αvβ6 Peptide 1-AD07511-PK/PD) | 0.605 |

TABLE 18.2

Percentage of DUX4 knockdown in diaphragm for mice of Example 6 tcompared o Positive Control (Tamoxifen Only) (Group 2).

| Diaphragm Day 22 | % Knockdown DUX4 |
|---|---|
| Group 3 (1 mg/kg SM45b-AD07511-PK/PD) | 0.484 |
| Group 4 (5 mg/kg SM45b-AD07511-PK/PD) | 0.577 |
| Group 11 (1 mg/kg SM45b-AD07778-PK/PD) | 0.462 |
| Group 12 (5 mg/kg SM45b-AD07778-PK/PD) | 0.473 |
| Group 13 (1 mg/kg αvβ6 Peptide 1-AD07511-PK/PD) | 0.463 |
| Group 14 (5 mg/kg αvβ6 Peptide 1-AD07511-PK/PD) | 0.650 |

TABLE 18.3

Percentage of DUX4 knockdown in gastrocnemius for mice of Example 6 compared to Positive Control (Tamoxifen Only) (Group 2).

| Gastrocnemius Day 22 | % Knockdown DUX4 |
|---|---|
| Group 3 (1 mg/kg SM45b-AD07511-PK/PD) | 0.456 |
| Group 4 (5 mg/kg SM45b-AD07511-PK/PD) | 0.716 |
| Group 11 (1 mg/kg SM45b-AD07778-PK/PD) | 0.551 |
| Group 12 (5 mg/kg SM45b-AD07778-PK/PD) | 0.553 |
| Group 13 (1 mg/kg αvβ6 Peptide 1-AD07511-PK/PD) | 0.701 |
| Group 14 (5 mg/kg αvβ6 Peptide 1-AD07511-PK/PD) | 0.692 |

TABLE 18.4

Percentage of DUX4 knockdown in masseter for mice of Example 6 compared to Positive Control (Tamoxifen Only) (Group 2).

| Masseter Day 22 | % Knockdown DUX4 |
|---|---|
| Group 3 (1 mg/kg SM45b-AD07511-PK/PD) | 0.183 |
| Group 4 (5 mg/kg SM45b-AD07511-PK/PD) | 0.388 |
| Group 11 (1 mg/kg SM45b-AD07778-PK/PD) | 0.301 |
| Group 12 (5 mg/kg SM45b-AD07778-PK/PD) | 0.245 |
| Group 13 (1 mg/kg αvβ6 Peptide 1-AD07511-PK/PD) | 0.398 |
| Group 14 (5 mg/kg αvβ6 Peptide 1-AD07511-PK/PD) | 0.580 |

TABLE 18.5

Percentage of DUX4 knockdown in TA (tibialis anterior) for mice of Example 6 compared to Positive Control (Tamoxifen Only) (Group 2).

| TA Day 22 | % Knockdown DUX4 |
|---|---|
| Group 3 (1 mg/kg SM45b-AD07511-PK/PD) | 0.623 |
| Group 4 (5 mg/kg SM45b-AD07511-PK/PD) | 0.634 |
| Group 11 (1 mg/kg SM45b-AD07778-PK/PD) | 0.527 |
| Group 12 (5 mg/kg SM45b-AD07778-PK/PD) | 0.565 |
| Group 13 (1 mg/kg αvβ6 Peptide 1-AD07511-PK/PD) | 0.614 |
| Group 14 (5 mg/kg αvβ6 Peptide 1-AD07511-PK/PD) | 0.676 |

TABLE 18.6

Percentage of DUX4 knockdown in trapezius for mice of Example 6 compared to Positive Control (Tamoxifen Only) (Group 2).

| Trapezius Day 22 | % Knockdown DUX4 |
|---|---|
| Group 3 (1 mg/kg SM45b-AD07511-PK/PD) | 0.552 |
| Group 4 (5 mg/kg SM45b-AD07511-PK/PD) | 0.676 |
| Group 11 (1 mg/kg SM45b-AD07778-PK/PD) | 0.646 |
| Group 12 (5 mg/kg SM45b-AD07778-PK/PD) | 0.610 |
| Group 13 (1 mg/kg αvβ6 Peptide 1-AD07511-PK/PD) | 0.683 |
| Group 14 (5 mg/kg αvβ6 Peptide 1-AD07511-PK/PD) | 0.581 |

TABLE 18.7

Percentage of DUX4 knockdown in triceps for mice of Example 6 compared to Positive Control (Tamoxifen Only) (Group 2).

| Triceps Day 22 | % Knockdown DUX4 |
|---|---|
| Group 3 (1 mg/kg SM45b-AD07511-PK/PD) | 0.639 |
| Group 4 (5 mg/kg SM45b-AD07511-PK/PD) | 0.718 |
| Group 11 (1 mg/kg SM45b-AD07778-PK/PD) | 0.602 |
| Group 12 (5 mg/kg SM45b-AD07778-PK/PD) | 0.638 |
| Group 13 (1 mg/kg αvβ6 Peptide 1-AD07511-PK/PD) | 0.645 |
| Group 14 (5 mg/kg αvβ6 Peptide 1-AD07511-PK/PD) | 0.705 |

TABLE 19.1

Average relative Wfdc3 expression in biceps for mice of Example 6 normalized to Baseline (Group 1).

| Biceps Day 22 | Relative Wfdc3 Expression | Low (error) | High (error) |
|---|---|---|---|
| Group 1 (Baseline) | 1.000 | 0.868 | 6.549 |
| Group 2 (Positive Control (Tamoxifen only)) | 21.742 | 2.185 | 2.429 |
| Group 3 (1 mg/kg SM45b-AD07511-PK/PD) | 10.061 | 2.600 | 3.506 |
| Group 4 (5 mg/kg SM45b-AD07511-PK/PD) | 3.302 | 1.613 | 3.154 |
| Group 11 (1 mg/kg SM45b-AD07778-PK/PD) | 4.360 | 2.022 | 3.769 |
| Group 12 (5 mg/kg SM45b-AD07778-PK/PD) | 0.778 | 0.318 | 0.538 |
| Group 13 (1 mg/kg αvβ6 Peptide 1-AD07511-PK/PD) | 9.153 | 3.716 | 6.257 |
| Group 14 (5 mg/kg αvβ6 Peptide 1-AD07511-PK/PD) | 5.444 | 2.062 | 3.319 |

Average relative Wfdc3 mRNA transcript levels in harvested tissue were similarly determined as shown in the following Tables for carious muscle types:

TABLE 19.2

Average relative Wfdc3 expression in diaphragm for mice of Example 6 normalized to Baseline (Group 1).

| Diaphragm Day 22 | Relative Wfdc3 Expression | Low (error) | High (error) |
|---|---|---|---|
| Group 1 (Baseline) | 1.000 | 0.747 | 2.954 |
| Group 2 (Positive Control (Tamoxifen only)) | 19.044 | 3.445 | 4.206 |
| Group 3 (1 mg/kg SM45b-AD07511-PK/PD) | 6.596 | 2.343 | 3.634 |
| Group 4 (5 mg/kg SM45b-AD07511-PK/PD) | 0.640 | 0.393 | 1.016 |
| Group 11 (1 mg/kg SM45b-AD07778-PK/PD) | 1.688 | 0.839 | 1.668 |
| Group 12 (5 mg/kg SM45b-AD07778-PK/PD) | 0.108 | 0.049 | 0.088 |
| Group 13 (1 mg/kg αvβ6 Peptide 1-AD07511-PK/PD) | 5.007 | 2.475 | 4.895 |
| Group 14 (5 mg/kg αvβ6 Peptide 1-AD07511-PK/PD) | 1.127 | 0.542 | 1.044 |

TABLE 19.3

Average relative Wfdc3 expression in gastrocnemius for mice of Example 6 normalized to Baseline (Group 1).

| Gastrocnemius Day 22 | Relative Wfdc3 Expression | Low (error) | High (error) |
|---|---|---|---|
| Group 1 (Baseline) | 1.000 | 0.773 | 3.403 |
| Group 2 (Positive Control (Tamoxifen only)) | 8.502 | 1.568 | 1.923 |
| Group 3 (1 mg/kg SM45b-AD07511-PK/PD) | 3.528 | 0.689 | 0.857 |
| Group 4 (5 mg/kg SM45b-AD07511-PK/PD) | 0.787 | 0.415 | 0.877 |
| Group 11 (1 mg/kg SM45b-AD07778-PK/PD) | 1.238 | 0.472 | 0.763 |
| Group 12 (5 mg/kg SM45b-AD07778-PK/PD) | 0.213 | 0.100 | 0.189 |
| Group 13 (1 mg/kg αvβ6 Peptide 1-AD07511-PK/PD) | 2.801 | 0.666 | 0.873 |
| Group 14 (5 mg/kg αvβ6 Peptide 1-AD07511-PK/PD) | 1.707 | 0.455 | 0.620 |

TABLE 19.4

Average relative Wfdc3 expression in masseter for mice of Example 6 normalized to Baseline (Group 1).

| Masseter Day 22 | Relative Wfdc3 Expression | Low (error) | High (error) |
|---|---|---|---|
| Group 1 (Baseline) | 1.000 | 0.766 | 3.276 |
| Group 2 (Positive Control (Tamoxifen only)) | 10.813 | 4.217 | 6.913 |
| Group 3 (1 mg/kg SM45b-AD07511-PK/PD) | 4.561 | 1.194 | 1.618 |
| Group 4 (5 mg/kg SM45b-AD07511-PK/PD) | 0.854 | 0.563 | 1.653 |

TABLE 19.4-continued

Average relative Wfdc3 expression in masseter for mice of Example 6 normalized to Baseline (Group 1).

| | Masseter Day 22 | | |
|---|---|---|---|
| | Relative Wfdc3 Expression | Low (error) | High (error) |
| Group 11 (1 mg/kg SM45b-AD07778-PK/PD) | 1.391 | 0.400 | 0.561 |
| Group 12 (5 mg/kg SM45b-AD07778-PK/PD) | 0.141 | 0.065 | 0.122 |
| Group 13 (1 mg/kg αvβ6 Peptide 1-AD07511-PK/PD) | 2.251 | 0.824 | 1.299 |
| Group 14 (5 mg/kg αvβ6 Peptide 1-AD07511-PK/PD) | 0.778 | 0.450 | 1.065 |

TABLE 19.5

Average relative Wfdc3 expression in TA (tibialis anterior) for mice of Example 6 normalized to Baseline (Group 1).

| | TA Day 22 | | |
|---|---|---|---|
| | Relative Wfdc3 Expression | Low (error) | High (error) |
| Group 1 (Baseline) | 1.000 | 0.866 | 6.475 |
| Group 2 (Positive Control (Tamoxifen only)) | 23.367 | 3.417 | 4.002 |
| Group 3 (1 mg/kg SM45b-AD07511-PK/PD) | 5.417 | 1.188 | 1.521 |
| Group 4 (5 mg/kg SM45b-AD07511-PK/PD) | 1.153 | 0.647 | 1.474 |
| Group 11 (1 mg/kg SM45b-AD07778-PK/PD) | 1.800 | 0.639 | 0.990 |
| Group 12 (5 mg/kg SM45b-AD07778-PK/PD) | 0.263 | 0.122 | 0.229 |
| Group 13 (1 mg/kg αvβ6 Peptide 1-AD07511-PK/PD) | 4.666 | 1.699 | 2.672 |
| Group 14 (5 mg/kg αvβ6 Peptide 1-AD07511-PK/PD) | 2.429 | 0.512 | 0.650 |

TABLE 19.6

Average relative Wfdc3 expression in trapezius for mice of Example 6n ormalized to Baseline (Group 1).

| | Trapezius Day 22 | | |
|---|---|---|---|
| | Relative Wfdc3 Expression | Low (error) | High (error) |
| Group 1 (Baseline) | 1.000 | 0.820 | 4.552 |
| Group 2 (Positive Control (Tamoxifen only)) | 20.944 | 3.702 | 4.497 |
| Group 3 (1 mg/kg SM45b-AD07511-PK/PD) | 4.452 | 1.705 | 2.763 |
| Group 4 (5 mg/kg SM45b-AD07511-PK/PD) | 0.586 | 0.386 | 1.128 |
| Group 11 (1 mg/kg SM45b-AD07778-PK/PD) | 1.072 | 0.503 | 0.949 |
| Group 12 (5 mg/kg SM45b-AD07778-PK/PD) | 0.122 | 0.060 | 0.119 |
| Group 13 (1 mg/kg αvβ6 Peptide 1-AD07511-PK/PD) | 3.512 | 1.804 | 3.709 |
| Group 14 (5 mg/kg αvβ6 Peptide 1-AD07511-PK/PD) | 1.000 | 0.538 | 1.162 |

TABLE 19.7

Average relative Wfdc3 expression in triceps for mice of Example 6 normalized to Baseline (Group 1).

| | Triceps Day 22 | | |
|---|---|---|---|
| | Relative Wfdc3 Expression | Low (error) | High (error) |
| Group 1 (Baseline) | 1.000 | 0.810 | 4.255 |
| Group 2 (Positive Control (Tamoxifen only)) | 23.534 | 5.125 | 6.552 |
| Group 3 (1 mg/kg SM45b-AD07511-PK/PD) | 4.148 | 1.492 | 2.330 |
| Group 4 (5 mg/kg SM45b-AD07511-PK/PD) | 0.796 | 0.449 | 1.028 |
| Group 11 (1 mg/kg SM45b-AD07778-PK/PD) | 1.006 | 0.550 | 1.212 |
| Group 12 (5 mg/kg SM45b-AD07778-PK/PD) | 0.136 | 0.053 | 0.087 |
| Group 13 (1 mg/kg αvβ6 Peptide 1-AD07511-PK/PD) | 3.284 | 1.485 | 2.712 |
| Group 14 (5 mg/kg αvβ6 Peptide 1-AD07511-PK/PD) | 1.241 | 0.633 | 1.290 |

For the DUX4 RNAi agents shown in the data Tables above, AD07511 included nucleotide sequences designed to inhibit a DUX4 gene at position 1437 of the gene; and AD077778 included nucleotide sequences designed to inhibit a DUX4 gene at position 408 of the gene.

As shown above, both of these DUX4 RNAi agents preserved bodyweight and showed meaningful reductions in DUX4 gene expression.

Example 7. In Vivo Administration of RNAi Agents Targeting DUX4 in FSHD-Like Transgenic Mice The FSHD-like transgenic mouse model as described in Example 2 were used to assess DUX4 RNAi agents. DUX4 RNAi agents that included a sense strand and an antisense strand were synthesized according to phosphoramidite technology on solid phase in accordance with general procedures known in the art and commonly used in oligonucleotide synthesis, as set forth in Example 1 herein.

On Study Day 1, mice were injected between the skin and muscle (i.e. subcutaneous injections) into the loose skin region over the neck and shoulder area with either isotonic saline (vehicle control) or a DUX4 RNAi agent formulated in isotonic saline. Starting on day 4, an oral gavage of 100 µL/20 g mouse of either corn oil (negative control) or tamoxifen dissolved in corn oil (1 mg/mL) was administered three times per week (days 4, 6, 8, 10, 12, 15, 17, and 19) to induce increased expression of DUX4. The dosing regimen and details are set forth in the following Table:

TABLE 20

Dosing Groups for mice of Example 7.

| Group | RNAi agent and Dose | RNAi agent Dosing Regimen | Induction Agent Administration | Induction Agent Dosing Regimen |
|---|---|---|---|---|
| 1 | Baseline (no RNAi agent, saline injection) | N/A | Corn oil (negative control) | 3 times per week starting on day 4 |
| 2 | Positive Control (no RNAi agent, saline injection) | N/A | Tamoxifen | 3 times per week starting on day 4 |
| 3 | αvβ6 Peptide 1-AD07511-LP38b | 1 mg/kg administered on days 1 and 7 | Tamoxifen | 3 times per week starting on day 4 |
| 4 | αvβ6 Peptide 1-AD07511-LP38b | 5 mg/kg administered on days 1 and 7 | Tamoxifen | 3 times per week starting on day 4 |
| 5 | αvβ6 Peptide 1-AD07776-LP38b | 1 mg/kg administered on days 1 and 7 | Tamoxifen | 3 times per week starting on day 4 |
| 6 | αvβ6 Peptide 1-AD07776-LP38b | 5 mg/kg administered on days 1 and 7 | Tamoxifen | 3 times per week starting on day 4 |

The RNAi agents in Example 7 (Groups 3-6) were synthesized having nucleotide sequences directed to target the DUX4 gene, and included a functionalized amine reactive group ($NH_2$-$C_6$) at the 5' terminal end of the sense strand to facilitate conjugation to the skeletal muscle cell receptor peptide referred to as Peptide 1 (See, e.g., Example 6, above, for structural information and related information).

The DUX4 RNAi agents in Example 7 were further synthesized with a disulfide functional group (C6-SS-C6) at the 3' terminal end of the sense strand to facilitate conjugation to the PK/PD modulator (LP38b). (See, e.g., Example 6, above, for structural information and related information).

The modified RNAi agent nucleotide sequences were synthesized as shown herein in Table 3, Table 4.1, Table 4.6, and Tables 5.1, Table 5.2, Table 5.3, and Table 5.4 (showing the fully modified conjugate).

For the DUX4 RNAi agents shown above, AD07511 (Groups 3 and 4) included nucleotide sequences designed to inhibit a DUX4 gene at position 1437 of the gene; and AD07776 (Groups 5 and 6) included nucleotide sequences designed to inhibit a DUX4 gene at position 408 of the gene.

Figure 7:
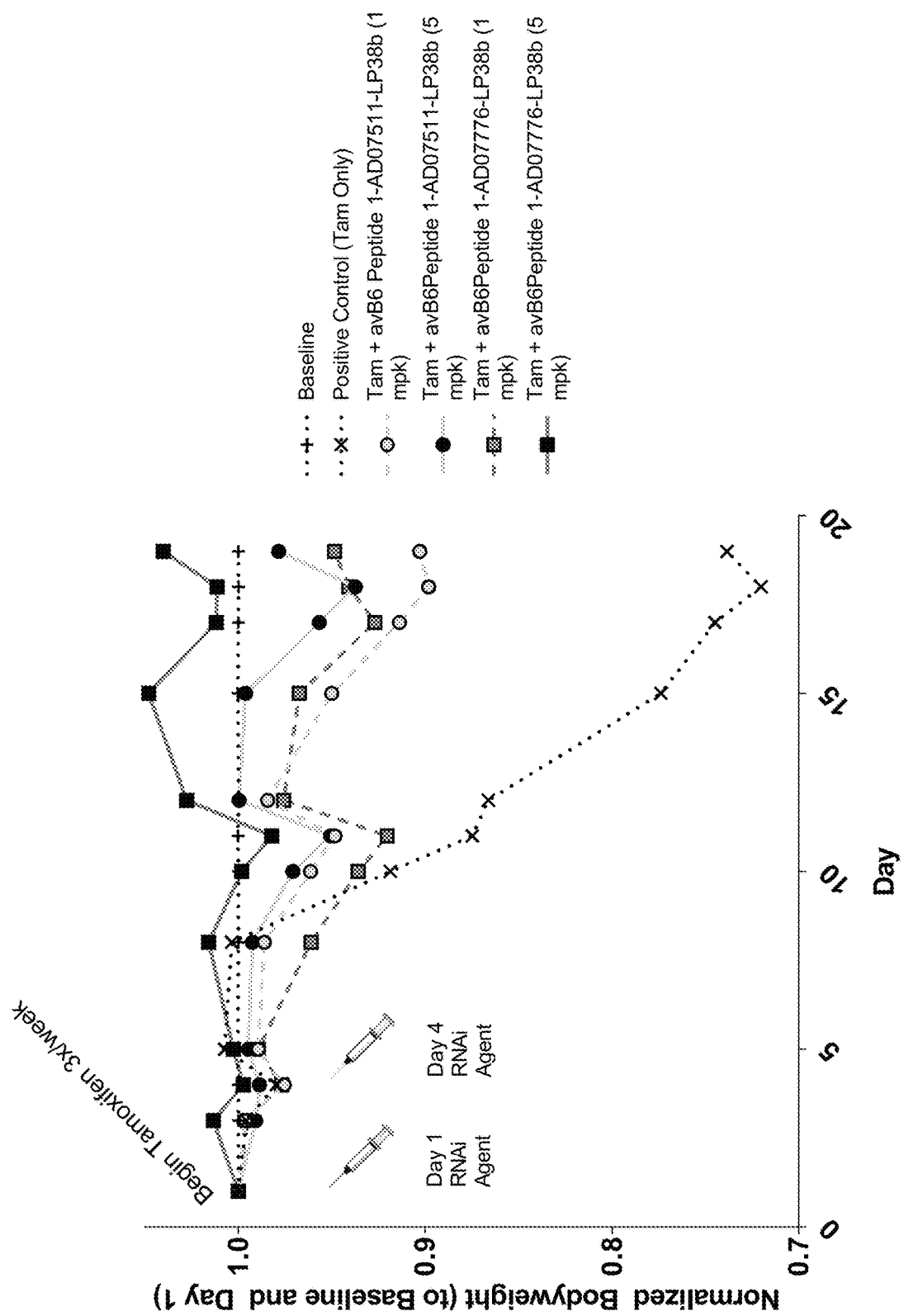
FIG. 7. Graph depicting mean bodyweights of FSHD-like model mice, as more fully described in Example 7.

Body weight measurements were taken on days 1, 3, 4, 5, 8, 10, 11, 12, 15, 17, 18, and 19, and were normalized to Day 1 (pre-tamoxifen administration) and baseline, as shown in FIG. 7. Bodyweight was preserved above positive control levels in all groups treated with 1 or 5 mg/kg RNAi agent.

Six mice were dosed in each Group (n=6). On Day 19, animals were sacrificed and muscles were harvested, processed, and analyzed in accordance with the procedures described in Example 2. Average relative DUX4 expression in harvested tissue is shown in the following Tables for gastrocnemius and triceps:

TABLE 21.1

Average relative DUX4 expression in gastrocnemius for mice of Example 7 normalized to Baseline (Group 1).

| | Gastrocnemius Day 19 | |
|---|---|---|
| | Relative DUX4 Expression | Standard Deviation (+/-) |
| Group 1 (Baseline) | 1.000 | 0.215 |
| Group 2 (Positive Control (Tamoxifen only)) | 1.486 | 0.325 |
| Group 3 (AD07511, 1 mg/kg) | 0.919 | 0.200 |
| Group 4 (AD07511, 5 mg/kg) | 0.879 | 0.241 |

TABLE 21.1-continued

Average relative DUX4 expression in gastrocnemius for mice of Example 7 normalized to Baseline (Group 1).

| | Gastrocnemius Day 19 | |
|---|---|---|
| | Relative DUX4 Expression | Standard Deviation (+/-) |
| Group 5 (AD07776, 1 mg/kg) | 1.474 | 0.615 |
| Group 6 (AD07776, 5 mg/kg) | 1.136 | 0.540 |

TABLE 21.2

Average relative DUX4 expression in triceps for mice of Example 7 normalized to Baseline (Group 1).

| | Triceps Day 19 | |
|---|---|---|
| | Relative DUX4 Expression | Standard Deviation (+/-) |
| Group 1 (Baseline) | 1.000 | 0.217 |
| Group 2 (Positive Control (Tamoxifen only)) | 1.654 | 0.675 |
| Group 3 (AD07511, 1 mg/kg) | 0.777 | 0.091 |
| Group 4 (AD07511, 5 mg/kg) | 0.968 | 0.620 |
| Group 5 (AD07776, 1 mg/kg) | 1.145 | 0.285 |
| Group 6 (AD07776, 5 mg/kg) | 0.968 | 0.620 |

Average relative Wfdc3 mRNA transcript levels in harvested tissue were similarly determined as shown in the following Tables for various gastrocnemius and triceps:

TABLE 22.1

Average relative Wfdc3 expression in gastrocnemius for mice of Example 7 normalized to Baseline (Group 1).

| | Gastrocnemius Day 19 | | |
|---|---|---|---|
| | Relative Wfdc3 Expression | Low (error) | High (error) |
| Group 1 (Baseline) | 1.000 | 0.810 | 4.259 |
| Group 2 (Positive Control (Tamoxifen only)) | 7.684 | 3.764 | 7.376 |
| Group 3 (AD07511, 1 mg/kg) | 5.999 | 1.891 | 2.762 |
| Group 4 (AD07511, 5 mg/kg) | 2.742 | 0.649 | 0.851 |
| Group 5 (AD07776, 1 mg/kg) | 3.628 | 0.735 | 0.922 |
| Group 6 (AD07776, 5 mg/kg) | 1.537 | 0.467 | 0.672 |

TABLE 22.2

Average relative Wfdc3 expression in triceps for mice of Example 7 normalized to Baseline (Group 1).

| | Triceps Day 19 | | |
| --- | --- | --- | --- |
| | Relative Wfdc3 Expression | Low (error) | High (error) |
| Group 1 (Baseline) | 1.000 | 0.899 | 8.915 |
| Group 2 (Positive Control (Tamoxifen only)) | 16.942 | 4.319 | 5.797 |
| Group 3 (AD07511, 1 mg/kg) | 5.014 | 1.291 | 1.738 |
| Group 4 (AD07511, 5 mg/kg) | 0.958 | 0.396 | 0.676 |
| Group 5 (AD07776, 1 mg/kg) | 1.334 | 0.668 | 1.339 |
| Group 6 (AD07776, 5 mg/kg) | 0.131 | 0.071 | 0.156 |

To further illustrate inhibition levels, the data in Tables 22.1 and 22.2 above were compared solely to the positive control (tamoxifen only) group, which shows the following relative inhibition levels for the various Groups:

TABLE 23.1

Relative average Wfdc3 expression in gastrocnemius for mice of Example 7 normalized to Positive Control (Group 2).

| | Gastrocnemius Day 22 Relative Wfdc3 Expression |
| --- | --- |
| Group 2 (Positive Control (Tamoxifen only)) | 1.000 |
| Group 3 (AD07511, 1 mg/kg) | 0.781 |
| Group 4 (AD07511, 5 mg/kg) | 0.357 |
| Group 5 (AD07776, 1 mg/kg) | 0.472 |
| Group 6 (AD07776, 5 mg/kg) | 0.200 |

TABLE 23.2

Average relative Wfdc3 expression in triceps for mice of Example 7 normalized to Positive Control (Group 2).

| | Triceps Day 22 Relative Wfdc3 Expression |
| --- | --- |
| Group 2 (Positive Control (Tamoxifen only)) | 1.000 |
| Group 3 (AD07511, 1 mg/kg) | 0.296 |
| Group 4 (AD07511, 5 mg/kg) | 0.057 |
| Group 5 (AD07776, 1 mg/kg) | 0.079 |
| Group 6 (AD07776, 5 mg/kg) | 0.008 |

Figure 8:
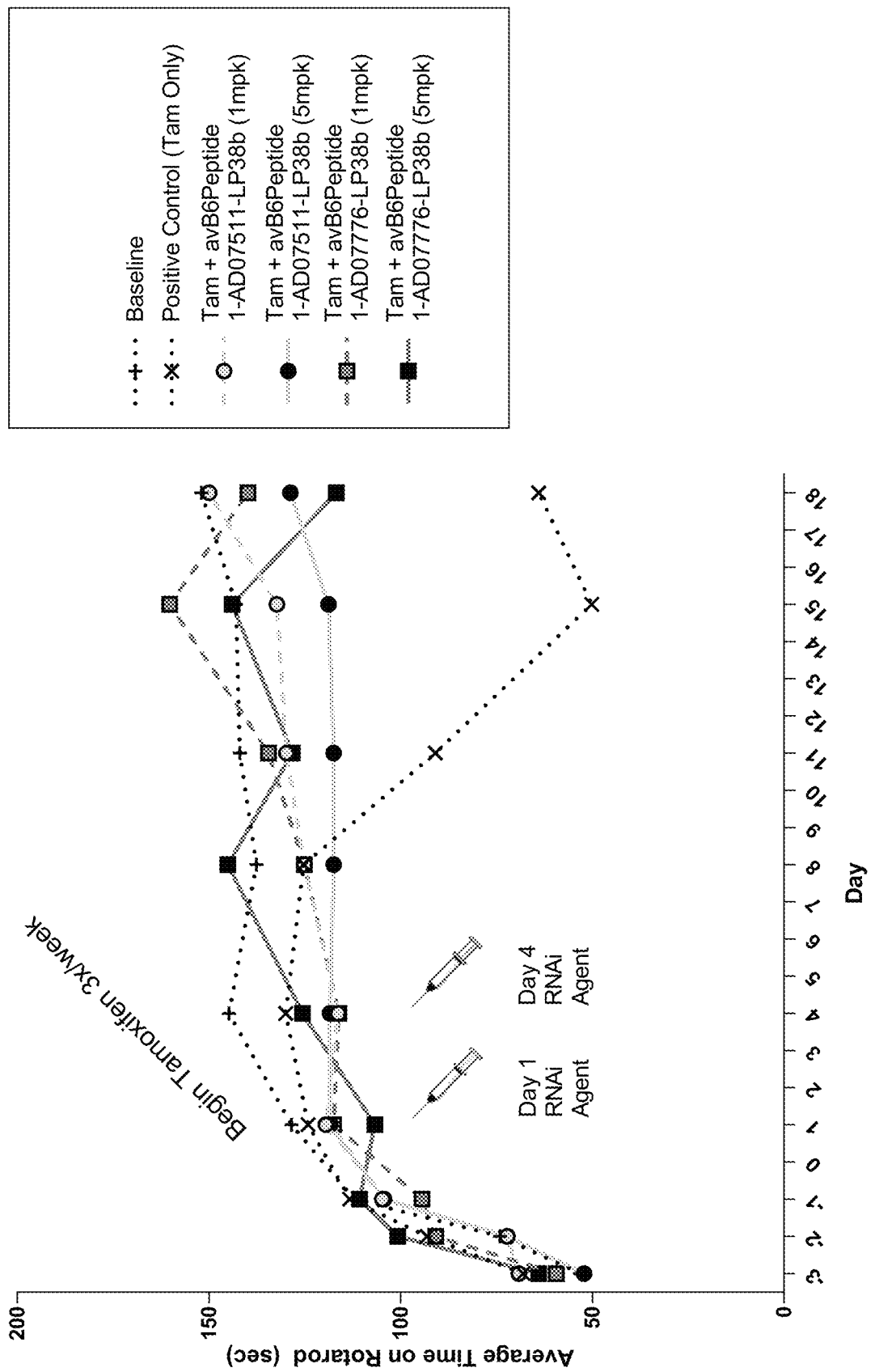
FIG. 8. Graph depicting time on Rotarod apparatus of FSHD-like model mice, as more fully described in Example 7.

The mice in Example 7 were further subjected to the Rotarod apparatus to conduct a gross motor coordination assessment, as describe in Example 2 above. As shown in FIG. 8, throughout the duration of the study the animals dosed with the DUX4 RNAi agents (Groups 3-6) were able to maintain their balance and gross motor function on the Rotarod apparatus similar to the negative control saline group that was not administered tamoxifen. Conversely, the animals dosed with tamoxifen but no DUX4 RNAi agent began falling off the Rotarod apparatus much faster starting around day 11, indicating a loss of muscle function.

As evidenced by the data shown above, both of the DUX4 RNAi agents show substantial inhibition of DUX4 gene expression, and preservation of gross motor function and bodyweight in the model mice dosed with the DUX4 RNAi agents.

Example 8. In Vivo Administration of RNAi Agents Targeting DUX4 in FSHD-Like Transgenic Mice The FSHD-like transgenic mouse model as described in Example 2 were used to assess DUX4 RNAi agents. DUX4 RNAi agents that included a sense strand and an antisense strand were synthesized according to phosphoramidite technology on solid phase in accordance with general procedures known in the art and commonly used in oligonucleotide synthesis, as set forth in Example 1 herein.

On Study Day 1, mice were injected between the skin and muscle (i.e. subcutaneous injections) into the loose skin region over the neck and shoulder area with either isotonic saline (vehicle control) or a DUX4 RNAi agent formulated in isotonic saline. Starting on day 4, an oral gavage of 100 µL/20 g mouse of either corn oil (negative control) or tamoxifen dissolved in corn oil (1 mg/mL) was administered three times per week (days 4, 6, 8, 10, 12, 15, 17, and 19) to induce increased expression of DUX4. The dosing regimen and details are set forth in the following Table:

TABLE 24

Dosing Groups for mice of Example 8.

| Group | RNAi agent and Dose | RNAi agent Dosing Regimen | Induction Agent Administration | Induction Agent Dosing Regimen |
| --- | --- | --- | --- | --- |
| 1 | Baseline (no RNAi agent, saline injection) | N/A | Corn oil (negative control) | 3 times per week starting on day 4 |
| 2 | Positive Control (no RNAi agent, saline injection) | N/A | Tamoxifen | 3 times per week starting on day 4 |
| 3 | SM45b-L4-AD07511-Bis(PEG47 + C22) | 1 mg/kg administered on days 1 and 7 | Tamoxifen | 3 times per week starting on day 4 |
| 4 | SM45b-L4-AD07778-Bis(PEG47 + C22) | 1 mg/kg administered on days 1 and 7 | Tamoxifen | 3 times per week starting on day 4 |
| 5 | αvβ6 Peptide 1-AD07511-LP29b | 1 mg/kg administered on days 1 and 7 | Tamoxifen | 3 times per week starting on day 4 |
| 6 | αvβ6 Peptide 1-AD07778-LP29b | 1 mg/kg administered on days 1 and 7 | Tamoxifen | 3 times per week starting on day 4 |
| 7 | αvβ6 Peptide 1-AD07511-LP38b | 1 mg/kg administered on days 1 and 7 | Tamoxifen | 3 times per week starting on day 4 |

TABLE 24-continued

Dosing Groups for mice of Example 8.

| Group | RNAi agent and Dose | RNAi agent Dosing Regimen | Induction Agent Administration | Induction Agent Dosing Regimen |
|---|---|---|---|---|
| 8 | αvβ6 Peptide 1-AD07578-LP38b | 1 mg/kg administered on days 1 and 7 | Tamoxifen | 3 times per week starting on day 4 |

The RNAi agents in Example 8 (Groups 3-8) were synthesized having nucleotide sequences directed to target the DUX4 gene, and included a functionalized amine reactive group ($NH_2$-$C_6$) at the 5' terminal end of the sense strand to facilitate conjugation to the respective targeting ligand or linker.

For Groups 3-4, the targeting ligand selected was the small molecule skeletal muscle receptor SM45b, which was synthesized as an azide, which allowed for convenient coupling to Linker L4. (See, e.g., Example 3, above, for structural and related information for SM45-p and L4).

For Groups 5-8, Peptide 1 was conjugated to the sense strand of the DUX4 RNAi agent. Peptide 1 was linked to the (NH2-C6) functionalized RNAi agent via an amide coupling reaction at the 5' terminal end of the sense strand (See Example 6 for structural information.)

The DUX4 RNAi agents in Example 6 were further synthesized with a disulfide functional group (C6-SS-C6) at the 3' terminal end of the sense strand to facilitate conjugation to a PK/PD modulator.

For Groups 3-4, a Bis(PEG47+C22) moiety was attached to the 3' terminal end of the sense strand to serve as a pharmacokinetic/pharmacodynamic (PK/PD) modulator (See, e.g., Example 3, above, for structural information and related information).

For Groups 5-6, an LP29b moiety was attached to the 3' terminal end of the sense strand to serve as a pharmacokinetic/pharmacodynamic (PK/PD) modulator, having the following structure:

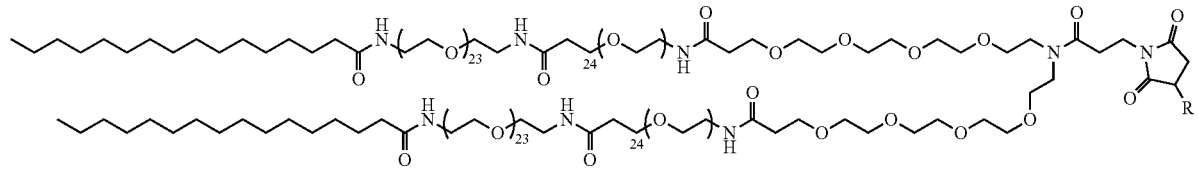

wherein R comprises the DUX4 RNAi agent.

LP29-p was linked to the 3' end of the sense strand by reducing the terminal 3' disulfide bond of the (C6-SS-C6) functional group and coupling the maleimide of LP29-p to the terminal 3' thiol via Michael addition. For Groups 7-8, an LP38b moiety was attached to the 3' terminal end of the sense strand to serve as a pharmacokinetic/pharmacodynamic (PK/PD) modulator. (See, e.g., Example 6, above, for structural information and related information).

The modified RNAi agent nucleotide sequences were synthesized as shown herein in Table 3, Table 4.1, Table 4.6, and Tables 5.1, Table 5.2, Table 5.3, and Table 5.4 (showing the fully modified conjugate).

Nine mice were dosed in each Group (n=9), except for the Positive Control (tamoxifen and saline, with no DUX4 RNAi agent administered) which had 12 mice (n=12). On day 22, animals were sacrificed and muscles were harvested, processed, and analyzed in accordance with the procedures described in Example 2.

Figure 9:
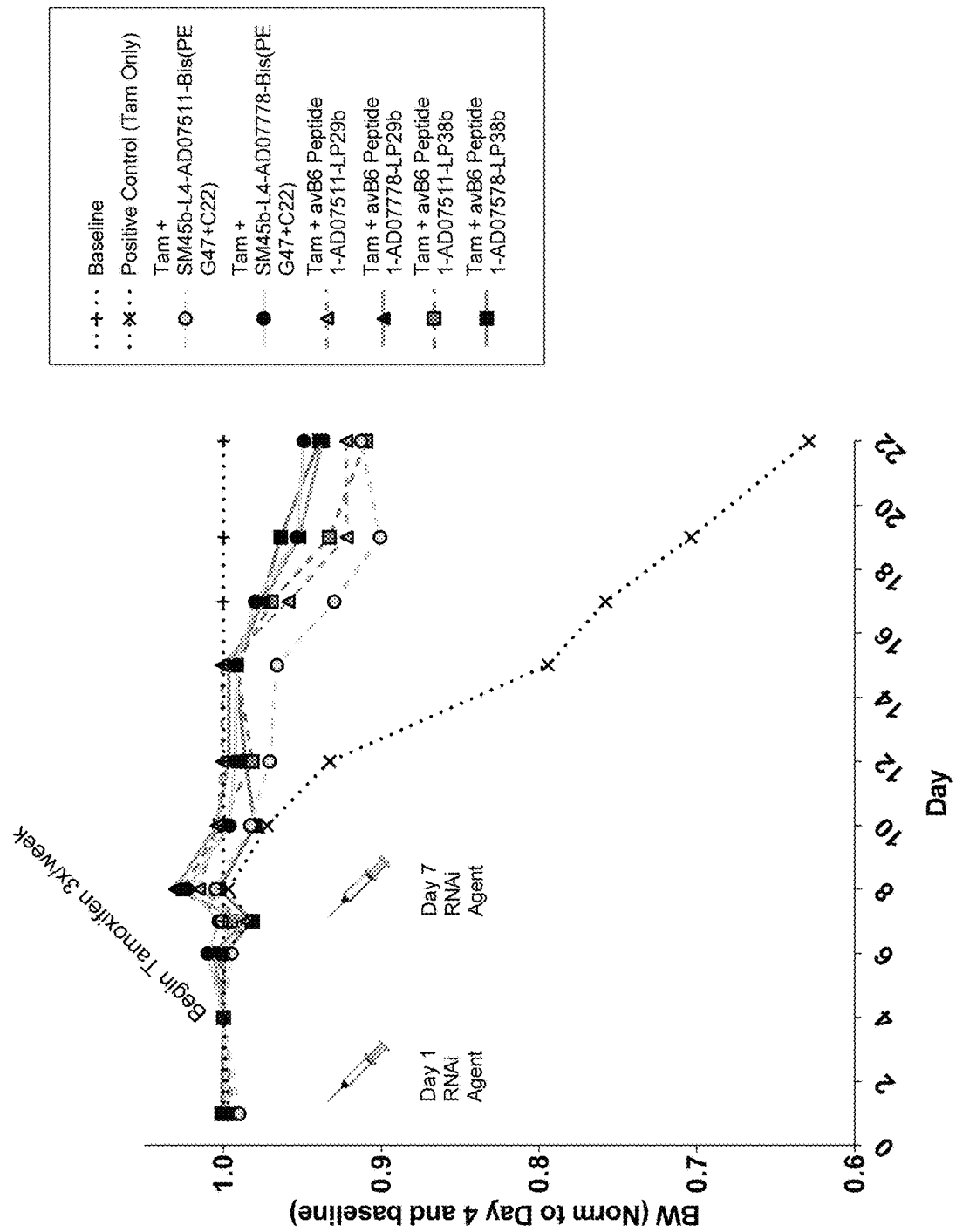
FIG. 9. Graph depicting mean bodyweights of FSHD-like model mice, as more fully described in Example 8.
Figure 10:
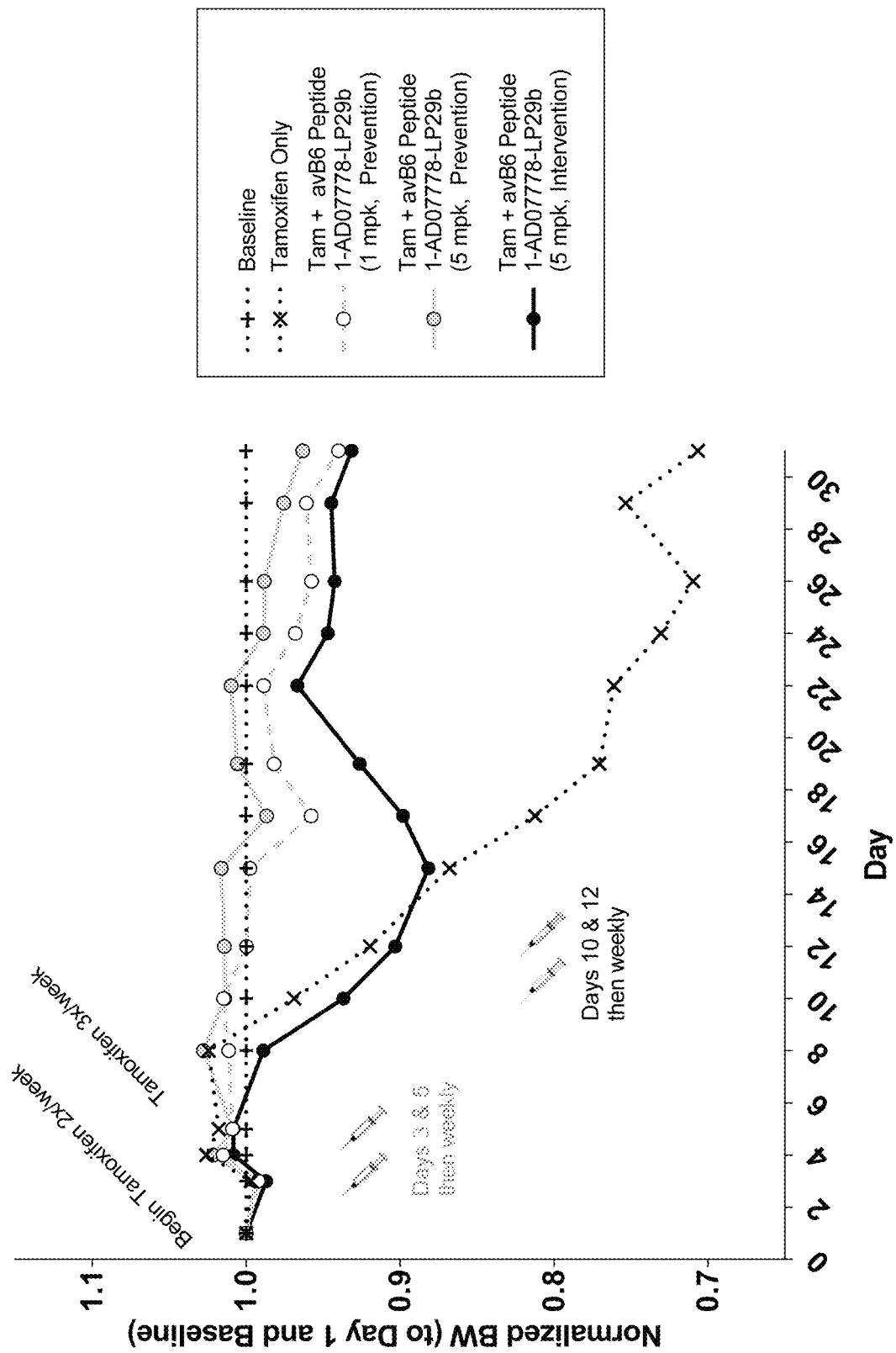
FIG. 10. Graph depicting mean bodyweights of FSHD-like model mice, as more fully described in Example 9.

Body weight measurements were taken on days 1, 4, 6, 7, 8, 10, 12, 15, 17, 19 and 22, and were normalized to day 4 (pre-tamoxifen administration) and baseline, as shown in FIG. 9.

Average relative DUX4 expression in harvested tissue was examined, as shown in the following Tables for various muscle types:

TABLE 25.1

Average relative DUX4 expression in biceps for mice of Example 8 normalized to Baseline (Group 1).

| | Biceps Day 22 | |
|---|---|---|
| | Relative DUX4 Expression | Standard Deviation (+/−) |
| Group 1 (Baseline) | 1.000 | 0.831 |
| Group 2 (Positive Control (Tamoxifen only)) | 1.311 | 0.478 |
| Group 3 (1 mg/kg SM45b-AD07511-Bis(PEG47 + C22)) | 0.705 | 0.313 |
| Group 4 (1 mg/kg SM45b-AD07778-Bis(PEG47 + C22)) | 0.788 | 0.254 |
| Group 5 (1 mg/kg αvβ6 Peptide 1-AD07511-LP29b) | 0.399 | 0.172 |
| Group 6 (1 mg/kg αvβ6 Peptide 1-AD07778-LP29b) | 0.405 | 0.262 |

TABLE 25.1-continued

Average relative DUX4 expression in biceps for mice of Example 8 normalized to Baseline (Group 1).

| | Biceps Day 22 | |
|---|---|---|
| | Relative DUX4 Expression | Standard Deviation (+/−) |
| Group 7 (1 mg/kg αvβ6 Peptide 1-AD07511-LP38b) | 0.580 | 0.275 |
| Group 8 (1 mg/kg αvβ6 Peptide 1-AD07778-LP38b) | 0.374 | 0.228 |

TABLE 25.2

Average relative DUX4 expression in diaphragm for mice of Example 8 normalized to Baseline (Group 1).

| | Diaphragm Day 22 | |
|---|---|---|
| | Relative DUX4 Expression | Standard Deviation (+/−) |
| Group 1 (Baseline) | 1.000 | 0.373 |
| Group 2 (Positive Control (Tamoxifen only)) | 2.628 | 0.681 |
| Group 3 (1 mg/kg SM45b-AD07511-Bis(PEG47 + C22)) | 0.926 | 0.353 |
| Group 4 (1 mg/kg SM45b-AD07778-Bis(PEG47 + C22)) | 1.098 | 0.366 |
| Group 5 (1 mg/kg αvβ6 Peptide 1-AD07511-LP29b) | 0.990 | 0.360 |
| Group 6 (1 mg/kg αvβ6 Peptide 1-AD07778-LP29b) | 0.866 | 0.372 |
| Group 7 (1 mg/kg αvβ6 Peptide 1-AD07511-LP38b) | 1.053 | 0.333 |
| Group 8 (1 mg/kg αvβ6 Peptide 1-AD07778-LP38b) | 0.787 | 0.382 |

TABLE 25.3

Average relative DUX4 expression in gastrocnemius for mice of Example 8 normalized to Baseline (Group 1).

| | Gastrocnemius Day 22 | |
|---|---|---|
| | Relative DUX4 Expression | Standard Deviation (+/−) |
| Group 1 (Baseline) | 1.000 | 0.328 |
| Group 2 (Positive Control (Tamoxifen only)) | 2.274 | 0.757 |
| Group 3 (1 mg/kg SM45b-AD07511-Bis(PEG47 + C22)) | 0.585 | 0.207 |
| Group 4 (1 mg/kg SM45b-AD07778-Bis(PEG47 + C22)) | 0.764 | 0.162 |
| Group 5 (1 mg/kg αvβ6 Peptide 1-AD07511-LP29b) | 0.615 | 0.218 |
| Group 6 (1 mg/kg αvβ6 Peptide 1-AD07778-LP29b) | 0.631 | 0.212 |
| Group 7 (1 mg/kg αvβ6 Peptide 1-AD07511-LP38b) | 0.705 | 0.239 |
| Group 8 (1 mg/kg αvβ6 Peptide 1-AD07778-LP38b) | 0.727 | 0.330 |

TABLE 25.4

Average relative DUX4 expression in masseter for mice of Example 8 normalized to Baseline (Group 1).

| | Masseter Day 22 | |
|---|---|---|
| | Relative DUX4 Expression | Standard Deviation (+/−) |
| Group 1 (Baseline) | 1.000 | 0.300 |
| Group 2 (Positive Control (Tamoxifen only)) | 1.330 | 0.318 |
| Group 3 (1 mg/kg SM45b-AD07511-Bis(PEG47 + C22)) | 0.852 | 0.243 |
| Group 4 (1 mg/kg SM45b-AD07778-Bis(PEG47 + C22)) | 0.876 | 0.221 |
| Group 5 (1 mg/kg αvβ6 Peptide 1-AD07511-LP29b) | 0.533 | 0.111 |
| Group 6 (1 mg/kg αvβ6 Peptide 1-AD07778-LP29b) | 0.534 | 0.068 |
| Group 7 (1 mg/kg αvβ6 Peptide 1-AD07511-LP38b) | 0.613 | 0.248 |
| Group 8 (1 mg/kg αvβ6 Peptide 1-AD07778-LP38b) | 0.610 | 0.156 |

TABLE 25.5

Average relative DUX4 expression in TA (tibialis anterior) for mice of Example 8 normalized to Baseline (Group 1).

| | TA Day 22 | |
|---|---|---|
| | Relative DUX4 Expression | Standard Deviation (+/−) |
| Group 1 (Baseline) | 1.000 | 0.211 |
| Group 2 (Positive Control (Tamoxifen only)) | 1.516 | 0.297 |
| Group 3 (1 mg/kg SM45b-AD07511-Bis(PEG47 + C22)) | 0.616 | 0.195 |
| Group 4 (1 mg/kg SM45b-AD07778-Bis(PEG47 + C22)) | 0.654 | 0.159 |
| Group 5 (1 mg/kg αvβ6 Peptide 1-AD07511-LP29b) | 0.484 | 0.167 |
| Group 6 (1 mg/kg αvβ6 Peptide 1-AD07778-LP29b) | 0.573 | 0.303 |
| Group 7 (1 mg/kg αvβ6 Peptide 1-AD07511-LP38b) | 0.495 | 0.218 |
| Group 8 (1 mg/kg αvβ6 Peptide 1-AD07778-LP38b) | 0.556 | 0.184 |

TABLE 25.6

Average relative DUX4 expression in trapezius for mice of Example 8 normalized to Baseline (Group 1).

| | Trapezius Day 22 | |
|---|---|---|
| | Relative DUX4 Expression | Standard Deviation (+/−) |
| Group 1 (Baseline) | 1.000 | 0.340 |
| Group 2 (Positive Control (Tamoxifen only)) | 2.181 | 0.466 |
| Group 3 (1 mg/kg SM45b-AD07511-Bis(PEG47 + C22)) | 0.508 | 0.233 |
| Group 4 (1 mg/kg SM45b-AD07778-Bis(PEG47 + C22)) | 0.622 | 0.277 |
| Group 5 (1 mg/kg αvβ6 Peptide 1-AD07511-LP29b) | 0.562 | 0.179 |
| Group 6 (1 mg/kg αvβ6 Peptide 1-AD07778-LP29b) | 0.567 | 0.214 |
| Group 7 (1 mg/kg αvβ6 Peptide 1-AD07511-LP38b) | 0.603 | 0.322 |
| Group 8 (1 mg/kg αvβ6 Peptide 1-AD07778-LP38b) | 0.633 | 0.218 |

TABLE 25.7

Average relative DUX4 expression in triceps for mice of Example 8 normalized to Baseline (Group 1).

| | Triceps Day 22 | |
|---|---|---|
| | Relative DUX4 Expression | Standard Deviation (+/−) |
| Group 1 (Baseline) | 1.000 | 0.387 |
| Group 2 (Positive Control (Tamoxifen only)) | 2.331 | 1.000 |
| Group 3 (1 mg/kg SM45b-AD07511-Bis(PEG47 + C22)) | 0.508 | 0.243 |
| Group 4 (1 mg/kg SM45b-AD07778-Bis(PEG47 + C22)) | 0.649 | 0.109 |
| Group 5 (1 mg/kg αvβ6 Peptide 1-AD07511-LP29b) | 0.569 | 0.189 |
| Group 6 (1 mg/kg αvβ6 Peptide 1-AD07778-LP29b) | 0.601 | 0.265 |
| Group 7 (1 mg/kg αvβ6 Peptide 1-AD07511-LP38b) | 0.679 | 0.300 |
| Group 8 (1 mg/kg αvβ6 Peptide 1-AD07778-LP38b) | 0.848 | 0.359 |

Average relative Wfdc3 mRNA transcript levels in harvested tissue were similarly determined as shown in the following Tables for various muscle types:

TABLE 26.1

Average relative Wfdc3 expression in biceps for mice of Example 6 normalized to Baseline (Group 1).

| | Biceps Day 22 | | |
|---|---|---|---|
| | Relative Wfdc3 Expression | Low (error) | High (error) |
| Group 1 (Baseline) | 1.000 | 0.821 | 4.586 |
| Group 2 (Positive Control (Tamoxifen only)) | 16.434 | 2.039 | 2.327 |
| Group 3 (1 mg/kg SM45b-AD07511-Bis(PEG47 + C22)) | 4.778 | 2.175 | 3.994 |
| Group 4 (1 mg/kg SM45b-AD07778-Bis(PEG47 + C22)) | 3.760 | 1.353 | 2.114 |
| Group 5 (1 mg/kg αvβ6 Peptide 1-AD07511-LP29b) | 6.146 | 1.610 | 2.181 |
| Group 6 (1 mg/kg αvβ6 Peptide 1-AD07778-LP29b) | 2.722 | 1.090 | 1.819 |
| Group 7 (1 mg/kg αvβ6 Peptide 1-AD07511-LP38b) | 6.513 | 2.463 | 3.962 |
| Group 8 (1 mg/kg αvβ6 Peptide 1-AD07778-LP38b) | 3.041 | 1.072 | 1.655 |

TABLE 26.2

Average relative Wfdc3 expression in diaphragm for mice of Example 6 normalized to Baseline (Group 1).

| | Diaphragm Day 22 | | |
|---|---|---|---|
| | Relative Wfdc3 Expression | Low (error) | High (error) |
| Group 1 (Baseline) | 1.000 | 0.769 | 3.338 |
| Group 2 (Positive Control (Tamoxifen only)) | 21.913 | 2.959 | 3.421 |
| Group 3 (1 mg/kg SM45b-AD07511-Bis(PEG47 + C22)) | 4.848 | 2.284 | 4.320 |
| Group 4 (1 mg/kg SM45b-AD07778-Bis(PEG47 + C22)) | 2.795 | 1.346 | 2.598 |
| Group 5 (1 mg/kg αvβ6 Peptide 1-AD07511-LP29b) | 5.240 | 1.774 | 2.682 |
| Group 6 (1 mg/kg αvβ6 Peptide 1-AD07778-LP29b) | 1.306 | 0.621 | 1.185 |
| Group 7 (1 mg/kg αvβ6 Peptide 1-AD07511-LP38b) | 5.245 | 2.932 | 6.646 |
| Group 8 (1 mg/kg αvβ6 Peptide 1-AD07778-LP38b) | 1.618 | 1.003 | 2.642 |

TABLE 26.3

Average relative Wfdc3 expression in gastrocnemius for mice of Example 6 normalized to Baseline (Group 1).

| | Gastrocnemius Day 22 | | |
|---|---|---|---|
| | Relative Wfdc3 Expression | Low (error) | High (error) |
| Group 1 (Baseline) | 1.000 | 0.674 | 2.064 |
| Group 2 (Positive Control (Tamoxifen only)) | 8.357 | 1.679 | 2.102 |
| Group 3 (1 mg/kg SM45b-AD07511-Bis(PEG47 + C22)) | 2.326 | 0.537 | 0.698 |
| Group 4 (1 mg/kg SM45b-AD07778-Bis(PEG47 + C22)) | 1.455 | 0.464 | 0.681 |
| Group 5 (1 mg/kg αvβ6 Peptide 1-AD07511-LP29b) | 2.382 | 0.597 | 0.797 |
| Group 6 (1 mg/kg αvβ6 Peptide 1-AD07778-LP29b) | 1.130 | 0.420 | 0.669 |
| Group 7 (1 mg/kg αvβ6 Peptide 1-AD07511-LP38b) | 2.440 | 0.814 | 1.221 |
| Group 8 (1 mg/kg αvβ6 Peptide 1-AD07778-LP38) | 1.126 | 0.468 | 0.800 |

TABLE 26.4

Average relative Wfdc3 expression in masseter for mice of Example 6 normalized to Baseline (Group 1).

| | Masseter Day 22 | | |
|---|---|---|---|
| | Relative Wfdc3 Expression | Low (error) | High (error) |
| Group 1 (Baseline) | 1.000 | 0.724 | 2.625 |
| Group 2 (Positive Control (Tamoxifen only)) | 9.662 | 1.776 | 2.175 |
| Group 3 (1 mg/kg SM45b-AD07511-Bis(PEG47 + C22)) | 2.818 | 0.911 | 1.347 |
| Group 4 (1 mg/kg SM45b-AD07778-Bis(PEG47 + C22)) | 1.574 | 0.598 | 0.965 |
| Group 5 (1 mg/kg αvβ6 Peptide 1-AD07511-LP29b) | 1.716 | 0.602 | 0.928 |
| Group 6 (1 mg/kg αvβ6 Peptide 1-AD07778-LP29b) | 0.700 | 0.294 | 0.507 |
| Group 7 (1 mg/kg αvβ6 Peptide 1-AD07511-LP38b) | 1.836 | 0.884 | 1.704 |
| Group 8 (1 mg/kg αvβ6 Peptide 1-AD07778-LP38b) | 0.570 | 0.271 | 0.516 |

TABLE 26.5

Average relative Wfdc3 expression in TA (tibialis anterior) for mice of Example 6 normalized to Baseline (Group 1).

| | TA Day 22 | | |
|---|---|---|---|
| | Relative Wfdc3 Expression | Low (error) | High (error) |
| Group 1 (Baseline) | 1.000 | 0.825 | 4.714 |
| Group 2 (Positive Control (Tamoxifen only)) | 16.122 | 2.924 | 3.571 |
| Group 3 (1 mg/kg SM45b-AD07511-Bis(PEG47 + C22)) | 3.474 | 1.193 | 1.817 |
| Group 4 (1 mg/kg SM45b-AD07778-Bis(PEG47 + C22)) | 1.697 | 0.618 | 0.971 |
| Group 5 (1 mg/kg αvβ6 Peptide 1-AD07511-LP29b) | 4.008 | 0.925 | 1.202 |
| Group 6 (1 mg/kg αvβ6 Peptide 1-AD07778-LP29b) | 1.539 | 0.793 | 1.634 |
| Group 7 (1 mg/kg αvβ6 Peptide 1-AD07511-LP38b) | 4.097 | 1.537 | 2.459 |
| Group 8 (1 mg/kg αvβ6 Peptide 1-AD07778-LP38b) | 1.553 | 0.560 | 0.876 |

TABLE 26.6

Average relative Wfdc3 expression in trapezius for mice of Example 6 normalized to Baseline (Group 1).

| | Trapezius Day 22 | | |
|---|---|---|---|
| | Relative Wfdc3 Expression | Low (error) | High (error) |
| Group 1 (Baseline) | 1.000 | 0.757 | 3.112 |
| Group 2 (Positive Control (Tamoxifen only)) | 13.635 | 2.965 | 3.790 |
| Group 3 (1 mg/kg SM45b-AD07511-Bis(PEG47 + C22)) | 1.929 | 1.009 | 2.115 |
| Group 4 (1 mg/kg SM45b-AD07778-Bis(PEG47 + C22)) | 1.222 | 0.553 | 1.010 |
| Group 5 (1 mg/kg αvβ6 Peptide 1-AD07511-LP29b) | 1.834 | 0.609 | 0.911 |
| Group 6 (1 mg/kg αvβ6 Peptide 1-AD07778-LP29b) | 0.552 | 0.272 | 0.534 |
| Group 7 (1 mg/kg αvβ6 Peptide 1-AD07511-LP38b) | 2.258 | 1.166 | 2.410 |
| Group 8 (1 mg/kg αvβ6 Peptide 1-AD07778-LP38b) | 0.632 | 0.321 | 0.651 |

TABLE 267

Average relative Wfdc3 expression in triceps for mice of Example 6 normalized to Baseline (Group 1).

| | Triceps Day 22 | | |
|---|---|---|---|
| | Relative Wfdc3 Expression | Low (error) | High (error) |
| Group 1 (Baseline) | 1.000 | 0.648 | 1.842 |
| Group 2 (Positive Control (Tamoxifen only)) | 13.188 | 2.581 | 3.209 |
| Group 3 (1 mg/kg SM45b-AD07511-Bis(PEG47 + C22)) | 1.742 | 0.614 | 0.948 |
| Group 4 (1 mg/kg SM45b-AD07778-Bis(PEG47 + C22)) | 0.792 | 0.427 | 0.926 |
| Group 5 (1 mg/kg αvβ6 Peptide 1-AD07511-LP29b) | 1.702 | 0.573 | 0.865 |
| Group 6 (1 mg/kg αvβ6 Peptide 1-AD07778-LP29b) | 0.517 | 0.229 | 0.411 |
| Group 7 (1 mg/kg αvβ6 Peptide 1-AD07511-LP38b) | 1.606 | 0.962 | 2.399 |
| Group 8 (1 mg/kg αvβ6 Peptide 1-AD07778-LP38b) | 0.590 | 0.322 | 0.707 |

For the DUX4 RNAi agents shown in the data Tables above, AD07511 included nucleotide sequences designed to inhibit a DUX4 gene at position 1437 of the gene; and AD077778 included nucleotide sequences designed to inhibit a DUX4 gene at position 408 of the gene. As shown above, both of these DUX4 RNAi agents show meaningful reductions in DUX4 gene expression in each of the three formats examined.

Example 9. In Vivo Administration of RNAi Agents Targeting DUX4 in FSHD-Like Transgenic Mice The FSHD-like transgenic mouse model as described in Example 2 were used. The DUX4 RNAi agent assessed was DUX4 RNAi agent AD07778 linked to the targeting ligand of peptide 1 and the PK/PD modulator LP29b (see AC000448 in Table 5.4 for fully modified and conjugated sense and antisense strand structure), which was synthesized according to phosphoramidite technology on solid phase in accordance with general procedures known in the art and commonly used in oligonucleotide synthesis, as set forth in Example 1 herein.

The objective of this study was to assess dose response and timing effect of this DUX4 RNAi agent on the knock-down of DUX4 mRNA expression, the reduction of biomarkers of DUX4 protein activity, and pharmacodynamic effect after a twice weekly subcutaneous dose followed by weekly subcutaneous doses in FLExDUX4/HSA-MCM mice.

Two administration strategies were employed with the study: prevention and intervention.

During the prevention strategy (Groups C and D below) the DUX4 RNAi agent was administered within 2 days of initiation of tamoxifen administration. In this way, the DUX4 RNAi agent was believed to be delivered to skeletal muscle cells (myofibers) as DUX4 expression was induced and increasing.

During the intervention strategy (Group E below), the DUX4 RNAi agent was administered after manifestation of the FSHD-like phenotype (by Day 10 after initiation of tamoxifen administration). In this way, the DUX4 RNAi agent was delivered to myofibers after DUX4 expression had already begun to take myotoxic effect.

The dosing regimen and details are set forth in the following Table 27:

TABLE 27

Dosing Groups for mice of Example 9.

| Group | RNAi agent and Dose | RNAi agent Dosing Regimen | Induction Agent Administration | Induction Agent Dosing Regimen |
|---|---|---|---|---|
| A | Baseline (no RNAi agent, saline injection) | N/A | Corn oil (negative control) | Day 1, and then 2 times per week for the first week and 3 times per week beginning at week 2 |
| B | Positive Control (no RNAi agent, saline injection) | N/A | Tamoxifen | Day 1, and then 2 times per week for the first week and 3 times per week beginning at week 2 |
| C | (Prevention study) αvβ6 Peptide 1-AD07778-LP29b | 1 mg/kg administered on days 3, 5, 10, 17, and 25 | Tamoxifen | Day 1, and then 2 times per week for the first week and 3 times per week beginning at week 2 |
| D | (Prevention study) αvβ6 Peptide 1-AD07778-LP29b | 5 mg/kg administered on days 3, 5, 10, 17, and 25 | Tamoxifen | Day 1, and then 2 times per week for the first week and 3 times per week beginning at week 2 |
| E | (Intervention study) Saline (no RNAi agent) for first two doses, followed by administration of Peptide 1-AD07778-LP29b | Saline (no RNAi Agent) administered on days 3 and 5. 5 mg/kg of the RNAi agent administered on days 10, 17, and 25 | Tamoxifen | Day 1, and then 2 times per week for the first week and 3 times per week beginning at week 2 |

Each mouse was administered corn oil control or 1 mg/mL tamoxifen solution via oral gavage at a dose volume of 100 μL per 20 g body weight (5 mg/kg) twice weekly during Week 1 and three times weekly during Weeks 2 through 4.

The RNAi agent in Example 9 (Groups C, D, and E) were synthesized having nucleotide sequences directed to target the DUX4 gene, and included a functionalized amine reactive group ($NH_2$-$C_6$) at the 5' terminal end of the sense strand to facilitate conjugation to the respective targeting ligand or linker. Peptide 1 was conjugated to the sense strand of the DUX4 RNAi agent. Peptide 1 was linked to the ($NH_2$-$C_6$) functionalized RNAi agent via an amide coupling reaction at the 5' terminal end of the sense strand (See Example 6 for structural information.)

The DUX4 RNAi agents in Example 6 were further synthesized with a disulfide functional group (C6-SS-C6) at the 3' terminal end of the sense strand to facilitate conjugation to a PK/PD modulator. An LP29b moiety was attached to the 3' terminal end of the sense strand to serve as a pharmacokinetic/pharmacodynamic (PK/PD) modulator, having the following structure:

The modified RNAi agent nucleotide sequences were synthetized as shown herein in Table 3, Table 4.1, Table 4.6, and Tables 5.1, Table 5.2, Table 5.3, and Table 5.4 (showing the fully modified conjugate).

Six mice were dosed in Group A (n=6), which involved no tamoxifen. Ten mice were dosed in Groups B, C, D, and E (n=10).

Body weight measurements were taken on days of tamoxifen and RNAi agent administration (Days 1, 3, 4, 5, 8, 10, 12, 15, 17, 19, 22, 24, 26, 29, and 31). To control for individual variance, each individual animal's bodyweight was normalized to Day 1 and then to the mean of the baseline group's bodyweight at each time point. A two-way ANOVA followed by a Dunnett's multiple comparison test was used to determine significant differences between group body weights at each time point.

Bodyweight did not significantly differ between groups until Day 10. On Day 10, animals administered tamoxifen only tended to have lower bodyweights compared to baseline and had significantly lower bodyweights than those administered 1 or 5 mg/kg of the RNAi agent beginning on Day 3 (Groups C and D; p=0.0294, p=0.0010, and p=0.0012,

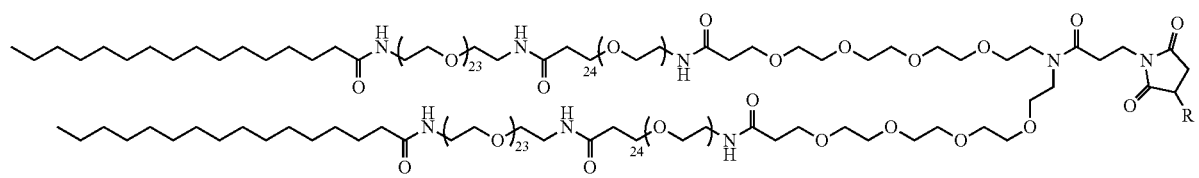

wherein R comprises the DUX4 RNAi agent.

The maleimide LP29-p was linked to the 3' end of the sense strand by reducing the terminal 3' disulfide bond and performing Michael addition to the terminal 3' thiol to synthesize the RNAi agent.

respectively). By Day 12, animals administered tamoxifen only (Group B) and the group with tamoxifen and 5 mg/kg RNAi agent administered for the first time on Day 10 (Group E) had significantly lower bodyweight compared to baseline animals (Group A) and those administered 1 or 5 mg/kg on Day 3 (Groups C and D). On Day 17, bodyweight loss ceased for animals administered in Group E, while bodyweight loss continued for animals administered tamoxifen only (Group B). While Group E mean bodyweight was significantly lower than baseline and animals administered 1 or 5 mg/kg DUX4 RNAi agent beginning on Day 3 (Groups A, C, and D; p<0.05 for all respective comparisons), it was also significantly higher than mean bodyweight of animals administered tamoxifen only (Group B, p=0.0003). After day 22, bodyweight for animals of Group E that were administered DUX4 RNAi agent beginning on Day 10 remained statistically equivalent to Groups C and D through Day 31

On day 31, animals were sacrificed and muscles were harvested, processed, and analyzed in accordance with the procedures described in Example 2. Average relative DUX4 expression in harvested tissue was examined, as shown in the following Tables for various muscle types:

TABLE 28.1

Average relative DUX4 expression in biceps for mice of Example 9 normalized to Baseline (Group A).

| | Biceps Day 31 | |
|---|---|---|
| | Relative DUX4 Expression | Standard Deviation (+/−) |
| Group A (Baseline) | 1.000 | 0.306 |
| Group B (Positive Control (Tamoxifen only)) | 1.929 | 0.794 |
| Group C (1 mg/kg αvβ6 Peptide 1-AD07778-LP29) | 0.868 | 0.255 |
| Group D (5 mg/kg αvβ6 Peptide 1-AD07778-LP29) | 1.050 | 0.327 |
| Group E (5 mg/kg αvβ6 Peptide 1-AD07778-LP29 dosed starting day 10 after two saline doses on days 3 and 5 | 0.715 | 0.223 |

TABLE 28.2

Average relative DUX4 expression in gastrocnemius for mice of Example 9 normalized to Baseline (Group A).

| | Gastrocnemius Day 31 | |
|---|---|---|
| | Relative DUX4 Expression | Standard Deviation (+/−) |
| Group A (Baseline) | 1.000 | 0.283 |
| Group B (Positive Control (Tamoxifen only)) | 1.912 | 1.101 |
| Group C (1 mg/kg αvβ6 Peptide 1-AD07778-LP29) | 0.888 | 0.455 |
| Group D (5 mg/kg αvβ6 Peptide 1-AD07778-LP29) | 0.716 | 0.288 |
| Group E (5 mg/kg αvβ6 Peptide 1-AD07778-LP29 dosed starting day 10 after two saline doses on days 3 and 5 | 0.789 | 0.419 |

TABLE 28.3

Average relative DUX4 expression in masseter for mice of Example 9 normalized to Baseline (Group A).

| | Masseter Day 31 | |
|---|---|---|
| | Relative DUX4 Expression | Standard Deviation (+/−) |
| Group A (Baseline) | 1.000 | 0.246 |
| Group B (Positive Control (Tamoxifen only)) | 1.444 | 0.467 |
| Group C (1 mg/kg αvβ6 Peptide 1-AD07778-LP29) | 0.843 | 0.410 |
| Group D (5 mg/kg αvβ6 Peptide 1-AD07778-LP29) | 0.666 | 0.168 |
| Group E (5 mg/kg αvβ6 Peptide 1-AD07778-LP29 dosed starting day 10 after two saline doses on days 3 and 5 | 0.841 | 0.176 |

TABLE 28.4

Average relative DUX4 expression in TA (tibialis anterior) for mice of Example 9 normalized to Baseline (Group A).

| | TA Day 31 | |
|---|---|---|
| | Relative DUX4 Expression | Standard Deviation (+/−) |
| Group A (Baseline) | 1.000 | 0.338 |
| Group B (Positive Control (Tamoxifen only)) | 1.907 | 0.808 |
| Group C (1 mg/kg αvβ6 Peptide 1-AD07778-LP29) | 0.953 | 0.312 |
| Group D (5 mg/kg αvβ6 Peptide 1-AD07778-LP29) | 0.834 | 0.281 |
| Group E (5 mg/kg αvβ6 Peptide 1-AD07778-LP29 dosed starting day 10 after two saline doses on days 3 and 5 | 0.808 | 0.311 |

TABLE 28.5

Average relative DUX4 expression in trapezius for mice of Example 9 normalized to Baseline (Group A).

| | Trapezius Day 31 | |
|---|---|---|
| | Relative DUX4 Expression | Standard Deviation (+/−) |
| Group A (Baseline) | 1.000 | 0.258 |
| Group B (Positive Control (Tamoxifen only)) | 2.679 | 2.189 |
| Group C (1 mg/kg αvβ6 Peptide 1-AD07778-LP29) | 0.931 | 0.564 |
| Group D (5 mg/kg αvβ6 Peptide 1-AD07778-LP29) | 0.890 | 0.241 |
| Group E (5 mg/kg αvβ6 Peptide 1-AD07778-LP29 dosed starting day 10 after two saline doses on days 3 and 5 | 0.857 | 0.199 |

TABLE 28.6

Average relative DUX4 expression in triceps for mice of Example 9 normalized to Baseline (Group A).

| | Triceps Day 31 | |
|---|---|---|
| | Relative DUX4 Expression | Standard Deviation (+/−) |
| Group A (Baseline) | 1.000 | 0.227 |
| Group B (Positive Control (Tamoxifen only)) | 2.565 | 2.000 |

TABLE 28.6-continued

Average relative DUX4 expression in triceps for mice of Example 9 normalized to Baseline (Group A).

|  | Triceps Day 31 | |
| --- | --- | --- |
|  | Relative DUX4 Expression | Standard Deviation (+/−) |
| Group C (1 mg/kg αvβ6 Peptide 1-AD07778-LP29) | 0.972 | 0.358 |
| Group D (5 mg/kg αvβ6 Peptide 1-AD07778-LP29) | 0.633 | 0.222 |
| Group E (5 mg/kg αvβ6 Peptide 1-AD07778-LP29 dosed starting day 10 after two saline doses on days 3 and 5 | 0.793 | 0.259 |

Average relative Wfdc3 mRNA transcript levels and Myo1g mRNA transcript levels in harvested tissue were similarly determined for various muscle types. All individual and group Wfdc3 and Myo1g relative expression values were normalized to respective mean relative expression levels from the baseline group (Group A). The tamoxifen administration (Group B) resulted in a dramatic and significant increase in Wfdc3 (4.891-11.772-fold) and Myo1g (2.139-12.744-fold) expression in all muscles assessed (p<0.001 for all respective comparisons). In tamoxifen-induced animals, the DUX4 RNAi agent Peptide 1-AD07778-LP29 administered at 1 or 5 mg/kg beginning on Day 3 (Groups C and D) and beginning on Day 10 (Group E) prevented Wfdc3 and Myo1g expression increase or reduced relative Wfdc3 and Myo1g expression to or below baseline. Administration of the DUX4 RNAi agent resulted in Wfdc3 and Myo1g mean relative expression levels that were significantly lower than tamoxifen only (Group B) regardless of dose level or administration timing (Groups C, D and E; p<0.0001 for all respective comparisons).

Additionally, the histology of the tissue samples were analyzed. Muscle sections were cut from formalin-fixed gastrocnemius, TA, and triceps collected on days of harvest and stained using H&E and PSR. In gastrocnemius, TA, and triceps, administration of tamoxifen induced a dramatic increase in centrally located nuclei, indicating active muscle repair, and fibrosis in FLExDUX4/HSA-MCM animals (Group B). Generally, fewer centralized nuclei and less fibrosis was observed in muscle sections from animals administered tamoxifen and DUX4 RNAi agent-treated animals (Groups C, D, and E) when compared to those administered tamoxifen only (Group B). Indeed, muscle sections from the animals of Groups C, D, and E had similar morphology to those of the baseline group (Group A). Animals of Group E (administered tamoxifen beginning on Day 1, then DUX4 RNAi agent beginning on Day 10) tended to exhibit slightly more fibrosis than those of Groups C and D.

As shown herein, the DUX4 RNAi agent administered, using either prevention or intervention strategy, was sufficient to return DUX4 expression levels to baseline, prevent or reduce increased expression of DUX4 target genes and markers of DUX4 activity (Wfdc3 and Myo1g), prevent bodyweight loss and return bodyweight to baseline levels, and reduce signs of myotoxicity (fibrosis, increased central nuclei, elevated serum creatinine kinase, muscle weight loss-4 of 9 muscles) thereby alleviating the FSHD-like phenotype observed in the FLExDUX4/HSA-MCM transgenic mouse model when administered tamoxifen via oral gavage.

Example 10. In Vivo Administration of RNAi Agents Targeting DUX4 in FSHD-Like Transgenic Mice The FSHD-like transgenic mouse model as described in Example 2 were used. The DUX4 RNAi agent assessed was DUX4 RNAi agent AD07778 linked to the targeting ligand of peptide 1 and the PK/PD modulator LP29b (see AC000448 in Table 5.4 for fully modified and conjugated sense and antisense strand structure), which was synthesized according to phosphoramidite technology on solid phase in accordance with general procedures known in the art and commonly used in oligonucleotide synthesis, as set forth in Example 1 herein.

The dosing regimen and details are set forth in the following Table 29:

TABLE 29

Dosing Groups for mice of Example 10.

| Group | RNAi agent and Dose | RNAi agent Dosing Regimen | Induction Agent Administration | Induction Agent Dosing Regimen |
| --- | --- | --- | --- | --- |
| 1 | Baseline (no RNAi agent, saline injection) | N/A | Corn oil (negative control) | Day 1, and then 2 times per week for the first week and 3 times per week beginning at week 2 |
| 2 | Positive Control (no RNAi agent, saline injection) | N/A | Tamoxifen | Day 1, and then 2 times per week for the first week and 3 times per week beginning at week 2 |
| 3 | (Prevention study) αvβ6 Peptide 1-AD07778-LP29b | 1 mg/kg administered on days 1 and 4 | Tamoxifen | Day 1, and then 2 times per week for the first week and 3 times per week beginning at week 2 |
| 4 | (Prevention study) αvβ6 Peptide 1-AD07778-LP29b | 5 mg/kg administered on days 1 and 4 | Tamoxifen | Day 1, and then 2 times per week for the first week and 3 times per week beginning at week 2 |

TABLE 29-continued

Dosing Groups for mice of Example 10.

| Group | RNAi agent and Dose | RNAi agent Dosing Regimen | Induction Agent Administration | Induction Agent Dosing Regimen |
|---|---|---|---|---|
| 5 | (Intervention study) Saline (no RNAi agent) for first two doses, followed by administration of αvβ6 Peptide 1-AD07778-LP29b | Saline (no RNAi Agent) administered on days 3 and 5. 5 mg/kg of the RNAi agent administered on days 10 and 12 | Tamoxifen | Day 1, and then 2 times per week for the first week and 3 times per week beginning at week 2 |

Each mouse was administered corn oil control or 1 mg/mL tamoxifen solution via oral gavage at a dose volume of 100 μL per 20 g body weight (5 mg/kg) twice weekly during Week 1 and three times weekly during Weeks 2 through 4.

The RNAi agent in Example 10 (Groups 2 and 4-6) was synthesized having nucleotide sequences directed to target the DUX4 gene, and included a functionalized amine reactive group ($NH_2$-$C_6$) at the 5' terminal end of the sense strand to facilitate conjugation to the respective targeting ligand or linker. Peptide 1 was conjugated to the sense strand of the DUX4 RNAi agent. Peptide 1 was linked to the ($NH_2$-$C_6$) functionalized RNAi agent via an amide coupling reaction at the 5' terminal end of the sense strand (See Example 6 for structural information.)

The DUX4 RNAi agents in Example 6 were further synthesized with a disulfide functional group (C6-SS-C6) at the 3' terminal end of the sense strand to facilitate conjugation to a PK/PD modulator. An LP29b moiety was attached to the 3' terminal end of the sense strand to serve as a pharmacokinetic/pharmacodynamic (PK/PD) modulator, having the following structure:

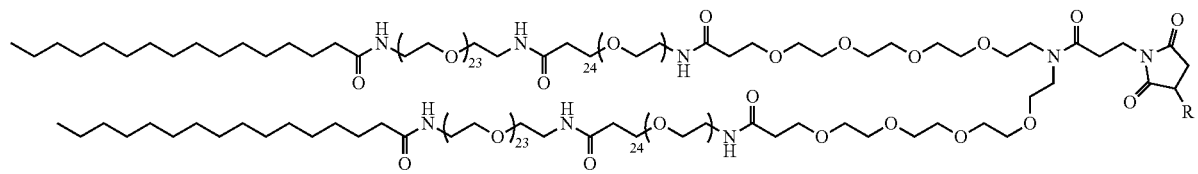

wherein R comprises the DUX4 RNAi agent.

The maleimide LP29-p was linked to the 3' end of the sense strand by reducing the terminal 3' disulfide bond and performing Michael addition to the terminal 3' thiol to synthesize the RNAi agent.

The modified RNAi agent nucleotide sequences were synthesized as shown herein in Table 3, Table 4.1, Table 4.6, and Tables 5.1, Table 5.2, Table 5.3, and Table 5.4 (showing the fully modified conjugate).

Six mice were dosed in Group 1 (n=6), ten mice were dosed in Group 2 (n=10), and eight mice were dosed in each of groups 3-5 (n=8).

On Day 26, animals were sacrificed and muscles were harvested, processed, and analyzed in accordance with the procedures described in Example 2. Average relative DUX4 expression in harvested tissue is shown in the following Tables for gastrocnemius and triceps:

TABLE 30.1

Average relative DUX4 expression in gastrocnemius for mice of Example 10 normalized to Baseline (Group 1).

| | Gastrocnemius Day 26 | |
|---|---|---|
| | Relative DUX4 Expression | Standard Deviation (+/−) |
| Group 1 (Baseline) | 1.000 | 0.213 |
| Group 2 (Positive Control (Tamoxifen only)) | 1.520 | 0.268 |
| Group 3 (1 mg/kg αvβ6 Peptide 1-AD07778-LP29), dosing days 1 and 4 | 0.868 | 0.223 |
| Group 4 (5 mg/kg αvβ6 Peptide 1-AD07778-LP29), dosing days 1 and 4 | 0.909 | 0.224 |
| Group 5 (5 mg/kg αvβ6 Peptide 1-AD07778-LP29), dosing days 10 and 12 | 1.059 | 0.201 |

TABLE 30.2

Average relative DUX4 expression in triceps for mice of Example 10 normalized to Baseline (Group 1).

| | Triceps Day 26 | |
|---|---|---|
| | Relative DUX4 Expression | Standard Deviation (+/−) |
| Group 1 (Baseline) | 1.000 | 0.419 |
| Group 2 (Positive Control (Tamoxifen only)) | 1.216 | 0.353 |
| Group 3 (1 mg/kg αvβ6 Peptide 1-AD07778-LP29), dosing days 1 and 4 | 0.755 | 0.198 |
| Group 4 (5 mg/kg αvβ6 Peptide 1-AD07778-LP29), dosing days 1 and 4 | 0.583 | 0.126 |
| Group 5 (5 mg/kg αvβ6 Peptide 1-AD07778-LP29), dosing days 10 and 12 | 1.009 | 0.217 |

Average relative Wfdc3 mRNA transcript levels in harvested tissue were similarly determined as shown in the following Tables for various gastrocnemius and triceps:

TABLE 31.1

Average relative Wfdc3 expression in gastrocnemius for mice of Example 10 normalized to Baseline (Group 1).

| | Gastrocnemius Day 26 | | |
|---|---|---|---|
| | Relative Wfdc3 Expression | Low (error) | High (error) |
| Group 1 (Baseline) | 1.000 | 0.238 | 0.312 |
| Group 2 (Positive Control (Tamoxifen only)) | 3.562 | 0.399 | 0.450 |
| Group 3 (1 mg/kg αvβ6 Peptide 1-AD07778-LP29), dosing days 1 and 4 | 1.187 | 0.399 | 0.600 |
| Group 4 (5 mg/kg αvβ6 Peptide 1-AD07778-LP29), dosing days 1 and 4 | 0.320 | 0.103 | 0.151 |
| Group 5 (5 mg/kg αvβ6 Peptide 1-AD07778-LP29), dosing days 10 and 12 | 0.459 | 0.281 | 0.725 |

TABLE 31.2

Average relative Wfdc3 expression in triceps for mice of Example 10 normalized to Baseline (Group 1).

| | Triceps Day 26 | | |
|---|---|---|---|
| | Relative Wfdc3 Expression | Low (error) | High (error) |
| Group 1 (Baseline) | 1.000 | 0.453 | 0.828 |
| Group 2 (Positive Control (Tamoxifen only)) | 2.726 | 0.938 | 1.429 |
| Group 3 (1 mg/kg αvβ6 Peptide 1-AD07778-LP29), dosing days 1 and 4 | 0.699 | 0.281 | 0.469 |
| Group 4 (5 mg/kg αvβ6 Peptide 1-AD07778-LP29), dosing days 1 and 4 | 0.075 | 0.027 | 0.043 |
| Group 5 (5 mg/kg αvβ6 Peptide 1-AD07778-LP29), dosing days 10 and 12 | 0.147 | 0.110 | 0.430 |

Average relative Myo1g mRNA transcript levels in harvested tissue were similarly determined as shown in the following Tables for various gastrocnemius and triceps:

TABLE 32.1

Average relative Myo1g expression in gastrocnemius for mice of Example 10 normalized to Baseline (Group 1).

| | Gastrocnemius Day 26 | | |
|---|---|---|---|
| | Relative Myo1g Expression | Low (error) | High (error) |
| Group 1 (Baseline) | 1.000 | 0.079 | 0.086 |
| Group 2 (Positive Control (Tamoxifen only)) | 1.685 | 0.163 | 0.180 |
| Group 3 (1 mg/kg αvβ6 Peptide 1-AD07778-LP29), dosing days 1 and 4 | 0.977 | 0.337 | 0.515 |
| Group 4 (5 mg/kg αvβ6 Peptide 1-AD07778-LP29), dosing days 1 and 4 | 0.284 | 0.117 | 0.198 |
| Group 5 (5 mg/kg αvβ6 Peptide 1-AD07778-LP29), dosing days 10 and 12 | 0.392 | 0.166 | 0.288 |

TABLE 32.2

Average relative Myo1g expression in triceps for mice of Example 10 normalized to Baseline (Group 1).

| | Triceps Day 26 | | |
|---|---|---|---|
| | Relative Myo1g Expression | Low (error) | High (error) |
| Group 1 (Baseline) | 1.000 | 0.249 | 0.332 |
| Group 2 (Positive Control (Tamoxifen only)) | 1.375 | 0.275 | 0.343 |
| Group 3 (1 mg/kg αvβ6 Peptide 1-AD07778-LP29), dosing days 1 and 4 | 0.701 | 0.293 | 0.504 |
| Group 4 (5 mg/kg αvβ6 Peptide 1-AD07778-LP29), dosing days 1 and 4 | 0.160 | 0.079 | 0.156 |
| Group 5 (5 mg/kg αvβ6 Peptide 1-AD07778-LP29), dosing days 10 and 12 | 0.293 | 0.175 | 0.432 |

Figure 12:
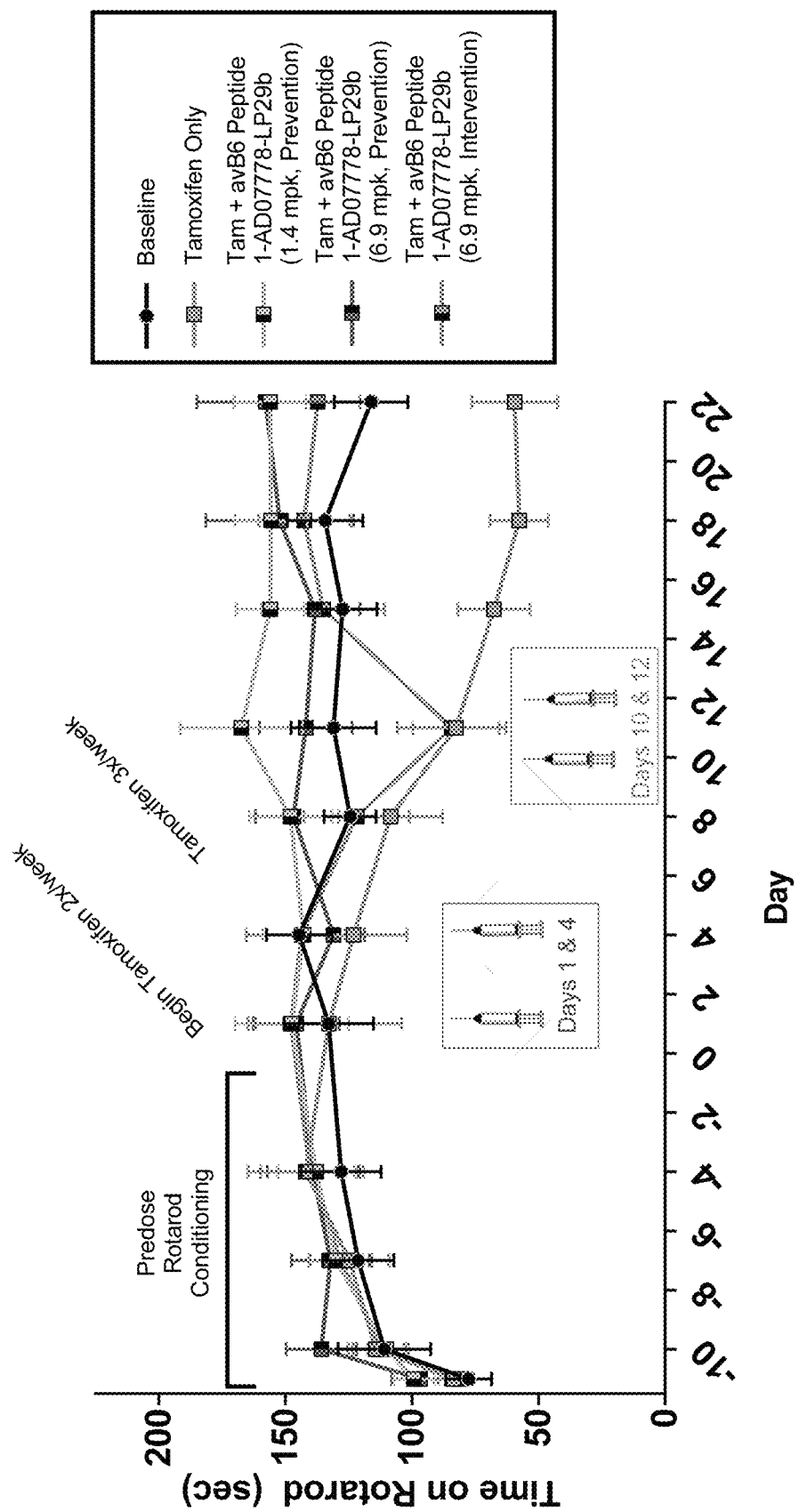
FIG. 12. Graph depicting time on Rotarod apparatus of FSHD-like model mice, as more fully described in Example 10.
Figure 13:
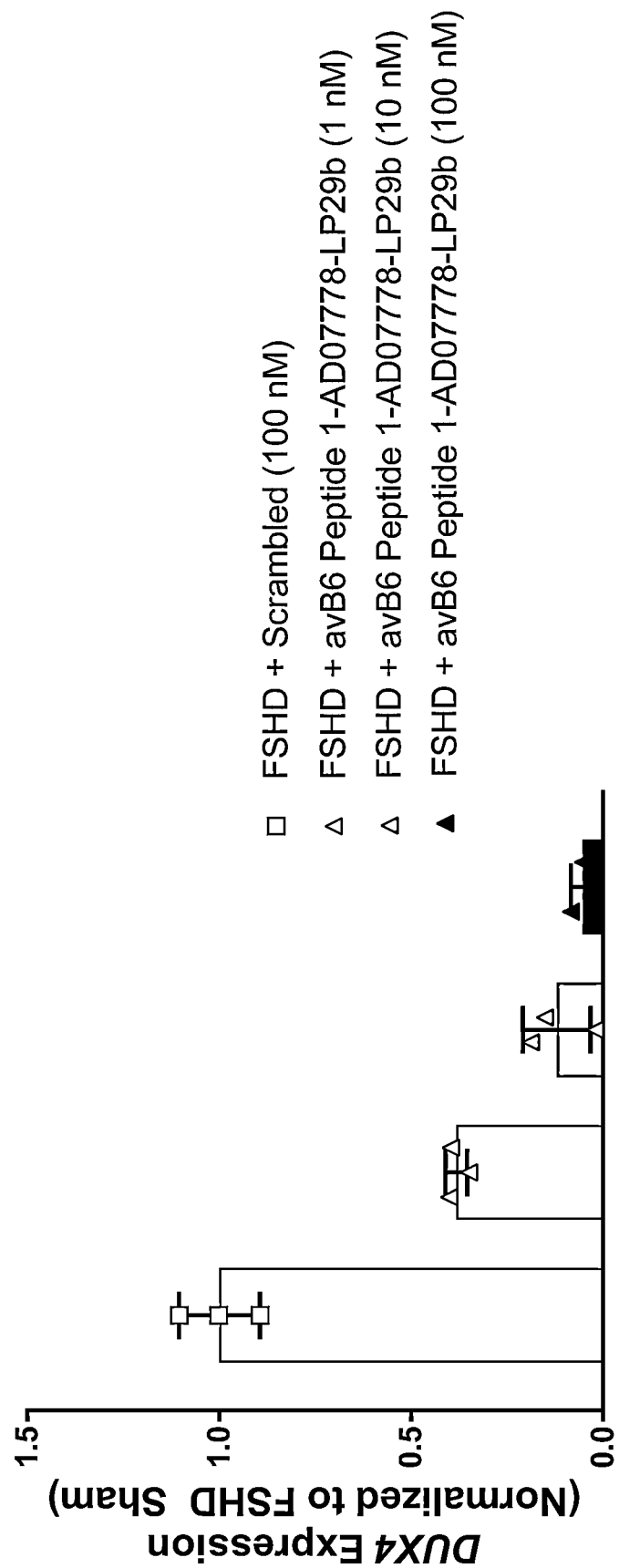
FIG. 13. Graph depicting DUX4 expression in patient-derived myotubules, as more fully described in Example 11.
Figure 14:
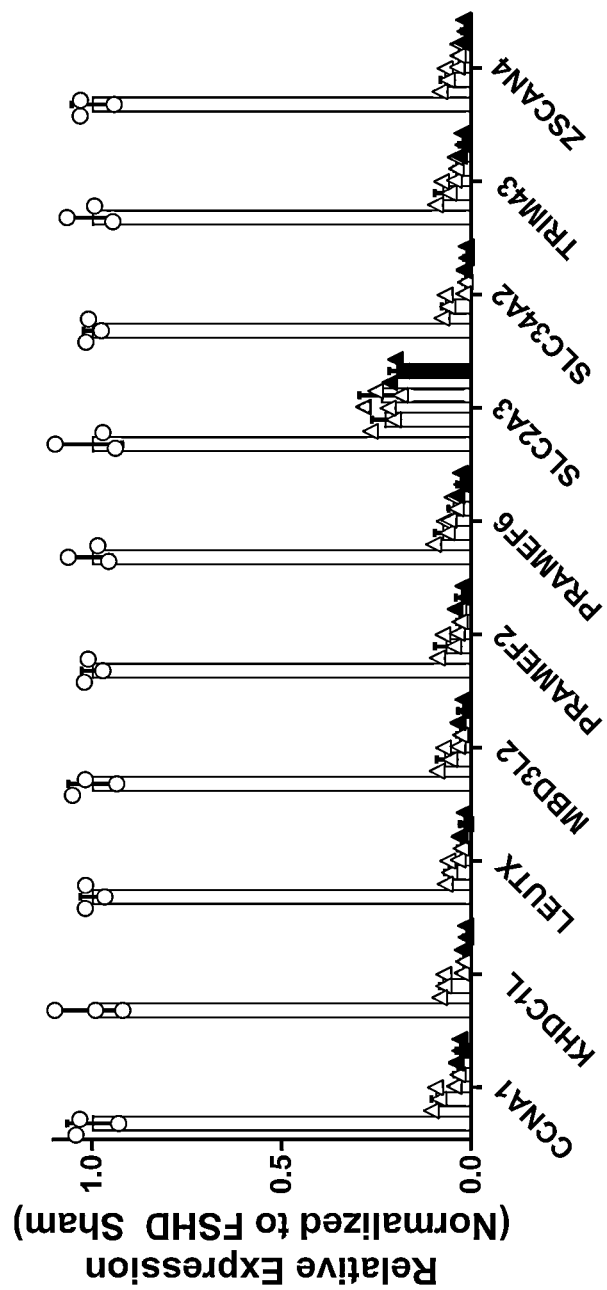
FIG. 14. Graph depicting relative gene expression of several biomarker genes known to be related to FSHD in patient-derived myotubules, as more fully described in Example 11.
Figure 16A:
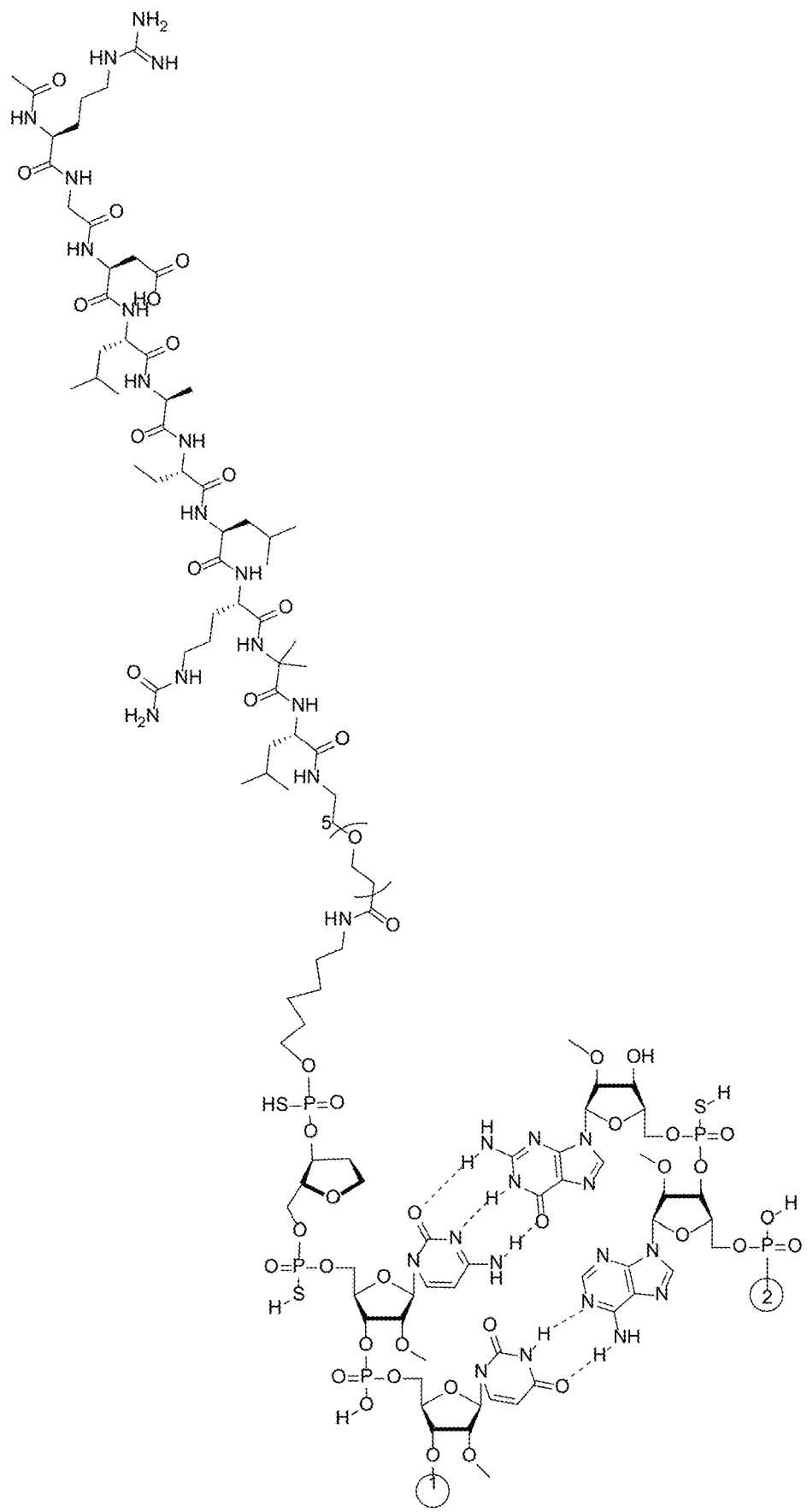
Figure 16B:
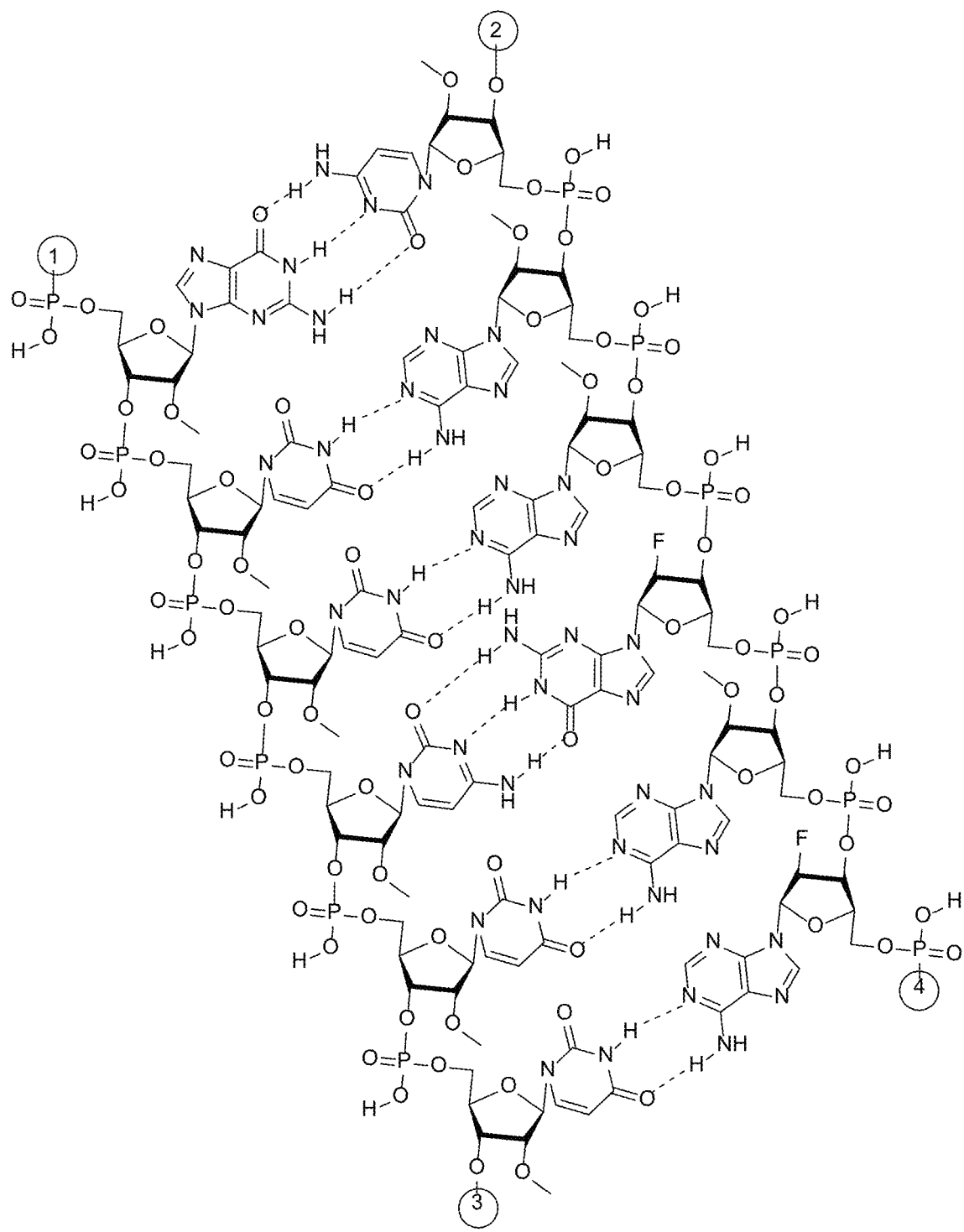
Figure 16C:
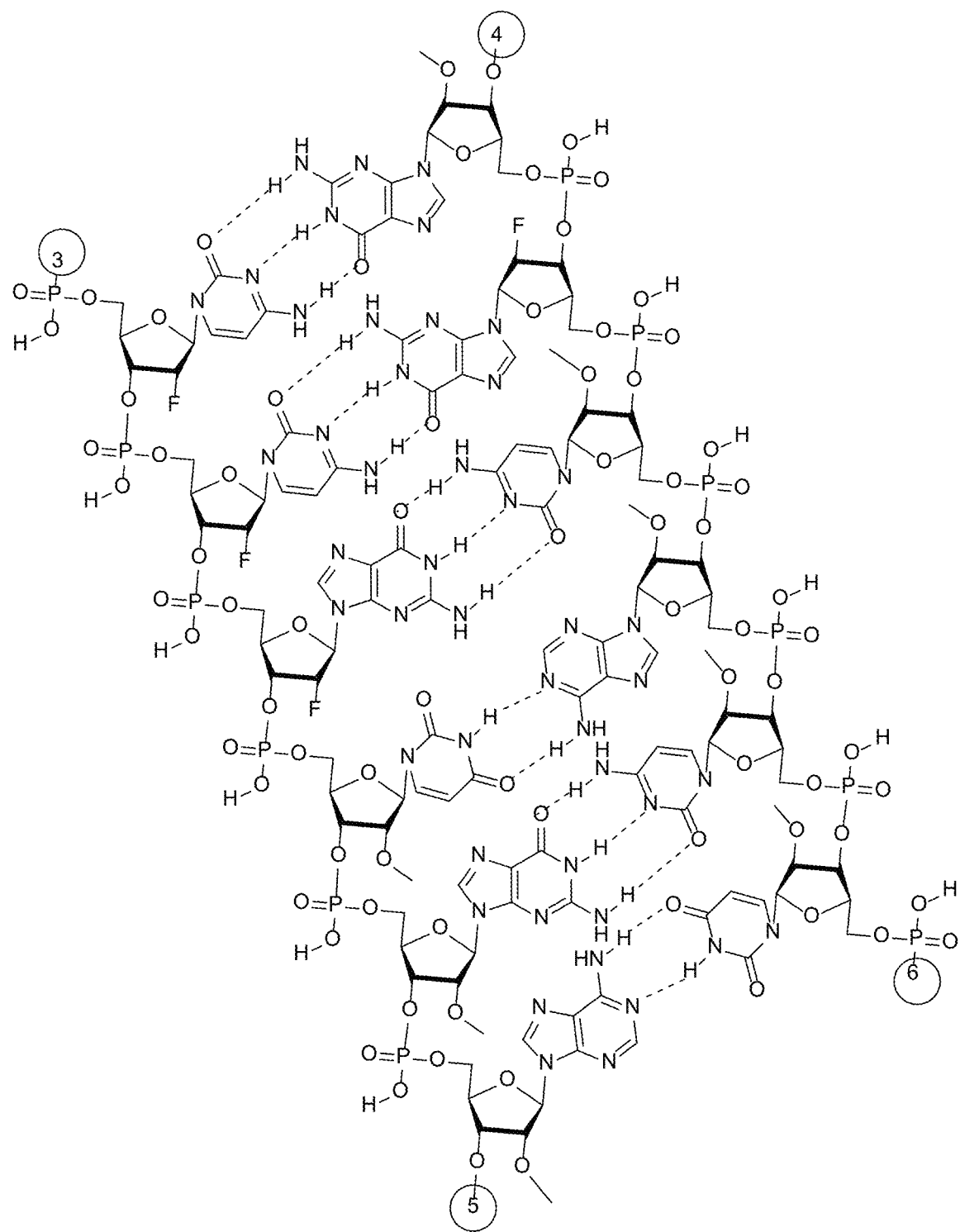
Figure 16D:
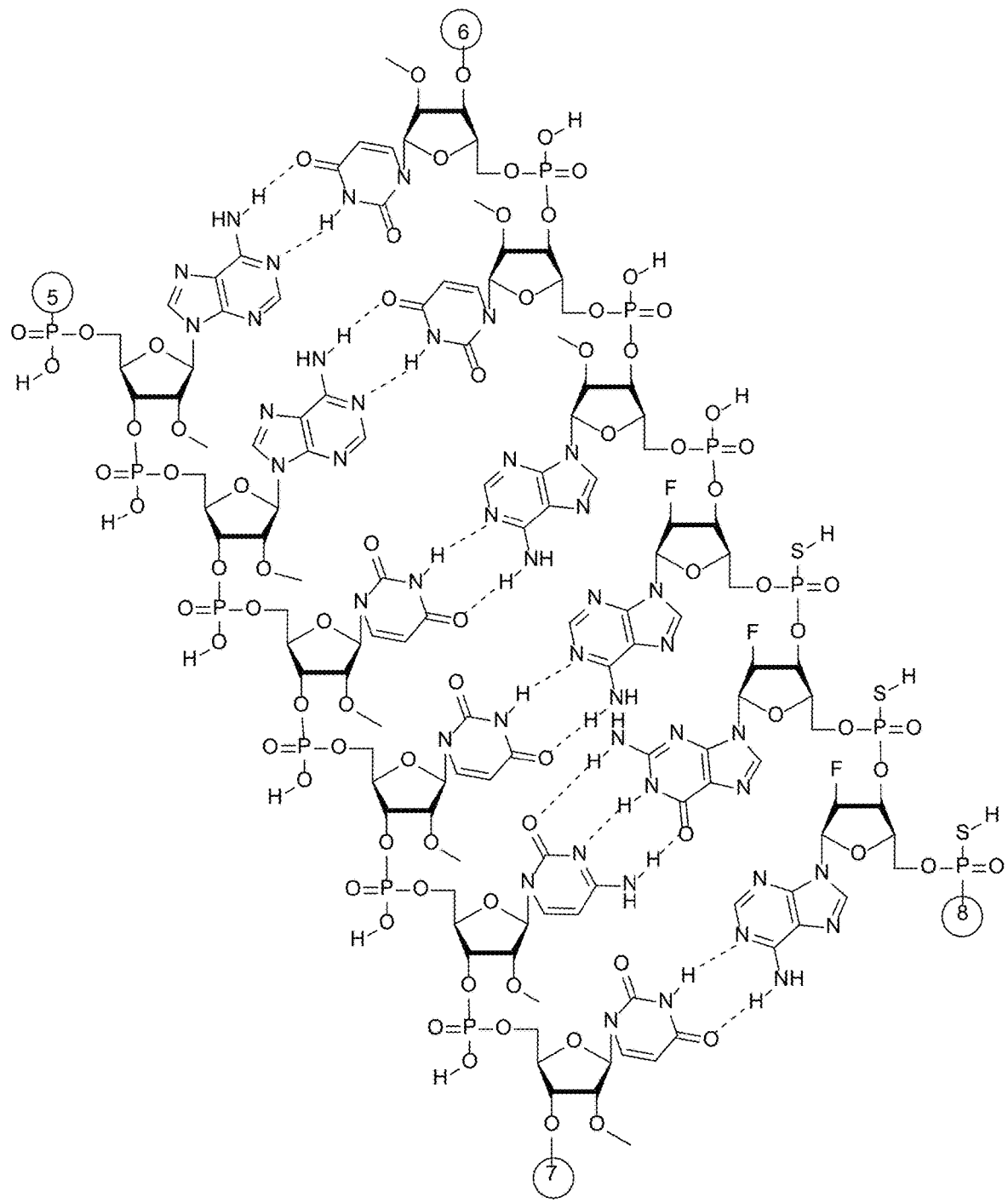
Figure 16E:
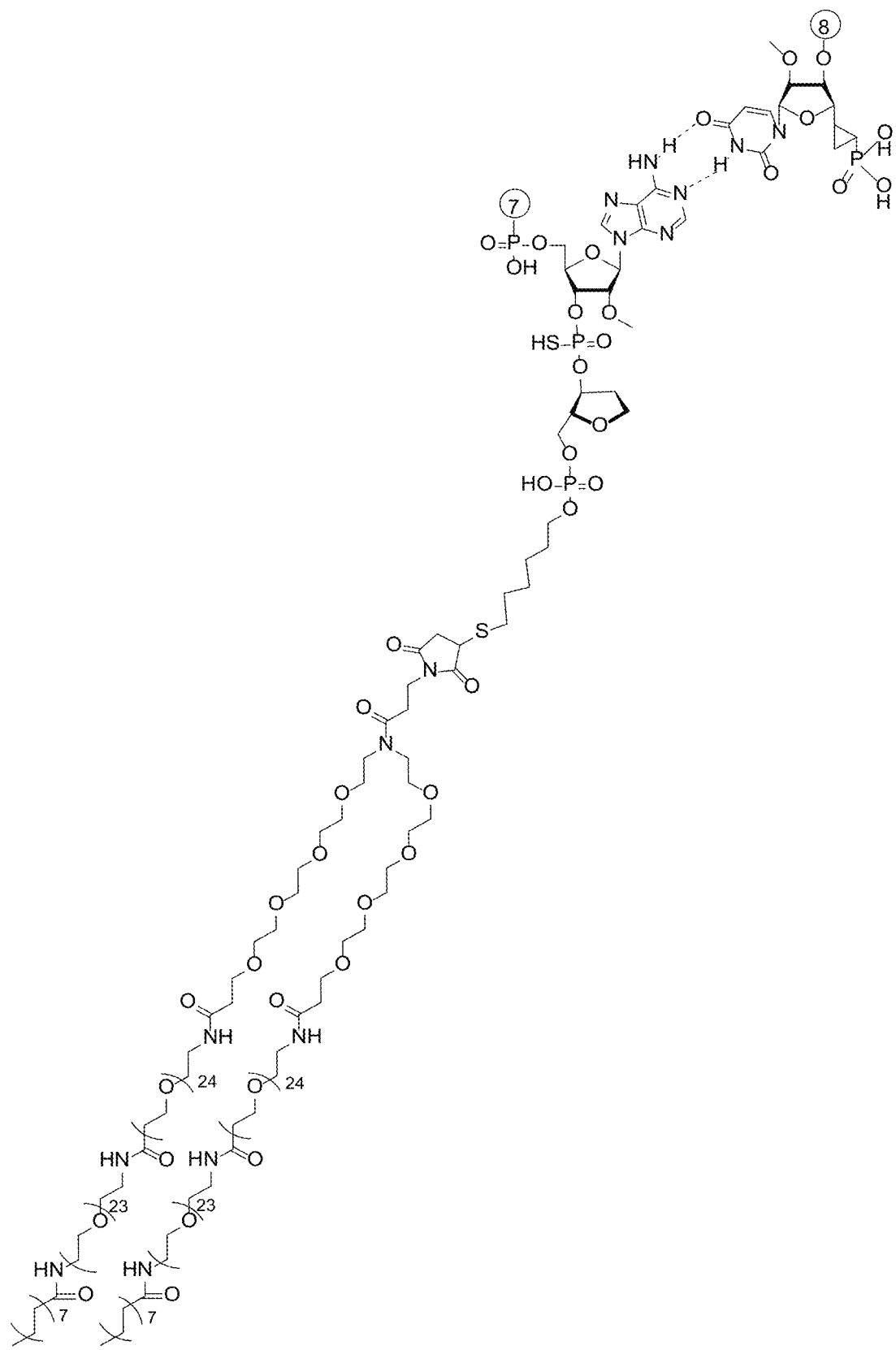
Figure 17A:
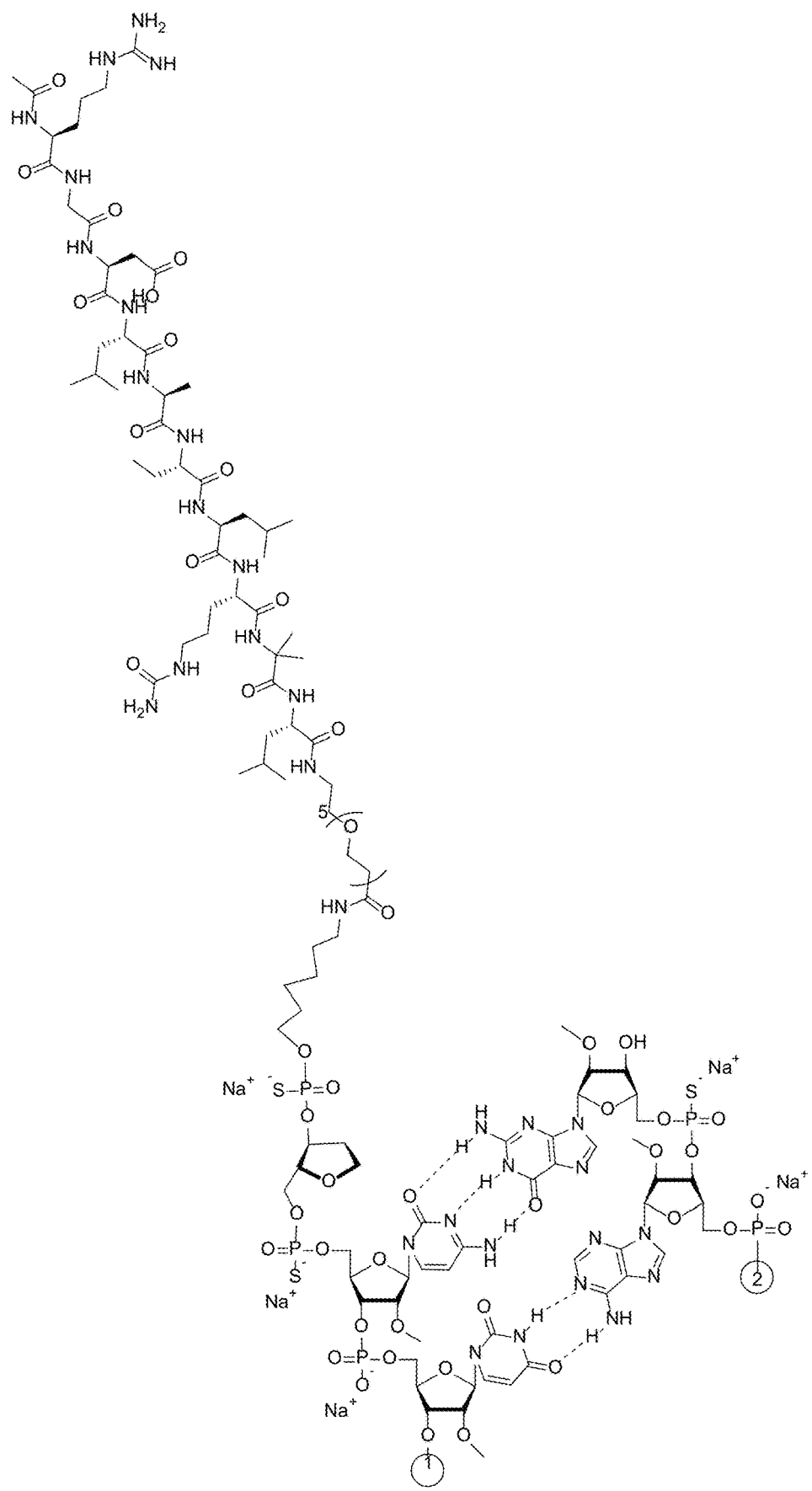
Figure 17B:
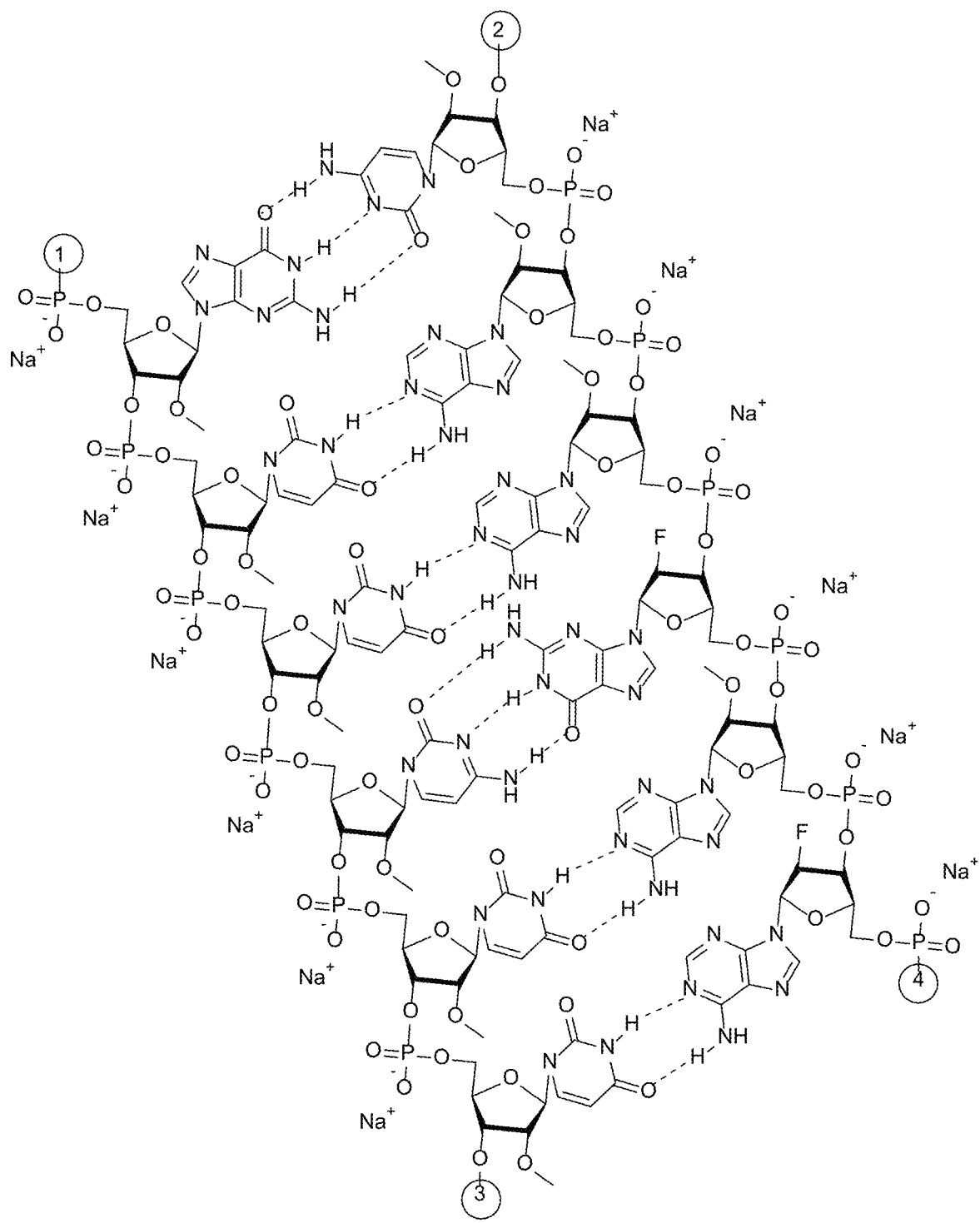
Figure 17C:
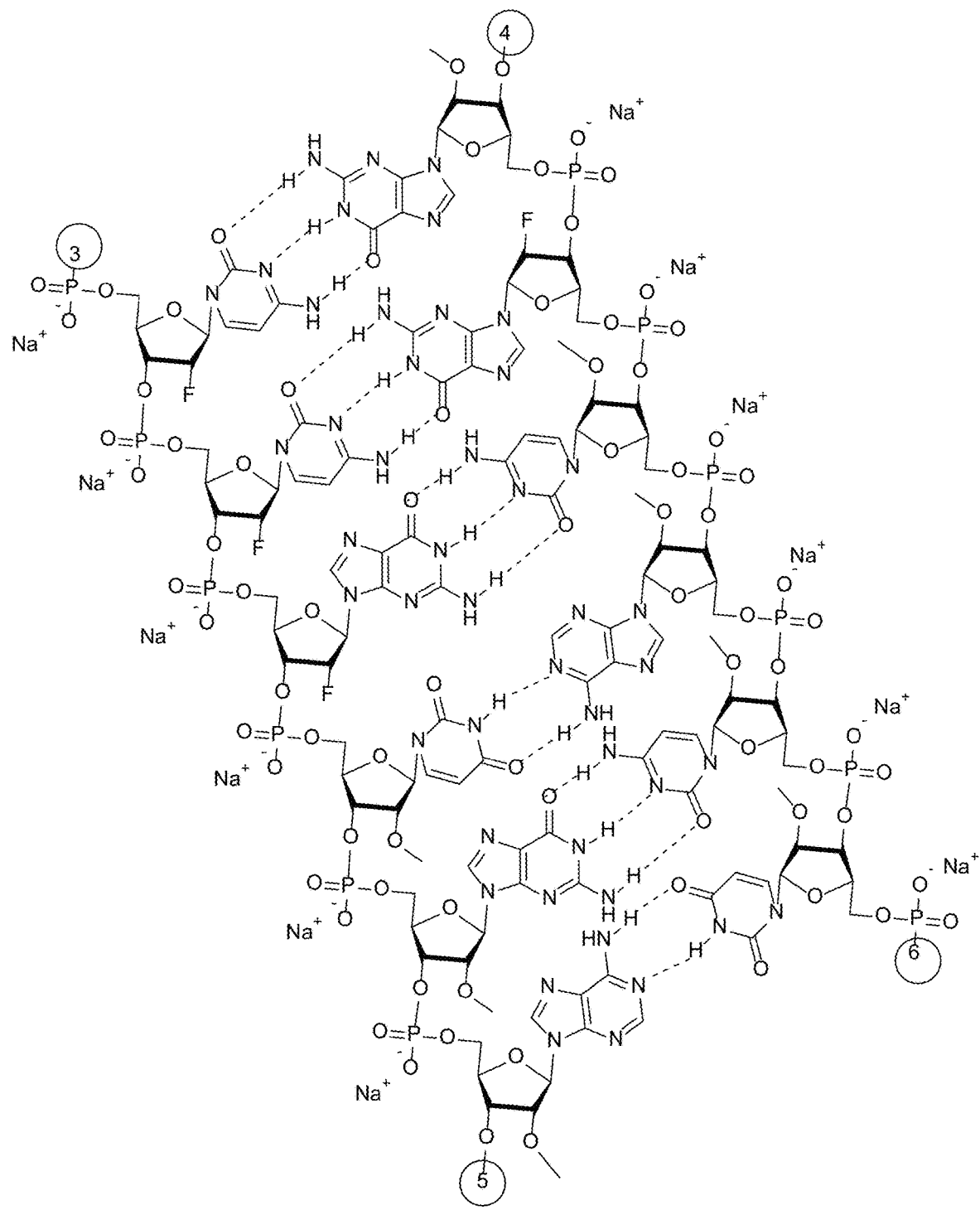
Figure 17D:
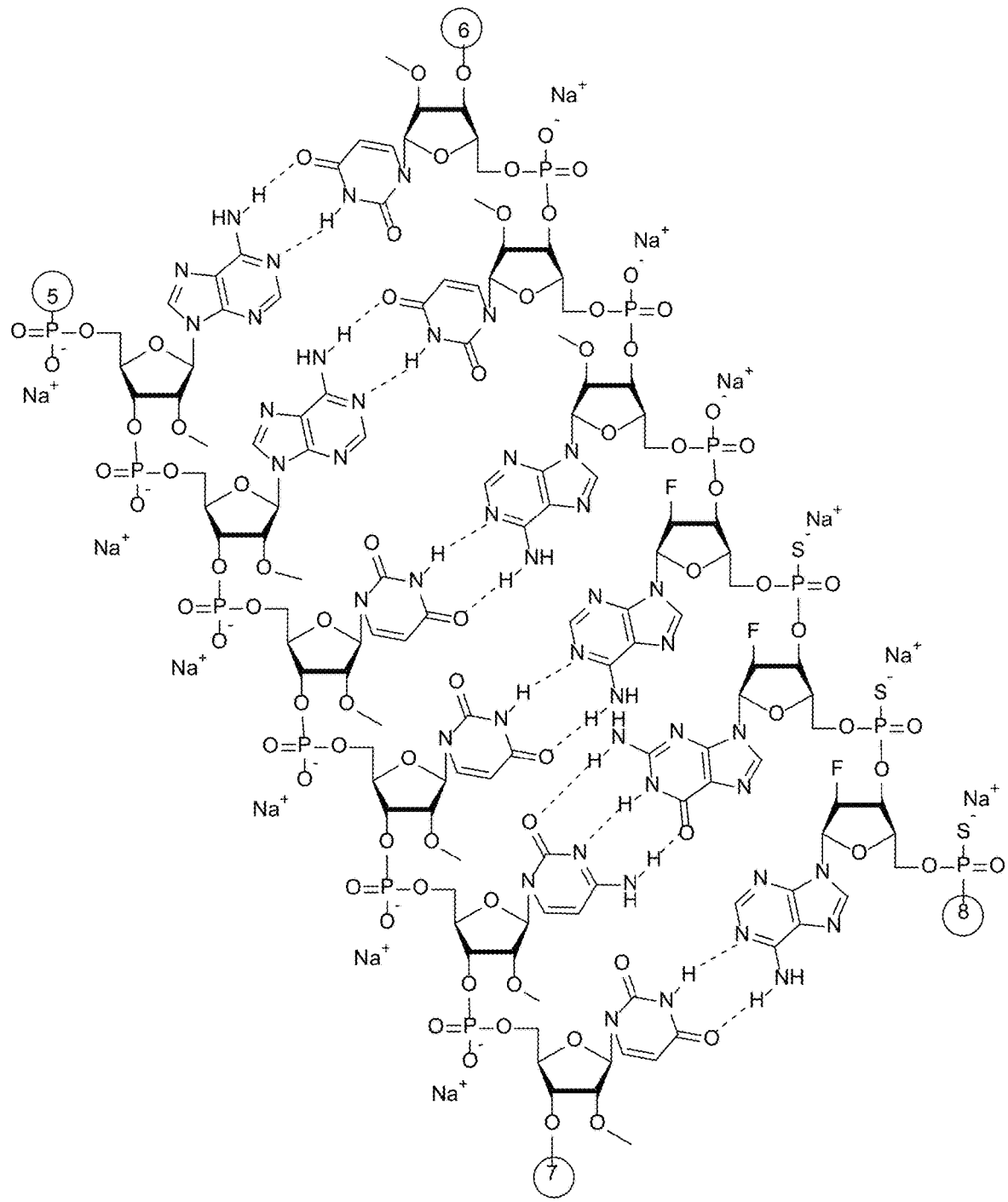
Figure 17E:
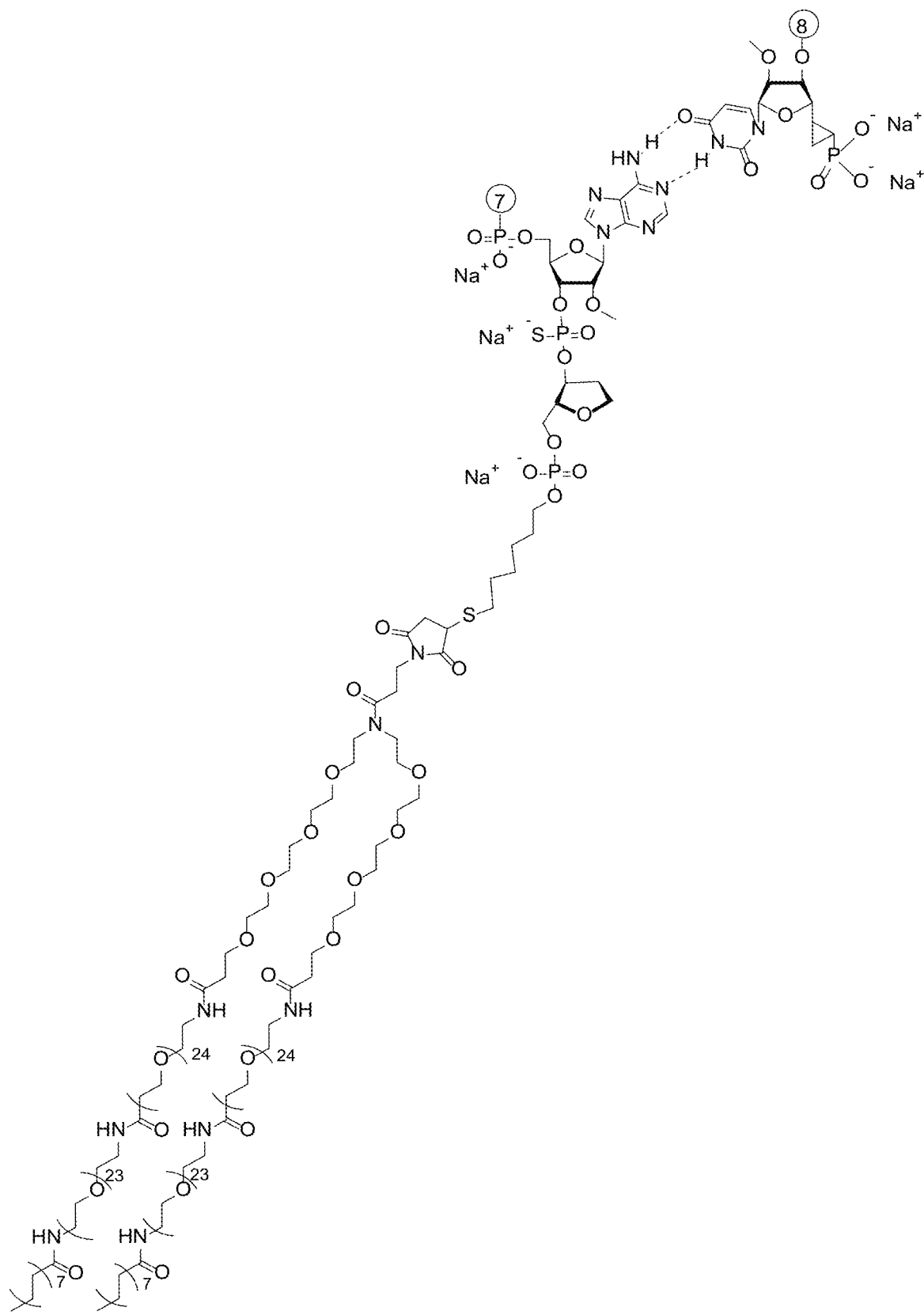
Figure 18A:
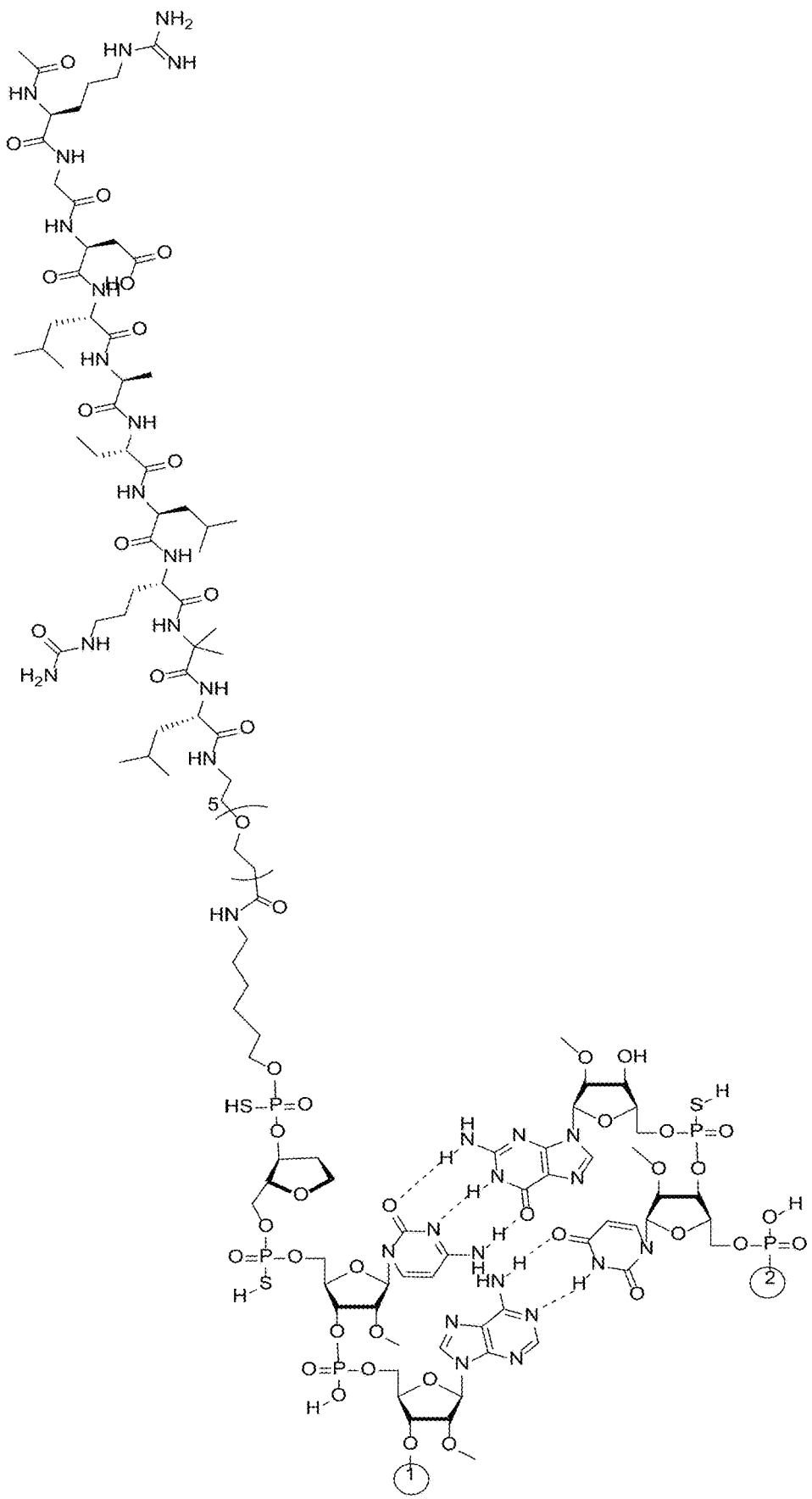
Figure 18B:
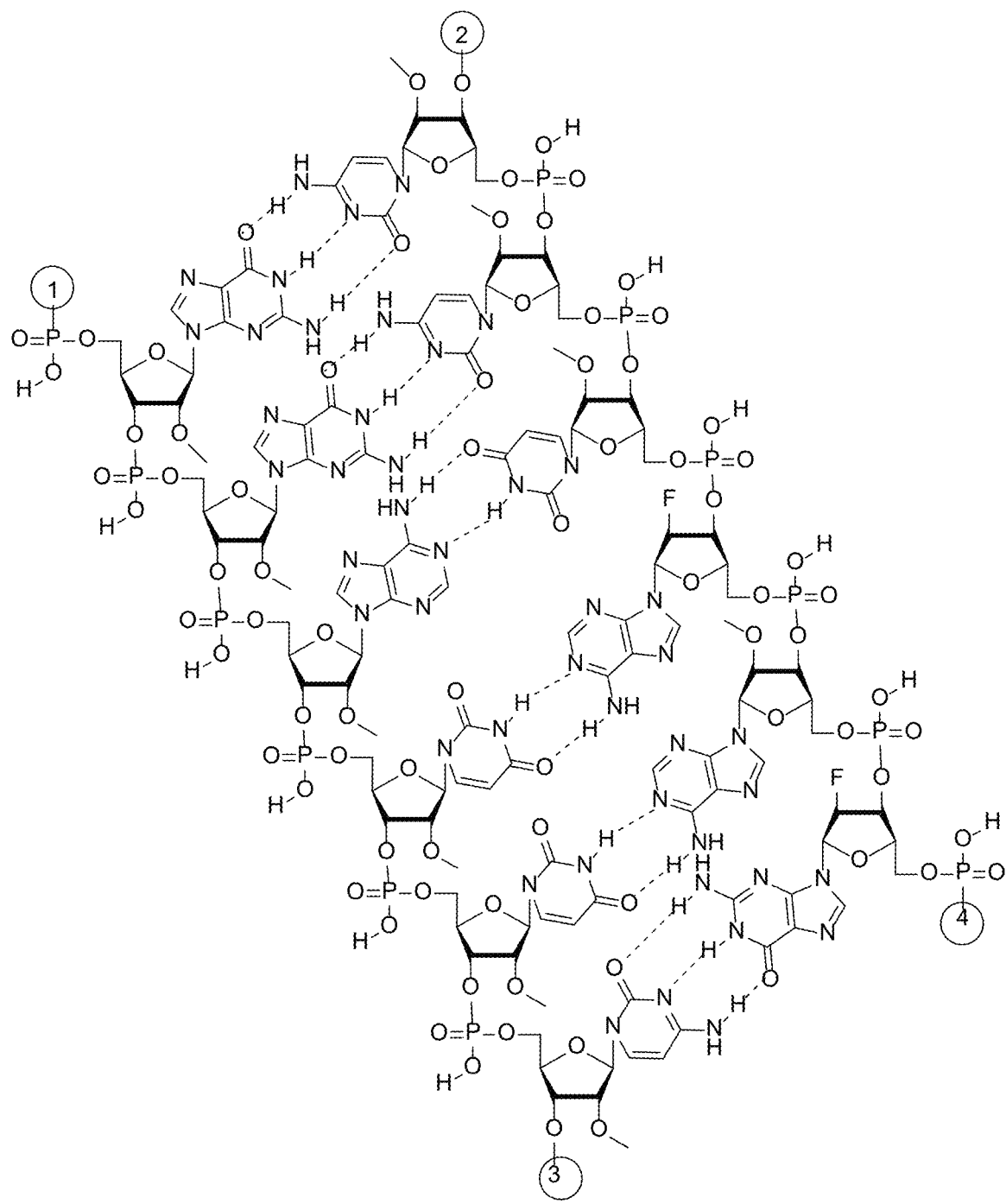
Figure 18C:
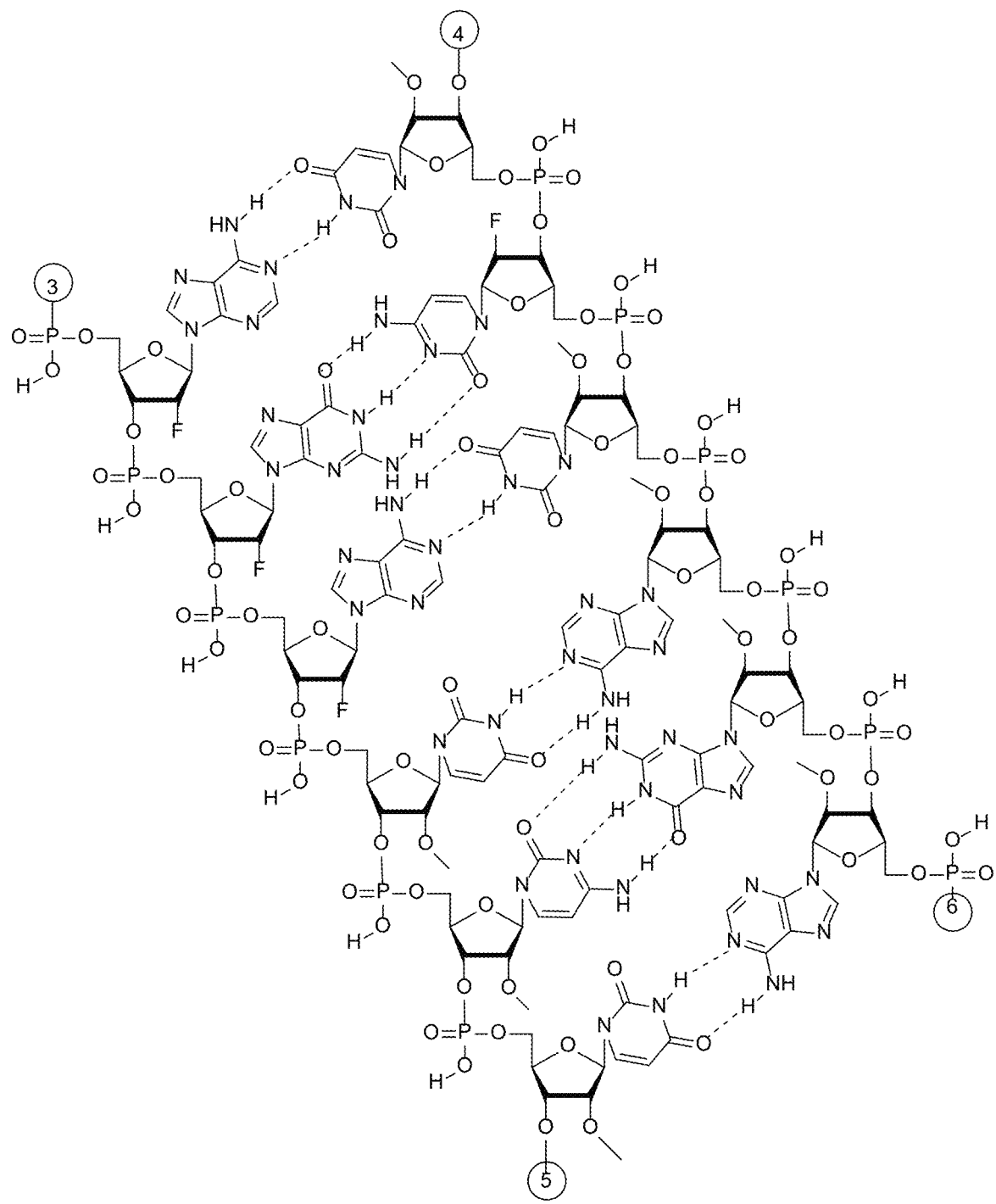
Figure 18D:
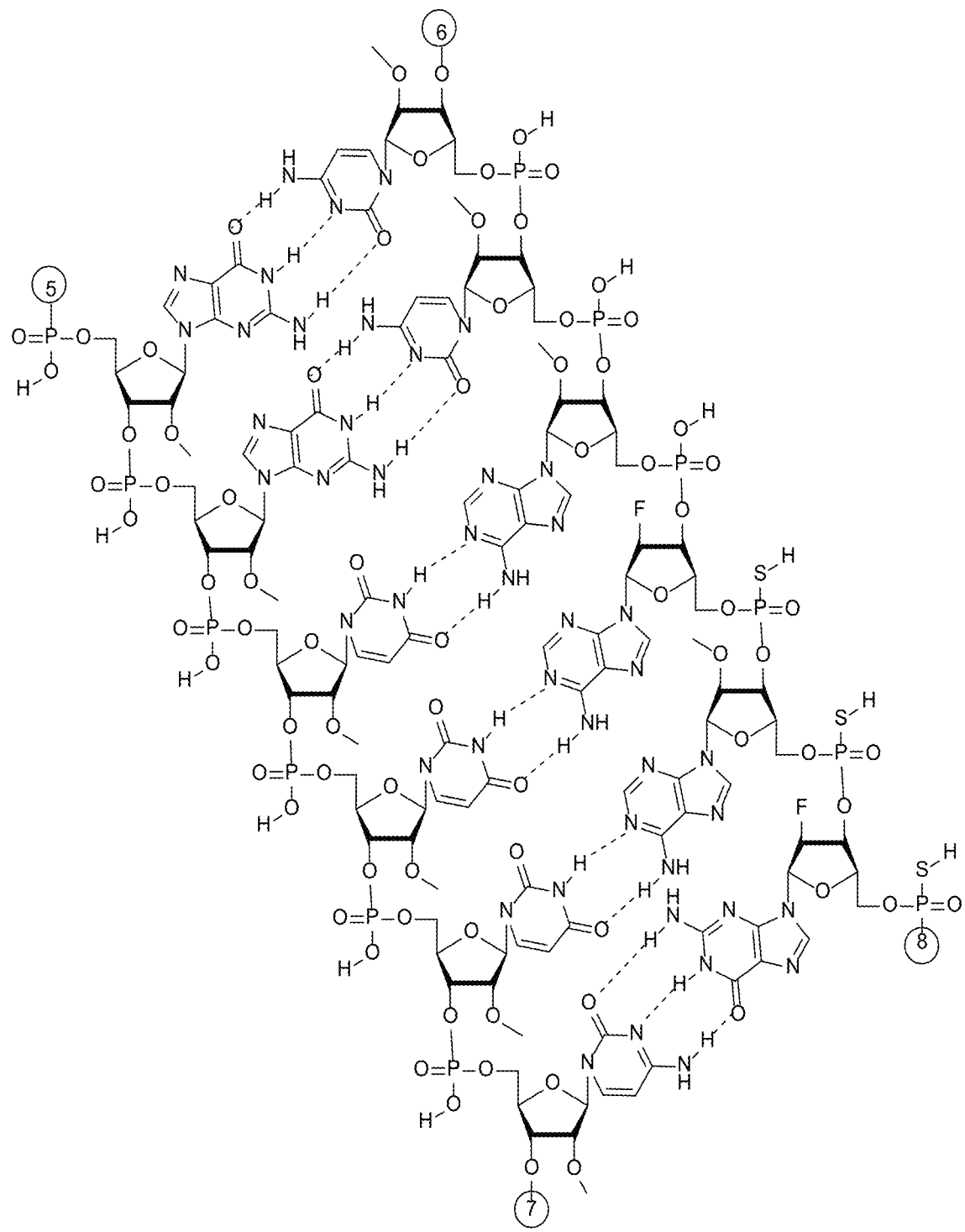
Figure 18E:
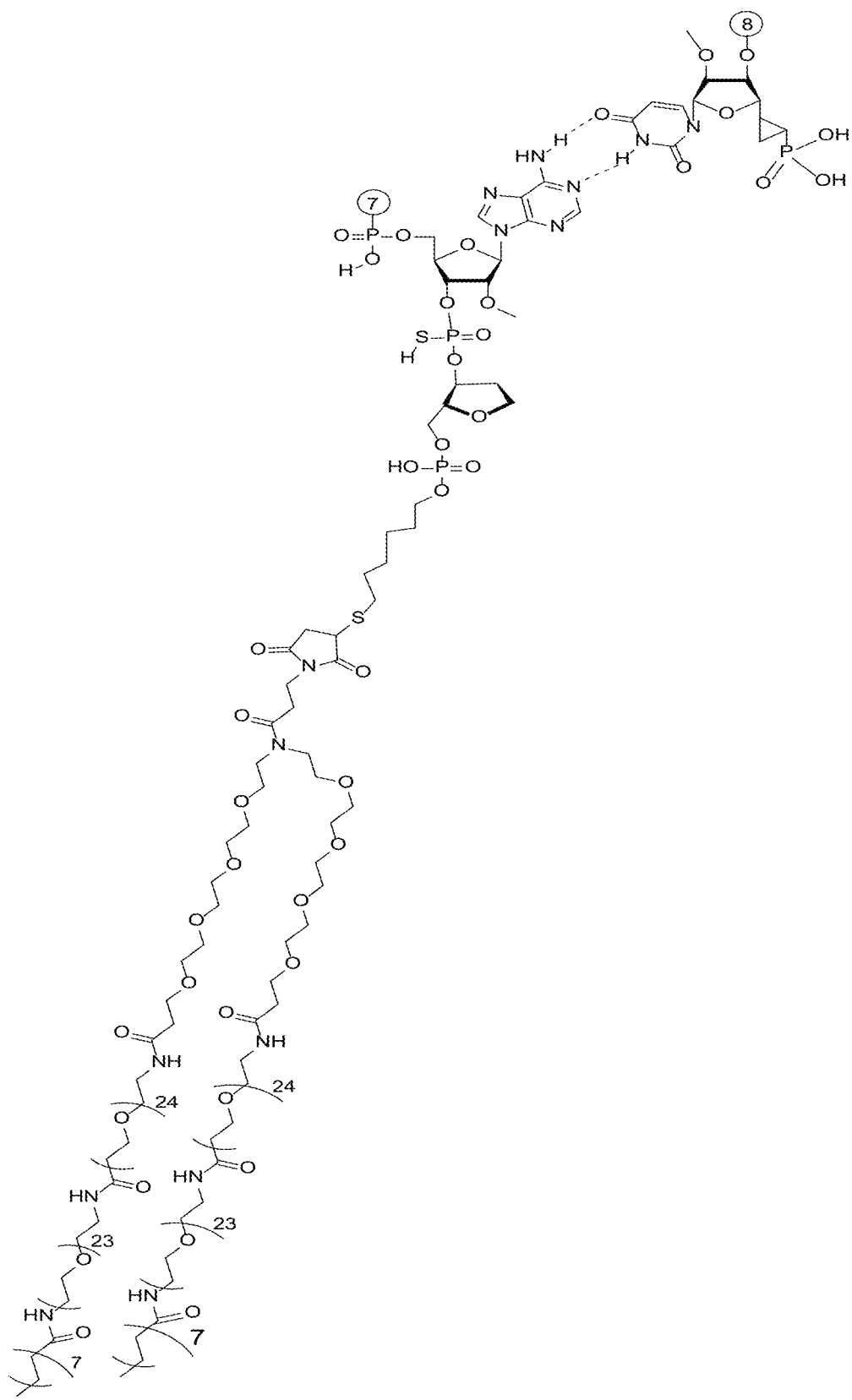
Figure 19A:
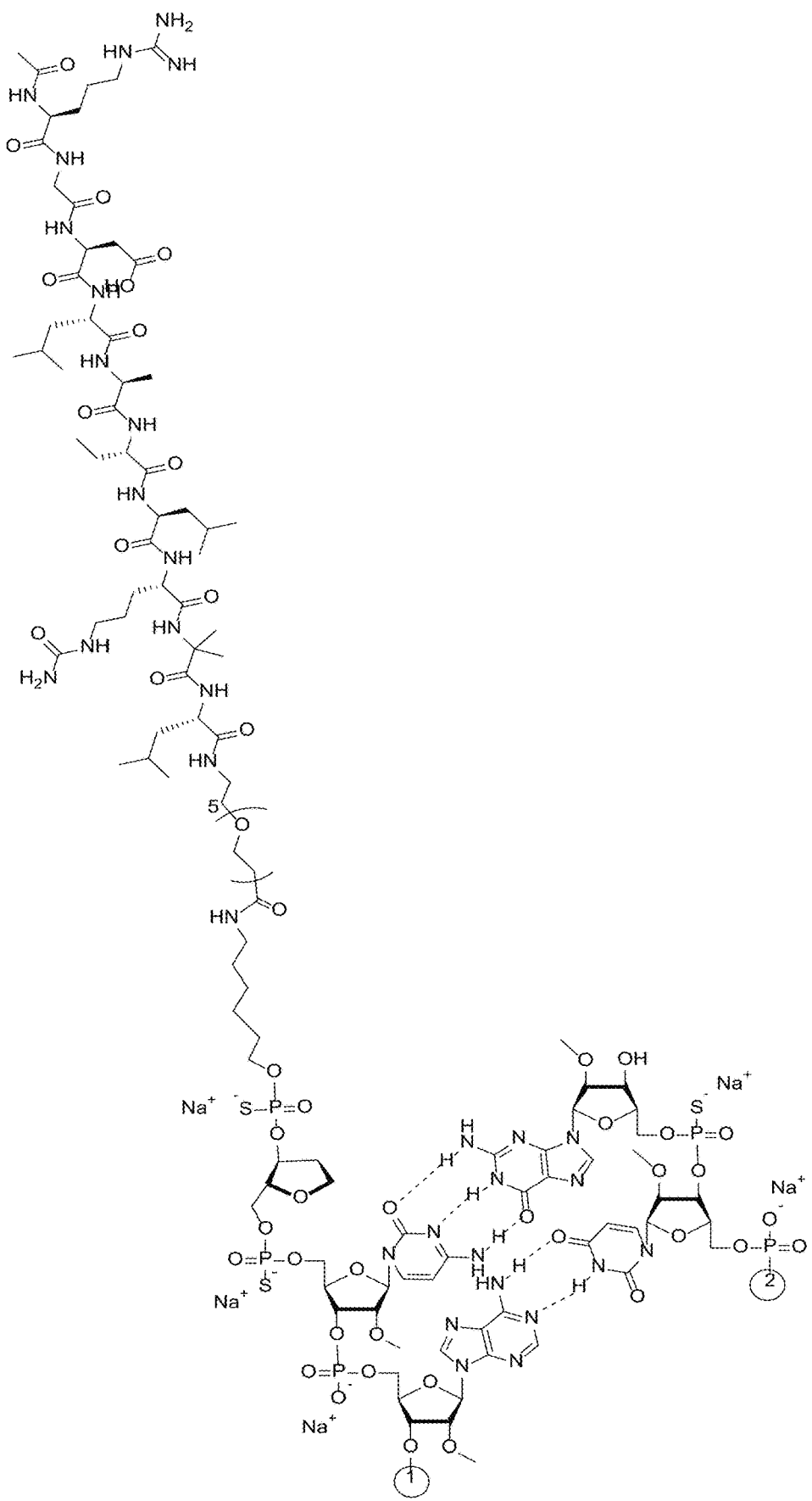
Figure 19B:
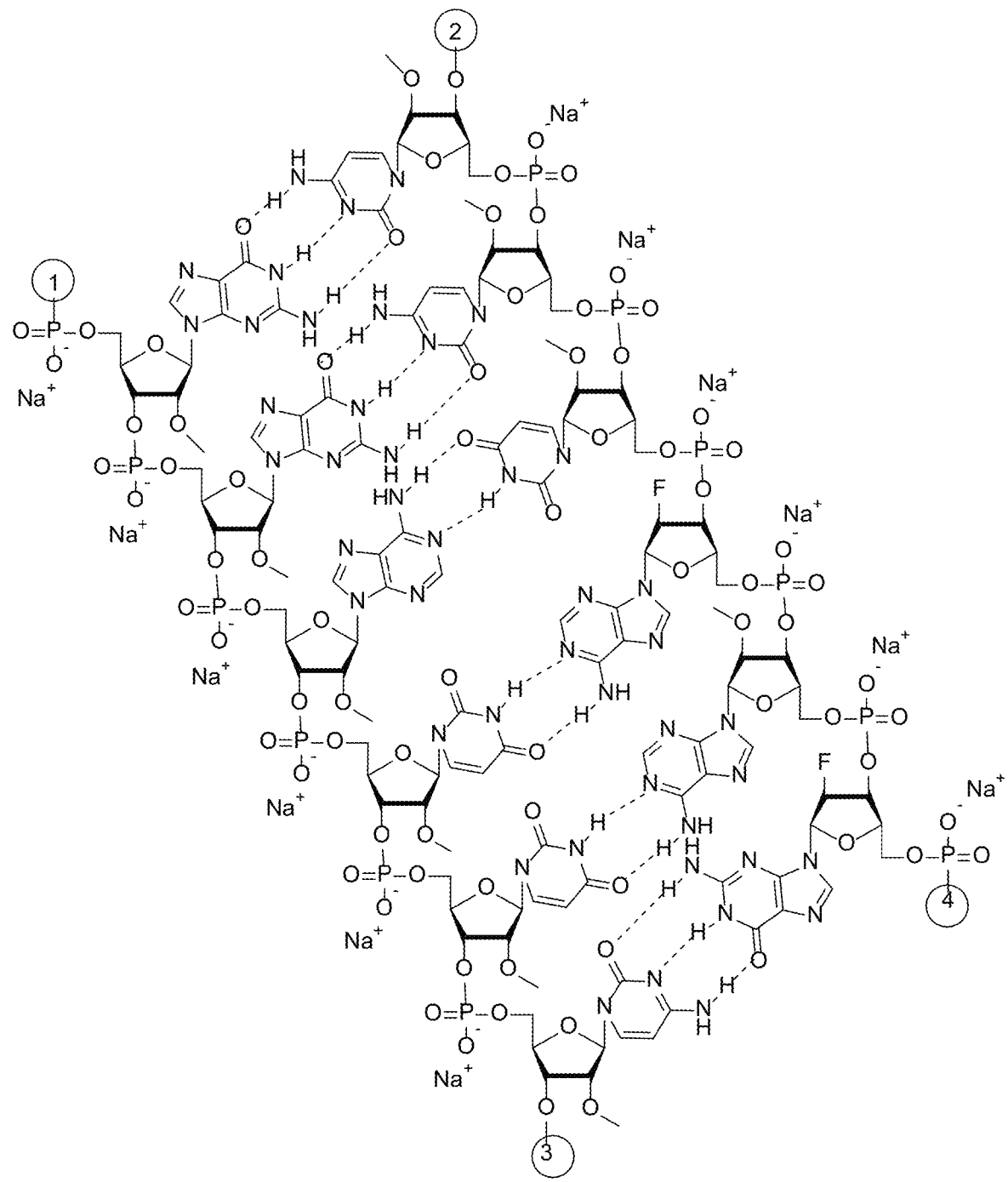
Figure 19C:
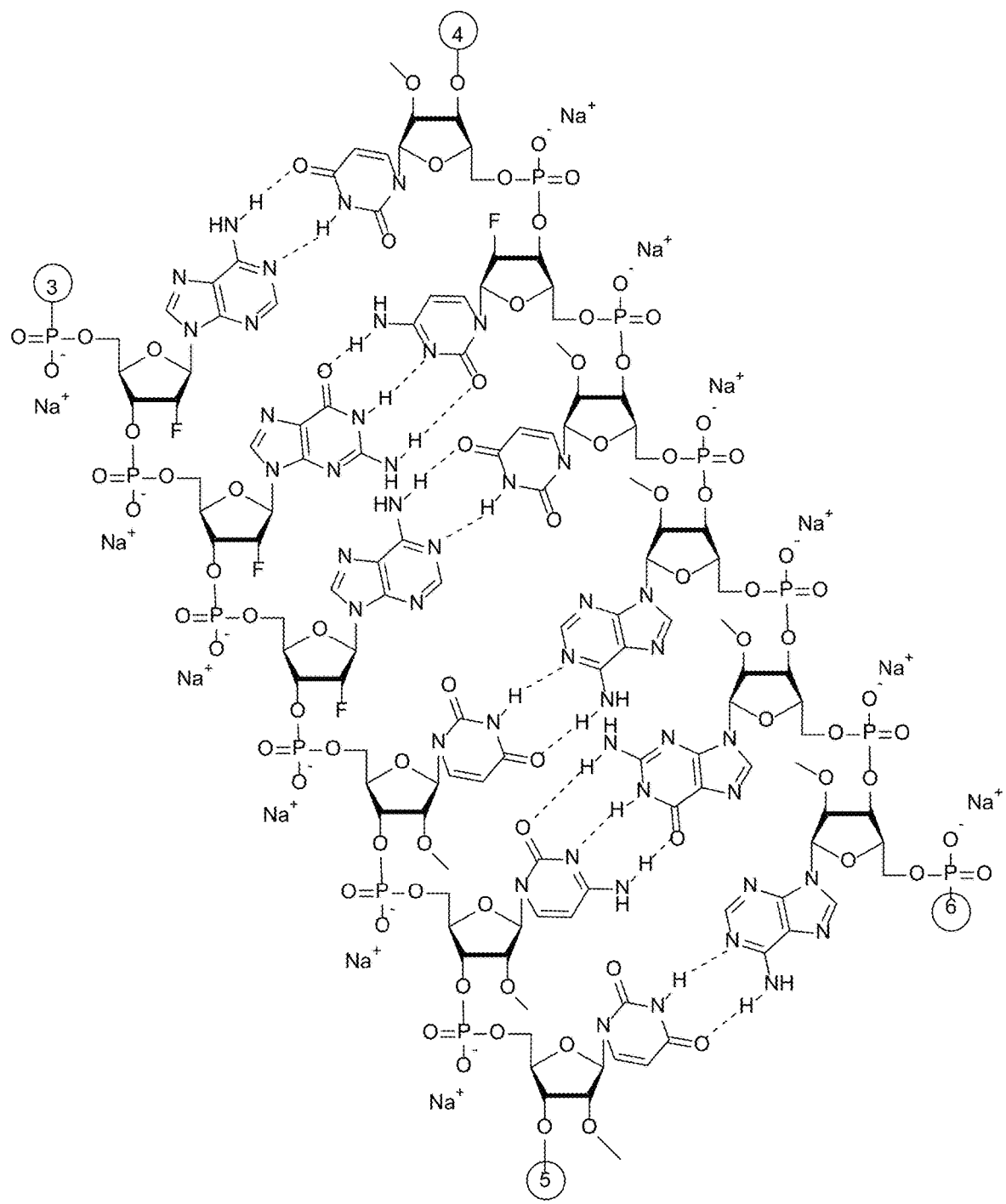
Figure 19D:
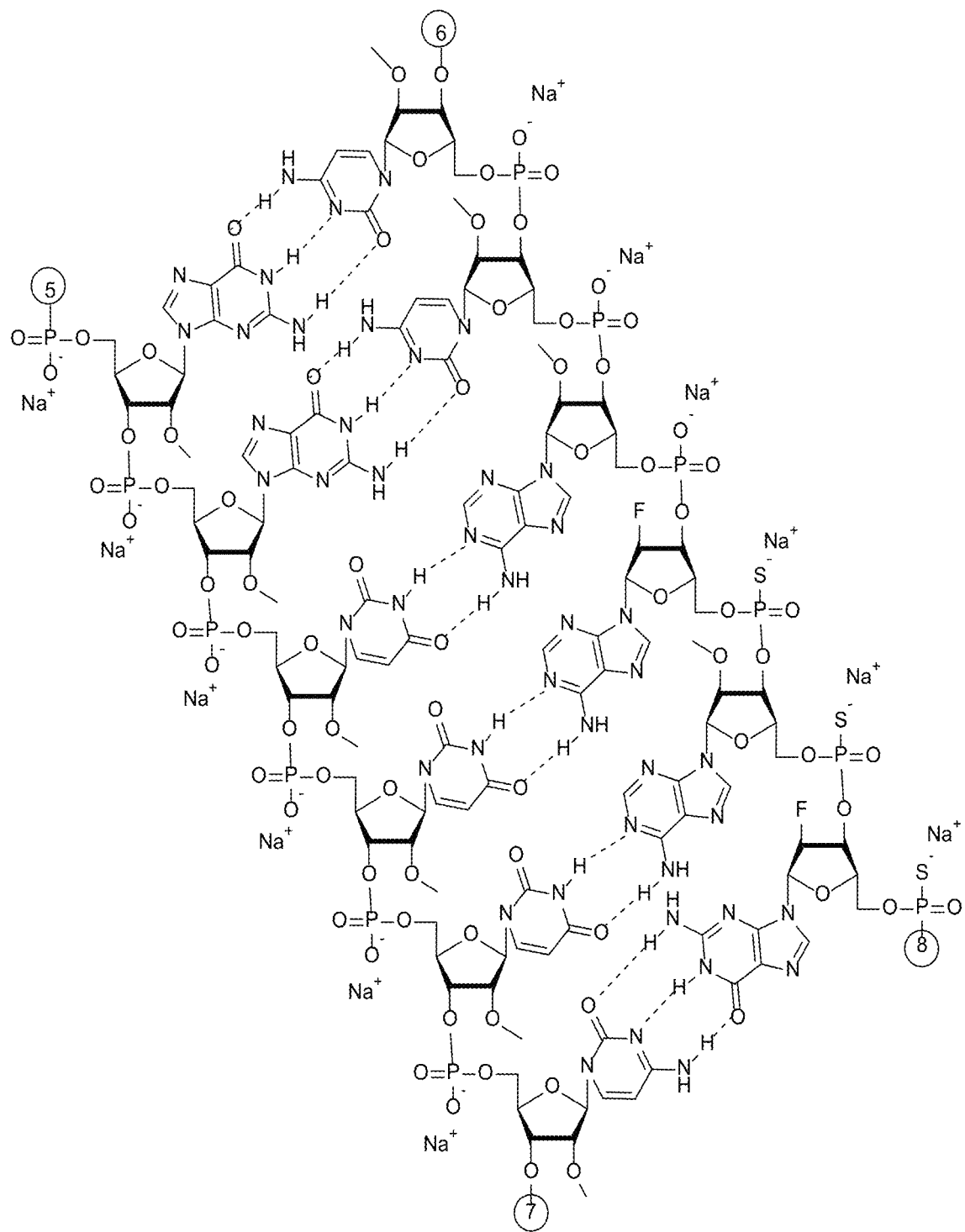
Figure 19E:
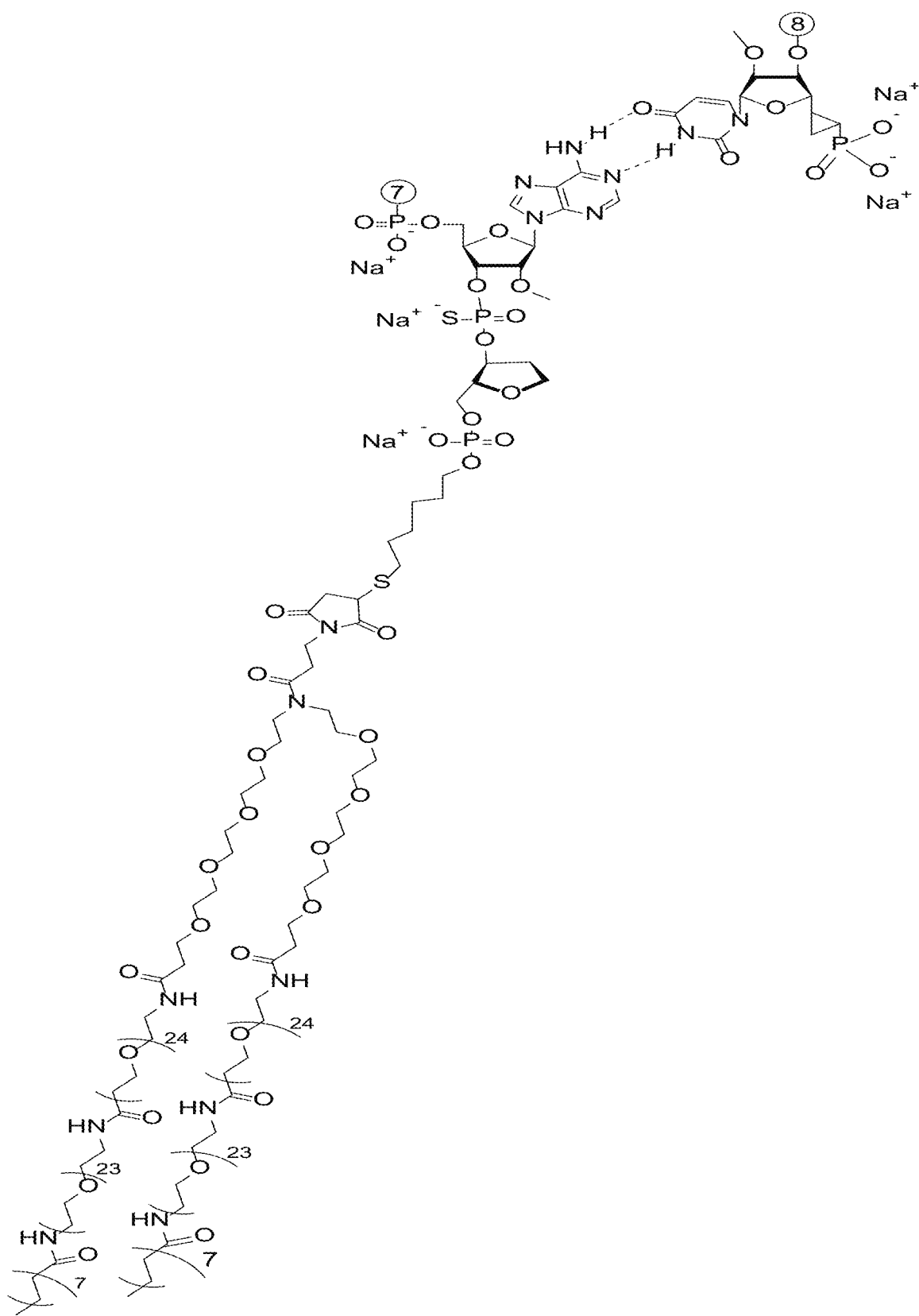
Figure 20A:
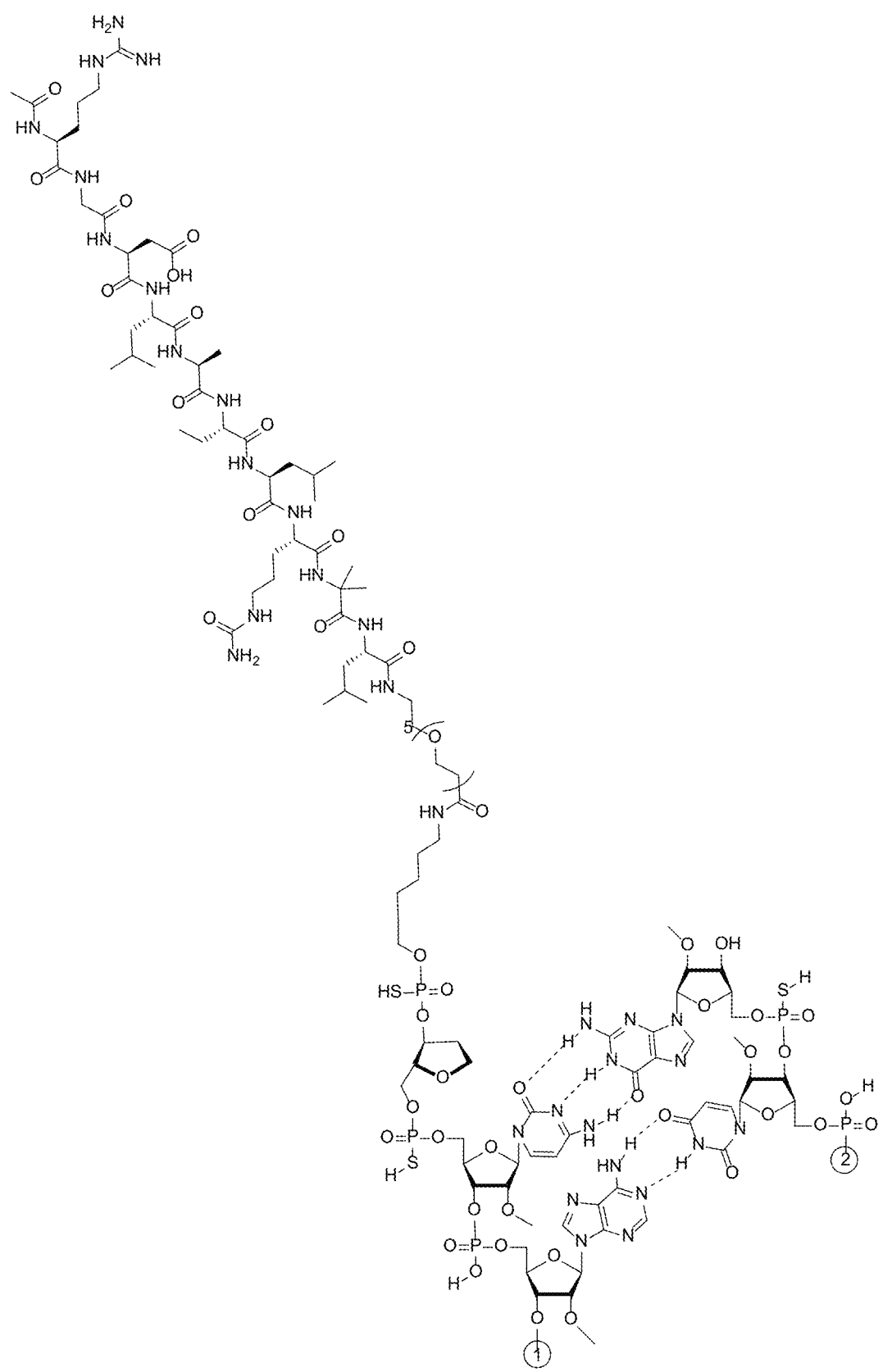
Figure 20B:
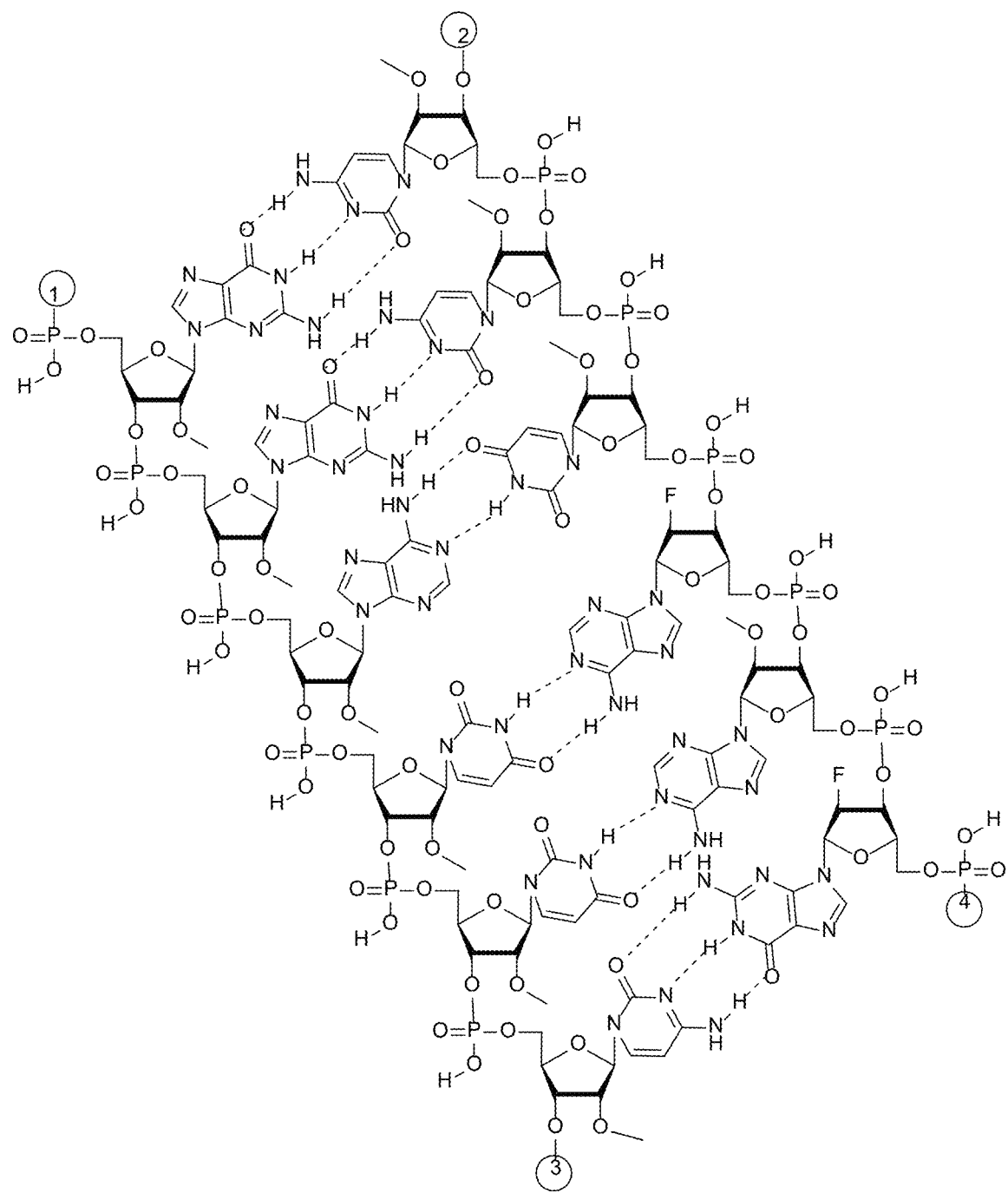
Figure 20C:
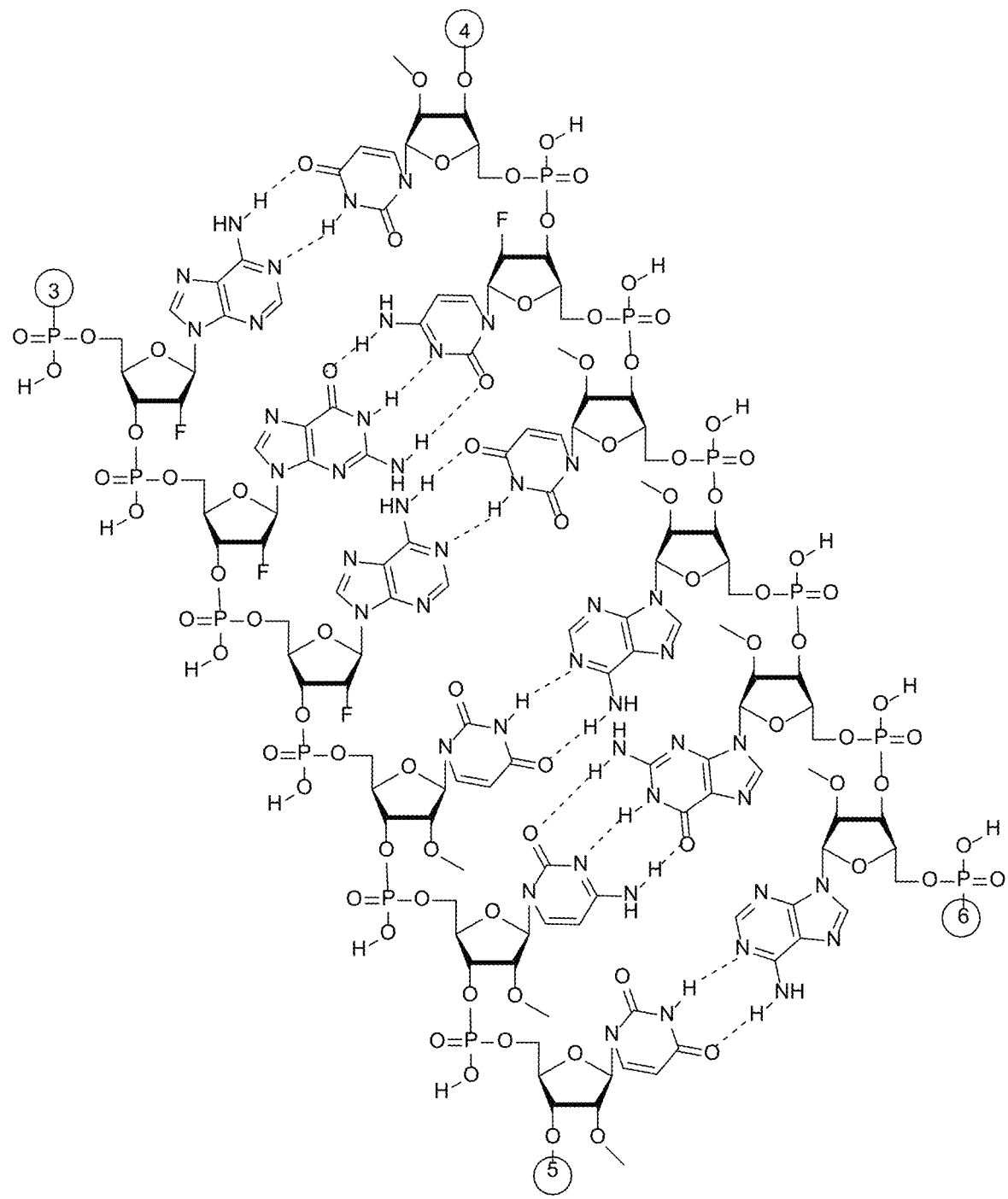
Figure 20D:
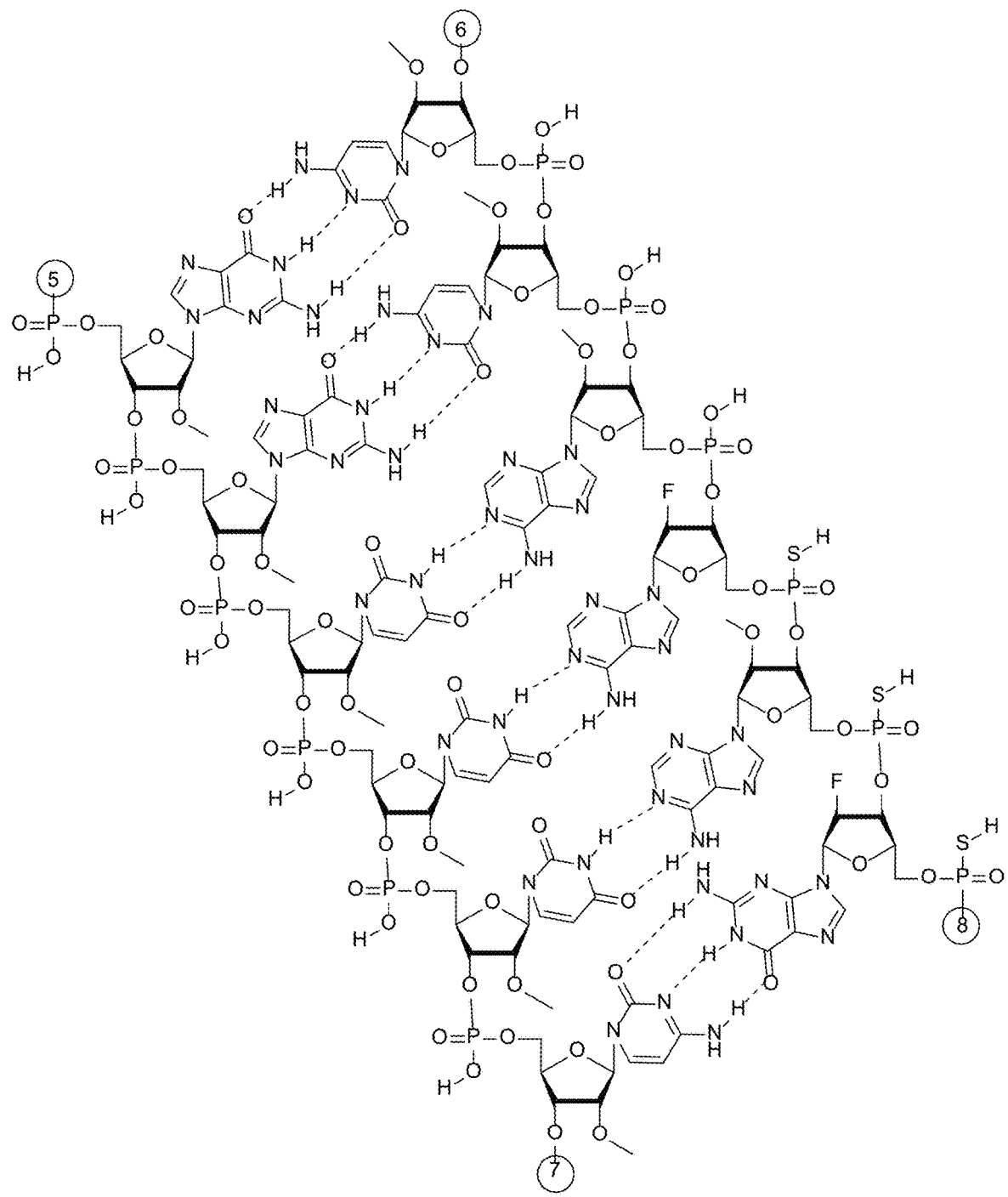
Figure 20E:
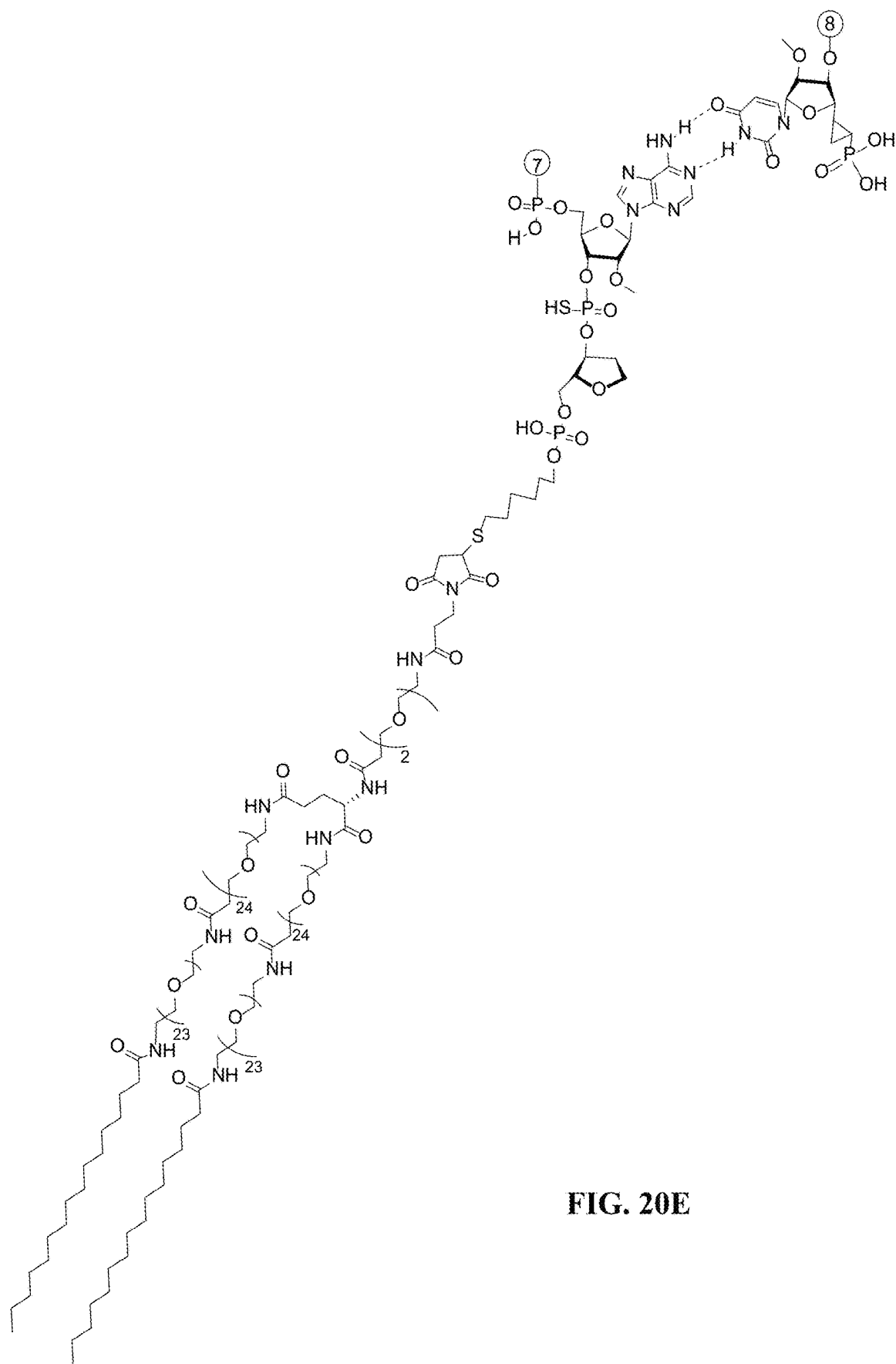
Figure 21A:
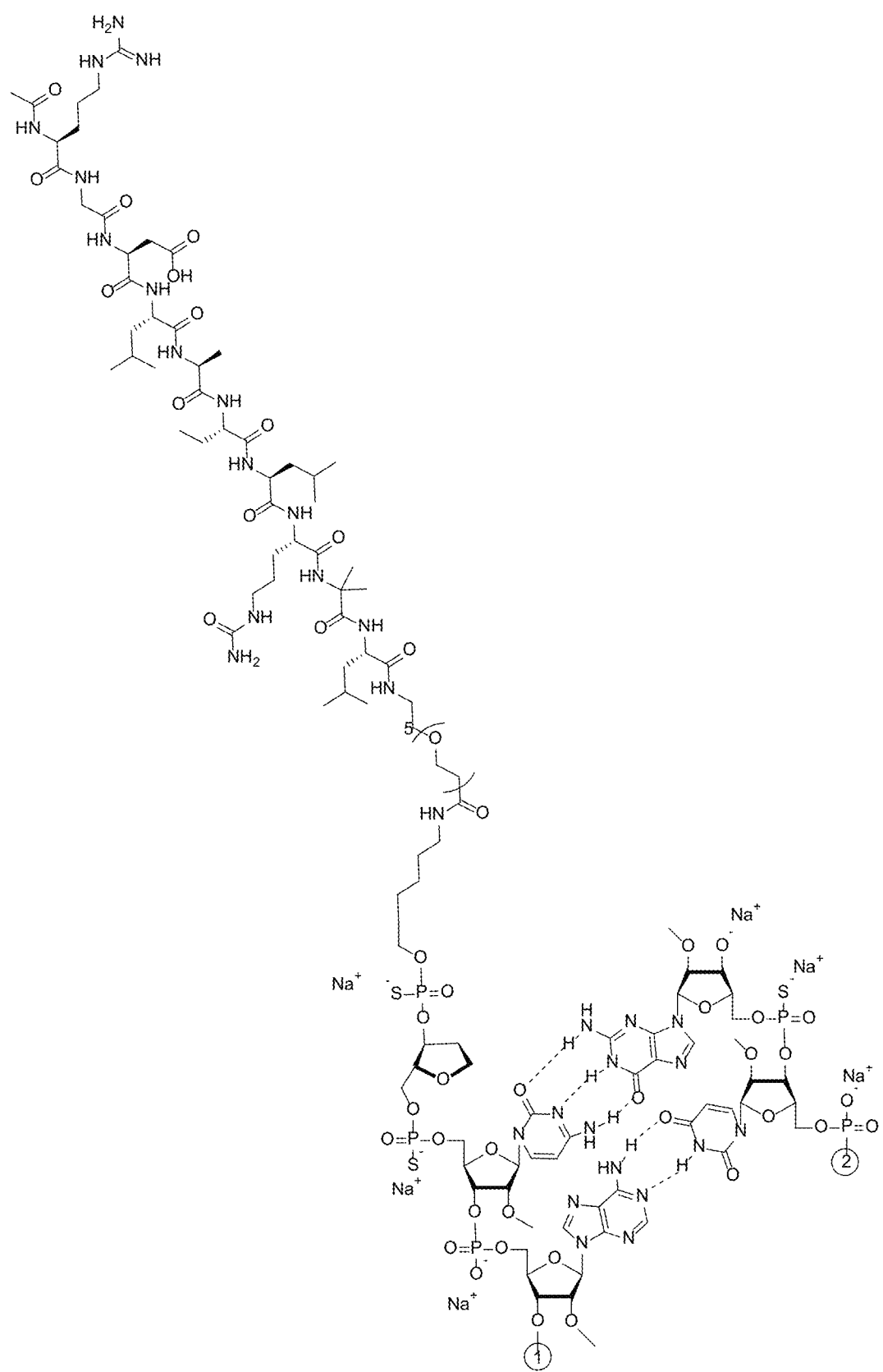
Figure 21B:
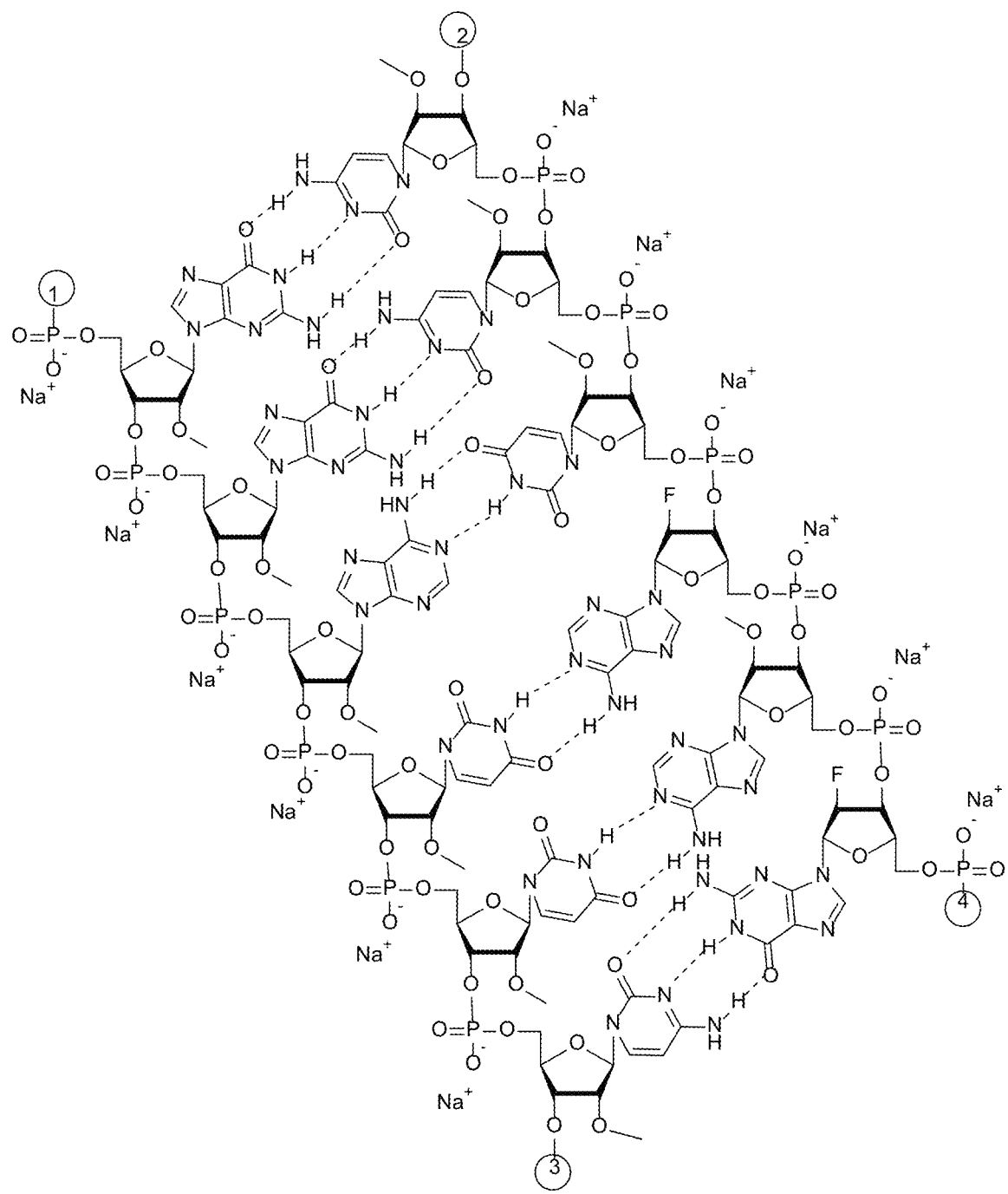
Figure 21C:
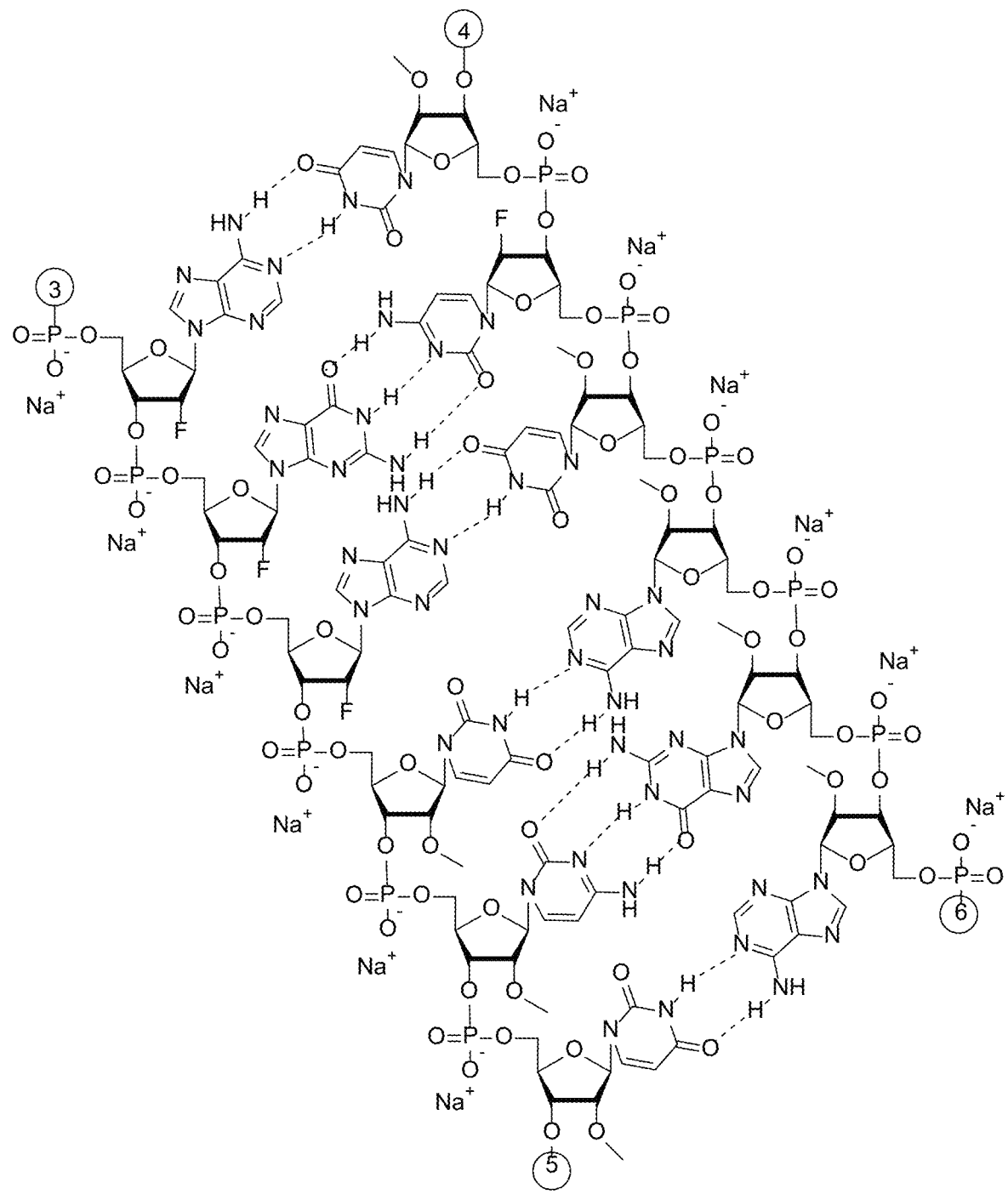
Figure 21D:
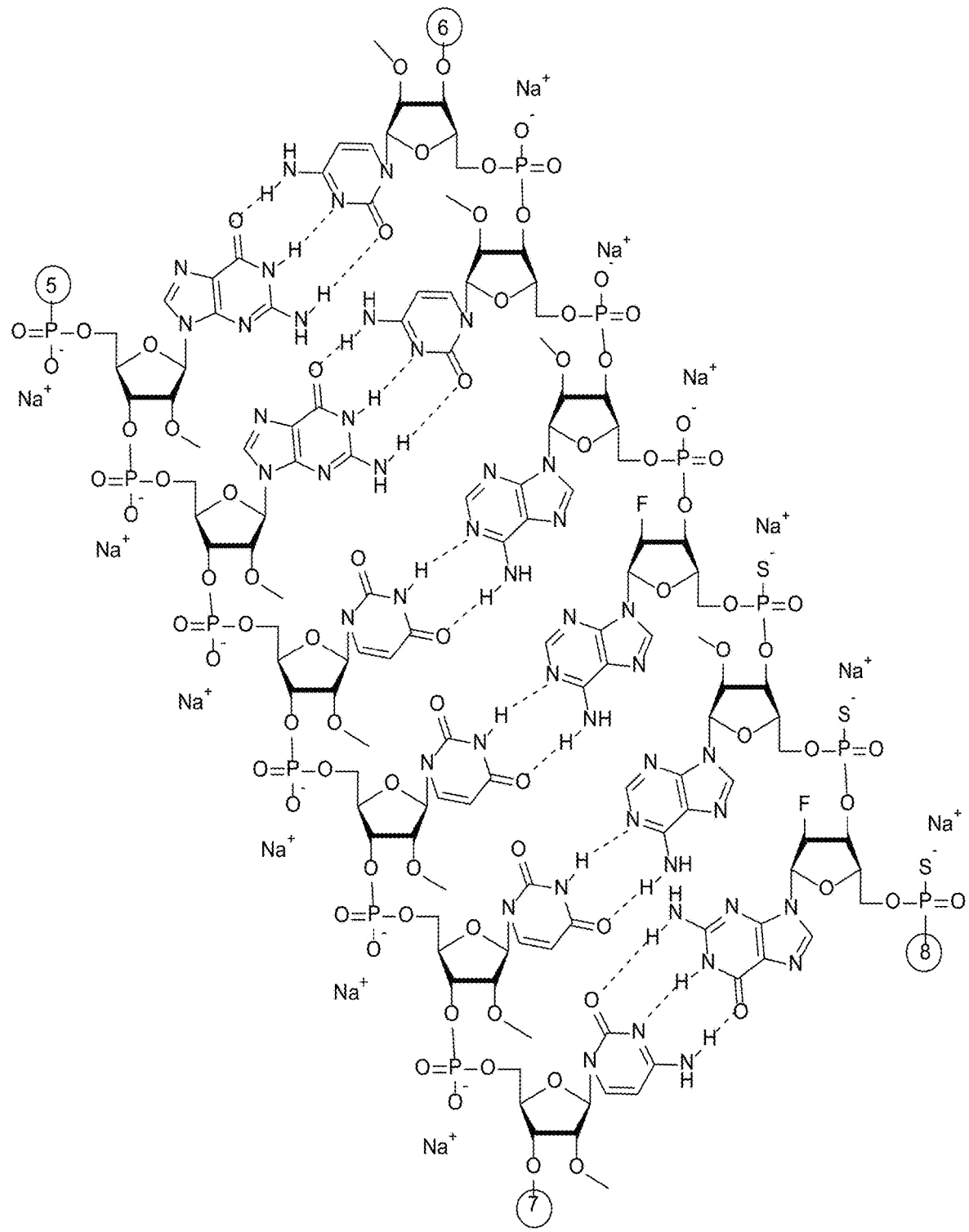
Figure 21E:
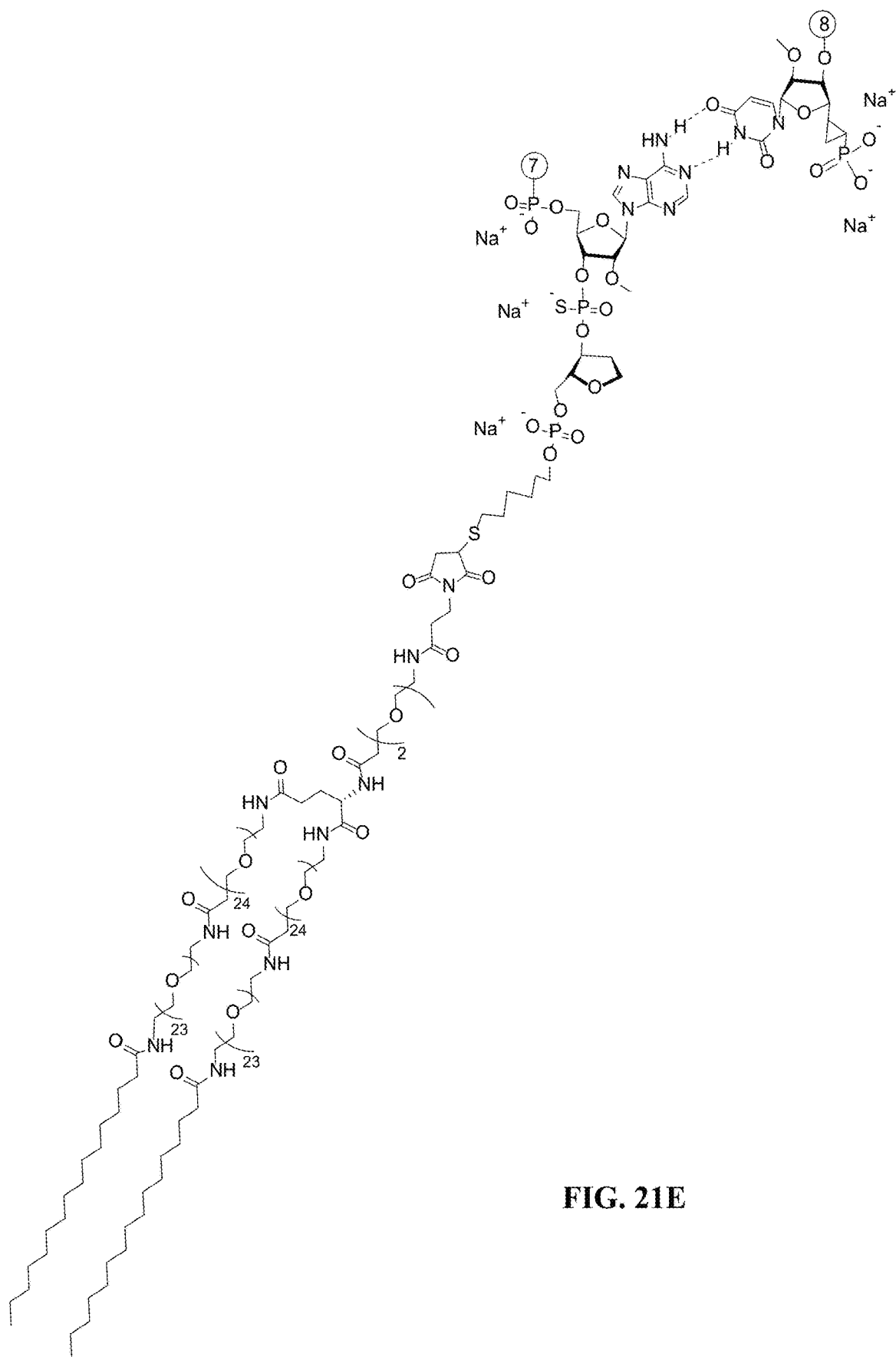

The mice in Example 10 were further subjected to the Rotarod apparatus to conduct a gross motor coordination assessment, as describe in Example 2 above. As shown in FIG. 12, throughout the duration of the study the animals dosed with the DUX4 RNAi agents (Groups 3-5) were able to maintain their balance and gross motor function on the Rotarod apparatus more similar to the negative control saline group that was not administered tamoxifen (Group 1). Conversely, the animals dosed with tamoxifen but no DUX4 RNAi agent (Group 2) were unable to maintain balance and motor function for long and began falling off the Rotarod apparatus much sooner by day 11 (as compared to Groups 1, 3 and 4) indicating a loss of muscle function in the animals of Group 2. The animals dosed with tamoxifen but no DUX4 RNAi agent until Day 10 (Group 5) similarly were unable to maintain balance and motor function for long and began falling off the Rotarod apparatus more quickly by day 11; however, following DUX4 RNAi agent dosing (began day 10), by day 15, these animals were able to maintain balance and motor function sufficient to stay on the Rotarod apparatus for comparable time to the animals of Groups 1, 3, and 4 indicating an initial loss of muscle function in the animals of Group 5 that was reversed by the administration of the DUX4 RNAi agent.

As evidenced by the data shown above, the DUX4 RNAi agent showed substantial inhibition of DUX4 gene expression and preservation gross motor function or reversed gross motor function loss (as shown by Group 5 beginning around day 15) in the model mice.

Example 11. In Vitro Inhibition DUX4 RNAi Agents in Patient-Derived Myotubes

Frozen untransformed FSHD patient-derived myoblasts were acquired from the NIGMS Human Genetic Cell Repository at the Coriell Institute for Medical Research (Camden, NJ). Upon differentiation into myotubes in vitro, these cells have been shown to express relatively high levels of DUX4 and target genes of DUX4 protein. The FSHD patient-derived myoblasts were then expanded and differentiated into myotubes in vitro.

The objective of this study was to assess dose response of this DUX4 RNAi agent on the knockdown of DUX4 mRNA expression and the reduction of biomarkers of DUX4 protein activity in FSHD patient-derived myotubes following transfection.

The FSHD patient-derived myoblasts were expanded and differentiated into myotubes in vitro. The DUX4 RNAi agent was transfected into differentiating myotubes using a commercially available lipofectamine transfection reagent (RNAiMAX; Thermo). Myotube cultures were harvested once mature myotube morphology was observed and DUX4 and DUX4 target gene relative expression examined.

The DUX4 RNAi agent assessed in patient-derived myotubes was DUX4 RNAi agent AD07778 linked to the targeting ligand of peptide 1 and the PK/PD modulator LP29b (see AC000448 in Table 5.4 for fully modified and conjugated sense and antisense strand structure), which was synthesized according to phosphoramidite technology on solid phase in accordance with general procedures known in the art and commonly used in oligonucleotide synthesis, as set forth in Example 1 herein.

The DUX4 RNAi agent was tested at 1.0, 10, and 100 nM concentrations. A "scrambled control" was also evaluated, which included the same targeting ligands and PK/PD modifier as the DUX4 RNAi agent AD07778 linked to the targeting ligand of peptide 1 and the PK/PD modulator LP29b, but the scrambled control was modified in a manner such that it was expected to have no activity and would not inhibit DUX4 gene expression.

Figure 11:
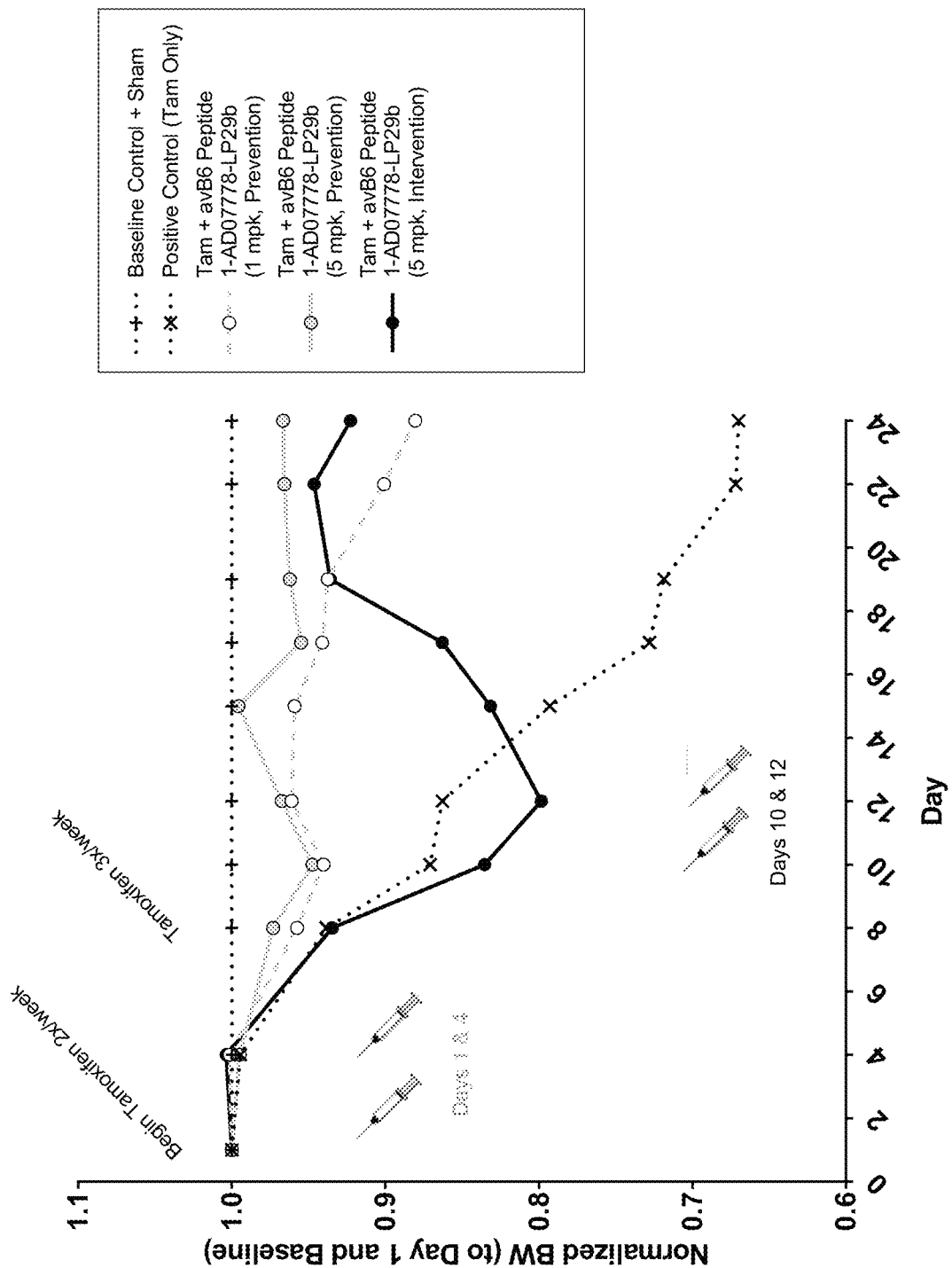
FIG. 11. Graph depicting mean bodyweights of FSHD-like model mice, as more fully described in Example 10.

FIG. 11 shows a dose-dependent inhibition of the patient-derived myotubes with the DUX4 RNAi agent, suggesting that the DUX4 RNAi agent is effective to reduce DUX4 protein expression by elimination of DUX4 mRNA in human muscle cells. The data were normalized against "scrambled control.".

Additionally, certain biomarkers of DUX4 expression were evaluated to determine how they were impacted by the DUX4 RNAi agent. These include CCNA1, KHDC1L, LEUTX, MDB3L2, PRAMEF2, PRAMEF6, SLC2A3, SLC34A2, TRIM43, and ZSCAN4. These genes are known gene targets of the DUX4 transcription factor and whose increased expression has been characterized in FSHD patient muscle biopsies as markers of increased DUX4 expression. As shown in FIG. 12, cells in which the DUX4 RNAi agent was administered also showed reductions in expression levels for these FSHD biomarker genes.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. An RNAi agent for inhibiting expression of a double homeobox 4 (DUX4) gene, comprising:
   i. an antisense strand consisting of the nucleotide sequence cPrpusGfsasAfaccagauCfuGfaAfuccusg (SEQ ID NO: 99); and
   ii. a sense strand comprising the nucleotide sequence caggauucAfGfAfucugguuuca (SEQ ID NO: 147); wherein a represents 2'-O-methyl adenosine, c represents 2'-O-methyl cytidine, g represents 2'-O-methyl guanosine, and u represents 2'-O-methyl uridine; Af represents 2'-fluoro adenosine, Cf represents 2'-fluoro cytidine, Gf represents 2'-fluoro guanosine, and Uf represents 2'-fluoro uridine; cPrpu represents a 5'-cyclopropyl phosphonate-2'-O-methyl uridine; and s represents a phosphorothioate linkage.

2. The RNAi agent of claim 1, wherein the sense strand comprises a targeting ligand having the structure:

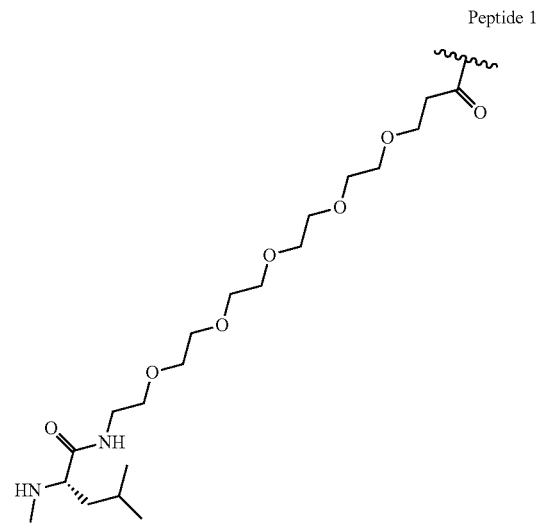

Peptide 1

-continued

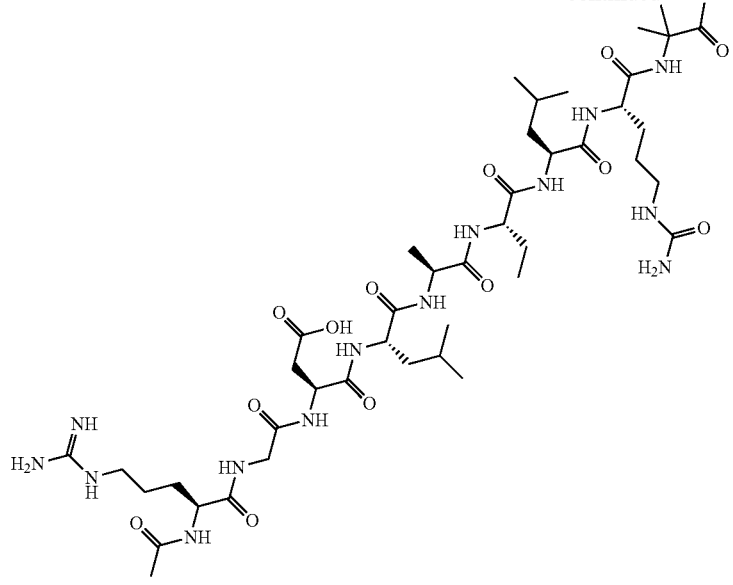

αvβ6 or a pharmaceutically acceptable salt thereof, wherein ⁀ indicates the point of connection to the RNAi agent.

3. The RNAi agent of claim 2, wherein the targeting ligand is linked to the 5′ terminal end of the sense strand.

4. The RNAi agent of claim 1, wherein the RNAi agent is further linked to a pharmacokinetic/pharmacodynamic (PK/PD) modulator.

5. The RNAi agent of claim 4, wherein the PK/PD modulator is linked to the sense strand.

6. The RNAi agent of claim 5, wherein the PK/PD modulator is linked to the 3′ terminal end of the sense strand.

7. The RNAi agent of claim 4, wherein the PK/PD modulator is:

2′-fluoro guanosine, and Uf represents 2′-fluoro uridine; cPrpu represents a 5′-cyclopropyl phosphonate-2′-O-methyl uridine; s represents a phosphorothioate linkage, and (invAb)s represents

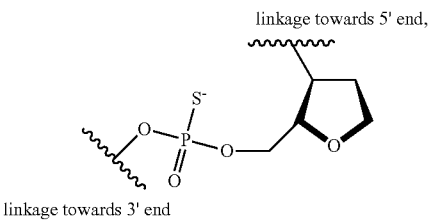

LP 29b

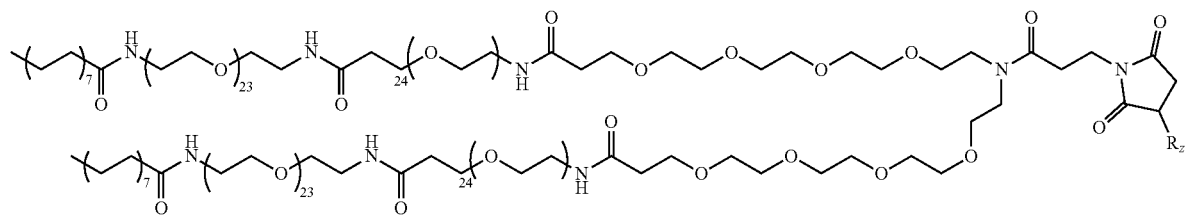

wherein $R_z$ comprises the RNAi agent.

8. An RNAi agent for inhibiting expression of a double homeobox 4 (DUX4) gene, comprising:
  i. an antisense strand consisting of the nucleotide sequence cPrpusGfsasAfaccagauCfuGfaAfuccusg (SEQ ID NO: 99); and
  ii. a sense strand comprising the nucleotide sequence αvβ6-peptide 1-(NH-C6)s(invAb)scaggauucAfGfA-fucugguuucas(invAb)(C6-S)-LP29b (SEQ ID NO:236);
wherein a represents 2′-O-methyl adenosine, c represents 2′-O-methyl cytidine, g represents 2′-O-methyl guanosine, and u represents 2′-O-methyl uridine; Af represents 2′-fluoro adenosine, Cf represents 2′-fluoro cytidine, Gf represents (C6-S) represents linkage towards 5′ end of oligonucleotide    linkage towards 3′ end of, oligonucleotide

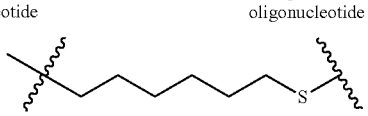

LP29b represents

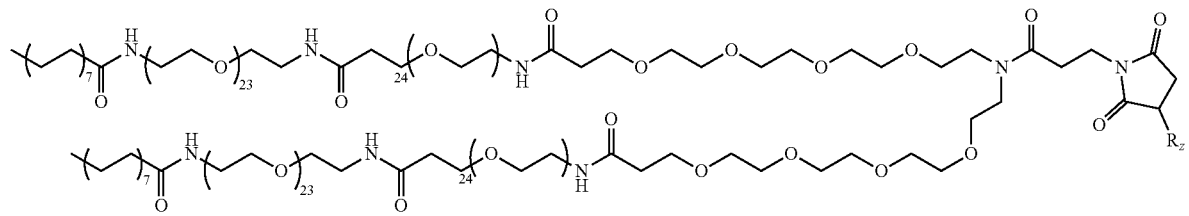

wherein $R_z$ is the remainder of the RNAi agent, (NH-C6)s represents

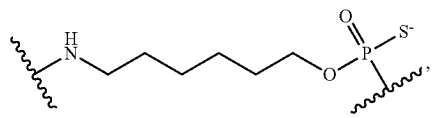 [SMILES: *NCCCCCCOP(*)(=O)[S-]]

αvβ6-peptide 1 represents

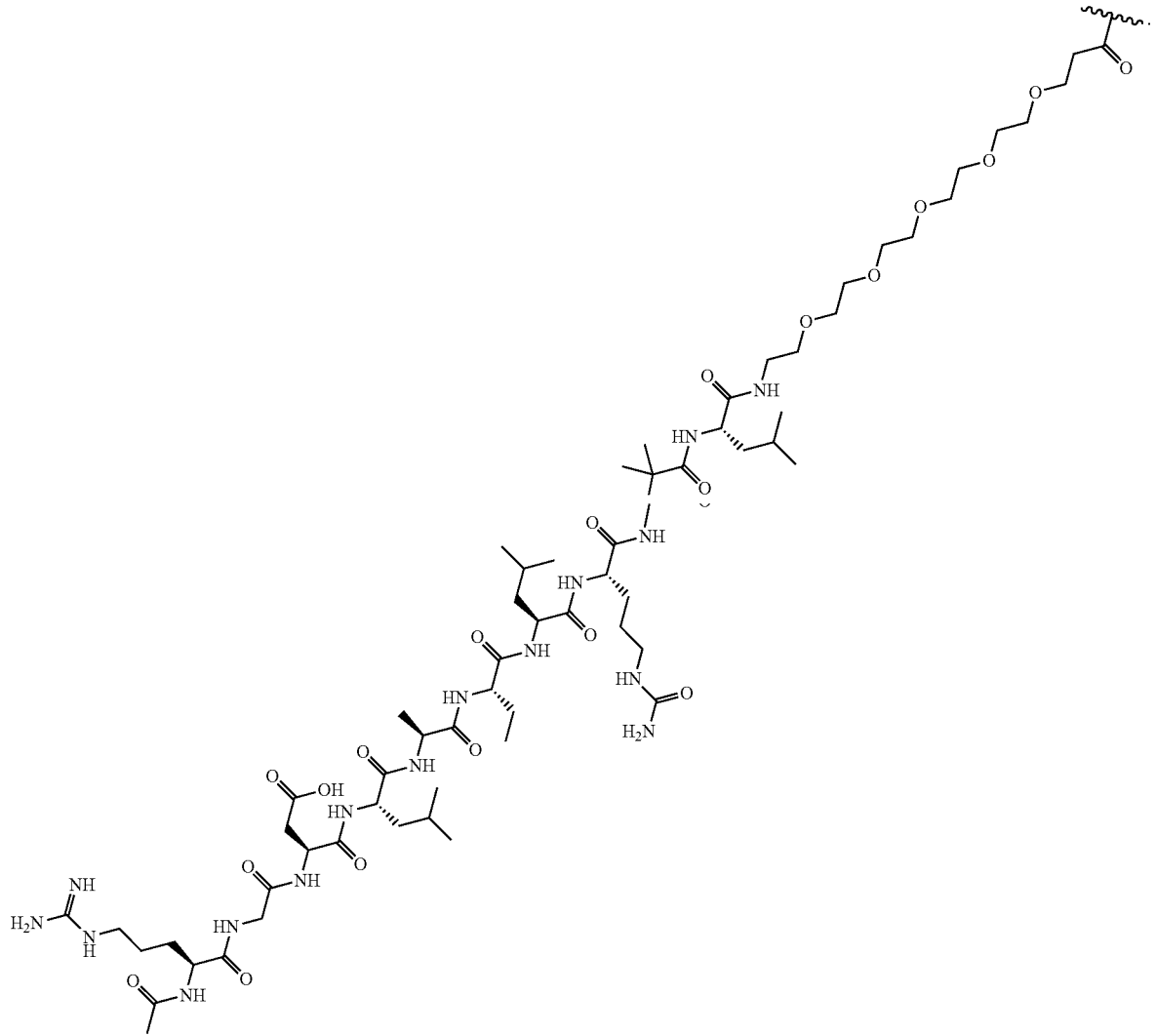 [SMILES: *C(=O)CCOCCOCCOCCOCCOCCNC(=O)[C@H](CC(C)C)NC(=O)C(C)(C)NC(=O)[C@H](CCCNC(N)=O)NC(=O)[C@H](CC(C)C)NC(=O)[C@H](CC)NC(=O)[C@H](C)NC(=O)[C@H](CC(C)C)NC(=O)[C@H](CC(=O)O)NC(=O)CNC(=O)[C@H](CCCNC(=N)N)NC(C)=O]

9. The RNAi agent of claim 8, wherein the RNAi agent is a pharmaceutically acceptable salt.

10. The RNAi agent of claim 9, wherein the RNAi agent is in the sodium salt form.

11. A pharmaceutical composition comprising the RNAi agent of claim 1, wherein the composition further comprises a pharmaceutically acceptable excipient.

12. A method for inhibiting expression of a DUX4 gene in a cell, the method comprising introducing into a cell an effective amount of the RNAi agent of claim 1.

13. The method of claim 12, wherein the cell is within a subject.

14. The method of claim 13, wherein the subject is a human subject.

15. The method of claim 14, wherein the DUX4 gene expression is inhibited by at least about 40% in the skeletal muscle cells of the subject.

16. The method of claim 12, wherein the subject's DUX4 protein levels are reduced by at least about 40%.

17. The method of claim 12, wherein the DUX4 gene expression is reduced in one or more of paraspinal, facial, torso, abdominal, and limb muscle tissues of the subject.

18. The method of claim 12, wherein the DUX4 gene expression is reduced in one or more of the triceps, biceps, quadriceps, gastrocnemius, soleus, EDL (extensor digitorum longus), TA (Tibialis anterior), or diaphragm of the subject.

19. The method of claim 12, wherein the RNAi agent is administered at a dose of about 0.5 mg/kg to about 20.0 mg/kg of body weight.

20. A method of treating one or more symptoms or diseases that can be ameliorated at least in part by a reduction in DUX4 protein levels or a reduction in DUX4 mRNA levels, the method comprising administering to a human subject in need thereof a therapeutically effective amount of the pharmaceutical composition of claim 11.

21. The method of claim 20, wherein the disease is Facioscapulohumeral Muscular Dystrophy (FSHD).

22. The method of claim 21, wherein the RNAi agent is administered by subcutaneous (SQ) injection.

* * * * *